US00RE50753E

(19) United States
(12) Reissued Patent
Barouch et al.

(10) Patent Number: US RE50,753 E
(45) Date of Reissued Patent: Jan. 20, 2026

(54) RECOMBINANT ADENOVIRUSES AND USE THEREOF

(71) Applicants: Beth Israel Deaconess Medical Center, Inc., Boston, MA (US); Washington University, St. Louis, MO (US)

(72) Inventors: Dan H. Barouch, Newton, MA (US); Herbert Virgin, IV, St. Louis, MO (US); Peter Abbink, Winthrop, MA (US)

(73) Assignee: Beth Israel Deaconess Medical Center, Inc., Boston, MA (US)

(21) Appl. No.: 17/934,479

(22) Filed: Sep. 22, 2022

Related U.S. Patent Documents

Reissue of:
(64) Patent No.: 10,781,427
Issued: Sep. 22, 2020
Appl. No.: 16/159,336
Filed: Oct. 12, 2018

U.S. Applications:
(63) Continuation of application No. 14/443,299, filed as application No. PCT/US2013/070353 on Nov. 15, 2013, now Pat. No. 10,106,781.

(60) Provisional application No. 61/727,455, filed on Nov. 16, 2012.

(51) Int. Cl.
*C12N 7/00* (2006.01)
*A61K 39/00* (2006.01)
*A61K 39/12* (2006.01)

(52) U.S. Cl.
CPC ..... *C12N 7/00* (2013.01); *A61K 39/00* (2013.01); *A61K 39/12* (2013.01)

(58) Field of Classification Search
CPC ..... C12N 7/00; C12N 2710/10042; C12N 2710/10321; C12N 2710/10343; C12N 2740/15034; C12N 15/861; A61K 39/00; A61K 39/12; A61K 2039/5256; A61K 2039/5258
See application file for complete search history.

(56) References Cited

U.S. PATENT DOCUMENTS

| | | | |
|---|---|---|---|
| 4,695,623 | A | 9/1987 | Stabinsky |
| 7,247,472 | B2 | 7/2007 | Wilson et al. |
| 9,718,863 | B2 | 8/2017 | Colloca et al. |
| 10,106,781 | B2 | 10/2018 | Barouch et al. |
| 2004/0136963 | A1 | 7/2004 | Wilson et al. |
| 2005/0232900 | A1 | 10/2005 | Vogels et al. |
| 2010/0034774 | A1 | 2/2010 | Vogels et al. |
| 2011/0000480 | A1 | 1/2011 | Turner et al. |
| 2011/0306090 | A1 | 12/2011 | Francky et al. |
| 2012/0027788 | A1 | 2/2012 | Colloca et al. |
| 2012/0076812 | A1 | 3/2012 | Barouch et al. |
| 2014/0348791 | A1 | 11/2014 | Barouch et al. |
| 2015/0291935 | A1 | 10/2015 | Barouch et al. |
| 2017/0119872 | A1 | 5/2017 | O'Hagan et al. |
| 2019/0136205 | A1 | 5/2019 | Barouch et al. |

FOREIGN PATENT DOCUMENTS

| | | | |
|---|---|---|---|
| CN | 1578678 | A | 2/2005 |
| EP | 1944043 | A1 | 7/2008 |
| JP | 2005-523730 | A | 8/2005 |
| WO | WO-97/00326 | A1 | 1/1997 |
| WO | WO-00/70071 | A1 | 11/2000 |
| WO | WO-01/02607 | A1 | 1/2001 |
| WO | WO-02/22080 | A2 | 3/2002 |
| WO | WO-02/40665 | A2 | 5/2002 |
| WO | WO-03/046124 | A3 | 6/2003 |
| WO | WO-2003046124 | A2 | 6/2003 |
| WO | WO-2004001032 | A2 | 12/2003 |
| WO | WO-2007/104792 | A2 | 9/2007 |
| WO | WO-2008/010864 | A2 | 1/2008 |
| WO | WO-2008/010864 | A3 | 5/2008 |
| WO | WO-2011/057248 | A2 | 5/2011 |
| WO | WO-2011/057254 | A2 | 5/2011 |
| WO | WO-2011/057248 | A3 | 9/2011 |
| WO | WO-2011/129468 | A1 | 10/2011 |
| WO | WO-2012/021730 | A2 | 2/2012 |
| WO | WO-2012/024351 | A2 | 2/2012 |
| WO | WO-2012/024351 | A3 | 5/2012 |
| WO | WO-2014/078688 | A2 | 5/2014 |
| WO | WO-2014/078688 | A3 | 7/2014 |

OTHER PUBLICATIONS

Avvakumov N et al. "Comprehensive sequence analysis of the E1A proteins of human and simian adenoviruses." Virology 329: 477-492. (Year: 2004).*

GenBank, "KM591901.1—Rhesus adenovirus 51, complete genome." Available online at < https://www.ncbi.nlm.nih.gov/nuccore/KM591901.1/ >. Downloaded from the Internet Jul. 10, 2024. (Year: 2015).*

GenBank, "KM591902.1—Rhesus adenovirus 52, complete genome." Available online at < https://www.ncbi.nlm.nih.gov/nuccore/KM591902.1/ >. Downloaded from the Internet Jul. 10, 2024. (Year: 2015).*

GenBank, "KM591903.1—Rhesus adenovirus 53, complete genome." Available online at < https://www.ncbi.nlm.nih.gov/nuccore/KM591903.1/ >. Downloaded from the Internet Jul. 10, 2024. (Year: 2015).*

Abbink P et al. "Construction and Evaluation of Novel Rhesus Monkey Adenovirus Vaccine Vectors." J Virol 89: 1512-1522. (Year: 2015).*

(Continued)

*Primary Examiner* — Lora E Barnhart Driscoll
(74) *Attorney, Agent, or Firm* — Clark & Elbing LLP

(57) ABSTRACT

The present invention relates to recombinant adenoviruses and vectors thereof. In particular, the adenoviruses are novel simian adenoviruses having a low seroprevalence and high immunogenicity relative to other adenoviruses and vectors thereof. The invention also provides methods for production of the adenoviruses and for the treatment of diseases by administering the adenoviral vector(s) to a subject (e.g., a human).

69 Claims, 26 Drawing Sheets

Specification includes a Sequence Listing.

(56) References Cited

OTHER PUBLICATIONS

PubMed, "Construction and Evaluation of Novel Rhesus Monkey Adenovirus Vaccine Vectors." Available online at < https://pubmed.ncbi.nlm.nih.gov/25410856/ >. Downloaded from the Internet Jul. 10, 2024. (Year: 2014).*
English Translation of Office Action for Japanese Patent Application No. 2022-057870, mailed Jul. 4, 2023 (8 pages).
Abbink et al. "Rapid Cloning of Novel Rhesus Adenoviral Vaccine Vectors," J Virol. 92(6):e01924-17 (2018) (11 pages).
Bangari et al. "Development of nonhuman adenoviruses as vaccine vectors," Vaccine 24(7):849-62 (2006) (21 pages).
Communication Pursuant to Rules 70(2) and 70a(2) EPC for International Patent Application No. PCT/US2013/070353, dated Jul. 5, 2016 (1 page).
Dicks et al. "A novel chimpanzee adenovirus vector with low human seroprevalence: improved systems for vector derivation and comparative immunogenicity," PLOS One 7(7):e40385 (Jul. 2012) (12 pages).
Examination Review Report for Singaporean Patent Application No. 11201503864T, dated Apr. 22, 2019 (4 pages).
Extended European Search Report for European Patent Application No. 13854932.4, mailed Jun. 17, 2016 (8 pages).
Finkbeiner, et al., "Metagenomic analysis of human diarrhea: viral detection and discovery," PLoS Pathog. 4(2):e1000011 (2008) (9 pages).
Geisbert et al. "Recombinant adenovirus serotype 26 (Ad26) and Ad35 vaccine vectors bypass immunity to Ad5 and protect nonhuman primates against ebolavirus challenge," J Virol. 85(9):4222-33 (2011).
Handley et al., "Pathogenic simian immunodeficiency virus infection is associated with expansion of the enteric virome," Cell. 151(2):253-66 (Oct. 2012).
Holterman et al., "Novel replication-incompetent vector derived from adenovirus type 11 (Ad11) for vaccination and gene therapy: low seroprevalence and non-cross-reactivity with Ad5," J Virol. 78(23):13207-15 (2004).
International Search Report and Written Opinion for International Application No. PCT/US2018/064978 dated Apr. 24, 2019 (20 pages).
International Search Report and Written Opinion for International Patent Application No. PCT/US13/70353, mailed May 12, 2014 (17 pages).
Kass-Eisler et al., "Circumventing the immune response to adenovirus-mediated gene therapy," Gene Ther. 3(2):154-62 (1996) (10 pages).
Lemckert et al., "Immunogenicity of heterologous prime-boost regimens involving recombinant adenovirus serotype 11 (Ad11) and Ad35 vaccine vectors in the presence of anti-ad5 immunity," J Virol. 79(15):9694-701 (2005).
Liu et al., "Modulation of DNA vaccine-elicited $CD8^+$ T-lymphocyte epitope immunodominance hierarchies," J Virol. 80(24):11991-7 (2006).
Notice of Reasons for Rejection for Japanese Patent Application No. 2015-542833, mailed Sep. 5, 2017 (20 pages).
Office Action for Chinese Patent Application No. 201380068078.0, mailed Apr. 4, 2018 (5 pages).
Office Action for Israeli Patent Application No. 238847, dated May 27, 2019 (5 pages).
Office Action for Japanese Patent Application No. 2015-542833, mailed Apr. 22, 2020 (4 pages).
Office Action for Japanese Patent Application No. 2015-542833, mailed Aug. 7, 2018 (8 pages).
Office Action for Japanese Patent Application No. 2018-038380, Mar. 12, 2019 (28 pages).
Setoguchi et al., "Intraperitoneal In Vivo Gene Therapy to Deliver alpha1-Antitrypsin to the Systemic Circulation," Am J Respir Cell Mol Biol. 10(4):369-77 (1994).
Shiver et al., "Replication-incompetent adenoviral vaccine vector elicits effective anti-immunodeficiency-virus immunity," Nature. 415(6869):331-5 (2002).
Yei et al., "Adenovirus-mediated Gene Transfer for Cystic Fibrosis: Quantitative Evaluation of Repeated in Vivo Vector Administration to the Lung," Gene Ther. 1(3):192-200 (1994).
International Preliminary Report on Patentability for International Application No. PCT/US2018/064978, dated Jun. 16, 2020 (9 pages).
Communication Pursuant to 164(1) EPC for European Patent Application No. 18889863.9, dated Nov. 3, 2021 (22 pages).
"UniProtKB: Q5C8P9," UniProtKB, <https://www.uniprot.org/uniprot/Q5C8P9> (2005) (7 pages).
Pantó et al., "Taxonomy Proposal For Old World Monkey Adenoviruses: Characterisation of Several Non-Human, Non-Ape Primate Adenovirus Lineages," Arch Virol. 160: 3165-77 (2015) (14 pages).
Extended European Search Report for European Patent Application No. 18889863.9, dated Mar. 10, 2022 (24 pages).
International Search Report and Written Opinion for International Application No. PCT/US02/33645, mailed Sep. 30, 2003 (4 pages).
International Search Report and Written Opinion for International Application No. PCT/US2007/010347, mailed May 3, 2008 (4 pages).
International Search Report and Written Opinion for International Application No. PCT/US2010/055991, mailed Jun. 30, 2011 (6 pages).
International Search Report and Written Opinion for International Application No. PCT/US2011/048006, mailed Apr. 9, 2012 (3 pages).
International Search Report and Written Opinion for International Application No. PCT/US13/70353, mailed May 12, 2014 (3 pages).
Wu et al., "Flexibility of the adenovirus fiber is required for efficient receptor interaction," J Virol. 77(13):7225-35 (Jul. 2003).
Morris et al., "Simian adenoviruses as vaccine vectors," Future Virol. 11(9):649-659 (Sep. 2016).
Awasthi et al., "A Dual-Modality Herpes Simplex Virus 2 Vaccine for Preventing Genital Herpes by Using Glycoprotein C and D Subunit Antigens To Induce Potent Antibody Responses and Adenovirus Vectors Containing Capsid and Tegument Proteins as T Cell Immunogens," J Virol. 89(16):8497-509 (Aug. 2015).
Office Action for Japanese Patent Application No. 2022-057870, Jan. 10, 2023 (3 pages).
Abbink et al., "Comparative seroprevalence and immunogenicity of six rare serotype recombinant adenovirus vaccine vectors from subgroups B and D," J Virol. 81(9):4654-63 (2007).
Abbink et al., "Development of Novel Simian Adenovirus Based Vaccine Vectors." Poster. 2013. <http://epostersonline.s3.amazonaws.com>. Retrieved on Apr. 16, 2014 (1 page).
Bangari and Mittal. "Development of nonhuman adenoviruses as vaccine vectors,"Vaccine 24(7):849-62 (2006) (21 pages).
Barouch et al., "Immunogenicity of recombinant adenovirus serotype 35 vaccine in the presence of pre-existing anti-Ad5 immunity." J Immunol. 172(10):6290-7 (2004) (9 pages).
Barouch et al., "International seroepidemiology of adenovirus serotypes 5, 26, 35, and 48 in pediatric and adult populations," Vaccine. 29(32):5203-9 (2011) (14 pages).
Communication Pursuant to 94(3) EPC for European Patent Application No. 13854932.4, dated Sep. 28, 2017 (8 pages).
Communication Pursuant to Rules 70(2) and 70a(2)EPC for International Patent Application No. PCT/US 13/70353, dated Jul. 5, 2016 (1 page).
EMBOSS Needle, "Pairwise Sequence Alignment (PROTEIN)." http://www.ebi.ac.uk/Tools/psa/emboss_needle/, retrieved Aug. 18, 2017 (40 pages).
Geisbert et al., "Recombinant adenovirus serotype 26 (Ad26) and Ad35 vaccine vectors bypass immunity to Ad5 anti protect nonhuman primates against ebolavirus challenge," J Virol. 85(9):4222-33 (2011).
GenBank Accession No. AF326321.1. Retrieved on Apr. 16, 2014 (3 pages).
GanBank Accession No. AY771780.1. Retrieved on Apr. 16, 2014 (15 pages).

(56) References Cited

OTHER PUBLICATIONS

GenBank Accession No. AZ111781.1. Retrieved on Jul. 13, 2016 (2 pages).
GenBank Accession No. JA453575.1. Retrieved on Jul. 13, 2016 (8 pages).
GenBank Accession No. AY771780. Retrieved Oct. 24, 2017 (17 pages).
Hayes, "Zika virus outside Africa," Emerg Infect Dis. 15(9):1347-50 (2009).
Holterman et al., "Novel replication-incompetent vector derived from adenovirus type 11 (Ad11) for vaccination and gene therapy: low seroprevalence and non-cross-reactivity with Ads," J Virol. 78(23):13207-15 (2004).
International Preliminary Report on Patentability for International Patent Application No. PCT/US2013/070353. dated May 19, 2015 (8 pages).
International Search Report and Written Opinion for International Patent Application No. PCT/US13/70353. dated May 12, 2014 (17 pages).
Kovacs et al., "Complete genome sequence of simian adenovirus 1: an Old World monkey adenovirus with two fiber genes," Journal of General Virology. 86(6):1681-6 (2005).
Lemckert et al., "Immunogenicity of heterologous prime-boost regimens involving recombinant adenovirus scrotype 11 (Ad11) and Ad35 vaccine vectors in the presence of anti-ad5 immunity," J Virol. 79(15):9694-701 (2005).
Letvin et al., "Prospects for vaccine protection against HIV-1 infection and AIDS." Annu Rev Immunol. 20:73-99 (2002).
Liu et al. "Modulation of DNA vaccine-elicited CD8+ T-lymphocyte epitope immunodominanee hierarchies." J Virol. 80(24):11991-7 (2006).
Notice of Reasons for Rejection for Japanese Patent Application No. 2015-542833, dated Sep. 5, 2017 (20 pages).
Office Action for Chinese Patent Application No. 201380068078.0, dated Apr. 4, 2018 (5 pages).
Ostapchuk et al., "Pseudopackaging of adenovirus type 5 genomes into capsids containing the hexon proteins of adenovirus serotypes B, D, or E," J Virol. 75(1):45-51 (2001).
Search Report for Singaporean Application No. 11201503864T, dated Feb. 29, 2016 (3 pages).
Shiver et al., "Recent advances in the development of HIV-1 vaccines using replication-incompetent adenovirus vectors," Annu Rev Med. 55:355-72 (2004).
Sprangers et al., "Quantifying adenovirus-neutralizing antibodies by luciferase transgene detection: addressing preexisting immunity to vaccine and gene therapy vectors,"J Clin Microbiol. 41(11):5046-52 (2003).
Sumida et al., "Neutralizing antibodies to adenovirus serotype 5 vaccine vectors are directed primarily against the adenovirus hexon protein," J Immunol. 174(11):7179-85 (2005).
Tripp et al., "Development of a Zika vaccine," Expert Rev Vaccines. 15(9):1083-5 (2016).
Vogels et al., "Replication-deficient human adenovirus type 35 vectors for gene transfer and vaccination: efficient human cell infection and bypass of preexisting adenovirus immunity," J Virol. 77(15):8263-71 (2003).
Wodrich et al., "Switch from capsid protein import to adenovirus assembly by cleavage of nuclear transport signals," EMBO J. 22(23):6245-55 (2003).
Written Opinion for Singaporean Application No. 11201503864T, dated Apr. 1, 2016 (6 pages).
Dicks et al., "A novel chimpanzee adenovirus vector with low human seroprevalence: improved systems for vector derivation and comparative immunogenicity," PLoS One 7(7):e40385 (2012) (12 pages).
Office Action for Israeli Patent Application No. 238847, dated May 27, 2019 (7 pages).
Examination Report for Australian Patent Application No. 2018229561, dated Jun. 21, 2019 (4 pages).
Examination Review Report for Singapore Patent Application No. 11201503864T, dated Apr. 22, 2019 (4 pages).
First Examination Report for New Zealand Patent Application No. 708144, dated Mar. 13, 2019 (5 pages).
Office Action for Japanese Patent Application No. 2018-038380, dated Mar. 12, 2019 (28 pages).
Extended European Search Report for European Patent Application No. 19179450.2, dated Oct. 9, 2019 (7 pages).
GenBank Accession No. AZI11781.1. Retrieved Jan. 7, 2020 (2 Pages).
"Sequence alignment results, EMBOSS Needle/Pairwise Sequence Alignment/EMBLE-EBI website," <https://www.ebi.ac.uk/Tools/psa/emboss needle/nucleotide.html>, retrieved on Feb. 15, 2019 (10 pages).
Abbink et al., "Construction and Evaluation of Novel Rhesus Monkey adenovirus Vaccine Vectors," J Virol. 89(3):1512-22 (2015) (11 pages).
EMBOSS Needle, "Pairwise Sequence Alignment (NUCLEOTIDE)," www.ebi.ac.uk/Tools/psa/emboss_needle/nucleotide.html, retrieved Feb. 28, 2019 (10 pages).
Foy et al., "Probable Non-Vector-borne Transmission of Zika Virus, Colorado, USA," Emerg Infect Dis. 17(5):880-2 (2011) (7 pages).
Kubo, "The Task of Isolating and Identifying Human Pathogenic Viruses," Seikatsu Eisei. 50(5):381-6 (2006) (English language abstract included).
Kuno et al., "Full-length sequencing and genomic characterization of Bagaza. Kedougou, and Zika viruses," Arch Virol. 152(4):687-96 (2007).
Larocca et al., "Vaccine protection against Zika virus from Brazil," Nature. 536(7617):474-8 (2016) (15 pages).
Office Action for Japanese Patent Application No. 2018-038380, dated Mar. 10, 2020 (16 pages).
Poland et al., "Development of vaccines against Zika virus," Lancet Infect Dis. 18(7):e211-e219 (2018) (9 pages).
Communication pursuant to Article 94(3) EPC for European Application No. 1979450.2. dated May 13, 2020 (5 pages).
Kass-Eisler et al., "The Impact of Developmental Stage, Route of Administration and the Immune System on Adenovirus-Mediated Gene Transfer," Gene Ther. 1(6):395-402 (1994).
Office Action for Japanese Patent Application No. 2015-542833, dated Apr. 22, 2020 (4 pages).
Setoguchi et al., "Intraperitoneal In Vivo Gene Therapy to Deliver alphal-Antitrysin to the Systemic Circulation," Am J Respir Cell Mol Biol. 10(4):369-77 (1994).
Zabner et al., "Safety and efficacy of repetitive adenovirus-mediated transfer of CFTR cDNA to airway epithelia of primates and cotton rats," Nat Genet. 6(1):75-83 (1994).

* cited by examiner sAd4287 human
Total=144
sAd4287 monkey
Total=108 sAd4287 human
Total=144
sAd4287 monkey
Total=108 sAd4312 human
Total=144
sAd4312 monkey
Total=108
<18
18-200
201-1000
>1000

RECOMBINANT ADENOVIRUSES AND USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

STATEMENT AS TO FEDERALLY FUNDED RESEARCH

This invention was made with government support under Grant Nos. AI078526, AI096040, and OD011170, awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Dec. 24, 2019, is named 01948-219003_Sequence_Listing_12_24_19_ST25 and is 600,226 bytes in size.

BACKGROUND OF THE INVENTION

Recombinant adenoviral vectors have been used in the development of vaccines. To date, approximately 55 different adenovirus serotypes have been identified. The subgroup C adenoviruses have been most extensively studied for applications such as vaccination and gene therapy. Adenovirus serotypes 2 and 5 (Ad2 and Ad5), in particular, are widely used in the field. Importantly, Ad5 vector-based vaccines have been shown to elicit potent and protective immune responses in a variety of animal models. Moreover, large-scale clinical trials for HIV vaccination using Ad5-based recombinant vectors are ongoing (see, e.g., WO 01/02607; WO 02/22080; Shiver et al., Nature. 415:331-335, 2002; Letvin et al., Annu. Rev. Immunol. 20:73-99, 2002; and Shiver and Emini, Annu. Rev. Med. 55:355, 2004).

The usefulness of recombinant Ad5 vector-based vaccines for HIV and other pathogens, however, may be limited due to high pre-existing anti-Ad5 immunity in human populations. The presence of anti-Ad5 immunity has been correlated with a reduction in the immunogenicity of Ad5-based vaccines in studies in mice and rhesus monkeys. Early data from phase-1 clinical trials show that this problem may also occur in humans. Although both Ad5-specific neutralizing antibodies (NAbs) and $CD8^+$ T lymphocytes contribute to anti-Ad5 immunity, the Ad5-specific NAbs appear to play the primary role in this process (Sumida et al., J. Virol., 174:7179-7185, 2004).

Accordingly, there is an unmet need in the field for alternative adenoviral vectors that have low seroprevalence and potent immunogenicity.

SUMMARY OF THE INVENTION

The entire genomes of three novel simian adenoviruses (sAds), sAd4287, sAd4310A, and sAd4312, have been identified and their entire genomes determined. These adenoviruses exhibit both surprisingly low seroprevalence and potent immunogenicity, which suggests that these viruses may be useful as novel vaccine vector candidates. In a first aspect, this invention features isolated polynucleotides including a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 1-3, or its complement. SEQ ID NOs: 1, 2, and 3 are the full-length genome sequence of wild-type sAd4287, sAd4310A, and sAd4312, respectively. The isolated polynucleotides of the invention may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, or 35000 or more contiguous or non-contiguous nucleotides of a reference polynucleotide molecule (e.g., SEQ ID NOs: 1-3).

In some embodiments, the isolated polynucleotides of the invention include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 4-12, or its complement. SEQ NOs: 4-12 feature the nucleotide sequences encoding the fiber-1, fiber-2, and hexon proteins of wild-type sAd4287, sAd4310A, and sAd4312. Accordingly, in some embodiments, the nucleotide sequence encoding all or a portion of the fiber-1 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-1 protein of wild-type sAd4287, sAd4310A, or sAd4312, which corresponds to SEQ ID NO: 4, 5, and 6, respectively. In some embodiments, the nucleotide sequence encoding all or a portion of the fiber-2 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-2 protein of wild-type sAd4287, sAd4310A, or sAd4312, which corresponds to SEQ ID NO: 7, 8, and 9, respectively. In some embodiments, the nucleotide sequence encoding all or a portion of the hexon protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the hexon protein of wild-type sAd4287, sAd4, 310A, or sAd4312, which corresponds to SEQ ID NO: 10, 11, and 12, respectively. In some embodiments, the nucleotide sequence can be at least 90% identical (e.g., at least 91%, 92%, 93%, or 94% identical), at least 95% identical (e.g., at least 96%, 97%, 98%, or 99% identical), or 100% identical to all or a portion of one or more hexon protein hypervariable regions (HVRs) (e.g., HVR1 (nt 403 to nt 489), HVR2 (nt 520 to nt 537), HVR3 (nt 592 to nt 618), HVR4 (nt 706 to nt 744), HVR5 (nt 763 to 786), HVR6 (nt 856 to nt 874), and/or HVR7 (nt 1201 to nt 1296) of sAd4287 hexon protein (SEQ ID NO: 10); HVR1 (nt 403 to nt 477), HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12)).

In some embodiments, the one or more nucleotide sequences encoding one or more hexon protein hypervariable regions (HVRs) of the invention have been substituted with that of another virus (e.g., HVR1 (nt 403 to nt 489), HVR2 (nt 520 to nt 537), HVR3 (nt 592 to nt 618), HVR4 (nt 706 to nt 744). HVR5 (nt 763 to 786), HVR6 (nt 856 to nt 874), and/or HVR7 (nt 1201 to nt 1296) of sAd4287 hexon protein (SEQ ID NO: 10); HVR1 (nt 403 to nt 477). HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12)) substituted with the corresponding HVR sequences of one or more other viruses, e.g., an adenovirus, e.g., an adenovirus that has a lower seroprevalence compared to that of Ad5, such as subgroup B (Ad11, Ad34, Ad35, and Ad50) and subgroup D (Ad15, Ad24, Ad26, Ad48, and Ad49) adenoviruses as well as simian adenoviruses (e.g., Pan9, also known as AdC68)). In other embodiments, the nucleotide sequence includes an adenoviral vector backbone of Ad5, Ad11, Ad15, Ad24, Ad26, Ad34, Ad48, Ad49, Ad50, or Pan9/AdC68 having a substitution of all or a portion of one or more of the above hexon HVRs of sAd4287, sAd4310A, and/or sAd4312.

In some embodiments, the isolated polynucleotides of the invention include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 13-18, or its complement. SEQ ID NOs: 13-18 feature the nucleotide sequences encoding the knob domain of the fiber-1 and fiber-2 proteins of wild-type sAd4287, sAd4310A, and sAd4312. In some embodiments, the nucleotide sequence encoding all or a portion of the knob domain of fiber-1 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-1 protein of wild-type sAd4287, sAd4310A, or sAd4312, which corresponds to SEQ ID NO: 13, 14, and 15, respectively. In some embodiments, the nucleotide sequence encoding all or a portion of the knob domain of fiber-2 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-2 protein of wild-type sAd4287, sAd4310A, or sAd4312, which corresponds to SEQ ID NO: 16, 17, and 18, respectively. In some embodiments, one or more nucleotide sequences encoding a knob domain of a fiber protein (e.g., a fiber-1 or fiber-2 protein) of the invention (SEQ ID NOs: 13-18) have been substituted with that of another virus.

In a second aspect, the invention features recombinant vectors including an isolated polynucleotide of the invention, the recombinant vectors including a nucleotide sequence that is at least 90% identical (e.g., at least 91%, 92%, 93%, or 94% identical), at least 95% identical (e.g., at least 96%. 97%, 98%, or 99% identical), or 100% identical to all or a portion of any one of SEQ ID NOs: 34-51. In some embodiments, the vector is an sAd4297 adenoviral vector including all or a portion of any one of SEQ ID NOs: 34-39. In some embodiments, the vector is an sAd4310A adenoviral vector including all or a portion of any one of SEQ ID NOs: 40-45. In some embodiments, the vector is an sAd4312 adenoviral vector including all or a portion of any one of SEQ ID NOs: 46-51. In other embodiments, more than one (e.g., 2, 3, or 4) of the vectors described by SEQ ID NOs: 34-51 may be used to establish a plasmid system for the generation of a recombinant adenovirus of the invention.

In an embodiment of the first or second aspect of the invention, the isolated polynucleotides and/or recombinant vectors are used to generate recombinant adenoviruses wherein all or a portion of the adenoviruses is derived from any one of SEQ ID NOs: 1-3. In some embodiments, the recombinant adenovirus includes an isolated polynucleotide including a deletion in or of the E1 region (e.g., nt 474 to nt 3085 of sAd4287 (SEQ ID NO: 1); nt 474 to nt 3088 of sAd4310A (SEQ ID NO: 2); and nt 487 to nt 3100 of sAd4312 (SEQ ID NO: 3)). A recombinant adenoviral vector that includes this deletion is rendered replication-defective. In some embodiments, the replication-defective virus may also include a deletion in or of the E3 region (e.g., nt 25973 to nt 28596 of sAd4287 (SEQ ID NO: 1); nt 25915 to nt 28496 of sAd4310A (SEQ ID NO: 2); and nt 25947 to nt 28561 of sAd4312 (SEQ ID NO: 3)) and/or E4 region (e.g., nt 31852 to nt 34752 of sAd4287 (SEQ ID NO: 1); nt 31750 to nt 34048 of sAd4310A (SEQ ID NO: 2); and nt 31818 to nt 34116 of sAd4312 (SEQ ID NO: 3)). In other embodiments, the recombinant adenovirus includes one or more of the E1, E3, and/or E4 regions and is replication-competent.

According to a preferred embodiment, the recombinant adenovirus further includes a heterologous nucleotide sequence encoding an antigenic or therapeutic gene product of interest, or fragment thereof. In some embodiments, the antigenic gene product, or fragment thereof, includes a bacterial, viral, parasitic, or fungal protein, or fragment thereof.

The bacterial protein, or fragment thereof, may be from Mycobacterium tuberculosis, Mycobacterium Bovis, Mycobacterium africanum, Mycobacterium microti, Mycobacterium leprae, Pseudomonas aeruginosa, Salmonella typhimurium, Escherichia coil, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani, or Bacillus anthracis. Examples of preferred gene products, or fragments thereof, from Mycobacterium strains include 10.4, 85A, 85E, 85C, CFP-10, Rv3871, and ESAT-6 gene products or fragments thereof.

The viral protein, or fragment thereof, may be from a virus of the Retroviridae family, which includes the human immunodeficiency virus (HIV; e.g., types 1 and 2), and human T-lymphotropic virus Types I and II (HTLV-1 and HTLV-2, respectively); Flaviviridae family (e.g., a member of the Flavivirus, Pestivirus, and Hepacivirus genera), which includes the hepatitis C virus (HCV), Yellow fever virus, tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey island virus, Dakar bat virus, Montana myotis leukoencephalitis virus, Phnom Penh bat virus, Rio Bravo virus, Tamana bat virus, and the Cell fusing agent virus; Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Cliveros virus, Paraná virus, Pichinde virus, Pirital virus, Sabiá virus, Tacaribe virus, Tamiami virus, Whitewater Arroyo virus, Chapare virus, and Lujo virus; Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barman Forest virus, O'nyong'nyong virus, and the chikungunya virus; Poxviridae family (e.g., a member of the Orthopoxvirus genus), which includes the smallpox virus, monkeypox virus, and vaccinia virus; Herpesviridae family; which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); Orthomyxoviridae family, which includes the influenza virus (A, B, and C), such as the H5N1 avian influenza virus or H1N1 swine flu; Coronaviridae family, which includes the severe acute respiratory syndrome (SARS) virus; Rhabdoviridae family, which includes the rabies virus and vesicular stomatitis virus (VSV); Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; Picornaviridae family, which includes the poliovirus, human enterovirus (A, B, C, and D), hepatitis A virus, and the coxsackievirus; Hepadnaviridae family, which includes the hepatitis B virus; Papillomaviridae family, which includes the human papiliomavirus; Parvoviridae family, which includes the adeno-associated virus; Astroviridae family, which includes the astrovirus; Polyomaviridae family, which includes the JC virus, BK virus, and SV40 virus; Calciviridae family, which includes the Norwalk virus; or Reoviridae family, which includes the rotavirus. In a preferred embodiment, the viral protein, or fragment thereof, is from human immunodeficiency virus (HIV), human papiliomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, or Marburg virus. In a most preferred embodiment, the viral protein, or fragment thereof, from HIV is Gag, Pol, Env, Nef, Tat, Rev, Vif, Vpr, or Vpu.

The parasitic protein, or fragment thereof, may be from Toxoplasma gondii, Plasmodium falciparum, Plasmodium vivax, Plasmodium ovale, Plasmodium malariae, Trypanosome spp., or Legionella spp. Examples of particularly preferred parasitic proteins that may be cloned into the vectors of the present invention include those from Plasmodium falciparum, such as the circumsparozoite (CS) protein and Liver Specific Antigens 1 or 3 (SA-1 or LSA-3).

The fungal protein, or fragment thereof, may be from Aspergillus, Blastomyces dermatitidis, Candida, Coccidioides immitis, Cryptococcus neoformans, Histoplasma capsulatum var. capsulatum, Paracoccidioides brasiliensis, Sporothrix schenckii, Zygomycetes spp., Absidia corymbifera, Rhizomucor pusillus, or Rhizopus arrhizus. Examples of fungal gene products, or fragments thereof, include any cell wall mannoprotein (e.g., Afmp1 of Aspergillus fumigatus) or surface-expressed glycoprotein (e.g., SOWgp of Coccidioides immitis).

The therapeutic gene products, or fragments thereof, may be interferon (IFN) proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and/or colony stimulating factors, or fragments thereof.

A third aspect of the invention features a method of treating a subject (e.g., a human) having a disease (e.g., HIV or cancer) by administering a recombinant sAd adenovirus vector of the second aspect of the invention to the subject. In a preferred embodiment, the recombinant sAd adenovirus of the invention includes an antigenic gene product, or fragment thereof, that promotes an immune response against an infective agent in a subject at risk of exposure to, or exposed to, the infective agent. In some embodiments, the infective agent is a bacterium, a virus, a parasite, or a fungus, such as those described above. In one non-limiting example, the administration of a sAd adenovirus of the invention expressing an HIV Gag protein, or fragment thereof, to an HIV-positive subject or a subject with acquired immune deficiency syndrome (AIDS) can stimulate an immune response in the subject against HIV, thereby treating the subject. In another embodiment, the recombinant sAd adenovirus of the invention includes a therapeutic gene product, or fragment thereof, such as an interferon (IFN) protein, or fragment thereof, that provides therapy to a subject having a disease caused by a non-infective agent, such as cancer, by stimulating a favorable immune response in the subject against neoplasia and/or by providing gene therapy, thereby treating the subject. Other non-limiting examples of diseases that may be treated include any human health disease, such as tuberculosis, leprosy, typhoid fever, pneumonia, meningitis, staphylococcal scalded skin syndrome (SSSS), Ritter's, disease, tularemia (rabbit fever), brucellosis, Glanders disease, bubonic plague, septicemic plague, pneumonic plague, diphtheria, pertussis (whooping cough), tetanus, anthrax, hepatitis, smallpox, monkeypox, measles, mumps, rubella, chicken pox, polio, rabies, Japanese encephalitis, herpes, mononucleosis, influenza, Ebola virus disease, hemorrhagic fever, yellow fever, Marburg virus disease, toxoplasmosis, malaria, trypanosomiasis, legionellosis, aspergillosis, blastomycosis, candidiasis (thrush), coccidioidomycosis, cryptococcosis, histoplasmosis, paracoccidioidomycosis, sporotrichosis, or sinus-orbital zygomycosis. Treatment of these diseases may be by administration of a recombinant sAd vector of the invention that encodes or expresses on its surface an immune response-stimulating antigen from the selected infective agent.

In some embodiments, the recombinant adenovirus or adenoviral vector is administered Intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. In one preferred embodiment, the recombinant adenovirus or adenoviral vector is administered as a pharmaceutical composition that includes a pharmaceutically acceptable carrier, diluent, or excipients, and may optionally include an adjuvant. In some embodiments, the subject is administered at least one dose (e.g., 1, 2, 3, 4, 5, 6, 7, 8, 9, 10, or more doses) of the composition. In other embodiments, the subject is administered at least two doses (e.g., 2, 3, 4, 5, 6, 7, 8, 9, 10, or more doses) of the composition. In yet another embodiment, the pharmaceutical composition is administered to the subject as a prime boost or in a prime boost regimen. The subject can be administered at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{14}$ vp/dose. The pharmaceutical composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, 20 years or longer post- diagnosis or post-exposure or to the infective agent. When treating disease (e.g., AIDS or cancer), the pharmaceutical compositions of the invention may be administered to the subject either before the occurrence of symptoms or a definitive diagnosis or after diagnosis or symptoms become evident. The pharmaceutical composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In a fourth aspect, the invention features a method of producing a recombinant adenovirus of the invention that includes culturing a cell in a suitable medium; transfecting the cell with an isolated polynucleotide of the first aspect of the invention or a recombinant vector of the second aspect of the invention; allowing replication of the polynucleotide or vector in the cell; and harvesting the produced recombinant adenovirus from the medium and/or cell. In some embodiments, the cell is a bacterial, plant, or mammalian cell. In a preferred embodiment, the mammalian cell is a PER.55K cell or a Chinese hamster ovary (CHO) cell.

Definitions

By "adenovirus" is meant a medium-sized (90-100 nm), nonenveloped icoshedral virus that includes a capsid and a double-stranded linear DNA genome. The adenovirus can be a naturally occurring, but isolated, adenovirus (e.g., sAd4287, sAd4310A, or sAd4312) or a recombinant adenovirus (e.g., replication-defective or replication competent sAd4287, sAd4310A, or sAd4312, or a chimeric variant thereof).

As used herein, by "administering" is meant a method of giving a dosage of a pharmaceutical composition (e.g., a recombinant adenovirus of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

Throughout this specification and claims, the word "comprise," or variations such as "comprises" or "comprising," will be understood to imply the inclusion of a stated integer or group of integers but not the exclusion of any other integer or group of integers.

By "deletion" of an adenoviral genomic region is meant the partial or complete removal, the disruption (e.g., by an insertion mutation), or the functional inactivation (e.g., by a missense mutation) of a specified genomic region (e.g., the E1, E2, E3, and/or E4 region), or any specific open-reading frame within the specified region.

By "gene product" is meant to include mRNAs or other nucleic acids (e.g., microRNAs) transcribed from a gene as well as polypeptides translated from those mRNAs. In some embodiments, the gene product is from a virus (e.g., HIV) and many include, for example, any one or more of the viral proteins, or fragments thereof, described in, for example, pending U.S. Pub. No, 2012/0076812. In some embodiments, the gene product is a therapeutic gene product, including, but not limited to, interferon proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and colony stimulating factors.

By "heterologous nucleic acid molecule" is meant any exogenous nucleic acid molecule that can be incorporated into, for example, an adenovirus of the invention, or polynucleotide or vector thereof, for subsequent expression of a gene product of interest, or fragment thereof, encoded by the heterologous nucleic acid molecule. In a preferred embodiment, the heterologous nucleic acid molecule encodes an antigenic or therapeutic gene product, or fragment thereof, that is a bacterial, viral, parasitic, or fungal protein, or fragment thereof (e.g., a nucleic acid molecule encoding one or more HIV or SIV Gag, Pol, Env, Net, Tat, Rev, Vif, Vpr, or Vpu gene products, or fragments thereof). The heterologous nucleic acid molecule is one that is not normally associated with the other nucleic acid molecules found in the wild-type adenovirus.

By "isolated" is meant separated, recovered, or purified from a component of its natural environment.

By "pharmaceutical composition" is meant any composition that contains a therapeutically or biologically active agent, such as a recombinant adenoviral vector of the invention, preferably including a heterologous nucleotide sequence encoding an antigenic or therapeutic gene product of interest, or fragment thereof, that is suitable for administration to a subject and that treats a disease (e.g., cancer or AIDS) or reduces or ameliorates one or more symptoms of the disease. For the purposes of this invention, pharmaceutical compositions include vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy (21$^{st}$ ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "portion" or "fragment" is meant a part of a whole. A portion may comprise at least 10%, 20%, 30%, 40%, 50%, 60%, 70%, 80%, 90%, or 95% of the entire length of an polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000 or more contiguous nucleotides of a reference polynucleotide molecule. For polypeptides, for example, a portion may include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, or 350 or more contiguous amino acids of a reference polypeptide molecule.

By "promotes an immune response" is meant eliciting a humoral response (e.g., the production of antibodies) or a cellular response (e.g., the activation of T cells, macrophages, neutrophils, and natural killer cells) directed against, for example, one or more infective agents (e.g., a bacterium, virus, parasite, fungus, or combination thereof) or protein targets in a subject to which the pharmaceutical composition (e.g., a vaccine) has been administered.

By "recombinant" with respect to a vector or virus, is meant a vector or virus that has been manipulated in vitro, such as a vector or virus that includes a heterologous nucleotide sequence (e.g., a sequence encoding an antigenic or therapeutic gene product) or a vector or virus bearing an alteration, disruption, or deletion in a viral E1, E3, and/or E4 region relative to a wild-type viral E1, E3, and/or E4 region.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

A "subject" is a vertebrate, such as a mammal (e.g., primates and humans). Mammals also include, but are not limited to, farm animals (such as cows), sport animals (e.g., horses), pets (such as cats, and dogs), mice, and rats. A subject to be treated according to the methods described herein (e.g., a subject having a disease such as cancer and/or a disease caused by an infective agent, e.g., a bacterium, virus, fungus, or parasite) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been subjected to standard tests or may have been identified, without examination, as one at high risk due to the presence of one or more risk factors (e.g., exposure to a biological agent, such as a virus).

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "vaccine," as used herein, is defined as material used to provoke an immune response and may confer immunity after administration of the vaccine to a subject.

By "vector" is meant a composition that includes one or more genes (non-structural or structural), or fragments thereof, from a viral species, such as an adenoviral species (e.g., sAd4287, sAd4310A, or sAd4312), that may be used to transmit one or more heterologous genes from a viral or non-viral source to a host or subject. The nucleic acid material of the viral vector may be encapsulated, e.g., in a lipid membrane or by structural proteins (e.g., capsid proteins), that may include one or more viral polypeptides (e.g., a glycoprotein). The viral vector can be used to infect cells of a subject, which, in turn, promotes the translation of the heterologous gene(s) of the viral vector into a protein product.

The term "virus," as used herein, is defined as an infectious agent that is unable to grow or reproduce outside a host cell and that infects mammals (e.g., humans) or birds.

Other features and advantages of the invention will be apparent from the following Detailed Description, the drawings, and the claims.

DETAILED DESCRIPTION

Figure 1:
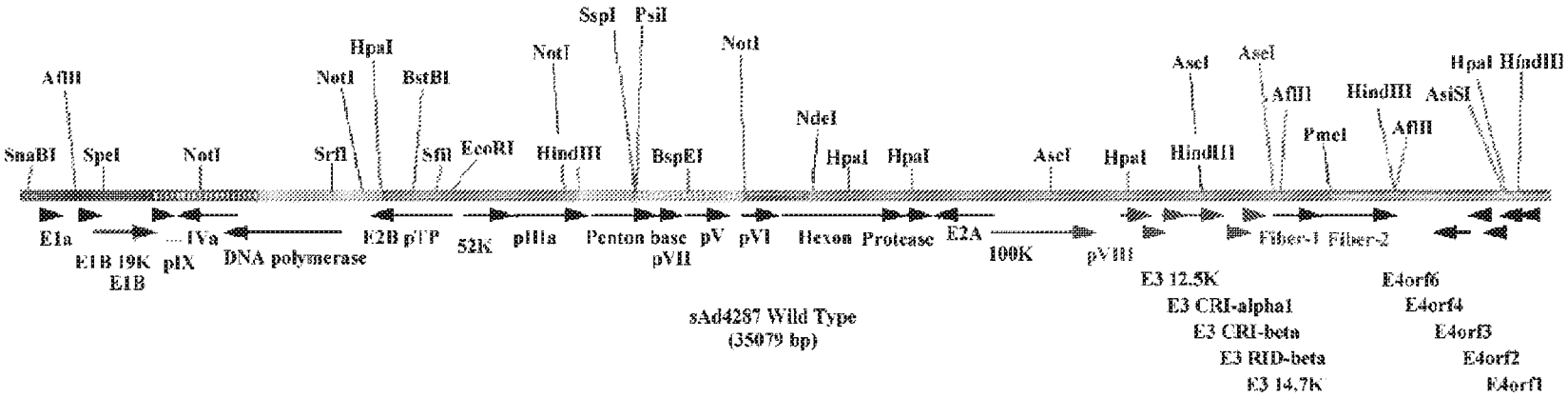
FIG. 1 is a schematic map of the genomic organization of sAd4287.

We have previously identified a variety of novel viruses, including several novel adenoviruses, from rhesus monkeys as part of a metagenomics study (Handley et al. Cell, 151(2):253-266, 2012). In the present invention, we isolated, amplified, and purified three novel simian adenoviruses (sAds), sAd4287, sAd4310 #13-1 (sAd4310A), and sAd4312. The three skis were obtained from the rhesus monkey metagenomics study described above. These viruses are entirely novel and their full sequences have never previously peen reported. As these viruses have not yet been officially "named," they do not yet have an official adenovirus number. Accordingly, the nomenclature used throughout represents our internal laboratory designation.

The complete genome sequence of the novel sAds as well as the vector systems we generated for each of the viruses is described in detail below. We generated recombinant sAd4287, sAd4310A, and sAd4312 vectors expressing a variety of transgenes, including luciferase and SIV Gag. In addition, we demonstrated that these vectors (i) have extremely and surprisingly low seroprevalence in human populations and (ii) exhibit potent immunogenicity in mice. This combination of low baseline anti-vector immunity and potent immunogenicity suggests that these novel adenoviral vectors can be useful in the generation of vaccines against diseases, such as cancer and those caused by an infective agent.

Polynucleotides of the Invention

As a first aspect, the invention provides polynucleotide sequences related to the three novel sAds (sAd4287, sAd4310A, and sAd4312). The isolated polynucleotides may include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of the full-length genome sequence of wild-type sAd4287 (SEQ ID NO: 1), sAd4310A (SEQ ID NO: 2), or sAd4312 (SEQ ID NO: 3), or their complement. The isolated polynucleotides of the invention may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000 or more contiguous or non-contiguous nucleotides of SEQ ID NOs: 1-3.

In some embodiments, the polynucleotides of the invention may be used as primers that are between 10-100 nucleotides in length, more particularly between 10-30 nucleotides in length (e.g., 10, 11, 12, 13, 14, 15, 16, 17, 18, 19, 20, 21, 22, 23, 24, 25, 26, 27, 28, 29, or 30 nucleotides in length), and can be at least 90% identical (e.g., at least 91%, 92%, 93%, or 94% identical), at least 95% identical (e.g., at least 96%, 97%, 98%, or 99% identical), or 100% identical to any one of SEQ ID NOs: 52-123.

In some embodiments, the polynucleotides of the invention include all or a portion of the nucleotide sequence encoding the fiber-1, fiber-2; and/or hexon protein of wild-type sAd4287, sAd4310A, and/or sAd4312. In some embodiments, the nucleotide sequence encoding all or a portion of the fiber-1 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-1 protein of wild-type sAd4287, sAd4310A, or sAd4312, which corresponds to SEQ ID NO: 4, 5, and 6, respectively. The polypeptide sequences of the fiber-1 protein of wild-type sAd4287, sAd4310A, and sAd4312 correspond to SEQ ID NOs: 19, 20, and 21, respectively. In some embodiments, the nucleotide sequence encoding all or a portion of the fiber-2 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-2 protein of wild-type sAd4287, sAd4310A, or sAd4312, which corresponds to SEQ ID NO: 7, 8, and 9, respectively. The polypeptide sequences of the fiber-2 protein of wild-type sAd4287, sAd4310A, and sAd4312 correspond to SEQ ID NOs: 22, 23, and 24, respectively. In some embodiments, the nucleotide sequence encoding all or a portion of the hexon protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the hexon protein of wild-type sAd4287, sAd4310A, or sAd4312, which corresponds to SEQ ID NO: 10, 11, and 12, respectively. The polypeptide sequences of the hexon protein of wild-type sAd4287, sAd4310A, and sAd4312 correspond to SEQ ID NOs: 25, 26, and 27, respectively.

In other embodiments, the polynucleotides of the invention include all or a portion of the nucleotide sequence encoding the knob domain of fiber-1 of wild-type sAd4287, sAd4310A, and/or sAd4312. In some embodiments, the nucleotide sequence encoding all or a portion of the knob domain of fiber-1 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-1 protein of wild-type sAd4287, sAd4310A, or sAd4312, which corresponds to SEQ ID NO: 13, 14, or 15, respectively. The polypeptide sequences of the knob domain of the fiber-1 protein of wild-type sAd4287, sAd4310A, and sAd4312 correspond to SEQ ID NOs: 28, 29, and 30, respectively. In some embodiments, the nucleotide sequence encoding all or a portion of the knob domain of fiber-2 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-2 protein of wild-type sAd4287, sAd4310A, or sAd4312, which corresponds to SEQ ID NO: 16, 17, and 18, respectively. The polypeptide sequences of the knob domain of the fiber-2 protein of wild-type sAd4287, sAd4310A, and sAd4312 correspond to SEQ ID NOs: 31, 32, and 33, respectively.

In other embodiments, the polynucleotides of the invention include all or a portion of one or more of the nucleotide sequences encoding the fiber-1, fiber-2, hexon, fiber-1 knob, and/or fiber-2 knob proteins of sAd4287, sAd4310A, and/or sAd4312 and nucleotide sequence from one or more adenoviral vectors including Ad11, Ad15, Ad24, Ad26, Ad34, Ad35, Ad48, Ad49, Ad50, and/or Pan9 (also known as AdC68) directed to the generation of chimeric adenoviral vectors, as discussed below. In other embodiments, the polynucleotides of the invention include all or a portion of one or more of the nucleotide sequences encoding the fiber-1, fiber-2, hexon, fiber-1 knob, and/or fiber-2 knob proteins of sAd4287, sAd4310A, and/or sAd4312 and nucleotide sequence that can be at least 90% identical (e.g., at least 91%, 92%, 93%, or 94% identical), at least 95% identical (e.g., at least 96%, 97%, 98%, or 99% identical), or 100% identical to nucleotide sequence from one or more adenoviral vectors including Ad11, Ad15, Ad24, Ad26, Ad34, Ad35, Ad48, Ad49, Ad50, and/or Pan9 (also known as AdC68). In other embodiments, the polynucleotides of the invention include nucleotide sequence from one or more adenoviral vectors including Ad5, Ad11, Ad15, Ad24, Ad26, Ad34, Ad35, Ad48, Ad49, Ad50, and/or Pan9 (also known as AdC68) and all or a portion of one or more of a nucleotide sequence that can be at least 90% identical (e.g., at least 91%, 92%, 93%, or 94% identical), at least 95% identical (e.g., at least 96%, 97%, 98%, or 99% identical), or 100% identical to all or a portion of one or more of the nucleotide sequences encoding the fiber-1, fiber-2, hexon, fiber-1 knob, and/or fiber-2 knob proteins of sAd4287, sAd4310A, and/or sAd4312.

Vectors of the Invention

The present invention also features recombinant vectors including any one or more of the polynucleotides described above. In some embodiments, one vector of the invention can be used in conjunction with one or more other vectors (e.g., 1, 2, 3, or more vectors) of the invention as a vector system, which can be used to generate recombinant replication-defective sAds (rdsAds) or replication-competent sAds (rcsAds) of the invention. Accordingly, the invention features novel adenovirus vector systems for each of the three novel sAds (sAd4287, sAd4310A, and sAd4312) described herein. Such vector systems to generate replication-defective adenoviruses are known in the art and have been applied to generate replication competent adenovirus-free batches based of, for example, Ad5, Ad11, Ad35 and Ad49 (see, e.g., WO 97/00326, WO 00/70071; WO 02/40665; U.S. Pub. No. 2005/0232900, all incorporated herein by reference). However, the vectors and vector systems of the present invention, applied towards the sAds sAd4287, sAd4310A, and sAd4312 are novel.

Figure 7:
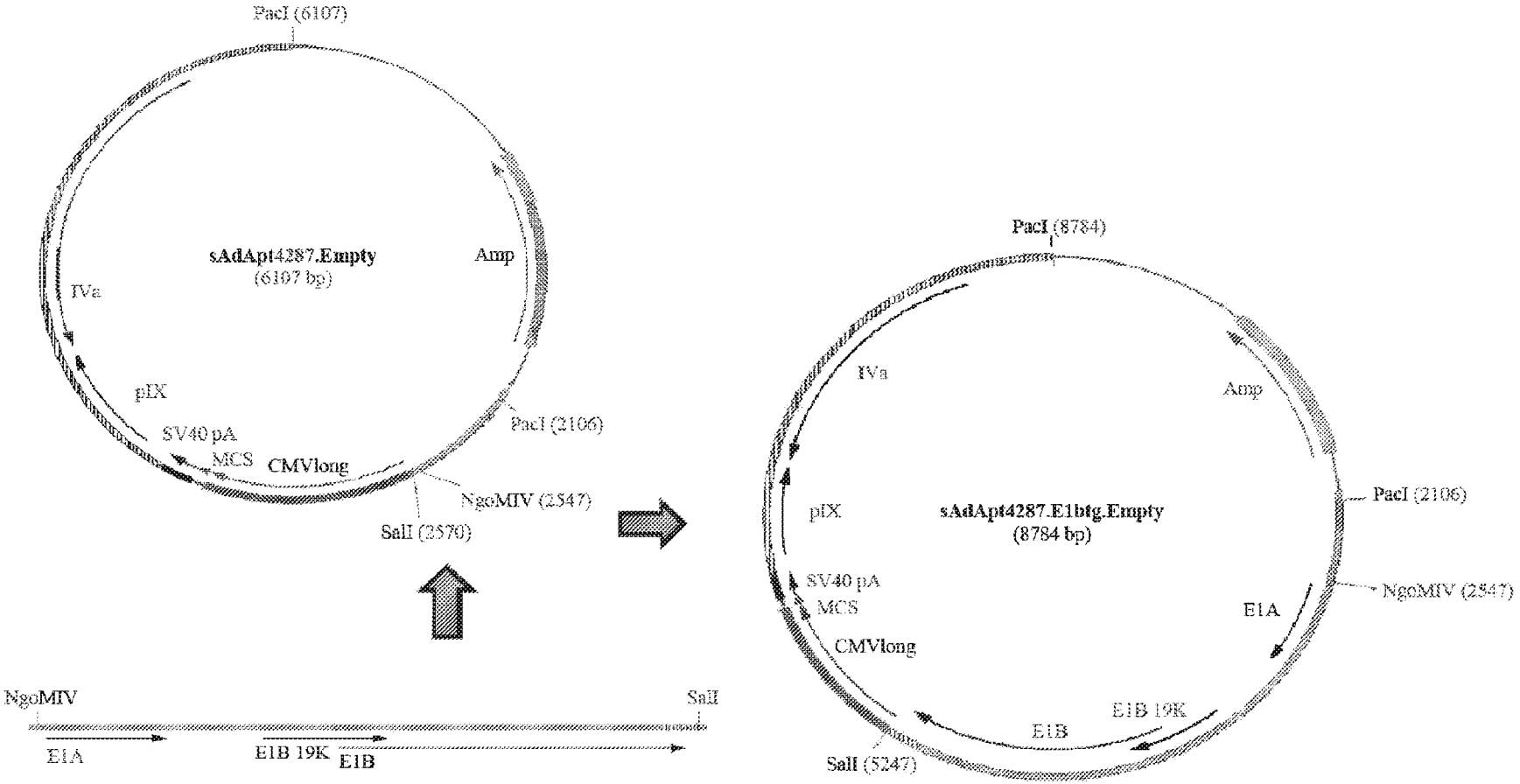
FIG. 7 illustrates the cloning strategy used to obtain plasmid sAdApt4287.E1btg.Empty and a schematic map of sAdApt4287.E1btg.Empty relative to that of its parental plasmid sAdApt4287.Empty.
Figure 14:
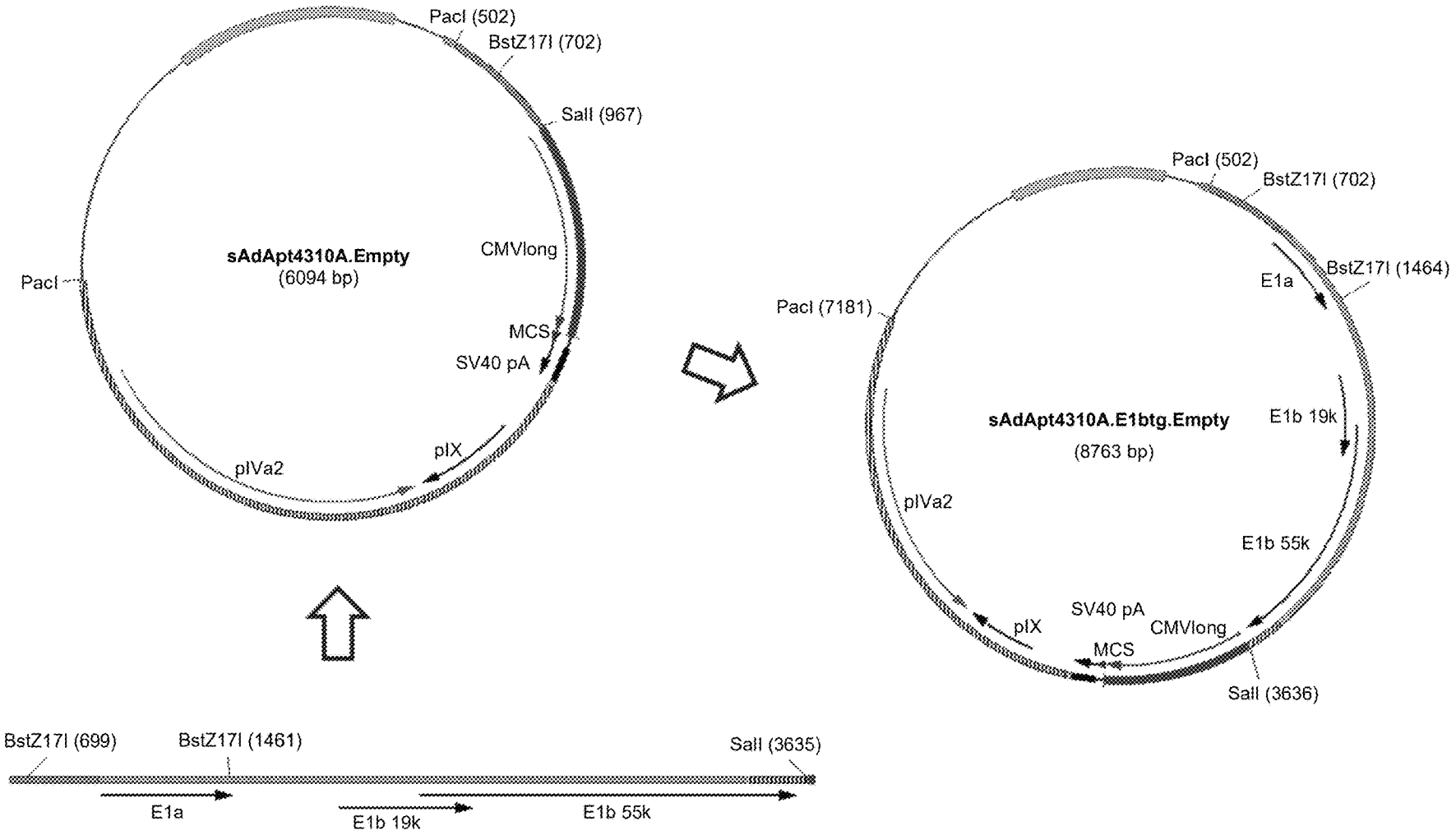
FIG. 14 illustrates the cloning strategy used to obtain plasmid sAdApt4310A.E1btg.Empty and a schematic map of sAdApt4310A.E1btg.Empty relative to that of its parental plasmid sAdApt4310A.Empty.
Figure 21:
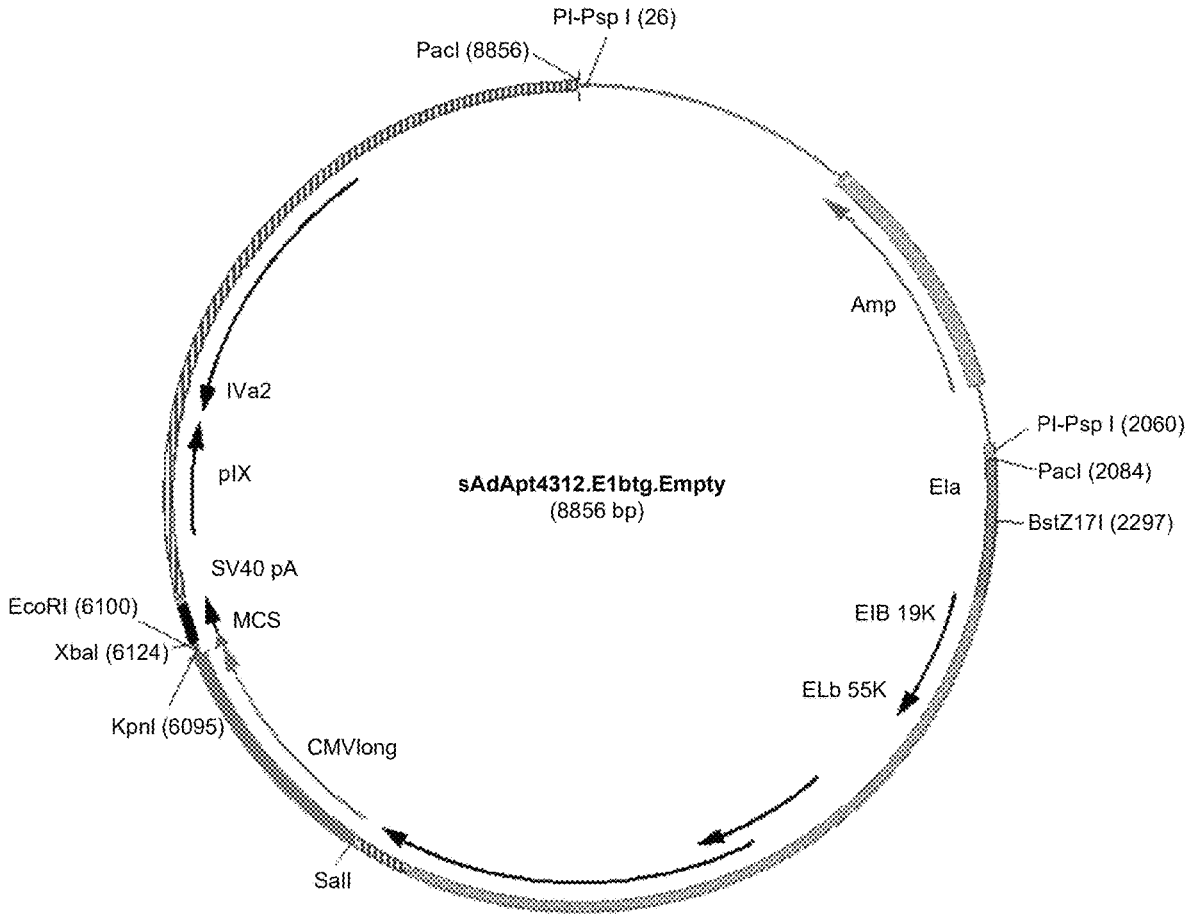
FIG. 21 is a schematic map of plasmid sAdApt4312.E1btg.Empty.

In some embodiments, the vectors of the invention can contain the E1 region (e.g., nt 474 to nt 3065 of sAd4287 (SEQ ID NO: 1); nt 474 to nt 3088 of sAd4310A (SEQ ID NO: 2); and nt 487 to nt 3100 of sAd4312 (SEQ ID NO: 3)) of the specific sAd (e.g., sAd4287, sAd4310A, and sAd4312) for the purposes of producing replication-competent sAd (rcsAd). Such vectors are exemplified, for example, in the .E1btg.Empty vectors of the invention (see, e.g., FIGS. 7, 14, and 21, which depict the .E1btg.Empty vectors of the invention for each of the three novel adenoviruses).

Figure 2:
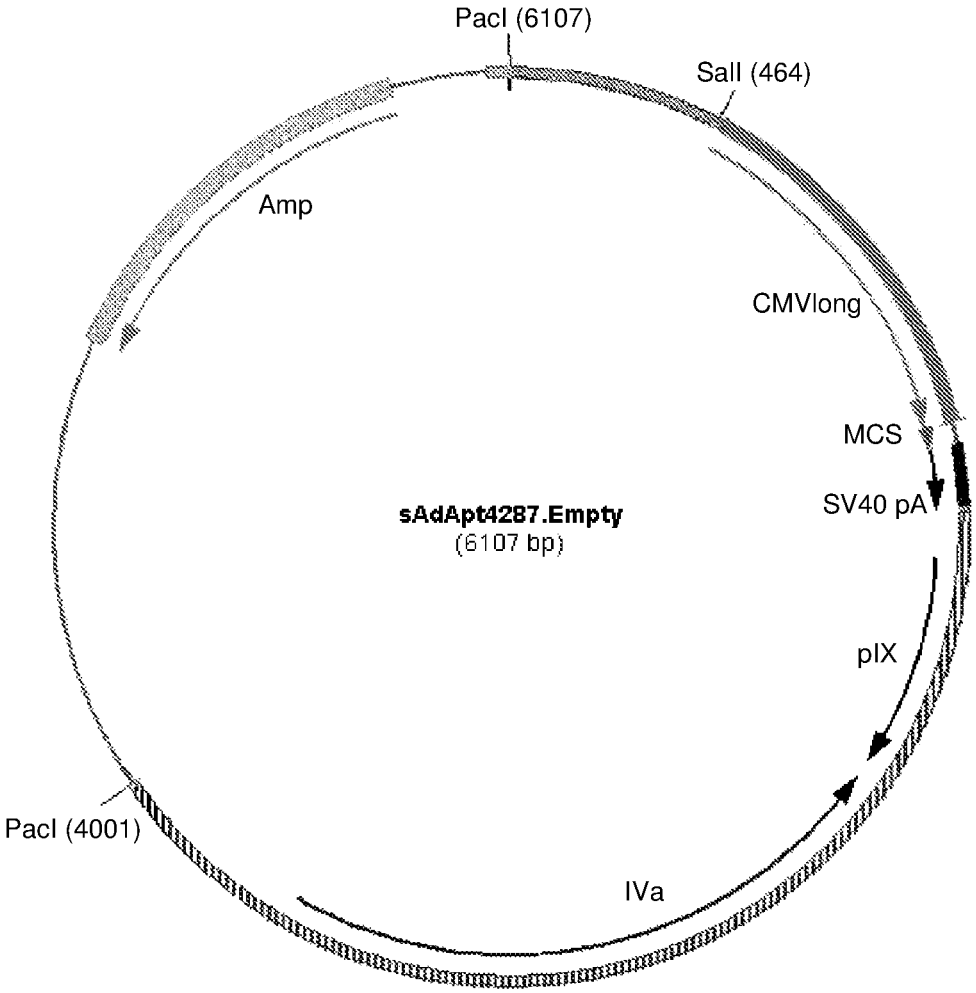
FIG. 2 is a schematic map of plasmid sAdApt4287.Empty.
Figure 3:
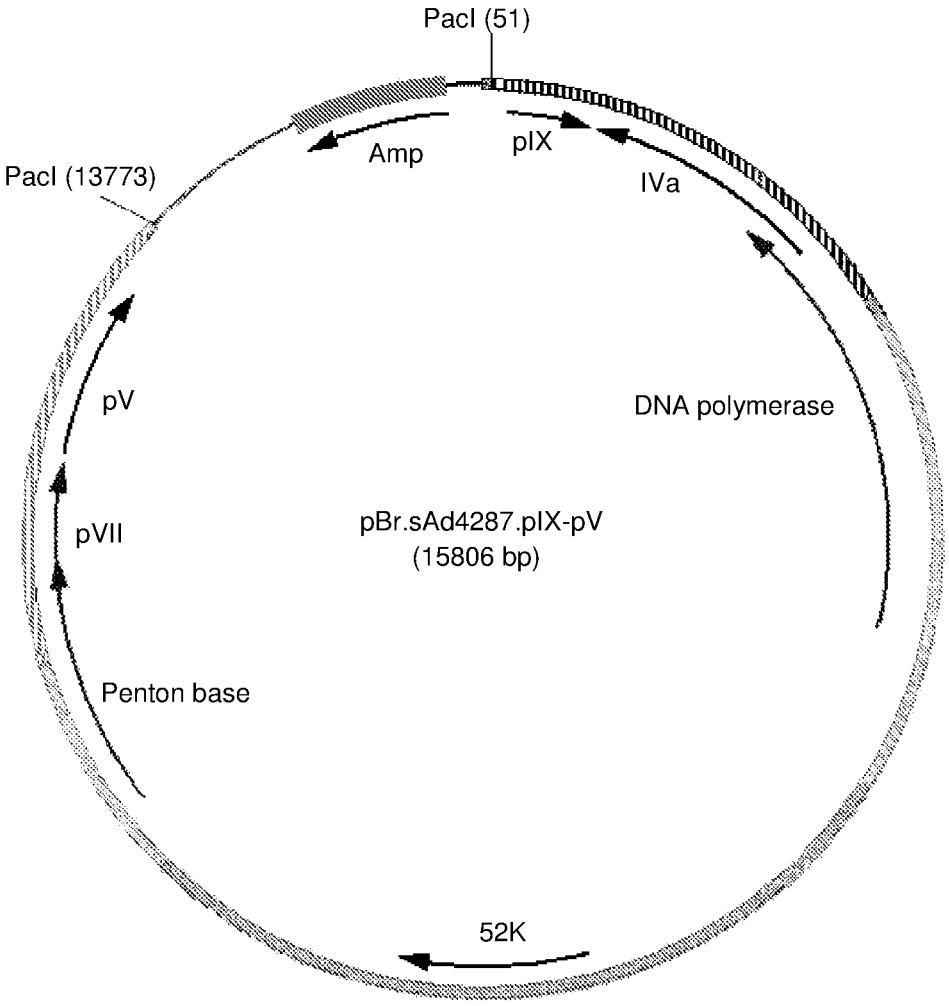
FIG. 3 is a schematic map of plasmid pBr/sAd4287.pIX-pV.
Figure 9:
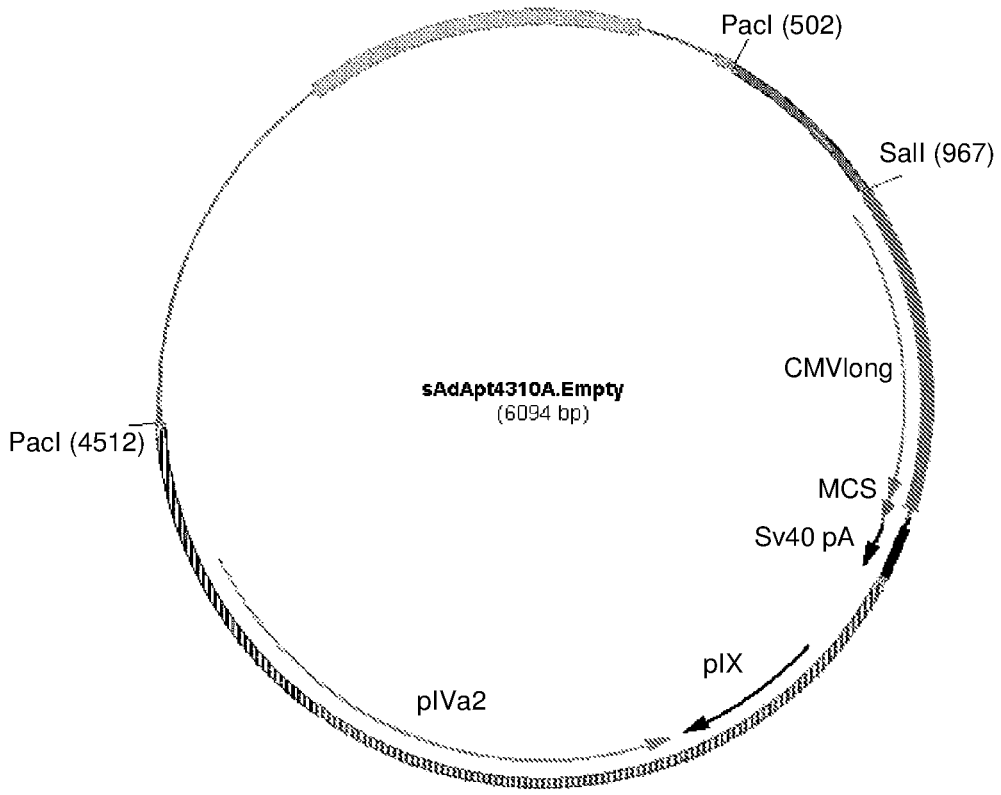
FIG. 9 is a schematic map of plasmid sAdApt4310A.Empty.
Figure 16:
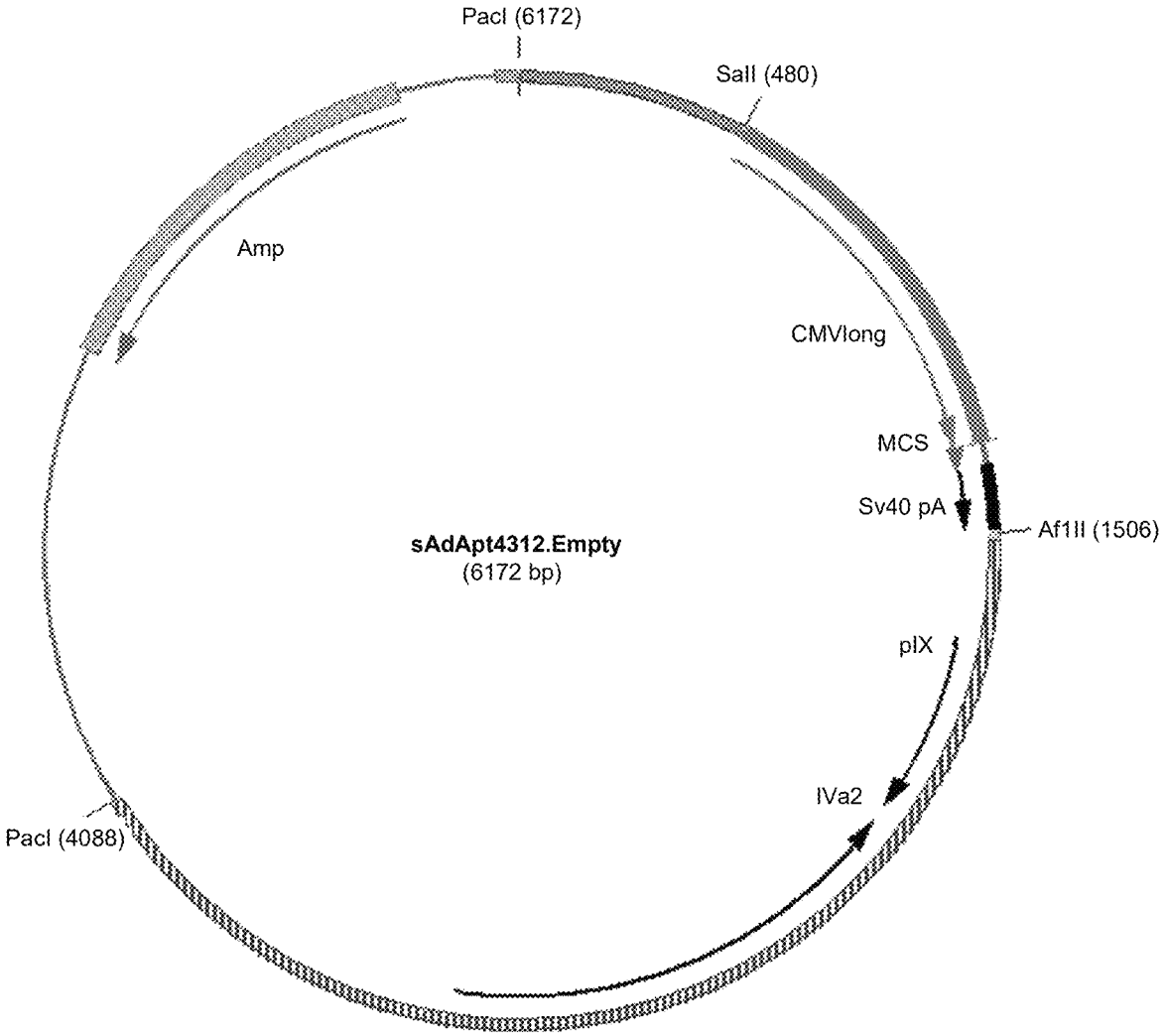
FIG. 16 is a schematic map of plasmid sAdApt4312.Empty.

In some embodiments, the vectors of the invention can contain the left-end sAd sequences and an expression/transgene cassette (see, e.g., FIG. 3, depicting the pBr/sAd4287.pIX-pV vector that includes the left part of the sAd4287 genome from approximately pIX to pV). In some embodiments, the expression cassette of the vector replaces or disrupts the E1 region of the specific adenovirus. In preferred embodiments, the expression cassette includes a promoter (e.g., a CMV promoter, e.g., a CMVlong promoter) that stimulates expression of a transgene, and optionally a poly-adenylation signal (e.g., a heterologous nucleotide sequence encoding an antigenic gene product of interest, e.g., a bacterial, viral, parasitic, fungal, or therapeutic protein, or fragment thereof) (see, e.g., FIGS. 2, 9, and 16, depicting .Empty vectors of the invention for each of the three novel adenoviruses). The E1 region can be deleted (either partially or completely), disrupted, or rendered inactive, by one or more mutations.

Figure 10:
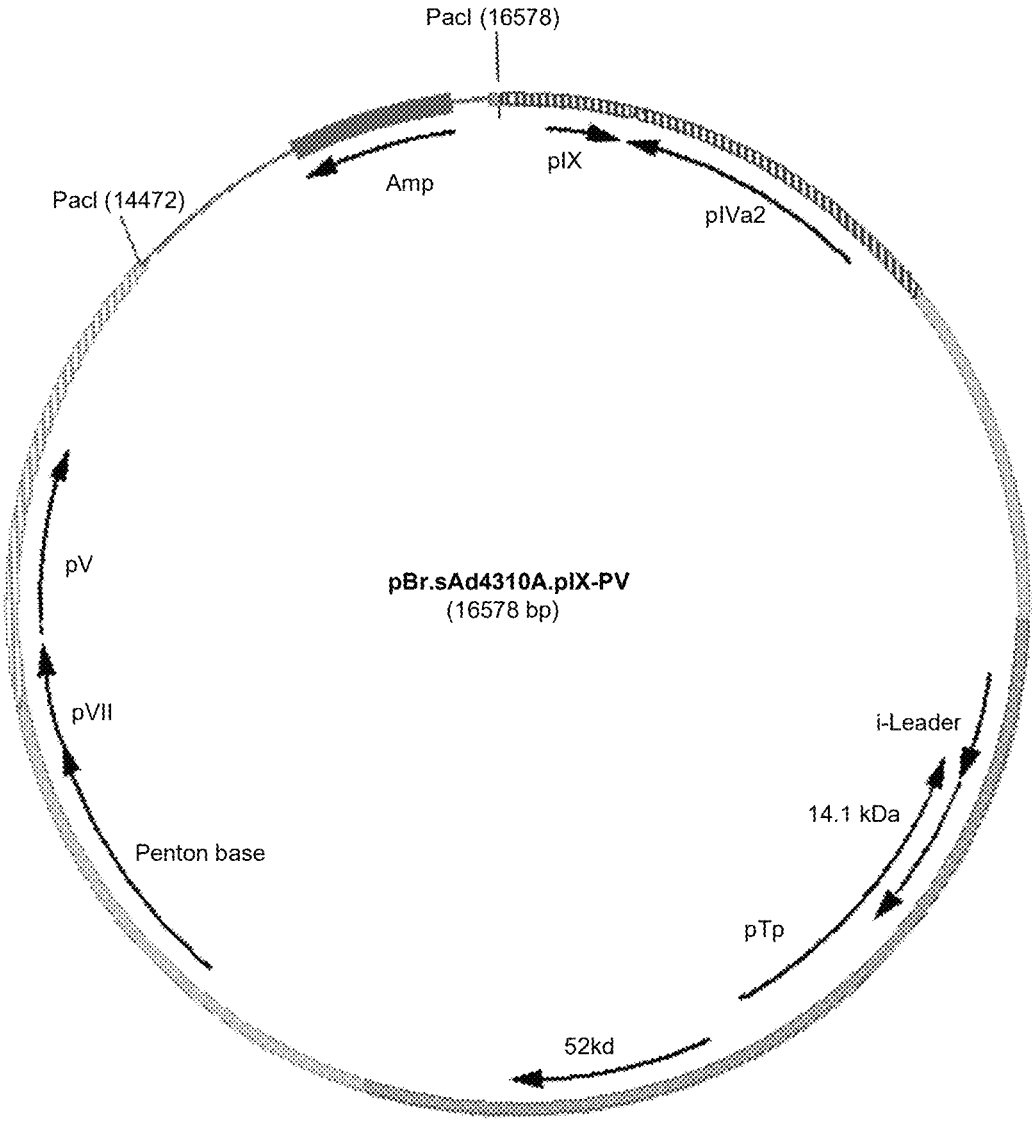
FIG. 10 is a schematic map of plasmid pBr/sAd4310A.pIX-pV.
Figure 17:
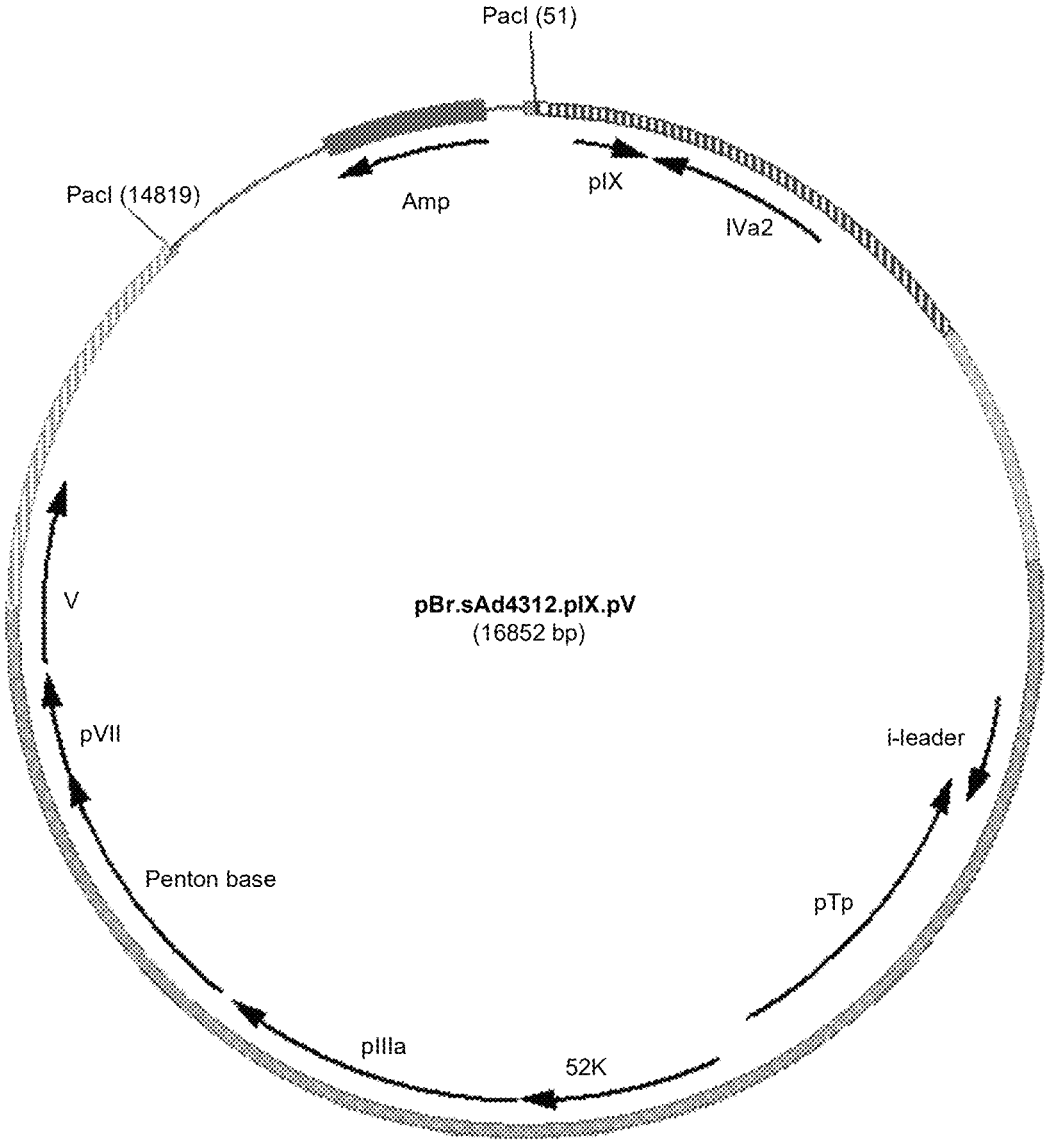
FIG. 17 is a schematic map of plasmid pBr/sAd4312.pIX-pV.

In some embodiments, the vectors of the invention can contain the left part of the sAd sequences (see, e.g., FIG. 3, depicting the pBr/sAd4287.pIX-pV vector that includes the left part of the sAd4287 genome from approximately pIX to pV), which includes the penton base and 52 K coding regions of the sAd (see, e.g., FIGS. 3, 10, and 17, depicting the .pIX-pV vectors of the invention for each of the three novel adenoviruses).

Figure 4:
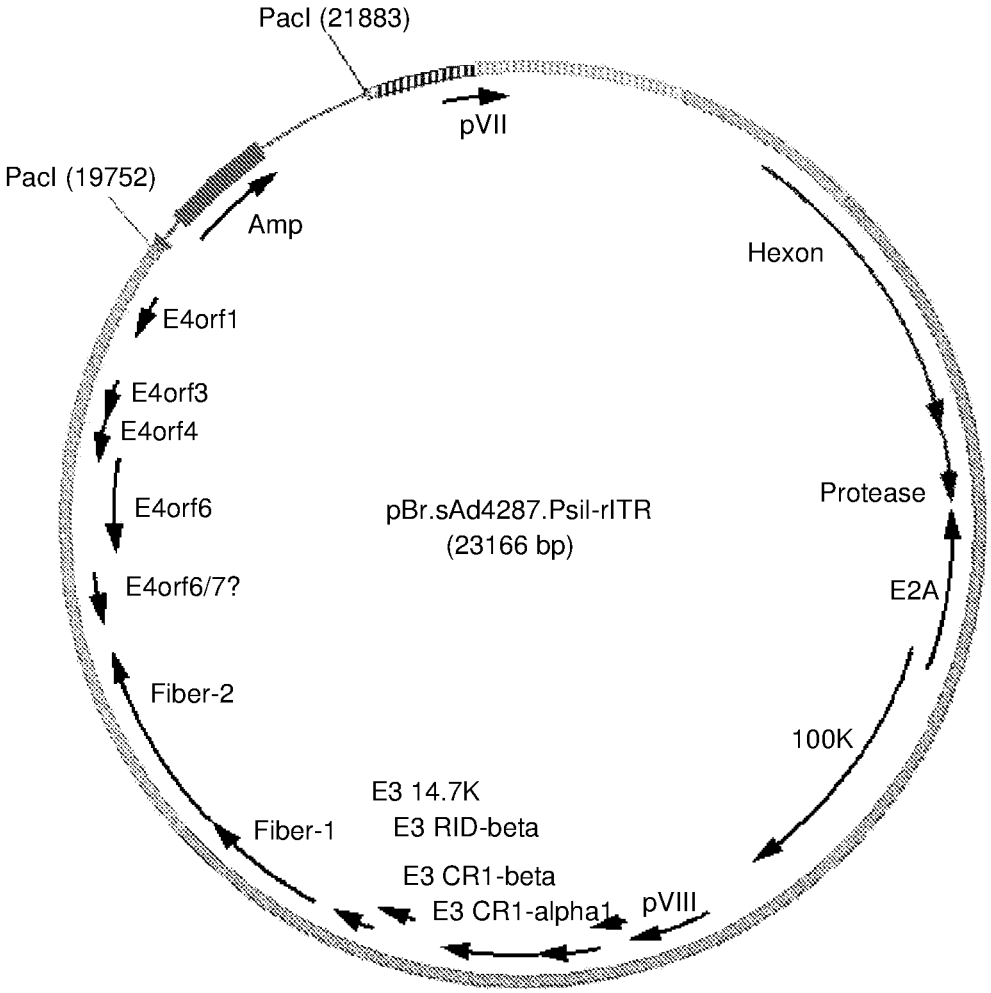
FIG. 4 is a schematic map of plasmid pBr/sAd4287.PsiI-rITR.
Figure 5:
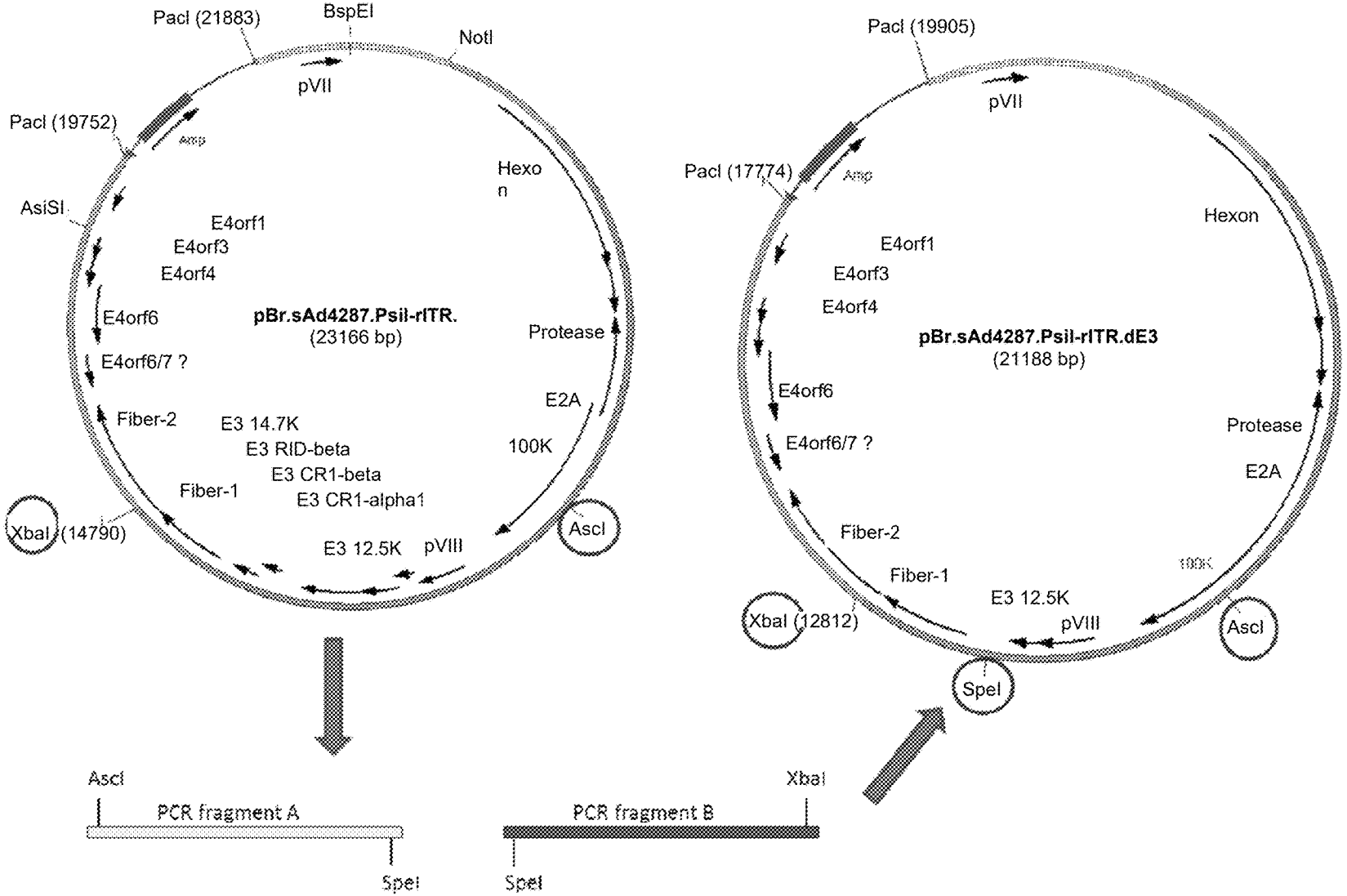
FIG. 5 illustrates the cloning strategy used to obtain plasmid pBr/sAd4287.PsiI-rITR.dE3 and a schematic map of pBr/sAd42.87.PsiI-rITR.dE3 relative to that of its parental plasmid pBr/sAd4287.PsiI-rITR.
Figure 6:
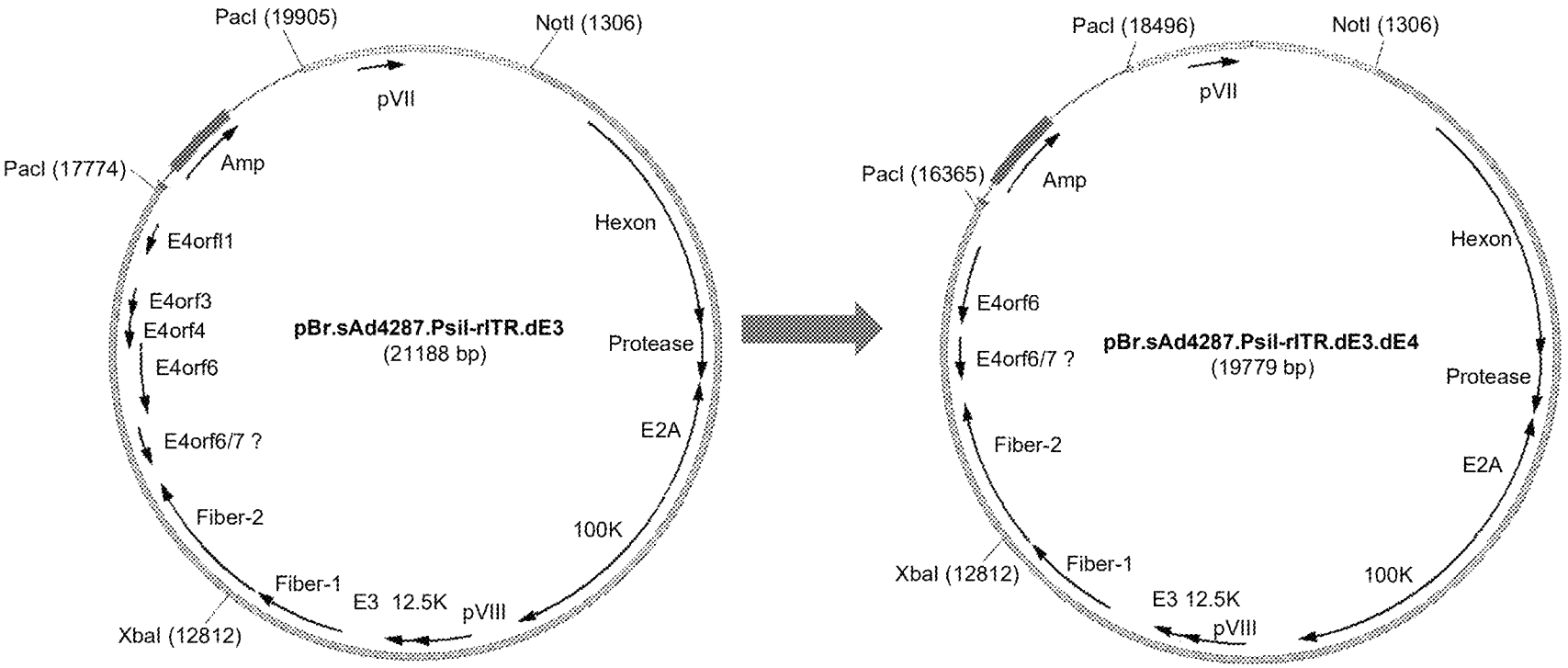
FIG. 6 shows a schematic map of plasmid pBr/sAd4287.PsiI-rITR.dE3.dE4 relative to that of its parental plasmid pBr/sAd4287.PsiI-rITR.dE3.
Figure 11:
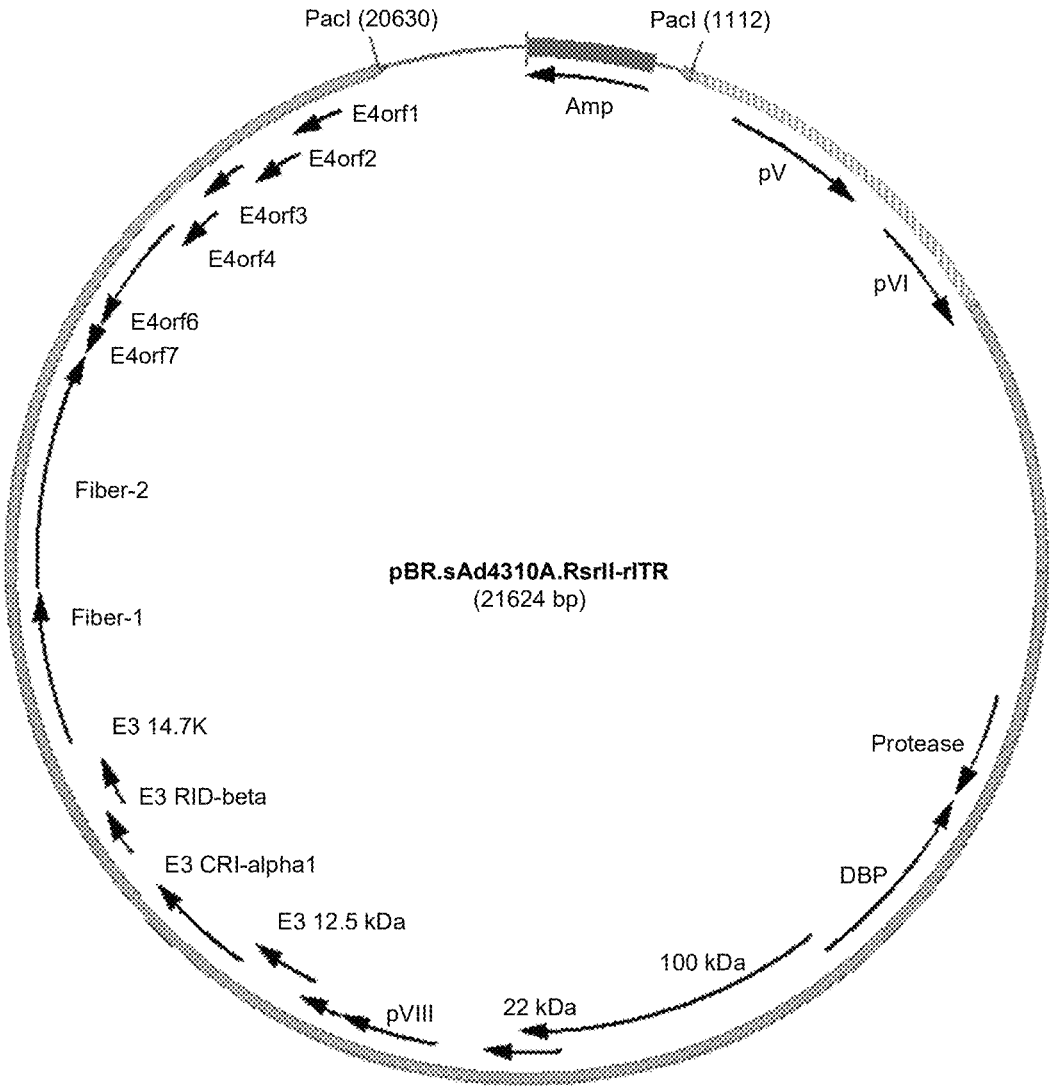
FIG. 11 is a schematic map of plasmid pBr/sAd4310A.RsrII-rITR.
Figure 12:
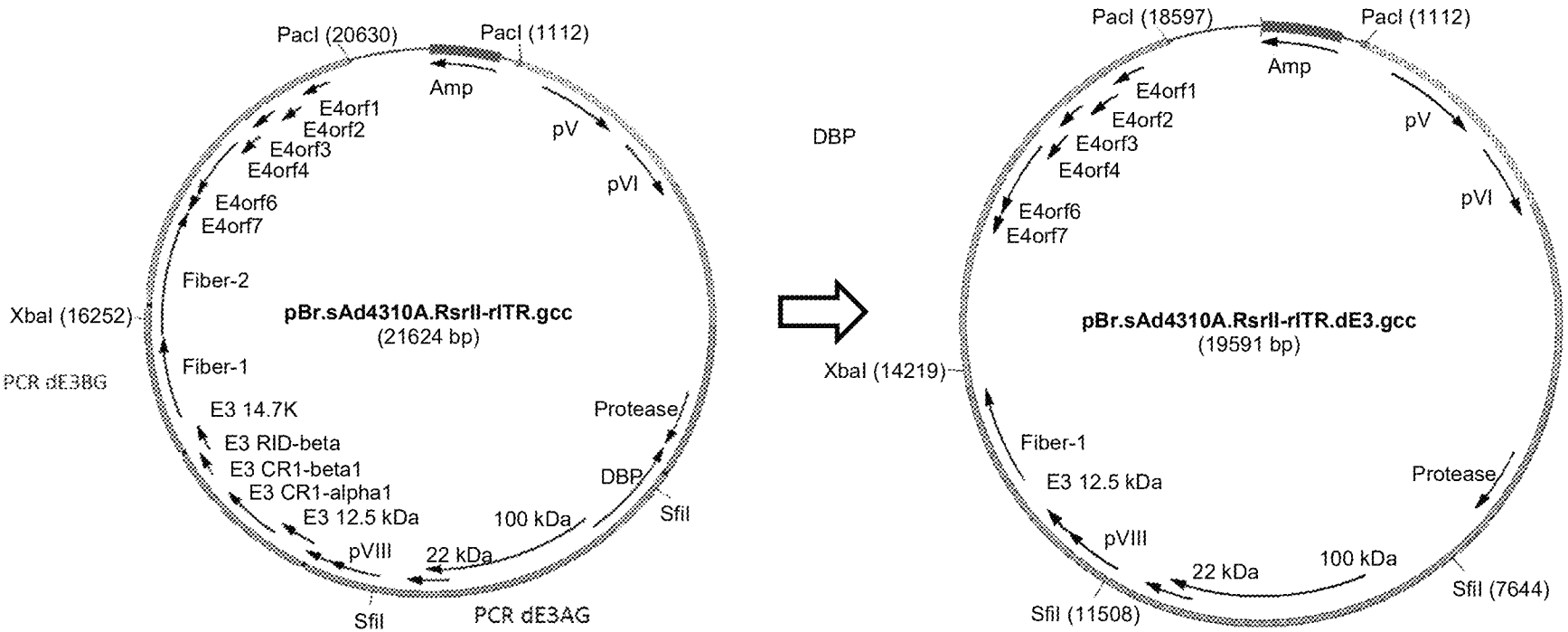
FIG. 12 shows a schematic map of pBr/sAd4310A.RsrII-rITR.dE3 relative to that of its parental plasmid pBr/sAd4310A.RsrII-rITR.
Figure 13:
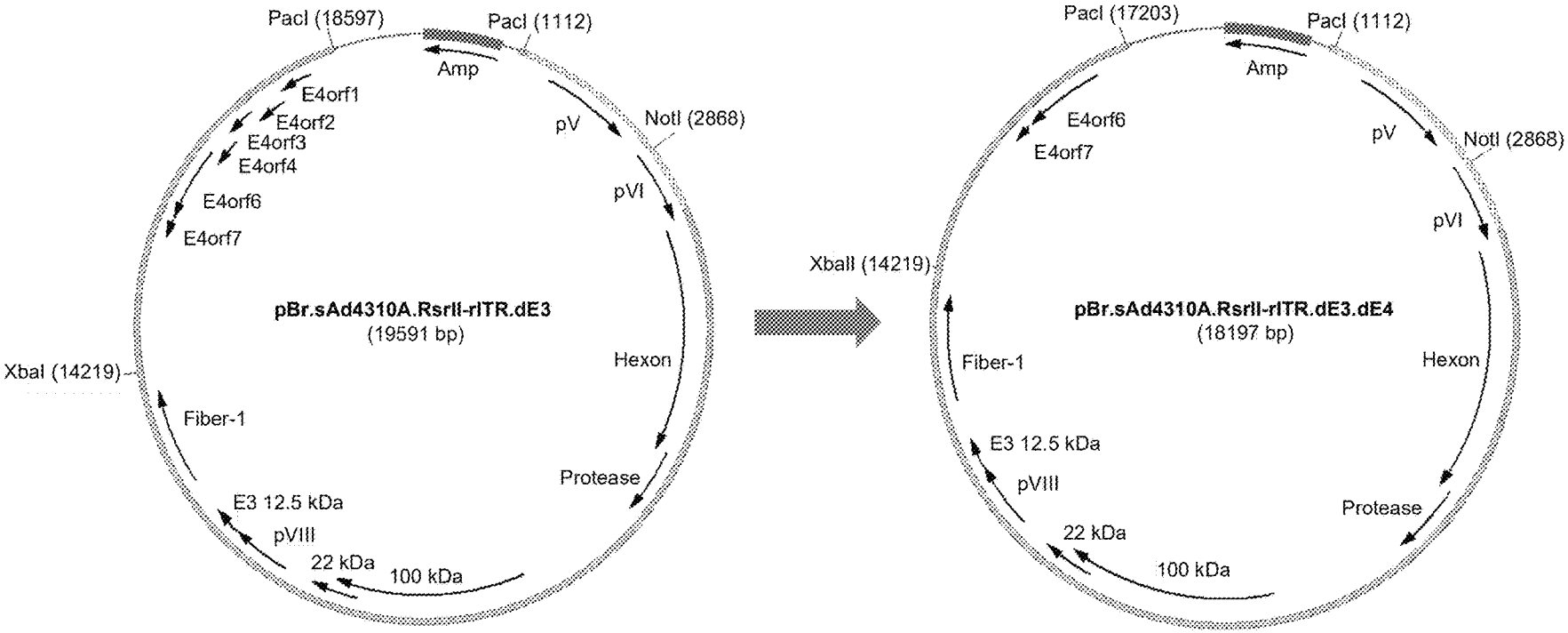
FIG. 13 shows a schematic map of plasmid pBr/sAd4310A.RsrII-rITR.dE3.dE4 relative to that of its parental plasmid pBr/sAd4310A.RsrII-rITR.dE3.
Figure 18:
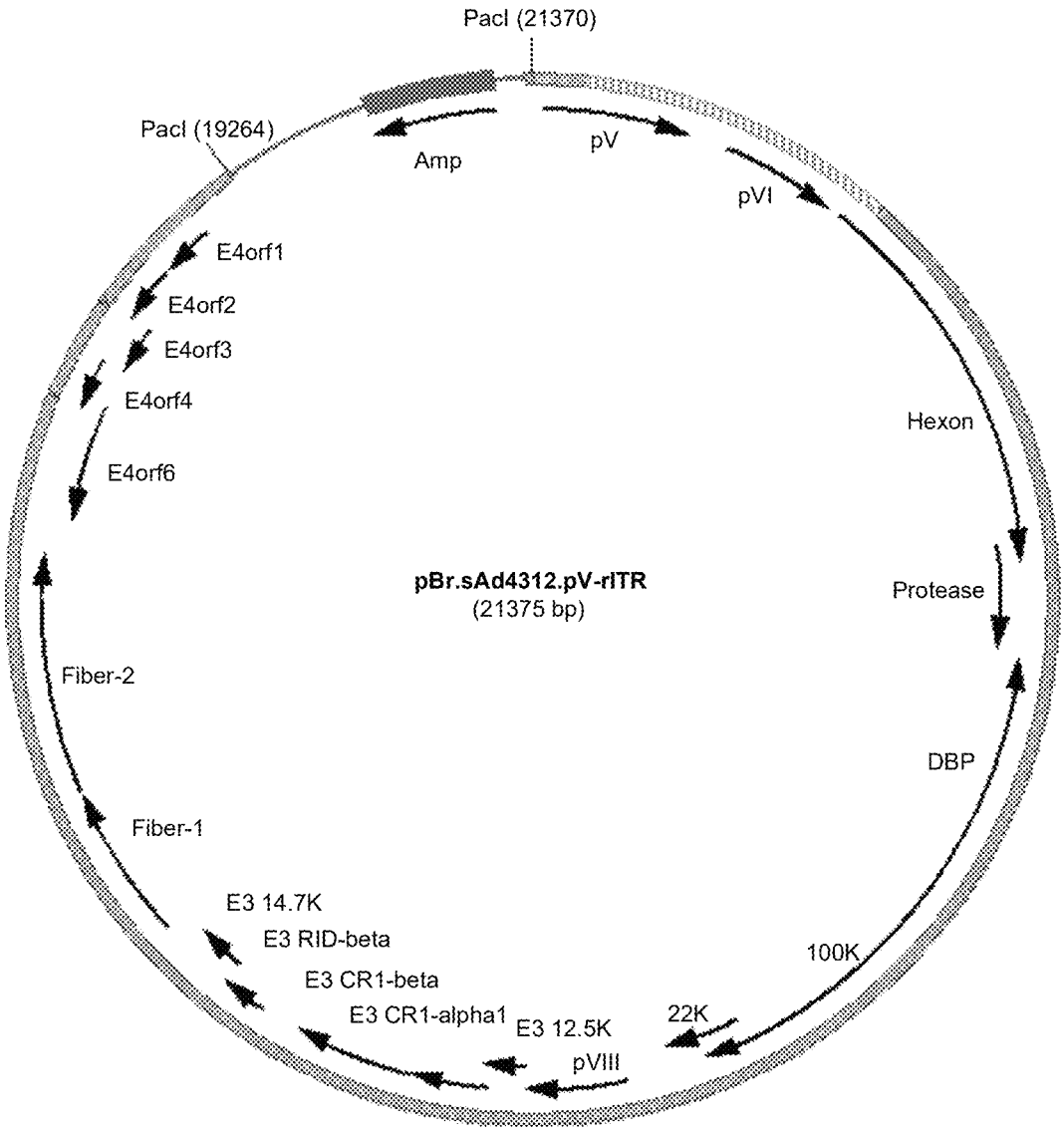
FIG. 18 is a schematic map of plasmid pBr/sAd4312.pV-rITR.
Figure 19:
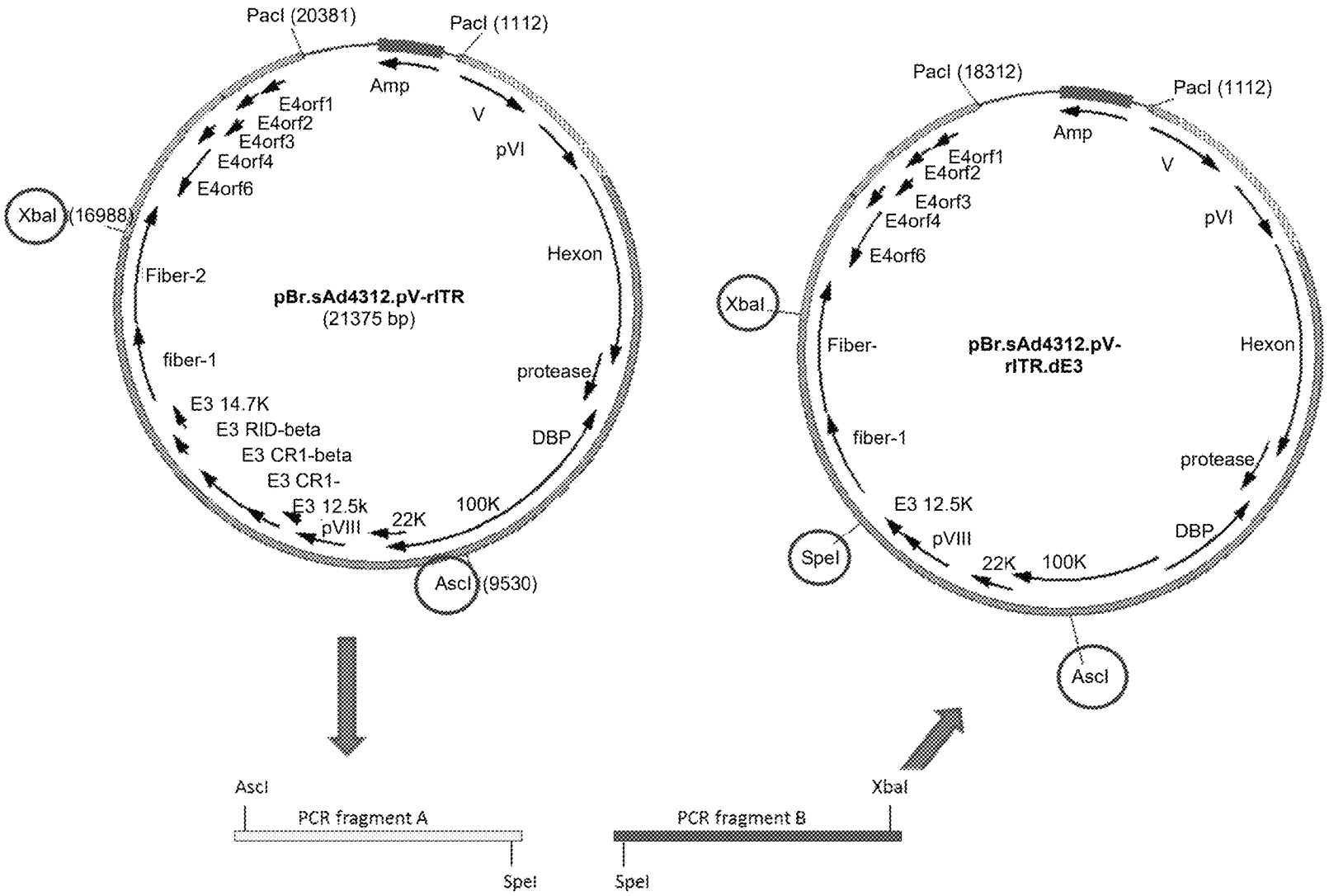
FIG. 19 illustrates the cloning strategy used to obtain plasmid pBr/sAd4312.pV-rITR.dE3 and a schematic map of pBr/sAd4312.pV-rITR.dE3 relative to that of its parental plasmid pBr/sAd4312.pV-rITR.
Figure 20:
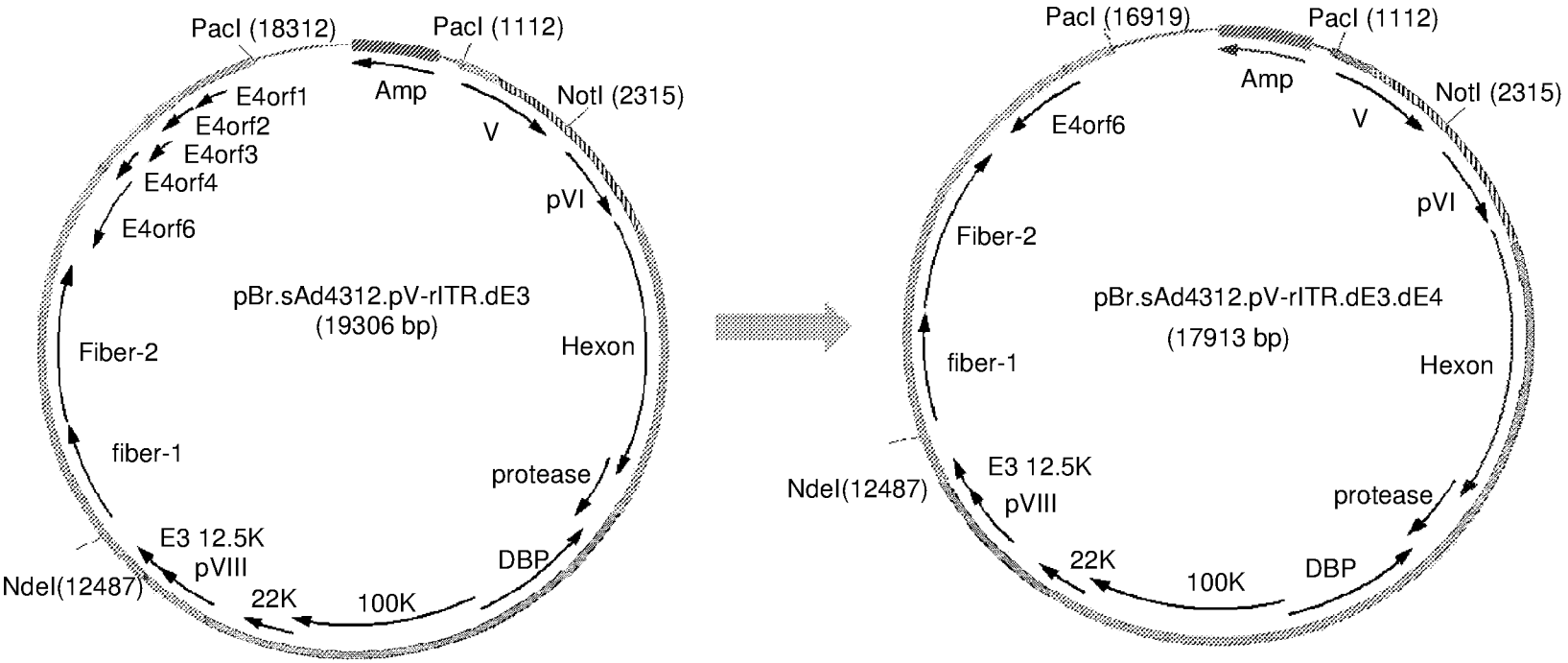
FIG. 20 shows a schematic map of plasmid pBr/sAd4312.pV-rITR.dE3.dE4 relative to that of its parental plasmid pBr/sAd4312.pV-rITR.dE3.

In other embodiments, the vectors of the invention can contain the right part of the sAd sequences (see, e.g., FIG. 4, depicting the pBr/sAd4287,PsiI.rITR vector that includes the right part of the sAd4287 genome from approximately pVII to the right ITR (rITR)) (see, e.g., FIGS. 4, 11, and 18, depicting the .pV-rITR vectors of the invention for each of the three novel adenoviruses). In some embodiments, these vectors may further have a deleted, disrupted, or mutated E3 (e.g., nt 25973 to nt 28596 of sAd4287 (SEQ ID NO: 1); nt 25915 to nt 28496 of sAd4310A (SEQ ID NO: 2): and nt 25947 to nt 28561 of sAd4312 (SEQ ID NO: 3); see FIGS. 5, 12, and 19, depicting the .dE3 vectors of the invention for each of the three novel adenoviruses) and/or E4 region (e.g., nt 31652 to nt 34752 of sAd4267 (SEQ ID NO: 1); nt 31750 to nt 34048 of sAd4310A (SEQ ID NO: 2); and nt 31818 to nt 34116 of sAd4312 (SEQ ID NO: 3); see FIGS. 6, 13, and 20, depicting the .dE3.dE4 vectors of the invention for each of the three novel adenoviruses), which are not required for replication and packaging of the adenoviral particle. Deletion of the E3 region is generally preferred if large transgene sequences are to be incorporated into the vector since the genome size which can be packaged into a functional particle is limited to approximately 105% of the wild type size. Although not applied herein, it is to be understood that other modifications may be introduced in the adenoviral genome, such as deletion of the E2A region, or most if not all of the entire E4 region. In some embodiments, a cell transfected with a vector of the invention can complement these deficiencies by delivering the functionality of the missing regions. The E2A region can be provided by, for instance, a temperature sensitive E2A mutant, or by delivering the E4 functions. Cells that can be used to complement a deficiency of an adenoviral gene (e.g., a E1, E3, and/or E4 deletion) of a vector of the invention include, for example, PER.55K, PER.C6®, and 293 cells. All such systems are known in the art and such modifications of the adenoviral genomes are within the scope of the present invention, which in principal relates to the three novel sAd4287, sAd4310A, and sAd4312 genomic sequences, and the use thereof. As described above, any one vector of the invention can be used in conjunction with one or more other vectors of the invention. In some embodiments, vectors are used which encode both left and right sides of the sAd genome in order to generate a given sAd of the invention.

The present invention also features vectors for the generation of chimeric adenoviruses which include a portion of the sAd4287, sAd4310A, or sAd4312 genome as well as a portion of the genome of one or more other viruses. In some embodiments, the chimeric adenoviral vectors of the invention may include a substitution of all or a portion of the hexon and/or fiber protein. In some embodiments, the portion of the hexon protein substituted with that of another virus is one or more of the hexon protein hypervariable regions (HVRs), for example, HVR1 (nt 403 to nt 489), HVR2 (nt 520 to nt 537), HVR3 (nt 592 to nt 618), HVR4 (nt 706 to nt 744), HVR5 (nt 763 to 786), HVR6 (nt 856 to nt 874), and/or HVR7 nt 1201 to nt 1296) of sAd4287 hexon protein (SEQ ID NO: 10); HVR1 (nt 403 to nt 477), HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12). In some embodiments, the portion of the fiber protein substituted with that of another virus is the fiber knob domain. In some embodiments, the substituted regions are replaced with a region derived from an adenovirus that has a lower seroprevalence compared to that of Ad5, such as subgroup B (Ad11, Ad34, Ad35, and Ad50) and subgroup D (Ad15, Ad24, Ad26, Ad48, and Ad49) adenoviruses as well as simian adenoviruses (e.g., Pan9, also known as AdC68). In some embodiments, an adenoviral vector backbone of Ad5, Ad11, Ad15, Ad24, Ad26, Ad34, Ad48, Ad49, Ad50, or Pan9/AdC68 includes a substitution of all or a portion of one or more of the above hexon HVRs of sAd4287, sAd4310A, and/or sAd4312.

Adenoviruses of the Invention

As discussed above, a recombinant adenovirus of the invention derived, at least in part, from sAd4287, sAd4310A, and/or sAd4312 can be generated using the above-described vectors of the invention. These adenoviruses may be rcsAds or rdsAds. rdsAds will include a deleted, disrupted, or mutational inactivation of the E1 region, and may further include a deletion, disruption, or mutational inactivation of the E2, E3, and/or E4 regions. In some embodiments, the adenovirus of the invention may include an antigenic or therapeutic gene product, or fragment thereof, including a bacterial, viral, parasitic, or fungal protein, or fragment thereof. In a preferred embodiment, the antigenic gene product, or fragment thereof, when expressed in a host, or host cells, is capable of eliciting a strong immune response. In some embodiments, the bacterial protein, or fragment thereof, may be derived from Mycobacterium tuberculosis, Mycobacterium bovis, Mycobacterium africanum, Mycobacterium microti, Mycobacterium leprae, Pseudomonas aeruginosa, Salmonella typhimurium, Escherichia coil, Klebsiella pneumoniae, Streptococcus pneumoniae, Staphylococcus aureus, Francisella tularensis, Brucella, Burkholderia mallei, Yersinia pestis, Corynebacterium Neisseria meningitidis, Bordetella pertussis, Clostridium tetani, or Bacillus anthracis. In some embodiments, the viral protein, or fragment thereof, may be derived from a virus of a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae, and Reoviridae. In some embodiments, the virus is human immunodeficiency virus (HIV), human papillomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, or Marburg virus. In some embodiments, the parasitic protein, or fragment thereof, is from Toxoplasma gondii, Plasmodium falciparum, Plasmodium vivax, Plasmodium ovale, Plasmodium malariae, Trypanosome spp., or Legionella spp. In some embodiments, the fungal protein, or fragment thereof, is from Aspergillus, Blastomyces dermatitidis, Candida, Coccidioides immitis, Cryptococcus neoformans, Histoplasma capsulatum var. capsulatum, Paracoccidioides brasiliensis, Sporothrix schenckii, Zygomycetes spp., Absidia corymbifera, Rhizomucor pusillus, or Rhizopus arrhizus. In some embodiments, the therapeutic gene products may be interferon (IFN) proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and/or colony stimulating factors (see, e.g., U.S. Pat. No. 6,054,288, incorporated by reference herein). In some embodiments, the IFN protein has an amino acid sequence substantially identical (e.g., at least 70%, 75%, 80%, 85%, 90%, 95%, 96%, 97%, 98%, 99%, or even 100% identical) to the sequence of a human IFN-α (e.g., IFN-α-1α, IFN-α-1b, IFN-α-2α, IFN-α-2b, and consensus IFN-α (conIFN-α); FIG. 1), a human IFN-β (e.g., IFN-β-1a and IFN-β-1b), a human IFN-γ), or an IFN-τ or a polypeptide that demonstrates the same or similar biological activity to an interferon (e.g., at least 50%, 60%, 70%, 75%, 80%, 85%, 90%, 95%, or 100% of the activity of a human IFN-α, a human IFN-β, a human IFN-γ, an IFN-τ, or a conIFN-α (see, e.g., U.S. Pat. No. 4,695,623 and U.S. Pub. No. 2011/0000480, incorporated by reference herein, for examples of specific IFN sequences).

Non-limiting examples of bacterial gene products, or fragments thereof, include 10.4, 85A, 85B, 86C, CFP-10, Rv3871, and ESAT-6 gene products, or fragments thereof, of Mycobacterium, O, H, and K antigens, or fragments thereof, of E. coli; and protective antigen (PA), or fragments thereof, of Bacillus anthracis. Non-limiting examples of viral gene products, or fragments thereof, include Gag, Pol, Nef, Tat, Rev, Vif, Vpr, or Vpu, or fragments thereof, of HIV and other retroviruses (see, e.g., U.S. Pub. No. 2012/0076812, incorporated by reference herein); 9D antigen, or fragments thereof, of HSV; Env, or fragments thereof, of all envelope protein-containing viruses. Non-limiting examples of parasitic gene products, or fragments thereof, include circumsporozoite (CS) protein, gamete surface proteins Pfs230 and Pfs48/45, and Liver Specific Antigens 1 or 3 (LSA-1 or LSA-3), or fragments thereof, of Plasmodium falciparum. Non-limiting examples of fungal gene products, or fragments thereof, include any cell wall mannoprotein (e.g., Afmp1 of Aspergillus fumigatus) or surface-expressed glycoprotein (e.g., SOWgp of Coccidioides immitis).

Methods of Prophylaxis or Treatment Using Compositions of the Invention

The pharmaceutical compositions of the invention can be used as vaccines for treating a subject (e.g., a human) with a disease (e.g., cancer or a disease caused by an infective agent, e.g., AIDS). In particular, the compositions of the invention car be used to treat (pre- or post-exposure) infection by bacteria, including Mycobacterium tuberculosis, Mycobacterium bovis, Mycobacterium africanum, Mycobacterium microti, Mycobacterium leprae, Pseudomonas aeruginosa, Salmonella typhimurium, Escherichia coli, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani, or Bacillus anthracis; viruses of a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae, and Reoviridae; parasites, including Toxoplasma gondii, Plasmodium falciparum, Plasmodium vivax, Plasmodium ovale, Plasmodium malariae, Trypanosoma spp., or Legionella spp.; and fungi, including Aspergillus, Blastomyces dermatitidis, Candida, Coccidioides immitis, Cryptococcus neoformans, Histoplasma capsulatum var. capsulatum, Paracoccidioides brasiliensis, Sporothrix schenckii, Zygomycetes spp., Absidia corymbifera, Rhizomucor pusillus, or Rhizopus arrhizus.

Accordingly, in other non-limiting embodiments, the pharmaceutical compositions of the invention can be used to treat a subject (e.g., a human) with acquired immune deficiency syndrome (AIDS), cancer, tuberculosis, leprosy, typhoid fever, pneumonia, meningitis, staphylococcal scalded skin syndrome (SSSS), Ritter's disease, tularemia (rabbit fever), brucellosis, Glanders disease, bubonic plague, septicemic plague, pneumonic plague, diphtheria, pertussis (whooping cough), tetanus, anthrax, hepatitis, smallpox, monkeypox, measles, mumps, rubella, chicken pox, polio, rabies, Japanese encephalitis, herpes, mononucleosis, influenza, Ebola virus disease, hemorrhagic fever, yellow fever, Marburg virus disease, toxoplasmosis, malaria, trypanosomiasis, legionellosis, aspergillosis, blastomycosis, candidiasis (thrush), coccidioidomycosis, cryptococcosis, histoplasmosis, paracoccidioidomycosis, sporotrichosis, or sinus-orbital zygomycosis.

Pharmaceutical Formulation and Administration of the Compositions of the Invention Administration The pharmaceutical compositions of the invention can be administered to a subject (e.g., a human), pre- or post-exposure to an infective agent (e.g., bacteria, viruses, parasites, fungi) or pre- or post-diagnosis of a disease of a disease without an etiology traceable to an infective, agent (e.g., cancer), to treat, prevent, ameliorate, inhibit the progression of, or reduce the severity of one or more symptoms of the disease in the subject. For example, the compositions of the invention can be administered to a subject to treat having AIDS. Examples of symptoms of diseases caused by a viral infection, such as AIDS, that can be treated using the compositions of the invention include, for example, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, for example, a physician during a physical examination or by other tests and methods known in the art.

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-exposure prophylaxis or after a subject has been diagnosed with a disease having a disease without an etiology traceable to an infective agent (e.g., cancer) or a subject exposed to an infective agent, such as a bacterium, virus, parasite, or fungus. The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis or post-exposure to the infective agent.

When treating disease (e.g., AIDS or cancer), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the recombinant replication-defective sAd vector containing a heterologous nucleic acid encoding an antigenic gene product, or fragment thereof, (e.g., an sAd4287, sAd4310A, or sAd4312 HIV Gag delivery vector) and, if desired, one or more immunomodulatory agents, such as in a sealed package of tablets or capsules, or in a suitable dry powder inhaler (DPI) capable of administering one or more doses.

Dosages

The dose of the compositions of the invention (e.g., the number of antigenic gene product-encoding recombinant sAd vectors) or the number of treatments using the compositions of the invention may be increased or decreased based on the severity of, occurrence of, or progression of, the disease in the subject (e.g., based on the severity of one or more symptoms of, e.g., viral infection or cancer).

The pharmaceutical compositions of the invention can be administered in a therapeutically effective amount that provides an immunogenic and/or protective effect against an infective agent or target protein for a disease caused by a non-infective agent. For example, the subject can be administered at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{11}$ vp/dose.

Viral particles include nucleic acid molecules encoding an antigenic gene product or fragment thereof (e.g., viral structural and non-structural proteins) and are surrounded by a protective coat (a protein-based capsid with hexon and fiber proteins, which may be derived from a single sAd of the invention or a chimeric variant thereof). Viral particle number can be measured based on, for example, lysis of vector particles, followed by measurement of the absorbance at 260 nm (see, e.g., Steel, Curr. Opin. Biotech., 1999).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of the antigenic or therapeutic gene product, or fragment thereof (e.g., a level of an antigenic gene product that elicits an immune response without undue adverse physiological effects in the host caused by the antigenic gene product).

In addition, single or multiple administrations of the compositions of the present invention may be given (pre- or post-exposure and/or pre- or post-diagnosis) to a subject (e.g., one administration or administration two or more times). For example, subjects who are particularly susceptible to, for example, viral infection may require multiple treatments to establish and/or maintain protection against the virus. Levels of induced immunity provided by the pharmaceutical compositions described herein can be monitored by, for example, measuring amounts of neutralizing secretory and serum antibodies. The dosages may then be adjusted or repeated as necessary to trigger the desired level of immune response. For example, the immune response triggered by a single administration (prime) of a composition of the invention may not sufficiently potent and/or persistent to provide effective protection. Accordingly, in some embodiments, repeated administration (boost), such that a prime boost regimen is established, can significantly enhance humoral and cellular responses to the antigen of the composition.

Alternatively, the efficacy of treatment can be determined by monitoring the level of the antigenic or therapeutic gene product, or fragment thereof, expressed in a subject (e.g., a human) following administration of the compositions of the invention. For example, the blood or lymph of a subject can be tested for antigenic or therapeutic gene product, or fragment thereof, using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of the compositions of the invention may achieve protection, pre exposure or pre-diagnosis. In addition, a single dose administered post-exposure or post-diagnosis can function as a treatment according to the present invention.

A single dose of the compositions of the invention can also be used to achieve therapy in subjects being treated for a disease. Multiple doses (e.g., 2, 3, 4, 5, or more doses) can also be administered, in necessary, to these subjects.

Carriers, Excipients, Diluents

The compositions of the invention include sAd5 vectors containing a heterologous nucleic acid molecule encoding an antigenic or therapeutic gene product, or fragment thereof. Therapeutic formulations of the compositions of the invention are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

EXAMPLES

The following examples are to illustrate the invention. They are not meant to limit the invention in any way.

The practice of this invention may employ, unless otherwise indicated, conventional techniques of molecular biology, cell biology, and recombinant DNA, which are within the skill of the person skilled in the art (see, e.g., Green and Sambrook. Molecular Cloning: A Laboratory Manuel, $4^{th}$ edition, 2012; Ausubel, et al. Current Protocols in Molecular Biology, 1987; Methods in Enzymology. Academic Press, Inc.; and MacPherson et al. PCR2: A Practical Approach, 1995).

Example 1. Sequence of Simian Adenovirus sAd4287

The total genome sequence of simian adenovirus sAd4287 was determined following the isolation, amplification, and purification of the novel virus obtained from the rhesus monkey metagenomics study of Handley et al. (Cell. 151(2):253-266, 2012). The obtained sequence of the sAd4287 genome (35079 nucleotides (nt)) is given as SEQ ID NO: 1. A schematic genome structure of sAd4287 is depicted in FIG. 1. Using the full genomic sequence in an NCBI web-based BLAST search, the most closely related virus to sAd4287 was identified as simian adenovirus 1 (sAd1) ATCC VR-195 (query coverage: 93%; maximum identity: 98%). NCBI web-based BLAST searches were also performed to assess homology of three major capsid proteins of sAd4287 (fiber-1, fiber-2, and hexon proteins). The most closely related protein to sAd4287 fiber-1 was identified as sAd1 fiber-1 (query coverage: 100%; maximum identity: 74%). The most closely related protein to sAd4287 fiber-2 was identified as sAd7 long fiber (query coverage: 100%; maximum identity: 97%). The most closely related protein to sAd4287 hexon was identified as sAd1 hexon (query coverage: 100%; maximum identity: 93%).

Example 2. Generation of Recombinant sAd4287 Viruses

Here, the construction of an sAd4287 plasmid-based system to generate recombinant sAd4287 vectors in a safe and efficient manner is described. The plasmid system consists of a first plasmid, referred to as an adapter plasmid, which contains sAd4287 nucleotides 1 to 460 including the left inverted terminal repeat (lITR) and packaging signal, an expression cassette and an sAd4287 fragment corresponding to nucleotides 2966 to 5466. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al, J. Virol. 81(9): 4654-4663, 2007), albeit now generated to comprise the sAd4287-derived sequences instead of the Ad26-derived sequences. Furthermore, the system consists of other plasmids together constituting sAd4287 sequences between nucleotide 2966 and 35079 that may be deleted for E1 region (nt 474 to nt 3085 of SEQ ID NO: 1), E3 region (nt 25973 to nt 28596 of SEQ ID NO: 1), and/or E4 region (nt 31852 to nt 34752 of SEQ ID NO: 1) sequences.

Generation of Adapter Plasmid sAdApt4287.Empty

Plasmids that were used for harboring the sAd4287 sequences were prepared. Primers (sAd4287.1A.fwd and sAd4287.1A.rev, SEQ ID NOs: 52 and 53, respectively) were designed to obtain the first 460 nucleotides of sAd4287 by PCR, with PacI and SalI at the 5'- and 3'-end of the resulting PCR product, respectively. A second set of primers (sAd4287.1B.fwd and sAd4287.1B.rev, SEQ ID NOs: 54 and 55, respectively) was designed to obtain pIX (nt 2966) through 2.5 kb upstream (nt 5466), with AfIII and PacI designed on the 5'- and 3'-end, respectively. A third set of PCR primers (sAd4287.TGC.fwd and sAd4287.TGC.rev, SEQ ID NOs: 56 and 57, respectively) were designed to obtain the transgene cassette from AdApter plasmid pAdApt26.Empty (Abbink, et al. J. Virol. 81(9): 4654-4663, 2007) from start of the CMV to end of the polyA with a SalI and AfIII site designed on the 5'- and 3'-end, respectively. These three PCR fragments were ligated together with the pAdApt bacterial backbone obtained by PacI digestion from pAdApt26 in a 4-point ligation, resulting in sAdApt4287.Empty (SEQ ID NO: 34). A schematic map of sAdApt4287.Empty is depicted in FIG. 2. This adapter plasmid contains left-end sAd4287 sequences (1-460 and 2966-5466) with the E1 region replaced by an expression/transgene cassette including the CMV promoter.

Generation of pBr/sAd4287.pIX-pV

To enable cloning of an sAd4287 HpaI-HindIII restriction fragment, which encompasses the 52K protein of sAd4287, a new plasmid was generated by inserting two PCR fragments in a pBr backbone. For this, primers (SEQ ID NOs: 58 and 59) were designed to obtain a PCR fragment from start of pIX over the HpaI site in wild-type sAd4287 (nt 2966 to nt 8311) with a PacI and a SbfI designed on the 5'- and 3'-end, respectively. A second PCR fragment was generated from HindIII (nt 12761) to the end of PCR (nt 16679), with a SbfI and PacI site designed on the 5'- and 3'-end, respectively. The second PCR fragment was generated using a second primer set (SEQ ID NOs: 60 and 61). These PCR fragments were ligated (PacI-SbfI-PacI) into a pBr backbone, obtained from pBr/Ad26.SfiI (see, e.g., WO 2007/104792) by PacI digestion, resulting in the pBr/sAd4287.pIX-pV shuttle vector. Finally, the sAd4287 HpaI-HindIII restriction fragment obtained from the sAd4287 wild-type genome was ligated into the pBr/sAd4287.pIX-pV shuttle vector digested with HpaI-HindIII, resulting in the complete pBr/sAd4287.pIX-pV plasmid (SEQ ID NO: 35). A schematic map of pBr/sAd4287.pIX-pV is depicted in FIG. 3.

Generation of pBr/sAd4287.PsiI-rITR pBr/sAd4287.PsiI-rITR contains sAd4287 sequences from the PsiI site at nucleotide 14053 to the end of the right inverted terminal repeat (rITR). To enable cloning of this sequence first a new plasmid was generated by inserting two PCR fragments in a pBr backbone. The two PCR fragments were generated such that they could be ligated together and cloned into a pBr-based backbone using the PacI restriction site. Primers were designed to obtain a PCR fragment from before PsiI site at nt 14053 to ~4 kb upstream over the NdeI site (nt 18186) at nt 18234, with a PacI and a SbfI site designed on the 5'- and 3'-end, respectively. A second set of primers was designed to obtain a PCR fragment from before PmeI site at nt30022 until the end of rITR at nt35079, with an SbfI and PacI site designed at the 5'- and 3'-end, respectively. The sequences of the primers used to generate these two PCR fragments is set forth in SEQ ID NOs: 62-65. These PCR fragments were ligated into a pBr backbone obtained from pBr/Ad26.SfiI by PacI-SbfI digestion, resulting in the pBr/sAd4287.PsiI-rITR shuttle vector. Finally, the NotI-AsiSI fragment (nt 16639-nt 34032) was obtained from the wild-type sAd4287 genome and ligated into the pBr/sAd4287.PsiI.rITR shuttle vector, resulting in the complete pBr/sAd4287.PsiI-rITR plasmid (SEQ ID NO: 36). A schematic map of pBr/sAd4287.PsiI-rITR is depicted in FIG. 4.

Generation of pBr/sAd4287.PsiI-rITR.dE3 pBr/sAd4287.PsiI-rITR was modified to delete part of the E3 region, which spans approximately nt 25973 to nt 28596 of sAd4287, and which is not required for replication and packaging of the adenoviral particle. To create the pBr/sAd4287.PsiI-rITR.dE3, two PCR fragments were generated. The first PCR fragment contained the pVIII from AscI to 140 bp after the polyA of pVIII (nt 8291-11192). The forward primer (SEQ ID NO: 66) was directed against the ApaLI in 100K and the reverse primer (SEQ ID NO: 67) has a SpeI site designed in it. The second PCR contains the Fiber region starting 100 bp before the polyA of the E3 region until the unique XbaI restriction site in the Fiber-2 region (nt 13177-14824). The forward primer, directed 100 bp in front of the polyA of E3, will have a SpeI site designed in it (SEQ ID NO: 68). The reverse primer was directed to the XbaI site (SEQ ID NO: 69). These two PCR fragments were ligated into pBr/sAd4287.PsiI-rITR with a 3-point ligation, with AscI-SpeI-XbaI, to generate pBr/sAd4287.PsiI-rITR.dE3 (SEQ ID NO: 37). FIG. 5 depicts a schematic map of pBr/sAd4287.PsiI-rITR.dE3 as well as an overview of the cloning strategy set forth above to generate the E3-deleted plasmid.

Generation of pBr/sAd4287.PsiI-rITR.dE3.dE4 pBr/sAd4287.PsiI-rITR.dE3 was modified to delete part of the E4 region, which spans approximately nt 31852 to nt 34752 of sAd4287, and specifically E4orf1-E4orf4. The modified plasmid, pBr/sAd4287.PsiI-rITR.dE3.dE4 (SEQ ID NO: 38), resulted in an enlarged cloning capacity with a 1409 bp gain of space. To create the pBr/sAd4287.PsiI-rITR.dE3.dE4, two PCR products were generated. The first PCR fragment starts at the XbaI site until the start of E4orf6. The sequences of the forward and reverse primers used to generate this first PCR fragment are set forth in SEQ ID NOs: 72 and 73, respectively. The second PCR fragment starts directly in front of the E4orf1 until the NotI site. The sequences of the forward and reverse primers used to operate this second PCR fragment are set forth in SEQ ID NOs: 74 and 75, respectively. These PCR fragments have 30-bp overlaps with flanking regions at the XbaI and Not I site and a 15-bp overlap with each other (30 bp total). The PCR fragments were assembled into pBr/sAd4287.PsiI-rITR.dE3 digested with XbaI and NotI by Gibson Assembly (New England BioLabs), resulting in pBr/sAd4287.PsiI-rITR.dE3.dE4. FIG. 6 depicts a schematic map of pBr/sAd4287.PsiI-rITR.dE3.dE4 relative to pBr/sAd4287.PsiI-rITR.dE3.

Generation of sAdApt4287.E1btg.Empty

To clone the E1 region of sAd4287 (approximately nt 474 to nt 3085 of SEQ ID NO: 1) into sAdApt4257.Empty for the purposes of producing replication-competent sAd4287 (rcsAd4287), a PCR fragment was generated from the wild-type sAd4287 with the forward primer (SEQ ID NO: 70) starting ~30 bp before the NgoMIV site in the lITR region until ~10 bp after the polyA of the E1 region (nt 218 to nt 3137). The reverse primer (SEQ ID NO: 71) has a ~30 bp overlap with the start of the CMV promoter in the sAdApt4287.Empty and includes the SaII restriction site. This PCR fragment was cloned into sAdApt4257.Empty, digested with NgoMIV and SaII, with Gibson Assembly (New England BioLabs), resulting in sAdApt4287.E1btg.Empty (SEQ ID NO: 39). A schematic map of sAdApt4287.E1btg.Empty and the cloning strategy described above is depicted in FIG. 7.

Example 3. Sequence of Simian Adenovirus sAd4310 #13-1 (sAd4310A)

Figure 8:
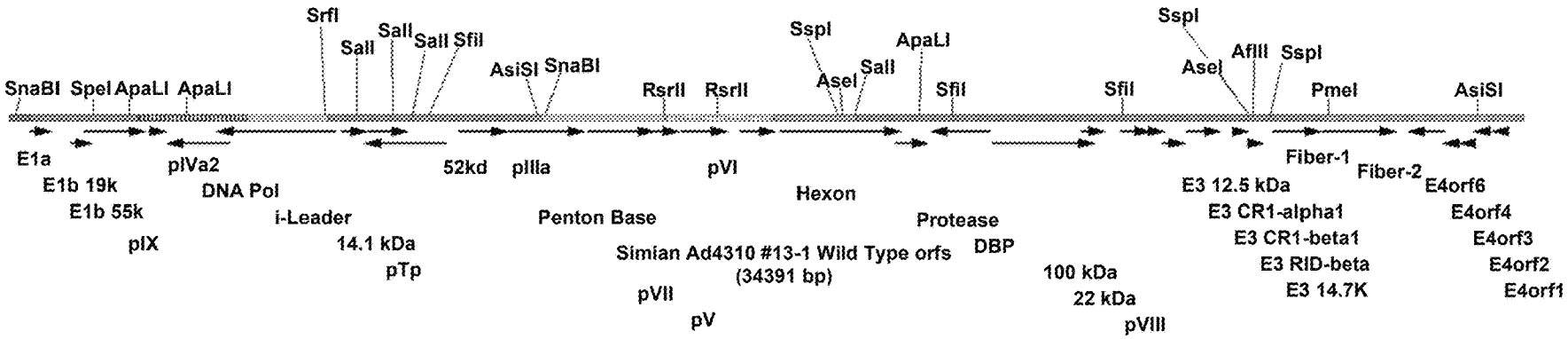
FIG. 8 is a schematic map of the genomic organization of sAd4310 #13-1 (sAd4310A).

The total genome sequence of simian adenovirus sAd4310 #13-1 (sAd4310A) was determined as described above for sAd4287. The obtained sequence of the sAd4310A genome (34391 nucleotides) is given as SEQ ID NO: 2. A schematic map of the genome structure of sAd4310A is depicted in FIG. 8. Using the full genomic sequence in an NCBI web-based BLAST search, the most closely related virus to sAd4310A was identified as simian adenovirus 1 (sAd1) ATCC VR-195 (query coverage: 97%; maximum identity: 98%). NCBI web-based BLAST searches were also performed to assess homology of three major capsid proteins of sAd4310A (fiber-1, fiber-2, and hexon proteins). The most closely related protein to sAd4310A fiber-1 was identified as sAd1 fiber-1 (query coverage: 100%; maximum identity: 99%). The most closely related protein to sAd4310A fiber-2 was identified as sAd1 fiber-2 (query coverage: 100%; maximum identity: 99%). The most closely related protein to sAd4310A hexon was identified as human Ad31 hexon (query coverage: 100%; maximum identity: 87%).

Example 4. Generation of Recombinant sAd4310A Viruses

Here, the construction of an sAd4310A plasmid-based system to generate recombinant sAd4310A vectors in a safe and efficient manner is described. The plasmid system consists of a first plasmid, referred to as an adapter plasmid, which contains sAd4310A nucleotides 1 to 461 including the left inverted terminal repeat (lITR) and packaging signal, an expression cassette and an sAd4310A fragment corresponding to nucleotides 2903 to 5410. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al. J. Virol. 81(9): 4654-4663, 2007), albeit now generated to comprise the sAd4310A-derived sequences instead of the Ad26-derived sequences. Furthermore, the system consists of other plasmids together constituting sAd4310A sequences between nucleotide 2903 and 34391 that may be deleted for E1 region (nt 474 to nt 3088 of SEQ ID NO: 2), E3 region (nt 25915 to nt 28496 of SEC) ID NO: 2), and/or E4 region (nt 31750 to nt 34048 of SEQ ID NO: 2) sequences.

Generation of Adapter Plasmid sAdApt4310A.Empty

Plasmids that were used for harboring the sAd4310A sequences were prepared. Primers (sAd4310A.1A.fwd and sAd4310A.1A.rev, SEQ ID NOs: 76 and 77, respectively) were designed to obtain the first 461 nucleotides of sAd4310A by PCR, with PacI and SaII at the 5'- and 3'-end of the resulting PCR product, respectively. A second set of primers (sAd4310A.1B.fwd and sAd4310A.1B.rev, SEQ ID NOs: 78 and 79, respectively) was designed to obtain pIX (nt 2903) through approximately 2.5 kb upstream (nt 5410), with AfIII and PacI designed on the 5'- and 3'-end, respectively. A third set of PCR primers (sAd4310A.TGC.fwd and sAd4310A.TGC.rev, SEQ ID NOs: 80 and 81, respectively) were designed to obtain the transgene cassette from AdApter plasmid pAdApt26.Empty (Abbink, et al. J. Virol. 81(9): 4654-4663, 2007) from start of the CMV to end of the polyA with a SaII and AfIII site designed on the 5'- and 3'-end, respectively. These three PCR fragments were ligated together with the pAdApt bacterial backbone obtained by PacI digestion from pAdApt26 in a 4-point ligation, resulting in sAdApt4310A.Empty (SEQ ID NO: 40). A schematic map of sAdApt4310A.Empty is depicted in FIG. 9. This adapter plasmid contains left-end sAd4310A sequences (1-451 and 2903-5410) with the E1 region replaced by an expression/transgene cassette including the CMV promoter.

Generation of pBr/sAd4310A.pIX-pV

To enable cloning of an sAd4310A SrfI-SnaBI restriction fragment, which encompasses the 52K protein of sAd4310A, a new plasmid was generated by inserting two PCR fragments in a pBr backbone. For this, primers (SEQ ID NOs: 82 and 83) were designed to obtain a PCR fragment from start of pIX over the SrfI site in wild-type sAd4310A (nt 2903 to nt 7224) with a PacI and a SbfI designed on the 5'- and 3'-end, respectively. A second PCR fragment was generated tram SnaBI (nt 12098) in pIIIa to pVI (nt 17365), with a SbfI and PacI site designed on the 5'- and 3'-end, respectively. The second PCR fragment was generated using a second primer set (SEQ ID NOs: 84 and 85). These PCR fragments were ligated (PacI-SbfI-PacI) into a pBr backbone, obtained from pBr/Ad26.SfiI (see, e.g., WO 2007/104792) by PacI digestion, resulting in the pBr/sAd4310A.pIX-pV shuttle vector. Finally, the sAd4310A SrfI-SnaBI restriction fragment obtained from the sAd4310A wild-type genome was ligated into the pBr/sAd4310A.pIX-pV shuttle vector digested with SrfI-SnaBI, resulting in the complete pBr/sAd4310A.pIX-pV plasmid (SEQ ID NO: 41). A schematic map of pBr/sAd4310A.pIX-pV is depicted in FIG. 10.

Generation of pBr/sAd4310A.RSrII-rITR pBr/sAd431 0A.RsrII-rITR contains sAd431 0A sequences from the RsrII site at nucleotide 14882 to the end of the right inverted terminal repeat (rITR) at nucleotide 34391. To enable cloning of this sequence first a new plasmid was generated by inserting two PCR fragments in a pBr backbone. The two PCR fragments were generated such that they could be ligated together and cloned into a pBr-based backbone using the Paci restriction site. Primers (sAd431 0A.3A.fwd and sAd431 0A.3A.rev, SEQ ID NOs: 86 and 87, respectively) were designed to obtain a PCR fragment from the RsrII site at nt 14882 to 4.5 kb upstream over the Sal I site (nt 19189) to nt 19224, with a Paci and a SbfI site designed on the 5' and 3'-end, respectively. A second set of primers (sAd431 0A.3B.fwd and sAd431 0A.3B.rev, SEQ ID NOs: 88 and 89, respectively) was designed to obtain a PCR fragment from before the PmeI site at nt 29829 until the end of the rITR at nt 34391, with an SbfI and Paci site designed at the 5'- and 3'-end, respectively. These PCR fragments were ligated into a TOPO® vector using the commercially available ZERO BLUNT® TOPO® PCR Cloning Kit (Invitrogen). The two PCR fragments were digested as PCR fragments or from the TOPO® clone with Paci and SbfI and subsequently ligated into a pBr backbone obtained from pBr/Ad26.SfiI digested with Paci. Finally, SalI-XbaI fragment (nt 19190-nt 30014) was obtained from the wild-type sAd431 0A genome and ligated into the pBr/sAd431 0A.RsrII.rITR shuttle vector, resulting in the complete pBr/sAd431 0A.RsrII-rITR plasmid (SEQ ID NO: 42). A schematic map of pBr/sAd431 0A.RsrII-rITR is depicted in FIG. 11.

Generation of pBr/sAd4310A.RsrII-rITR.dE3 pBr/sAd4310A.RsrII-rITR was modified to delete part of the E3 region, which spans approximately nt 25915 to nt 28496 of sAd4310A, and which is not required for replication and packaging of the adenoviral particle. To create the pBr/sAd4310A.RsrII-rITR.dE3 with Gibson Assembly, two PCR fragments were generated. The first PCR fragment (dE3AG) contained from approximately 50 bp before the SfiI site at nt 7644 to 140 bp after the polyA of pVIII. The forward primer and reverse primer have sequences set forth in SEQ ID NOs: 90 and 91, respectively, wherein the reverse primer was designed to have an approximately 25-bp overlap with the second PCR fragment. The second PCR fragment (dE3BG) starts at nt 14641 (approximately 100 bp before the polyA of the E3 region) until approximately 50 bp after the XbaI site at nt 16252. The forward primer and reverse primer for the second PCR have sequences set forth in SEQ ID NOs: 92 and 93, respectively, wherein the forward primer was designed to have an approximately 25-bp overlap with the first PCR fragment. The two PCR fragments were assembled with Gibson Assembly, with the pBr/sAd4310A.RsrII.rITR digested with SfiI and XbaI. The resulting plasmid, pBr/sAd4310A.RsrII.rITR.dE3 (SEQ ID NO: 43), is depicted in FIG. 12, along with the parental plasmid, pDr/sAd4310A.RsrII.rITR.

Generation of pBr/sAd4310A.RsrII-rITR.dE3.dE4 pBr/sAd4310A.RsrII-rITR.dE3 was modified to delete part of the E4 region, which spans approximately nt 31750 to nt 34048 of sAd4310A, and specifically E4orf1-E4orf4. The modified plasmid, pBr/sAd4310A.RsrII-rITR.CE3.dE4 (SEQ ID NO: 44), resulted in an enlarged cloning capacity with a 1394 bp pain of space. To create the pBr/sAd4310A.RsrII-rITR.dE3.dE4 plasmid, two PCR products were generated. The first PCR fragment starts at the XbaI site until the start of E4orf6. The sequences of the forward and reverse primers used to generate this first PCR fragment are set forth in SEQ ID NOs: 96 and 97, respectively. The second PCR fragment starts directly in front of the E4orf1 until the NotI site. The sequences of the forward and reverse primers used to generate this second PCR fragment are set forth in SEQ ID NOs: 98 and 99, respectively. These PCR fragments have 30-bp overlaps with flanking regions at the XbaI and Not I site and a 15-bp overlap with each other (30 bp total). The PCR fragments were assembled by Gibson Assembly (New England BioLabs) into pBr/sAd4310A.RsrII-rITR.dE3 digested with XbaI and NotI, resulting in pBr/sAd4310A.RsrII-rITR.dE3.dE4 (SEQ ID NO: 44). FIG. 13 depicts a schematic map of pBr/sAd4310A.RsrII-rITR.dE3.dE4 relative to the parental plasmid pBr/sAd4310A.RsrII-rITR.dE3.

Generation of sAdApt4310A.E1btg.Empty

To clone the E1 region of sAd4310A (nt 474 to nt 3088 of SEQ ID NO: 2) into sAdApt4310A.Empty for the purposes of producing replication-competent sAd4310A (rcsAd4310A), a PCR fragment was generated from the wild-type sAd4310A with the forward primer (SEQ ID NO: 94) starting ~40 bp before the BstZ17I site in the lITR region ~10 bp after the polyA of the E1 region (nt 150 to nt 3131). The reverse primer (SEQ ID NO: 95) has a ~30 bp overlap with the start of the CMV promoter in the sAdApt4310A.Empty and includes the SalI restriction site. This PCR fragment was cloned into sAdApt4310A.Empty, digested with BstZ17I and SalI, with Gibson Assembly (New England BioLabs), resulting in sAdApt4310A.E1btg.Empty (SEQ ID NO: 45). A schematic map of sAdApt4310A.E1btg.Empty and the cloning strategy described above is depicted in FIG. 14.

Example 5. Sequence of Simian Adenovirus sAd4312

Figure 15:
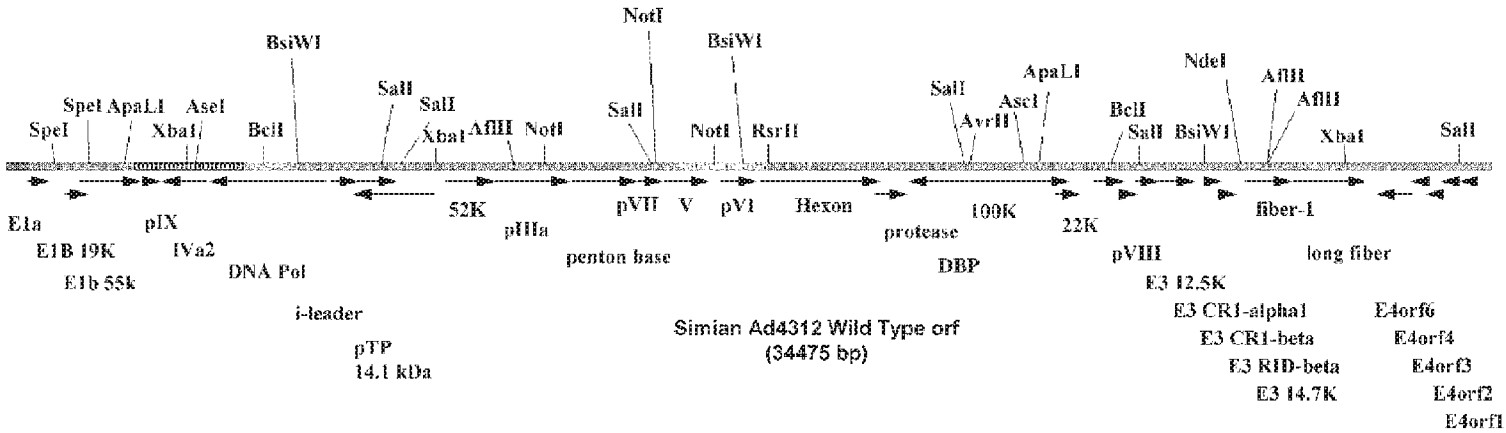
FIG. 15 is a schematic map of the genomic organization of sAd4312.

The total genome sequence of simian adenovirus sAd4312 was determined as described above for sAd4287 and sAd4310A. The obtained sequence of the sAd4312 genome (34475 nucleotides) is given as SEQ ID NO: 3. A schematic map of the genome structure of sAd4312 is depicted in FIG. 15. Using the full genomic sequence in an NCBI web-based BLAST search, the most closely related virus to sAd4312 was identified as simian adenovirus 1 (sAd1) ATCC VR-195 (query coverage: 90%; maximum identity: 98%). NCBI web-based BLAST searches were also performed to assess homology of three major capsid proteins of sAd4312 (fiber-1, fiber-2, and hexon proteins). The most closely related protein to sAd4312 fiber-1 was identified as human Ad52 fiber-1 (query coverage: 100%; maximum identity: 99%). The most closely related protein to sAd4312 fiber-2 was identified as sAd7 lone fiber (query coverage: 99%; maximum identity: 73%). The most closely related protein to sAd4312 hexon was identified as human Ad40 hexon (query coverage: 100%; maximum identity: 89%).

Example 6. Generation of Recombinant sAd4312 Viruses

Here, the construction of an sAd4312 plasmid-based system to generate recombinant sAd4312 vectors in a safe and efficient manner is described. The plasmid system consists of a first plasmid, referred to as an adapter plasmid, which contains sAd4312 nucleotides 1 to 472 including the left inverted terminal repeat (lITR) and packaging signal, an expression cassette and an sAd4312 fragment corresponding to nucleotides 2939 to 5510. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al. J. Virol. 81(9): 4654-4663, 2007), albeit now generated to comprise the sAd4312-derived sequences instead of the Ad26-derived sequences. Furthermore, the system consists of other plasmids together constituting sAd4312 sequences between nucleotide 2939 and 344475 that may be deleted for E1 region (nt 487 to nt 3100 of SEQ ID NO: 3), E3 region (nt 25947 to nt 28561 SEQ ID NO: 3), and/or E4 region (nt 31818 to nt 34116 SEQ ID NO: 3) sequences.

Generation of Adapter Plasmid sAdApt4312.Empty

Plasmids that were used for harboring the sAd4312 sequences were prepared. Primers (sAd4312.1A.fwd and sAd4312.1A.rev, SEQ ID NOs: 100 and 101, respectively) were designed to obtain the first 472 nucleotides of sAd4312 by PCR, with PacI and SalI at the 5'- and 3'-end of the resulting PCR product, respectively. A second set of primers (sAd4312.1B.fwd and sAd4312.1B.rev, SEQ ID NOs: 102 and 103, respectively) was designed to obtain pIX (nt 2939) through approximately 2.5 kb upstream (nt 5510), with AfIII and PacI designed on the 5- and 3'-end, respectively. A third set of PCR primers (sAd4312.TGC.fwd and sAd4312.TGC.rev, SEQ ID NOs: 104 and 105, respectively) were designed to obtain the transgene cassette from AdApter plasmid pAdApt26.Empty (Abbink, et al. J. Virol. 81(9): 4654-4663, 2007) from start of the PCR to end of the polyA with a SalI and AfIII site designed on the 5- and 3'-end, respectively. These three PCR fragments were ligated together with the pAdApt bacterial backbone obtained by PacI digestion from pAdApt26 in a 4-point ligation, resulting in sAdApt4312.Empty (SEQ ID NO: 46). A schematic map of sAdApt4312.Empty is depicted in FIG. 16. This adapter plasmid contains left-end sAd4312 sequences (1-472 and 2939-5510) with the E1 region replaced by an expression/transgene cassette including the CMV promoter.

Generation of pBr/sAd4312.pIX-pV

To enable cloning of an sAd4312 BsiWI-BsiWI restriction fragment, a new plasmid was generated by inserting two PCR fragments in a pBr backbone. For this, primers (SEQ ID NOs: 106 and 107) were designed to obtain a PCR fragment from start of pIX over the BsiWI site in wild-type sAd4312 (nt 2939 to nt 6791) with a Paci and a NdeI designed on the 5'- and 3'-end, respectively. A second PCR fragment was generated from pV (nt 15564) to the RsrII site at the end of pVI (nt 17698), with a NdeI and Paci site designed on the 5'- and 3'-end, respectively. The second PCR fragment was generated using a second primer set (SEQ ID NOs: 108 and 109). These PCR fragments were cloned into a TOPO® vector using the commercially available ZERO BLUNT® TOPO® PCR Cloning Kit (Invitrogen), resulting in the pBr/sAd4312.pIX-pV shuttle vector. Finally, the sAd4312 BsiWI-BsiWI restriction fragment obtained from the sAd4312 wild-type genome was ligated into the pBr/sAd4312.pIX-pV shuttle vector digested with BsiWI and screened for orientation, resulting in the complete pBr/sAd4312.pIX-pV plasmid (SEQ ID NO: 47). A schematic map of pBr/sAd4312.pIX-pV is depicted in FIG. 17.

Generation of pBr/sAd4312.pV-rITR pBr/sAd4312.pV-rITR contains sAd4312 sequences from the start of pV at nucleotide 15215 to the end of the right inverted terminal repeat (rITR) at nucleotide 34475. To enable cloning of this sequence first a new plasmid was generated by inserting two PCR fragments in a pBr backbone. The two PCR fragments were generated such that they could be ligated together and cloned into a pBr-based backbone using the Paci restriction site. Primers (sAd4312.3A.fwd and sAd4312.3A.rev, SEQ ID NOs: 110 and 111, respectively) were designed to obtain a PCR fragment from the start of pV at nt 15215 to 2.5 kb upstream over the RsrII site to nt 17698, with a Paci and a SbfI site designed on the 5'- and 3'end, respectively. A second set of primers (sAd4312.3B.fwd and sAd4312.3B.rev, SEQ ID NOs: 112 and 113, respectively) was designed to obtain a PCR fragment from before the XbaI site at nt 31015 until the end of the rITR at nt 34475, with an SbfI and Paci site designed at the 5'- and 3'-end, respectively. These PCR fragments were ligated into a TOPO® vector using the commercially available ZERO BLUNT® TOPO® PCR Cloning Kit (Invitrogen). The two PCR fragments were digested from the TOPO® clones with SbfI and Paci and subsequently ligated into a pBr backbone obtained from pBr/Ad26.SfiI digested with Paci, resulting in the pBr/sAd4312.pV-rITR shuttle vector. Finally, the NotI-XbaI fragment (nt 16412-nt 31083) was obtained from the wild-type sAd4312 genome and ligated into the pBr/sAd4312.pV-rITR shuttle vector, resulting in the complete pBr/sAd4312.pV-rITR plasmid (SEQ ID NO: 48). A schematic 1 o map of pBr/sAd4312.pV-rITR is depicted in FIG. 18.

Generation of pBr/sAd4312.pV-rITR.dE3 pBr/sAd4312.pV-rITR was modified to delete part of the E3 region, which spans approximately nt 487 to nt 3100 of sAd4312, and which is not required for replication and packaging of the adenoviral particle. To create the pBr/sAd4312.pV-rITR.dE3, two PCR fragments were generated. The first PCR fragment contains the pVIII from AscI to 140 bp after the polyA of pVIII (nt 9859 to nt 12302). The forward primer (sAd4312.dE3A.fwd, SEQ ID NO: 114) is directed against the AscI in 100K, and the reverse primer (sAd4312.dE3A.rev, SEQ ID NO: 115) has a SpeI site designed in it.

The second PCR contains the fiber region starting 100 bp before the polyA of the E3 region until the unique restriction site, XbaI, in the fiber-2 region (nt 14378 to nt 17020). The forward primer (sAd4312.dE3B.fwd, SEQ ID NO: 116), directed 100 bp in front of the polyA of E3, has a SpeI site designed in it. The reverse primer (sAd4312.dE3B.fwd, SEQ ID NO: 117) is directed to the XbaI site. These two PCR fragments were ligated into pBr/sAd4312.pV-rITR with a 3-point ligation, with AscI-SpeI-XbaI. The resulting plasmid, pBr/sAd4312.pV-rITR.dE3 (SEQ ID NO: 49), is depicted in FIG. 19, along with the parental plasmid, pBr/sAd4312.pV-rITR.

Generation of pBr/sAd4312.pV-rITR.dE3.dE4 pBr/sAd4312/pV-rITR.dE3 was modified to delete part of the E4 region, which spans approximately nt 25947 to nt 28561 of sAd4312, and specifically E4orf1-E4orf4. The modified plasmid, pBr/sAd4312.pV-rITR.dE3.dE4 (SEQ ID NO: 50), resulted in an enlarged cloning capacity with a 1393 bp gain of space. To create the pBr/sAd4312.pV-rITR.dE3.dE4 plasmid, two PCR products were generated. The first PCR fragment starts at the NdeI site until the start of E4orf6. The sequences of the forward and reverse primers used to generate this first PCR fragment are set forth in SEQ ID NOs: 120 and 121, respectively. The second PCR fragment starts directly in front of the E4orf1 until the NotI site. The sequences of the forward and reverse primers used to generate this second PCR fragment are set forth in SEQ ID NOs: 122 and 123, respectively. These PCR fragments have 30-bp overlaps with flanking regions at the NdeI and NotI site and a 15-bp overlap with each other (30 bp total). The PCR fragments were assembled into pBr/sAd4312.pV-rITR.dE3 digested with XbaI and NotI, resulting in pBr/sAd4312.pV-rITR.dE3.dE4 (SEQ ID NO: 50). FIG. 20 depicts a schematic map of pBr/sAd4312.pV-rITR.dE3.dE4 and that of the parental plasmid, pBr/sAd4312.pV-rITR.dE3.

Generation of sAdApt4312.E1btg.Empty

To clone the E1 region of sAd4312 (nt 487 to 3100 SEQ ID NO: 3) into sAdApt4312.Empty for the purposes of producing replication-competent sAd4312 (rcsAd4312), a PCR fragment was generated from the wild-type sAd4312 which included the complete E1 region of sAd4312. The forward primer (SEQ ID NO: 118) is directed to ~40 bp in front of the first BstZ17I site in the lITR region. The reverse primer (SEQ ID NO: 119) has a ~30 bp overlap with the start of the CMV promoter in the sAdApt4312.Empty. The generated PCR fragment was cloned into sAdApt4312.Empty, digested with BstZ17I and SalI, with Gibson Assembly (New England BioLabs), resulting in sAdApt4312.E1btg.Empty (SEQ ID NO: 51). In this cloning step, only the AdApt plasmid was digested; the PCR product was not digested with restriction enzymes. A schematic map of sAdApt4312.E1btg.Empty and the cloning strategy described above is depicted in FIG. 21.

Figures 22A, 22B, 22C:
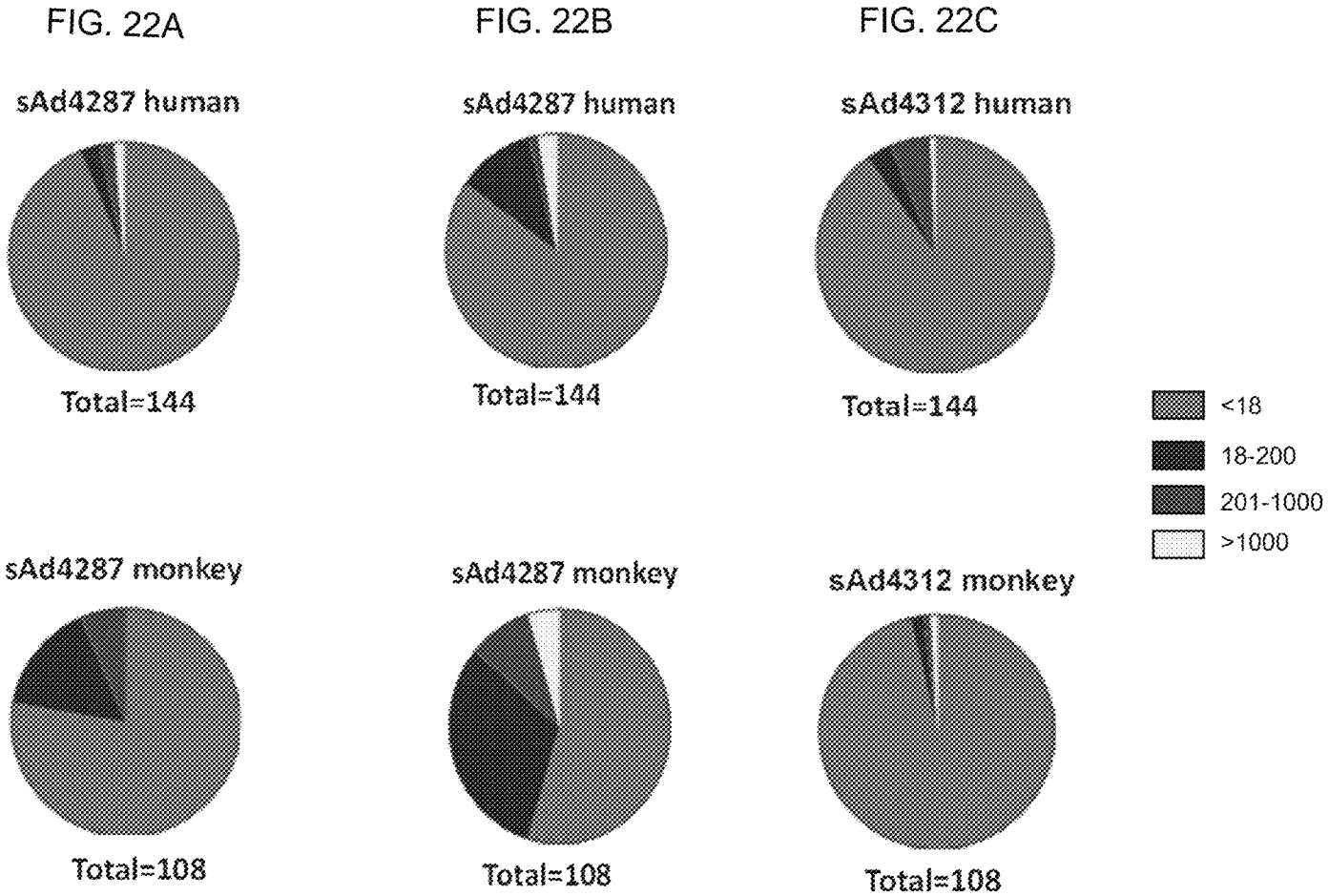
FIG. 22A is a pie chart showing the relative sAd4287-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high, and >1000=high), as assessed by luciferase-based virus neutralization assays, is shown.
FIG. 22B is a pie chart showing the relative sAd4310A-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high and >1000=high), as assessed by luciferase-based virus neutralization assays, is shown.
FIG. 22C is a pie chart showing the relative sAd4312-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high, and >1000=high), as assessed by luciferase-based virus neutralization assays, is shown.

Example 7. Seroprevalence of sAd4287, sAd4310A, and sAd4312 in sub-Saharan Humans and Rhesus Monkeys We next evaluated sAd4287, sAd4310A, and sAd4312 titers in 144 sub-Saharan humans and 108 rhesus monkeys (FIGS. 22A-22C). Adenovirus-specific neutralizing antibody (NAb) titers were determined by luciferase-based virus neutralization assays as previously described (Sprangers et al. J. Clin. Microbiol. 41: 5046-5052, 2003; Barouch et al. Vaccine. 29: 5203-5209, 2011). Titers of <18 are regarded as negative by this assay, 18-200 is low, 201-1000 is high, and >1000 is considered very high. It is suspected that titers >200 will likely be suppressive, according to data known in the art. Representative pie charts summarizing the relative number of individuals (humans or monkeys) that fall within each of the four titer categories are depicted for each of the three adenoviruses tested (see FIGS. 22A-22C).

The results of the seroprevalence studies clearly indicate that the majority of both sub-Saharan humans and rhesus monkeys tested exhibited negative (<18) or low (18-200) NAb titers for each of the three adenoviruses tested (sAd4287, sAd4310A, and sAd4312). These seroprevalence studies indicate that the sAd4287, sAd4310A, and sAd4312 vectors have extremely and surprisingly low seroprevalence in human populations (e.g., sub-Saharan human populations) and monkey populations (e.g., rhesus monkey populations). The extremely low seroprevalence of the sAd vectors of the invention are in marked contrast to the relatively high seroprevalence of Ad5 in human populations. Accordingly, these studies indicate a distinct advantage of using a vaccine comprising all or a portion of a recombinant sAd4287, sAd4310A, and sAd4312, as the neutralizing activities in the majority of both humans and monkeys alike are unlikely to hamper the efficacy of the vaccine.

Example 8. Determination of Cellular Responses to Recombinant Adenoviruses of the Invention in Mice We next studied whether recombinant replication-defective adenoviruses based on simian adenoviruses of the invention (e.g., sAd4287 or sAd4310A) were able to elicit a significant immune response in vivo. For this, vectors were generated that all contained the SIVmac239 Gag insert from Simian Immunodeficiency Virus (SIV). Recombinant DNA, such as the required adapter plasmids, and the recombinant viruses were generated generally as described (Lemckert et al. J. Virol. 79:9694-9701, 2005).

Figure 23A:
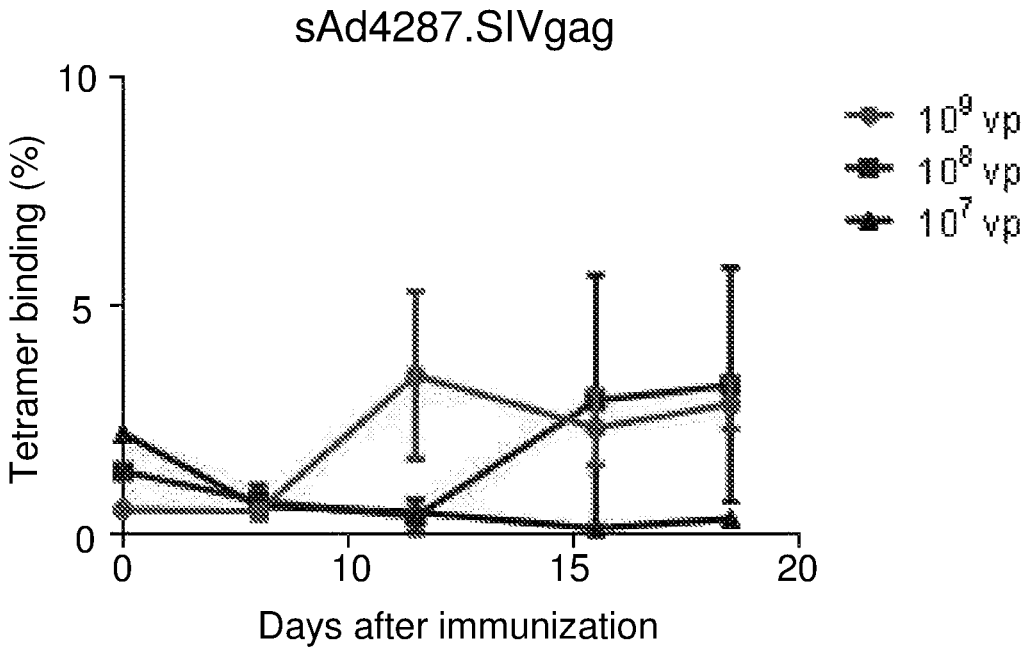
FIG. 23A is a graph showing the cellular responses induced by sAd4287 vectors bearing SIVmac239 Gag in C57BL/6 mice immunized with $10^7$, $10^8$, and $10^9$ viral particles (vp) of the vector, as assessed by measuring the $CD8^+$ T cell response via $D^b$/AL11 tetramer binding assays at days 0, 7, 14, 21, and 28 post-immunization.
Figure 23B:
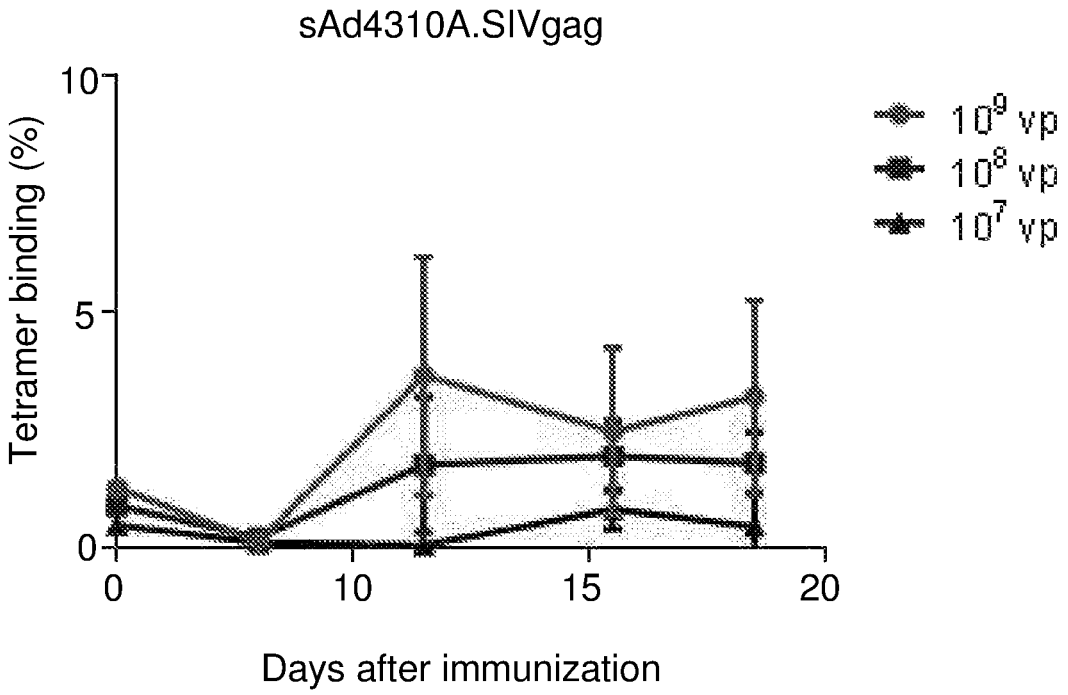
FIG. 23B is a graph showing the cellular responses induced by sAd4310A vectors bearing SIVmac239 Gag in C57BL/6 mice immunized with $10^7$, $10^8$, and $10^9$ viral particles (vp) of the vector, as assessed by measuring the $CD8^+$ T cell response via $D^b$/AL11 tetramer binding assays at days 0, 7, 14, 21, and 28 post-immunization.

C57BL/6 mice were injected intramuscularly with different amounts of viral vectors: $10^7$, $10^8$, and $10^9$ viral particles (vp). All vaccination procedures and cellular immune responses were performed and measured by assessing the $CD8^+$ T cell response via $D^b$/AL11 tetramer binding assays as previously described (Barouch et al. J. Immunol. 172: 6290-6297, 2004). Tetrameric H-2Db complexes folded around the immunodominant SIV Gag AL11 epitope (AAVKNWMTQTL; SEQ ID NO: 124) (Liu et al., J. Viral. 80: 11991-11997, 2006) were prepared and SIV Gag-specific $CD8^+$ T lymphocyte responses were measured on days 0, 7, 14, 21, and 28 post-immunization. For immunogenicity experiments with sAd4287 and sAd4310A, the results are shown in FIGS. 23A and 23B. From these results, it can be concluded that the adenoviral vectors of the invention exhibit potent immunogenicity in mice, especially with $10^8$ or $10^9$ vp doses.

Figure 24A:
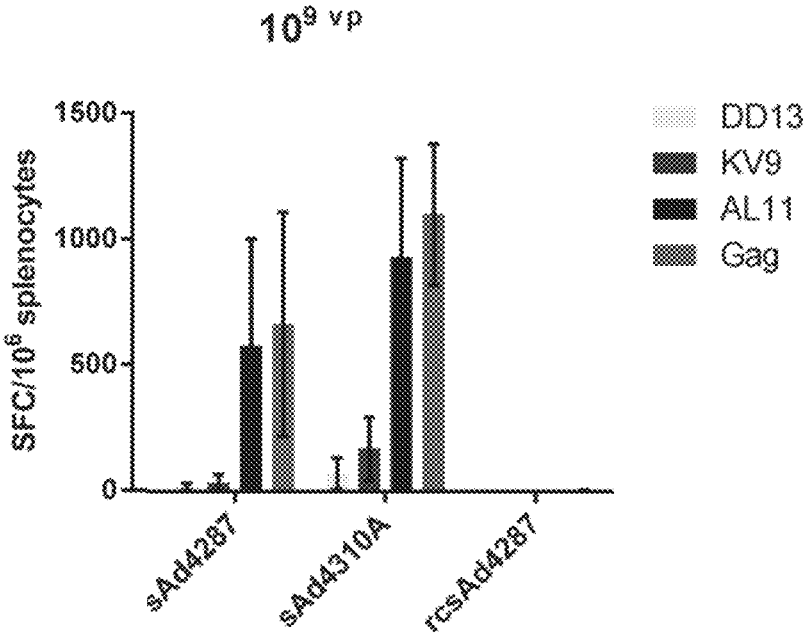
FIG. 24A is a graph showing the cellular responses induced by sAd4287, sAd4310A, and replication-competent sAd4287 (rcsAd4287) at $10^9$ vp as determined by IFN-γ ELISPOT assays using splenocytes from C57BL/6 mice on day 28 post-immunization. IFN-γ ELISPOT responses were measured to overlapping Gag peptides (Gag), the dominant $CD8^+$ T cell epitope AL11, the sub-dominant $CD8^+$ epitope KV9, and the $CD4^+$ T cell epitope DD13.
Figure 24B:
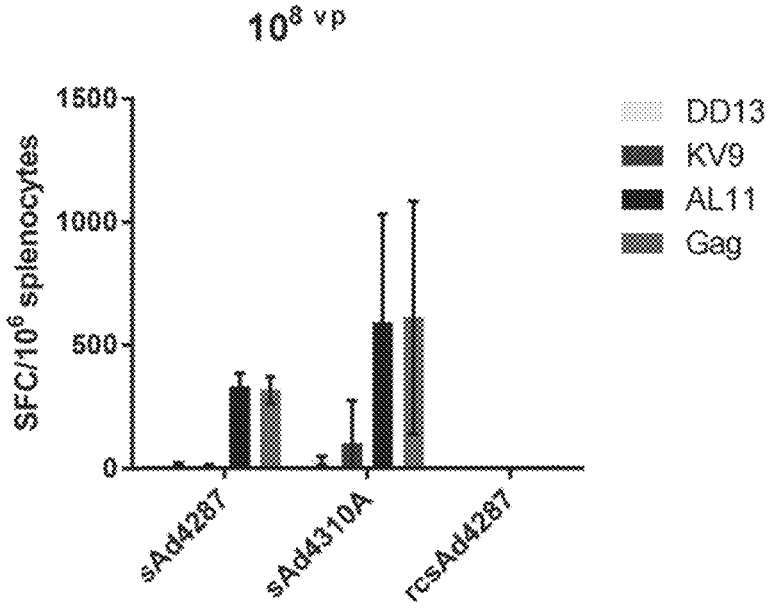
FIG. 24B is a graph showing the cellular responses induced by sAd4287, sAd4310A, and rcsAd4287 at $10^8$ vp as determined by IFN-γ ELISPOT assays using splenocytes from C57BL/6 mice on day 28 post-immunization. IFN-γ ELISPOT responses were measured to Gag, the dominant $CD8^+$ T cell epitope AL11, the sub-dominant $CD8^+$ T epitope KV9, and the $CD4^+$ T cell epitope DD13.
Figure 24C:
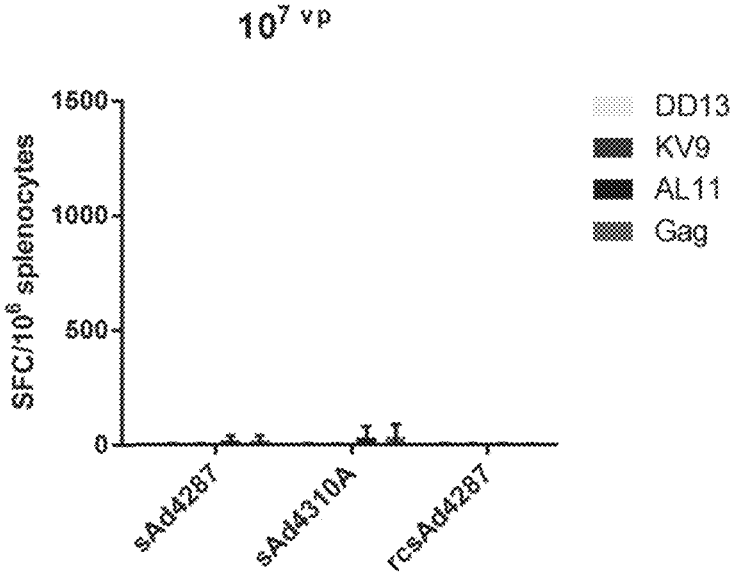
FIG. 24C is a graph showing the cellular responses induced by sAd4287, sAd4310A, and rcsAd4287 at $10^7$ vp as determined by IFN-γ ELISPOT assays using splenocytes from C57BL/6 mice on day 28 post-immunization. IFN-γ ELISPOT responses were measured to Gag, the dominant $CD8^+$ T cell epitope AL11, the sub-dominant $CD8^+$ T epitope KV9, and the $CD4^+$ T cell epitope DD13.

To evaluate functional responses, splenocytes from day 28 were utilized in IFN-γ ELISPOT assays. IFN-γ ELISPOT responses were measured to overlapping Gag peptides (Gag), the dominant CD8+ T cell epitope AL11 (AAVKNWMTQTL; SEQ ID NO: 124), the sub-dominant $CD8^+$ T epitope KV9 (KSLYNTVCV; SEQ ID NO: 125), and the CO4+ T cell epitope DD13 (DRFYKSLRAEQTD; SEQ ID NO: 126) (Liu et al., J. Virol. 80: 11991-11997, 2006) at $10^7$, $10^8$, and $10^9$ vp of viral vectors (sAd4287, sAd431 0A, and rcsAd4287). As depicted in FIGS. 24A-24C, the IFN-γ ELISPOT responses increased with increasing amounts of vp, and both Gag and AL11 responses were elevated relative to the responses to KV9 or DD13 epitopes. In addition, these functional responses were elicited only when replication-defective adenoviruses of the invention were used (e.g., sAd4287 and sAd4310A), but not when replication-competent adenoviruses of the invention were used (e.g., rcsAd4287). Collectively, the studies of cellular responses to the recombinant adenoviral vectors of the invention clearly indicate potent immunogenicity in mice.

The combination of low baseline anti-vector immunity (low seroprevalence), potent immunogenicity, and novel biology suggests that the novel adenoviral vectors of the invention can be useful as novel vaccine candidates against human or veterinary pathogens, including, but not limited to, HIV, SIV, cancer, malaria, and tuberculosis, in addition to utility in gene therapy and/or diagnostics.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

SEQUENCE LISTING

```
Sequence total quantity: 126
SEQ ID NO: 1            moltype = DNA  length = 35079
FEATURE                 Location/Qualifiers
source                  1..35079
                        mol_type = genomic DNA
                        organism = Simian Adenovirus 4287 (sAd4287) Wild Type
SEQUENCE: 1
catcatcaat aatatacctt attctggaaa cgtgccaata tgataatgag cggggaggag  60
cgaggcgggg ccggggtgac gtgcggtgac gcggggtgac gcggggtggc gcgagggcgg  120
ggcgggagtg gggaggcgct tagtttttac gtatgcggaa ggaggtttta taccggaagt  180
tgggtaattt gggcgtatat ttgtaagttt tgtgtaattt ggcgcgaaaa ccgggtaatg  240
aggaagttga ggttaatatg tactttttat gactgggcgg aatttctgct gatcagcagt  300
gaactttggg cgctgacggg gaggtttcgc tacgtggcag taccacgaga aggctcaaag  360
gtcccattta ttgtactcct cagcgttttc gctgggtatt taaacgctgt cagatcatca  420
agaggccact cttgagtgcc ggcgagtaga gttttctcct ccgcgctgcc gcgatgaggc  480
tggttcccga gatgtacggt gttttctgca gcgagacggc ccggaactca gatgagctgc  540
ttaatacaga tctgctggat gttcccaact cgcctgtggc ttcgcctccg tcgcttcatg  600
atcttttcga tgtggaagtg gatccaccgc aagatcccaa cgaggacgcg gtaaacagta  660
tgttccctga atgtctgttt gaggcggctg aggagggttc tcacagcagt gaagagagca  720
gacggggaga ggaactggac ttgaaatgct acgaggaatg tctgccttct agcgattctg  780
aaacggaaca gacaggggga gacggctgtg agtcggcaat gaaaaatgaa cttgtattag  840
actgtccaga acatcctggt catggctgcc gtgcctgtgc ttttcataga aatgccagcg  900
gaaatcctga gactctatgt gctctgtgtt atctgcgcct taccagcgat tttgtataca  960
gtaagtaaag tgttttcatt ggcgtacggt aggggattcg ttgaagtgct ttgtgactta  1020
ttatgtgtca ttatttctag gtgacgtgtc cgacgtggaa ggggaaggag atagatcagg  1080
ggctgctaat tctccttgca ctttgggggc tgtggttcca gctggcatta ttaaacccgt  1140
ggcggtcaga gtctcaggca gacggtgcgc agttgaaaaa attgaagact tgctgcagga  1200
agaacagacg caacctttgg acctgtccat gaaacgccct aagctgactt aagtgtgttt  1260
attgtatgca ataaaagtgt tgatctttga actgtgttta tgtgttgggt gtgtctgtgg  1320
gtatataagc aggtggatgg gaagtgagag cacagctgct tcagatggat ctgctaggag  1380
acctaagaga atttggcgtg gttcggcgct tgttggagtt ggcctctgac agaacttcca  1440
agttttggag gttttgtttt ggctcaacgc ttagcaacgt gctatatagg gtcaagaagg  1500
agcaggagac gcagtttgct aggctgttgg ccgatactcc tggagttttt gtggctctgg  1560
atctaggcca tcactctctt ttccaagaga aaattatcaa aaacctaact tttacgtctc  1620
ctggccgcac ggttgcttcc gctgccttta ttacctatat tttggatcaa tggagcaaca  1680
gcggcagcca cctgtcgtgg gagtacatgc tggattacat gtcgatggcg ctgtggaggg  1740
ccatgctgcg gaggagggtt tgcatttact tgcgggcgca gcctccgcgg ctgggccgag  1800
tggaggagga ggacgagccg ggagagatgg agaacctgag ggccgggctg gaccctccaa  1860
cggaggacta ggtgctgagg atgatcctga agaggggact agtgggggag ctaggaaaaa  1920
gcaaaaaact gagcctgaac ctagaaactt tttgaatgag ttgactgtaa gcctgatgaa  1980
tcggcagcgt cctgagacgg tgttttgggc tgagttggag gatgagttca agaaggggga  2040
attgaacctc ttgtacaagt atgggtttga gcagttgaaa actcactggt tggagccgtg  2100
ggaggacatg gaaatggctc tagacacctt tgctaaagtg gctctgcggc cggataaagt  2160
ttacactatt cgccgcactg ttaatataaa aaagagtgtt tatgttatcg gtcatggagc  2220
tctggtgcag gtgcagaccc cagaccgggt ggctttcaat tgcggcatgc agagtttggg  2280
ccccggggtg ataggtttga atggagttac atttcaaaat gtcaggttta ctggtgatga  2340
ttttaatggc tctgtgtttg tgactagcac ccagctaacc ctccacggtg tttacttttt  2400
taactttaac aatacatgtg tggagtcatg gggtagggtg tctctgaggg gctgcagttt  2460
tcatggttgc tggaaggcgg tggtgggaag aattaaaagt gtcatgtctg tgaagaaatg  2520
catatttgaa cgctgtgtga tagctctagc agtagagggg tacggacgga tcaggaataa  2580
cgccgcatct gagaatggat gttttctttt gctgaaaggt acggccagcg ttaagcataa  2640
tatgatttgc ggcagcggcc tgtgcccctc gcagctctta acttgcgcag atggaaactg  2700
tcacaccttg cgcaccgtgc acatagtgtc ccactcgcgc cgcacctggc caacatttga  2760
gcacaatatg ctcatgcgtt gcgccgttca cctaggtgct agacgcggcg tgtttatgcc  2820
ttatcaatgt aactttagtc atactaagat tttgctggaa actgattcct tccctcgagt  2880
atgtttcaat ggggtgtttg acatgtcaat ggaacttttt aaagtgataa gatatgatga  2940
aaccaagtct cgttgtcgct catgtgaatg cggagctaat catttgaggt tgtatcctgt  3000
aaccctgaac gtcaccgagg agctgaggac ggaccaccac atgctgtctt gcctgcgtac  3060
cgactatgaa tccagtgatg aggagtgagg tgaggggcgg agccacaaag ggtataaagg  3120
ggcatgaagg gtggacgcgg tgtttcaaaa tgagcgggac gacggacggc aatgcgtttg  3180
agggggggagt gttcagccca tatctgacat ctcgtcttcc ttcctgggca ggagtgcgtc  3240
agaatgtagt gggctccacc gtggacggac ggccggtcgc ccctgcaaat tccgccaccc  3300
tcacctatgc caccgtggga tcatcgttgg acactgccgc ggcagctgcc gcttctgctg  3360
ccgcttctac tgctcgcggc atggcggctg attttggact atataaccaa ctggccactg  3420
cagctgtggc gtctcggtct ctggttcaag aagatgccct gaatgtgatc ttgactcgcc  3480
tggagatcat gtcacgtcgc ctggacgaac tggctgcgca gatatcccaa gctaaccccg  3540
ataccgcttc agaatcttaa ataaagacaa acaaatttgt tgaaaagtaa aatggcttta  3600
tttgtttttt ttggctcggt aggctcgggt ccacctgtct cggtcgttaa ggactttgtg  3660
```

-continued

```
tatgttttcc aaaacacggt acagatgggc ttggatgttc aagtacatgg gcatgaggcc  3720
atctttgggg tggagatagg accactgaag agcgtcatgt tccggggtgg tattgtaaat  3780
cacccagtcg tagcagggtt tttgagcgtg gaactggaat atgtccttca ggagcaggct  3840
aatggccaag ggcagcccct tagtgtaggt gtttacaaag cggttgagct gggagggatg  3900
catgcggggg gagatgatat gcatcttggc ttggattttg aggttagcta tgttaccacc  3960
caggtctctg cgggggttca tgttatgaag gaccaccagc acggtgtagc cggtgcactt  4020
ggggaacttg tcatgcagtt tggaggggaa ggcgtggaag aatttagata ccccccttgtg  4080
cccccctagg ttttccatgc actcatccat aataatggca atgggacccc tggcggccgc  4140
tttagcaaac acgttttggg ggttggaaac atcatagttt tgctctagag tgagctcatc  4200
ataggccatc tttacaaagc ggggtaggag ggtgcccgac tgggggatga tagttccatc  4260
tgggcctgga gcgtagttgc cctcacagat ctgcatctcc caggccttaa tttccgaggg  4320
ggggatcatg tccacctggg gggcgataaa gaacacggtt tctggcgggg gattgatgag  4380
ctgggtggaa agcaagttac gcaatagctg ggatttgccg caaccggtgg ggccgtagat  4440
gaccccgatg acgggttgca gctggtagtt cagagaggaa cagctgccgt cggggcgcag  4500
gagggggccc acatcgttca tcatgcttct gacatgttta ttttcactca ctaagttttg  4560
caagagcctc tccccaccca gggataagag ttcttccagg ctgttgaagt gtttcagcgg  4620
tttcaggccg tcggccatgg gcatcttttc aagcgactga cgaagcaagt acagtcggtc  4680
ccagagctcg gtgacgtgct ctatggaatc tcgatccagc agacttcttg gttgcggggg  4740
ttgggccgac tttcgctgta gggcaccagc cggtgggcgt ccagggccgc gagggttctg  4800
tccttccagg gtctcagcgt tcgggtgagg gtggtctcgg tgacggtgaa gggatgagcc  4860
ccgggctggg cgcttgcgag ggtgcgcttc aggctcatcc tgctggtgct gaagcgggcg  4920
tcgtctccct gtgagtcggc cagatagcaa cgaagcatga ggtcgtagct gagggactcg  4980
gccgcgtgtc ccttggcgcg cagctttccc ttggaaacgt gctgacattt ggtgcagtgc  5040
agacacttga gggcgtagag ttttggggcc aggaagaccg actcgggcga gtaggcgtcg  5100
gctccgcact gagcgcagac ggtctcgcac tccaccagcc acgtgagctc gggtttagcg  5160
ggatcaaaaa ccaagttgcc tccatttttt ttgatgcgtt tcttaccttg cgtctccatg  5220
agtctgtgtc ccgcttccgt gacaaaaagg ctgtcggtgt ccccgtagac cgacttgagg  5280
gggcgatctt ccaaaggtgt tccgaggtct tccgcgtaca ggaactggga ccactccgag  5340
acaaaggctc gggtccaggc taacacgaag gaggcgatct gcgaggggta tctgtcgttt  5400
tcaatgaggg ggtccacctt ttccagggtg tgcagacaca ggtcgtcctc ctccgcgtcc  5460
acgaaggtga ttggcttgta agtgtaggtc acgtgacccg cacccccccca aggggtataa  5520
aagggggcgt gcccactctc cccgtcactt tcttccgcat cgctgtggac cagagccagc  5580
tgttcgggtg agtaggccct ctcaaaagcc ggcatgattt cggcgctcaa gttgtcagtt  5640
tctacaaacg aggtggattt gatattcacg tgccccgcgg cgatgctttt gatggtggag  5700
gggtccatct gatcagaaaa cacgatcttt ttattgtcaa gtttggtggc gaaagacccg  5760
tagagggcgt tggaaagcaa cttggcgatg gagcgcaggg tctgattttt ctcccgatcg  5820
gccctctcct tggcagcgat gttgagttgc acgtactcgc gagccacgca ccgccactcg  5880
gggaacacgg cggtgcgctc gtcgggcagg atgcgcacgt gccagccgcg gttgtgcagg  5940
gtgatgaggt ccacgctggt ggccacctcc ccgcggaggg gctcgttggt ccaacacaat  6000
cgcccccctt ttctggagca gaacggaggc aggggatcta gcaagttggc gggcgggggg  6060
tcggcgtcga tggtaaatat gccgggtagc agaattttat taaaataatc gatttcggtg  6120
tccgtgtctt gcaacgcgtc ttcccacttc ttcaccgcca gggccctttc gtagggattc  6180
aggggcggtc cccagggcat ggggtgggtc agggccgagg cgtacatgcc gcagatgtcg  6240
tacacgtaca ggggctccct caacaccccg atgtaagtgg ggtaacagcg ccccccgcgg  6300
atgctggctc gcacgtagtc gtacatctcg tgagagggag ccatgagccc gtctcccaag  6360
tgggtcttgt ggggtttctc ggcccggtag aggatctgcc tgaagatggc gtgggagttg  6420
gaagagatgg tggggcgttg gaagacatta aagttggctc cgggcagtcc cacggagtct  6480
tggatgaact gggcgtagga ttcccggagc ttgtccacca gggctgcggt taccagcacg  6540
tcgagagcgc agtagtccaa cgtctcgcgg accaggttgt aggccgtctc ttgtttttc  6600
tcccacagtt cgcgattgag gaggtattcc tcgcggtctt tccagtactc ttcggcggga  6660
aatccttttt cgtccgctcg gtaagaacct aacatgtaaa attcgttcac ggctttgtat  6720
ggacaacagc ctttttctac cggcagggcg tacgcttgag cggcctttct gagagaggtg  6780
tgggtgaggg cgaaggtgtc ccgcaccatc actttcaggt actgatgttt gaagtccgtg  6840
tcgtcgcagg caccctgttc ccacagcgtg aagtcggtgc gctttttctg cctgggattg  6900
gggagggcga atgtgacgtc gttaaaaagg attttcccgg agcggggcat gaagttgcga  6960
gagatcctga agggtccggg cacgtccgag cggttgttga tgacttgtgc cgccaggacg  7020
atctcgtcga agccgttgat gttgtggccc acgatgtaaa gttcgataaa gcgcggctgt  7080
cccttgaggg ccggcgcttt tttcaactcc tcgtaggtga gacagtccgg cgaggagaga  7140
cccagctccg cccgggccca gtcggagagc tgagggttag ccgcgaggaa agagctccat  7200
aggtcaaggg ctagcagagt ttgcaagcgg tcgcggaact cgcgaaactt tttccccacg  7260
gccattttct ccggcgtcac cacgtagaaa gtgcaggggc ggtcgttcca gacgtcccat  7320
cggagctcta gggccagctc gcaggcttgg cgaacgaggg tctcctcgcc cgagacgtgc  7380
atgaccagca tgaagggtac caactgtttc ccgaacgagc ccatccatgt gtaggtttct  7440
acgtcgtagg tgacaaagag ccgctgggcg cgcgcgtggg agccgatcgg gaagaagctg  7500
atctcctgcc accagttgga ggaatgggtg ttgatgtggt gaaagtagaa gtcccgccgg  7560
cgcacagagc attcgtgctg atgtttgtaa aagcgaccgc agtagtcgca gcgctgcacg  7620
ctctgtatct cctgaatgag atgcgctttt cgcccgcgca ccagaaaccg gagggggaag  7680
ttgagacggg gggcttgtgg ggcggcatcc cattcgcctt ggcggtggga gtctgcgtct  7740
gcgtcctcct tctctgggtg gacgacggtg ggacgacaca cgccccgggt gccgcaagtc  7800
cagatctccg ccacggaggg gcgcaggcgc tgcaggaggg gacgcagctg cccgctgtcc  7860
agggagtcga gggcggccgc gctgaggtcg gcgggaagcg tttgcaagtt cactttcaga  7920
agaccggtaa gagcgtgagc caggtgcaga tggtacttga tttccagggg ggtgttggaa  7980
gaggcgtcca cggcgtagag gaggccgtgt ccgcgcgggg ccaccaccgt gccccgagga  8040
ggttttatct caatcgtcga gggcgagcgc cgggggggtag aggcggctct gcgccggggg  8100
gcagcggagg cagcggcacg ttttcgtgag gatttggcag cggttgatga cgagcccgga  8160
gactgctggc gtgggcgacg acgcggcggt tgaggtcctg gatgtgccgt ctctgcgtga  8220
agaccaccgg cccccgggtc ctgaacctga aagagagttc cacagaatca atgtctgcat  8280
cgttaacggc ggcctgcctg aggatctcct gtacgtcgcc cgagttgtct tgataggcga  8340
tctcggccat gaactgctcc acttcttcct cgcggaggtc gccgtggccc gctcgctcca  8400
```

-continued

```
cggtggcggc caggtcgttg gagatgcgac gcatgagttg agagaaggcg ttgaggccgt  8460
tctcgttcca cacgcggctg tacaccacgt tgccgaagga gtcgcgcgct cgcatgacca  8520
cctgggccac gttgagttcc acgtggcggg cgaagacggc gtagtttctg aggcgctgga  8580
agaggtagtt gagcgtggtg gcgatgtgct cgcagacgaa gaagtacatg atccagcgcc  8640
gcagggtcat ctcgttgatg tctccgatgg cttcgagacg ctccatggcc tcgtagaagt  8700
cgacggcgaa gttgaaaaat tgggagttgc gggcggccac cgtgagttct tcttgcagga  8760
ggcggatgag atcggcgacc gtgtcgcgca cctcctgctc gaaagcgccc cgaggcgcct  8820
ctgcttcttc ctccggctcc tcctcttcca ggggcacggg ttcctccggc agctctgcga  8880
cggggacggg gcggcgacgt cgtcgtctga ccggcaggcg gtccacgaag cgctcgatca  8940
tttcgccgcg ccggcgacgc atggtctcgg tgacggcgcg tccgttttcg cgaggtcgca  9000
gttcgaagac gccgccgcgc agagcgcccc cgtgcaggga gggtaagtgg ttagggccgt  9060
cgggcaggga cacggcgctg acgatgcatt ttatcaattg ctgcgtaggc actccgtgca  9120
gggatctgag aacgtcgagg tcgacgggat ccgagaactt ctctaagaaa gcgtctatcc  9180
aatcgcagtc gcaaggtaag ctgaggacag tgggtcgctg gggggcgtcc gcgggcagtt  9240
gggaggtgat gctgctgatg atgtaattaa agtaggcggt cttcaggcgg cggatggtgg  9300
cgaggaggac cacgtctttg ggcccggcct gttgaatgcg caggcgctcg gccatgcccc  9360
aggcctcgct ctgacagcga cgcaggtctt tgtagtagtc ttgcatcagt ctctccaccg  9420
gaacctctgc ttctcccctg tctgccatgc gagtcgagcc gaacccccgc aggggctgca  9480
gcaacgctag gtcggccacg acccttcgg ccagcacggc ctgttgaatc tgcgtgaggg  9540
tggtctggaa gtcgtccagg tccacgaagc ggtgataggc ccccgtgttg atggtgtagg  9600
tgcagttggc catgacggac cagttgacga cttgcatacc gggttgggtg atctccgtgt  9660
acttgaggcg cgagtaggcg cgggactcga acacgtagtc gttgcatgtg cgcaccagat  9720
actggtagcc gaccaggaag tgaggaggcg gctctcggta caggggccag ccgacggtgg  9780
cgggggcgcc gggggacagg tcgtccagca tgaggcgatg gtagtggtag atgtagcggg  9840
agagccaggt gatgccggcc gaggtggtcg cggccctggt gaattcccgg acgcggttcc  9900
agatgttgcg caggggacgg aagcgttcca tggtgggcac gctctgcccc gtgaggcggg  9960
cgcagtcctg tacgctctag atggaaaaaa gacagggcgg tcatcgactc ccttccgtag  10020
cttgggggt aaagtcgcaa gggtgcggcg gcggggaacc ccggttcgag accggccgga  10080
tccgccgctc ccgatgcgcc tggccccgca tccacgacgt ccgcgccgag acccagccgc  10140
gacgctctgc cccaatacgg aggggagtct tttggtgttt tttcgtagat gcatccggtg  10200
ctgcggcaga tgcgacctca gacgcccacc accaccgccg cggcggcagt aaacctgagc  10260
ggaggcggtg acagggaggt ggaggagctg gctttagacc tggaagaggg agaggggctg  10320
gcccggctgg gagcgccgtc cccagagaga caccctaggg ttcagctcgt gagggacgcc  10380
aggcaggctt ttgtgccgaa gcagaacctg tttagggacc gcagcggtca ggaggcggag  10440
gagatgcgcg attgcaggtt tcgggcgggt agagagctga gggcgggctt cgatcgcgag  10500
cggctcctga gggcggagga tttcgagccc gacgagcgtt ctggggtgag cccggcccgc  10560
gctcacgtct cggcggccaa cctggtgagc gcgtacgagc agacggtgaa cgaggagcgc  10620
aacttccaaa agagctttaa caatcacgtg aggaccctga tcgcgaggga ggaggtgacc  10680
atcgggctga tgcatctgtg ggacttcgtg gaggcctacg tgcagaaccc ggccagcaaa  10740
cctctgacgg cccagctgtt cctgatcgtg cagcacagcc gcgacaacga gacgttccgc  10800
gacgccatgt tgaacatcgc ggagcccgag ggtcgctggc tcttggatct gattaacatc  10860
ctgcagagca tcgtggtgca ggagaggggt ctgagtttag cggacaaggt ggcggccatt  10920
aactattcga tgcagagcct ggggaagttc tacgctcgca agatctacaa gagcccttac  10980
gtgcccatag acaaggaggt gaagatagac agcttttaca tgcgcatggc gctaaaggtg  11040
ctgacgctga gcgacgacct cggcgtgtac cgtaacgaca agatccacaa ggcggtgagc  11100
gccagccgcc ggcgggagct gagcgacagg gagctgatgc acagcctgca gagggcgctg  11160
gcgggcgccg gggacgagga gcgtgaggct tactttgaca tgggagccga tctgcagtgg  11220
cgtcccagcg cgcgcgcctt ggaggcggcg ggttatcccg acgaggagga tcgggacgat  11280
ttggaggagg caggcgagta cgaggacgaa gcctgaccgg gcaggtgttg ttttagatgc  11340
agcggccggc ggacggggcc accgcggatc ccgcactttt ggcatccatg cagagtcaac  11400
cttcgggcgt gaccgcctcc gatgactggg cggcggccat ggaccgcatc atggcgctga  11460
ccacccgcaa ccccgaggct tttaggcagc aaccccaggc caaccgtttt tcggccatct  11520
tggaagcggt ggtgccctcc cgcaccaacc ccacacacga gaaagtcctg actatcgtga  11580
acgccctggt agacagcaag gccatccgcc gcgacgaggc gggcttgatt tacaacgctc  11640
tgctggaacg ggtggcgcgc tacaacagca ctaacgttca gaccaatctg gatcgcctca  11700
ccaccgacgt gaaggaggcg ctggctcaga aggagcggtt tctgagggac agcaatctgg  11760
gctctctggt ggcactcaac gccttcctga gcacgcagcc ggccaacgtg ccccgcgggc  11820
aggaggacta cgtgagcttc atcagcgctc tgaggctgct ggtgtccgag gtgccccaga  11880
gcgaggtgta tcagtctggg ccggattact tcttccagac gtcccgacag ggcttgcaaa  11940
cggtgaacct gactcaggcc tttaaaaact tgcaaggcat gtggggcgtt aaggccccgg  12000
tgggcgatcg agccaccatc tccagtctgc tgacccccaa cactcgcctg ctgctgctct  12060
tgatcgcgcc gttcaccaac agtagcacta tcagccgtga ctcgtacctg ggtcatctca  12120
tcactttgta ccgcgaggcc atcggtcagg ctcagattga cgagcataca tatcaggaga  12180
tcactaacgt gagccgggcc ctgggtcagg aagataccgg cagcctggaa gccacgttga  12240
actttttgct aaccaaccgg aggcaaaaaa taccctccca gtttacgtta agcgccgagg  12300
aggagaggat tctgcgatac gtgcagcagt ccgtgagtct gtacttgatg cgggagggcg  12360
ccaccgcttc cacggcttta gacatgacgg ctcggaacat ggaaccgtcc ttttactccg  12420
cccaccggcc gttcattaac cgtctgatgg actacttcca tcgcgcggcc gccatgaacg  12480
gggagtattt taccaatgcc atcctgaatc cgcattggat gcccccgtcc ggcttctaca  12540
ccggcgagtt tgacctgccc gaagccgacg acggctttct ttgggacgac gtgtccgaca  12600
gcattttcac gccgggcaat cgccgattcc agaagaagga gggcggagac gagctccccc  12660
tctccagcgt ggaggcggcc tctaggggag agagtccctt tcccagtctg tcttccgcca  12720
gcagtggtcg ggtaacgcgc ccgcggttgc cgggggagag cgactacctg aacgacccct  12780
tgctgcggcc ggctaggaag aaaaatttcc ccaacaacgg ggtggaaagc ttggtggata  12840
aaatgaatcg ttggaagacc tacgcccagg agcagcggga gtgggaggac agtcagccgc  12900
gaccgctggt tccgccgcac tggcgtcgtc agagagaaga cccggacgac tccgcagacg  12960
atagtagcgt gttggacctg ggagggagcg gagccaaccc ctttgctcac ttgcaaccca  13020
aggggcgttc gagccgcctc tactaataaa aaagaagcgg aaacttacca gagccatggc  13080
cacagcgtgt gtgctttctt cctctctttc ttcctcggcg cggcagaatg agaagagcgg  13140
```

-continued

```
tgagagtcac gccggcggcg tatgagggtc cgcccccttc ttacgaaagc gtgatgggat  13200
cagcgaacgt gccggccacg ctggaggcgc cttacgttcc tcccagatac ctgggaccta  13260
cggagggcag aaacagcatc cgttactccg agctggcacc cctgtacgat accaccaagg  13320
tgtacctggt ggacaacaag tcggcggaca tcgcctccct gaattatcaa aacgatcaca  13380
gcaactttct gactaccgtg gtgcagaaca atgacttcac cccgacggag gcgggcacgc  13440
agaccattaa ctttgacgag cgttcccgct ggggcggtca gctgaaaacc atcctgcaca  13500
ccaacatgcc caacatcaac gagttcatgt ccaccaacaa gttcagggct aagctgatgg  13560
tagaaaaaag taatgcggaa actcggcagc cccgatacga gtggttcgag tttaccattc  13620
cagagggcaa ctattccgaa actatgacta tcgatctcat gaataacgcg atcgtggaca  13680
attacctgca agtggggaga cagaacgggg tgctggaaag cgatatcggc gtgaaattcg  13740
ataccagaaa cttccgactg gggtgggatc ccgtgaccaa gctggtgatg ccaggcgtgt  13800
acaccaacga ggcttttcac cccgacatcg tgctgctgcc ggggtgcggt gtggacttca  13860
ctcagagccg tttgagtaac ctgttaggaa ttagaaagcg ccgccccttc caagagggct  13920
ttcaaatcat gtatgaggac ctggagggag gtaatatacc cgccttactg gacgtgtcga  13980
agtacgaagc tagcatacaa cgcgccaaag cggagggtag agagattcgg ggagacacct  14040
ttgcggtagc tccccaggac ctggaaatag tgcctttaac taaagacagc aaagacagaa  14100
gctacaatat tataaacaac acgacggaca ccctgtatcg gagctggttt ctggcttaca  14160
actacggaga ccccgagaaa ggagtgagat catggaccat actcaccacc acggacgtga  14220
cctgtggctc gcagcaagtg tactggtccc tgccggatat gatgcaagac ccggtcacct  14280
tccgcccctc cacccaagtc agcaacttcc cggtggtggg caccgagctg ctgcccgtcc  14340
atgccaagag cttctacaac gagcaggccg tctactcgca acttattcgc cagtccaccg  14400
cgcttaccca cgtgttcaat cgctttcccg agaaccagat tctggtgcgc cctcccgctc  14460
ctaccattac caccgtcagt gaaaacgttc ccgccctcac agatcacgga accctgccgc  14520
tgcgcagcag tatcagtgga gttcagcgcg tgaccatcac cgacgccaga cgtcgaacct  14580
gcccctacgt ttacaaagcg cttggcgtgg tggctcctaa agttctttct agtcgcacct  14640
tctaaaaaca tgtccatcct catctctccc gataacaaca ccggctgggg actgggctcc  14700
ggcaagatgt acggcggagc caaaaggcgc tccagtcagc acccagttcg agttcggggc  14760
cacttccgcg ctccttgggg agcttacaag cgaggactct cgggtcgaac ggctgtagac  14820
gataccatag atgccgtgat tgccgacgcc cgccggtaca accccggacc ggtcgctagc  14880
gccgcctcca ccgtggattc cgtgatcgac agcgtggtag ccggcgctcg ggcctatgct  14940
cgccgcaaga ggcggctgca tcggagacgt cgccccaccg ccgccatgct ggcagccaga  15000
gccgtgctga gacgggcccg gagggtaggc aggagggcta tgcgccgcgc tgccgccaac  15060
gccgccgccg ggagggcccg ccgacaggct gcccgccagg ctgctgccgc catcgctagc  15120
atggccagac ccaggagagg gaacgtgtac tgggtgcgcg attctgtgac gggagtccga  15180
gtgccggtgc gcagccgacc tccccgaagt tagaagatcc aagctgcgaa gacggcggta  15240
ctgagtctcc ctgttgttat cagcccaaca tgagcaagcg caagtttaaa gaagaactgc  15300
tgcagacgct ggtgcctgag atctatggcc ctccggacgt gaagcctgac attaagcccc  15360
gcgatatcaa gcgtgttaaa aagcgggaaa agaaagagga actcgcggtg gtagacgatg  15420
gcggagtgga atttattagg agtttcgccc cgcggcgcag ggttcaatgg aaagggcgac  15480
gggtacaacg cgttttgagg ccgggcaccg cggtagtttt taccccggga gagcggtcgg  15540
ccgttagggg ttttaaaagg cagtacgacg aggtgtacgg cgacgaggac atattggaac  15600
aggcggctca acagatcgga gaatttgcct atggaaagcg ctcgcgtcgc gaagacctgg  15660
ccatcgcctt agacagcggc aaccccacgc ccagcctcaa acccgtgacg ctgcagcagg  15720
tgcttcccgt gagcgccagc acggacagca agaggggaat aaaaagagaa atggaagatc  15780
tgcagcctac catccagctc atggttccta aacggcagag gctggaagag gtcctggaga  15840
agatgaaagt ggaccccagc atagagccgg acgttaaagt caggccgatc aaagaagtgg  15900
cccctggact cggggtgcag acggtggata tccagatccc cgtcacgtca gcttcgaccg  15960
ccgtggaagc catggaaacg caaaccgaaa cccccgccgt ggttggtacc aaagaagtgg  16020
cgttgcaaac cgacccctgg tacgaatttg ccgcccccccg gcgtcagagg cgacccgctc  16080
gttacggccc cgccaacgcc atcatgccag aatatgcgct gcatccgtct atcctgccca  16140
ccccccggcta ccggggagtg acgtatcgcc cgtcaggaac ccgccgccga acccgtcgcc  16200
gccgccgctc ccgtcgcgct ctggcccccg tgtcggtgcg ccgcgtaaca cgccggggaa  16260
agacagtcac cattcccaac ccgcgctacc accctagcat cctttaatga ctctgccgtt  16320
ttgcagatgg ctctgacttg ccgcgtgcgc cttcccgttc cgcactatcg aggaagatct  16380
cgtcgtagga gaggcatggc gggcagtggt cgccggcggg ctttgcgcag gcgcatgaaa  16440
ggcggaattt tacccgcttt gatacccata atcgccgccg ccatcggtgc catacccggc  16500
gtcgcttcag tggccttgca agcagctcgt aataaataaa cgaaggcttt tgcacttatg  16560
tcctggtcct gactatttta tgcagaaaga gcatggaaga catcaatttt acgtcgctgg  16620
ctccgcggca cggctcgcgg ccgctcatgg gcacctggaa cgacatcggc accagtcagc  16680
tcaacggggg cgctttcaat tgggggagcc tttggagcgg cattaaaaac tttggctcca  16740
cgattaaatc ctacggcagc aaagcctgga acagtagtgc tggtcagatg ctccgagata  16800
aactgaagga caccaacttc caagaaaaag tggtcaatgg ggtggtgacc ggcatccacg  16860
gtgcggtaga tctcgccaac caagcggtgc agaaagagat tgacaggcgt ttggaaaact  16920
cgcgggtgcc gccgcagagg ggggatgagg tggaggtcga ggaagtagaa gtagaggaaa  16980
agctgccccc gctggagaaa gttcccggtg cacctccgag gccgcagaag cggcccaggc  17040
cagaactaga agaaactctg gtgacggaga gcaaggagcc tccctcgtac gagcaagcct  17100
tgaaagaggg cgcctctcca ccctcctacc cgatgactaa gccgatcgca cccatggctc  17160
gaccggtgta cggcaaggat tacaagcccg tcacgctaga gctgccccca ccgccccctt  17220
cgcgtccgac ggtgcctccg ctgcctgccc cgtcggcggg tcccgagtct gcaccatccg  17280
ctgtgcctct gccagccgcc cgtcccgtgg ccgtggccac tgccaggaac cccagaggcc  17340
agagaggagc caactggcaa agcacgctga acagcatcgt gggcctgggg gtgaaaagcc  17400
tgaaacgccg ccgttgctat tattaaaaag tgtagctaaa aaatttcccg ttgtatacgc  17460
ctcctatgtt accgccagag acgcgtgact gtcgccgcga gcgccgcttc caagatggcc  17520
accccatcga tgatgccgca gtggtcttac atgcacatcg ccggccagga cgcctcggag  17580
tacctgagtc ccggcctcgt gcagtttgcc cgcgccaccg acacctactt cagcttggga  17640
aacaagttta gaaaccccac cgtggccccc acccacgatg tgaccacgga ccgctcgcag  17700
aggctgaccc tgcgctttgt gcccgtagac cgggaggaca ccgcgtactc ttacaaagtg  17760
cgctacacgc tggccgtagg ggacaaccga gtgctggaca tggccagcac ctactttgac  17820
atccgggggg tgctggatcg gggtcccagc ttcaagccct actccggcac cgcttacaac  17880
```

-continued

```
tccctggctc ccaagggcgc ccccaatcct gcagaatggg ccgataccaa cgacagcaac  17940
aaactgaaag tgaggggtca ggcgcctttt gtcagtactt acggttctgc tacggcgctt  18000
acaaaagatg ggatacaggt gggagtggat acttccgaag catctcaggc tgtttatgcc  18060
gacagaagtt accagccaga accccaaatt ggagagacag agtggaacag cgaagtgggt  18120
aatgacgaca gagtggcggg aagggtgcta aagaaaacaa ctcccatgtt cccttgttac  18180
ggttcatatg ccaagcccac caacgaaaaa ggcggacaag caatacagcc caccgccggc  18240
aacggcgata atcaggctgt agagttacaa ttctttgcca ctactagcac tcccactgcg  18300
ccaaaggcag tattgtacgc ggaggacgtg gccattgaag ctccagatac tcacttagtg  18360
tttaagccaa cagtagtcgc gggaactaca agttcggaag ctctgctaac ccaacaagcc  18420
gcacctaacc gcccaaacta cattgccttt agagataact ttattggtct catgtactac  18480
aattcaaccg ggaatatggg agtactggcc ggacaagcat ctcagctcaa tgcagtggtt  18540
gatcttcagg acagaaacac cgaactgtca tatcagctaa tgctggatgc tctgggagat  18600
cgcagtcggt acttttctat gtggaatcaa gctgtagata gctatgatcc agatgtaaga  18660
attgtagaaa accacggtgt ggaagacgaa ctgcctaatt attgcttccc actaggcggg  18720
atggtagtaa cggacactta caaagccata aaggtaaatg gaagcggatg gacggctaat  18780
actgacgttt tcagcgagag agtagaaata ggctcaggta acctgtttgc catggaaatt  18840
aacttgcaag ctaatctgtg gcgcagtttc ttgtattcca acataggact gtacctcccg  18900
gactctttaa aattaacccc tgacaacatc acgctccctg agaacaaaaa tacctaccag  18960
tatatgaacg gtcgcgtaac accacccggg ctcgtggaca cctacgttaa cgtgggtgcg  19020
cgctggtccc ccgatgttat ggacagcatt aaccctttta accaccaccg caacgccggg  19080
ctccgctacc gttccatgct cctgggaaac ggacgctacg taccccttcca cattcaggtg  19140
ccccagaaat tctttgcaat taaaaacctg ctgctgctcc ccggttccta tacctacgag  19200
tggaatttcc gcaaggacgt gaacatgatt ttgcaaagct cgctgggtaa cgacctgcga  19260
gttgacgggg ccagcatacg cttcgacagc atcaacctgt atgctaactt tttccccatg  19320
gcccacaaca cggcctccac cctggaagcc atgctgcgca acgacaccaa tgaccagtcc  19380
ttcaacgact acctgtgcgc ggccaacatg ctgtatccca tccccgccaa cgccaccagc  19440
gtgcccatct ccatcccgtc tcgcaactgg gccgccttta ggggttggag tttcacccgc  19500
ctcaaaacca aggaaacccc ctcgctgggc tctggcttcg acccctactt cgtctactca  19560
ggctccattc cctacctgga cggcactttc tatcttaacc acactttcaa aaaggtgtct  19620
atcatgttcg attcctcggt cagctggccc ggcaacgacc gcctgctgac gcccaacgag  19680
ttcgaaatca agcgttcggt ggacggtgaa gggtacaacg tggcccagag caacatgacc  19740
aaggactggt tcctggttca aatgctcagc cattacaaca tcggttacca gggcttctat  19800
gtgcccgaga actacaagga ccgcatgtac tccttcttta ggaacttcca acccatgagt  19860
cgccaagtcg tggactcagt ggcttacagg gactactacc aggacgttaa gctcccctac  19920
cagcacaaca actcagggtt cgtgggctac atgggtccca ccatgcgaga ggggcaggcc  19980
tacccggcca actatcctta tcccctaatc ggagagactg ctgtacccag cctgacgcag  20040
aaaaagttcc tctgcgaccg ggtgatgtgg aggataccct tctctagcaa cttcatgtct  20100
atgggctccc tcaccgacct ggggcagaac atgctgtacg ccaactccgc tcacgccttg  20160
gacatgacct ttgaggtgga tcccatggat gagcccacgc ttctctatgt tctgtttgaa  20220
gtcttcgacg tggtgcgcat ccaccagccg caccgcggcg tcatcgaggc cgtctacctg  20280
cgcacacctt tctctgccgg taacgccacc acctaaagaa gccgatgggc tccagcgaac  20340
aggagctgca ggccattgtt cgcgacctgg gctgcgggcc ctactttttg ggcaccttcg  20400
acaagcggtt ccccggcttc atgtcccctc acaagccggc ctgtgccatc gttaacacgg  20460
ccggacggga aaccgggggg gtccactggc tcgccttcgc ctggaacccg cgtaaccgca  20520
cctgctacct gttcgaccct tttggtttct ccgacgaaag gctgaagcag atctaccagt  20580
tcgagtacga ggggctcctc cagcgcagcg ctctggcctc cacgcccgac cactgcgtca  20640
ccctggaaaa gtccacccag acggtccagg ggcccctctc ggcgcgcctgc gggctcttct  20700
gttgcatgtt tttgcacgcc ttcgtgcact ggcctcacac ccccatggat cacaacccca  20760
ccatggatct gctcaccgga gtgcccaaca gcatgcttca cagcccccag gtcgcccccca  20820
ccctgcgccg taaccaggaa cacctgtatc gctttctggg gaaacactct gcctatttcc  20880
gccgccatcg gcagcgcatc gaacaggcca cggccttcga aagcatgagc caaagagtgt  20940
aatcaataaa aaccattttt atttgacatg atacgcgctt ctggcgtttt tattaaaaat  21000
cgaagggttc gagggagggg tcctcgtgcc cgctggggag ggacacgttg cgatactgga  21060
atcgggcgct ccaacgaaac tcggggatca ccagtcgcgg caggggcacg tcttccaggt  21120
tctgcttcca aaactgtcgc accagctgca gggctcccat cacgtcgggc gccgatatct  21180
tgaagtcgca gttagggccg gagctcccgc ggctgttccg gaacacgggg ttggcacact  21240
ggaacaccat cacgctgggg ttgtgaatac tagccagggc cgtcggatcg gtcacctccg  21300
acgcatccag atcctcggcg ttgctcaggg cgaacggggt cagcttgcac atctgccgcc  21360
cgatctgggg caccaggtcg ggtttgttga ggcaatcgca gcgcagaggg atcaggatgc  21420
gtcgctgccc gcgttgcatg atagggtaac tcgccgccag gaactcctcc atctgacgga  21480
aggccatctg ggccttaacg ccctcggtga aaaacagccc acaggacttg ctagaaaata  21540
cgttattgcc gcagttaatg tcttccgcgc agcagcgtgc atcttcgttc ttcagctgaa  21600
ccacgttacg cccccagcgg ttctggacca ccttggcttt cgtaggatgc tccttcagcg  21660
cccgctgccc gttctcgctg gtcacatcca tttccaccac gtgctccttg cagaccatct  21720
ccactccgtg gaagcaaaac aggacgccct cctgccgggt attgcgatgc tcccaaacgg  21780
cacacccggt gggctcccag ctcttgtgtt ttacccccgc gtaggcttcc atgtaagcca  21840
tgaggaatct gcccatcagc tcggtgaagg tcttctgatt ggtgaaggtt agcggcaggc  21900
cgcggtgctc ctcgttcaac caagtttgac agatcttgcg gtacaccgtt ccctggtcgg  21960
gcagaaactt aaaagccgct ctgctgtcgt tgtccacgtg gaacttctcc attaacatca  22020
tcatggtttc catacccttc tcccacgctg acaccagcgg tttgctgtcg gggttcttca  22080
ccaacacggc ggtagagggg ccctcgccgg ccccgacgtc cttcatggtc attctttgaa  22140
actccacgga gccgtccgcg cgacgtactc tgcgcaccgg agggtagctg aagcccacct  22200
ccaccacggt gccttcgccc tcgctgtcgg aaacgatctc cggggatggc ggcggtgcgg  22260
gtgtcgcctt gcgagccttc ttcttgggag ggagctgagg cgcctcctgc tcgcgctcgg  22320
ggctcatctc ccgcaagtag ggggttatgg agctgcctgc ttggttctga cggttggcca  22380
ttgtatccta ggcagaaaga catggagctt atgcgcgagg aaactttaac cgccccgtcc  22440
cccgtcagcg acgaagatgt catcgtcgaa caggacccgg gctacgttac gccgcccgag  22500
gatctggagg ggcctgaccg gcgcgacgct agtgagcggc aggaaaatga gaaagaggag  22560
gcctgctacc tcctggaagg cgacgttttg ctaaagcatt tcgccaggca gagcaccata  22620
```

-continued

```
gttaaggagg ccttgcaaga ccgctccgag gtgcccttgg acgtcgccgc gctctcccag  22680
gcctacgagg cgaacctttt ctcgcctcga gtgcctccga agagacagcc caacggcacc  22740
tgcgagccca acccgcgact caacttctac cccgtgttcg ccgtaccaga ggcgctggcc  22800
acctatcaca tttttttcaa aaaccaacgc atccccctat cgtgccgggc caaccgcacc  22860
gcggccgata ggaatctcag gcttaaaaac ggagccaaca tacctgatat cacgtcgctg  22920
gaggaagtgc ccaagatttt cgagggtctg ggtcgagatg agaagcgggc ggcgaacgct  22980
ctgcagaaag aacagaaaga gagtcagaac gtgctggtgg agctggaggg ggacaacgcg  23040
cgtctggccg tcctcaaacg ctgcatagaa gtctcccact tcgcctaccc cgccctcaac  23100
ttgccaccca aagttatgaa atcggtcatg gatcagctgc tcatcaagag agctgagccc  23160
ctggatcccg accaccccga ggcggaaaac tcagaggacg gaaagcccgt cgtcagcgac  23220
gaggagctcg agcggtggct ggaaaccagg gacccccaac agttgcaaga gaggcgcaag  23280
atgatgatgg cggccgtgct ggtcaccgtg gagctggaat gcctgcaacg gtttttcagc  23340
gacgtggaga cgctacgcaa aatcggggaa tccctgcact acaccttccg ccagggctac  23400
gtccgccagg cctgcaagat ctccaacgtg gagctcagca acctggtctc ctacatgggc  23460
atcctccacg agaaccggct ggggcagagc gtgctgcact gcaccttgca aggcgaggcg  23520
cggcgggact acgtgcgaga ctgcatctac ctcttcctca ccctcacctg gcagaccgcc  23580
atgggcgtct ggcagcagtg cttggaagag agaaacctca aagagctaga caaactcctc  23640
tgccgccagc ggcgcgccct gtggtccggt ttcagcgagc gcacggtcgc cagcgctctg  23700
gcggacatca tcttcccgga gcgcctgatg aaaaccttgc aaaacggcct gccggatttc  23760
atcagtcaaa gcattttgca aaacttccgc tcttttgtcc tggaacgctc cgggatcttg  23820
cccgccatga gctgcgcgct accttctgac tttgtccccc tctcctaccg cgagtgccct  23880
cccccactgt ggagccactg ctacctcttc caactggcca actttctggc ctaccactcc  23940
gacctcatgg aagacgtaag cggagagggt ttactggagt gccactgccg ctgcaacctg  24000
tgcacccccc acagatcgct ggcctgcaac accgagctac tcagcgaaac ccaggtcata  24060
ggtaccttcg agatccaggg gccccagcag caagagggtg cttccggctt gaagctcact  24120
ccggcgctgt ggacctcggc ttacttacgc aaatttgtag ccgaggacta ccacgcccac  24180
aaaattcagt tttacgaaga ccaatctcaa ccaccgaaag ccccccctcac ggcctgcgtc  24240
atcacccaga gcaagatcct ggcccaattg caatccatca accaagcgcg ccgcgatttc  24300
cttttgaaaa agggtcgggg ggtgtatctg gacccccaga ccggcgagga actcaacccg  24360
tccacactct ccgtcgaagc agcccccccg agacatgccg cccaagggaa ccgccaagca  24420
gctgatcgct cggcagagag cgaagaagca agagctgctc cagcagcagg tggaggacga  24480
ggaagagatg tgggacagcc aggcagagga ggtgtcagag gacgaggagg agatggaaag  24540
ctgggacagc ctagacgagg aggaggacga gctttcagag gaagaggcga ccgaagaaaa  24600
accacctgca tccagcgcgc cttctctgag ccgacagccg aagccccggc ccccgacgcc  24660
cccggccggc tcactcaaag ccagccgtag gtgggacgcc accgaatctc cagcggcagc  24720
ggcaacggca gcgggtaagg ccaaacgcga gcggcggggg tattgctcct ggcgggccca  24780
caaaagcagt attgtgaact gcttgcaaca ctgcgggggga aacatctcct ttgcccgacg  24840
ctacctcctc ttccatcacg gtgtggcctt ccctcgcaac gttctctatt attaccgtca  24900
tctctacagc ccctacgaaa cgctcggaga aaaaagctaa ggcctcctcc gccgcgagga  24960
aaaactccgc cgccgctgcc gccgccaagg atccaccggc caccgaggag ctgagaaagc  25020
gcatctttcc cactctgtat gctatctttc agcaaagccg cgggcagcac cctcagcgcg  25080
aactgaaaat aaaaaaccgc tccttccgct cgctcacccg cagctgtctg taccacaaga  25140
gagaagacca gctgcagcgc accctggacg acgccgaagc actgttcagc aaatactgct  25200
cagcgtctct taaagactaa aagacccgcg ctttttcccc ctcggccgcc aaaacccacg  25260
tcatcgccag catgagcaag gagattccca ccccctacat gtggagctat cagccccaga  25320
tgggcctggc cgcgggggcc gcccaggact actccagcaa gatgaactgg ctcagcgccg  25380
gcccccacat gatctcacga gttaacggca tccgagccca ccgaaaccag attctcttag  25440
aacaggcggc aatcaccgcc acaccccggc gccaactcaa cccgcctagt tggcccgccg  25500
cccaggtgta tcaggaaaat ccccgcccga ccacagtcct cctgccacgc gacgcggagg  25560
ccgaagtcct catgactaac tctggggtac aattagcggg cgggtccagg tacgccaggt  25620
acagaggtcg ggccgctcct tactctcccg ggagtataaa gagggtgatc attcgaggcc  25680
gaggtatcca gctcaacgac gagacggtga gctcctcaac cggtctcaga cctgacggag  25740
tcttccagct cggaggagcg ggccgctctt ccttcaccac tcgccaggcc tacctgaccc  25800
tgcagagctc ttcctcgcag ccgcgctccg ggggaatcgg cactctccag ttcgtggaag  25860
agttcgttcc ctccgtctac ttcaacccct tctccggctc gcctggacgc tacccggacg  25920
ccttcattcc caactttgac gcagtgagtg aatccgtgga cggctacgac tgatgacaga  25980
tggtgcggcc gtgagagctc ggctgcgaca tctgcatcac tgccgtcagc ctcgctgcta  26040
cgctcgggag gcgatcgtct tcagctactt tgagctgccg gacgagcacc ctcagggtcc  26100
ggctcacggg ttgaaactcg agatcgagaa cgcgctcgag tctcgcctca tcgacacctt  26160
caccgcccga cctctcctgg tagaaatcga acgcgggatc actaccatca ccctgttctg  26220
catctgcccc acgcccggat tacatgaaga tctgtgctgt catctttgcg ctcagtttaa  26280
taaaaactga actttttgcc gcaccttcaa cgccacgcgt cgtttctcca aaagttgtcg  26340
acagctcttc agtcagaggt atacgagaaa ctgtttattt ttacaactct actacttttc  26400
tcacccttaa ctgctcctgc actaacgaac taattcagtg gttcgcgaac ggctcactct  26460
gccaagtctt ttttaattct gctgttcttc ctgagtttgg ctcctttgcg tgtggaaatt  26520
ctaccccctc caccttaacc attgcggcgc ccttttcgga aatccagtat ttttgtattg  26580
gggcgggagg taaaccgggt tgtattcacc gcttgtttgt aaagccattt gttgcttcaa  26640
ttcccattaa cacttcactt tcctctaata catacttacc taccttacat tctactcacc  26700
cctcctggca acctcttatt ggcctcacgg cttttatttc cgttgtttta ctaaacttta  26760
taattcttaa caaactttct taaacatgct tgccattttg cttctgctcg ttactttaac  26820
gtccgcagat taccacaatg taattgtacg agaaaacagt ttacaaaacc catcacaggt  26880
atatgttaaa gcaggctcta acttaacttt acaatccttc tattcgcctt accctgagga  26940
catgccacgt gttacttggt acttagaagt ttttgattcg ctatttgaaa ggcatacgat  27000
tcctccattt tttacaggcg ttatactttg tgacatttct ggtgacatac agcatgtgtg  27060
gaaccattgg cctttacaat ttaattgcat aaataaaagc ttacatatta ttaatctcaa  27120
accaagtgat gaaggccttt acaatgtgaa ggttttaaag gacagcattc agcataatac  27180
atactttcga gtgcatgtag taagttttcc aagacctgaa tgtaacatca ccactacata  27240
tctttcagat gactactgcc ttattaacat tgattgctct caattaccat accctgctaa  27300
ggtctattat aatggcaatg aaagtaagct gcattactac ttatctgaac gcggtggcca  27360
```

```
gccaaacctt ccaaattact ttactgttgg gtatcgatat agagatctcc gacaaaatta  27420
tacagttgaa tatccattta atgaactatg tacagagata attgctcttg aaacagggtc  27480
tgattttatg ccaattttta tagttaccct agtggtgagc attatagtta ttgtgatggg  27540
catcacatat cttatttatc actgtaggac tttaaagacc aaaaccaaaa ccaaaaccaa  27600
gcctcctgaa atccgtttgc tttaattttt tccagaatgg tagctgcttt cttcattttt  27660
ctctgtatac caatcatctg cgcctccaca acttttgccg ctgtttccca cctggaacca  27720
gactgtctac cacctttttgt tgtatacctg atactgactt ttgtggtctg tacagccatt  27780
accagcatag cctgcttttt tgtaacaatt ttccaagccg ccgattatct ctacgtacgg  27840
tttgcttatt ttagacatca ccccgagtat cggaatcaaa acgtagcttc tttactttgt  27900
ctagcatgat tcgcctattt atactgcaca ctctgtttac cctcgcaaaa tgtcattgcc  27960
cttttaccaa accttggtcc ttttacacct gttacgatgt actgcccgaa acccctattg  28020
cctggcttta cgtagccaca gcggttttag tttttgtagc aacctgcatt ggcgttaaac  28080
tgtacttcta cttaaaaatt ggatggcttc atcccccaga agatttaccc cgatatcctc  28140
ttgttaataa ctttcaacag cctctgccgc ctcctgatcc tcttccgcga gctccctccg  28200
ttgttagcta ctttcaactc accggtggag atgactgact ctcaggacat tgatattagt  28260
gtggaaagaa tagccgctca gcgtcagcga gaaactcggg tgctggagta ctttgaacta  28320
cagcagctta aagagtccca ctggtgtgag aaaggagtgc tgtgtcatgt taagcaggca  28380
gccctttctt acgatgtcag ccttcaggga catgaactgt cttacacttt gccttcgcaa  28440
aaacaaacct tctgcaccat gatgggctct acctccatca caatcaccca acaaaccgga  28500
cctgttgagg gagctatcct gtgtcactgt cacgcgcctg attgtatgcc caaactaatt  28560
agaactctct gtgccttagg tgatatattt aaaatgtaag tcagtatcaa taaacttacc  28620
ttaaatttga cagcagtttt ttggtaacat cattcagcag caccacttta ccctcttccc  28680
aactctcgta tgggacgtga tggtgggcgg caaacttcct ccaaacccta aaacaaatat  28740
taatatccac ttccttgtcc ttacccacaa ttttcatctt ttcatagatg aaaagaacca  28800
gagttgatga agacttcaac cccgtctacc cttatgactc cacatccact cctgcggtcc  28860
cctttatatc ccccccgttt gtaaacagcg atggtcttca ggaaaaccct cctggagtct  28920
taagtttacg aatagctaaa cccttgtatt ttgacatgga aaggaaacta gcgctttcac  28980
ttggaagagg attggcaatt acctccaccg gacagctaga aagcacacag agcgtgcaaa  29040
ccacccctcc attagttgtc aacaacagca acacgcttgt cctgcgttat tcctccccgt  29100
taggcttatc gggtgacaat ttaatactaa attgctccga tcctctccgc gtagtaaaca  29160
acagcctgac attcagctac ctatctccac ttcgttttga aggtggcagt cttacattca  29220
attacacatc tccccttaaa ctgttgaaca gcagccttgc gatcggaata aattccaaca  29280
aaggtctcgg caatgacagc gatgaacttt ctgtcaaact aacatcagat ctaaagttta  29340
acaacgatgg aaaaatagct tttggtatac aaagcctgtg taccaccccc acagccgcct  29400
ctaactgtac cgtttttacc aacggtgatt ctttactctg tttatgttta accaaatgtg  29460
gagctcacgt gttaggaagt gtgagtttaa ccggaatgca aggaaccata acagccatga  29520
cacagaacta cattagtatt caatttctat ttgacaacaa tggtgcgttg acttcatcac  29580
cgctcctcaa caacaacact tggggtatac ggcaaaacga cacttcgtcc gctaaccccg  29640
cctacaatgc tcttgcattt atgcctaaca gcactgtata tgtaagaggt caaagtggtg  29700
agcccagaaa taactattac acccaaacat accttagggg aaacgttaaa aagccaatta  29760
tccttaccgt tacctacaac tcggctgctt caggttattc actaactttt aaatgggatg  29820
ctgtagtaac agaaaaattt gccactccaa catcttcttt ttgctatatt acagaacaat  29880
aaattcctat taccccacca attcgttttt ttcagatgaa acgggccaga gttgatgaag  29940
acttcaaccc agtgtaccct tatgaccccc catacgctcc cgttatgccc ttcattactc  30000
cacctttttac ctcctcggat gggttgcagg aaaaaccact tggagtgtta agtttaaact  30060
acaaggatcc cattactaca caaaatggat ctctcacgtt gaaaatagga aacggcctca  30120
ctctagacaa ccagggacaa ttaacatcaa ctgctgggga agtagagcct ccgctcacta  30180
atgctaacaa caaacttgca ctagcctata gcgaaccatt agcagtaaaa agcaaccgct  30240
taactttatc acacaccgcc ccccttgtcg ttgctaataa ttctttagcg ttgcaagttt  30300
cagaacctat ttttataaat gacgatgaca agctagccct gcagacagcc gcccccccttg  30360
taactaacgc tggcaccctt cgcttacaga gcgccgcccc tttaggattg gttgaaaata  30420
ctcttagact gctgttttct aaacccttgt atttgcaaaa tgattttctt gcattaggca  30480
ttgaacgccc cctggctata gcagccgcag gtactctagc actacaactc actcctccat  30540
taaagactaa cgatgacggg ctgacactat ccacagtcga gccattaact gtaaaaaacg  30600
gaaacttagg cttgcaaata tctcgccctt tggttgttca aaacagcagc ctttcgcttg  30660
ctattacccc cccgctgcgt ctatttaaca gcgaccccgt tcttggtttg ggctttactt  30720
ttcccctagc cgtgacagac aacctactct ccttaaacat gggagacggt gttaaactaa  30780
cctataataa actaacagcc aatttgggta gggatttaca atttgaaaac ggtgccattg  30840
ccgtaacgct tactgccgaa tcacctttgc aatacactaa caaacttcaa ctgaatattg  30900
gagctggcct tcgttacaat ggagccagca gaaaactaga tgtaaacatt aaccaaaata  30960
agggcttaac ttgggacaac gatgcagtta ttcccaaatt aggatcaggt ttacaattcg  31020
accctaatgg taacatcgct gttatccctg aaaccgtaaa gccgcaaacg ttatggacaa  31080
ctgcagatcc atcgcctaac tgctcagtgt accaggactt ggacgccagg ctgtggctcg  31140
ctcttgttaa aagtggtgac atggttcatg gaagcattgc tctaaaagcc ctaaaaggaa  31200
cgttgctaaa tcctacagca agctacatct ccattgtgat atatttttac agcaacggag  31260
tcaggcgtac caactatccc acgtttgaca acgaaggcac cttagctaac agcgctacct  31320
ggggataccg agaggggcaa tctgctaaca ctaatgtaac caatgccact gaatttatgc  31380
ccagctcaac caggtacccc gtgaataaag gagacaatat tcagaatcaa tctttttcat  31440
acacctgtat caaaggagat ttcgctatgc ctgtcccgtt ccgtgtaaca tataatcatg  31500
ccctggaagg atactccctt aagttcacct ggcgcgttgt agccaaccaa gcttttgata  31560
ttccttgctg ttccttttca tacatcacag aataaaccac tttttaaaat ttttcttttt  31620
attttacacg cacagtaagg cttcctcccc ccttccattt gacagcatac accagcctct  31680
ccccccttcat ggcagtaaac tgctgcgagc cagtccggta tttgggagtt aaaatccaaa  31740
cagtctcttt ggtgatgaaa cgtcgatccg tgatggacac aaatccctgg ggcaggtttt  31800
ccagcgtttc ggtaaaaaac tgcacaccgc cctacaaaac aaacaggttc aggctctcca  31860
tgggttatct ccccgatcaa actcagacag ggtaaaggtg cggtgatgtt ccactaaacc  31920
acgcaggtgg cgctgtctga acctctcggt gcgactcctg tgaggctggt aagaagttag  31980
attgtccagt agcctcacag catggatgat cagtttacgt gtacgtctgg cgcaacagcg  32040
catctgaatc tcactgagat tccggcaaga atcgcacacc atcacaatca ggttgttcat  32100
```

```
gatcccatag ctgaacacgc tccagccaaa gctcattcgc tccaacagcg ccaccgcgtg  32160
tccgtccaac cttactttaa cataaatcag gtgtctgccg cgtacaaaca tactacccgc  32220
atacagaact tcccggggca aacccctgtt caccacctgc ctgtaccagg gaaacctcac  32280
atttatcagg gagccataga tagccatttt aaaccaatta gctaacaccg ccccaccagc  32340
tctacactga agagaaccgg gagagttaca atgacagtga ataatccatc tctcataacc  32400
cctgatggtc tgatggaaat ccagcacacc gccctacaaa acaaacaggt tcaggctctc  32460
catgggttat ctccccgatc aaactcagac agggtaaagg tgcggtgatg ttccactaaa  32520
ccacgcaggt ggcgctgtct gaacctctcg gtgcgactcc tgtgaggctg gtaagaagtt  32580
agattgtcca gtagcctcac agcatggatg atcagtttac gtgtacgtct ggcgcaacag  32640
cgcatctgaa tctcactgag attccggcaa gaatcgcaca ccatcacaat caggttgttc  32700
atgatcccat agctgaacac gctccagcca aagctcattc gctccaacag cgccaccgcg  32760
tgtccgtcca accttacttt aacataaatc aggtgtctgc cgcgtacaaa catactaccc  32820
gcatacagaa cttcccgggg caaacccctg ttcaccacct gcctgtacca gggaaacctc  32880
acatttatca gggagccata gatagccatt ttaaaccaat tagctaacac cgccccacca  32940
gctctacact gaagagaacc gggagagtta caatgacagt gaataatcca tctctcataa  33000
cccctgatgg tctgatggaa atccagatct aacgtggcac agcagataca cactctcata  33060
tacattttca tcacatggtt ttcccaggcc gttaaaatac aatcccaata cacgggccac  33120
tcctgcagta caataaagct aatacaagat ggtatactcc tcacctcact aacattgtgc  33180
atgttcatat tttcacattc taagtaccga gagttctcct ctacaacagc actgctgcgg  33240
tcctcacaag gtggtagctg gtgacgatcg taaggagcca gtctgcaacg ataccgtctg  33300
tcgcgctgca tcgtagacca gagaccgacg cacctcctgg tacttgtggt agcagaacca  33360
cgtccgctgc caacaggtat ccacgtaacg ccggtccctg cgtcgcgcgc gctctgttct  33420
caatgcaaaa tgcagccact cttgtaatcc acacagatcc ctctcggcct ccgggaggat  33480
acacacttca aacctacaaa tgtctcggta cagttccaaa cacgaagtga gggcgagttc  33540
caaccaagac aggcaggctg gtctatcccg acacactgga ggtggaggaa gacacggaag  33600
aggcatgtta ttccaagcga ttcaccaacg ggtcgaaatg aagatcccga agatgacaac  33660
ggtcgcctcc ggagccctga tggaatttaa cagccaaatc aaacattatg cgattttcca  33720
ggctatcgat cgcggcctcc aaaagagcct ggacccgcac ttccacaaac accagcaaag  33780
caaaagcgtt attatcaaac tcttcgatca tcaagctgca agactgtaca atgcccaagt  33840
aattttcatt tctccactcg cgaatgatgt cgcggcaaat agtctgaagg ttcatgccgt  33900
gcatattaaa aagctccgaa agggcgccct ctatagccat gcgtagacac accatcatga  33960
ctgcaagata tcgggctcct gagacacctg cagcagattt aacagaccca ggtcaggttg  34020
ctctccgcga tcgcgaatct ccatccgcaa ggtcatttgc aaataattaa atagatctgc  34080
gccgactaaa tctgttaact ccgcgttagg aactaaatca ggtgtggcta cgcagcacaa  34140
aagttccagg gatggcgcca aactcactag aaccgctccc gagtagcaaa actgatgaat  34200
gggagtaaca cagtgtaaaa tgttcagcca aaaatcacta agccgctcct ttaaaaagtc  34260
cagtacttct atattcagtt cgtgcaagta ctgaagcaac tgtgtgggaa tatgcacaac  34320
aaaaaaaata gggcggctca gatacatgtt gacctaaaat aaaaagaatc attaaactaa  34380
agaagcttgg cgaacggtgg gataaatgac acgttccagc agcaggcaag caaccggctg  34440
tccccgggaa ccgcggtaaa attcatccga atgattaaaa agaacaacag aaacttccca  34500
ccatgtactc ggttggatct cctgagcaca gagcaatacc cccctcacat tcatatccgc  34560
cacagaaaaa aagcgtccca gatacccagc gggaatatcc aacgacagct gcaaagacag  34620
caaaacaatc cctctgggag caatcacaaa atcctccggt gaaaaaagca catacatatt  34680
agaataaccc tgctgctggg gcaaaaaggc ccgtcgtccc agcaaatgca cataaatatg  34740
ttcatcagcc attgccccgt cttaccgcgt aaacagccac gaaaaattcg agctaaaatc  34800
cacccaacag cctatagcta tatatacact ccgcccaatg acgctaatac cgcaccaccc  34860
accgccaaag ttcacccaca cccacgaaac ccgcgaaaat ccagcgccgt cagcacttcc  34920
gcaatttcag tctcacaacg tcacttccgc gcgccttttc acattcccac acccgcccac  34980
aaaccccgcg tcaccgcccg tcaccccggc cccgcctcgc tcctccccgc tcattatcat  35040
attggcacgt ttccagaata aggtatatta ttgatgatg                         35079
```

```
SEQ ID NO: 2            moltype = DNA  length = 34391
FEATURE                 Location/Qualifiers
source                  1..34391
                        mol_type = genomic DNA
                        organism = Simian Adenovirus 4310A (sAd4310A) Wild Type
SEQUENCE: 2
catcatcaat aatatacctt attctggaaa cgtgccaata tgataatgag cggggaggag  60
cgaggcgggg ccggggtgac gtgcggtgac gcggggtgac gcggggtggc gcgagggcgg  120
ggcgggtgtg cggaggcgct tagtttttac gtatgcggaa ggaggtttta taccggaagt  180
tgggtaattt gggcgtatac ttgtaagttt tgtgtagttt ggcgcgaaaa ccgggtaatg  240
aggaagttga ggttaatatg tactttttat gactgggcgg aatttctgct gatcagcagt  300
gaactttggg cgctgacggg gaggtttcgc tacgtggcag taccacgaga aggctcaaag  360
gtcccattta ttgtactcct cagcgttttc gctgggtatt taaacgctgt cagatcatca  420
agaggccact cttgagtgcc ggcgagtaga gttttctcct ccgcgctgcc gcgatgaggc  480
tggttcccga gatgtacggt gttttctgca gcgagacggc ccggaactca gatgagctgc  540
tgaattcaga cctgctggaa atttcgaatt cgcctgtgct tttgccgccg tcacttcacg  600
acctgtttga tgtggaagtg gaccctccgg aagatcccaa cgaggacgcg gtaaatacta  660
tgtttccaga atgtctgttt gaggcggctg aggagggttc ttacagcggt gaagacggcg  720
ggcagggaga ggaagtggac ctgaagtgct acgaggaatg tctaccttct agcgattctg  780
aaacggaaca gacaggggga gatggctgtg ctgaacctgt tgtgaaaaat gaacttgtat  840
tagactgtcc tgataatcct ggtcacggtt gccgcgcctg tgattttcat agaaatgcca  900
gtggaaatcc tgagactcta tgtgctctgt gttacctgcg ccttaccagc cattgtgtat  960
acagtaagta gaaacttttt cgctttgtgc atgctggtgg gatttttaaa gtgcgttggg  1020
cttattgttg cgtaatgttt tacaggcgac gtgtctgacg cggaagggga tggagataga  1080
tcaggctctg ctggttctcc ttgcactttg ggggctgtgg ttccagatgg cattattaaa  1140
cccgtggcgg taagagtttc aggcagacgg tgtgcggtcg aaaaaattga agacttgctg  1200
caggaggaac agatgcaacc tttggacctg tccctgaaac gccctaagct gacctaagag  1260
tgtttattgt atgcaataaa aagtgttgat ctttgaactg tgtttatgtg ttgggtgtgt  1320
```

-continued

```
ctgtgggtat ataagcaggt ggatgggaag tgagagcaca gctgcttcag atggatctgc  1380
taggagacct gagggaattt ggcgtggttc ggcgcttgct ggagttggcc tctgacagaa  1440
cttccaagtt ttggaggttt tgttttggct caacgcttag caacgtgcta tatagggtca  1500
agaaggagca ggagacgcag tttgctaggc tgttggccga tactcctgga gtttttgtgg  1560
ctctggatct aggccatcac tctcttttcc aagagaaaat tatcaaaaac ttaactttta  1620
cgtctcctgg tcgcacggtt gcttccgctg cctttattac ctatattttg gatcaatgga  1680
gcaacagcgg cagtcacctg tcgtgggagt acatgctgga ttacatgtcg atggcgctgt  1740
ggagggccat gctgcggagg agggtttgca tttacttgcg ggcgcagcct ccgcggctgg  1800
accgagtgga ggaggaggac gagccggggg agaccgagaa cctgagggcc gggctggacc  1860
ctccaacgga ggactaggtg ctgaggatga tcccgaagag gggactagtg gggctaggaa  1920
gaagcaaaag actgagtctg aacctcgaaa ctttttgaat gagttgactg tgagtttgat  1980
gaatcgtcag cgtccggaga caattttctg gtctgaattg gaggaggaat tcaggagggg  2040
ggaactgaac ctgctataca agtatgggtt tgaacagttg aaaactcact ggttggagcc  2100
gtgggaggat tttgaaaccg ccttggacac ttttgctaaa gtggctctgc gaccggataa  2160
ggtttacact atccgccgca ctgttaacat aaagaagagt gtttatgtta taggccatgg  2220
agctctggtg caggtgcaaa ccgccgaccg ggtggccttt agttgcggca tgcaaaatct  2280
gggccccggg gtgataggct taaatggtgt aacatttcac aatgtaaggt ttactggtga  2340
aagttttaac ggctctgtgt ttgcaaataa cacacagctg acgctccacg gcgtttactt  2400
ttttaacttt aataacacat gtgtggagtc gtggggcagg gtgtctttga ggggctgctg  2460
ttttcacggc tgctggaagg cggtggtggg aagacttaaa agtgtaacat ctgtaaaaaa  2520
atgcgtgttt gagcgctgtg tgttggcttt aaccgtggag ggctgtggac gcattaggaa  2580
taatgcagcg tctgagaatg gatgtttcct tttgctaaaa ggcacggcta gcgttaagca  2640
taacatgata tgcggcagcg gtttgtaccc ttcgcagctg ttaacttgcg cggatggaaa  2700
ctgtcagacc ctgcgcaccg tgcacatagc gtcccaccag cgacgcgcct ggccaacatt  2760
cgagcacaat atgcttatgc gctgtgccgt tcacctgggc cctaggcgag gcgtgtttgt  2820
gccttaccag tgtaacttta gccataccaa gtttttacta gaacctgaca ccttctctcg  2880
agtgtgtttc aacggggttt ttgacatgtc aatggaactg tttaaagtga taagatatga  2940
tgaatccaag tctcgttgtc gcccatgtga atgcggagct aatcatttga ggttgtatcc  3000
tgtaactctg aacgtcaccg aggagctgag aacggaccac cacatgctgt cttgcctgcg  3060
cactgactat gaatccagcg acgaggagtg aggtgagggg cggagccaaa cgggtataaa  3120
ggggcgtgag gggtcggtgc ggtgtttcaa aatgagcggg acgacggacg gcaatgcgtt  3180
tgagggggga gtgttcagcc catatctgac atctcgtctt ccttcctggg caggagtgcg  3240
tcagaatgta gtgggatcca ccgtggacgg acgaccggtg gctcctgcaa attccgccac  3300
cctcacctat gccaccgtgg gatcatcgtt ggacactgcc gcggcagctg ccgcttctgc  3360
tgccgcttct actgctcgcg gcatggcggc tgattttgga ctgtataacc aactggccac  3420
tgcagctgtg gcgtctcggt ccctggttca agaagatgcc ctgaatgtga ttctgactcg  3480
cctggagatc atgtcacgcc gcctggacga actggctgcg cagatatcct caactaaccc  3540
cgataccact tcagaacctt aaataaagac aaacaaattt gttgaaaagt aaaatggctt  3600
tatttgtttt tttggctcgg taggctcggg tccacctgtc ccggtcgtta aggaccttgt  3660
gtatgttttc caagacccgg tacagatggg cttggatgtt caagtacatg ggcatgaggc  3720
catctcgggg gtggagatag gaccattgca gagcgtcatg ctccggggtg gtgttgtaaa  3780
taacccagtc gtagcagggt ttctgagcgt ggaactggaa gatgtccttt aggagcaggc  3840
tgatggccaa gggcagcccc ttagtgtagg tgttaacaaa gcggttaagc tgggagggat  3900
gcatgcgggg ggagatgata tgcatcttgg cttgaatttt gaggttagct atgttaccac  3960
ctaggtccct gcggggttc atgttatgaa ggaccaccag cacggtgtag ccggtgcact  4020
tggggaactt gtcatgcagt ttggagggga aggcgtggaa gaatttagag accccccttgt  4080
ggcctcctag gttttccatg cactcatcca taatgatggc aatgggaccc ctggcggccg  4140
ctttggcaaa cacgttttgg gggttggaaa catcatagtt ttgctctaga gtgagctcat  4200
cataggccat cttaacaaag cggggtagga gggtgcccga ctgggggatg atagttccat  4260
ctgggcctgg ggcgtagttg ccctcacaaa tctgcatttc ccaggcctta atttccgagg  4320
ggggtatcat gtccacctgg ggggcgataa agaacacggt ttctggcggg ggattgatga  4380
gctgggtgga aagcaagtta cgcaacagtt gggatttgcc gcaaccggtg ggaccgtaga  4440
tgaccccgat gacgggttgc agctggtagt tgagagagga acagctgccg tcggggcgca  4500
ggagggggc tacatcgttc atcatgcttc tgacatgttt attttcactc actaagtttt  4560
gcaagagcct ctccccaccc agggataaga gttcttccag gctgttgaag tgtttcagcg  4620
gtttcaggcc gtctgccatg ggcatctttt caagcgactg acgaagcaag tacagtcggt  4680
cccagagctc ggtgacgtgc tctatggaat ctcgatccag cagacttctt ggttgcgggg  4740
gttgggccga ctttcgctgt agggcaccag ccggtgggcg tccagggccg cgagggttct  4800
gtccttccag ggtctcagcg ttcgggtgag ggtggtctcg gtgacggtga agggatgagc  4860
cccgggctgg gcgcttgcga gggtgcgctt caggctcatc ctgctggtgc tgaagcgggc  4920
gtcgtctccc tgtgagtcgg ccagatagca acgaagcatg aggtcgtagc tgagggactc  4980
ggccgcgtgt cccttggcgc gcagctttcc cttggaaacg tgctgacatt tggtgcagtg  5040
cagacacttg agggcgtaga gtttgggggc caggaagacc gactcggacg agtaggcgtc  5100
ggctccgcac tgagcgcaga cggtctcgca ctccaccagc cacgtgagct cgggtttagc  5160
gggatcaaaa accaagttgc ctccattttt tttgatgcgt ttcttacctt gcgtctccat  5220
gagtctgtgt cccgcttccg tgacaaaaag gctgtcggtg tccccgtaga ccgacttgag  5280
ggggcgatct tccaaaggtg ttccgagatc ttccgcgtac aggaactggg accactccga  5340
gacaaaggct cgggtccagg ctaacacgaa ggaggcgatc tgcgaggggt atctgtcgtt  5400
ttcaatgagg gggtccacct tttccagggt gtgcagacac aggtcgtcct cctccgcgtc  5460
cacgaaggtg attggcttgt aagtgtaggt cacgtgaccc gcaccccccc aaggggtata  5520
aaagggggcg tgcccactct ccccgtcact ttcttccgca tcgctgtgga ccagagccag  5580
ctgttcgggt gagtaggccc tctcaaaagc cggcatgatt tcggcgctca agttgtcagt  5640
ttctacaaac gaggaggatt tgatattcac gtgccccgcg gcgatgcttt tgatggtgga  5700
ggggtccatc tgatcagaaa acacgatctt tttattgtca agtttggtgg cgaaagaccc  5760
gtagagggcg ttggaaagca acttggcgat ggagcgcagg gtctgatttt tctcccgatc  5820
ggccctctcc ttggcggcga tgttgagttg cacgtactcg cgagccacgc accgccactc  5880
ggggaacacg gcggtgcgct cgtcgggcag gatgcgcacg tgccagccgc ggttgtgcag  5940
ggtgatgagg tccacgctgg tggccacctc cccgcggagg ggctcgttgg tccaacacaa  6000
tcgcccccct tttctggagc agaacggagg caggggatct agcaagttgg cgggcggggg  6060
```

```
gtcggcgtcg atggtaaata tgccgggtag cagaatttta ttaaaataat cgatttcggt  6120
gtccgtgtct tgcaacgcgt cttcccactt cttcaccgcc agggcccttt cgtagggatt  6180
taggggcggt ccccagggca tggggtgggt cagggccgag gcgtacatgc cgcagatgtc  6240
gtacacgtac aggggctccc tcaacacccc gatgtaagtg gggtaacagc gccccccgcg  6300
gatgctggct cgcacgtagt cgtacatctc gtgagaggga gccatgagcc cgtctcccaa  6360
gtgggtcttg tggggtttct cggcccggta gaggatctgc ctgaagatgg cgtgggagtt  6420
ggaagagatg gtggggcgtt ggaagacgtt aaagttggct ccgggcagtc ccacggagtc  6480
ttggatgaat tgggcgtagg attcccggag cttgtccacc agggctgcgg ttaccagcac  6540
gtcgagagcg cagtagtcca acgtctcgcg gaccaggttg taggccgtct cttgtttttt  6600
ctcccacagt tcgcggttga ggaggtattc ctcgcggtct ttccagtact cttcggcggg  6660
aaatcctttt tcgtccgctc ggtaagaacc taacatgtaa aattcgttca cggctttgta  6720
tggacaacag cctttttcta ccggcagggc gtacgcttga gcggcctttc tgagagaggt  6780
gtgggtgagg gcgaaggtgt cccgcaccat cactttcagg tactgatgtt tgaagtccgt  6840
gtcgtcgcag gcaccctgtt cccacagcgt gaagtcggtg cgctttttct gcctgggatt  6900
ggggagggcg aaggtgacgt cgttaaagag gattttcccg gcgcggggca tgaagttgcg  6960
agagatcctg aagggtccgg gcacgtccga gcggttgttg atgacttgcg ccgccaggac  7020
gatctcatcg aagccgttga tgttgtggcc cacgatgtaa agttcgataa agcgcggctg  7080
tcccttgagg gccggcgctt ttttcaactc ctcgtaggtg agacagtccg gcgaggacag  7140
acccagctca gcccgggccc agtcggagag ttgaggatta gccgcgagga aggaactcca  7200
tagatccaag gccaggagag tttgcaagcg gtcgcggaac tcgcggaact ttttgcccac  7260
ggccattttc tccggcgtta ccacgtaaaa ggtgtcgggg cggttgttcc agacgtccca  7320
tcggagctct agggccagct cgcaggcttg gcgaacgagg gtctcctcgc ccgagacgtg  7380
catgaccagc atgaagggta ccaactgttt cccgaacgag cccatccatg tgtaggtttc  7440
tacgtcgtag gtgacaaaga gccgctgggt gcgcgcgtgg gagccgatcg ggaagaagct  7500
gatctcctgc caccagctgg aggaatgggt gttgatgtgg tgaaagtaga agtcccgccg  7560
gcgcacagag cattcgtgct gatgtttgta aaagcgaccg cagtagtcgc agcgttgcac  7620
gctctgtatc tcctgaatga gatgcgcttt tcgcccgcgc accagaaacc ggagggggaa  7680
gttgagactg gggcttggtg gggcggcatc cccttcgcct tggcggtggg agtctgcgtc  7740
tgcgcccttc ttctctgggt ggacgacggt ggggacgacg acgccccggg tgccgcaagt  7800
ccagatctcc gccacggagg ggcgcaggcg ctgcaggagg gggcgcagct gcccgctgtc  7860
cagggagtcg agggcggccg cgctgaggtc gacgggaagc gtttgcaagt tcactttcag  7920
aagaccggta agagcgtgag ccaggtgcag atggtacttg atttccaggg gggtgttgga  7980
agaggcgtcc acggcgtaga ggaggccgtg tccgcgcggg gtcaccaccg tgccccgagg  8040
aggttttatc tcactcgtcg agggcgagcg ccgggtggta gaggcggctc tgcgccgggg  8100
ggcagcggag gcagaggcac gttttcgtga ggattcggca gcggttgatg acgagcccgg  8160
agactgctgg cgtgggcgac gacgcggcgg ttgaggtcct ggatgtgctg tctctgcgtg  8220
aagaccaccg gtccccgggt cctgaacctg aaagagagtt ccacagaatc aatgtctgca  8280
tcgttaacgg cggcctgcct gaggatctcc tgtacgtcgc ccgagttgtc ttgataggcg  8340
atctcggcca tgaactgctc cacttcttcc tcgcggaggt cgccgtggcc cgctcgctcc  8400
acggtggcgg ccaggtcgtt ggagatgcga cgcatgagtt gagagaaggc gttgaggccg  8460
ttctcgttcc acacgcggct gtacaccacg tttccgaagg agtcgcgcgc tcgcatgacc  8520
acctgggcca cgttgagttc cacgtggcgg gcgaagacgg cgtagtttct gaggcgctgg  8580
aagaggtagt tgagcgtggt ggcgatgtgc tcgcagacga agaagtacat gatccagcgc  8640
cgcagggtca tctcgttgat gtctccgatg gcttcgagac gctccatggc ctcgtagaag  8700
tcgacggcga agttgaaaaa ttgggagttg cgggcggcca ccgtgagttc ttcttgcagg  8760
aggcggatga gatcggcgac cgtgtcgcgc acctcctgct cgaaagcgcc ccgaggcgcc  8820
tctgcttctt cctccggctc ctcctcttcc aggggcacgg gttcctccgg cagctctgcg  8880
acggggacgg ggcggcgacg tcgtcgtctg accggcaggc ggtccacgaa gcgctcgatc  8940
atttcgccgc gccggcgacg catggtctcg gtgacggcgc gtccgttttc gcgaggtcgc  9000
agttcgaaga cgccgccgcg cagagcgccc ccgtgcaggg agggtaagtg gttagggccg  9060
tcgggcaggg acacggcgct gacgatgcat tttatcaatt gctgcgtagg cactccgtgc  9120
agggatctga gaacgtcgag gtcgacggga tccgagaact tctctaggaa agcgtctatc  9180
caatcgcaat cgcaaggtaa gctgaggacg gtgggccgct gggggggctc cgcgggcagt  9240
tgggaggtga tgctgctgat gatgtaatta aagtaggcgg tcttcaggcg gcggatggtg  9300
gcgaggagga ccacgtcttt gggcccggcc tgttgaatgc gcaggcgctc ggccatgccc  9360
caggcctcgc tctgacagcg acgcaggtct ttgtagtagt cttgcatcag tctctccacc  9420
ggaacctctg cttctcccct gtctgccatg cgagtcgagc cgaagccccg caggggctgc  9480
agcaacgcta ggtcggccac gaccctctcg gccagcacgg cctgttgaat ctgcgtgagg  9540
gtggtctgga agtcgtccag gtccacgaag cggtgatagg cccccgtgtt gatggtgtag  9600
gtgcagttgg ccataacgga ccagttgacg acttgcatgc cgggttgggt gatctccgtg  9660
tacttgaggc gcgagtaggc gcgggactcg aacacgtagt cgttgcatgt gcgcaccaga  9720
tactggtagc cgaccaggaa gtgaggaggc ggttctcggt acaggggcca gccgacggtg  9780
gcgggggcgc cgggggacag gtcgtccagc atgaggcggt ggtagtggta gatgtagcgg  9840
gagagccagg tgatgccggc cgaggtggtc gcggccctgg tgaattcgcg gacgcggttc  9900
cagatgttgc gcagggggcg aaagcgctcc atggtgggca cgctctgccc cgtgaggcgg  9960
gcgcaatctt gtacgctcta gatggaaaaa agacagggcg gtcatcgact cccttccgta  10020
gctcgggggg taaagtcgca agggtgcggc ggcggggaac cccggttcga gaccggccgg  10080
atccgccgct cccgatgcgc ctggccccgc atccacgacg tccgcgccga gacccagccg  10140
cgacgctccg ccccaatacg gaggggagtc ttttggtgtt ttttcgtaga tgcatccggt  10200
gctgcggcag atgcgacctc agacgcccac caccaccgcc gcggcggcag taaacctgag  10260
cggaggcggt gacagggagg aggaggagct ggctttagac ctggaagagg gagaggggtt  10320
ggcccggctg ggagcgccgt ccccagagag acaccctagg gttcagctcg tgagggacgc  10380
caggcaggct tttgtgccga agcagaacct gtttagggac cgcagcggtc aggaggcgga  10440
ggagatgcgc gattgcaggt ttcgcgcggg cagagagctg agggcgggct tcgatcgcga  10500
gcggctcctg agggcggagg atttcgagcc cgacgagcgt tctggggtga gcccggcccg  10560
cgctcacgtc tcggcggcca acctggtgag cgcgtacgag cagacggtga acgaggagcg  10620
caacttccaa aagagcttta acaatcacgt gaggaccctg atcgcgaggg aggaggtgac  10680
catcgggctg atgcatctgt gggacttcgt ggaggcctac gtgcagaacc cggccagcaa  10740
acctctgacg gcccagctgt tcctgatcgt gcagcacagc cgcgacaacg agacgttccg  10800
```

```
cgacgccatg ttgaacatcg cggagcccga gggtcgctgg ctcttggatc tgattaacat  10860
cctgcagagc atcgtggtgc aggagagggg gctgagttta gcggacaagg tggcggccat  10920
taactattcg atgcagagcc tggggaagtt ctacgctcgc aagatctaca agagccctta  10980
cgtgcccata gacaaggagg tgaagataga cagcttttac atgcgcatgg cgctgaaggt  11040
gctgacgctg agcgacgatc tcggcgtgta ccgtaacgac aagatccaca aggcggtgag  11100
cgccagccgc cggcgggagc tgagcgacag ggagctgatg cacagcctgc agagggcgct  11160
ggcgggcgcc ggggacgagg agcgcgaggc ttacttcgac atgggagccg atctgcagtg  11220
gcgtcccagc gcgcgcgcct tggaggcggc gggctacccc gacgaggagg accgggatga  11280
tttggaggag gcaggcgagt acgaggacga agcctgaccg ggcaggtgtt gttttagatg  11340
cagcggccgg cggacggggc caccgcggat cccgcacttt tggcatccat gcagagtcaa  11400
ccttcgggcg tgaccgcctc cgatgactgg gcggcggcca tggaccgcat catggcgctg  11460
accacccgca accccgaggc ttttaggcag caaccccagg ccaaccgttt ttcggccata  11520
ttggaagcgg tggtaccgtc gcgcaccaac cccacacacg agaaagtcct gactatcgtg  11580
aacgccctgg tagacagcaa agctatccgc cgcgacgagg cggggctgat ctacaacgct  11640
ctgttggaac gggtggcgcg ctacaacagc actaacttgc agaccaatct ggatcgcctc  11700
accacggacg tgaaggaggc gctggctcag aaggagcggt ttctgaggga tagcaatctg  11760
ggttctctgg tggcactgaa cgcctttctg agcacgcagc cggccaacgt gccccgcggg  11820
caggaggatt acgtgagctt catcagcgct ctgagactgc tggtgtccga ggtgccccag  11880
agcgaggtgt accagtctgg gccggattac ttttttcaga cgtcccgaca gggcttgcaa  11940
acggtgaacc tgactcaggc ctttaaaaac ttgcaaggta tgtggggcgt caaggccccg  12000
gtgggcgatc gcgccactat ctccagtctg ctgacccccca acactcgcct gctgctgctc  12060
ttgatcgcac cgttcaccaa cagtagcact atcagccgtg actcgtacct gggtcatctc  12120
atcactctgt accgcgaggc catcggccag gctcagatcg acgagcatac gtatcaggag  12180
atcactaacg tgagccgggc cctgggtcag gaagataccg gcagcctgga agccacgttg  12240
aactttttgc taaccaaccg gaggcaaaaa ataccctccc agttcacgtt aagcgccgag  12300
gaggagagga ttctgcgata cgtgcagcag tccgtgagcc tgtacttgat gcgcgagggc  12360
gccaccgctt ccacggcttt agacatgacg gctcggaaca tggaaccgtc cttttactcc  12420
gcccaccggc cgttcattaa ccgtctgatg gactacttcc atcgtgcggc cgccatgaac  12480
ggggagtact tcaccaatgc catcctgaat ccgcattgga tgcccccgtc cggcttctac  12540
accggggagt ttgacctgcc cgaagccgac gacggctttc tgtgggacga cgtgtccgat  12600
agcattttca cgccggggaa tcgccgattc cagaagaagg agggcggaga cgagctcccc  12660
ctctccagcg tggaggctgc ctctagggga gagagcccct ttcccagtct gtcttccgcc  12720
agtagcggtc gggtaacgcg cccgcggttg ccgggggaga gcgactacct gaacgacccc  12780
ttgctgcgac cggctagaaa gaaaaatttc cccaacaacg gggtggaaag cttggtggat  12840
aaaatgaatc gttggaagac ctacgcccag gagcagcggg agtgggagga cagtcagccg  12900
cgaccgctgg ttccgccgca ctggcgtcgc cagagagaag acccggacga ctccgcagac  12960
gatagtagcg tgttggacct gggagggagc ggagccaacc cctttgctca cttgcaaccc  13020
aaggggcgtt cgagtcgcct ctactaataa aaaagacgcg gaaacttacc agagccatgg  13080
ccacagcgtg tgtcctttct tcctctcttt cttcctcggc gcggcagaat gagaagagcg  13140
gtgagagtca cgccggcggc gtatgagggt ccgccccctt cttacgaaag cgtgatggga  13200
tcagcgaacg tgccggccac gctggaggcg ccttacgttc ctcccagata cctgggacct  13260
accgagggca gaaacagcat ccgttactcc gagctggcgc ccctgtacga taccaccaag  13320
gtgtacctgg tggacaacaa gtcggcggac atcgcctccc tgaattacca aaacgaccac  13380
agcaactttc tgaccaccgt ggtgcagaac aatgacttca ccccgacgga ggcgggcacg  13440
cagaccatta actttgacga gcgttcccgc tggggcggtc agctgaaaac catcctgcac  13500
accaacatgc ccaacatcaa cgagttcatg tccaccaaca agttcagggc caggctgatg  13560
gttaaaaagg tagaaaacca gcctcccgag tacgaatggt ttgagttcac catccccgag  13620
ggcaactatt ccgagactat gactatcgat ctgatgaaca atgcgatcgt ggacaattac  13680
ctgcaagtgg ggaggcagaa cggggtattg gaaagcgata tcggtgtgaa atttgatacc  13740
agaaacttcc gactggggtg ggatcccgtg accaagctgg taatgccagg cgtgtacacc  13800
aacgaggctt ttcaccccga catcgtgctg ctgccggggt gcggcgtgga tttcactcag  13860
agccgcttga gtaacctgtt aggaatcagg aagcgccgtc ccttccagga gggctttcag  13920
atcatgtatg aggacctgga gggaggtaac attcccgctc tactagatgt gacaaagtac  13980
gaacaaagtg tacagcgagc caaggcggaa gggcgagaga ttcgcggaga cacttttgcc  14040
gtgtctcccc aggatttggt tatagagccg ttagagcatg acagcaaaaa tcgtagttac  14100
aatcttttgc ccaacaaaac cgacacggcc tatcgcagct ggtttttggc ttacaactac  14160
ggagaccccg agaaaggagt gagatcatgg accatactca ccaccacgga cgtgacctgc  14220
ggctcgcagc aagtgtactg gtccctgccg gatatgatgc aagacccggt caccttccgc  14280
ccctccaccc aagtcagcaa cttcccggtg gtgggcaccg agctgctgcc cgtccatgcc  14340
aagagcttct acaacgagca ggccgtctac tcgcaactca ttcgccagtc caccgcgctt  14400
acccacgtgt tcaatcgttt tcccgagaac cagattctgg tgcgccctcc cgctcctacc  14460
attaccaccg tcagtgaaaa cgttcccgcc ctcacagatc acggaaccct accgctgcgc  14520
agcagtatca gtggagttca gcgcgtgacc atcaccgacg ccagacgtcg aacctgcccc  14580
tacgtttaca aagcgctcgg cgtggtggcc cctaaagttc tctctagtcg cacctttaa  14640
acatgtccat tctcatctct cccgataaca acaccggctg gggattgggc tccggcaaga  14700
tgtacggcgg ggctaagcga cgctccagtc agcatcccgt tcgcgttcgg ggtcacttcc  14760
gcgctccctg gggagcttac aagcgaggac tctctggccg aacggctgta gacgatacca  14820
tagatgccgt gattgccgac gcccgccggt acaaccccgg accggtcgct agcgccgcct  14880
ccaccgtgga ttccgtgatc gacagcgtgg tggccagcgc cagggcctat gctcgccgca  14940
agaggcggct gcatcggaaa cgtcgcccca ccgccgccat gctagcagcc agggccgtgc  15000
tgaggcgggc ccggagggta ggcaggaggg ctatgcgccg cgctgccgcc aacgccgccg  15060
ggagggcccg cagacaagcc gcccgccagg ccgccgctgc catcgctagc atggccagac  15120
ccaggagagg gaacgtgtac tgggtgcgcg attctgtaac gggagtccga gtgccggtgc  15180
gcagccgacc tccccgaagt tagaagatcc aagctgcgaa gacggcggta ctgagtctcc  15240
ctgttgttat tagcccaaca tgagcaagcg caagtttaaa gaagaactgc tgcagacgct  15300
ggtgcctgag atctatggcc ctccggacgt gaagcctgac attaagcccc gcgatatcaa  15360
gcgtgttaaa aagcgggaaa aaaaagagga acttgcggcg gtagacgatg gcggtgtaga  15420
atttattagg agtttcgccc cacggcgcag ggttcaatgg aaagggcggc gtgtacaacg  15480
cgttctgagg ccgggcaccg cggtagtttt taccccggga gagcggtcgg ccgttagggg  15540
```

-continued

```
tttcaagcgg cagtacgatg aggtgtacgg cgacgaagac atactggaac aggcggctca  15600
gcagattgga gaattcgctt atggcaaacg ttctcggcgc gaagacctgg ccatcgcctt  15660
ggacagcggc aatcccacac ccagcctcaa acccgtgacg ctgcaacagg tgcttcccgt  15720
gagcgccagt actgacagca aaagggggat taaaagagag atggaagagc tgcaacccac  15780
catccaactt atggtcccta aacgacagag gttggaagag gtcctggaga agatgaaagt  15840
ggaccccagc atagagccgg atgtgaaagt gaggcctatt aaggaagtgg cccccggtct  15900
tggggtgcaa acggtggaca ttcaaatccc cgtcacgtcc gcttcaacag cggtggaagc  15960
catggaaacg caaacggaag cccccgccgt cacggtcggt accagggaag tggcgttgca  16020
aacggaaccc tggtacgaat acgccacccc taggcgtcag aggcggtccg cccgttacgg  16080
acccgtcaac gccatcatgc ccgagtacgc gctacatccg tctatccggc ccactcccgg  16140
ctaccgggga gtgacgtatc gcccgtcagg aactcgccgc cgttaccgtc gccgccgtcg  16200
ctctcgccgc gctctggccc cagtgtcggt gcggcgcgtg acccgccagg ggaaaacagt  16260
caccatcccc aacccgcgct accaccctag cattctttaa tgactctgcc gttttgcaga  16320
tggctctgac ttgccgcgtg cgccttcccg ttctgcacta tcgaggaaga tctcgtcgta  16380
ggagaggcat ggcgggcagt ggtcgccggc gggctttgcg caggcgcatg aaaggcggaa  16440
ttttacccgc cctaatacct ataatcgccg ccgccatagg cgccataccc ggcgtcgctt  16500
cagtggcctt gcaagcagct cgtaataaat aaacgaaggc ttttgcactt atgtcctggt  16560
cctgactatt ttatgcagaa aaagcatgga agacatcaat tttacgtcgc tggctccgcg  16620
gcaaggctcg cggccgctca tgggcacctg gaacgacatc ggcaccagtc agctcaacgg  16680
gggcgctttc aattgggggga gcctttggag cggcattaaa aactttggct ccacgattaa  16740
atcctacggc agcaaagcct ggaacagtag tgctggtcaa atgctccgag ataaactgaa  16800
ggacaccaac ttccaagaga aagtggtcaa cggggtggtg accggcatac acggcgcggt  16860
agatcttgcc aaccaagcgg tgcagaaaga gattgacagg cgattggaaa actcgcgggt  16920
gccgccgcag agaggggatg aggtggaggt cgaggaagta gaagtagagg aaaagctgcc  16980
ccccttggag aaagttcccg gtgcgattcc aaggccgcag aagcggccaa ggccagaact  17040
agaagaaact ctggtgacgg agagcaagga gcctccctcg tacgagcaag ccttaaaaga  17100
gggcgcttca ccctacccga tgaccaaacc gatcgcgcct atggctcggc cggtgtacgg  17160
gaaggactac aaacctgtca cgctagaact tcctccgcca ctcccttcgc gtcctacggt  17220
gcctcccatg ccagcgccgt cggccggtcc cgtgtctgca ccttccgcag cgcctctgcc  17280
agccgcccgc ccagtggccg tggccactgc cagaaacccc agaggccaga gaggagccaa  17340
ctggcaaaac acgctgaaca gcatcgtggg cctgggagtt aaaagcctga aacgccgccg  17400
ttgctattat taaaaaagtg tagctaaaaa atctcccgtt gtatacgcct cctatgttac  17460
cgccagagac gtgtgactgt cgtcgcgagc agcgctttca agatggccac cccatcgatg  17520
atgccgcagt ggtcttacat gcacatcgcc gggcaggacg cctcggagta tctgagcccc  17580
ggtcttgtgc agtttgcccg cgccaccgac acctacttca gcttgggaaa caagtttaga  17640
aatcccaccg tggcccccac gcacgatgtg accacggatc gttcgcagag gctgactctg  17700
cgctttgtac cggtagaccg tgaggatact gcctattctt acaaagttcg gtatacgtta  17760
gccgtaggag acaacagggt gctggacatg gccagtactt actttgacat ccgcggtgtt  17820
cttgaccgcg gtccaagctt taaaccgtat accggaacgg catacaatgc cttggctcca  17880
aagggcgctc caaatgcttg ccagtggaca acgaccaacg ggggcaataa aacgaacact  17940
tttgcccaag cccctttaat aggcacggct attgacggaa ccaacggact gcagattggg  18000
caagataatg gacaagctgt ttatgctgac aaaacctttc aacccgaacc acaagtggga  18060
gaatctcagt ggaatactaa tccaaccaca aacgcagcag gacgcgtgtt aaaaacaact  18120
actcgcatgc tgccttgcta tggttctttt gcaaggccca ccaatgagaa agggggtcaa  18180
gcttcaggag acgttacctt ccaatttttc gacactgcct cggacaatgg caacaaccct  18240
aaggtggtgc tatatggaga agacgtcaac attgaatcgc ctgacacaca cttaatctac  18300
aaacccaccg ctgacaacac aaactctgaa aacctttttgg gtcaacaggc cgctccaaac  18360
agagccaatt acattgcctt tcgggacaac ttcattggac taatgtacta taattcaaca  18420
ggaaacatgg gagtgttggc agggcaggct tcccaactaa atgctgtggt agacttgcaa  18480
gacagaaaca ctgagctttc ctaccaactc atgttagatg caataggaga ccggagtcgt  18540
tacttttcaa tgtggaacca agcagtggac agctatgatc cagatgtgcg aattattgaa  18600
aatcatggcg ttgaggacga actgccaaat tactgcttcc ctcttaacgc tcaaggaatt  18660
gctaacacct ataaaggcgt taagaaaaac aacggcaatt gggcgaaaga cgacgcagta  18720
gtagaaacta acgaaattgg cataggaaat gtttttgcca tggagataaa tttaactgct  18780
aacttgtggc gaaactttct gtattccaat attgctttgt acctgccaga ctcctacaag  18840
tattcaccgg gaaacataac cttacccgaa aacaaaaaca gttacaatta cattaatggt  18900
cgagtaacag ctcctggtct ggtagacacc tttgtaaaca ttggcgcgcg atggtctccc  18960
gaccccatgg acaacgtgaa tccttttaat caccatcgca atgctggtct gcgttatcgc  19020
tccatgcttc taggcaacgg ccgctacgtg cccttccaca ttcaggtgcc tcaaaaattc  19080
tttgccatta agaacctgct tctgctgcct gggtcctaca cctacgagtg gaacttcaga  19140
aaagatgtaa acatgatctt gcagagcacg ctgggcaacg acctccgtgt cgacggggcc  19200
agcgtcagat tcgacagcat taacctctac gctaatttct tccccatggc acataacacc  19260
gcttccaccc tggaggctat gttacgcaac gacaccaacg accagtcctt taatgactac  19320
ctctgcgcgg ccaacatgct ataccccatt cctgccaatg ccaccagtgt gcccatctcc  19380
atcccctctc gcaactgggc agctttcaga gggtggagtt tcacccgcct caaaacaaaa  19440
gaaacccccct cgctgggttc cggatttgat ccatactttg tttactcagg ctccattccc  19500
tacctggatg gtaccttcta cctgaaccac accttcaaaa aggtgtctat tatgttcgac  19560
tcttctgtga gctggcccgg caacgaccgc ctgctgaccc ctaatgagtt tgaaattaag  19620
cgctcggtgg acggagaagg atacaatgta gcccagagca acatgaccaa agactggttc  19680
ttaattcaaa tgctcagcca ctacaacatt ggttaccaag ggttttacgt gcccgaggct  19740
tacaaagaca gaatgtactc ctttttaga aacttccaac ctatgagtag acaggtagtg  19800
gatgcagatc ggtatgaaca atacaaaaaa gtcaccgttg agtatcaaca taataattct  19860
ggttttgtgg gatacatggg acccaccatg agggaagggc aggcttatcc agcgaattac  19920
ccttatcctc ttattggaga caccgccgtg cccagcctga cccagaaaaa gttcctctgt  19980
gaccgcacca tgtggagaat ccccttctct agcaacttca tgtctatggg ggccctcacc  20040
gacctggggc agaacatgct gtacgccaat tccgctcacg ccttggatat gacctttgag  20100
gtggacccca tggatgagcc cacgcttctc tatgttctgt ttgaagtctt cgacgtggtg  20160
cgcatccacc agccgcaccg cggcgtcatc gaggccgtct acctgcgcac acctttctct  20220
gccggtaacg ccaccacata agaagcaaat gggctccagc gaacaggagc tgcgggccat  20280
```

```
tattcgcgac ctgggctgcg gaccctactt tttgggcacc ttcgacaagc gtttccccgg  20340
attcatgtcc ccccagaagc cggcctgtgc catagtcaac acggccgggc gggagaccgg  20400
gggggttcac tggctcgcct tcgcctggaa cccgcgcaac cgcacctgct acctgttcga  20460
cccttttggt ttttccgacg aaaggctgaa gcaaatctac cagttcgaat acgaaggact  20520
cctcaagcgc agcgctctgg cctccacgcc cgaccactgc gtcaccctgg aaaaatccac  20580
ccaaacggtg caggggcccc tctcggccgc ctgcgggctt ttctgttgca tgtttttgca  20640
cgccttcgtg cactggcctc acaaccccat ggagcgcaac cccaccatgg atctgctcac  20700
cggagtgccc aacagcatgc ttcacagccc ccaggtcgcc cccaccctgc gccgtaacca  20760
ggaacacctg tatcgctttc tggggaaaca ctctgcctat ttccgccgcc accggcagcg  20820
catcgagcag gccacggcct ttgaaagcat gagccaaaga gtgtaatcaa taaaaaccat  20880
ttttatttaa catgatacgc gcttctggcg tttttattaa aaatcgaacg gttcgaggga  20940
ggggtcctcg tgcccgctgg gaagggacac gttgcggtac tggaaacggg cgctccaacg  21000
aaactcgggg atcaccagcc gcggcagggg cacgtcttct aggttctgct tccagaactg  21060
ccgcaccagc tgcagggctc ccatgacgtc gggcgccgag atcttgaagt cgcagttagg  21120
gccggagccc ccgcggctgt tgcggaacac ggggttggca cactggaaca ccagcacgct  21180
ggggttgtaa atactggcca gggccgttgg gtcggtcacc tccgacgcat ccagatcctc  21240
ggcattgctc agggcgaacg gagtcagctt gcacatctgc cgtccgatct ggggcaccag  21300
gtcgggtttg ttgaggcaat cgcagcgcag agggattagg atgcgacgct gcccgcgttg  21360
catgataggg taactcgccg ccaggaactc ctccatctga cggaaggcca tctgggcctt  21420
ggtaccctcg gtgaaaaata gcccacagga cttgctagaa aatacgttat tgccgcagtt  21480
gatgtcttcc gcgcagcagc gtgcatcttc gttcttcagc tgaaccacgt tacgccccca  21540
gcggttctgg accaccttgg ctttcgtagg atgctccttc aacgcccgct gaccgttctc  21600
gctggtcaca tccatttcca ccacgtgctc cttgcagacc atctccactc cgtggaagca  21660
gaacaggacg ccctcctgct gggtattgcg atgctcccaa acggcacatc cggtgggctc  21720
ccagctcttg cgtttcaccc ccgcgtatgc ttccatgtaa gccatgagga atctgcccat  21780
cagctcggtg aaggtcttct ggttggtgaa ggttagcggc aggccgcggt gctcctcgtt  21840
caaccaagtt tgacagattt tgcggtacac ggctccctgg tcgggcagaa acttaaaagc  21900
cgctctgctc tcgttgtcca cgtggaactt ctccatcaac atcgtcatga cttccatgcc  21960
cttctcccac gccgtcacca acggttcggt cccggggttc ttcaccaaca cggcggtgga  22020
ggggccctcg ccggccccga cgtccttcat ggtcattctt tggaactcca cggtgccgtc  22080
cgcgcggcgt actctgcgca tcggagggta gctgaagccc acctccacca cggtgccttc  22140
gccctcgctg tcggaaacga tctccgggga tggcggcggc gcgggtgtcg ccttgcgagc  22200
cttcttcttg ggagggagcg gaggcacctc ctgctcgcgc tcggggctca tctcccgcaa  22260
gtagggggta atggagcttc cgggttggtt ctgacggttg gccattgtat cctaggcaga  22320
aagacatgga tcttatgcgc gaggaaactt taaccgcccc gtcccccgtc agcgacgaag  22380
aggtcatcgt cgaacaggac ccgggctacg ttacgccgcc cgaggatctg gagtccccct  22440
tagacgaccg acgcgacgct agtgagcggc aggaaaatga gaaagaggag gaggagggct  22500
gctacctcct ggaaggcgac gtcttgctaa agcatttcgc caggcagagc accatactca  22560
aggaggcctt gcaagaccgc tccgaggtgc ccttggacgt cgccgcgctc tcccaggcct  22620
acgaggcgaa ccttttctcg ccccgagtgc ctccgaagag acagcccaac ggcacctgcg  22680
agcccaaccc gcgactcaac ttctaccccg tgttcgccgt gcccgaggcg ctggccacct  22740
accacatctt tttcaaaaac cagcgcattc ccctttcctg ccgggccaac cgcaccgcag  22800
ccgataggaa gctaacactc agaaacggag ccagcatacc tgatatcacg tcactggagg  22860
aagtgcctaa gatcttcgag ggtctgggtc gagatgagaa gcgggcggcg aacgctctgc  22920
agaaagaaca gaaagagagt cagaacgtgc tggtggagct ggagggggac aacgcgcgtc  22980
tggccgtcct caaacgctgc atagaagtct cccacttcgc ctaccccgcc ctcaacttgc  23040
cacccaaagt tatgaaatcg gtcatggatc agctgctcat caagagagct gagcccctgg  23100
atcccgacca ccccgaggcg gaaaactcag aggacggaaa gcccgtcgtc agcgacgagg  23160
agctcgagcg gtggctggaa accggggacc cccaacagtt gcaagagagg cgcaagatga  23220
tgatggcggc cgtgctggtc accgtggagc tggaatgcct gcaacggttt ttcagcgacg  23280
tggagacgct acgcaaaatc ggggagtccc tgcactacac cttccgccag ggctacgtcc  23340
gccaggcctg caagatctcc aacgtggagc tcagcaacct ggtctcctac atgggcatcc  23400
tccacgagaa ccggctgggg cagagcgtgc tgcactgcac cttgcaaggc gaggcgcggc  23460
gggactacgt ccgcgactgc atctacctct tcctcaccct cacctggcag accgccatgg  23520
gcgtctggca gcagtgcttg gaagagagaa acctcaaaga gctagacaaa ctcctctgcc  23580
gccagcggcg ggccctctgg accggtttca gcgagcgcac ggtcgcctgc gccctggcag  23640
acattatctt cccggagcgc ctgatgaaaa ccttgcagaa cggcctgccg gattttatca  23700
gtcaaagtat tttgcaaaac ttccgctcct tcgttctgga gcgctccggg atcttgcccg  23760
ccatgagctg cgcgctgcct tctgactttg tccccctttc ctaccgcgag tgtcctcccc  23820
ccctgtggag ccactgctac ctcttccaac tggccaactt tctggcctac cactccgacc  23880
tcatggaaga cgtgagcgga gaggggctgc tcgagtgcca ctgccgctgc aacctctgca  23940
ccccccacag atcgctggcc tgcaacaccg agctgctcag cgaaacccag gtcataggta  24000
ccttcgagat ccaggggccc cagcagcaag agggtgcttc cggcttgaag ctcactccgg  24060
cgctgtggac ctcggcttac ttacgcaaat ttgtagccga ggactaccac gcccacaaaa  24120
ttcagttcta tgaagaccaa tctcgaccac ccaaagcccc cctcacggcc tgcgtcatca  24180
ctcagagcaa aatcctggcc caattgcaat ccatcaacca agcgcgccga gatttccttt  24240
tgaaaaaggg tcgggggtg tacctagacc cccagaccgg cgaggaactc aacccgtcca  24300
cactctccgt cgaagcagcc cccccgagac atgccgccca agggaaccgc caagcagctg  24360
atcgctcggc agagagcgaa gaagcaagag ctgctccagc agcagcagca ggtggaggac  24420
gaggaagagc tgtgggacag ccaggcagag gaggtgtcag aggacgagga ggagatggaa  24480
agctgggaca gcctagacga ggaggaggac gagctttcag aggaagaggc gaccgaagaa  24540
aaaccacctg catccagcgc gccttctctg agccgacagc cgaagccccg gcccccgacg  24600
cccccggccg gctcactcaa agccagccgt aggtgggacg ccaccggatc tccagcggca  24660
gcggcaacgg cagcgggtaa ggccaaacgc gagcggcggg ggtattgctc ctggcgggcc  24720
cacaaaagca gtatcgtgaa ctgcttgcaa cactgcgggg gaaacatctc ctttgcccga  24780
cgctacctcc tcttccatca cggtgtggcc ttccctcgca acgttctcta ttattaccgt  24840
catctctaca gcccctacga aacgctcgga gaaaaaagct aaggcctcct ctgccgcgag  24900
gaaaaactcc gccgccgctg ccgccgccaa ggatccgccg gccaccgagg agctgagaaa  24960
gcgcatcttt cccactctgt atgctatctt tcagcaaagc cgcgggcagc accctcagcg  25020
```

```
cgaactgaaa ataaaaaacc gctccttccg ctcactcacc cgcagctgtc tgtaccacaa  25080
gagagaagac cagctgcagc gcaccctgga cgacgccgaa gcactgttca gcaaatactg  25140
ctcagcgtct cttaaagact aaaagacccg cgctttttcc ccctcgggcg ccaaaaccca  25200
cgtcattgcc agcatgagca aggagattcc cacccccttac atgtggagct atcagcccca  25260
gatgggcctg gccgcggggg ccgcccagga ctactccagc aagatgaact ggctcagcgc  25320
cggcccccac atgatctcac gagttaacgg catccgagcc caccgaaacc agatcctctt  25380
agaacaggcg gcaatcaccg ccacaccccg gcgccaactc aacccgccca gttggcccgc  25440
cgcccaggtg tatcaggaaa ctccccgccc gaccacagtc ctcctgccac gcgacgcgga  25500
ggccgaagtc ctcatgacta actctggggt acaattagcg ggcgggtcca ggtacgccag  25560
gtacagaggt cgggccgctc cttactctcc cgggagtata aagagggtga tcattcgagg  25620
ccgaggtatc cagctcaacg acgaggcggt gagctcctca accggtctca gacctgacgg  25680
agtcttccag ctcggaggag cgggccgctc ttccttcacc actcgccagg cctacctgac  25740
cctgcagagc tcttcctcgc agccgcgctc cgggggaatc ggcactctcc agttcgtgga  25800
agagttcgtc ccctccgtct acttcaaccc gttttccggc tcacctggac gctacccgga  25860
cgccttcatt cccaactttg acgcagtgag tgaatccgtg gacggctacg actgatgaca  25920
gatggtgcgg ccgtgagagc tcggctgcga catctgcatc actgccgcca gcctcgctgc  25980
tacgctcggg aggcgatcgt gttcagctac tttgagctgc cggacgagca ccctcagggg  26040
ccggctcacg ggttgaaact cgagatcgag aacgcgctcg agtctcgcct catcgacgcc  26100
ttcaccgccc ggcctctcct ggtagaaacc gaacgcggga tcactaccat caccctgttc  26160
tgcatctgcc ccacgcccgg attacatgaa gatctgtgtt gtcatctttg cgctcagttt  26220
aataaaaact gaactgtttg ccgcaccttc aacgccatct gtgatttcta caacaaaaag  26280
ttcttctggc aaaggtacac aaactgtatt ttattctaat tctacctcat ctattgtgct  26340
gaactgcgcc tgcactaacg aacttatcca gtggattgca aacggtagtg tgtgcaagta  26400
cttttggggg aacgagatag ttagtagaaa taacagcctt tgcaagcact gcaactcctc  26460
cacactaatc ctttatcccc catttgttac tggatggtat atgtgcgttg gctccggttt  26520
aaatcctagt tgctttcata agtggtttct acaaaaagag acccttccca acaattctgt  26580
ttctttttc accctgtcct actgctgttc tccctctggt tactctttca aacctctaat  26640
tggtatttta gctttgatac tgataatctt tattaacttt ataataatta acaacttaca  26700
gtaaacatgc ttgttatcct cctgctcgcc acatttttcg ctctctctca cgccagaaca  26760
agtattgttg gcgcaggtta caatgcaact cttcaatctg cttacatgcc agattccgac  26820
cagatacccc atattacgtg gtacttacaa acctccaaac ctaattcttc attttatgaa  26880
ggaaacaaac tctgcgatga ctccgacaac aggacgcaca catttcccca cccttcacta  26940
caattcgaat gcgtaaacaa aagcttgaag ctttacaact taaagccttc agattctggc  27000
ttgtatcatg ctgtagttga aaaaagtaat ttagaagtcc acagtgatta cattgaattg  27060
atggttgtgg acctgccacc tccaaaatgt gaggtttcct cctcttacct tgaagttcaa  27120
ggcgtggatg cctactgcct catacacatt aactgcagca actctaaata tccagctaga  27180
atttactata atggacagga aagtaatctt ttttattatt taacaacaag cgctggtaac  27240
ggtaaacagt tacctgatta ttttactgct gttgttgaat tttccaccta cagagaaacg  27300
tatgccaagc ggccttacaa tttctcatac ccgtttaacg acctttgcaa tgaaatacaa  27360
gcgctcgaaa ctggaactga ttttactcca attttcattg ctgccattgt tgtgagctta  27420
attaccatta ttgtcagcct agcattttac tgcttttgca agcccaaaaa acctaagttt  27480
gaaaaactta aactaaaacc tgtcattcaa caagtgtgat tttgttttcc agcatggtag  27540
ctgcatttct acttctcctc tgtctaccca tcattttcgt ctcttcaact ttcgccgcag  27600
tttcccacct ggaaccagag tgcctaccgc cttttgacgt gtatctgatt ctcacctttg  27660
tttgttgtat atccatttgc agtatagcct gctttttat aacaatcttt caagccgccg  27720
actatcttta cgtgcgaatt gcttacttta gacaccatcc tgaatacaga aatcaaaacg  27780
ttgcctcctt actttgtttg gcatgattaa gctattgcta atacttaatt atttacccct  27840
aatcaactgt aattgtccat tcaccaaacc ctggtcattc tacacctgtt atgataaaat  27900
ccccgacact cctgttgctt ggctttacgc agccaccgcc gctttggtat ttgtatctac  27960
ttgccttgga gtaaaattgt attttattct acacactggg tggctacatc ccagagaaga  28020
tttacctaga catcctcttg taaacgcttt tcaattacag cctctgcctc ctcctgatct  28080
tcttcctcga gctccctcta ttgtgagcta ctttcaactc accggtggag atgactgact  28140
ctcaggacat taatattagt gtggaaagaa tagctgctca gcgtcagcga gaaacgcgag  28200
tgttggaata cctggaacta caacagctta aggagtccca ctggtgtgag aaaggagtgc  28260
tgtgtcatgt taagcaggca gccctttcct acgatgtcag cgttcaggga catgaactgt  28320
cttacacttt gcctttgcag aaacaaacct tctgcaccat gatgggctct acctccatca  28380
caatcaccca acaagccggg cctgtagagg gggctatcct ctgtcactgt cacgcacctg  28440
attgcatgtc caaactaatc aaaactctct gtgctttagg tgatattttt aaaatgtaaa  28500
tcataataaa cttaccttaa atttgacaac aattttctgg tgacatcatt cagcagcacc  28560
actttaccct cttcccagct ctcgtatggg atgcgatagt gggtggcaaa cttcctccaa  28620
accctaaaag aaatattggt atccacttcc ttgtcctcac ccacaatttt catcttttca  28680
tagatgaaaa gaaccagagt tgatgaagac ttcaaccccg tctaccccta tgacaccaca  28740
accactcctg cagttccctt tatatcaccc ccctttgtaa acagcgatgg tcttcaggaa  28800
aaccccccag gtgttttaag tctgcgaata gctaaacccc tatatttcga catggagaga  28860
aaactagccc tttcacttgg aagagggttg acaattaccg ccgccggaca attagaaagt  28920
acgcagagcg tacaaaccaa cccaccgttg ataattacca acaacaacac actgacccta  28980
cgtcattctc ccccttaaa cctaactgac aatagcttag tgctaggcta ctcgagtccg  29040
ctccgcgtca cagacaacaa acttacattt aacttcacat caccactccg ttatgaaaat  29100
gaaaacctta cttttaacta tacagagcct cttaaactta taaataacag ccttgccatt  29160
gacatcaatt cctcaaaagg ccttagtagc gtcggaggct cactagctgt aaacctgagt  29220
tcagacttaa agtttgacag caacggatcc atagcttttg gcatacaaac cctgtggacc  29280
gctccgacct cgactggcaa ctgcaccgtc tacagcgagg gcgattccct acttagtctc  29340
tgtttaacca aatgcggagc tcacgtctta ggaagtgtaa gtttaaccgg tttaacagga  29400
accataaccc aaatgactga tatttctgtc accattcaat ttacatttga caacaatggt  29460
aagctactaa gctctccgct tataaacaac gcctttagta ttcgacagaa tgacagtacg  29520
gcctcaaacc ctacctacaa cgccctggcg tttatgccta acagtaccat atatgcaaga  29580
gggggaggtg gtgaaccacg aaacaactac tacgtccaaa cgtatcttag gggaaatgtt  29640
caaaaaccaa tcattcttac tgtaacctac aactcagccg ccacaggata ttccttatct  29700
tttaagtgga ctgctcttgc acgtgaaaag tttgcaaccc caacaacttc gttttgctac  29760
```

```
attacagaac aataaaaccg tgtaccccac cgtttcgttt ttttcagatg aaacgggcga  29820
gagttgatga agacttcaac ccagtgtacc cttatgaccc cccacatgct cccgttatgc  29880
ccttcattac tccacctttt acctcctcgg atgggttgca ggaaaaacca cttggagtgt  29940
taagtttaaa ctacagagat cccattacta cgcaaaatgg gtctcttaca gttaaactag  30000
gaaacggcct cactctagac aaccagggac aactaacatc aaccgctggg gaagtagaac  30060
ctccactcac taacgctaac aacaaacttg cactggtcta tagcgatcct ttagcagtaa  30120
agcgcaacag cctaacctta tcgcacaccg ctccccttgt tattgctgat aactctttag  30180
cattgcaagt ttcagagcct atttttataa atgacaagga caaactagcc ctgcaaacag  30240
ccgcgcccct tgtaactaac gctggcaccc ttcgcttaca aagcgccgcc cctttaggca  30300
ttgcagacca aaccctaaaa ctcctgttta ccaacccttt gtacttgcag aataactttc  30360
tcacgttagc cattgaacga ccccttgcca ttaccaatag tggaaagctg gctctacagc  30420
tctccccacc gctacaaaca gcagacacag gcttgacttt gcaaaccaac gtgccattaa  30480
ctgtaagcaa cgggacccta ggcttagcca taaagcgccc acttattgtt caggacaaca  30540
acttgttttt ggacttcaga gctcccctgc gtcttttcaa cagcgacccc gtactagggc  30600
ttaactttta cacccctctt gcagtgcgcg atgaggcgct cactgttaac acaggccgcg  30660
gcctcacagt gagttacgat ggtttaattt taaatcttgg taaggatctt cgctttgaca  30720
acaacaccgt ttctgtcgct cttagtgctg ctttgccttt acaatacact gatcagcttc  30780
gccttaacgt gggcgctggg ctgcgttaca atccagtgag taaaaaattg gacgtgaacc  30840
ccaatcaaaa caagggttta acctgggaaa atgactacct cattgtaaag ctaggaaatg  30900
gattaggttt tgatggcaat ggaaacatag ctgtttctcc tcaagttaca tcgcctgaca  30960
ccttatggac cactgccgat ccatccccca attgttccat ctacactgat ttagatgcca  31020
aaatgtggct ctcgttggta aaacaagggg gtgtggttca cggttctgtt gctttaaaag  31080
cattgaaagg aaccctattg agtcctacgg aaagtgccat tgttattata ctacattttg  31140
acaattatgg agtgcgaatt ctcaattatc ccactttggg cactcaaggc acgttgggaa  31200
ataatgcaac ttggggttat aggcagggag aatctgcaga cactaatgta ctcaatgcac  31260
tagcatttat gcccagttca aaaaggtacc caagagggcg tggaagcgaa gttcagaatc  31320
aaactgtggg ctacacttgt atacagggtg acctttctat gcccgtaccg taccaaatac  31380
agtacaacta tggaccaact ggctactcct ttaaatttat ttggagaact gtttcaagac  31440
aaccatttga catcccatgc tgtttttctt cttacattac ggaagaataa aacaactttt  31500
ccttttttatt ttctttttat tttacacgca cagtaaggct tcctccaccc ttccatttga  31560
cagcatacac cagcctctcc cccttcatgg cagtaaactg ctgcgagcca gtccggtatt  31620
tgggagttaa gatccaaaca gtctctttgg taatcagatg tcgatccgtg atggacacaa  31680
atccctgggg caggttctcc aacgtttcgg tgaaaaactg catgccgccc tacaaaacaa  31740
acaggttcag gctctccacg ggttatctcc ccgatcaaac tcagacaggg taaaggtgcg  31800
atgatgttcc actaaaccac gcaggtggcg ctgtctgaac ctctcggtgc gactcctgtg  31860
aggctggtaa gaagttagat tgtccagcag cctcacagca tggatcatca gtctacgagt  31920
gcgtctggcg cagcagcgca tctgaatctc actgagattc cggcaagaat cgcacaccat  31980
cacaatcagg ttgttcatga tcccatagct gaacacgctc cagccaaagc tcattcgctc  32040
caacagcgcc accgcgtgtc cgtccaacct tactttaaca taaatcaggt gtctgccgcg  32100
tacaaacatg ctacccgcat acagaacctc cggggcagt cccctgttca ccacctgcct  32160
gtaccaggga aacctcacat ttatcaggga gccatagata gccatcttaa accaattagc  32220
taacaccgcc ccaccagctc tacactgaag agaaccggga gagttacaat gacagtgaat  32280
aatccatctc tcataacccc taatggtctg atggaaatcc agatctaacg tggcacagca  32340
gatacacact ttcatataca ttttcatcac atgtttttcc caggccgtta aaatacaatc  32400
ccaatacacg ggccactcct gcagtacaat aaagctaata caagatggta tactcctcac  32460
ctcactaaca ttgtgcatgt tcatattttc acattctaag taccgagagc tctcctctac  32520
aacagcactg ccgcggtcct cacaaggtgg tagctggtga caattgtagg gagccagtct  32580
gcagcgatac cgtctgtcgc gttgcatcgt agaccaggga ccgacgcact tcctcgtact  32640
tgtagtagca gaaccacgtc cgctgccagc acgtctccaa gtaacgccgg tccctgcgtc  32700
gctcacgctc cctcctcaac gcaaagtgca accactcttg taatccacac agatccctct  32760
cggcctccgg ggcgatgcac acctcaaacc tacagatgtc tcggtacagt tccaaacacg  32820
tagtgagggc gagttccaac caagacagac agcctgatct atcccgacac actggaggtg  32880
gaggaagaca cggaagaggc atgttattcc aagcgattca ccaacgggtc gaaatgaaga  32940
tcccgaagat gacaacggtc gcctccggag ccctgatgga atttaacagc cagatcaaac  33000
attatgcgat tttccaggct atcaatcgcg gcctccaaaa gagcctggac ccgcacttcc  33060
acaaacacca gcaaagcaaa agcgttatta tcaaactctt cgatcatcaa gctgcaggac  33120
tgtacaatgc ccaagtaatt ttcatttctc cactcgcgaa tgatgtcgcg gcaaatagtc  33180
tgaaggttca tgccgtgcat attaaaaagc tccgaaaggg cgccctctat agccatgcgt  33240
agacacacca tcatgactgc aagatatcgg gctcctgaga cacctgcagc agatttaaca  33300
gacccaggtc aggttgctct ccgcgatcgc gaatctccat ccgcaaggtc atttgcaaat  33360
aattaaatag atctgcgccg actaaatctg ttaactccgc gctaggaact aaatcaggtg  33420
tggctatgca gcacaaaagt tccagggatg gcgccaaact cactagaacc gctcccgagt  33480
agcaaaactg atgaatggga gtaacacagt gtaaaatgtt cagccaaaaa tcactaagct  33540
gctcctttaa aaagtccagt acttctatat tcagtccgtg caagtactga agcaactgtg  33600
cgggaatatg cacagcaaaa aaaatagggc ggctcagata catgttgacc taaaataaaa  33660
ataaacatta aactaaagaa gcttggcgaa cggtgggata tatgacacgc tccagcagca  33720
ggcaagcaac cggctgtccc cgggaaccgc ggtaaaattc atccgaatga ttaaaaagaa  33780
caacagaaac ttcccaccat gtactcggtt ggatctcctg agcacacagc aatacccccc  33840
tcacattcat atccgccaca gaaaaaaaac gtcccagata cccagtggga atatccaacg  33900
acagctgcaa agacagcaaa ataatccctc tgggagcaag cacaaaatcc tccggtgaaa  33960
aaagaacata catattagaa taaccctgtt gctggggcaa aaaggcccga cgtcccagca  34020
aatgcacata tatgtgttga tcagccattg ccccgtctta ccgcgtataa agccacgaaa  34080
aagtcgagct aaaatccacc caacagccta tagctatata tacactccgc ccaatgacgc  34140
taacaccgta ccacccacga ccaaagttca cccacaccca caaaacccgc gaaaatccag  34200
cgccgtcagc acttccgcaa tttcagtctc acaacgtcac ttccgcgcgc ctttttcac  34260
tattcccaca cccgccctcg cgccaccccg cgtcaccccg cgtcaccgca cgtcaccccg  34320
gccccgcctc gctcctcccc gctcattatc atattggcac gtttccagaa taaggtatat  34380
tattgatgat g                                                       34391
```

```
SEQ ID NO: 3            moltype = DNA  length = 34475
FEATURE                 Location/Qualifiers
source                  1..34475
                        mol_type = genomic DNA
                        organism = Simian Adenovirus 4312 (sAd4312) Wild Type
SEQUENCE: 3
catcatcaat aatatacctt attctggaaa cgtgccaata tgataatgag tggggaggag  60
cgaggcgggg ccggggtggg gtgaggcggg gccggggtgg ggtgagggtg acgtcggggc  120
gggcggggcg gccgacgtgt gtggggaggc gcgtagtgtt tacgtatgcg gaaggaggtt  180
ttataccgga agatgggtaa tttgggcgta tacttgtaag ttttgtgtaa tttggcgcga  240
aaactgggta atgaggaagt tgaggttaat atgtactttt tatgactggg cggaatttct  300
gctgttcagc agtgaacttt gggcgctgac ggggaggttt cgctacgtgg cagtaccacg  360
agaaggctca aaggtcccat ttattgtact cctcagcgtt ttcgccgggt atttaaacgc  420
tgtcagatca tcaagaggcc actcttgagt gctggcgagt agagttttct cctccgcgct  480
gccacaatga ggctggtccc cgagatgttt ggtgtttttt gcgacgaggc ggcgcggaac  540
tcagatgacc tgctgaattc agatttgctg gaaattccca attcgcctgt ggcttcgcct  600
ccgtcacttc acgacctttt cgatgtggaa gtggatcctc cggcagatcc caacgaggac  660
gcggtaaata gtatgtttcc cgaatgtctg ttcgaggcgg ctgacgaggg tagcgacagc  720
ggtggagaga gtggacaggg tgaggaactg gacttaaaat gctacgagga atgcataccg  780
tctagcgatt ctgaaacgga acaaacaggg ggagatggct gcgctgagcc aactgagaaa  840
aatgaactta tattagactg tcctgaacat cctggtcatg gctgccgtgc ctgtgctttt  900
catagagatg ccagtggaaa tcctgaaact ctatgtgctc tgtgttacct gcgtcttacc  960
ggcaattttg tatacagtaa gtaggttttt tactttgtgt acggtaggga agtttttgta  1020
aagtgtgtta tgacttattg cttgtgtaat gttttacagg tgacgtgtct gatgtggagg  1080
agggagataa gtcagtccat actagttctc cttgcacttt gggggctgtg gttccagata  1140
atgttattaa acccgtggcg gtcagagtat caggcaggcg gtgtgcagtc gaaaaaattg  1200
aagacttgct gcaggaagag cagatgcaac ctttggacct gtccctcaaa cgccctaaga  1260
tgacctaagc ctgtttattg agtgcaataa aactgttgat ctttgaactg tgtttatgtg  1320
ttgggtgtgt ctgtggatat ataagcaggt ggatgggaag tgagagcaca tctgccttga  1380
tggatctgtt ggggaacttg cgggaatttg acgtggttcg tcgcttgctg gagttggcct  1440
ccgacaaaac ttccaggctt tggaggtttt ggtttggctc aacgcttagc agcgtagtgt  1500
acagggtcaa gaaggagcag gaggggcaat tttctaggct gttggctgat attcctggag  1560
tttttgtggc tctggattta ggccatcaca gtctttttca agagaaaatt gtcaaaagct  1620
taactttctc gtctcctggc cgcacggttg tttcagcagc ctttattacc tatattttgg  1680
atcaatggag cagcagcggc agccacctgt cgtgggatta catgctggat tacctggcaa  1740
tggccctgtg gagggccatg ctgcggagga gggtttgcat ttactcgcgg gcgcagcctc  1800
cgcggctgga tcgagtggtg gaggaggacg agccggacga gaccgagaac ctgagagccg  1860
gcctggaccc tccaatggaa gactaggtgc agaggataat cctgaagagg gaactagtgg  1920
gggtgctaga aaaaagcaaa aaaccgagac tgagcctaga aactttttga atgagctgac  1980
tgtgagtttg atgaatcgcc atcgtcccga gacaattttc tggtctgagt tggaggaaga  2040
gtttaggaag ggggatttga acctgctgta caagtatggg ttcgaacagt tgaagactca  2100
ctggttggag ccgtgggagg attttgaaac cgctctggac acttttgcta aagtggcttt  2160
gcggccggat aaagtttata ctatccgctg cactgttaat ataaggaaaa gtgtttatgt  2220
tataggccat ggagcactgg tgcaggtgga gaccgccgat cgggtggctt tcaactgcgg  2280
catgcagaat ctgggccctg gggtgatagg tgttaatggt gtcacgtttc agaacgtgag  2340
gttcgcgggt gaaagcttta gcggctccgt gtttgcaaat aacacacagc tcactctcca  2400
cggcgtttac ttttttaact ttaacaatac atgtgtggag tcgtggggca gggcgtcctt  2460
gaggggctgc acttttcacg gttgctggaa ggcggtggtg ggaagactga aaagtgtaac  2520
gtctgtgaaa aaatgcatat tcgagcggtg tgtgctagct gtaaccgtgg aagggcatgg  2580
acgcattaga aacaacgcag cgtctgagaa tgggtgtttt cttttactga aaggcacggc  2640
cagcgttaag cataacatga tctgtggcag tgggctgtac ccgtcgcagt tgttaacctg  2700
cgcggatgga aactgccaga cattgcgcac cgtgcacata gtgtctcacc cgcgtcgcca  2760
ctggccaacg tttgagcaca acttgcttat gcgttgtacg gtccatctgg ggcctagacg  2820
gggcatgttt gtgccttttc agtgtaactt tagccacact aagatcttac tagaagcaga  2880
tgccttcact cgagtgtgtt tcaatggggt gtttgacatg tcggtggaaa tttttaaagt  2940
gataagatat gatgaatcca agtctcgttg tcgcccctgt gaatgcggag ctaatcattt  3000
gaggttgtat cccgcgaccc tgaacgtaac cgaggagctg agggccgacc accacatgtt  3060
gtcctgcttg cgcaccgact atgagtccag cgacgaagag tgaggtgagg ggcggagcca  3120
caaagggtat aaagggtcag gatgggtggg cacaggtatt caaaatgagc gggacgacgg  3180
acggcaacgc gtttgagggg ggagtgttca gcccatatct gacatctcgt cttccttcct  3240
gggcaggagt gcgtcagaat gtagtgggct ccaccgtgga cggacggccg gtcgcccctg  3300
cgaattccgc cacccttacc tatgccaccg tgggatcacc gttggacact gccgcggcag  3360
ccgcagcttc tgctgccgct tctactgctc gcggtatggc ggctgacttt ggactttata  3420
accaactggc taccgcggct gtggcatctc gcactctggt tcaagaagat gccctgagcg  3480
tggttctgct tcgactggaa gatctgtctc gtcgcttgga tcagctggct gcgcagatat  3540
ccccacctaa ccccgatact actcaagaat cttaaataaa gacaaacaga tttgttgaaa  3600
ataaatggct ttatttgttt tttttggctc gataggctcg ggtccacctg tcccggtcgt  3660
taaggacttt gtgtatgctt tccaagaccc ggtacagatg ggcttggatg tttagataca  3720
tgggcatgag gccatcccgg gggtggagat aggaccattg cagagcgtca tgctccgggg  3780
tggtgttgta gatgacccag tcgtagcagg gtttttgggc gtggaactga aaaatgtcct  3840
tgagaagcag gctgatggcc aggggcagac ccttagtgta ggtgttcaca aagcggttga  3900
gctgggaggg atgcatgcgg ggagagatga tatgcatctt agcctggatt ttcaggttag  3960
ctatgttgcc ccccaggtcc cttcgagggt tcatattgtg gaggaccacc agaacggtgt  4020
agccggtaca cttgggaaac ttatcgtgca gtttggaggg gaaggcgtga aagaatttgg  4080
aaacccctttt gtgaccacct aagttttcca tgcactcgtc catgataatg gcgatgggcc  4140
ccttggcggc agctttagcg aacacgttgt gggggttgga aacatcatag ttttgctcta  4200
gagttagctc gtcataggcc atttttacga agcggggtag gagggtgcca gactgaggga  4260
cgatagttcc atctggcccc ggtgcgtaat taccctcgca gatctgcatc tcccaagctt  4320
taatttccga gggagggatc atgtccacct ggggggcgat aaagaacacg gtttctggcg  4380
```

-continued

```
ggggattaat gagctgggtg gaaagcaggt tgcgcaagag ctgagacttg ccgcaaccgg  4440
tgggaccgta gatgaccccg atgacgggct gcagctggta gttgagagag gagcagctgc  4500
cgtcggggcg taggagggga gccacctcgt tcatcatgct tcttacatgt ttattttcac  4560
tgactaagct ttgcaagagc ctctccccac ccagggacaa gagttcttcc aggctgttga  4620
agtgtttcag cggtttcagg ccgtcggcca tgggcatctt ttcaagcgac tgacgaagca  4680
agtacagccg gtcccagagc tcggtgacgt gctctatgga atctcgatcc agcagacttc  4740
ttggttgcgg gggttgggcc gactttcgct gtagggtacg agccggtggg cgtccagggc  4800
cgcgagggtt ttgtccttcc agggtctcag cgtccgggtg agggtggtct cggtgacggt  4860
gaacggatga gccccgggct gggcgcttgc cagggtgcgc ttcaggctca tccggctggt  4920
gctgaagcgg gcgtcgtctc cctgggaatc ggccagatag caacggagca tgaggtcgta  4980
gctaagggat tcggccgcgt gtcccttggc gcgcagtttt cccttggaaa catgctggca  5040
tctggtgcag tgtaaacact tgagggcgta cagcttgggg gcgaggaaga cggactcggg  5100
cgagtaggcg tcggccccgc actcggcgca gacggtttca cactccacca gccacgtgag  5160
ctcgggtttg tcggggtcaa aaaccaggtt gcctccattt tttttgatgc gtttcttacc  5220
ttgcgtctcc atgagcctgt gacccgcttc ggtgacaaaa aggctgtctg tgtctccgta  5280
gaccgacttg agggggcgtt cttccaaggg cgtgccgcgg tcttctgcgt acaaaaactg  5340
ggaccactcc gaaacgaagg ccctggtcca cgctaacacg aaggatgcga tctgcgaggg  5400
gtatctgtcg ttctcaatga ggggatccac cttttccagg gtatgcagac acaggtcgtc  5460
ctcctccgcg tccacaaagg tgattggctt gtaagtgtag gtcacgtgac cggcgccccc  5520
cggaggggta taaaaggggg cgtgcccacc ctccccgtca ctttcttccg catcgctgtg  5580
gaccagagcc agctgttcgg gtgagtaggc cctctcaaag gccggcatga cttcggcact  5640
caagttgtca gtttctacaa acgaggagga tttgatgttc acgtgccccg cggcgatgct  5700
tttgatggtg gagtggtcca tctggtcaga aaacacgatc tttttgttgt caagtttggt  5760
ggcaaaagac ccatagaggg cgttggaaag caacttggcg atggagcgca gggtctgatt  5820
tttttcccga tcggcccttt ccttcgcggc gatgtttaat tgcacgtact cgcgggccac  5880
gcatcgccat tccgggaaca cggcggtgcg ctcgtcgggc aggatgcgca cgcgccagcc  5940
gcgattgtgc agggtgatca tgtccacgct ggtggccacc tccccccgga ggggctcgtt  6000
ggtccaacac aatctccctc cttttctgga gcagaacgga gggaggggat ctaggaggtt  6060
ggcgtgcggg gggtcggcgt cgatggtgaa gatgccaggc aggagaactt tattaaagta  6120
atcgatctcg gtttccacgt cttgcaacgc ctcctcccat ctctttaccg ccagggccct  6180
ctcgtagggg ttcaggggcg ccccccaggg catggggtgg gtgagagccg aggcgtacat  6240
gccacagatg tcatagacgt agaggggctc ccgtaggacc ccgatgtaag tgggataaca  6300
gcgccccccg cggatgctgg cccgcacgta gtcgtacatc tcgtgagatg gggccaggag  6360
accctctccc aagtgggtct tgtggggctt ctccgcccgg tagaggatct gcctgaagat  6420
ggcgtgggag ttggaagaga tggtgggccg ttggaagacg ttaaagttgg cccgcggcag  6480
ccccaccgag tcttcgatga actgggcgta ggattcctgg agtttgttca cgagggcggc  6540
ggtgaccagc acgtccaggg cgcagtaatc cagggtctcg cggaccaggt tgtaggagct  6600
ctcttgtttt ttctcccaca gttcgcggtt gaggaggtat tcctcgcggt ctttccagta  6660
ctcttcggcg ggaaatcctt tttcgtccgc tcggtaagaa cctaacatgt aaaactcgtt  6720
caccgctttg tatggacaac agcctttctc taccggcagg gcgtacgcct gagcggcctt  6780
tctgagagaa gtgtgggtga gggcgaaggt gtcccgcacc atgactttca ggtactgatg  6840
tttgaagtcc gtgtcgtcgc agcttccttg ttcccacagg ctgaagtcgg tgcgcttttt  6900
ctgcctcggg ttggggaggg cgaaagtgac atcgttaaac aagattttcc cggcgcgggg  6960
cataaagttg cgagagattc tgaagggccc tggcacgtcc gagcggttgt tgatgacctg  7020
cgccgccagg acgatctcgt cgaagccgtt gatgttatgc cccacgatgt acagttctat  7080
gaagcgcggc tgtcccttga gggcgggcgc ttttttcagt tcctcgtagg tgagggactc  7140
gggagaggcg agccccagct ccgcgcgggc ccagtcggcc agttgagggt tagccgcgag  7200
gaaggaattc cagagctccg aggccagaag agtttgcaag cgatcgcgaa actcgcggaa  7260
ctttttcccc acggccattt tttctggcgt gaccacgtag aaagtggcgg agcgatcgtt  7320
ccagacgtcc cacttgagct cccgggccag ctcgcaggcc tgacgcacga gagtttcctc  7380
gcccgagacg tgcatgacca acatgaaagg cactaactgt tttccgaacg cgcccatcca  7440
cgtgtaggtc tctacatcgt aggtgacaaa gagccgttgg gtgcgtgcgt gggagccgat  7500
cggaaagaag ctgatctcct gccaccagct ggaggaatgg gtgttgatgt ggtgaaagta  7560
gaagtcccgc cggcgcacag agcattcgtg ctggtgtttg taaaagcgac cgcagtagtc  7620
gcagcgctgc acgctctgta tttcttgaat gagatgcact tttcgcccgc gaaccagaaa  7680
tcggagggga aagttgagcc cgggggatgg tggagtcgcg tccccttcgc cttggcggtg  7740
ggcgtctgcg tctgcgtcct gtttttctgg gtggacgacg gtggggacga cgacgccccg  7800
ggttccgcaa gtccagattt cagcgacgga ggggcgcaga cgcagaagga gggggcgcag  7860
ttgcccgctg tccagagagt cgaggaaagc gacgctgagg tcagcgggga gcgtttgcaa  7920
attcactttc aagagaccgg taagagcgtg agccaggtgg agatgatact tgatttccag  7980
gggggtgttg gaagaggcgt ccacgccgta caagaggccg tgtccgcgcg gagccaccac  8040
ggttccccgc ggaggtttta tctcactcgc cgagggcgag cgccgggggg tagaggcggc  8100
tctgcgccgg gtggtagcgg aggcagaggc acgttttcgt gaggattcgg cagcggctga  8160
tgacgcgctc ggagactgct ggcgtgggcg acgacgcggc ggttgaggtc ctggatgtgc  8220
tgcctctgcg tgaagaccac cggtcccctg gtcctgaacc tgaaagagag ttccacagag  8280
tcaatgtctg catcgttaac ggccgcctgc ctgaggatct cctgcacgtc gcccgagttg  8340
tcttggtagg cgatctcggc catgaactgt tcgacttctt cttcgcggag gtcgccgtgg  8400
cccgcgcgtt ctacggtggc ggccaggtcg ttagagatgc gacgcatgag ctgggagaag  8460
gcgttgaggc cgttctcgtt ccacacgcgg ctgtacacca cgttaccgaa ggagtcgcgc  8520
gctcgcatga ccacctgcgc cacgttgagt tccacgtggc gggcgaagac ggcgtagttt  8580
ctgaggcgct ggaagaggta gttgagcgtg gtggcgatgt gctcgcagac gaagaagtac  8640
atgatccagc gcctcagagt ctgctcgttg atgtctccga tggcttcgag gcgttccatg  8700
gcctcgtaga agtcgacggc gaagttgaaa aattgggagt tgcgggcggc caccgtgagt  8760
tcttcttgca ggaggcggat gagatcggcg acggtgtcgc gcacctcctg ttcgaaagcg  8820
ccccgaggcg cctctgcttc ttcctccagc tcctcctctt ccaggggcac aggttcctcc  8880
ggcacctctg cggcggggac ggggcggcga cgtcgtcgtc tgaccggcag tcggtccacg  8940
aagcgttcga tcatttcacc gcgccggcga cgcatggtct cggtgacggc gcgtccgttt  9000
tcgcggggac gcagttcgaa gacgccgccg cgcagagcgc ccccgtgcag ggagggtaag  9060
tggttagggc cgtcgggcag agacacggcg ctgacgatgc attttatcaa ttgttgcgta  9120
```

```
ggcactccgt gcagggatct gagaacgtcg aggtcgacgg gatccgaaaa cttctctagg  9180
aaagcgtcta tccaatcgca atcgcaaggt aagctgagga cggtgggccg ctgggggcg  9240
tccgcgggta gttgggaggt gatgctgctg atgatgtaat taaagtaggc ggttttcagg  9300
cggcggatgg tggcgaggag gaccacgtct ttgggcccgg cctgttgaat gcgcaggcgc  9360
tcggccatcc cccaggcctc gctctgacag cgacgcaggt ctttgtagta gtcttgcatc  9420
agtctctcca ccggaatctc tgcttctccc ctgtctgcca tgcgagtcga gccgtacccc  9480
cgcaagggct gcagcaacgc taggtctgcc actactcttt cggccagcac ggcctgttga  9540
atctgcgtga gggtggcctg gaagtcgtcc aggtccacga agcggtggta ggctcccgtg  9600
ttgatggtgt aggtgcagtt ggccatgacg gaccagttga cgacttggat gccgggttgg  9660
gtgatctccg tgtacttgag gcgcgagtag gccctggact cgaacacgta gtcgttgcat  9720
gcgcgcacca gatactggta gccgacgaga aagtgcggag gcggttcccg atacaggggc  9780
cagcccacgg tggcgggggc tccgggggcc aggtcttcca gcatgaggcg gtggtagtgg  9840
tacacgtatc gagagagcca ggtgatgccg gctgaggtgg tggcggccct ggtgaactcg  9900
cggacgcggt tccagatgtt gcgcaggggg cggaagcgtt ccatggtggg cacgctctgt  9960
cccgtcaggc gcgcgcaatc ctgtacgctc tagatggaga aaagacaggg cggtcatcga  10020
ctcccgtccg tagctgggag gtaaagtcgc aagggtgcgg cggcggggaa ccccggttcg  10080
agaccggctg gatccgccgt tcccgatgcg cctggccccg catccacgac gttcgcgccg  10140
agacccagcc gcggcacacc gccccaatac ggaggggagt cttttggtgt tttttcatag  10200
atgcatccgg tgctgcgaca gatgcgaccc cagacgccca ctgctactac cgccgcggcg  10260
gcagtaaacc tgagcggagg cggtgacagg gaggacgaag agctggcttt agacctggaa  10320
gagggagagg gtctggcgcg actgggcgcc ccctcccccg agagacaccc cagggtccag  10380
ctcgtgaggg atgcgagaca ggcttttgta ccgcggcaga acctgtttag ggaccgcagc  10440
ggccaggagg cggaggagat gcgcgattgt cggtttcggg cgggcagaga gctgagggcg  10500
gggttcgacc gggagcggtt gctgcgggcg gaggatttcg aacccgacga gcggtcgggg  10560
gtgagtccgg cccgagccca cgtgtcggcc gccaacctgg tgagtgcgta tgagcagacg  10620
gtgaacgagg agcgtaactt tcaaaagagc tttaataatc acgttcggac cctcatcgcg  10680
agggaggagg tggccatcgg gctgatgcat ctgtgggact tcgtggaggc ctacgtgcag  10740
aacccggcga gcaagcccct gacggctcag ctgttcctga tcgtgcagca cagccgcgac  10800
aacgagacgt ttcgcgacgc catgctcaac atcgccgagc ccgagggccg ctggctcttg  10860
gatcttatca acatcttgca gagcatcgtg gttcaggaga ggggtctcag cttagcggac  10920
aaggtggcgg ccattaacta ctccatgcag agtctgggaa aattctacgc tcgcaagatc  10980
tacaagagcc cctacgtgcc catagacaag gaggtgaaga tagacagctt ttacatgcgc  11040
atggcgctga aggtgctgac gctgagcgac gatctcggcg tgtaccgtaa cgacaagatc  11100
cacaaggcgg tgagcgccag ccgccggcgg gagctgagcg atagggagct gatgcacagc  11160
ctgcagaggg cgctggcggg tgccggggac gaggagcgcg agacttactt cgatatggga  11220
gcggacttac agtggaaacc cagcgcccga gcgttggagg cggcgggcta ccgtggcgac  11280
gaggatcggg atgactttga ggaggcaggc gagtacgagg acgaagcctg accgggcagg  11340
tgttgtttta gatgcagcgt ccggcggacg gggccaccgt ggatcccgcg cttttggcat  11400
ccatgcagag tcaacctacg ggcgtgaccg cctccgatga ctgggcggcg gccatggacc  11460
gcatcatggc actgaccacc cgcaaccccg aggcttttag gcagcaaccc caggccaacc  11520
gtttttcggc catcttggaa gcggtagtgc cgtctcgcac taatccgacc cacgaaaagg  11580
ttttaactat cgtgaacgcg ctggtagaca gcaaggccat ccgccgcgac gaggcggggc  11640
tgatttacaa cgctctgctg gaacgcgtgg cgcgctacaa cagcactaac gtgcagacca  11700
atctggaccg cctcaccacg gacgtgaagg aagcgttggc tcagaaggag cggttcttaa  11760
gggacagcaa tctgggttct ctggtggcgc tgaacgcttt tctgagcacg cagccggcga  11820
acgtaccccg cgggcaggag gactacgtga gcttcatcag cgctctgaga ctgctcgttt  11880
ccgaggtgcc gcagagcgag gtgtaccagt cgggacctga ctacttcttc cagacgtccc  11940
gacagggctt gcaaacggtg aacctgactc aggcttttaa aaacttgcaa ggcatgtggg  12000
gcgtgaaggc gccggttggc gatcgcgcga ccatttccag cctgctgacc cccaacacga  12060
gactgctgtt gcttttaatc gccccgttca ccaacagcag caccatcagc cgcgactcgt  12120
acctgggcca tctcatcact ctgtaccgag aggccatagg tcaggctcag attgacgagc  12180
atacgtatca agagatcacc aatgtgagcc gagccctggg tcaggaagac accggcagtt  12240
tggaagccac gctaaacttt ctgctgacca atcggagaca aaagattccc tcgcagtaca  12300
cgttaagcgc cgaggaggag aggattctgc gctacgtgca gcagtccgtg agcctgtact  12360
tgatgcggga gggtgctacc gcttccacgg ccttggacat gacggctcga aacatggaac  12420
cgtcttttta ctcagcccac cgtccgttca tcaatcgcct gatggactac ttccatcgcg  12480
cggccgccat gaacggggag tatttcacca atgccatctt gaatccgcat tggatgcctc  12540
cgtccggttt ctacaccggg gagttcgacc tgcccgaggc cgacgacggc tttctgtggg  12600
acgatgtgtc cgacagcatt tttacgccag gtaacagtcg tttccataaa aaggaagggg  12660
gagacgaact tccccttcg agtgtggagg cggcctccag gggggagagc ccctttcca  12720
gcttgtcttc cgtgagtagc ggtcgggtga cgcgcccacg cttgccgggg gagagcgact  12780
acctaaacga ccctttgctg cgaccggcta aaaagaaaaa ttttcccaac aacggggtgg  12840
aaagcttggt ggataaaatg aatcgttgga agacctacgc tcaggagcag cgggagtggg  12900
aggacagtca gccccgaccg ctggtcccgc cgcactggcg ccgccagaga gaagacccgg  12960
acgactccgc agacgatagt agcgtgttgg acttgggagg gagcggagcc aaccccttg  13020
ctcacttgca acccaagggg cgcttgagtc gcctgtacta ataaaaagaa agcggaaacg  13080
taccagagcc atggccacag cgtgtgtcct ttcttcctct ctttcctcct cggcgcggca  13140
gaatgagaag agcggtgaga gtcacgccgg cggtgtatgc cgagggtccg cccccttctt  13200
acgaaagcgt gatgggatca gcgaacgtgc cggccacgct ggaggcgcct tacgttcctc  13260
ccagatacct gggacctacc gagggcagaa acagcatccg ttactccgag ctggcccccc  13320
tgtacgatac caccaaggtg tacctggtgg acaacaagtc ggcggacatc gcctccctga  13380
attaccaaaa cgaccacagc aacttcctga ccaccgtggt gcagaacaat gacttcaccc  13440
cgacggaggc gggcacgcaa accattaact ttgacgagcg ttcccgctgg ggcggtcagc  13500
tgaaaaccat cctgcacacc aacatgccca acatcaacga gtttatgtcc accaacaagt  13560
ttagggccag gttgatggta gagaagacta gcggccagcc gcccaaatac gagtggttcg  13620
agttcaccat tcccgagggt aactactccg agaccatgac tatcgatctc atgaataacg  13680
cgatcgtgga caattacctg caagttggaa ggcaaaacgg ggtattggag agcgacatag  13740
gagtaaaatt tgataccagg aacttccgac tggggtggga tccggtgacc aagctggtga  13800
tgcctggcgt gtacaccaac gaggcttttc accccgatat cgtgctgctt ccggggtgcg  13860
```

-continued

```
gagtggactt tacgcagagc cgcttgagta acctgttagg aatcaggaag cgccgtccct  13920
ttcaggaggg ctttcagatt atgtatgagg acttggaggg aggtaatatt ccaggcctgc  13980
tagacgtgcc ggcctatgaa caaagcttac aacaggccca agaggaggga agagtcactc  14040
gcggagacac ctttgccacg gctcccaacg aggtagtgat taagccctta ttgaaagaca  14100
gtaaggatag aagttataat attataaccg acaccacgga cactttgtac cggagttggt  14160
ttctggctta caactacggg gaccccgaaa acggagtgag atcatggacc atactcacca  14220
ccacggacgt gacctgcggc tcgcagcaag tgtactggtc cctgccggat atgatgcaag  14280
acccagtcac cttccgcccc tccacccaag tcagcaactt tccggtggtg ggcactgagc  14340
tgttgcccgt tcacgccaag agcttctaca acgagcaggc tgtttattcg caactcattc  14400
gccagtctac cgcgcttacc cacgtattca accgtttccc cgagaaccag attctcgtgc  14460
gccctcccgc tcctaccatt accaccgtga gtgaaaacgt tcccgccctc acagatcacg  14520
gaaccctgcc gctgcgcagc agtatcagtg gagttcagcg cgtgaccatc accgacgcca  14580
gacgtcgaac ctgcccttac gtttacaaag cgctcggcgt agtggcccca aaagtgctct  14640
ctagtcgcac cttctaaaac atgtccattc tcatctctcc cgataacaac accggctggg  14700
gactgggctc cggcaagatg tatggcgggg cgaagcggcg ctccagtcag caccctgttc  14760
gcgttcgggg tcatttccgc gctccctggg gagcttacaa acgaggactc tcgggccgaa  14820
cggcggtaga cgacaccatt gacgccgtca ttgccgatgc ccgccggtat aaccccggaa  14880
cggtcgctag cgccgcctcc accgtggatt ccgtgatcga cagcgtggtg gccggcgcca  14940
gggcctacgc tcgccgcaaa aggcggctgc accgcaggcg tcgacccacg gccgccatgc  15000
tggccgccag ggccgtgctg agacgggccc gcagggtagg caggagggcc atgcgccgcg  15060
cggccgccaa cgctgccgcc gggagggccc gcaggcaagc cgccagccgg gccgccgccg  15120
ccatcgctaa catggccaga cccaggagag ggaacgttta ctgggtgcgc gattctgtga  15180
cgggagtcag agtgccggtg cgcagccgac ctccccgaag ttagaagacc aaaggtgcga  15240
agacggcgta ctgagtctcc ctgttgttat cagcccaaca tgagcaagcg caagtttaaa  15300
gaagaactcc tgcagaccct ggctcctgaa atctatggcc ctccggacgt gaagcccgac  15360
attaagcccc gcgatatcaa gcgtgttaaa aagcgggaaa aaaaagagga actcgcggtg  15420
gtagacgatg gcggggtaga atttattaga agtttcgccc cgcgacgcag ggtgcagtgg  15480
aaagggcggc gcgtgcaacg cgttctcagg ccaggcaccg cggtagtttt tactccggga  15540
gagcggtcgg ctgtcagggg tttcaagcgg caatatgacg aggtgtacgg cgacgaagac  15600
atcctggaac aggcggctca gcagattgga gaattcgcct acggaaagcg gtctcgccgc  15660
gaagacctgg ccattgcctt ggacagtggc aaccccaccc ccagcctcaa acccgtcacg  15720
ctgcagcagg tgctccccgt gagcgcgagc acggagagca aaaggggaat caagagagag  15780
atggaagatc tgaagcccac catccaactt atggtcccta aacgacagaa gctggaggag  15840
gttctggaaa acatgaaagt ggaccccagc atagagccgg atgtaaaagt gaggcctatt  15900
aaggaagtgg ctccgggtct cggggtgcaa acggtggaca ttcagatccc agtcagatcc  15960
gcttcgaccg ccgtggaagc catggaaacg caaaccgaaa ctccggtcgc ggccggtacc  16020
agagaagtgg ctttgcaaac ggagccctgg tacgaataca ccgctcctcg gcgccagagg  16080
cggcgttacg gcccggcaaa tgccatcatg ccagagtatg cgctgcaccc gtctatccga  16140
cccacccccg gctaccgggg ggtaacgtat cgcccgtcgc caacccgacg ccgttatcgt  16200
cgccgccgcc gttctcgtcg cgctctggcg cccgtgtccg tgcgacgcgt aacgcgccgg  16260
ggaagaacag tcaccatccc taacccgcgc taccacccta gcattcttta atgactctgc  16320
cgttttgcag atggctctga cttgccgcgt gcgccttccc gttctgcact atcgaggaag  16380
atctcgtcgt aggagaggca tggcggggag cggccgccgt cgggctttac gcaggcgcat  16440
gaaaggcgga attttgcccg cactgattcc cataattgcc gccgccattg gggcgatacc  16500
cggcgttgct tcagtggcct tgcaagcagc tcgtaataaa taaacgaagg cttttcaact  16560
tatgacctgg tcctgactat tttatgcaga aaaagcatgg aagacatcaa ttttacgtcg  16620
ctggctccgc ggcaaggctc acgcccgctc atgggcacct ggaacgacat cggcagcagc  16680
cagctcaacg ggggcgcttt caattggggg agcctttgga gcggcattaa aaactttggc  16740
tccgcgatta aatcctacgg cagcaaagcc tggaacagta gtactggtca gatgctccgg  16800
gataaactga aggacacaaa ctttcaagag aaagtggtca acggggtggt gaccggcatc  16860
cacggcgcgg tggatctcgc taatcaagcg gtgcaaaaag agatagacag acgatgggaa  16920
aactcgcggg tgcctccgca gagaggggac gaagtggagg tggaggaagt agaagtcgag  16980
gagaaactgc ccccgctaga gaaagttccc ggggcgccgc ccaggccaca gaagcgtccc  17040
cggccggatc tggaagaaac tttagtgacg gaaaccatcg aacctccctc gtacgaacaa  17100
gctttaaagg agggcgcctc tccttacccc atgactaagc ccatcgcgcc catggcgcgt  17160
ccggtgtacg gaaaagatca caagccagta acgttagagc taccccccacc acccccttcc  17220
cgtcctacgg tgcctccgtt acccgccccg tcggcaggtc ccagctctgc accatccgca  17280
gctcctgcac caaccgctcg cccggtggcc gtggcaaccg ccagagcccc cagaggatcc  17340
aactggcaaa gcacgctgaa cagcatcgtg ggcttgggag tgaaaaccct aaaacgccgc  17400
cgctgctatt attaaagagt gtagctaaaa atttcccgtt gtatacgcct cctatgttac  17460
cgccagagac gcgtgactgg tcgccgctcc gccgctttca agatggccac cccatcgatg  17520
atgccgcagt ggtcttacat gcacatcgcc ggccaggacg cctcggagta cctgagtccc  17580
ggcctggtgc agtttgcccg cgccaccgaa agctacttca gcttgggaaa caagtttaga  17640
aaccccaccg tggcccccac gcacgatgta accacggacc gctcgcagag gctgacactg  17700
cgcttcgtgc ccgtagaccg ggaggacacc gcgtactcct acaaagtgcg cttcaccctc  17760
gccgtagggg acaacagggt gctggacatg gccagcacgt actttgacat ccggggaatg  17820
ctggaccgag ggcccagctt taaaccctac tcgggaactg cctacaattc gctggcacct  17880
aagggcgctc ccaaccctag tcaatggact actaccaacg gagggaataa aacaaattca  17940
tttgcccaag catcctacat aggtcaaagc ctgtcgaaag acggggtgca agtagcagta  18000
gatacagccg ctgggggggc tgcagtatat gctgacaaaa cgtttcaacc agaaccccaa  18060
gtaggaatat cacaatggaa tgaaaatcct actacaaatg ctgcaggaag aattttaaag  18120
cctactaccg caatgcgtcc atgctacggt tcatacgctt accccaccaa cgaaaaaggt  18180
gggcaggtaa aaatcactga ccctaacaat gacaaaaccg gcgctaataa cgttagctta  18240
aatttttca acactgccgc tgacaatggg aataacaatc caaaagtagt actctacagc  18300
gaagatgtaa atttagaagg gccagatacc caccttgttt ttaagccaga tgtaactggc  18360
gacgcaacca gtgcagaaac cctgttaggt caacaagcag ctcccaatcg tccaaactac  18420
attgggttca gggacaactt tattggcctg atgtactaca attcaactgg aaacatggga  18480
gtgctagcag gtcaggcttc tcagctaaac gccgtagtgg atcttcaaga cagaaatacc  18540
gaattgtcat atcagctaat gcttgacgct ttgggtgaca gaagtcggta cttttctatg  18600
```

```
tggaatcaag cagtggacag ctacgatcct gacgttagaa tcatagaaaa tcatggagta  18660
gaagacgaac ttccaaatta ttgttttccg ttaaatggac aggggatttc gaatacatac  18720
aaaggtgtga aatataacac aaacacttgg acgcaagaca ctgatgtagt cacaaccaat  18780
gaaatttcca ttggcaacat ttttgccatg gaaataaacc tggcggctaa cttgtggcgc  18840
agctttctgt actccaatgt cgccctgtac ttgccagatt cctacaaata cactcccgac  18900
aatattgaac ttcctacaaa caagaacagc tacggctaca ttaacggaag ggtaaccgcc  18960
cccactgcca tcgacactta cgttaacatc ggcgcccggt ggtctccgga ccccatggac  19020
aacgttaacc ctttcaacca ccaccgcaac gccggcttgc gataccgctc catgctgctg  19080
ggcaacggtc gctacgtacc cttccacatt caggtgcccc agaaattttt tgccattaaa  19140
aacctgcttc tgcttcccgg gtcctacacc tacgagtgga acttcaggaa agatgtaaac  19200
atgatcttgc agagcacctt gggcaacgac ctccgcgttg acggagctag cgtgaggttt  19260
gacagcatta acctctacgc taacttcttc cccatggccc acaacacggc ctccaccttg  19320
gaagccatgc tgcgcaacga caccaacgac cagtccttta atgattacct gtgcgcggcc  19380
aacatgctgt accccatccc cgccaatgcc accagcgtgc cgatctccat tccctcacgc  19440
aactgggccg ccttcagagg ttggagtttc actcgcctga aaaccaagga gacccccctcg  19500
ctgggctccg gtttcgaccc atactttgtt tactccggga gcattcccta cctggacgga  19560
actttctacc tgaaccacac cttcaaaaag gtgtctatta tgtttgactc ctccgtgagc  19620
tggcccggta acgaccgctt gctaaccccc aacgagttcg aaatcaaacg ctcggtggac  19680
ggagagggtt acaatgtagc ccagagcaac atgaccaaag actggttttt aattcaaatg  19740
ctaagccact ataacattgg ctaccaagga ttctacgtgc ctgaagccta caaggacaga  19800
atgtactcct tctttagaaa cttccaaccc atgagccgcc aggtagtaga cacggtaaac  19860
tatgctaact acaaggaagt aacaatgcca ttccagcaca acaactcagg cttcgtgggg  19920
tacatgggac ctaccatgag agaggggcag gcctacccgg ctaattatcc ctacccccta  19980
atcggagcca ctgccgtgcc cagcctgaca cagaaaaagt ttctctgcga tcgaacaatg  20040
tggaggattc ccttctctag caacttcatg tccatggggg ctctcaccga cctggggcag  20100
aacatgctgt acgctaactc cgctcacgcc ttggacatga cctttgaggt ggaccccatg  20160
gatgagccca cgcttctcta tgttctgttt gaagtcttcg acgtggtgcg cattcaccag  20220
ccgcaccgcg gcgtcatcga ggccgtctac ctgcgcacac ctttctctgc cggtaacgcc  20280
accacctaag aagctgatgg gctccagcga acaggagctg cgggccattg ttcgcgacct  20340
gggctgcggg ccctactttt tgggcacctt cgacaagcgc ttccccggct tcatgtcccc  20400
ccacaagccg gcctgcgcca tcgtcaacac ggccggacgc gagaccgggg gggttcactg  20460
gctcgccttt gcctggaacc cgcgtaacca cacctgctac ctgttcgacc cttttggttt  20520
ttctgacgaa aggcttaaac agatttacca gttcgagtac gaggggctcc ttaaacgcag  20580
cgctctggcc tccacgcccg accactgcgt caccctggag aagtccaccc aaacggttca  20640
gggtcccctc tcggcggcct gcggactctt ttgttgcatg tttttgcatg ctttcgtcca  20700
ctggccgaac acccccatgg accgcaaccc cactatggat ctgctcacgg gagtgcctaa  20760
cagcatgctt cacagccctc aggtcgcacc caccctgcgt cgcaatcagg aacagctgta  20820
tgcttttctg ggaaaacatt ctgcctactt tcgccgccac cggcagcgca tagaacaggc  20880
cacggccttt gaaagcatga gtcaaagagt gtaatcaata aaatcaactt ttattttaca  20940
tcacacgcgc ttctggcgtt ttcttaaaaa tcaaagggtt cgggggaggg gtcgtcgtgc  21000
ccgctgggca gggacacgtt gcgatactgg aagcgggggc tccagcggaa ctcggggatc  21060
gccagccggg gcagaggcac ttcttccagg ttctgcttcc aaaactgccg caccagctgg  21120
agggctccca ttacgtcggg cgccgagatc ttgaagtcgc agttggggcc cgagcttccg  21180
cggctgttgc gaaacacggg gttggcacac tggaacacca gcacgctcgg gtagttgata  21240
ctggccaggg ccgttgcgtc ggtcaccgcc gttacatcca gatcctccgc gttggtcagg  21300
gcgaagggag tcagcttgca catctgccgc ccgatgtggg gcacgccgtc atgcttgttg  21360
aggcagtcgc aacgcagggg aatcagaatg cgatgctggc cgcgttgcat ctgagggtag  21420
ttggcccgca agaacgcttc catctgacgg aaggccgtct gggctttcat tccctcggtg  21480
tagaaaagac cgcaggactt gctagaaaat acattattgc cgcaggtgac gtcttccgcg  21540
cagcagcggg cgtcttcgtt ctttagctgc accacgttgc gaccccaccg gttctgtacc  21600
accttggccc tcgtgggctg ctccttcagc gcccgctggc cgttttcgct ggtcacatcc  21660
atttccaaca cgtgctcctt acacaccatt tccactccgt ggaagcagaa caggacgccc  21720
tcctgctggg tattgcgatg ctcccacacg gcgcagcctg tggcctccca gctcttatgc  21780
ttcacccccg cgtagttttc catgtaagcc atcaggaatc tgcccatcat ctcggtaaag  21840
gttttctgac tggtgaaggt caaaggcaag ccgcggtgct cttcgttcag ccacgtttga  21900
cagatcttgc ggtacgtggc gccctgatcc ggcagaaact taaacgcccc cttgctctcg  21960
ttgtccacgt ggaacttttc catcagcatt agcataactt ccataccctt ctcccacgcc  22020
gtcaccagcg gtgtgctgtc ggggttcttc accaacatgg tagaagggcc ctcgccggcc  22080
ctgaagtcgc tcatactcat tttttgaaac tccacagtgc cgtccgcacg acggacccgg  22140
cgcatcggag ggtagctgaa gccaacctcc accagggtgc cttcgctctc gctgtcggag  22200
acgatctccg gggagggcgg cggcgcgggt gtcgacttgc gagccttctt cttgggagga  22260
agcggtggcg cctcttggtc gcgctcggga ctcatctccc tcaagtaggg ggtgatggag  22320
cttcctgctt ggttctgacg gttggccatt gtatcctagg cagaaacaca tggagcttat  22380
gcgcgaggaa actttaaccg ccccgtcccc cgtcaacgac gaagaggtca tcatcgaaca  22440
ggacccgggc tacgttactc cgcccgagga tctggagggg cctttagacg accggcgcga  22500
cgctagtgag cagcaggaaa atgagaaaga ggaagcctgc tacctcctgg aaggcgacgt  22560
gttgctaaaa catttcgcca ggcagagcac catagtgaag gaggctttgc aagaccgctc  22620
ggaggtgccc ttggacgtcg ccgcgctctc ccaggcctac gaggcgaacc tcttctcgcc  22680
ccgagtgcct ccgaagagac agcccaacgg cacctgcgag cccaacccgc gccttaactt  22740
ctaccccgtg ttcgccgtgc ccgaggcgct ggccacctac cacatttttt tcaagaacca  22800
gcgcatcccg ctctcgtgcc gggccaaccg caccgcggcc gatagaaagc tgagactcaa  22860
aaacggagct agcatacctg atatcacgtc cctggaggaa gtgcctaaga tcttcgaagg  22920
tctgggtcga gacgagaaac gggcggcaaa cgctctgcag aaagaacaga aggacagtca  22980
gaacgtgctg gtggaactgg agggggacaa tgcgcgtctg gccgttctca agcgctgcat  23040
agaagtttcc cacttcgcct accctgccct gaacctgccg cccaaagtca tgcgctcggt  23100
catggaccag ctgctcatca agagagctga gcccctgaac cccgagcacc ccgaggcgga  23160
gaactcggag gacggaaagc ccgtcgtcag cgacgaggag ctcgagcggt ggctggacag  23220
cacggacccc gagcagttgc aagagcggcg caaaatgatg atggcggccg tcctggtcac  23280
cgttgagctg gagtgcctgc agcggttttt tagcgacgtg gaaacgctgc gtaaaatcgg  23340
```

```
agagtccctg cactacacct tccgccaggg ctacgtccgc caggcctgca agatctccaa  23400
cgtggagctc agcaacctgg tctcctacat gggcatcctc cacgagaacc ggctgggaca  23460
gagcgtgctg cactgcacct tgcaaggcga ggcgcggcgg gactacgtgc gagactgcgt  23520
ctacctcttc ctcactctca cctggcagac cgccatggga gtgtggcagc agtgcttgga  23580
agacagaaac ctcaaagagc tagacaaact cctctgccgc cagcggcgcg ccctgtggtc  23640
cggtttcagc gagcgcacgg tcgccagcgc tctggcggac atcatcttcc cggagcgcct  23700
gatgaaaacc ttgcaaaacg gcctgccgga tttcatcagt caaagcattt tgcaaaactt  23760
ccgctctttt gtcctggaac gctccgggat attgcccgcc atgagctgcg cgctaccttc  23820
tgactttgtc cccctctcct accgcgagtg ccctccccca ctgtggagcc actgctacct  23880
cttccaactg gccaactttc tggcctacca ctccgacctc atggaagacg taagcggaga  23940
gggtttactg gagtgccact gccgctgcaa cctgtgcacc ccccacagat cgctggcctg  24000
caacaccgag ctactcagcg aaacccaggt cataggtacc ttcgagatcc aggggcccca  24060
gcagcaagag ggtgcttccg gcttgaagct cactccggcg ctgtggacct cggcttactt  24120
acgcaaattt gtagccgagg actaccacgc ccacaaaatt cagttttacg aagaccaatc  24180
tcgaccaccg aaagcccccc tcacggcctg cgtcatcacc cagagcaaga tcctggccca  24240
attgcaatcc atcaaccaag cgcgccgcga tttccttttg aaaaagggtc gggggggtgta  24300
cctggacccc cagaccggcg aggaactcaa cccgtccaca ctctccgtcg aagcagcccc  24360
cccgagacat gccgcccaag ggaaccgcca agcagctgat cgctcggcag agagcgaaga  24420
agcaagagct gctccagcag caggtggagg acgaggaaga gatgtgggac agccaggcag  24480
aggaggtgtc agaggacgag gaggagatgg aaagctggga cagcctagac gaggaggagg  24540
acgagctttc agaggaagag gcgaccgaag aaaaaccacc tgcatccagc gcgccttctc  24600
tgagccgaca gccgaagccc cggcccccga cgcccccggc cggctcactc aaagccagcc  24660
gtaggtggga cgccaccgaa tctccagcgg cagcggcaac ggcagcgggt aaggccaaac  24720
gcgagcggcg ggggtattgc tcctggcggg cccacaaaag cagtattgtg aactgcttgc  24780
aacactgcgg gggaaacatc tcctttgccc gacgctacct cctcttccat cacggtgtgg  24840
ccttccctcg caacgttctc tattattacc gtcatctcta cagcccctac gaaacgctcg  24900
gagaaaaaag ctaaggcctc ctccgccgcg aggaaaaact ccgccgccgc tgccgccgcc  24960
aaggatccac cggccaccga agagctgaga aagcgcatct ttcccactct gtatgctatc  25020
tttcagcaaa gccgcgggca gcaccctcag cgcgaactga aaataaaaaa ccgctccttc  25080
cgctcgctca cccgcagctg tctgtaccac aagagagaag accagctgca gcgcaccctg  25140
gacgacgccg aagcactgtt cagcaaatac tgctcagcgt ctcttaaaga ctaaaagacc  25200
cgcgcttttt ccccctcggc cgccaaaacc cacgtcatcg ccagcatgag caaggagatt  25260
cccacccccct acatgtggag ctatcagccc cagatgggcc tggccgcggg ggccgcccag  25320
gactactcca gcaagatgaa ctggctcagc gccggccccc acatgatctc acgagttaac  25380
ggcatccgag cccaccgaaa ccagattctc ttagaacagg cggcaatcac cgccacaccc  25440
cggcgccaac tcaacccgcc tagttggccc gccgcccagg tgtatcagga aaatccccgc  25500
ccgaccacag tcctcctgcc acgcgacgcg gaggccgaag tcctcatgac taactctggg  25560
gtacaattag cgggcgggtc caggtacgcc aggtacagag gtcgggccgc tccttactct  25620
cccgggagta taaagagggt gatcattcga ggccgaggta tccagctcaa cgacgagacg  25680
gtgagctcct caaccggtct cagacctgac ggagtcttcc agctcggagg agcaggccgc  25740
tcttccttca ccactcgcca ggcctacctg accctgcaga gctcttcctc gcagccgcgc  25800
tccgggggaa tcggcactct ccagttcgtg gaagagttcg ttccctccgt ctacttcaac  25860
cccttctccg gctcgcctgg acgctacccg gacgccttca ttcccaactt tgacgcagtg  25920
agtgaatccg tggacggcta cgactgatga cagatggtgc ggccgtgaga gctcggctgc  25980
gacatctgca tcactgccgt cagcctcgct gctacgctcg ggaggcgatc gtgttcagct  26040
actttgagct gccggacgag caccctcagg gtccggctca cgggttgaaa ctcgagatcg  26100
agaacgcgct cgagtctcgc ctcatcgaca ccttcaccgc ccgacctctc ctggtagaaa  26160
tccaacgggg gatcactacc atcaccctgt tctgcatctg ccccacgccc ggattacatg  26220
aagatctgtg ttgtcatctt tgcgctcagt ttaataaaaa ctgaactttt tgccgcacct  26280
tcaacgccac gcgttgtttc tccaacagtc gacgatagct cttcaattaa aggtacccga  26340
gaaactgttt attttgacaa ttctactact tctcttatcc ttaactgttc ttgcactaac  26400
gaactaattc agtggttcgc caacggttca ctctgcaaag ttttccttga ctctgcgata  26460
cttcccggat ttagcagctc tgcgtgtgat aattctaccc cctccacctt aaccatcaca  26520
aagccatttt cagaagtcca gtatttttgt attggagcgg ggggtaaacc gggctgtatt  26580
caccgcttct ttctggagac atttgttgct tcgattccca ttaacacttc actttcctct  26640
aatacatact taactacctt acattctact cacccctcct ggaaacctct tattggcctc  26700
acagctttta tttccgttgt tttactaaac tttataattc ttaacaaact ttcttaaaca  26760
tgcttgccat tttgcttctg ctcgttactt taacctccgc agattaccac aatgcaattg  26820
tacgagaaaa cagtttacaa aacccatcac aggtatatgt taaagcaggt tctaacttaa  26880
ctctacaatc cttctattcg ccttaccctg aggacatgcc acgtgtcacc tggtacttag  26940
aagtttttga ttcgctattt gaaagacata caattcctcc atttttaca ggcgttatac  27000
tttgtgacat ttctggtgac atacagcatg tgtggaacca ttggccttta caatttaatt  27060
gcataaataa aagcttacat attatcaatc tcaaaccaag tgatgaaggc ctttacaatg  27120
tgaaggtttt aaagggcagc attcagcata atacatactt tcgtgtgcat gtagtaagtt  27180
ttccaaaacc tgaatgtaac atcaccacta catatctttc agatgactac tgccttatta  27240
acattgattg ctctcaatta ccataccctg ctaaggtcta ttataatggc aatgaaagta  27300
agctgcatta ctacttatct gaacgcggtg gccaaccaaa ccttccaaat tactttactg  27360
ttgggtatcg atatagagat ctccgacaga attatacagt tgaatatcca tttaatgaac  27420
tctgtacaga tataattgct cttgaaacag ggtctgattt tacgccaatt tttatagtta  27480
ccctagtggt gagcattata gttattgtga tgggcatcac atatcttatt tatcactgta  27540
ggactttaaa aaccaaaacc aaaaccaagc ctcctgaaat ccgtctgctt taattttttc  27600
cagaatggta gctgctttct tcattctcct ctgtatacca atcatctgcg cctccacaac  27660
ttttgccgct gtttcccacc tggaaccaga ctgtctacca ccttttgttg tatacctaat  27720
actgactttt gtggtctgta cagccattac cagtatagcc tgctttttg taacaatttt  27780
ccaagccgcc gattacctct acgtacggtt tgcttacttt agacatcacc ccgagtatcg  27840
gaatcaaaac gtagcctctc tgctttgttt agcatgattc gcatttttat actttgtaag  27900
ctctttacca ccacaatatg tcaatgccct tttaccaaac cctggtcctt ttacacttgt  27960
tataatgtat tacccgaaac ccccattgcc tggctttacg tagccacagc ggctttagtt  28020
tttgtagcaa cctgcattgg cgttaaactg tacttttact taaaaattgg atggcttcat  28080
```

-continued

```
cccccagaag atttaccccg atatcctctt gttaataact ttcaacagcc tctaccgcct  28140
cctgatcttc cgcgagctcc ctccgttgtt agctactttc aactcaccgg tggagatgac  28200
tgacactcag gacattaaca ttactgtgga aagaatagct gctcagcgtc agcgagagac  28260
gcgggtgatg gagtacgtgg aactacagca gcttaaagag tcccactggt gtgaaaaagg  28320
agtgctttgc catgttaagc aagcagccct ttcttacgat gtcagcactc agggacatga  28380
actgtcctac actttgcctt tacagaaaca aaccttctgc accatgatgg gctctacctc  28440
cattacaatc agccaacaaa ccggacctgt cgagggggct atcctgtgtc actgtcacgc  28500
gcctgattgt atgcccaaac taatcagaac tctttgtgct ttaggtgata tatttaaaat  28560
atagatagta tcaataaact taccttaaat ttgacagcaa ttttttggta tcatcattca  28620
gcagcaccac tttaccctct tcccaactct catatgggat atgatggtgg gcggcaaact  28680
tcctccaaac cctgaaagaa atatcggtat ccacttcctt gtcctcaccc acaattttca  28740
tcttttcata gatgaaaaga acccgagttg atgaagactt caaccccgtc tacccttatg  28800
acaccacaac cactccagcc gttcctttca tatcaccccc gtttgtaaac agtgacggtc  28860
ttcaggaaaa cccccccgga gttttaagcc tgcgaatagc taaacccctg tattttgaca  28920
tggagagaaa actagccctt tcacttggaa gagggttaac aattaccgcg aacggacaat  28980
tagaaagcac ccagagcgtg cagactaacc cgccgttaac tgtcaccaat aacaacacac  29040
ttatcctacg ccactcctcc cctttaatcc taactgacaa taatttaacc gtaggcttct  29100
caagtcctct ccgtgttata gacaacaaac tgacattcac ttttacctca cctctccgtt  29160
atgaaaacga aacccttacc ttcaattaca cagagcccct tacacttatg aacagcaacc  29220
ttgcgcttaa cgtaaactcc tctaaaggcc ttagggttga cgggggctca ctaggtacaa  29280
acttaagtcc ggacttaagg tttaacagca gtggagccat agcttttggt atacaaaccc  29340
tatggacacc cccgacctca aatcctaact gcaccgttta caccgaaagc gattccttac  29400
ttagtctctg cttaactaaa tgcggagctc acgttttagg aagtgtaagc ttaaccgggg  29460
tagcaggtac catgataaac atggctgaaa cttcgcttgc tattgaattt acgtttgacg  29520
acactggaaa actacttcac tcaccacttg ttaacaccac ttttagcatt cgtcagggcg  29580
acagccccgc ctcaaatcct acctacaatg ctctagcatt tatgccaaac agtaccctct  29640
acgctagagg aggaagtggt gaaccccgaa acaattacta cgtccaaaca tacctcaggg  29700
gaaatgttca gagaccgatt accctcactg ttactttcaa ctcagccgcc acgggatatt  29760
ccttatcttt taagtggact gctgttgcac gtgaaaaatt tgcagctcct gcaacttcat  29820
tttgctacat taccgaacaa taaaaccctg tgttcccacc gtttcgtttt ttccagatga  29880
aacgggccag agttgatgaa gacttcaatc ccgtgtaccc ttacgatccc ccttacgccc  29940
ccattatgcc gtttattacc ccgccgttta catcttcaga tgggttacag gaaaaaccac  30000
ttggtgtttt aagtttaaaa tacaaggatc ctatcactac acaaaatggt tctctaaccc  30060
ttaaattagg aaacgggctg aacattaaca accagggcca acttacatca tctgctgggg  30120
aagtcgagcc tcccctcacc aatgctgaca acaagctggc cttagcctac agcgaccctc  30180
tgacattaaa aaacagccgt ctaacactgt ctcacaatgc cccacttgca attaacaata  30240
attctctaag tttggaagta tcagagccta tatttataaa taacgacaac aaactgtctc  30300
tgaaagctga cgcccccctg acaaccagcg ctggaaccct ccgcctgcaa agcgctgctc  30360
cattaggact tgctgaacag acactaaagc tgctgttttc taaccctttg tacttgcgag  30420
gtgacttcct tacattagcc attgaacgcc cattggctgt aacagcagac gggctattat  30480
cacttgccct caaccctccg ctcacaacaa ctaacacagg cttagctctc tctaccgcgg  30540
ttccattaac tgttaccaac gggaacctta gcctaaacgt aaaacggccg tttattatac  30600
aggacggcag cctttacatg gattttagac ccccactata tctgtttaac agcgagccac  30660
aacttggtgt taattttaat gcccctctaa ctgttagaga taacggccta gctataaaca  30720
ccggagacgg gctaacagta acgtataata aactaacatt aaacctcggt agagacttgc  30780
aatatgaaaa tggagctgca gctgttaagc taagtaccgc ccctcctcta cagtatacta  30840
ctcaactgca gctgaatttg ggagcgggct tacgtctagg tcctactagg aacttagacg  30900
tggccattaa ccacaataaa gggttagcgt gggaaaacaa tgaagtggtt actaaattag  30960
gacaaggcct ttactttgat tcctccggaa gcatagcttt atcgcctaca aaccccagac  31020
cagatacttt atggaccacg gccgatcctt cgccaaactg cactgtatat gaatcacttg  31080
actctagact gtggctagcg cttgttaaat gtgggggaat ggtacacggc agcatagccc  31140
tacaagctga aaaaggccaa ttgctgcgtc ctactgctag ttttatctcc atcgtaattt  31200
acttctacag tgatggggtc cgtcgcacca actaccctac aattggcaat gatgagggta  31260
ctctggccaa cagcgctact tggggctaca gacaagggca atctgcagac accaacgtca  31320
ccaatgctgt tgaattcatg cctagtttac acagatatcc tataaatcag ggagacaata  31380
ttaaaaacca aatgataact tacacttgca tacaaggcaa cgtgaacatg ccagtaccct  31440
tgaaaatcac gttcaatcat gctcttgaag gctactcctt aaagtttaca tggcgtgtgg  31500
tggctaatga aaagtttgat attccttgct gttcgttttc ttacattaca gaacaataaa  31560
acaacttttt tatttttcat ttcttttatt ttacacgcac agtaagactt cctccccccct  31620
tccatttaac agcgtacacc agcctttccc ccttcatggc ggtaaacttc tgtgagttag  31680
tccggtattt gggagttaaa atccaaacag gctctttggt gattaaacgt tgatccgtga  31740
tggacacaaa tccctgagac aggtcctcca acgttgcggt aaaaaactga acgccgccct  31800
acaaaacaaa cagttcaggc tctccacggg ttatcacccc gatcaaactc agacagagta  31860
aaggtgcggt gatgttccac aagaccgcgc aagtggcgct gtctaaagct ctcagtgcga  31920
cttctatgcg gctggtagga tgttacatta tccaacagcc tcacagcgcg gattattagt  31980
ctacgagtgc gcctggcgca gcagcgcatc tgaatttcag tcaagtcttg acaagaagcg  32040
cataccataa caatcaggtt gttcatgatc ccatagctaa acgcgctcca gccaaaactc  32100
attcgctcca acagcaccac cgcgtgtccg tcaagtctta cttttacata aacaaggtgt  32160
ctgccacgta catacatgct acccgcatac aaaacttccc ggggcaaacc tctattcacc  32220
acctgtctgt accagggaaa cctgatgttt atcagggaac catagatggc cattttaaac  32280
cagttagcca gcaccacccc gccagctcta cactgaaggg aaccgggaga gttacaatga  32340
cagtggatca tccacctctc gtaaccccta attacctgat taaaatccaa atctaacgtg  32400
gcacaacaga tacacactct cataaacatt ttcatgacat gtttttccca ggatgttaaa  32460
atacaatccc aatacacggg ccactcctgt aatacaataa agctaatgca tgatggaacg  32520
ctcctcacct cactaacatt gtgcatgttt acattttcac actctaagta ccgagtcctc  32580
tcctcaacag ccgcagtgtc gcgctcctca cacggtggta gctgatgaca attgtaaggg  32640
gccagtctgc agcgatatcg tctgtcgcgc tgcatcgtaa aacagggacc gtctcacttc  32700
ctcgtacttc caatagcaga accacgtccg ctgccagcag gtttccacga accgccgatc  32760
ccttcgtcgt tcacgctccc tcctcaacgc aaaatgcagc cactcctgca atccacacaa  32820
```

```
atccctctcg gcctccggag tcatgcacac ctcataccta tatatgtctc ggtacagttc  32880
caaacacgaa gtaagggcga gctccaacca acacaaacag gctgatttat cccgacacac  32940
tggaggtgga ggaagacacg gaagaggcat gttattccaa gcgatccggc aaaggatcaa  33000
agtgcagatc ccgaagatgg caacgctcgc ctccggagcc ctggtgaaat ttaacggcca  33060
aatcaaacat tatgcggttt tccaaactat caatcgccgc ctccaaaagg gcctgaaccc  33120
gcacttccac aatcaccagc aaagcaaaag cgtgattatc aaagtcttca atcatcagat  33180
ggcatgactg tacaatgccc aaataattct catttctcca ctcgcgaata gtgtcgcggc  33240
agatcgtctg aaggtccatg ccatgcatgt taaaaagctc ccagagggcg ccctctaccg  33300
acatgcgtag acacaccatc atgactgcaa aatatcaggc tcctgagaca cctgcagcag  33360
atttaacaga tcaaagtcag gttgctgtcc gcggtcacga atctccatgc gcaaagccat  33420
ttgcaaaaaa ttatataggt ctgtgccaac tagctctgtt aattccgcgt taggaagcaa  33480
atcaggtgag gctatgcagc acaaaagttg cagggaaggc gccaaactca gtaaaaccgc  33540
tccagaataa caaaattgat gaagcggagt cacacagtgt aaaatgtgca accaaaaatc  33600
attcagctgc tcttttaaat agtccagtac ttctatattc aatccgtgca agtactgaag  33660
caactgcgcg ggaacagtca cattaaaaaa aatggggcgg ctcaaataca tgtcgaccta  33720
aaataaaaat aatcattaaa ccagagaagc ttgacgaatg gaaggataaa atacacgctc  33780
cagcaaaagg caggcaaccg gctgtccccg agaaccgtaa aaaaattcat ccgaatgatt  33840
aaaaagaacc acagaaattt cccaccatgt actcggttgt aactcctgag cacacagcaa  33900
cacccccta acgttcatgt ccgccactga aaaaagacgt cccaaatacc caggtggaat  33960
gtcaagagac aactgcagag acagcaaaac aacccctctg ggagcgatca taaactcctc  34020
cggtgagaaa agcgcataca aattagaata accctgttgc tggggcaaaa tagcccggcg  34080
gcccagcaaa tggacataaa tatgttcagc agccatcgcc ccgtcttacc gcgtaaaaag  34140
ccagaaaaat ccagctaact acactctaca gcctattact atatatactc tcctcccact  34200
gacgctatac caccccgccc acgtccaaag ttcacccacg cccaaaaaac ccgcgaaaat  34260
ccagcgccgt cagcacttcc gcaattgtag tctctcaacg tcacttccgc gcgccttttc  34320
cctattccca cacacgcccg cggacttcgc cccgcccgcc ctcgcgccac cccgcgtcac  34380
cccgcgtcac cgcacgtcac cccggccccg cctcgctcct ccccactcat tatcatattg  34440
gcacgtttcc agaataaggt atattattga tgatg                             34475
```

SEQ ID NO: 4 moltype = DNA length = 1092
FEATURE Location/Qualifiers
source 1..1092
mol_type = other DNA
note = Synthetic oligonucleotide sAd4287 Fiber-1
organism = synthetic construct
SEQUENCE: 4

```
atgaaaagaa ccagagttga tgaagacttc aaccccgtct acccttatga ctccacatcc  60
actcctgcgg tccccttat atcccccccg tttgtaaaca gcgatggtct tcaggaaaac  120
cctcctggag tcttaagttt acgaatagct aaacccttgt attttgacat ggaaaggaaa  180
ctagcgcttt cacttggaag aggattggca attacctcca ccggacagct agaaagcaca  240
cagagcgtgc aaaccacccc tccattagtt gtcaacaaca gcaacacgct tgtcctgcgt  300
tattcctccc cgttaggctt atcgggtgac aatttaatac taaattgctc cgatcctctc  360
cgcgtagtaa acaacagcct gacattcagc tacctatctc cacttcgttt tgaaggtggc  420
agtcttacat tcaattacac atctcccctt aaactgttga acagcagcct tgcgatcgga  480
ataaattcca acaaaggtct cggcaatgac agcgatgaac tttctgtcaa actaacatca  540
gatctaaagt ttaacaacga tggaaaaata gcttttggta tacaaagcct gtgtaccacc  600
cccacagccg cctctaactg taccgttttt accaacggtg attctttact ctgtttatgt  660
ttaaccaaat gtggagctca cgtgttagga agtgtgagtt taaccggaat gcaaggaacc  720
ataacagcca tgacacagaa ctacattagt attcaatttc tatttgacaa caatggtgcg  780
ttgacttcat caccgctcct caacaacaac acttggggta tacggcaaaa cgacacttcg  840
tccgctaacc ccgcctacaa tgctcttgca tttatgccta acagcactgt atatgtaaga  900
ggtcaaagtg gtgagcccag aaataactat tacacccaaa catacctag gggaaacgtt  960
aaaaagccaa ttatccttac cgttacctac aactcggctg cttcaggtta ttcactaact  1020
tttaaatggg atgctgtagt aacagaaaaa tttgccactc caacatcttc tttttgctat  1080
attacagaac aa                                                      1092
```

SEQ ID NO: 5 moltype = DNA length = 1089
FEATURE Location/Qualifiers
source 1..1089
mol_type = other DNA
note = Synthetic oligonucleotide sAd4310A Fiber-1
organism = synthetic construct
SEQUENCE: 5

```
atgaaaagaa ccagagttga tgaagacttc aaccccgtct acccctatga caccacaacc  60
actcctgcag ttccctttat atcacccccc tttgtaaaca gcgatggtct tcaggaaaac  120
cccccaggtg ttttaagtct gcgaatagct aaacccctat atttcgacat ggagagaaaa  180
ctagcccttt cacttggaag agggttgaca attaccgccg ccggacaatt agaaagtacg  240
cagagcgtac aaaccaaccc accgttgata attaccaaca acaacacact gaccctacgt  300
cattctcccc ccttaaacct aactgacaat agcttagtgc taggctactc gagtccgctc  360
cgcgtcacag acaacaaact tacatttaac ttcacatcac cactccgtta tgaaaatgaa  420
aaccttactt ttaactatac agagcctctt aaacttataa ataacagcct tgccattgac  480
atcaattcct caaaaggcct tagtagcgtc ggaggctcac tagctgtaaa cctgagttca  540
gacttaaagt ttgacagcaa cggatccata gcttttggca tacaaaccct gtggaccgct  600
ccgacctcga ctggcaactg caccgtctac agcgagggcg attccctact tagtctctgt  660
ttaaccaaat gcggagctca cgtcttagga agtgtaagtt taaccggttt aacaggaacc  720
ataacccaaa tgactgatat ttctgtcacc attcaattta catttgacaa caatggtaag  780
ctactaagct ctccgcttat aaacaacgcc tttagtattc gacagaatga cagtacggcc  840
tcaaacccta cctacaacgc cctggcgttt atgcctaaca gtaccatata tgcaagaggg  900
ggaggtggtg aaccacgaaa caactactac gtccaaacgt atcttagggg aaatgttcaa  960
```

```
aaaccaatca ttcttactgt aacctacaac tcagccgcca caggatattc cttatctttt  1020
aagtggactg ctcttgcacg tgaaaagttt gcaaccccaa caacttcgtt ttgctacatt  1080
acagaacaa                                                          1089

SEQ ID NO: 6            moltype = DNA  length = 1089
FEATURE                 Location/Qualifiers
source                  1..1089
                        mol_type = other DNA
                        note = Synthetic oligonucleotide sAd4312 Fiber-1
                        organism = synthetic construct
SEQUENCE: 6
atgaaaagaa cccgagttga tgaagacttc aaccccgtct acccttatga caccacaacc  60
actccagccg ttcctttcat atcacccccg tttgtaaaca gtgacggtct tcaggaaaac  120
ccccccggag ttttaagcct gcgaatagct aaacccctgt attttgacat ggagagaaaa  180
ctagcccttt cacttggaag agggttaaca attaccgcga acggacaatt agaaagcacc  240
cagagcgtgc agactaaccc gccgttaact gtcaccaata acaacacact tatcctacgc  300
cactcctccc ctttaatcct aactgacaat aatttaaccg taggcttctc aagtcctctc  360
cgtgttatag acaacaaact gacattcact tttacctcac ctctccgtta tgaaaacgaa  420
acccttacct tcaattacac agagcccctt acacttatga acagcaacct tgcgcttaac  480
gtaaactcct ctaaaggcct tagggttgac gggggctcac taggtacaaa cttaagtccg  540
gacttaaggt ttaacagcag tggagccata gcttttggta tacaaaccct atggacaccc  600
ccgacctcaa atcctaactg caccgtttac accgaaagcg attccttact tagtctctgc  660
ttaactaaat gcggagctca cgttttagga agtgtaagct taaccggggt agcaggtacc  720
atgataaaca tggctgaaac ttcgcttgct attgaattta cgtttgacga cactggaaaa  780
ctacttcact caccacttgt taacaccact tttagcattc gtcagggcga cagccccgcc  840
tcaaatccta cctacaatgc tctagcattt atgccaaaca gtaccctcta cgctagagga  900
ggaagtggtg aaccccgaaa caattactac gtccaaacat acctcagggg aaatgttcag  960
agaccgatta ccctcactgt tactttcaac tcagccgcca cgggatattc cttatctttt  1020
aagtggactg ctgttgcacg tgaaaaattt gcagctcctg caacttcatt ttgctacatt  1080
accgaacaa                                                          1089

SEQ ID NO: 7            moltype = DNA  length = 1677
FEATURE                 Location/Qualifiers
source                  1..1677
                        mol_type = other DNA
                        note = Synthetic oligonucleotide sAd4287 Fiber-2
                        organism = synthetic construct
SEQUENCE: 7
atgaaacggg ccagagttga tgaagacttc aacccagtgt acccttatga ccccccatac  60
gctcccgtta tgcccttcat tactccacct tttacctcct cggatgggtt gcaggaaaaa  120
ccacttggag tgttaagttt aaactacaag gatcccatta ctacacaaaa tggatctctc  180
acgttgaaaa taggaaacgg cctcactcta gacaaccagg gacaattaac atcaactgct  240
ggggaagtag agcctccgct cactaatgct aacaacaaac ttgcactagc ctatagcgaa  300
ccattagcag taaaaagcaa ccgcttaact ttatcacaca ccgccccccct tgtcgttgct  360
aataattctt tagcgttgca agtttcagaa cctattttta taaatgacga tgacaagcta  420
gccctgcaga cagccgcccc ccttgtaact aacgctggca cccttcgctt acagagcgcc  480
gcccctttag gattggttga aaatactctt agactgctgt tttctaaacc cttgtatttg  540
caaaatgatt ttcttgcatt aggcattgaa cgcccccctgg ctatagcagc cgcaggtact  600
ctagcactac aactcactcc tccattaaag actaacgatg acgggctgac actatccaca  660
gtcgagccat taactgtaaa aaacggaaac ttaggcttgc aaatatctcg ccctttggtt  720
gttcaaaaca gcagcctttc gcttgctatt acccccccgc tgcgtctatt taacagcgac  780
cccgttcttg gtttgggctt tacttttccc ctagccgtga cagacaacct actctcctta  840
aacatgggag acggtgttaa actaacctat aataaactaa cagccaattt gggtagggat  900
ttacaatttg aaaacggtgc cattgccgta acgcttactg ccgaatcacc tttgcaatac  960
actaacaaac ttcaactgaa tattggagct ggccttcgtt acaatggagc cagcagaaaa  1020
ctagatgtaa acattaacca aaataagggc ttaacttggg acaacgatgc agttattccc  1080
aaattaggat caggtttaca attcgaccct aatggtaaca tcgctgttat ccctgaaacc  1140
gtaaagccgc aaacgttatg gacaactgca gatccatcgc ctaactgctc agtgtaccag  1200
gacttggacg ccaggctgtg gctcgctctt gttaaaagtg gtgacatggt tcatggaagc  1260
attgctctaa aagccctaaa aggaacgttg ctaaatccta cagcaagcta catctccatt  1320
gtgatatatt tttacagcaa cggagtcagg cgtaccaact atcccacgtt tgacaacgaa  1380
ggcaccttag ctaacagcgc tacctgggga taccgagagg ggcaatctgc taacactaat  1440
gtaaccaatg ccactgaatt tatgcccagc tcaaccaggt accccgtgaa taaaggagac  1500
aatattcaga atcaatcttt ttcatacacc tgtatcaaag gagatttcgc tatgcctgtc  1560
ccgttccgtg taacatataa tcatgccctg gaaggatact cccttaagtt cacctggcgc  1620
gttgtagcca accaagcttt tgatattcct tgctgttcct tttcatacat cacagaa     1677

SEQ ID NO: 8            moltype = DNA  length = 1680
FEATURE                 Location/Qualifiers
source                  1..1680
                        mol_type = other DNA
                        note = Synthetic oligonucleotide sAd4310A Fiber-2
                        organism = synthetic construct
SEQUENCE: 8
atgaaacggg cgagagttga tgaagacttc aacccagtgt acccttatga ccccccacat  60
gctcccgtta tgcccttcat tactccacct tttacctcct cggatgggtt gcaggaaaaa  120
ccacttggag tgttaagttt aaactacaga gatcccatta ctacgcaaaa tgggtctctt  180
acagttaaac taggaaacgg cctcactcta gacaaccagg gacaactaac atcaaccgct  240
ggggaagtag aacctccact cactaacgct aacaacaaac ttgcactggt ctatagcgat  300
```

```
cctttagcag taaagcgcaa cagcctaacc ttatcgcaca ccgctcccct tgttattgct  360
gataactctt tagcattgca agtttcagag cctattttta taaatgacaa ggacaaacta  420
gccctgcaaa cagccgcgcc ccttgtaact aacgctggca cccttcgctt acaaagcgcc  480
gccccttag gcattgcaga ccaaacccta aaactcctgt ttaccaaccc tttgtacttg  540
cagaataact ttctcacgtt agccattgaa cgaccccttg ccattaccaa tagtggaaag  600
ctggctctac agctctcccc accgctacaa acagcagaca caggcttgac tttgcaaacc  660
aacgtgccat taactgtaag caacgggacc ctaggcttag ccataaagcg cccacttatt  720
gttcaggaca acaacttgtt tttggacttc agagctcccc tgcgtctttt caacagcgac  780
cccgtactag ggcttaactt ttacacccct cttgcagtgc gcgatgaggc gctcactgtt  840
aacacaggcc gcggcctcac agtgagttac gatggtttaa ttttaaatct tggtaaggat  900
cttcgctttg acaacaacac cgtttctgtc gctcttagtg ctgctttgcc tttacaatac  960
actgatcagc ttcgccttaa cgtgggcgct gggctgcgtt acaatccagt gagtaaaaaa  1020
ttggacgtga accccaatca aaacaagggt ttaacctggg aaaatgacta cctcattgta  1080
aagctaggaa atggattagg ttttgatggc aatggaaaca tagctgtttc tcctcaagtt  1140
acatcgcctg acaccttatg gaccactgcc gatccatccc ccaattgttc catctacact  1200
gatttagatg ccaaaatgtg gctctcgttg gtaaaacaag ggggtgtggt tcacggttct  1260
gttgctttaa aagcattgaa aggaacccta ttgagtccta cggaaagtgc cattgttatt  1320
atactacatt ttgacaatta tggagtgcga attctcaatt atcccacttt gggcactcaa  1380
ggcacgttgg gaaataatgc aacttggggt tataggcagg gagaatctgc agacactaat  1440
gtactcaatg cactagcatt tatgcccagt tcaaaaaggt acccaagagg gcgtggaagc  1500
gaagttcaga atcaaactgt gggctacact tgtatacagg gtgacctttc tatgcccgta  1560
ccgtaccaaa tacagtacaa ctatggacca actggctact cctttaaatt tatttggaga  1620
actgtttcaa gacaaccatt tgacatccca tgctgttttt tctcttacat tacggaagaa  1680
```

```
SEQ ID NO: 9            moltype = DNA  length = 1680
FEATURE                 Location/Qualifiers
source                  1..1680
                        mol_type = other DNA
                        note = Synthetic oligonucleotide sAd4312 Fiber-2
                        organism = synthetic construct
SEQUENCE: 9
atgaaacggg ccagagttga tgaagacttc aatcccgtgt acccttacga tccccccttac  60
gcccccatta tgccgtttat taccccgccg tttacatctt cagatgggtt acaggaaaaa  120
ccacttggtg ttttaagttt aaaatacaag gatcctatca ctacacaaaa tggttctcta  180
acccttaaat taggaaacgg gctgaacatt aacaaccagg gccaacttac atcatctgct  240
ggggaagtcg agcctcccct caccaatgct gacaacaagc tggccttagc ctacagcgac  300
cctctgacat taaaaaacag ccgtctaaca ctgtctcaca atgccccact tgcaattaac  360
aataattctc taagtttgga agtatcagag cctatattta taaataacga caacaaactg  420
tctctgaaag ctgacgcccc cctgacaacc agcgctggaa ccctccgcct gcaaagcgct  480
gctccattag gacttgctga acagacacta aagctgctgt tttctaaccc tttgtacttg  540
cgaggtgact tccttacatt agccattgaa cgcccattgg ctgtaacagc agacgggcta  600
ttatcacttg ccctcaaccc tccgctcaca acaactaaca caggcttagc tctctctacc  660
gcggttccat taactgttac caacgggaac cttagcctaa acgtaaaacg gccgtttatt  720
atacaggacg gcagccttta catggatttt agacccccac tatatctgtt taacagcgag  780
ccacaacttg gtgttaattt taatgcccct ctaactgtta gagataacgg cctagctata  840
aacaccggag acgggctaac agtaacgtat aataaactaa cattaaacct cggtagagac  900
ttgcaatatg aaaatggagc tgcagctgtt aagctaagta ccgcccctcc tctacagtat  960
actactcaac tgcagctgaa tttgggagcg ggcttacgtc taggtcctac taggaactta  1020
gacgtggcca ttaaccacaa taaagggtta gcgtgggaaa acaatgaagt ggttactaaa  1080
ttaggacaag gcctttactt tgattcctcc ggaagcatag ctttatcgcc tacaaacccc  1140
agaccagata ctttatggac cacggccgat ccttcgccaa actgcactgt atatgaatca  1200
cttgactcta gactgtggct agcgcttgtt aaatgtgggg gaatggtaca cggcagcata  1260
gccctacaag ctgaaaaagg ccaattgctg cgtcctactg ctagttttat ctccatcgta  1320
atttacttct acagtgatgg ggtccgtcgc accaactacc ctacaattgg caatgatgag  1380
ggtactctgg ccaacagcgc tacttggggc tacagacaag ggcaatctgc agacaccaac  1440
gtcaccaatg ctgttgaatt catgcctagt ttacacagat atcctataaa tcagggagac  1500
aatattaaaa accaaatgat aacttacact tgcatacaag gcaacgtgaa catgccagta  1560
cccttgaaaa tcacgttcaa tcatgctctt gaaggctact ccttaaagtt tacatggcgt  1620
gtggtggcta atgaaaagtt tgatattcct tgctgttcgt tttcttacat tacagaacaa  1680
```

```
SEQ ID NO: 10           moltype = DNA  length = 2799
FEATURE                 Location/Qualifiers
source                  1..2799
                        mol_type = other DNA
                        note = Synthetic oligonucleotide sAd4287 Hexon
                        organism = synthetic construct
SEQUENCE: 10
atggccaccc catcgatgat gccgcagtgg tcttacatgc acatcgccgg ccaggacgcc  60
tcggagtacc tgagtcccgg cctcgtgcag tttgcccgcg ccaccgacac ctacttcagc  120
ttgggaaaca agtttagaaa ccccaccgtg gcccccaccc acgatgtgac cacggaccgc  180
tcgcagaggc tgaccctgcg ctttgtgccc gtagaccggg aggacaccgc gtactcttac  240
aaagtgcgct acacgctggc cgtaggggac aaccgagtgc tggacatggc cagcacctac  300
tttgacatcc ggggggtgct ggatcggggt cccagcttca agccctactc cggcaccgct  360
tacaactccc tggctcccaa gggcgccccc aatcctgcag aatgggccga taccaacgac  420
agcaacaaac tgaaagtgag gggtcaggcg ccttttgtca gtacttacgg ttctgctacg  480
gcgcttacaa aagatgggat acaggtggga gtggatactt ccgaagcatc tcaggctgtt  540
tatgccgaca gaagttacca gccagaaccc caaattggag agacagagtg gaacagcgaa  600
gtgggtaatg acgacagagt ggcgggaagg gtgctaaaga aaacaactcc catgttccct  660
tgttacggtt catatgccaa gcccaccaac gaaaaaggcg gacaagcaat acagcccacc  720
```

```
gccggcaacg gcgataatca ggctgtagag ttacaattct ttgccactac tagcactccc  780
actgcgccaa aggcagtatt gtacgcggag gacgtggcca ttgaagctcc agatactcac  840
ttagtgttta agccaacagt agtcgcggga actacaagtt cggaagctct gctaacccaa  900
caagccgcac ctaaccgccc aaactacatt gcctttagag ataactttat tggtctcatg  960
tactacaatt caaccgggaa tatgggagta ctggccggac aagcatctca gctcaatgca  1020
gtggttgatc ttcaggacag aaacaccgaa ctgtcatatc agctaatgct ggatgctctg  1080
ggagatcgca gtcggtactt ttctatgtgg aatcaagctg tagatagcta tgatccagat  1140
gtaagaattg tagaaaacca cggtgtggaa gacgaactgc ctaattattg cttcccacta  1200
ggcgggatgg tagtaacgga cacttacaaa gccataaagg taaatggaag cggatggacg  1260
gctaatactg acgttttcag cgagagagta gaaataggct caggtaacct gtttgccatg  1320
gaaattaact tgcaagctaa tctgtggcgc agtttcttgt attccaacat aggactgtac  1380
ctcccggact ctttaaaatt aacccctgac aacatcacgc tccctgagaa caaaaatacc  1440
taccagtata tgaacggtcg cgtaacacca cccgggctcg tggacaccta cgttaacgtg  1500
ggtgcgcgct ggtcccccga tgttatggac agcattaacc cttttaacca ccaccgcaac  1560
gccgggctcc gctaccgttc catgctcctg ggaaacggac gctacgtacc cttccacatt  1620
caggtgcccc agaaattctt tgcaattaaa aacctgctgc tgctccccgg ttcctatacc  1680
tacgagtgga atttccgcaa ggacgtgaac atgattttgc aaagctcgct gggtaacgac  1740
ctgcgagttg acggggccag catacgcttc gacagcatca acctgtatgc taacttttc  1800
cccatggccc acaacacggc ctccaccctg gaagccatgc tgcgcaacga caccaatgac  1860
cagtccttca acgactacct gtgcgcggcc aacatgctgt atcccatccc cgccaacgcc  1920
accagcgtgc ccatctccat cccgtctcgc aactgggccg cctttagggg ttggagtttc  1980
acccgcctca aaaccaagga aacccccctcg ctgggctctg gcttcgaccc ctacttcgtc  2040
tactcaggct ccattcccta cctggacggc actttctatc ttaaccacac tttcaaaaag  2100
gtgtctatca tgttcgattc ctcggtcagc tggcccggca acgaccgcct gctgacgccc  2160
aacgagttcg aaatcaagcg ttcggtggac ggtgaagggt acaacgtggc ccagagcaac  2220
atgaccaagg actggttcct ggttcaaatg ctcagccatt acaacatcgg ttaccagggc  2280
ttctatgtgc ccgagaacta caaggaccgc atgtactcct tctttaggaa cttccaaccc  2340
atgagtcgcc aagtcgtgga ctcagtggct tacagggact actaccagga cgttaagctc  2400
ccctaccagc acaacaactc agggttcgtg ggctacatgg gtcccaccat gcgagagggg  2460
caggcctacc cggccaacta tccttatccc ctaatcggag agactgctgt acccagcctg  2520
acgcagaaaa agttcctctg cgaccgggtg atgtggagga taccccttctc tagcaacttc  2580
atgtctatgg gctccctcac cgacctgggg cagaacatgc tgtacgccaa ctccgctcac  2640
gccttggaca tgacctttga ggtggatccc atggatgagc ccacgcttct ctatgttctg  2700
tttgaagtct tcgacgtggt gcgcatccac cagccgcacc gcggcgtcat cgaggccgtc  2760
tacctgcgca cacctttctc tgccggtaac gccaccacc                         2799
```

```
SEQ ID NO: 11          moltype = DNA  length = 2736
FEATURE                Location/Qualifiers
source                 1..2736
                       mol_type = other DNA
                       note = Synthetic oligonucleotide sAd4310A Hexon
                       organism = synthetic construct
SEQUENCE: 11
atggccaccc catcgatgat gccgcagtgg tcttacatgc acatcgccgg gcaggacgcc  60
tcggagtatc tgagccccgg tcttgtgcag tttgcccgcg ccaccgacac ctacttcagc  120
ttgggaaaca agtttagaaa tcccaccgtg gcccccacgc acgatgtgac cacggatcgt  180
tcgcagaggc tgactctgcg ctttgtaccg gtagaccgtg aggatactgc ctattcttac  240
aaagttcggt atacgttagc cgtaggagac aacagggtgc tggacatggc cagtacttac  300
tttgacatcc gcggtgttct tgaccgcggt ccaagcttta aaccgtatac cggaacggca  360
tacaatgcct tggctccaaa gggcgctcca aatgcttgcc agtggacaac gaccaacggg  420
ggcaataaaa cgaacacttt tgcccaagcc cctttaatag gcacggctat tgacggaacc  480
aacggactgc agattgggca agataatgga caagctgttt atgctgacaa aacctttcaa  540
cccgaaccac aagtgggaga atctcagtgg aatactaatc caaccacaaa cgcagcagga  600
cgcgtgttaa aaacaactac tcgcatgctg ccttgctatg gttcttttgc aaggcccacc  660
aatgagaaag ggggtcaagc ttcaggagac gttaccttcc aatttttcga cactgcctcg  720
gacaatggca acaaccctaa ggtggtgcta tatggagaag acgtcaacat tgaatcgcct  780
gacacacact taatctacaa acccaccgct gacaacacaa actctgaaaa ccttttgggt  840
caacaggccg ctccaaacag agccaattac attgcctttc gggacaactt cattggacta  900
atgtactata attcaacagg aaacatggga gtgttggcag ggcaggcttc ccaactaaat  960
gctgtggtag acttgcaaga cagaaacact gagctttcct accaactcat gttagatgca  1020
ataggagacc ggagtcgtta cttttcaatg tggaaccaag cagtggacag ctatgatcca  1080
gatgtgcgaa ttattgaaaa tcatggcgtt gaggacgaac tgccaaatta ctgcttccct  1140
cttaacgctc aaggaattgc taacacctat aaaggcgtta agaaaaacaa cggcaattgg  1200
gcgaaagacg acgcagtagt agaaactaac gaaattggca taggaaatgt ttttgccatg  1260
gagataaatt taactgctaa cttgtggcga aactttctgt attccaatat tgctttgtac  1320
ctgccagact cctacaagta ttcaccggga aacataacct tacccgaaaa caaaaacagt  1380
tacaattaca ttaatggtcg agtaacagct cctggtctgg tagacacctt tgtaaacatt  1440
ggcgcgcgat ggtctcccga ccccatggac aacgtgaatc cttttaatca ccatcgcaat  1500
gctggtctgc gttatcgctc catgcttcta ggcaacggcc gctacgtgcc cttccacatt  1560
caggtgcctc aaaaattctt tgccattaag aacctgcttc tgctgcctgg gtcctacacc  1620
tacgagtgga acttcagaaa agatgtaaac atgatcttgc agagcacgct gggcaacgac  1680
ctccgtgtcg acggggccag cgtcagattc gacagcatta acctctacgc taatttcttc  1740
cccatggcac ataacaccgc ttccaccctg gaggctatgt tacgcaacga caccaacgac  1800
cagtccttta atgactacct ctgcgcggcc aacatgctat accccattcc tgccaatgcc  1860
accagtgtgc ccatctccat cccctctcgc aactgggcag ctttcagagg gtggagtttc  1920
acccgcctca aaacaaaaga aacccccctcg ctgggttccg gatttgatcc atactttgtt  1980
tactcaggct ccattcccta cctggatggt accttctacc tgaaccacac cttcaaaaag  2040
gtgtctatta tgttcgactc ttctgtgagc tggcccggca acgaccgcct gctgacccct  2100
aatgagtttg aaattaagcg ctcggtggac ggagaaggat acaatgtagc ccagagcaac  2160
```

```
atgaccaaag actggttctt aattcaaatg ctcagccact acaacattgg ttaccaaggg  2220
ttttacgtgc ccgaggctta caaagacaga atgtactcct tttttagaaa cttccaacct  2280
atgagtagac aggtagtgga tgcagatcgg tatgaacaat acaaaaaagt caccgttgag  2340
tatcaacata ataattctgg ttttgtggga tacatgggac ccaccatgag ggaagggcag  2400
gcttatccag cgaattaccc ttatcctctt attggagaca ccgccgtgcc cagcctgacc  2460
cagaaaaagt tcctctgtga ccgcaccatg tggagaatcc ccttctctag caacttcatg  2520
tctatggggg ccctcaccga cctggggcag aacatgctgt acgccaattc cgctcacgcc  2580
ttggatatga cctttgaggt ggaccccatg gatgagccca cgcttctcta tgttctgttt  2640
gaagtcttcg acgtggtgcg catccaccag ccgcaccgcg gcgtcatcga ggccgtctac  2700
ctgcgcacac ctttctctgc cggtaacgcc accaca                            2736

SEQ ID NO: 12          moltype = DNA  length = 2784
FEATURE                Location/Qualifiers
source                 1..2784
                       mol_type = other DNA
                       note = Synthetic oligonucleotide sAd4312 Hexon
                       organism = synthetic construct
SEQUENCE: 12
atggccaccc catcgatgat gccgcagtgg tcttacatgc acatcgccgg ccaggacgcc  60
tcggagtacc tgagtcccgg cctggtgcag tttgcccgcg ccaccgaaag ctacttcagc  120
ttgggaaaca agtttagaaa ccccaccgtg gcccccacgc acgatgtaac cacggaccgc  180
tcgcagaggc tgacactgcg cttcgtgccc gtagaccggg aggacaccgc gtactcctac  240
aaagtgcgct tcaccctcgc cgtaggggac aacagggtgc tggacatggc cagcacgtac  300
tttgacatcc ggggaatgct ggaccgaggg cccagcttta aaccctactc gggaactgcc  360
tacaattcgc tggcacctaa gggcgctccc aaccctagtc aatggactac taccaacgga  420
gggaataaaa caaattcatt tgcccaagca tcctacatag gtcaaagcct gtcgaaagac  480
ggggtgcaag tagcagtaga tacagccgct gggggggctg cagtatatgc tgacaaaacg  540
tttcaaccag aaccccaagt aggaatatca caatggaatg aaaatcctac tacaaatgct  600
gcaggaagaa ttttaaagcc tactaccgca atgcgtccat gctacggttc atacgcttac  660
cccaccaacg aaaaaggtgg gcaggtaaaa atcactgacc ctaacaatga caaaaccggc  720
gctaataacg ttagcttaaa ttttttcaac actgccgctg acaatgggaa taacaatcca  780
aaagtagtac tctacagcga agatgtaaat ttagaagggc cagataccca ccttgttttt  840
aagccagatg taactggcga cgcaaccagt gcagaaaccc tgttaggtca acaagcagct  900
cccaatcgtc caaactacat tgggttcagg gacaacttta ttggcctgat gtactacaat  960
tcaactggaa acatgggagt gctagcaggt caggcttctc agctaaacgc cgtagtggat  1020
cttcaagaca gaaataccga attgtcatat cagctaatgc ttgacgcttt gggtgacaga  1080
agtcggtact tttctatgtg gaatcaagca gtggacagct acgatcctga cgttagaatc  1140
atagaaaatc atggagtaga agacgaactt ccaaattatt gttttccgtt aaatggacag  1200
gggatttcga atacatacaa aggtgtgaaa tataacacaa acacttggac gcaagacact  1260
gatgtagtca caaccaatga aatttccatt ggcaacattt ttgccatgga aataaacctg  1320
gcggctaact tgtggcgcag ctttctgtac tccaatgtcg ccctgtactt gccagattcc  1380
tacaaataca ctcccgacaa tattgaactt cctacaaaca agaacagcta cggctacatt  1440
aacggaaggg taaccgcccc cactgccatc gacacttacg ttaacatcgg cgcccggtgg  1500
tctccggacc ccatggacaa cgttaaccct ttcaaccacc accgcaacgc cggcttgcga  1560
taccgctcca tgctgctggg caacggtcgc tacgtaccct tccacattca ggtgccccag  1620
aaatttttg ccattaaaaa cctgcttctg cttcccgggt cctacaccta cgagtggaac  1680
ttcaggaaag atgtaaacat gatcttgcag agcaccttgg gcaacgacct ccgcgttgac  1740
ggagctagcg tgaggtttga cagcattaac ctctacgcta acttcttccc catggcccac  1800
aacacggcct ccaccttgga agccatgctg cgcaacgaca ccaacgacca gtcctttaat  1860
gattacctgt gcgcggccaa catgctgtac cccatccccg ccaatgccac cagcgtgccg  1920
atctccattc cctcacgcaa ctgggccgcc ttcagaggtt ggagtttcac tcgcctgaaa  1980
accaaggaga ccccctcgct gggctccggt ttcgacccat actttgttta ctccgggagc  2040
attccctacc tggacggaac tttctacctg aaccacacct tcaaaaaggt gtctattatg  2100
tttgactcct ccgtgagctg gcccggtaac gaccgcttgc taacccccaa cgagttcgaa  2160
atcaaacgct cggtggacgg agagggttac aatgtagccc agagcaacat gaccaaagac  2220
tggtttttaa ttcaaatgct aagccactat aacattggct accaaggatt ctacgtgcct  2280
gaagcctaca aggacagaat gtactccttc tttagaaact tccaacccat gagccgccag  2340
gtagtagaca cggtaaacta tgctaactac aaggaagtaa caatgccatt ccagcacaac  2400
aactcaggct tcgtggggta catgggacct accatgagag aggggcaggc ctacccggct  2460
aattatccct acccccctaat cggagccact gccgtgccca gcctgacaca gaaaaagttt  2520
ctctgcgatc gaacaatgtg gaggattccc ttctctagca acttcatgtc catgggggct  2580
ctcaccgacc tggggcagaa catgctgtac gctaactccg ctcacgcctt ggacatgacc  2640
tttgaggtgg accccatgga tgagcccacg cttctctatg ttctgtttga agtcttcgac  2700
gtggtgcgca ttcaccagcc gcaccgcggc gtcatcgagg ccgtctacct gcgcacacct  2760
ttctctgccg gtaacgccac cacc                                         2784

SEQ ID NO: 13          moltype = DNA  length = 492
FEATURE                Location/Qualifiers
source                 1..492
                       mol_type = other DNA
                       note = Synthetic oligonucleotide sAd4287 Fiber-1 Knob
                       organism = synthetic construct
SEQUENCE: 13
ctgtgtacca cccccacagc cgcctctaac tgtaccgttt ttaccaacgg tgattcttta  60
ctctgtttat gtttaaccaa atgtggagct cacgtgttag gaagtgtgag tttaaccgga  120
atgcaaggaa ccataacagc catgacacag aactacatta gtattcaatt tctatttgac  180
aacaatggtg cgttgacttc atcaccgctc ctcaacaaca acacttgggg tatacggcaa  240
aacgacactt cgtccgctaa ccccgcctac aatgctcttg catttatgcc taacagcact  300
gtatatgtaa gaggtcaaag tggtgagccc agaaataact attacaccca aacatacctt  360
```

```
aggggaaacg ttaaaaagcc aattatcctt accgttacct acaactcggc tgcttcaggt  420
tattcactaa cttttaaatg ggatgctgta gtaacagaaa aatttgccac tccaacatct  480
tctttttgct at                                                      492

SEQ ID NO: 14          moltype = DNA  length = 489
FEATURE                Location/Qualifiers
source                 1..489
                       mol_type = other DNA
                       note = Synthetic oligonucleotide sAd4310A Fiber-1 Knob
                       organism = synthetic construct
SEQUENCE: 14
ctgtggaccg ctccgacctc gactggcaac tgcaccgtct acagcgaggg cgattcccta  60
cttagtctct gtttaaccaa atgcggagct cacgtcttag gaagtgtaag tttaaccggt  120
ttaacaggaa ccataaccca aatgactgat atttctgtca ccattcaatt tacatttgac  180
aacaatggta agctactaag ctctccgctt ataaacaacg cctttagtat tcgacagaat  240
gacagtacgg cctcaaaccc tacctacaac gccctggcgt ttatgcctaa cagtaccata  300
tatgcaagag ggggaggtgg tgaaccacga aacaactact acgtccaaac gtatcttagg  360
ggaaatgttc aaaaaccaat cattcttact gtaacctaca actcagccgc cacaggatat  420
tccttatctt ttaagtggac tgctcttgca cgtgaaaagt ttgcaacccc aacaacttcg  480
ttttgctac                                                          489

SEQ ID NO: 15          moltype = DNA  length = 489
FEATURE                Location/Qualifiers
source                 1..489
                       mol_type = other DNA
                       note = Synthetic oligonucleotide sAd4312 Fiber-1 Knob
                       organism = synthetic construct
SEQUENCE: 15
ctatggacac ccccgacctc aaatcctaac tgcaccgttt acaccgaaag cgattcctta  60
cttagtctct gcttaactaa atgcggagct cacgttttag gaagtgtaag cttaaccggg  120
gtagcaggta ccatgataaa catggctgaa acttcgcttg ctattgaatt tacgtttgac  180
gacactggaa aactacttca ctcaccactt gttaacacca cttttagcat tcgtcagggc  240
gacagccccg cctcaaatcc tacctacaat gctctagcat ttatgccaaa cagtaccctc  300
tacgctagag gaggaagtgg tgaaccccga aacaattact acgtccaaac atacctcagg  360
ggaaatgttc agagaccgat taccctcact gttactttca actcagccgc cacgggatat  420
tccttatctt ttaagtggac tgctgttgca cgtgaaaaat ttgcagctcc tgcaacttca  480
ttttgctac                                                          489

SEQ ID NO: 16          moltype = DNA  length = 510
FEATURE                Location/Qualifiers
source                 1..510
                       mol_type = other DNA
                       note = Synthetic oligonucleotide sAd4287 Fiber-2 Knob
                       organism = synthetic construct
SEQUENCE: 16
tggacaactg cagatccatc gcctaactgc tcagtgtacc aggacttgga cgccaggctg  60
tggctcgctc ttgttaaaag tggtgacatg gttcatggaa gcattgctct aaaagcccta  120
aaaggaacgt tgctaaatcc tacagcaagc tacatctcca ttgtgatata tttttacagc  180
aacggagtca ggcgtaccaa ctatcccacg tttgacaacg aaggcacctt agctaacagc  240
gctacctggg gataccgaga ggggcaatct gctaacacta atgtaaccaa tgccactgaa  300
tttatgccca gctcaaccag gtaccccgtg aataaaggag acaatattca gaatcaatct  360
ttttcataca cctgtatcaa aggagatttc gctatgcctg tcccgttccg tgtaacatat  420
aatcatgccc tggaaggata ctcccttaag ttcacctggc gcgttgtagc caaccaagct  480
tttgatattc cttgctgttc cttttcatac                                   510

SEQ ID NO: 17          moltype = DNA  length = 513
FEATURE                Location/Qualifiers
source                 1..513
                       mol_type = other DNA
                       note = Synthetic oligonucleotide sAd4310A Fiber-2 Knob
                       organism = synthetic construct
SEQUENCE: 17
ttatggacca ctgccgatcc atcccccaat tgttccatct acactgattt agatgccaaa  60
atgtggctct cgttggtaaa acaagggggt gtggttcacg gttctgttgc tttaaaagca  120
ttgaaaggaa ccctattgag tcctacggaa agtgccattg ttattatact acattttgac  180
aattatggag tgcgaattct caattatccc actttgggca ctcaaggcac gttgggaaat  240
aatgcaactt ggggttatag gcagggagaa tctgcagaca ctaatgtact caatgcacta  300
gcatttatgc ccagttcaaa aaggtaccca agagggcgtg gaagcgaagt tcagaatcaa  360
actgtgggct acacttgtat acagggtgac ctttctatgc ccgtaccgta ccaaatacag  420
tacaactatg gaccaactgg ctactccttt aaatttattt ggagaactgt ttcaagacaa  480
ccatttgaca tcccatgctg ttttttctct tac                               513

SEQ ID NO: 18          moltype = DNA  length = 516
FEATURE                Location/Qualifiers
source                 1..516
                       mol_type = other DNA
                       note = Synthetic oligonucleotide sAd4312 Fiber-2 Knob
                       organism = synthetic construct
SEQUENCE: 18
```

```
ttatggacca cggccgatcc ttcgccaaac tgcactgtat atgaatcact tgactctaga  60
ctgtggctag cgcttgttaa atgtggggga atggtacacg gcagcatagc cctacaagct  120
gaaaaaggcc aattgctgcg tcctactgct agttttatct ccatcgtaat ttacttctac  180
agtgatgggg tccgtcgcac caactaccct acaattggca atgatgaggg tactctggcc  240
aacagcgcta cttggggcta cagacaaggg caatctgcag acaccaacgt caccaatgct  300
gttgaattca tgcctagttt acacagatat cctataaatc agggagacaa tattaaaaac  360
caaatgataa cttacacttg catacaaggc aacgtgaaca tgccagtacc cttgaaaatc  420
acgttcaatc atgctcttga aggctactcc ttaaagttta catggcgtgt ggtggctaat  480
gaaaagtttg atattccttg ctgttcgttt tcttac                            516

SEQ ID NO: 19          moltype = AA  length = 364
FEATURE                Location/Qualifiers
source                 1..364
                       mol_type = protein
                       note = Synthetic polypeptide sAd4287 Fiber-1
                       organism = synthetic construct
SEQUENCE: 19
MKRTRVDEDF NPVYPYDSTS TPAVPFISPP FVNSDGLQEN PPGVLSLRIA KPLYFDMERK  60
LALSLGRGLA ITSTGQLEST QSVQTTPPLV VNNSNTLVLR YSSPLGLSGD NLILNCSDPL  120
RVVNNSLTFS YLSPLRFEGG SLTFNYTSPL KLLNSSLAIG INSNKGLGND SDELSVKLTS  180
DLKFNNDGKI AFGIQSLCTT PTAASNCTVF TNGDSLLCLC LTKCGAHVLG SVSLTGMQGT  240
ITAMTQNYIS IQFLFDNNGA LTSSPLLNNN TWGIRQNDTS SANPAYNALA FMPNSTVYVR  300
GQSGEPRNNY YTQTYLRGNV KKPIILTVTY NSAASGYSLT FKWDAVVTEK FATPTSSFCY  360
ITEQ                                                               364

SEQ ID NO: 20          moltype = AA  length = 363
FEATURE                Location/Qualifiers
source                 1..363
                       mol_type = protein
                       note = Synthetic polypeptide sAd4310A Fiber-1
                       organism = synthetic construct
SEQUENCE: 20
MKRTRVDEDF NPVYPYDTTT TPAVPFISPP FVNSDGLQEN PPGVLSLRIA KPLYFDMERK  60
LALSLGRGLT ITAAGQLEST QSVQTNPPLI ITNNNTLTLR HSPPLNLTDN SLVLGYSSPL  120
RVTDNKLTFN FTSPLRYENE NLTFNYTEPL KLINNSLAID INSSKGLSSV GGSLAVNLSS  180
DLKFDSNGSI AFGIQTLWTA PTSTGNCTVY SEGDSLLSLC LTKCGAHVLG SVSLTGLTGT  240
ITQMTDISVT IQFTFDNNGK LLSSPLINNA FSIRQNDSTA SNPTYNALAF MPNSTIYARG  300
GGGEPRNNYY VQTYLRGNVQ KPIILTVTYN SAATGYSLSF KWTALAREKF ATPTTSFCYI  360
TEQ                                                                363

SEQ ID NO: 21          moltype = AA  length = 360
FEATURE                Location/Qualifiers
source                 1..360
                       mol_type = protein
                       note = Synthetic polypeptide sAd4312 Fiber-1
                       organism = synthetic construct
SEQUENCE: 21
MKRTRVDEDF NPVYPYDTTT TPAVPFISPP FVNSDGLQEN PPGVLSLRIA KPLYFDMERK  60
LALSLGRGLT ITANGQLEST QSVQTNPPLT VTNNNTLILR HSSPLILTDN NLTVGFSSPL  120
RVIDNKLTFT FTSPLRYENE TLTFNYTEPL TLMNSNLALN VNSSKGLRVD GGSLGTNLSP  180
DLRFNSSGAI AFGIQTLWTP PTSNPNCTVY TESDSLLSLC LTKCGAHVLG SVSLTGVAGT  240
MINMAETSLA IEFTFDDTGK LLHSPLVNTT FSIRQGDSPA SNPTYNALAF MPNSTLYARG  300
GSGEPRNNYY VQTYLRGNVQ RPITLTVTFN SAATGYSLSF KWTAVAREKF AAPATSFCYI  360

SEQ ID NO: 22          moltype = AA  length = 559
FEATURE                Location/Qualifiers
source                 1..559
                       mol_type = protein
                       note = Synthetic polypeptide sAd4287 Fiber-2
                       organism = synthetic construct
SEQUENCE: 22
MKRARVDEDF NPVYPYDPPY APVMPFITPP FTSSDGLQEK PLGVLSLNYK DPITTQNGSL  60
TLKIGNGLTL DNQGQLTSTA GEVEPPLTNA NNKLALAYSE PLAVKSNRLT LSHTAPLVVA  120
NNSLALQVSE PIFINDDDKL ALQTAAPLVT NAGTLRLQSA APLGLVENTL RLLFSKPLYL  180
QNDFLALGIE RPLAIAAAGT LALQLTPPLK TNDDGLTLST VEPLTVKNGN LGLQISRPLV  240
VQNSSLSLAI TPPLRLFNSD PVLGLGFTFP LAVTDNLLSL NMGDGVKLTY NKLTANLGRD  300
LQFENGAIAV TLTAESPLQY TNKLQLNIGA GLRYNGASRK LDVNINQNKG LTWDNDAVIP  360
KLGSGLQFDP NGNIAVIPET VKPQTLWTTA DPSPNCSVYQ DLDARLWLAL VKSGDMVHGS  420
IALKALKGTL LNPTASYISI VIYFYSNGVR RTNYPTFDNE GTLANSATWG YREGQSANTN  480
VTNATEFMPS STRYPVNKGD NIQNQSFSYT CIKGDFAMPV PFRVTYNHAL EGYSLKFTWR  540
VVANQAFDIP CCSFSYITE                                               559

SEQ ID NO: 23          moltype = AA  length = 560
FEATURE                Location/Qualifiers
source                 1..560
                       mol_type = protein
                       note = Synthetic polypeptide sAd4310A Fiber-2
                       organism = synthetic construct
SEQUENCE: 23
```

```
MKRARVDEDF NPVYPYDPPH APVMPFITPP FTSSDGLQEK PLGVLSLNYR DPITTQNGSL  60
TVKLGNGLTL DNQGQLTSTA GEVEPPLTNA NNKLALVYSD PLAVKRNSLT LSHTAPLVIA  120
DNSLALQVSE PIFINDKDKL ALQTAAPLVT NAGTLRLQSA APLGIADQTL KLLFTNPLYL  180
QNNFLTLAIE RPLAITNSGK LALQLSPPLQ TADTGLTLQT NVPLTVSNGT LGLAIKRPLI  240
VQDNNLFLDF RAPLRLFNSD PVLGLNFYTP LAVRDEALTV NTGRGLTVSY DGLILNLGKD  300
LRFDNNTVSV ALSAALPLQY TDQLRLNVGA GLRYNPVSKK LDVNPNQNKG LTWENDYLIV  360
KLGNGLGFDG NGNIAVSPQV TSPDTLWTTA DPSPNCSIYT DLDAKMWLSL VKQGGVVHGS  420
VALKALKGTL LSPTESAIVI ILHFDNYGVR ILNYPTLGTQ GTLGNNATWG YRQGESADTN  480
VLNALAFMPS SKRYPRGRGS EVQNQTVGYT CIQGDLSMPV PYQIQYNYGP TGYSFKFIWR  540
TVSRQPFDIP CCFFSYITEE                                              560

SEQ ID NO: 24          moltype = AA  length = 560
FEATURE                Location/Qualifiers
source                 1..560
                       mol_type = protein
                       note = Synthetic polypeptide sAd4312 Fiber-2
                       organism = synthetic construct
SEQUENCE: 24
MKRARVDEDF NPVYPYDPPY APIMPFITPP FTSSDGLQEK PLGVLSLKYK DPITTQNGSL  60
TLKLGNGLNI NNQGQLTSSA GEVEPPLTNA DNKLALAYSD PLTLKNSRLT LSHNAPLAIN  120
NNSLSLEVSE PIFINNDNKL SLKADAPLTT SAGTLRLQSA APLGLAEQTL KLLFSNPLYL  180
RGDFLTLAIE RPLAVTADGL LSLALNPPLT TTNTGLALST AVPLTVTNGN LSLNVKRPFI  240
IQDGSLYMDF RPPLYLFNSE PQLGVNFNAP LTVRDNGLAI NTGDGLTVTY NKLTLNLGRD  300
LQYENGAAAV KLSTAPPLQY TTQLQLNLGA GLRLGPTRNL DVAINHNKGL AWENNEVVTK  360
LGQGLYFDSS GSIALSPTNP RPDTLWTTAD PSPNCTVYES LDSRLWLALV KCGGMVHGSI  420
ALQAEKGQLL RPTASFISIV IYFYSDGVRR TNYPTIGNDE GTLANSATWG YRQGQSADTN  480
VTNAVEFMPS LHRYPINQGD NIKNQMITYT CIQGNVNMPV PLKITFNHAL EGYSLKFTWR  540
VVANEKFDIP CCSFSYITEQ                                              560

SEQ ID NO: 25          moltype = AA  length = 933
FEATURE                Location/Qualifiers
source                 1..933
                       mol_type = protein
                       note = Synthetic polypeptide sAd4287 Hexon
                       organism = synthetic construct
SEQUENCE: 25
MATPSMMPQW SYMHIAGQDA SEYLSPGLVQ FARATDTYFS LGNKFRNPTV APTHDVTTDR  60
SQRLTLRFVP VDREDTAYSY KVRYTLAVGD NRVLDMASTY FDIRGVLDRG PSFKPYSGTA  120
YNSLAPKGAP NPAEWADTND SNKLKVRGQA PFVSTYGSAT ALTKDGIQVG VDTSEASQAV  180
YADRSYQPEP QIGETEWNSE VGNDDRVAGR VLKKTTPMFP CYGSYAKPTN EKGGQAIQPT  240
AGNGDNQAVE LQFFATTSTP TAPKAVLYAE DVAIEAPDTH LVFKPTVVAG TTSSEALLTQ  300
QAAPNRPNYI AFRDNFIGLM YYNSTGNMGV LAGQASQLNA VVDLQDRNTE LSYQLMLDAL  360
GDRSRYFSMW NQAVDSYDPD VRIVENHGVE DELPNYCFPL GGMVVTDTYK AIKVNGSGWT  420
ANTDVFSERV EIGSGNLFAM EINLQANLWR SFLYSNIGLY LPDSLKLTPD NITLPENKNT  480
YQYMNGRVTP PGLVDTYVNV GARWSPDVMD SINPFNHHRN AGLRYRSMLL GNGRYVPFHI  540
QVPQKFFAIK NLLLLPGSYT YEWNFRKDVN MILQSSLGND LRVDGASIRF DSINLYANFF  600
PMAHNTASTL EAMLRNDTND QSFNDYLCAA NMLYPIPANA TSVPISIPSR NWAAFRGWSF  660
TRLKTKETPS LGSGFDPYFV YSGSIPYLDG TFYLNHTFKK VSIMFDSSVS WPGNDRLLTP  720
NEFEIKRSVD GEGYNVAQSN MTKDWFLVQM LSHYNIGYQG FYVPENYKDR MYSFFRNFQP  780
MSRQVVDSVA YRDYYQDVKL PYQHNNSGFV GYMGPTMREG QAYPANYPYP LIGETAVPSL  840
TQKKFLCDRV MWRIPFSSNF MSMGSLTDLG QNMLYANSAH ALDMTFEVDP MDEPTLLYVL  900
FEVFDVVRIH QPHRGVIEAV YLRTPFSAGN ATT                               933

SEQ ID NO: 26          moltype = AA  length = 912
FEATURE                Location/Qualifiers
source                 1..912
                       mol_type = protein
                       note = Synthetic polypeptide sAd4310A Hexon
                       organism = synthetic construct
SEQUENCE: 26
MATPSMMPQW SYMHIAGQDA SEYLSPGLVQ FARATDTYFS LGNKFRNPTV APTHDVTTDR  60
SQRLTLRFVP VDREDTAYSY KVRYTLAVGD NRVLDMASTY FDIRGVLDRG PSFKPYTGTA  120
YNALAPKGAP NACQWTTTNG GNKTNTFAQA PLIGTAIDGT NGLQIGQDNG QAVYADKTFQ  180
PEPQVGESQW NTNPTTNAAG RVLKTTTRML PCYGSFARPT NEKGGQASGD VTFQFFDTAS  240
DNGNNPKVVL YGEDVNIESP DTHLIYKPTA DNTNSENLLG QQAAPNRANY IAFRDNFIGL  300
MYYNSTGNMG VLAGQASQLN AVVDLQDRNT ELSYQLMLDA IGDRSRYFSM WNQAVDSYDP  360
DVRIIENHGV EDELPNYCFP LNAQGIANTY KGVKKNNGNW AKDDAVVETN EIGIGNVFAM  420
EINLTANLWR NFLYSNIALY LPDSYKYSPG NITLPENKNS YNYINGRVTA PGLVDTFVNI  480
GARWSPDPMD NVNPFNHHRN AGLRYRSMLL GNGRYVPFHI QVPQKFFAIK NLLLLPGSYT  540
YEWNFRKDVN MILQSTLGND LRVDGASVRF DSINLYANFF PMAHNTASTL EAMLRNDTND  600
QSFNDYLCAA NMLYPIPANA TSVPISIPSR NWAAFRGWSF TRLKTKETPS LGSGFDPYFV  660
YSGSIPYLDG TFYLNHTFKK VSIMFDSSVS WPGNDRLLTP NEFEIKRSVD GEGYNVAQSN  720
MTKDWFLIQM LSHYNIGYQG FYVPEAYKDR MYSFFRNFQP MSRQVVDADR YEQYKKVTVE  780
YQHNNSGFVG YMGPTMREGQ AYPANYPYPL IGDTAVPSLT QKKFLCDRTM WRIPFSSNFM  840
SMGALTDLGQ NMLYANSAHA LDMTFEVDPM DEPTLLYVLF EVFDVVRIHQ PHRGVIEAVY  900
LRTPFSAGNA TT                                                      912

SEQ ID NO: 27          moltype = AA  length = 928
FEATURE                Location/Qualifiers
```

```
source                  1..928
                        mol_type = protein
                        note = Synthetic polypeptide sAd4312 Hexon
                        organism = synthetic construct
SEQUENCE: 27
MATPSMMPQW SYMHIAGQDA SEYLSPGLVQ FARATESYFS LGNKFRNPTV APTHDVTTDR  60
SQRLTLRFVP VDREDTAYSY KVRFTLAVGD NRVLDMASTY FDIRGMLDRG PSFKPYSGTA  120
YNSLAPKGAP NPSQWTTTNG GNKTNSFAQA SYIGQSLSKD GVQVAVDTAA GGAAVYADKT  180
FQPEPQVGIS QWNENPTTNA AGRILKPTTA MRPCYGSYAY PTNEKGGQVK ITDPNNDKTG  240
ANNVSLNFFN TAADNGNNNP KVVLYSEDVN LEGPDTHLVF KPDVTGDATS AETLLGQQAA  300
PNRPNYIGFR DNFIGLMYYN STGNMGVLAG QASQLNAVVD LQDRNTELSY QLMLDALGDR  360
SRYFSMWNQA VDSYDPDVRI IENHGVEDEL PNYCFPLNGQ GISNTYKGVK YNTNTWTQDT  420
DVVTTNEISI GNIFAMEINL AANLWRSFLY SNVALYLPDS YKYTPDNIEL PTNKNSYGYI  480
NGRVTAPTAI DTYVNIGARW SPDPMDNVNP FNHHRNAGLR YRSMLLGNGR YVPFHIQVPQ  540
KFFAIKNLLL LPGSYTYEWN FRKDVNMILQ STLGNDLRVD GASVRFDSIN LYANFFPMAH  600
NTASTLEAML RNDTNDQSFN DYLCAANMLY PIPANATSVP ISIPSRNWAA FRGWSFTRLK  660
TKETPSLGSG FDPYFVYSGS IPYLDGTFYL NHTFKKVSIM FDSSVSWPGN DRLLTPNEFE  720
IKRSVDGEGY NVAQSNMTKD WFLIQMLSHY NIGYQGFYVP EAYKDRMYSF FRNFQPMSRQ  780
VVDTVNYANY KEVTMPFQHN NSGFVGYMGP TMREGQAYPA NYPYPLIGAT AVPSLTQKKF  840
LCDRTMWRIP FSSNFMSMGA LTDLGQNMLY ANSAHALDMT FEVDPMDEPT LLYVLFEVFD  900
VVRIHQPHRG VIEAVYLRTP FSAGNATT                                     928

SEQ ID NO: 28           moltype = AA  length = 168
FEATURE                 Location/Qualifiers
source                  1..168
                        mol_type = protein
                        note = Synthetic polypeptide sAd4287 Fiber-1 Knob
                        organism = synthetic construct
SEQUENCE: 28
LCTTPTAASN CTVFTNGDSL LCLCLTKCGA HVLGSVSLTG MQGTITAMTQ NYISIQFLFD  60
NNGALTSSPL LNNNTWGIRQ NDTSSANPAY NALAFMPNST VYVRGQSGEP RNNYYTQTYL  120
RGNVKKPIIL TVTYNSAASG YSLTFKWDAV VTEKFATPTS SFCYITEQ               168

SEQ ID NO: 29           moltype = AA  length = 163
FEATURE                 Location/Qualifiers
source                  1..163
                        mol_type = protein
                        note = Synthetic polypeptide sAd4310A Fiber-1 Knob
                        organism = synthetic construct
SEQUENCE: 29
LWTAPTSTGN CTVYSEGDSL LSLCLTKCGA HVLGSVSLTG LTGTITQMTD ISVTIQFTFD  60
NNGKLLSSPL INNAFSIRQN DSTASNPTYN ALAFMPNSTI YARGGGGEPR NNYYVQTYLR  120
GNVQKPIILT VTYNSAATGY SLSFKWTALA REKFATPTTS FCY                    163

SEQ ID NO: 30           moltype = AA  length = 163
FEATURE                 Location/Qualifiers
source                  1..163
                        mol_type = protein
                        note = Synthetic polypeptide sAd4312 Fiber-1 Knob
                        organism = synthetic construct
SEQUENCE: 30
LWTPPTSNPN CTVYTESDSL LSLCLTKCGA HVLGSVSLTG VAGTMINMAE TSLAIEFTFD  60
DTGKLLHSPL VNTTFSIRQG DSPASNPTYN ALAFMPNSTL YARGGSGEPR NNYYVQTYLR  120
GNVQRPITLT VTFNSAATGY SLSFKWTAVA REKFAAPATS FCY                    163

SEQ ID NO: 31           moltype = AA  length = 171
FEATURE                 Location/Qualifiers
source                  1..171
                        mol_type = protein
                        note = Synthetic polypeptide sAd4287 Fiber-2 Knob
                        organism = synthetic construct
SEQUENCE: 31
LWTTADPSPN CSVYQDLDAR LWLALVKSGD MVHGSIALKA LKGTLLNPTA SYISIVIYFY  60
SNGVRRTNYP TFDNEGTLAN SATWGYREGQ SANTNVTNAT EFMPSSTRYP VNKGDNIQNQ  120
SFSYTCIKGD FAMPVPFRVT YNHALEGYSL KFTWRVVANQ AFDIPCCSFS Y           171

SEQ ID NO: 32           moltype = AA  length = 171
FEATURE                 Location/Qualifiers
source                  1..171
                        mol_type = protein
                        note = Synthetic polypeptide sAd4310A Fiber-2 Knob
                        organism = synthetic construct
SEQUENCE: 32
LWTTADPSPN CSIYTDLDAK MWLSLVKQGG VVHGSVALKA LKGTLLSPTE SAIVIILHFD  60
NYGVRILNYP TLGTQGTLGN NATWGYRQGE SADTNVLNAL AFMPSSKRYP RGRGSEVQNQ  120
TVGYTCIQGD LSMPVPYQIQ YNYGPTGYSF KFIWRTVSRQ PFDIPCCFFS Y           171

SEQ ID NO: 33           moltype = AA  length = 172
FEATURE                 Location/Qualifiers
```

```
source                  1..172
                        mol_type = protein
                        note = Synthetic polypeptide sAd4312 Fiber-2 Knob
                        organism = synthetic construct
SEQUENCE: 33
LWTTADPSPN CTVYESLDSR LWLALVKCGG MVHGSIALQA EKGQLLRPTA SFISIVIYFY  60
SDGVRRTNYP TIGNDEGTLA NSATWGYRQG QSADTNVTNA VEFMPSLHRY PINQGDNIKN  120
QMITYTCIQG NVNMPVPLKI TFNHALEGYS LKFTWRVVAN EKFDIPCCSF SY          172

SEQ ID NO: 34           moltype = DNA  length = 6109
FEATURE                 Location/Qualifiers
source                  1..6109
                        mol_type = other DNA
                        note = Synthetic oligonucleotide sAdApt4287.Empty
                        organism = synthetic construct
SEQUENCE: 34
attaacatca tcaataatat accttattct ggaaacgtgc caatatgata atgagcgggg  60
aggagcgagg cggggccggg gtgacgtgcg gtgacgcggg gtgacgcggg gtggcgcgag  120
ggcggggcgg gagtggggag gcgcttagtt tttacgtatg cggaaggagg ttttataccg  180
gaagttgggt aatttgggcg tatatttgta agttttgtgt aatttggcgc gaaaaccggg  240
taatgaggaa gttgaggtta atatgtactt tttatgactg ggcggaattt ctgctgatca  300
gcagtgaact ttgggcgctg acggggaggt ttcgctacgt ggcagtacca cgagaaggct  360
caaaggtccc atttattgta ctcctcagcg ttttcgctgg gtatttaaac gctgtcagat  420
catcaagagg ccactcttga gtgccggcga gtagagtttt ctcctgtcga ctggtcaata  480
ttggccatta gccatattat tcattggtta tatagcataa atcaatattg gctattggcc  540
attgcatacg ttgtatccat atcataatat gtacatttat attggctcat gtccaacatt  600
accgccatgt tgacattgat tattgactag ttattaatag taatcaatta cggggtcatt  660
agttcatagc ccatatatgg agttccgcgt tacataactt acggtaaatg gcccgcctgg  720
ctgaccgccc aacgaccccc gcccattgac gtcaataatg acgtatgttc ccatagtaac  780
gccaataggg actttccatt gacgtcaatg ggtggagtat ttacggtaaa ctgcccactt  840
ggcagtacat caagtgtatc atatgccaag tacgccccct attgacgtca atgacggtaa  900
atggcccgcc tggcattatg cccagtacat gaccttatgg gactttccta cttggcagta  960
catctacgta ttagtcatcg ctattaccat ggtgatgcgg ttttggcagt acatcaatgg  1020
gcgtggatag cggtttgact cacggggatt tccaagtctc caccccattg acgtcaatgg  1080
gagtttgttt tggcaccaaa atcaacggga ctttccaaaa tgtcgtaaca actccgcccc  1140
attgacgcaa atgggcggta ggcgtgtacg gtgggaggtc tatataagca gagctcgttt  1200
agtgaaccgt cagatcgcct ggagacgcca tccacgctgt tttgacctcc atagaagaca  1260
ccgggaccga tccagcctcc gcggccggga acggtgcatt ggaagcttgg taccggtgaa  1320
ttcgctagcg ttaacggatc ctctagacga gatccgaact tgtttattgc agcttataat  1380
ggttacaaat aaagcaatag catcacaaat ttcacaaata aagcattttt ttcactgcat  1440
tctagttgtg gtttgtccaa actcatcaat gtatcttatc atgtctagat ccttaaggaa  1500
tgcggagcta atcatttgag gttgtatcct gtaaccctga acgtcaccga ggagctgagg  1560
acggaccacc acatgctgtc ttgcctgcgt accgactatg aatccagtga tgaggagtga  1620
ggtgaggggc ggagccacaa agggtataaa ggggcatgaa gggtggacgc ggtgtttcaa  1680
aatgagcggg acgacggacg gcaatgcgtt tgagggggga gtgttcagcc catatctgac  1740
atctcgtctt ccttcctggg caggagtgcg tcagaatgta gtgggctcca ccgtggacgg  1800
acggccggtc gcccctgcaa attccgccac cctcacctat gccaccgtgg gatcatcgtt  1860
ggacactgcc gcggcagctg ccgcttctgc tgccgcttct actgctcgcg gcatggcggc  1920
tgattttgga ctatataacc aactggccac tgcagctgtg gcgtctcggt ctctggttca  1980
agaagatgcc ctgaatgtga tcttgactcg cctggagatc atgtcacgtc gcctggacga  2040
actggctgcg cagatatccc aagctaaccc cgataccgct tcagaatctt aaataaagac  2100
aaacaaattt gttgaaaagt aaaatggctt tatttgtttt ttttggctcg gtaggctcgg  2160
gtccacctgt ctcggtcgtt aaggactttg tgtatgtttt ccaaaacacg gtacagatgg  2220
gcttggatgt tcaagtacat gggcatgagg ccatctttgg ggtggagata ggaccactga  2280
agagcgtcat gttccggggt ggtattgtaa atcacccagt cgtagcaggg tttttgagcg  2340
tggaactgga atatgtcctt caggagcagg ctaatggcca agggcagccc cttagtgtag  2400
gtgtttacaa agcggttgag ctgggaggga tgcatgcggg gggagatgat atgcatcttg  2460
gcttggattt tgaggttagc tatgttacca cccaggtctc tgcgggggtt catgttatga  2520
aggaccacca gcacggtgta gccggtgcac ttggggaact tgtcatgcag tttggagggg  2580
aaggcgtgga agaatttaga tacccccttg tgcccccccta ggttttccat gcactcatcc  2640
ataataatgg caatgggacc cctggcggcc gctttagcaa acacgttttg ggggttggaa  2700
acatcatagt tttgctctag agtgagctca tcataggcca tctttacaaa gcggggtagg  2760
agggtgcccg actgggggat gatagttcca tctgggcctg gagcgtagtt gccctcacag  2820
atctgcatct cccaggcctt aatttccgag gggggggatca tgtccacctg gggggcgata  2880
aagaacacgg tttctggcgg gggattgatg agctgggtgg aaagcaagtt acgcaatagc  2940
tgggatttgc cgcaaccggt ggggccgtag atgaccccga tgacgggttg cagctggtag  3000
ttcagagagg aacagctgcc gtcggggcgc aggagggggg ccacatcgtt catcatgctt  3060
ctgacatgtt tattttcact cactaagttt tgcaagagcc tctccccacc cagggataag  3120
agttcttcca ggctgttgaa gtgtttcagc ggtttcaggc cgtcggccat gggcatcttt  3180
tcaagcgact gacgaagcaa gtacagtcgg tcccagagct cggtgacgtg ctctatggaa  3240
tctcgatcca gcagacttct tggttgcggg ggttgggccg actttcgctg tagggcacca  3300
gccggtgggc gtccagggcc gcgagggttc tgtccttcca gggtctcagc gttcgggtga  3360
gggtggtctc ggtgacggtg aagggatgag ccccgggctg ggcgcttgcg agggtgcgct  3420
tcaggctcat cctgctggtg ctgaagcggg cgtcgtctcc ctgtgagtcg gccagatagc  3480
aacgaagcat gaggtcgtag ctgagggact cggccgcgtg tcccttggcg cgcagctttc  3540
ccttggaaac gtgctgacat ttggtgcagt gcagacactt gagggcgtag agttttgggg  3600
ccaggaagac cgactcgggc gagtaggcgt cggctccgca ctgagcgcag acggtctcgc  3660
actccaccag ccacgtgagc tcgggtttag cgggatcaaa aaccaagttg cctccatttt  3720
ttttgatgcg tttcttacct tgcgtctcca tgagtctgtg tcccgcttcc gtgacaaaaa  3780
```

```
ggctgtcggt gtccccgtag accgacttga gggggcgatc ttccaaaggt gttccgaggt  3840
cttccgcgta caggaactgg gaccactccg agacaaaggc tcgggtccag gctaacacga  3900
aggaggcgat ctgcgagggg tatctgtcgt tttcaatgag ggggtccacc ttttccaggg  3960
tgtgcagaca caggtcgtcc tcctccgcgt ccacgaagtt aattaattcg aacccataat  4020
acccataata gctgtttgcc atcgacgcga ggctggatgg ccttccccat tatgattctt  4080
ctcgcttccg gcggcatcgg gatgcccgcg ttgcaggcca tgctgtccag gcaggtagat  4140
gacgaccatc agggacagct tcaaggatcg ctcgcggctc ttaccagccc agcaaaaggc  4200
caggaaccgt aaaaaggccg cgttgctggc gtttttccat aggctccgcc cccctgacga  4260
gcatcacaaa aatcgacgct caagtcagag gtggcgaaac ccgacaggac tataaagata  4320
ccaggcgttt ccccctggaa gctccctcgt gcgctctcct gttccgaccc tgccgcttac  4380
cggatacctg tccgcctttc tcccttcggg aagcgtggcg ctttctcata gctcacgctg  4440
taggtatctc agttcggtgt aggtcgttcg ctccaagctg ggctgtgtgc acgaaccccc  4500
cgttcagccc gaccgctgcg ccttatccgg taactatcgt cttgagtcca acccggtaag  4560
acacgactta tcgccactgg cagcagccac tggtaacagg attagcagag cgaggtatgt  4620
aggcggtgct acagagttct tgaagtggtg gcctaactac ggctacacta gaaggacagt  4680
atttggtatc tgcgctctgc tgaagccagt taccttcgga aaaagagttg gtagctcttg  4740
atccggcaaa caaaccaccg ctggtagcgg tggtttttt gtttgcaagc agcagattac  4800
gcgcagaaaa aaaggatctc aagaagatcc tttgatcttt tctacggggt ctgacgctca  4860
gtggaacgaa aactcacgtt aagggatttt ggtcatgaga ttatcaaaaa ggatcttcac  4920
ctagatcctt ttaaattaaa aatgaagttt taaatcaatc taaagtatat atgagtaaac  4980
ttggtctgac agttaccaat gcttaatcag tgaggcacct atctcagcga tctgtctatt  5040
tcgttcatcc atagttgcct gactccccgt cgtgtagata actacgatac gggagggctt  5100
accatctggc cccagtgctg caatgatacc gcgagaccca cgctcaccgg ctccagattt  5160
atcagcaata aaccagccag ccggaagggc cgagcgcaga agtggtcctg caactttatc  5220
cgcctccatc cagtctatta attgttgccg ggaagctaga gtaagtagtt cgccagttaa  5280
tagtttgcgc aacgttgttg ccattgctgc aggcatcgtg gtgtcacgct cgtcgtttgg  5340
tatggcttca ttcagctccg gttcccaacg atcaaggcga gttacatgat cccccatgtt  5400
gtgcaaaaaa gcggttagct ccttcggtcc tccgatcgtt gtcagaagta agttggccgc  5460
agtgttatca ctcatggtta tggcagcact gcataattct cttactgtca tgccatccgt  5520
aagatgcttt tctgtgactg gtgagtactc aaccaagtca ttctgagaat agtgtatgcg  5580
gcgaccgagt tgctcttgcc cggcgtcaac acgggataat accgcgccac atagcagaac  5640
tttaaaagtg ctcatcattg gaaaacgttc ttcggggcga aaactctcaa ggatcttacc  5700
gctgttgaga tccagttcga tgtaacccac tcgtgcaccc aactgatctt cagcatcttt  5760
tactttcacc agcgtttctg ggtgagcaaa aacaggaagg caaaatgccg caaaaaaggg  5820
aataagggcg acacggaaat gttgaatact catactcttc ctttttcaat attattgaag  5880
catttatcag ggttattgtc tcatgagcgg atacatattt gaatgtattt agaaaaataa  5940
acaaataggg gttccgcgca catttccccg aaaagtgcca cctgacgtct aagaaaccat  6000
tattatcatg acattaacct ataaaaatag gcgtatcacg aggccctttc gtcttcaaga  6060
attggtcgat ggcaaacagc tattatgggt attatgggtt cgaattaat              6109
```

```
SEQ ID NO: 35          moltype = DNA  length = 15808
FEATURE                Location/Qualifiers
source                 1..15808
                       mol_type = other DNA
                       note = Synthetic oligonucleotide pBr/sAd4287.pIX-pV
                       organism = synthetic construct
SEQUENCE: 35
attaagaatg cggagctaat catttgaggt tgtatcctgt aaccctgaac gtcaccgagg  60
agctgaggac ggaccaccac atgctgtctt gcctgcgtac cgactatgaa tccagtgatg  120
aggagtgagg tgaggggcgg agccacaaag ggtataaagg ggcatgaagg gtggacgcgg  180
tgtttcaaaa tgagcgggac gacggacggc aatgcgtttg agggggggagt gttcagccca  240
tatctgacat ctcgtcttcc ttcctgggca ggagtgcgtc agaatgtagt gggctccacc  300
gtggacggac ggccggtcgc ccctgcaaat tccgccaccc tcacctatgc caccgtggga  360
tcatcgttgg acactgccgc ggcagctgcc gcttctgctg ccgcttctac tgctcgcggc  420
atggcggctg attttggact atataaccaa ctggccactg cagctgtggc gtctcggtct  480
ctggttcaag aagatgccct gaatgtgatc ttgactcgcc tggagatcat gtcacgtcgc  540
ctggacgaac tggctgcgca gatatcccaa gctaaccccg ataccgcttc agaatcttaa  600
ataaagacaa acaaatttgt tgaaaagtaa aatggcttta tttgtttttt ttggctcggt  660
aggctcgggt ccacctgtct cggtcgttaa ggactttgtg tatgttttcc aaaacacggt  720
acagatgggc ttggatgttc aagtacatgg gcatgaggcc atctttgggg tggagatagg  780
accactgaag agcgtcatgt tccggggtgg tattgtaaat cacccagtcg tagcagggtt  840
tttgagcgtg gaactggaat atgtccttca ggagcaggct aatggccaag ggcagcccct  900
tagtgtaggt gtttacaaag cggttgagct gggagggatg catgcggggg gagatgatat  960
gcatcttggc ttggattttg aggttagcta tgttaccacc caggtctctg cgggggttca  1020
tgttatgaag gaccaccagc acggtgtagc cggtgcactt ggggaacttg tcatgcagtt  1080
tggaggggaa ggcgtggaag aatttagata ccccccttgtg ccccccctagg ttttccatgc  1140
actcatccat aataatggca atgggacccc tggcggccgc tttagcaaac acgttttggg  1200
ggttggaaac atcatagttt tgctctagag tgagctcatc ataggccatc tttacaaagc  1260
ggggtaggag ggtgcccgac tgggggatga tagttccatc tgggcctgga gcgtagttgc  1320
cctcacagat ctgcatctcc caggccttaa tttccgaggg ggggatcatg tccacctggg  1380
gggcgataaa gaacacggtt tctggcgggg gattgatgag ctgggtggaa agcaagttac  1440
gcaatagctg ggatttgccg caaccggtgg ggccgtagat gaccccgatg acgggttgca  1500
gctggtagtt cagagaggaa cagctgccgt cggggcgcag gagggggggcc acatcgttca  1560
tcatgcttct gacatgttta ttttcactca ctaagttttg caagagcctc tccccaccca  1620
gggataagag ttcttccagg ctgttgaagt gtttcagcgg tttcaggccg tcggccatgg  1680
gcatcttttc aagcgactga cgaagcaagt acagtcggtc ccagagctcg gtgacgtgct  1740
ctatggaatc tcgatccagc agacttcttg gttgcggggg ttgggccgac tttcgctgta  1800
gggcaccagc cggtgggcgt ccagggccgc gagggttctg tccttccagg gtctcagcgt  1860
tcgggtgagg gtggtctcgg tgacggtgaa gggatgagcc ccgggctggg cgcttgcgag  1920
```

-continued

```
ggtgcgcttc aggctcatcc tgctggtgct gaagcgggcg tcgtctccct gtgagtcggc  1980
cagatagcaa cgaagcatga ggtcgtagct gagggactcg gccgcgtgtc ccttggcgcg  2040
cagctttccc ttggaaacgt gctgacattt ggtgcagtgc agacacttga gggcgtagag  2100
ttttggggcc aggaagaccg actcgggcga gtaggcgtcg gctccgcact gagcgcagac  2160
ggtctcgcac tccaccagcc acgtgagctc gggtttagcg ggatcaaaaa ccaagttgcc  2220
tccatttttt ttgatgcgtt tcttaccttg cgtctccatg agtctgtgtc ccgcttccgt  2280
gacaaaaagg ctgtcggtgt ccccgtagac cgacttgagg gggcgatctt ccaaaggtgt  2340
tccgaggtct tccgcgtaca ggaactggga ccactccgag acaaaggctc gggtccaggc  2400
taacacgaag gaggcgatct gcgaggggta tctgtcgttt tcaatgaggg ggtccacctt  2460
ttccagggtg tgcagacaca ggtcgtcctc ctccgcgtcc acgaaggtga ttggcttgta  2520
agtgtaggtc acgtgacccg cacccccca aggggtataa aaggggcgt gcccactctc  2580
cccgtcactt tcttccgcat cgctgtggac cagagccagc tgttcgggtg agtaggccct  2640
ctcaaaagcc ggcatgattt cggcgctcaa gttgtcagtt tctacaaacg aggtggattt  2700
gatattcacg tgccccgcgg cgatgctttt gatggtggag gggtccatct gatcagaaaa  2760
cacgatcttt ttattgtcaa gtttggtggc gaaagacccg tagagggcgt tggaaagcaa  2820
cttggcgatg gagcgcaggg tctgattttt ctcccgatcg gccctctcct tggcagcgat  2880
gttgagttgc acgtactcgc gagccacgca ccgccactcg gggaacacgg cggtgcgctc  2940
gtcgggcagg atgcgcacgt gccagccgcg gttgtgcagg gtgatgaggt ccacgctggt  3000
ggccacctcc ccgcggaggg gctcgttggt ccaacacaat cgcccccctt ttctggagca  3060
gaacggaggc aggggatcta gcaagttggc gggcgggggg tcggcgtcga tggtaaatat  3120
gccgggtagc agaattttat taaaataatc gatttcggtg tccgtgtctt gcaacgcgtc  3180
ttcccacttc ttcaccgcca gggccctttc gtagggattc aggggcggtc cccagggcat  3240
ggggtgggtc agggccgagg cgtacatgcc gcagatgtcg tacacgtaca ggggctccct  3300
caacaccccg atgtaagtgg ggtaacagcg ccccccgcgg atgctggctc gcacgtagtc  3360
gtacatctcg tgagagggag ccatgagccc gtctcccaag tgggtcttgt ggggtttctc  3420
ggcccggtag aggatctgcc tgaagatggc gtgggagttg gaagagatgg tggggcgttg  3480
gaagacatta aagttggctc cgggcagtcc cacggagtct tggatgaact gggcgtagga  3540
ttcccggagc ttgtccacca gggctgcggt taccagcacg tcgagagcgc agtagtccaa  3600
cgtctcgcgg accaggttgt aggccgtctc ttgtttttc tcccacagtt cgcgattgag  3660
gaggtattcc tcgcggtctt tccagtactc ttcggcggga aatccttttt cgtccgctcg  3720
gtaagaacct aacatgtaaa attcgttcac ggctttgtat ggacaacagc ctttttctac  3780
cggcagggcg tacgcttgag cggcctttct gagagaggtg tgggtgaggg cgaaggtgtc  3840
ccgcaccatc actttcaggt actgatgttt gaagtccgtg tcgtcgcagg caccctgttc  3900
ccacagcgtg aagtcggtgc gctttttctg cctgggattg gggagggcga atgtgacgtc  3960
gttaaaaagg attttcccgg agcggggcat gaagttgcga gagatcctga agggtccggg  4020
cacgtccgag cggttgttga tgacttgtgc cgccaggacg atctcgtcga agccgttgat  4080
gttgtggccc acgatgtaaa gttcgataaa gcgcggctgt cccttgaggg ccggcgcttt  4140
tttcaactcc tcgtaggtga gacagtccgg cgaggagaga cccagctccg cccgggccca  4200
gtcggagagc tgagggttag ccgcgaggaa agagctccat aggtcaaggg ctagcagagt  4260
ttgcaagcgg tcgcggaact cgcgaaactt tttccccacg gccattttct ccggcgtcac  4320
cacgtagaaa gtgcaggggc ggtcgttcca gacgtcccat cggagctcta gggccagctc  4380
gcaggcttgg cgaacgaggg tctcctcgcc cgagacgtgc atgaccagca tgaagggtac  4440
caactgtttc ccgaacgagc ccatccatgt gtaggtttct acgtcgtagg tgacaaagag  4500
ccgctgggcg cgcgcgtggg agccgatcgg gaagaagctg atctcctgcc accagttgga  4560
ggaatgggtg ttgatgtggt gaaagtagaa gtcccgccgg cgcacagagc attcgtgctg  4620
atgtttgtaa aagcgaccgc agtagtcgca gcgctgcacg ctctgtatct cctgaatgag  4680
atgcgctttt cgcccgcgca ccagaaaccg gagggggaag ttgagacggg gggcttgtgg  4740
ggcggcatcc cattcgcctt ggcggtggga gtctgcgtct gcgtcctcct tctctgggtg  4800
gacgacggtg gggacgacaa cgccccgggt gccgcaagtc cagatctccg ccacggaggg  4860
gcgcaggcgc tgcaggaggg gacgcagctg cccgctgtcc agggagtcga gggcggccgc  4920
gctgaggtcg gcgggaagcg tttgcaagtt cactttcaga agaccggtaa gagcgtgagc  4980
caggtgcaga tggtacttga tttccagggg ggtgttggaa gaggcgtcca cggcgtagag  5040
gaggccgtgt ccgcgcgggg ccaccaccgt gccccgagga ggttttatct caatcgtcga  5100
gggcgagcgc cgggggggtag aggcggctct gcgccggggg gcagcggagg cagcggcacg  5160
ttttcgtgag gatttggcag cggttgatga cgagcccgga gactgctggc gtgggcgacg  5220
acgcggcggt tgaggtcctg gatgtgccgt ctctgcgtga agaccaccgg cccccgggtc  5280
ctgaacctga aagagagttc cacagaatca atgtctgcat cgttaacggc ggcctgcctg  5340
aggatctcct gtacgtcgcc cgagttgtct tgataggcga tctcggccat gaactgctcc  5400
acttcttcct cgcggaggtc gccgtggccc gctcgctcca cggtggcggc caggtcgttg  5460
gagatgcgac gcatgagttg agagaaggcg ttgaggccgt tctcgttcca cacgcggctg  5520
tacaccacgt tgccgaagga gtcgcgcgct cgcatgacca cctgggccac gttgagttcc  5580
acgtggcggg cgaagacggc gtagtttctg aggcgctgga agaggtagtt gagcgtggtg  5640
gcgatgtgct cgcagacgaa gaagtacatg atccagcgcc gcagggtcat ctcgttgatg  5700
tctccgatgg cttcgagacg ctccatggcc tcgtagaagt cgacggcgaa gttgaaaaat  5760
tgggagttgc gggcggccac cgtgagttct tcttgcagga ggcggatgag atcggcgacc  5820
gtgtcgcgca cctcctgctc gaaagcgccc cgaggcgcct ctgcttcttc ctccggctcc  5880
tcctcttcca ggggcacggg ttcctccggc agctctgcga cggggacggg gcggcgacgt  5940
cgtcgtctga ccggcaggcg gtccacgaag cgctcgatca tttcgccgcg ccggcgacgc  6000
atggtctcgg tgacggcgcg tccgttttcg cgaggtcgca gttcgaagac gccgccgcgc  6060
agagcgcccc cgtgcaggga gggtaagtgg ttagggccgt cgggcaggga cacggcgctg  6120
acgatgcatt ttatcaattg ctgcgtaggc actccgtgca gggatctgag aacgtcgagg  6180
tcgacgggat ccgagaactt ctctaagaaa gcgtctatcc aatcgcagtc gcaaggtaag  6240
ctgaggacag tgggtcgctg gggggcgtcc gcgggcagtt gggaggtgat gctgctgatg  6300
atgtaattaa agtaggcggt cttcaggcgg cggatggtgg cgaggaggac cacgtctttg  6360
ggcccggcct gttgaatgcg caggcgctcg gccatgcccc aggcctcgct ctgacagcga  6420
cgcaggtctt tgtagtagtc ttgcatcagt ctctccaccg gaacctctgc ttctcccctg  6480
tctgccatgc gagtcgagcc gaacccccgc aggggctgca gcaacgctag gtcggccacg  6540
acccttttcgg ccagcacggc ctgttgaatc tgcgtgaggg tggtctggaa gtcgtccagg  6600
tccacgaagc ggtgataggc ccccgtgttg atggtgtagg tgcagttggc catgacggac  6660
```

-continued

```
cagttgacga cttgcatacc gggttgggtg atctccgtgt acttgaggcg cgagtaggcg  6720
cgggactcga acacgtagtc gttgcatgtg cgcaccagat actggtagcc gaccaggaag  6780
tgaggaggcg gctctcggta caggggccag ccgacggtgg cgggggcgcc gggggacagg  6840
tcgtccagca tgaggcgatg gtagtggtag atgtagcggg agagccaggt gatgccggcc  6900
gaggtggtcg cggccctggt gaattcccgg acgcggttcc agatgttgcg caggggacgg  6960
aagcgttcca tggtgggcac gctctgcccc gtgaggcggg cgcagtcctg tacgctctag  7020
atggaaaaaa gacagggcgg tcatcgactc ccttccgtag cttgggggt aaagtcgcaa  7080
gggtgcggcg gcggggaacc ccggttcgag accggccgga tccgccgctc ccgatgcgcc  7140
tggccccgca tccacgacgt ccgcgccgag acccagccgc gacgctctgc cccaatacgg  7200
aggggagtct tttggtgttt tttcgtagat gcatccggtg ctgcggcaga tgcgacctca  7260
gacgcccacc accaccgccg cggcggcagt aaacctgagc ggaggcggtg acagggaggt  7320
ggaggagctg gctttagacc tggaagaggg agaggggctg gcccggctgg gagcgccgtc  7380
cccagagaga caccctaggg ttcagctcgt gagggacgcc aggcaggctt ttgtgccgaa  7440
gcagaacctg tttagggacc gcagcggtca ggaggcggag gagatgcgcg attgcaggtt  7500
tcgggcgggt agagagctga gggcgggctt cgatcgcgag cggctcctga gggcggagga  7560
tttcgagccc gacgagcgtt ctggggtgag cccggcccgc gctcacgtct cggcggccaa  7620
cctggtgagc gcgtacgagc agacggtgaa cgaggagcgc aacttccaaa agagctttaa  7680
caatcacgtg aggaccctga tcgcgaggga ggaggtgacc atcgggctga tgcatctgtg  7740
ggacttcgtg gaggcctacg tgcagaaccc ggccagcaaa cctctgacgg cccagctgtt  7800
cctgatcgtg cagcacagcc gcgacaacga gacgttccgc gacgccatgt tgaacatcgc  7860
ggagcccgag ggtcgctggc tcttggatct gattaacatc ctgcagagca tcgtggtgca  7920
ggagaggggt ctgagtttag cggacaaggt ggcggccatt aactattcga tgcagagcct  7980
ggggaagttc tacgctcgca agatctacaa gagcccttac gtgcccatag acaaggaggt  8040
gaagatagac agcttttaca tgcgcatggc gctaaaggtg ctgacgctga gcgacgacct  8100
cggcgtgtac cgtaacgaca agatccacaa ggcggtgagc gccagccgcc ggcgggagct  8160
gagcgacagg gagctgatgc acagcctgca gagggcgctg gcgggcgccg gggacgagga  8220
gcgtgaggct tactttgaca tgggagccga tctgcagtgg cgtcccagcg cgcgcgcctt  8280
ggaggcggcg ggttatcccg acgaggagga tcgggacgat ttggaggagg caggcgagta  8340
cgaggacgaa gcctgaccgg gcaggtgttg ttttagatgc agcggccggc ggacggggcc  8400
accgcggatc ccgcactttt ggcatccatg cagagtcaac cttcgggcgt gaccgcctcc  8460
gatgactggg cggcggccat ggaccgcatc atggcgctga ccacccgcaa ccccgaggct  8520
tttaggcagc aaccccaggc caaccgtttt tcggccatct tggaagcggt ggtgccctcc  8580
cgcaccaacc ccacacacga gaaagtcctg actatcgtga acgccctggt agacagcaag  8640
gccatccgcc gcgacgaggc gggcttgatt tacaacgctc tgctggaacg ggtggcgcgc  8700
tacaacagca ctaacgttca gaccaatctg gatcgcctca ccaccgacgt gaaggaggcg  8760
ctggctcaga aggagcggtt tctgagggac agcaatctgg gctctctggt ggcactcaac  8820
gccttcctga gcacgcagcc ggccaacgtg ccccgcgggc aggaggacta cgtgagcttc  8880
atcagcgctc tgaggctgct ggtgtccgag gtgccccaga gcgaggtgta tcagtctggg  8940
ccggattact tcttccagac gtcccgacag ggcttgcaaa cggtgaacct gactcaggcc  9000
tttaaaaact tgcaaggcat gtggggcgtt aaggccccgg tgggcgatcg agccaccatc  9060
tccagtctgc tgacccccaa cactcgcctg ctgctgctct tgatcgcgcc gttcaccaac  9120
agtagcacta tcagccgtga ctcgtacctg ggtcatctca tcactttgta ccgcgaggcc  9180
atcggtcagg ctcagattga cgagcataca tatcaggaga tcactaacgt gagccgggcc  9240
ctgggtcagg aagataccgg cagcctggaa gccacgttga actttttgct aaccaaccgg  9300
aggcaaaaaa taccctccca gtttacgtta agcgccgagg aggagaggat tctgcgatac  9360
gtgcagcagt ccgtgagtct gtacttgatg cgggagggcg ccaccgcttc cacggcttta  9420
gacatgacgg ctcggaacat ggaaccgtcc ttttactccg cccaccggcc gttcattaac  9480
cgtctgatgg actacttcca tcgcgcggcc gccatgaacg gggagtattt taccaatgcc  9540
atcctgaatc cgcattggat gcccccgtcc ggcttctaca ccggcgagtt tgacctgccc  9600
gaagccgacg acggctttct ttgggacgac gtgtccgaca gcattttcac gccgggcaat  9660
cgccgattcc agaagaagga gggcggagac gagctccccc tctccagcgt ggaggcggcc  9720
tctaggggag agagtccctt tcccagtctg tcttccgcca gcagtggtcg ggtaacgcgc  9780
ccgcggttgc cgggggagag cgactacctg aacgacccct tgctgcggcc ggctaggaag  9840
aaaaatttcc ccaacaacgg ggtggaaagc ttggtggata aaatgaatcg ttggaagacc  9900
tacgcccagg agcagcggga gtgggaggac agtcagccgc gaccgctggt tccgccgcac  9960
tggcgtcgtc agagagaaga cccggacgac tccgcagacg atagtagcgt gttggacctg  10020
ggagggagcg gagccaaccc ctttgctcac ttgcaaccca aggggcgttc gagccgcctc  10080
tactaataaa aaagaagcgg aaacttacca gagccatggc cacagcgtgt gtgctttctt  10140
cctctctttc ttcctcggcg cggcagaatg agaagagcgg tgagagtcac gccggcggcg  10200
tatgagggtc cgcccccttc ttacgaaagc gtgatgggat cagcgaacgt gccggccacg  10260
ctggaggcgc cttacgttcc tcccagatac ctgggaccta cggagggcag aaacagcatc  10320
cgttactccg agctggcacc cctgtacgat accaccaagg tgtacctggt ggacaacaag  10380
tcggcggaca tcgcctccct gaattatcaa aacgatcaca gcaactttct gactaccgtg  10440
gtgcagaaca atgacttcac cccgacggag gcgggcacgc agaccattaa ctttgacgag  10500
cgttcccgct ggggcggtca gctgaaaacc atcctgcaca ccaacatgcc caacatcaac  10560
gagttcatgt ccaccaacaa gttcagggct aagctgatgg tagaaaaaag taatgcggaa  10620
actcggcagc cccgatacga gtggttcgag tttaccattc cagagggcaa ctattccgaa  10680
actatgacta tcgatctcat gaataacgcg atcgtggaca attacctgca agtggggaga  10740
cagaacgggg tgctggaaag cgatatcggc gtgaaattcg ataccagaaa cttccgactg  10800
gggtgggatc ccgtgaccaa gctggtgatg ccaggcgtgt acaccaacga ggcttttcac  10860
cccgacatcg tgctgctgcc ggggtgcggt gtggacttca ctcagagccg tttgagtaac  10920
ctgttaggaa ttagaaagcg ccgccccttc caagagggct ttcaaatcat gtatgaggac  10980
ctggagggag gtaatatacc cgccttactg gacgtgtcga agtacgaagc tagcatacaa  11040
cgcgccaaag cggagggtag agagattcgg ggagacacct ttgcggtagc tccccaggac  11100
ctggaaatag tgcctttaac taaagacagc aaagacagaa gctacaatat tataaacaac  11160
acgacggaca ccctgtatcg gagctggttt ctggcttaca actacggaga ccccgagaaa  11220
ggagtgagat catggaccat actcaccacc acggacgtga cctgtggctc gcagcaagtg  11280
tactggtccc tgccggatat gatgcaagac ccggtcacct tccgcccctc cacccaagtc  11340
agcaacttcc cggtggtggg caccgagctg ctgcccgtcc atgccaagag cttctacaac  11400
```

```
gagcaggccg tctactcgca acttattcgc cagtccaccg cgcttaccca cgtgttcaat  11460
cgctttcccg agaaccagat tctggtgcgc cctcccgctc ctaccattac caccgtcagt  11520
gaaaacgttc ccgccctcac agatcacgga accctgccgc tgcgcagcag tatcagtgga  11580
gttcagcgcg tgaccatcac cgacgccaga cgtcgaacct gcccctacgt ttacaaagcg  11640
cttggcgtgg tggctcctaa agttctttct agtcgcacct tctaaaaaca tgtccatcct  11700
catctctccc gataacaaca ccggctgggg actgggctcc ggcaagatgt acggcggagc  11760
caaaaggcgc tccagtcagc acccagttcg agttcggggc cacttccgcg ctccttgggg  11820
agcttacaag cgaggactct cgggtcgaac ggctgtagac gataccatag atgccgtgat  11880
tgccgacgcc cgccggtaca accccggacc ggtcgctagc gccgcctcca ccgtggattc  11940
cgtgatcgac agcgtggtag ccggcgctcg ggcctatgct cgccgcaaga ggcggctgca  12000
tcggagacgt cgccccaccg ccgccatgct ggcagccaga gccgtgctga gacgggcccg  12060
gagggtaggc aggagggcta tgcgccgcgc tgccgccaac gccgccgccg ggagggcccg  12120
ccgacaggct gcccgccagg ctgctgccgc catcgctagc atggccagac ccaggagagg  12180
gaacgtgtac tgggtgcgcg attctgtgac gggagtccga gtgccggtgc gcagccgacc  12240
tccccgaagt tagaagatcc aagctgcgaa gacggcggta ctgagtctcc ctgttgttat  12300
cagcccaaca tgagcaagcg caagtttaaa gaagaactgc tgcagacgct ggtgcctgag  12360
atctatggcc ctccggacgt gaagcctgac attaagcccc gcgatatcaa gcgtgttaaa  12420
aagcgggaaa agaaagagga actcgcggtg gtagacgatg gcggagtgga atttattagg  12480
agtttcgccc cgcggcgcag ggttcaatgg aaagggcgac gggtacaacg cgttttgagg  12540
ccgggcaccg cggtagtttt taccccggga gagcggtcgg ccgttagggg ttttaaaagg  12600
cagtacgacg aggtgtacgg cgacgaggac atattggaac aggcggctca acagatcgga  12660
gaatttgcct atggaaagcg ctcgcgtcgc gaagacctgg ccatcgcctt agacagcggc  12720
aaccccacgc ccagcctcaa acccgtgacg ctgcagcagg tgcttcccgt gagcgccagc  12780
acggacagca agaggggaat aaaaagagaa atggaagatc tgcagcctac catccagctc  12840
atggttccta aacggcagag gctggaagag gtcctggaga agatgaaagt ggaccccagc  12900
atagagccgg acgttaaagt caggccgatc aaagaagtgg cccctggact cggggtgcag  12960
acggtggata tccagatccc cgtcacgtca gcttcgaccg ccgtggaagc catggaaacg  13020
caaaccgaaa cccccgccgt ggttggtacc aaagaagtgg cgttgcaaac cgacccctgg  13080
tacgaatttg ccgcccccg gcgtcagagg cgacccgctc gttacggccc cgccaacgcc  13140
atcatgccag aatatgcgct gcatccgtct atcctgccca cccccggcta ccggggagtg  13200
acgtatcgcc cgtcaggaac ccgccgccga acccgtcgcc gccgccgctc ccgtcgcgct  13260
ctggcccccg tgtcggtgcg ccgcgtaaca cgccggggaa agacagtcac cattcccaac  13320
ccgcgctacc accctagcat cctttaatga ctctgccgtt ttgcagatgg ctctgacttg  13380
ccgcgtgcgc cttcccgttc cgcactatcg aggaagatct cgtcgtagga gaggcatggc  13440
gggcagtggt cgccggcggg ctttgcgcag gcgcatgaaa ggcggaattt tacccgcttt  13500
gatacccata atcgccgccg ccatcggtgc catacccggc gtcgcttcag tggccttgca  13560
agcagctcgt aataaataaa cgaaggcttt tgcacttatg tcctggtcct gactatttta  13620
tgcagaaaga gcatggaaga catcaatttt acgtcgctgg ctccgcggca cggctcgcgg  13680
ccgctcatgg gcacctggaa cgacatcggc accagtcagt taattaattc gaacccataa  13740
tacccataat agctgtttgc catcgacgcg aggctggatg gccttcccca ttatgattct  13800
tctcgcttcc ggcggcatcg ggatgcccgc gttgcaggcc atgctgtcca ggcaggtaga  13860
tgacgaccat cagggacagc ttcaaggcca gcaaaaggcc aggaaccgta aaaaggccgc  13920
gttgctggcg tttttccata ggctccgccc ccctgacgag catcacaaaa atcgacgctc  13980
aagtcagagg tggcgaaacc cgacaggact ataaagatac caggcgtttc cccctggaag  14040
ctccctcgtg cgctctcctg ttccgaccct gccgcttacc ggatacctgt ccgcctttct  14100
cccttcggga agcgtggcgc tttctcatag ctcacgctgt aggtatctca gttcggtgta  14160
ggtcgttcgc tccaagctgg gctgtgtgca cgaacccccc gttcagcccg accgctgcgc  14220
cttatccggt aactatcgtc ttgagtccaa cccggtaaga cacgacttat cgccactggc  14280
agcagccact ggtaacagga ttagcagagc gaggtatgta ggcggtgcta cagagttctt  14340
gaagtggtgg cctaactacg gctacactag aaggacagta tttggtatct gcgctctgct  14400
gaagccagtt accttcggaa aaagagttgg tagctcttga tccggcaaac aaaccaccgc  14460
tggtagcggt ggtttttttg tttgcaagca gcagattacg cgcagaaaaa aaggatctca  14520
agaagatcct ttgatctttt ctacggggtc tgacgctcag tggaacgaaa actcacgtta  14580
agggattttg gtcatgagat tatcaaaaag gatcttcacc tagatccttt taaattaaaa  14640
atgaagtttt aaatcaatct aaagtatata tgagtaaact tggtctgaca gttaccaatg  14700
cttaatcagt gaggcaccta tctcagcgat ctgtctattt cgttcatcca tagttgcctg  14760
actccccgtc gtgtagataa ctacgatacg ggagggctta ccatctggcc ccagtgctgc  14820
aatgataccg cgagacccac gctcaccggc tccagattta tcagcaataa accagccagc  14880
cggaagggcc gagcgcagaa gtggtcctgc aactttatcc gcctccatcc agtctattaa  14940
ttgttgccgg gaagctagag taagtagttc gccagttaat agtttgcgca acgttgttgc  15000
cattgctgca ggcatcgtgg tgtcacgctc gtcgtttggt atggcttcat tcagctccgg  15060
ttcccaacga tcaaggcgag ttacatgatc ccccatgttg tgcaaaaaag cggttagctc  15120
cttcggtcct ccgatcgttg tcagaagtaa gttggccgca gtgttatcac tcatggttat  15180
ggcagcactg cataattctc ttactgtcat gccatccgta agatgctttt ctgtgactgg  15240
tgagtactca accaagtcat tctgagaata gtgtatgcgg cgaccgagtt gctcttgccc  15300
ggcgtcaaca cgggataata ccgcgccaca tagcagaact ttaaaagtgc tcatcattgg  15360
aaaacgttct tcggggcgaa aactctcaag gatcttaccg ctgttgagat ccagttcgat  15420
gtaacccact cgtgcaccca actgatcttc agcatctttt actttcacca gcgtttctgg  15480
gtgagcaaaa acaggaaggc aaaatgccgc aaaaaaggga ataagggcga cacggaaatg  15540
ttgaatactc atactcttcc tttttcaata ttattgaagc atttatcagg gttattgtct  15600
catgagcgga tacatatttg aatgtattta gaaaaataaa caaatagggg ttccgcgcac  15660
atttccccga aaagtgccac ctgacgtcta agaaaccatt attatcatga cattaaccta  15720
taaaaatagg cgtatcacga ggccctttcg tcttcaagaa ttggtcgatg gcaaacagct  15780
attatgggta ttatgggttc gaattaat                                     15808
```

```
SEQ ID NO: 36          moltype = DNA  length = 23168
FEATURE                Location/Qualifiers
source                 1..23168
                       mol_type = other DNA
```

```
                        note = Synthetic oligonucleotide pBr/sAd4287.PsiI-rITR
                        organism = synthetic construct
SEQUENCE: 36
attaacccag gacctggaaa tagtgccttt aactaaagac agcaaagaca gaagctacaa  60
tattataaac aacacgacgg acaccctgta tcggagctgg tttctggctt acaactacgg  120
agaccccgag aaaggagtga gatcatggac catactcacc accacggacg tgacctgtgg  180
ctcgcagcaa gtgtactggt ccctgccgga tatgatgcaa gacccggtca ccttccgccc  240
ctccacccaa gtcagcaact tcccggtggt gggcaccgag ctgctgcccg tccatgccaa  300
gagcttctac aacgagcagg ccgtctactc gcaacttatt cgccagtcca ccgcgcttac  360
ccacgtgttc aatcgctttc ccgagaacca gattctggtg cgccctcccg ctcctaccat  420
taccaccgtc agtgaaaacg ttcccgccct cacagatcac ggaaccctgc cgctgcgcag  480
cagtatcagt ggagttcagc gcgtgaccat caccgacgcc agacgtcgaa cctgccccta  540
cgtttacaaa gcgcttggcg tggtggctcc taaagttctt tctagtcgca ccttctaaaa  600
acatgtccat cctcatctct cccgataaca acaccggctg gggactgggc tccggcaaga  660
tgtacggcgg agccaaaagg cgctccagtc agcacccagt tcgagttcgg ggccacttcc  720
gcgctccttg gggagcttac aagcgaggac tctcgggtcg aacggctgta gacgatacca  780
tagatgccgt gattgccgac gcccgccggt acaaccccgg accggtcgct agcgccgcct  840
ccaccgtgga ttccgtgatc gacagcgtgg tagccggcgc tcgggcctat gctcgccgca  900
agaggcggct gcatcggaga cgtcgcccca ccgccgccat gctggcagcc agagccgtgc  960
tgagacgggc ccggagggta ggcaggaggg ctatgcgccg cgctgccgcc aacgccgccg  1020
ccgggagggc ccgccgacag gctgcccgcc aggctgctgc cgccatcgct agcatggcca  1080
gacccaggag agggaacgtg tactgggtgc gcgattctgt gacgggagtc cgagtgccgg  1140
tgcgcagccg acctccccga agttagaaga tccaagctgc gaagacggcg gtactgagtc  1200
tccctgttgt tatcagccca acatgagcaa gcgcaagttt aaagaagaac tgctgcagac  1260
gctggtgcct gagatctatg gccctccgga cgtgaagcct gacattaagc cccgcgatat  1320
caagcgtgtt aaaaagcggg aaaagaaaga ggaactcgcg gtggtagacg atggcggagt  1380
ggaatttatt aggagtttcg cccgcggcg cagggttcaa tggaaagggc gacgggtaca  1440
acgcgttttg aggccgggca ccgcggtagt ttttaccccg ggagagcggt cggccgttag  1500
gggttttaaa aggcagtacg acgaggtgta cggcgacgag gacatattgg aacaggcggc  1560
tcaacagatc ggagaatttg cctatggaaa gcgctcgcgt cgcgaagacc tggccatcgc  1620
cttagacagc ggcaacccca cgcccagcct caaacccgtg acgctgcagc aggtgcttcc  1680
cgtgagcgcc agcacggaca gcaagagggg aataaaaaga gaaatggaag atctgcagcc  1740
taccatccag ctcatggttc ctaaacggca gaggctggaa gaggtcctgg agaagatgaa  1800
agtggacccc agcatagagc cggacgttaa agtcaggccg atcaaagaag tggcccctgg  1860
actcggggtg cagacggtgg atatccagat ccccgtcacg tcagcttcga ccgccgtgga  1920
agccatggaa acgcaaaccg aaacccccgc cgtggttggt accaaagaag tggcgttgca  1980
aaccgacccc tggtacgaat ttgccgcccc ccggcgtcag aggcgacccg ctcgttacgg  2040
ccccgccaac gccatcatgc cagaatatgc gctgcatccg tctatcctgc ccacccccgg  2100
ctaccgggga gtgacgtatc gcccgtcagg aacccgccgc cgaacccgtc gccgccgccg  2160
ctcccgtcgc gctctggccc ccgtgtcggt gcgccgcgta acacgccggg gaaagacagt  2220
caccattccc aacccgcgct accaccctag catcctttaa tgactctgcc gttttgcaga  2280
tggctctgac ttgccgcgtg cgccttcccg ttccgcacta tcgaggaaga tctcgtcgta  2340
ggagaggcat ggcgggcagt ggtcgccggc gggctttgcg caggcgcatg aaaggcggaa  2400
ttttacccgc tttgataccc ataatcgccg ccgccatcgg tgccataccc ggcgtcgctt  2460
cagtggcctt gcaagcagct cgtaataaat aaacgaaggc ttttgcactt atgtcctggt  2520
cctgactatt ttatgcagaa agagcatgga agacatcaat tttacgtcgc tggctccgcg  2580
gcacggctcg cggccgctca tgggcacctg gaacgacatc ggcaccagtc agctcaacgg  2640
gggcgctttc aattggggga gcctttggag cggcattaaa aactttggct ccacgattaa  2700
atcctacggc agcaaagcct ggaacagtag tgctggtcag atgctccgag ataaactgaa  2760
ggacaccaac ttccaagaaa aagtggtcaa tggggtggtg accggcatcc acggtgcggt  2820
agatctcgcc aaccaagcgg tgcagaaaga gattgacagg cgtttggaaa actcgcgggt  2880
gccgccgcag agggggggatg aggtggaggt cgaggaagta gaagtagagg aaaagctgcc  2940
cccgctggag aaagttcccg gtgcacctcc gaggccgcag aagcggccca ggccagaact  3000
agaagaaact ctggtgacgg agagcaagga gcctccctcg tacgagcaag ccttgaaaga  3060
gggcgcctct ccaccctcct acccgatgac taagccgatc gcacccatgg ctcgaccggt  3120
gtacggcaag gattacaagc ccgtcacgct agagctgccc ccaccgcccc cttcgcgtcc  3180
gacggtgcct ccgctgcctg ccccgtcggc gggtcccgag tctgcaccat ccgctgtgcc  3240
tctgccagcc gcccgtcccg tggccgtggc cactgccagg aaccccagag gccagagagg  3300
agccaactgg caaagcacgc tgaacagcat cgtgggcctg ggggtgaaaa gcctgaaacg  3360
ccgccgttgc tattattaaa aagtgtagct aaaaaatttc ccgttgtata cgcctcctat  3420
gttaccgcca gagacgcgtg actgtcgccg cgagcgccgc ttccaagatg gccaccccat  3480
cgatgatgcc gcagtggtct tacatgcaca tcgccggcca ggacgcctcg gagtacctga  3540
gtcccggcct cgtgcagttt gcccgcgcca ccgacaccta cttcagcttg ggaaacaagt  3600
ttagaaaccc caccgtggcc cccacccacg atgtgaccac ggaccgctcg cagaggctga  3660
ccctgcgctt tgtgcccgta gaccgggagg acaccgcgta ctcttacaaa gtgcgctaca  3720
cgctggccgt aggggacaac cgagtgctgg acatggccag cacctacttt gacatccggg  3780
gggtgctgga tcggggtccc agcttcaagc cctactccgg caccgcttac aactccctgg  3840
ctcccaaggg cgcccccaat cctgcagaat gggccgatac caacgacagc aacaaactga  3900
aagtgagggg tcaggcgcct tttgtcagta cttacggttc tgctacggcg cttacaaaag  3960
atgggataca ggtgggagtg gatacttccg aagcatctca ggctgtttat gccgacagaa  4020
gttaccagcc agaaccccaa attggagaga cagagtggaa cagcgaagtg ggtaatgacg  4080
acagagtggc gggaagggtg ctaaagaaaa caactcccat gttcccttgt tacggttcat  4140
atgccaagcc caccaacgaa aaaggcggac aagcaataca gcccaccgcc ggcaacggcg  4200
ataatcaggc tgtagagtta caattctttg ccactactag cactcccact gcgccaaagg  4260
cagtattgta cgcggaggac gtggccattg aagctccaga tactcactta gtgtttaagc  4320
caacagtagt cgcgggaact acaagttcgg aagctctgct aacccaacaa gccgcaccta  4380
accgcccaaa ctacattgcc tttagagata actttattgg tctcatgtac tacaattcaa  4440
ccgggaatat gggagtactg gccggacaag catctcagct caatgcagtg gttgatcttc  4500
aggacagaaa caccgaactg tcatatcagc taatgctgga tgctctggga gatcgcagtc  4560
```

```
ggtacttttc tatgtggaat caagctgtag atagctatga tccagatgta agaattgtag  4620
aaaaccacgg tgtggaagac gaactgccta attattgctt cccactaggc gggatggtag  4680
taacggacac ttacaaagcc ataaaggtaa atggaagcgg atggacggct aatactgacg  4740
ttttcagcga gagagtagaa ataggctcag gtaacctgtt tgccatggaa attaacttgc  4800
aagctaatct gtggcgcagt ttcttgtatt ccaacatagg actgtacctc ccggactctt  4860
taaaattaac ccctgacaac atcacgctcc ctgagaacaa aaatacctac cagtatatga  4920
acggtcgcgt aacaccaccc gggctcgtgg acacctacgt taacgtgggt gcgcgctggt  4980
cccccgatgt tatggacagc attaaccctt ttaaccacca ccgcaacgcc gggctccgct  5040
accgttccat gctcctggga aacggacgct acgtaccctt ccacattcag gtgccccaga  5100
aattctttgc aattaaaaac ctgctgctgc tccccggttc ctatacctac gagtggaatt  5160
tccgcaagga cgtgaacatg attttgcaaa gctcgctggg taacgacctg cgagttgacg  5220
gggccagcat acgcttcgac agcatcaacc tgtatgctaa ctttttcccc atggcccaca  5280
acacggcctc caccctggaa gccatgctgc gcaacgacac caatgaccag tccttcaacg  5340
actacctgtg cgcggccaac atgctgtatc ccatccccgc caacgccacc agcgtgccca  5400
tctccatccc gtctcgcaac tgggccgcct ttaggggttg gagtttcacc cgcctcaaaa  5460
ccaaggaaac cccctcgctg ggctctggct tcgaccccta cttcgtctac tcaggctcca  5520
ttccctacct ggacggcact ttctatctta accacacttt caaaaaggtg tctatcatgt  5580
tcgattcctc ggtcagctgg cccggcaacg accgcctgct gacgcccaac gagttcgaaa  5640
tcaagcgttc ggtggacggt gaagggtaca acgtggccca gagcaacatg accaaggact  5700
ggttcctggt tcaaatgctc agccattaca acatcggtta ccagggcttc tatgtgcccg  5760
agaactacaa ggaccgcatg tactccttct ttaggaactt ccaacccatg agtcgccaag  5820
tcgtggactc agtggcttac agggactact accaggacgt taagctcccc taccagcaca  5880
acaactcagg gttcgtgggc tacatgggtc ccaccatgcg agaggggcag gcctacccgg  5940
ccaactatcc ttatccccta atcggagaga ctgctgtacc cagcctgacg cagaaaaagt  6000
tcctctgcga ccgggtgatg tggaggatac ccttctctag caacttcatg tctatgggct  6060
ccctcaccga cctggggcag aacatgctgt acgccaactc cgctcacgcc ttggacatga  6120
cctttgaggt ggatcccatg gatgagccca cgcttctcta tgttctgttt gaagtcttcg  6180
acgtggtgcg catccaccag ccgcaccgcg gcgtcatcga ggccgtctac ctgcgcacac  6240
ctttctctgc cggtaacgcc accacctaaa gaagccgatg ggctccagcg aacaggagct  6300
gcaggccatt gttcgcgacc tgggctgcgg gccctacttt ttgggcacct tcgacaagcg  6360
gttccccggc ttcatgtccc ctcacaagcc ggcctgtgcc atcgttaaca cggccggacg  6420
ggaaaccggg ggggtccact ggctcgcctt cgcctggaac ccgcgtaacc gcacctgcta  6480
cctgttcgac ccttttggtt tctccgacga aaggctgaag cagatctacc agttcgagta  6540
cgaggggctc ctccagcgca gcgctctggc ctccacgccc gaccactgcg tcaccctgga  6600
aaagtccacc cagacggtcc aggggcccct ctcggccgcc tgcgggctct tctgttgcat  6660
gtttttgcac gccttcgtgc actggcctca cacccccatg gatcacaacc ccaccatgga  6720
tctgctcacc ggagtgccca acagcatgct tcacagcccc caggtcgccc ccaccctgcg  6780
ccgtaaccag gaacacctgt atcgctttct ggggaaacac tctgcctatt tccgccgcca  6840
tcggcagcgc atcgaacagg ccacggcctt cgaaagcatg agccaaagag tgtaatcaat  6900
aaaaaccatt tttatttgac atgatacgcg cttctggcgt ttttattaaa aatcgaaggg  6960
ttcgagggag gggtcctcgt gcccgctggg gagggacacg ttgcgatact ggaatcgggc  7020
gctccaacga aactcgggga tcaccagtcg cggcaggggc acgtcttcca ggttctgctt  7080
ccaaaactgt cgcaccagct gcagggctcc catcacgtcg ggcgccgata tcttgaagtc  7140
gcagttaggg ccggagctcc cgcggctgtt ccggaacacg gggttggcac actggaacac  7200
catcacgctg gggttgtgaa tactagccag ggccgtcgga tcggtcacct ccgacgcatc  7260
cagatcctcg gcgttgctca gggcgaacgg ggtcagcttg cacatctgcc gcccgatctg  7320
gggcaccagg tcgggtttgt tgaggcaatc gcagcgcaga gggatcagga tgcgtcgctg  7380
cccgcgttgc atgatagggt aactcgccgc caggaactcc tccatctgac ggaaggccat  7440
ctgggcctta acgccctcgg tgaaaaacag cccacaggac ttgctagaaa atacgttatt  7500
gccgcagtta atgtcttccg cgcagcagcg tgcatcttcg ttcttcagct gaaccacgtt  7560
acgcccccag cggttctgga ccaccttggc tttcgtagga tgctccttca gcgcccgctg  7620
cccgttctcg ctggtcacat ccatttccac cacgtgctcc ttgcagacca tctccactcc  7680
gtggaagcaa aacaggacgc cctcctgccg ggtattgcga tgctcccaaa cggcacaccc  7740
ggtgggctcc cagctcttgt gttttacccc cgcgtaggct tccatgtaag ccatgaggaa  7800
tctgcccatc agctcggtga aggtcttctg attggtgaag gttagcggca ggccgcggtg  7860
ctcctcgttc aaccaagttt gacagatctt gcggtacacc gttccctggt cgggcagaaa  7920
cttaaaagcc gctctgctgt cgttgtccac gtggaacttc tccattaaca tcatcatggt  7980
ttccataccc ttctcccacg ctgacaccag cggtttgctg tcggggttct tcaccaacac  8040
ggcggtagag gggccctcgc cggccccgac gtccttcatg gtcattcttt gaaactccac  8100
ggagccgtcc gcgcgacgta ctctgcgcac cggagggtag ctgaagccca cctccaccac  8160
ggtgccttcg ccctcgctgt cggaaacgat ctccggggat ggcggcggtg cgggtgtcgc  8220
cttgcgagcc ttcttcttgg gagggagctg aggcgcctcc tgctcgcgct cggggctcat  8280
ctcccgcaag tagggggtta tggagctgcc tgcttggttc tgacggttgg ccattgtatc  8340
ctaggcagaa agacatggag cttatgcgcg aggaaacttt aaccgccccg tcccccgtca  8400
gcgacgaaga tgtcatcgtc gaacaggacc cgggctacgt tacgccgccc gaggatctgg  8460
aggggcctga ccggcgcgac gctagtgagc ggcaggaaaa tgagaaagag gaggcctgct  8520
acctcctgga aggcgacgtt ttgctaaagc atttcgccag gcagagcacc atagttaagg  8580
aggccttgca agaccgctcc gaggtgccct tggacgtcgc cgcgctctcc caggcctacg  8640
aggcgaacct tttctcgcct cgagtgcctc cgaagagaca gcccaacggc acctgcgagc  8700
ccaacccgcg actcaacttc taccccgtgt tcgccgtacc agaggcgctg gccacctatc  8760
acatttttt caaaaaccaa cgcatccccc tatcgtgccg ggccaaccgc accgcggccg  8820
ataggaatct caggcttaaa aacggagcca acatacctga tatcacgtcg ctggaggaag  8880
tgcccaagat tttcgagggt ctgggtcgag atgagaagcg ggcggcgaac gctctgcaga  8940
aagaacagaa agagagtcag aacgtgctgg tggagctgga gggggacaac gcgcgtctgg  9000
ccgtcctcaa acgctgcata gaagtctccc acttcgccta ccccgccctc aacttgccac  9060
ccaaagttat gaaatcggtc atggatcagc tgctcatcaa gagagctgag cccctggatc  9120
ccgaccaccc cgaggcggaa aactcagagg acggaaagcc cgtcgtcagc gacgaggagc  9180
tcgagcggtg gctggaaacc agggaccccc aacagttgca agagaggcgc aagatgatga  9240
tggcggccgt gctggtcacc gtggagctgg aatgcctgca acggtttttc agcgacgtgg  9300
```

```
agacgctacg caaaatcggg gaatccctgc actacacctt ccgccagggc tacgtccgcc  9360
aggcctgcaa gatctccaac gtggagctca gcaacctggt ctcctacatg ggcatcctcc  9420
acgagaaccg gctggggcag agcgtgctgc actgcacctt gcaaggcgag gcgcggcggg  9480
actacgtgcg agactgcatc tacctcttcc tcaccctcac ctggcagacc gccatgggcg  9540
tctggcagca gtgcttggaa gagagaaacc tcaaagagct agacaaactc ctctgccgcc  9600
agcggcgcgc cctgtggtcc ggtttcagcg agcgcacggt cgccagcgct ctggcggaca  9660
tcatcttccc ggagcgcctg atgaaaacct tgcaaaacgg cctgccggat ttcatcagtc  9720
aaagcatttt gcaaaacttc cgctcttttg tcctggaacg ctccgggatc ttgcccgcca  9780
tgagctgcgc gctaccttct gactttgtcc ccctctccta ccgcgagtgc cctcccccac  9840
tgtggagcca ctgctacctc ttccaactgg ccaactttct ggcctaccac tccgacctca  9900
tggaagacgt aagcggagag ggtttactgg agtgccactg ccgctgcaac ctgtgcaccc  9960
cccacagatc gctggcctgc aacaccgagc tactcagcga aacccaggtc ataggtacct 10020
tcgagatcca ggggccccag cagcaagagg gtgcttccgg cttgaagctc actccggcgc 10080
tgtggacctc ggcttactta cgcaaatttg tagccgagga ctaccacgcc cacaaaattc 10140
agttttacga agaccaatct caaccaccga aagcccccct cacggcctgc gtcatcaccc 10200
agagcaagat cctggcccaa ttgcaatcca tcaaccaagc gcgccgcgat ttccttttga 10260
aaaagggtcg gggggtgtat ctggaccccc agaccggcga ggaactcaac ccgtccacac 10320
tctccgtcga agcagccccc ccgagacatg ccgcccaagg gaaccgccaa gcagctgatc 10380
gctcggcaga gagcgaagaa gcaagagctg ctccagcagc aggtggagga cgaggaagag 10440
atgtgggaca gccaggcaga ggaggtgtca gaggacgagg aggagatgga aagctgggac 10500
agcctagacg aggaggagga cgagctttca gaggaagagg cgaccgaaga aaaaccacct 10560
gcatccagcg cgccttctct gagccgacag ccgaagcccc ggcccccgac gcccccggcc 10620
ggctcactca aagccagccg taggtgggac gccaccgaat ctccagcggc agcggcaacg 10680
gcagcgggta aggccaaacg cgagcggcgg gggtattgct cctggcgggc ccacaaaagc 10740
agtattgtga actgcttgca acactgcggg ggaaacatct cctttgcccg acgctacctc 10800
ctcttccatc acggtgtggc cttccctcgc aacgttctct attattaccg tcatctctac 10860
agcccctacg aaacgctcgg agaaaaaagc taaggcctcc tccgccgcga ggaaaaactc 10920
cgccgccgct gccgccgcca aggatccacc ggccaccgag gagctgagaa agcgcatctt 10980
tcccactctg tatgctatct ttcagcaaag ccgcgggcag caccctcagc gcgaactgaa 11040
aataaaaaac cgctccttcc gctcgctcac ccgcagctgt ctgtaccaca agagagaaga 11100
ccagctgcag cgcaccctgg acgacgccga agcactgttc agcaaatact gctcagcgtc 11160
tcttaaagac taaaagaccc gcgctttttc cccctcggcc gccaaaaccc acgtcatcgc 11220
cagcatgagc aaggagattc ccacccccta catgtggagc tatcagcccc agatgggcct 11280
ggccgcgggg gccgcccagg actactccag caagatgaac tggctcagcg ccggccccca 11340
catgatctca cgagttaacg gcatccgagc ccaccgaaac cagattctct tagaacaggc 11400
ggcaatcacc gccacacccc ggcgccaact caacccgcct agttggcccg ccgcccaggt 11460
gtatcaggaa aatccccgcc cgaccacagt cctcctgcca cgcgacgcgg aggccgaagt 11520
cctcatgact aactctgggg tacaattagc gggcgggtcc aggtacgcca ggtacagagg 11580
tcgggccgct ccttactctc ccgggagtat aaagagggtg atcattcgag gccgaggtat 11640
ccagctcaac gacgagacgg tgagctcctc aaccggtctc agacctgacg gagtcttcca 11700
gctcggagga gcgggccgct cttccttcac cactcgccag gcctacctga ccctgcagag 11760
ctcttcctcg cagccgcgct ccgggggaat cggcactctc cagttcgtgg aagagttcgt 11820
tccctccgtc tacttcaacc ccttctccgg ctcgcctgga cgctacccgg acgccttcat 11880
tcccaacttt gacgcagtga gtgaatccgt ggacggctac gactgatgac agatggtgcg 11940
gccgtgagag ctcggctgcg acatctgcat cactgccgtc agcctcgctg ctacgctcgg 12000
gaggcgatcg tcttcagcta ctttgagctg ccggacgagc accctcaggg tccggctcac 12060
gggttgaaac tcgagatcga gaacgcgctc gagtctcgcc tcatcgacac cttcaccgcc 12120
cgacctctcc tggtagaaat cgaacgcggg atcactacca tcaccctgtt ctgcatctgc 12180
cccacgcccg gattacatga agatctgtgc tgtcatcttt gcgctcagtt taataaaaac 12240
tgaacttttt gccgcacctt caacgccacg cgtcgtttct ccaaaagttg tcgacagctc 12300
ttcagtcaga ggtatacgag aaactgttta tttttacaac tctactactt ttctcaccct 12360
taactgctcc tgcactaacg aactaattca gtggttcgcg aacggctcac tctgccaagt 12420
ctttttaat tctgctgttc ttcctgagtt tggctccttt gcgtgtggaa attctacccc 12480
ctccacctta accattgcgg cgccctttc ggaaatccag tatttttgta ttggggcggg 12540
aggtaaaccg ggttgtattc accgcttgtt tgtaaagcca tttgttgctt caattcccat 12600
taacacttca ctttcctcta atacatactt acctacctta cattctactc acccctcctg 12660
gcaacctctt attggcctca cggcttttat ttccgttgtt ttactaaact ttataattct 12720
taacaaactt tcttaaacat gcttgccatt ttgcttctgc tcgttacttt aacgtccgca 12780
gattaccaca atgtaattgt acgagaaaac agtttacaaa acccatcaca ggtatatgtt 12840
aaagcaggct ctaacttaac tttacaatcc ttctattcgc cttaccctga ggacatgcca 12900
cgtgttactt ggtacttaga agtttttgat tcgctatttg aaaggcatac gattcctcca 12960
ttttttacag gcgttatact ttgtgacatt tctggtgaca tacagcatgt gtggaaccat 13020
tggcctttac aatttaattg cataaataaa agcttacata ttattaatct caaaccaagt 13080
gatgaaggcc tttacaatgt gaaggtttta aaggacagca ttcagcataa tacatacttt 13140
cgagtgcatg tagtaagttt tccaagacct gaatgtaaca tcaccactac atatctttca 13200
gatgactact gccttattaa cattgattgc tctcaattac catacctgc taaggtctat 13260
tataatggca atgaaagtaa gctgcattac tacttatctg aacgcggtgg ccagccaaac 13320
cttccaaatt actttactgt tgggtatcga tatagagatc tccgacaaaa ttatacagtt 13380
gaatatccat ttaatgaact atgtacagag ataattgctc ttgaaacagg gtctgatttt 13440
atgccaattt ttatagttac cctagtggtg agcattatag ttattgtgat gggcatcaca 13500
tatcttattt atcactgtag gactttaaag accaaaacca aaaccaaaac caagcctcct 13560
gaaatccgtt tgctttaatt ttttccagaa tggtagctgc tttcttcatt tttctctgta 13620
taccaatcat ctgcgcctcc acaacttttg ccgctgtttc ccacctggaa ccagactgtc 13680
taccaccttt tgttgtatac ctgatactga cttttgtggt ctgtacagcc attaccagca 13740
tagcctgctt ttttgtaaca attttccaag ccgccgatta tctctacgta cggtttgctt 13800
attttagaca tcaccccgag tatcggaatc aaaacgtagc ttctttactt tgtctagcat 13860
gattcgccta tttatactgc acactctgtt taccctcgca aaatgtcatt gccctttac 13920
caaaccttgg tccttttaca cctgttacga tgtactgccc gaaaccccta ttgcctggct 13980
ttacgtagcc acagcggttt tagtttttgt agcaacctgc attggcgtta aactgtactt 14040
```

```
ctacttaaaa attggatggc ttcatccccc agaagattta ccccgatatc ctcttgttaa  14100
taactttcaa cagcctctgc cgcctcctga tcctcttccg cgagctccct ccgttgttag  14160
ctactttcaa ctcaccggtg gagatgactg actctcagga cattgatatt agtgtggaaa  14220
gaatagccgc tcagcgtcag cgagaaactc gggtgctgga gtactttgaa ctacagcagc  14280
ttaaagagtc ccactggtgt gagaaaggag tgctgtgtca tgttaagcag gcagcccttt  14340
cttacgatgt cagccttcag ggacatgaac tgtcttacac tttgccttcg caaaaacaaa  14400
ccttctgcac catgatgggc tctacctcca tcacaatcac ccaacaaacc ggacctgttg  14460
agggagctat cctgtgtcac tgtcacgcgc ctgattgtat gcccaaacta attagaactc  14520
tctgtgcctt aggtgatata tttaaaatgt aagtcagtat caataaactt accttaaatt  14580
tgacagcagt tttttggtaa catcattcag cagcaccact ttaccctctt cccaactctc  14640
gtatgggacg tgatggtggg cggcaaactt cctccaaacc ctaaaacaaa tattaatatc  14700
cacttccttg tccttaccca caattttcat cttttcatag atgaaaagaa ccagagttga  14760
tgaagacttc aaccccgtct acccttatga ctccacatcc actcctgcgg tccccttttat  14820
atcccccccg tttgtaaaca gcgatggtct tcaggaaaac cctcctggag tcttaagttt  14880
acgaatagct aaacccttgt attttgacat ggaaaggaaa ctagcgcttt cacttggaag  14940
aggattggca attacctcca ccggacagct agaaagcaca cagagcgtgc aaaccacccc  15000
tccattagtt gtcaacaaca gcaacacgct tgtcctgcgt tattcctccc cgttaggctt  15060
atcgggtgac aatttaatac taaattgctc cgatcctctc cgcgtagtaa acaacagcct  15120
gacattcagc tacctatctc cacttcgttt tgaaggtggc agtcttacat tcaattacac  15180
atctcccctt aaactgttga acagcagcct tgcgatcgga ataaattcca acaaaggtct  15240
cggcaatgac agcgatgaac tttctgtcaa actaacatca gatctaaagt ttaacaacga  15300
tggaaaaata gcttttggta tacaaagcct gtgtaccacc cccacagccg cctctaactg  15360
taccgttttt accaacggtg attctttact ctgtttatgt ttaaccaaat gtggagctca  15420
cgtgttagga agtgtgagtt taaccggaat gcaaggaacc ataacagcca tgacacagaa  15480
ctacattagt attcaatttc tatttgacaa caatggtgcg ttgacttcat caccgctcct  15540
caacaacaac acttggggta tacggcaaaa cgacacttcg tccgctaacc ccgcctacaa  15600
tgctcttgca tttatgccta acagcactgt atatgtaaga ggtcaaagtg gtgagcccag  15660
aaataactat tacacccaaa cataccttag gggaaacgtt aaaaagccaa ttatccttac  15720
cgttacctac aactcggctg cttcaggtta ttcactaact tttaaatggg atgctgtagt  15780
aacagaaaaa tttgccactc caacatcttc tttttgctat attacagaac aataaattcc  15840
tattacccca ccaattcgtt tttttcagat gaaacgggcc agagttgatg aagacttcaa  15900
cccagtgtac ccttatgacc ccccatacgc tcccgttatg cccttcatta ctccaccttt  15960
tacctcctcg gatgggttgc aggaaaaacc acttggagtg ttaagtttaa actacaagga  16020
tcccattact acacaaaatg gatctctcac gttgaaaata ggaaacggcc tcactctaga  16080
caaccaggga caattaacat caactgctgg ggaagtagag cctccgctca ctaatgctaa  16140
caacaaactt gcactagcct atagcgaacc attagcagta aaaagcaacc gcttaacttt  16200
atcacacacc gcccccttg tcgttgctaa taattcttta gcgttgcaag tttcagaacc  16260
tatttttata aatgacgatg acaagctagc cctgcagaca gccgcccccc ttgtaactaa  16320
cgctggcacc cttcgcttac agagcgccgc ccctttagga ttggttgaaa atactcttag  16380
actgctgttt tctaaaccct tgtatttgca aaatgatttt cttgcattag gcattgaacg  16440
ccccctggct atagcagccg caggtactct agcactacaa ctcactcctc cattaaagac  16500
taacgatgac gggctgacac tatccacagt cgagccatta actgtaaaaa acggaaactt  16560
aggcttgcaa atatctcgcc ctttggttgt tcaaaacagc agcctttcgc ttgctattac  16620
ccccccgctg cgtctattta acagcgaccc cgttcttggt ttgggcttta cttttcccct  16680
agccgtgaca gacaacctac tctccttaaa catgggagac ggtgttaaac taacctataa  16740
taaactaaca gccaatttgg gtagggattt acaatttgaa aacggtgcca ttgccgtaac  16800
gcttactgcc gaatcacctt tgcaatacac taacaaactt caactgaata ttggagctgg  16860
ccttcgttac aatggagcca gcagaaaact agatgtaaac attaaccaaa ataagggctt  16920
aacttgggac aacgatgcag ttattcccaa attaggatca ggtttacaat tcgaccctaa  16980
tggtaacatc gctgttatcc ctgaaaccgt aaagccgcaa acgttatgga caactgcaga  17040
tccatcgcct aactgctcag tgtaccagga cttggacgcc aggctgtggc tcgctcttgt  17100
taaaagtggt gacatggttc atggaagcat tgctctaaaa gccctaaaag gaacgttgct  17160
aaatcctaca gcaagctaca tctccattgt gatatatttt tacagcaacg gagtcaggcg  17220
taccaactat cccacgtttg acaacgaagg caccttagct aacagcgcta cctggggata  17280
ccgagagggg caatctgcta acactaatgt aaccaatgcc actgaattta tgcccagctc  17340
aaccaggtac cccgtgaata aaggagacaa tattcagaat caatcttttt catacacctg  17400
tatcaaagga gatttcgcta tgcctgtccc gttccgtgta acatataatc atgccctgga  17460
aggatactcc cttaagttca cctggcgcgt tgtagccaac caagcttttg atattccttg  17520
ctgttccttt tcatacatca cagaataaac cactttttaa aatttttctt tttattttac  17580
acgcacagta aggcttcctc ccccttcca tttgacagca tacaccagcc tctccccctt  17640
catggcagta aactgctgcg agccagtccg gtatttggga gttaaaatcc aaacagtctc  17700
tttggtgatg aaacgtcgat ccgtgatgga cacaaatccc tggggcaggt tttccagcgt  17760
ttcggtaaaa aactgcacac cgccctacaa aacaaacagg ttcaggctct ccatgggtta  17820
tctccccgat caaactcaga cagggtaaag gtgcggtgat gttccactaa accacgcagg  17880
tggcgctgtc tgaacctctc ggtgcgactc ctgtgaggct ggtaagaagt tagattgtcc  17940
agtagcctca cagcatggat gatcagttta cgtgtacgtc tggcgcaaca gcgcatctga  18000
atctcactga gattccggca agaatcgcac accatcacaa tcaggttgtt catgatccca  18060
tagctgaaca cgctccagcc aaagctcatt cgctccaaca gcgccaccgc gtgtccgtcc  18120
aaccttactt taacataaat caggtgtctg ccgcgtacaa acatactacc cgcatacaga  18180
acttcccggg gcaaacccct gttcaccacc tgcctgtacc agggaaacct cacatttatc  18240
agggagccat agatagccat tttaaaccaa ttagctaaca ccgccccacc agctctacac  18300
tgaagagaac cgggagagtt acaatgacag tgaataatcc atctctcata acccctgatg  18360
gtctgatgga aatccagcac accgccctac aaaacaaaca ggttcaggct ctccatgggt  18420
tatctccccg atcaaactca gacagggtaa aggtgcggtg atgttccact aaaccacgca  18480
ggtggcgctg tctgaacctc tcggtgcgac tcctgtgagg ctggtaagaa gttagattgt  18540
ccagtagcct cacagcatgg atgatcagtt tacgtgtacg tctggcgcaa cagcgcatct  18600
gaatctcact gagattccgg caagaatcgc acaccatcac aatcaggttg ttcatgatcc  18660
catagctgaa cacgctccag ccaaagctca ttcgctccaa cagcgccacc gcgtgtccgt  18720
ccaaccttac tttaacataa atcaggtgtc tgccgcgtac aaacatacta cccgcataca  18780
```

```
gaacttcccg gggcaaaccc ctgttcacca cctgcctgta ccagggaaac ctcacattta  18840
tcagggagcc atagatagcc attttaaacc aattagctaa caccgcccca ccagctctac  18900
actgaagaga accgggagag ttacaatgac agtgaataat ccatctctca taacccctga  18960
tggtctgatg gaaatccaga tctaacgtgg cacagcagat acacactctc atatacattt  19020
tcatcacatg gttttcccag gccgttaaaa tacaatccca atacacgggc cactcctgca  19080
gtacaataaa gctaatacaa gatggtatac tcctcacctc actaacattg tgcatgttca  19140
tattttcaca ttctaagtac cgagagttct cctctacaac agcactgctg cggtcctcac  19200
aaggtggtag ctggtgacga tcgtaaggag ccagtctgca acgataccgt ctgtcgcgct  19260
gcatcgtaga ccagagaccg acgcacctcc tggtacttgt ggtagcagaa ccacgtccgc  19320
tgccaacagg tatccacgta acgccggtcc ctgcgtcgcg cgcgctctgt tctcaatgca  19380
aaatgcagcc actcttgtaa tccacacaga tccctctcgg cctccgggag gatacacact  19440
tcaaacctac aaatgtctcg gtacagttcc aaacacgaag tgagggcgag ttccaaccaa  19500
gacaggcagg ctggtctatc ccgacacact ggaggtggag gaagacacgg aagaggcatg  19560
ttattccaag cgattcacca acgggtcgaa atgaagatcc cgaagatgac aacggtcgcc  19620
tccggagccc tgatggaatt taacagccaa atcaaacatt atgcgatttt ccaggctatc  19680
gatcgcggcc tccaaaagag cctggacccg cacttccaca aacaccagca aagcaaaagc  19740
gttattatca aactcttcga tcatcaagct gcaagactgt acaatgccca agtaattttc  19800
atttctccac tcgcgaatga tgtcgcggca aatagtctga aggttcatgc cgtgcatatt  19860
aaaaagctcc gaaagggcgc cctctatagc catgcgtaga cacaccatca tgactgcaag  19920
atatcgggct cctgagacac ctgcagcaga tttaacagac ccaggtcagg ttgctctccg  19980
cgatcgcgaa tctccatccg caaggtcatt tgcaaataat taaatagatc tgcgccgact  20040
aaatctgtta actccgcgtt aggaactaaa tcaggtgtgg ctacgcagca caaaagttcc  20100
agggatggcg ccaaactcac tagaaccgct cccgagtagc aaaactgatg aatgggagta  20160
acacagtgta aaatgttcag ccaaaaatca ctaagccgct cctttaaaaa gtccagtact  20220
tctatattca gttcgtgcaa gtactgaagc aactgtgtgg gaatatgcac aacaaaaaaa  20280
atagggcggc tcagatacat gttgacctaa aataaaaaga atcattaaac taaagaagct  20340
tggcgaacgg tgggataaat gacacgttcc agcagcaggc aagcaaccgg ctgtccccgg  20400
gaaccgcggt aaaattcatc cgaatgatta aaaagaacaa cagaaacttc ccaccatgta  20460
ctcggttgga tctcctgagc acagagcaat acccccctca cattcatatc cgccacagaa  20520
aaaaagcgtc ccagataccc agcgggaata tccaacgaca gctgcaaaga cagcaaaaca  20580
atccctctgg gagcaatcac aaaatcctcc ggtgaaaaaa gcacatacat attagaataa  20640
ccctgctgct ggggcaaaaa ggcccgtcgt cccagcaaat gcacataaat atgttcatca  20700
gccattgccc cgtcttaccg cgtaaacagc cacgaaaaat tcgagctaaa atccacccaa  20760
cagcctatag ctatatatac actccgccca atgacgctaa taccgcacca cccaccgcca  20820
aagttcaccc acacccacga aacccgcgaa aatccagcgc cgtcagcact tccgcaattt  20880
cagtctcaca acgtcacttc cgcgcgcctt ttcacattcc cacacccgcc cacaaacccc  20940
gcgtcaccgc ccgtcacccc ggccccgcct cgctcctccc cgctcattat catattggca  21000
cgtttccaga ataaggtata ttattgatga tgttaattaa ttcgaaccca taatacccat  21060
aatagctgtt tgccatcgac caattctccc atattcccgg ttgaattgta gtacatgaga  21120
ccaataaagt tatttgaaga cgaaagggcc tcgtgatacg cctattttta taggttaatg  21180
tcatgataat aatggtttct tagacgtcag gtggcacttt tcggggaaat gtgcgcggaa  21240
cccctatttg tttatttttc taaatacatt caaatatgta tccgctcatg agacaataac  21300
cctgataaat gcttcaataa tattgaaaaa ggaagagtat gagtattcaa catttccgtg  21360
tcgcccttat tccctttttt gcggcatttt gccttcctgt ttttgctcac ccagaaacgc  21420
tggtgaaagt aaaagatgct gaagatcagt tgggtgcacg agtgggttac atcgaactgg  21480
atctcaacag cggtaagatc cttgagagtt ttcgccccga agaacgtttt ccaatgatga  21540
gcacttttaa agttctgcta tgtggcgcgg tattatcccg tgttgacgcc gggcaagagc  21600
aactcggtcg ccgcatacac tattctcaga atgacttggt tgagtactca ccagtcacag  21660
aaaagcatct tacggatggc atgacagtaa gagaattatg cagtgctgcc ataaccatga  21720
gtgataacac tgcggccaac ttacttctga caacgatcgg aggaccgaag gagctaaccg  21780
ctttttttgca caacatgggg gatcatgtaa ctcgccttga tcgttgggaa ccggagctga  21840
atgaagccat accaaacgac gagcgtgaca ccacgatgcc tgcagcaatg gcaacaacgt  21900
tgcgcaaact attaactggc gaactactta ctctagcttc ccggcaacaa ttaatagact  21960
ggatggaggc ggataaagtt gcaggaccac ttctgcgctc ggcccttccg gctggctggt  22020
ttattgctga taaatctgga gccggtgagc gtgggtctcg cggtatcatt gcagcactgg  22080
ggccagatgg taagccctcc cgtatcgtag ttatctacac gacggggagt caggcaacta  22140
tggatgaacg aaatagacag atcgctgaga taggtgcctc actgattaag cattggtaac  22200
tgtcagacca agtttactca tatatacttt agattgattt aaaacttcat ttttaattta  22260
aaaggatcta ggtgaagatc ctttttgata atctcatgac caaaatccct taacgtgagt  22320
tttcgttcca ctgagcgtca gaccccgtag aaaagatcaa aggatcttct tgagatcctt  22380
tttttctgcg cgtaatctgc tgcttgcaaa caaaaaaacc accgctacca gcggtggttt  22440
gtttgccgga tcaagagcta ccaactcttt ttccgaaggt aactggcttc agcagagcgc  22500
agataccaaa tactgtcctt ctagtgtagc cgtagttagg ccaccacttc aagaactctg  22560
tagcaccgcc tacatacctc gctctgctaa tcctgttacc agtggctgct gccagtggcg  22620
ataagtcgtg tcttaccggg ttggactcaa gacgatagtt accggataag gcgcagcggt  22680
cgggctgaac gggggggttcg tgcacacagc ccagcttgga gcgaacgacc tacaccgaac  22740
tgagatacct acagcgtgag ctatgagaaa gcgccacgct tcccgaaggg agaaaggcgg  22800
acaggtatcc ggtaagcggc agggtcggaa caggagagcg cacgagggag cttccagggg  22860
gaaacgcctg gtatctttat agtcctgtcg ggtttcgcca cctctgactt gagcgtcgat  22920
ttttgtgatg ctcgtcaggg gggcggagcc tatggaaaaa cgccagcaac gcggcctttt  22980
tacggttcct ggccttttgc tggccttgaa gctgtccctg atggtcgtca tctacctgcc  23040
tggacagcat ggcctgcaac gcgggcatcc cgatgccgcc ggaagcgaga agaatcataa  23100
tggggaaggc catccagcct cgcgtcgatg gcaaacagct attatgggta ttatgggttc  23160
gaattaat                                                           23168
```

SEQ ID NO: 37 moltype = DNA length = 21190
FEATURE Location/Qualifiers
source 1..21190
mol_type = other DNA

```
                    note = Synthetic oligonucleotide pBr/sAd4287.PsiI-rITR.dE3
                    organism = synthetic construct
SEQUENCE: 37
attaacccag gacctggaaa tagtgccttt aactaaagac agcaaagaca gaagctacaa  60
tattataaac aacacgacgg acaccctgta tcggagctgg tttctggctt acaactacgg  120
agaccccgag aaaggagtga gatcatggac catactcacc accacggacg tgacctgtgg  180
ctcgcagcaa gtgtactggt ccctgccgga tatgatgcaa gacccggtca ccttccgccc  240
ctccacccaa gtcagcaact tcccggtggt gggcaccgag ctgctgcccg tccatgccaa  300
gagcttctac aacgagcagg ccgtctactc gcaacttatt cgccagtcca ccgcgcttac  360
ccacgtgttc aatcgctttc ccgagaacca gattctggtg cgccctcccg ctcctaccat  420
taccaccgtc agtgaaaacg ttcccgccct cacagatcac ggaaccctgc cgctgcgcag  480
cagtatcagt ggagttcagc gcgtgaccat caccgacgcc agacgtcgaa cctgccccta  540
cgtttacaaa gcgcttggcg tggtggctcc taaagttctt tctagtcgca ccttctaaaa  600
acatgtccat cctcatctct cccgataaca acaccggctg gggactgggc tccggcaaga  660
tgtacggcgg agccaaaagg cgctccagtc agcacccagt tcgagttcgg ggccacttcc  720
gcgctccttg gggagcttac aagcgaggac tctcgggtcg aacggctgta gacgatacca  780
tagatgccgt gattgccgac gcccgccggt acaaccccgg accggtcgct agcgccgcct  840
ccaccgtgga ttccgtgatc gacagcgtgg tagccggcgc tcgggcctat gctcgccgca  900
agaggcggct gcatcggaga cgtcgcccca ccgccgccat gctggcagcc agagccgtgc  960
tgagacgggc ccggagggta ggcaggaggg ctatgcgccg cgctgccgcc aacgccgccg  1020
ccgggagggc ccgccgacag gctgcccgcc aggctgctgc cgccatcgct agcatggcca  1080
gacccaggag agggaacgtg tactgggtgc gcgattctgt gacgggagtc cgagtgccgg  1140
tgcgcagccg acctccccga agttagaaga tccaagctgc gaagacggcg gtactgagtc  1200
tccctgttgt tatcagccca acatgagcaa gcgcaagttt aaagaagaac tgctgcagac  1260
gctggtgcct gagatctatg gccctccgga cgtgaagcct gacattaagc cccgcgatat  1320
caagcgtgtt aaaaagcggg aaaagaaaga ggaactcgcg gtggtagacg atggcggagt  1380
ggaatttatt aggagtttcg cccgcggcg cagggttcaa tggaaagggc gacgggtaca  1440
acgcgttttg aggccgggca ccgcggtagt ttttaccccg ggagagcggt cggccgttag  1500
gggttttaaa aggcagtacg acgaggtgta cggcgacgag gacatattgg aacaggcggc  1560
tcaacagatc ggagaatttg cctatggaaa gcgctcgcgt cgcgaagacc tggccatcgc  1620
cttagacagc ggcaacccca cgcccagcct caaacccgtg acgctgcagc aggtgcttcc  1680
cgtgagcgcc agcacggaca gcaagagggg aataaaaaga gaaatggaag atctgcagcc  1740
taccatccag ctcatggttc ctaaacggca gaggctggaa gaggtcctgg agaagatgaa  1800
agtggacccc agcatagagc cggacgttaa agtcaggccg atcaaagaag tggcccctgg  1860
actcggggtg cagacggtgg atatccagat ccccgtcacg tcagcttcga ccgccgtgga  1920
agccatggaa acgcaaaccg aaacccccgc cgtggttggt accaaagaag tggcgttgca  1980
aaccgacccc tggtacgaat ttgccgcccc ccggcgtcag aggcgacccg ctcgttacgg  2040
ccccgccaac gccatcatgc cagaatatgc gctgcatccg tctatcctgc ccacccccgg  2100
ctaccgggga gtgacgtatc gcccgtcagg aacccgccgc cgaacccgtc gccgccgccg  2160
ctcccgtcgc gctctggccc ccgtgtcggt gcgccgcgta acacgccggg gaaagacagt  2220
caccattccc aacccgcgct accaccctag catcctttaa tgactctgcc gttttgcaga  2280
tggctctgac ttgccgcgtg cgccttcccg ttccgcacta tcgaggaaga tctcgtcgta  2340
ggagaggcat ggcgggcagt ggtcgccggc gggctttgcg caggcgcatg aaaggcggaa  2400
ttttacccgc tttgataccc ataatcgccg ccgccatcgg tgccataccc ggcgtcgctt  2460
cagtggcctt gcaagcagct cgtaataaat aaacgaaggc ttttgcactt atgtcctggt  2520
cctgactatt ttatgcagaa agagcatgga agacatcaat tttacgtcgc tggctccgcg  2580
gcacggctcg cggccgctca tgggcacctg gaacgacatc ggcaccagtc agctcaacgg  2640
gggcgctttc aattggggga gcctttggag cggcattaaa aactttggct ccacgattaa  2700
atcctacggc agcaaagcct ggaacagtag tgctggtcag atgctccgag ataaactgaa  2760
ggacaccaac ttccaagaaa aagtggtcaa tggggtggtg accggcatcc acggtgcggt  2820
agatctcgcc aaccaagcgg tgcagaaaga gattgacagg cgtttggaaa actcgcgggt  2880
gccgccgcag agggggggatg aggtggaggt cgaggaagta gaagtagagg aaaagctgcc  2940
cccgctggag aaagttcccg gtgcacctcc gaggccgcag aagcggccca ggccagaact  3000
agaagaaact ctggtgacgg agagcaagga gcctccctcg tacgagcaag ccttgaaaga  3060
gggcgcctct ccaccctcct acccgatgac taagccgatc gcacccatgg ctcgaccggt  3120
gtacggcaag gattacaagc ccgtcacgct agagctgccc ccaccgcccc cttcgcgtcc  3180
gacggtgcct ccgctgcctg ccccgtcggc gggtcccgag tctgcaccat ccgctgtgcc  3240
tctgccagcc gcccgtcccg tggccgtggc cactgccagg aaccccagag gccagagagg  3300
agccaactgg caaagcacgc tgaacagcat cgtgggcctg ggggtgaaaa gcctgaaacg  3360
ccgccgttgc tattattaaa aagtgtagct aaaaaatttc ccgttgtata cgcctcctat  3420
gttaccgcca gagacgcgtg actgtcgccg cgagcgccgc ttccaagatg gccaccccat  3480
cgatgatgcc gcagtggtct tacatgcaca tcgccggcca ggacgcctcg gagtacctga  3540
gtcccggcct cgtgcagttt gcccgcgcca ccgacaccta cttcagcttg ggaaacaagt  3600
ttagaaaccc caccgtggcc cccacccacg atgtgaccac ggaccgctcg cagaggctga  3660
ccctgcgctt tgtgcccgta gaccgggagg acaccgcgta ctcttacaaa gtgcgctaca  3720
cgctggccgt aggggacaac cgagtgctgg acatggccag cacctacttt gacatccggg  3780
gggtgctgga tcggggtccc agcttcaagc cctactccgg caccgcttac aactccctgg  3840
ctcccaaggg cgcccccaat cctgcagaat gggccgatac caacgacagc aacaaactga  3900
aagtgagggg tcaggcgcct tttgtcagta cttacggttc tgctacggcg cttacaaaag  3960
atgggataca ggtgggagtg gatacttccg aagcatctca ggctgtttat gccgacagaa  4020
gttaccagcc agaaccccaa attggagaga cagagtggaa cagcgaagtg ggtaatgacg  4080
acagagtggc gggaagggtg ctaaagaaaa caactcccat gttcccttgt tacggttcat  4140
atgccaagcc caccaacgaa aaaggcggac aagcaataca gcccaccgcc ggcaacggcg  4200
ataatcaggc tgtagagtta caattctttg ccactactag cactcccact gcgccaaagg  4260
cagtattgta cgcggaggac gtggccattg aagctccaga tactcactta gtgtttaagc  4320
caacagtagt cgcgggaact acaagttcgg aagctctgct aacccaacaa gccgcaccta  4380
accgcccaaa ctacattgcc tttagagata actttattgg tctcatgtac tacaattcaa  4440
ccgggaatat gggagtactg gccggacaag catctcagct caatgcagtg gttgatcttc  4500
aggacagaaa caccgaactg tcatatcagc taatgctgga tgctctggga gatcgcagtc  4560
```

```
ggtacttttc tatgtggaat caagctgtag atagctatga tccagatgta agaattgtag  4620
aaaaccacgg tgtggaagac gaactgccta attattgctt cccactaggc gggatggtag  4680
taacggacac ttacaaagcc ataaaggtaa atggaagcgg atggacggct aatactgacg  4740
ttttcagcga gagagtagaa ataggctcag gtaacctgtt tgccatggaa attaacttgc  4800
aagctaatct gtggcgcagt ttcttgtatt ccaacatagg actgtacctc ccggactctt  4860
taaaattaac ccctgacaac atcacgctcc ctgagaacaa aaatacctac cagtatatga  4920
acggtcgcgt aacaccaccc gggctcgtgg acacctacgt taacgtgggt gcgcgctggt  4980
cccccgatgt tatggacagc attaaccctt ttaaccacca ccgcaacgcc gggctccgct  5040
accgttccat gctcctggga aacggacgct acgtaccctt ccacattcag gtgccccaga  5100
aattctttgc aattaaaaac ctgctgctgc tccccggttc ctatacctac gagtggaatt  5160
tccgcaagga cgtgaacatg attttgcaaa gctcgctggg taacgacctg cgagttgacg  5220
gggccagcat acgcttcgac agcatcaacc tgtatgctaa ctttttcccc atggcccaca  5280
acacggcctc caccctggaa gccatgctgc gcaacgacac caatgaccag tccttcaacg  5340
actacctgtg cgcggccaac atgctgtatc ccatccccgc caacgccacc agcgtgccca  5400
tctccatccc gtctcgcaac tgggccgcct ttaggggttg gagtttcacc cgcctcaaaa  5460
ccaaggaaac cccctcgctg ggctctggct tcgaccccta cttcgtctac tcaggctcca  5520
ttccctacct ggacggcact ttctatctta accacacttt caaaaaggtg tctatcatgt  5580
tcgattcctc ggtcagctgg cccggcaacg accgcctgct gacgcccaac gagttcgaaa  5640
tcaagcgttc ggtggacggt gaagggtaca acgtggccca gagcaacatg accaaggact  5700
ggttcctggt tcaaatgctc agccattaca acatcggtta ccagggcttc tatgtgcccg  5760
agaactacaa ggaccgcatg tactccttct ttaggaactt ccaacccatg agtcgccaag  5820
tcgtggactc agtggcttac agggactact accaggacgt taagctcccc taccagcaca  5880
acaactcagg gttcgtgggc tacatgggtc ccaccatgcg agaggggcag gcctacccgg  5940
ccaactatcc ttatccccta atcggagaga ctgctgtacc cagcctgacg cagaaaaagt  6000
tcctctgcga ccgggtgatg tggaggatac ccttctctag caacttcatg tctatgggct  6060
ccctcaccga cctggggcag aacatgctgt acgccaactc cgctcacgcc ttggacatga  6120
cctttgaggt ggatcccatg gatgagccca cgcttctcta tgttctgttt gaagtcttcg  6180
acgtggtgcg catccaccag ccgcaccgcg gcgtcatcga ggccgtctac ctgcgcacac  6240
ctttctctgc cggtaacgcc accacctaaa gaagccgatg ggctccagcg aacaggagct  6300
gcaggccatt gttcgcgacc tgggctgcgg gccctacttt ttgggcacct tcgacaagcg  6360
gttccccggc ttcatgtccc ctcacaagcc ggcctgtgcc atcgttaaca cggccggacg  6420
ggaaaccggg ggggtccact ggctcgcctt cgcctggaac ccgcgtaacc gcacctgcta  6480
cctgttcgac ccttttggtt tctccgacga aaggctgaag cagatctacc agttcgagta  6540
cgaggggctc ctccagcgca gcgctctggc ctccacgccc gaccactgcg tcaccctgga  6600
aaagtccacc cagacggtcc aggggcccct ctcggccgcc tgcgggctct tctgttgcat  6660
gtttttgcac gccttcgtgc actggcctca cacccccatg gatcacaacc ccaccatgga  6720
tctgctcacc ggagtgccca acagcatgct tcacagcccc caggtcgccc ccaccctgcg  6780
ccgtaaccag gaacacctgt atcgctttct ggggaaacac tctgcctatt tccgccgcca  6840
tcggcagcgc atcgaacagg ccacggcctt cgaaagcatg agccaaagag tgtaatcaat  6900
aaaaaccatt tttatttgac atgatacgcg cttctggcgt ttttattaaa aatcgaaggg  6960
ttcgagggag gggtcctcgt gcccgctggg gagggacacg ttgcgatact ggaatcgggc  7020
gctccaacga aactcgggga tcaccagtcg cggcaggggc acgtcttcca ggttctgctt  7080
ccaaaactgt cgcaccagct gcagggctcc catcacgtcg ggcgccgata tcttgaagtc  7140
gcagttaggg ccggagctcc cgcggctgtt ccggaacacg gggttggcac actggaacac  7200
catcacgctg gggttgtgaa tactagccag ggccgtcgga tcggtcacct ccgacgcatc  7260
cagatcctcg gcgttgctca gggcgaacgg ggtcagcttg cacatctgcc gcccgatctg  7320
gggcaccagg tcgggtttgt tgaggcaatc gcagcgcaga gggatcagga tgcgtcgctg  7380
cccgcgttgc atgatagggt aactcgccgc caggaactcc tccatctgac ggaaggccat  7440
ctgggcctta acgccctcgg tgaaaaacag cccacaggac ttgctagaaa atacgttatt  7500
gccgcagtta atgtcttccg cgcagcagcg tgcatcttcg ttcttcagct gaaccacgtt  7560
acgcccccag cggttctgga ccaccttggc tttcgtagga tgctccttca gcgcccgctg  7620
cccgttctcg ctggtcacat ccatttccac cacgtgctcc ttgcagacca tctccactcc  7680
gtggaagcaa aacaggacgc cctcctgccg ggtattgcga tgctcccaaa cggcacaccc  7740
ggtgggctcc cagctcttgt gttttacccc cgcgtaggct tccatgtaag ccatgaggaa  7800
tctgcccatc agctcggtga aggtcttctg attggtgaag gttagcggca ggccgcggtg  7860
ctcctcgttc aaccaagttt gacagatctt gcggtacacc gttccctggt cgggcagaaa  7920
cttaaaagcc gctctgctgt cgttgtccac gtggaacttc tccattaaca tcatcatggt  7980
ttccataccc ttctcccacg ctgacaccag cggtttgctg tcggggttct tcaccaacac  8040
ggcggtagag gggccctcgc cggccccgac gtccttcatg gtcattcttt gaaactccac  8100
ggagccgtcc gcgcgacgta ctctgcgcac cggagggtag ctgaagccca cctccaccac  8160
ggtgccttcg ccctcgctgt cggaaacgat ctccggggat ggcggcggtg cgggtgtcgc  8220
cttgcgagcc ttcttcttgg gagggagctg aggcgcctcc tgctcgcgct cggggctcat  8280
ctcccgcaag tagggggtta tggagctgcc tgcttggttc tgacggttgg ccattgtatc  8340
ctaggcagaa agacatggag cttatgcgcg aggaaacttt aaccgccccg tcccccgtca  8400
gcgacgaaga tgtcatcgtc gaacaggacc cgggctacgt tacgccgccc gaggatctgg  8460
aggggcctga ccggcgcgac gctagtgagc ggcaggaaaa tgagaaagag gaggcctgct  8520
acctcctgga aggcgacgtt ttgctaaagc atttcgccag gcagagcacc atagttaagg  8580
aggccttgca agaccgctcc gaggtgccct tggacgtcgc cgcgctctcc caggcctacg  8640
aggcgaacct tttctcgcct cgagtgcctc cgaagagaca gcccaacggc acctgcgagc  8700
ccaacccgcg actcaacttc taccccgtgt tcgccgtacc agaggcgctg gccacctatc  8760
acatttttt caaaaaccaa cgcatccccc tatcgtgccg ggccaaccgc accgcggccg  8820
ataggaatct caggcttaaa aacggagcca acatacctga tatcacgtcg ctggaggaag  8880
tgcccaagat tttcgagggt ctgggtcgag atgagaagcg ggcggcgaac gctctgcaga  8940
aagaacagaa agagagtcag aacgtgctgg tggagctgga gggggacaac gcgcgtctgg  9000
ccgtcctcaa acgctgcata gaagtctccc acttcgccta ccccgccctc aacttgccac  9060
ccaaagttat gaaatcggtc atggatcagc tgctcatcaa gagagctgag cccctggatc  9120
ccgaccaccc cgaggcggaa aactcagagg acggaaagcc cgtcgtcagc gacgaggagc  9180
tcgagcggtg gctggaaacc agggaccccc aacagttgca agagaggcgc aagatgatga  9240
tggcggccgt gctggtcacc gtggagctgg aatgcctgca acggtttttc agcgacgtgg  9300
```

-continued

```
agacgctacg caaaatcggg gaatccctgc actacacctt ccgccagggc tacgtccgcc  9360
aggcctgcaa gatctccaac gtggagctca gcaacctggt ctcctacatg ggcatcctcc  9420
acgagaaccg gctggggcag agcgtgctgc actgcacctt gcaaggcgag gcgcggcggg  9480
actacgtgcg agactgcatc tacctcttcc tcaccctcac ctggcagacc gccatgggcg  9540
tctggcagca gtgcttggaa gagagaaacc tcaaagagct agacaaactc ctctgccgcc  9600
agcggcgcgc cctgtggtcc ggtttcagcg agcgcacggt cgccagcgct ctggcggaca  9660
tcatcttccc ggagcgcctg atgaaaacct tgcaaaacgg cctgccggat ttcatcagtc  9720
aaagcatttt gcaaaacttc cgctcttttg tcctggaacg ctccgggatc ttgcccgcca  9780
tgagctgcgc gctaccttct gactttgtcc ccctctccta ccgcgagtgc cctcccccac  9840
tgtggagcca ctgctacctc ttccaactgg ccaactttct ggcctaccac tccgacctca  9900
tggaagacgt aagcggagag ggtttactgg agtgccactg ccgctgcaac ctgtgcaccc  9960
cccacagatc gctggcctgc aacaccgagc tactcagcga aacccaggtc ataggtacct 10020
tcgagatcca ggggccccag cagcaagagg gtgcttccgg cttgaagctc actccggcgc 10080
tgtggacctc ggcttactta cgcaaatttg tagccgagga ctaccacgcc cacaaaattc 10140
agttttacga agaccaatct caaccaccga aagcccccct cacggcctgc gtcatcaccc 10200
agagcaagat cctggcccaa ttgcaatcca tcaaccaagc gcgccgcgat ttccttttga 10260
aaaagggtcg gggggtgtat ctggaccccc agaccggcga ggaactcaac ccgtccacac 10320
tctccgtcga agcagccccc ccgagacatg ccgcccaagg gaaccgccaa gcagctgatc 10380
gctcggcaga gagcgaagaa gcaagagctg ctccagcagc aggtggagga cgaggaagag 10440
atgtgggaca gccaggcaga ggaggtgtca gaggacgagg aggagatgga aagctgggac 10500
agcctagacg aggaggagga cgagctttca gaggaagagg cgaccgaaga aaaaccacct 10560
gcatccagcg cgccttctct gagccgacag ccgaagcccc ggcccccgac gcccccggcc 10620
ggctcactca aagccagccg taggtgggac gccaccgaat ctccagcggc agcggcaacg 10680
gcagcgggta aggccaaacg cgagcggcgg gggtattgct cctggcgggc ccacaaaagc 10740
agtattgtga actgcttgca acactgcggg ggaaacatct cctttgcccg acgctacctc 10800
ctcttccatc acggtgtggc cttccctcgc aacgttctct attattaccg tcatctctac 10860
agcccctacg aaacgctcgg agaaaaaagc taaggcctcc tccgccgcga ggaaaaactc 10920
cgccgccgct gccgccgcca aggatccacc ggccaccgag gagctgagaa agcgcatctt 10980
tcccactctg tatgctatct ttcagcaaag ccgcgggcag caccctcagc gcgaactgaa 11040
aataaaaaac cgctccttcc gctcgctcac ccgcagctgt ctgtaccaca agagagaaga 11100
ccagctgcag cgcaccctgg acgacgccga agcactgttc agcaaatact gctcagcgtc 11160
tcttaaagac taaaagaccc gcgctttttc cccctcggcc gccaaaaccc acgtcatcgc 11220
cagcatgagc aaggagattc ccacccccta catgtggagc tatcagcccc agatgggcct 11280
ggccgcgggg gccgcccagg actactccag caagatgaac tggctcagcg ccggcccccа 11340
catgatctca cgagttaacg gcatccgagc ccaccgaaac cagattctct tagaacaggc 11400
ggcaatcacc gccacacccc ggcgccaact caacccgcct agttggcccg ccgcccaggt 11460
gtatcaggaa aatccccgcc cgaccacagt cctcctgcca cgcgacgcgg aggccgaagt 11520
cctcatgact aactctgggg tacaattagc gggcgggtcc aggtacgcca ggtacagagg 11580
tcgggccgct ccttactctc ccgggagtat aaagagggtg atcattcgag gccgaggtat 11640
ccagctcaac gacgagacgg tgagctcctc aaccggtctc agacctgacg gagtcttcca 11700
gctcggagga gcgggccgct cttccttcac cactcgccag gcctacctga ccctgcagag 11760
ctcttcctcg cagccgcgct ccgggggaat cggcactctc cagttcgtgg aagagttcgt 11820
tccctccgtc tacttcaacc ccttctccgg ctcgcctgga cgctacccgg acgccttcat 11880
tcccaacttt gacgcagtga gtgaatccgt ggacggctac gactgatgac agatggtgcg 11940
gccgtgagag ctcggctgcg acatctgcat cactgccgtc agcctcgctg ctacgctcgg 12000
gaggcgatcg tcttcagcta ctttgagctg ccggacgagc accctcaggg tccggctcac 12060
gggttgaaac tcgagatcga gaacgcgctc gagtctcgcc tcatcgacac cttcaccgcc 12120
cgacctctcc tggtagaaat cgaacgcggg atcactacca tcaccctgtt ctgcatctgc 12180
cccacgcccg gattacatga agatctgtgc tgtcatcttt gcgctcagtt taataaaaac 12240
tgaacttttt gccgcacctt caacgccacg cgtcgtttct ccaaaagttg tcgacagctc 12300
ttcagtcaga ggtatacgag aaactgttta tttttacaac tctactactt ttctcaccct 12360
taactgctcc tgcactaacg aactaattca gtggttcgcg aacggctcac tctgccaagt 12420
ctttttaat tctgctgttc ttcctgagtt tggctccttt gcgtgtggaa attctacact 12480
agtgggagct atcctgtgtc actgtcacgc gcctgattgt atgcccaaac taattagaac 12540
tctctgtgcc ttaggtgata tatttaaaat gtaagtcagt atcaataaac ttaccttaaa 12600
tttgacagca gtttttggt aacatcattc agcagcacca ctttaccctc ttcccaactc 12660
tcgtatggga cgtgatggtg ggcggcaaac ttcctccaaa ccctaaaaca aatattaata 12720
tccacttcct tgtccttacc cacaattttc atcttttcat agatgaaaag aaccagagtt 12780
gatgaagact tcaaccccgt ctacccttat gactccacat ccactcctgc ggtccccttt 12840
atatcccccc cgtttgtaaa cagcgatggt cttcaggaaa accctcctgg agtcttaagt 12900
ttacgaatag ctaaaccctt gtattttgac atggaaagga aactagcgct ttcacttgga 12960
agaggattgg caattacctc caccggacag ctagaaagca cacagagcgt gcaaaccacc 13020
cctccattag ttgtcaacaa cagcaacacg cttgtcctgc gttattcctc cccgttaggc 13080
ttatcgggtg acaatttaat actaaattgc tccgatcctc tccgcgtagt aaacaacagc 13140
ctgacattca gctacctatc tccacttcgt tttgaaggtg gcagtcttac attcaattac 13200
acatctcccc ttaaactgtt gaacagcagc cttgcgatcg gaataaattc caacaaaggt 13260
ctcggcaatg acagcgatga actttctgtc aaactaacat cagatctaaa gtttaacaac 13320
gatggaaaaa tagcttttgg tatacaaagc ctgtgtacca cccccacagc cgcctctaac 13380
tgtaccgttt ttaccaacgg tgattcttta ctctgtttat gtttaaccaa atgtggagct 13440
cacgtgttag gaagtgtgag tttaaccgga atgcaaggaa ccataacagc catgacacag 13500
aactacatta gtattcaatt tctatttgac aacaatggtg cgttgacttc atcaccgctc 13560
ctcaacaaca acacttgggg tatacggcaa aacgacactt cgtccgctaa ccccgcctac 13620
aatgctcttg catttatgcc taacagcact gtatatgtaa gaggtcaaag tggtgagccc 13680
agaaataact attacaccca aacatacctt aggggaaacg ttaaaaagcc aattatcctt 13740
accgttacct acaactcggc tgcttcaggt tattcactaa cttttaaatg ggatgctgta 13800
gtaacagaaa aatttgccac tccaacatct tctttttgct atattacaga acaataaatt 13860
cctattaccc caccaattcg tttttttcag atgaaacggg ccagagttga tgaagacttc 13920
aacccagtgt acccttatga ccccccatac gctcccgtta tgcccttcat tactccacct 13980
tttacctcct cggatgggtt gcaggaaaaa ccacttggag tgttaagttt aaactacaag 14040
```

```
gatcccatta ctacacaaaa tggatctctc acgttgaaaa taggaaacgg cctcactcta  14100
gacaaccagg gacaattaac atcaactgct ggggaagtag agcctccgct cactaatgct  14160
aacaacaaac ttgcactagc ctatagcgaa ccattagcag taaaaagcaa ccgcttaact  14220
ttatcacaca ccgcccccct tgtcgttgct aataattctt tagcgttgca agtttcagaa  14280
cctattttta taaatgacga tgacaagcta gccctgcaga cagccgcccc ccttgtaact  14340
aacgctggca cccttcgctt acagagcgcc gcccctttag gattggttga aaatactctt  14400
agactgctgt tttctaaacc cttgtatttg caaaatgatt ttcttgcatt aggcattgaa  14460
cgccccctgg ctatagcagc cgcaggtact ctagcactac aactcactcc tccattaaag  14520
actaacgatg acgggctgac actatccaca gtcgagccat taactgtaaa aaacggaaac  14580
ttaggcttgc aaatatctcg ccctttggtt gttcaaaaca gcagcctttc gcttgctatt  14640
acccccccgc tgcgtctatt taacagcgac cccgttcttg gtttgggctt tacttttccc  14700
ctagccgtga cagacaacct actctcctta aacatgggag acggtgttaa actaacctat  14760
aataaactaa cagccaattt gggtagggat ttacaatttg aaaacggtgc cattgccgta  14820
acgcttactg ccgaatcacc tttgcaatac actaacaaac ttcaactgaa tattggagct  14880
ggccttcgtt acaatggagc cagcagaaaa ctagatgtaa acattaacca aaataagggc  14940
ttaacttggg acaacgatgc agttattccc aaattaggat caggtttaca attcgaccct  15000
aatggtaaca tcgctgttat ccctgaaacc gtaaagccgc aaacgttatg gacaactgca  15060
gatccatcgc ctaactgctc agtgtaccag gacttggacg ccaggctgtg gctcgctctt  15120
gttaaaagtg gtgacatggt tcatggaagc attgctctaa aagccctaaa aggaacgttg  15180
ctaaatccta cagcaagcta catctccatt gtgatatatt tttacagcaa cggagtcagg  15240
cgtaccaact atcccacgtt tgacaacgaa ggcaccttag ctaacagcgc tacctgggga  15300
taccgagagg ggcaatctgc taacactaat gtaaccaatg ccactgaatt tatgcccagc  15360
tcaaccaggt accccgtgaa taaaggagac aatattcaga atcaatcttt ttcatacacc  15420
tgtatcaaag gagatttcgc tatgcctgtc ccgttccgtg taacatataa tcatgccctg  15480
gaaggatact cccttaagtt cacctggcgc gttgtagcca accaagcttt tgatattcct  15540
tgctgttcct tttcatacat cacagaataa accacttttt aaaatttttc tttttatttt  15600
acacgcacag taaggcttcc tcccccccttc catttgacag catacaccag cctctccccc  15660
ttcatggcag taaactgctg cgagccagtc cggtatttgg gagttaaaat ccaaacagtc  15720
tctttggtga tgaaacgtcg atccgtgatg gacacaaatc cctggggcag gttttccagc  15780
gtttcggtaa aaaactgcac accgccctac aaaacaaaca ggttcaggct ctccatgggt  15840
tatctccccg atcaaactca gacagggtaa aggtgcggtg atgttccact aaaccacgca  15900
ggtggcgctg tctgaacctc tcggtgcgac tcctgtgagg ctggtaagaa gttagattgt  15960
ccagtagcct cacagcatgg atgatcagtt tacgtgtacg tctggcgcaa cagcgcatct  16020
gaatctcact gagattccgg caagaatcgc acaccatcac aatcaggttg ttcatgatcc  16080
catagctgaa cacgctccag ccaaagctca ttcgctccaa cagcgccacc gcgtgtccgt  16140
ccaaccttac tttaacataa atcaggtgtc tgccgcgtac aaacatacta cccgcataca  16200
gaacttcccg gggcaaaccc ctgttcacca cctgcctgta ccagggaaac ctcacattta  16260
tcagggagcc atagatagcc attttaaacc aattagctaa caccgcccca ccagctctac  16320
actgaagaga accgggagag ttacaatgac agtgaataat ccatctctca taacccctga  16380
tggtctgatg gaaatccagc acaccgccct acaaaacaaa caggttcagg ctctccatgg  16440
gttatctccc cgatcaaact cagacagggt aaaggtgcgg tgatgttcca ctaaaccacg  16500
caggtggcgc tgtctgaacc tctcggtgcg actcctgtga ggctggtaag aagttagatt  16560
gtccagtagc ctcacagcat ggatgatcag tttacgtgta cgtctggcgc aacagcgcat  16620
ctgaatctca ctgagattcc ggcaagaatc gcacaccatc acaatcaggt tgttcatgat  16680
cccatagctg aacacgctcc agccaaagct cattcgctcc aacagcgcca ccgcgtgtcc  16740
gtccaacctt actttaacat aaatcaggtg tctgccgcgt acaaacatac tacccgcata  16800
cagaacttcc cggggcaaac ccctgttcac cacctgcctg taccagggaa acctcacatt  16860
tatcagggag ccatagatag ccattttaaa ccaattagct aacaccgccc caccagctct  16920
acactgaaga gaaccgggag agttacaatg acagtgaata atccatctct cataacccct  16980
gatggtctga tggaaatcca gatctaacgt ggcacagcag atacacactc tcatatacat  17040
tttcatcaca tggttttccc aggccgttaa aatacaatcc caatacacgg gccactcctg  17100
cagtacaata aagctaatac aagatggtat actcctcacc tcactaacat tgtgcatgtt  17160
catattttca cattctaagt accgagagtt ctcctctaca acagcactgc tgcggtcctc  17220
acaaggtggt agctggtgac gatcgtaagg agccagtctg caacgatacc gtctgtcgcg  17280
ctgcatcgta gaccagagac cgacgcacct cctggtactt gtggtagcag aaccacgtcc  17340
gctgccaaca ggtatccacg taacgccggt ccctgcgtcg cgcgcgctct gttctcaatg  17400
caaaatgcag ccactcttgt aatccacaca gatccctctc ggcctccggg aggatacaca  17460
cttcaaacct acaaatgtct cggtacagtt ccaaacacga agtgagggcg agttccaacc  17520
aagacaggca ggctggtcta tcccgacaca ctggaggtgg aggaagacac ggaagaggca  17580
tgttattcca agcgattcac caacgggtcg aaatgaagat cccgaagatg acaacggtcg  17640
cctccggagc cctgatggaa tttaacagcc aaatcaaaca ttatgcgatt ttccaggcta  17700
tcgatcgcgg cctccaaaag agcctggacc cgcacttcca caaacaccag caaagcaaaa  17760
gcgttattat caaactcttc gatcatcaag ctgcaagact gtacaatgcc caagtaattt  17820
tcatttctcc actcgcgaat gatgtcgcgg caaatagtct gaaggttcat gccgtgcata  17880
ttaaaaagct ccgaaagggc gccctctata gccatgcgta gacacaccat catgactgca  17940
agatatcggg ctcctgagac acctgcagca gatttaacag acccaggtca ggttgctctc  18000
cgcgatcgcg aatctccatc cgcaaggtca tttgcaaata attaaataga tctgcgccga  18060
ctaaatctgt taactccgcg ttaggaacta aatcaggtgt ggctacgcag cacaaaagtt  18120
ccagggatgg cgccaaactc actagaaccg ctcccgagta gcaaaactga tgaatgggag  18180
taacacagtg taaaatgttc agccaaaaat cactaagccg ctcctttaaa aagtccagta  18240
cttctatatt cagttcgtgc aagtactgaa gcaactgtgt gggaatatgc acaacaaaaa  18300
aaatagggcg gctcagatac atgttgacct aaaataaaaa gaatcattaa actaaagaag  18360
cttggcgaac ggtgggataa atgacacgtt ccagcagcag gcaagcaacc ggctgtcccc  18420
gggaaccgcg gtaaaattca tccgaatgat taaaaagaac aacagaaact tcccaccatg  18480
tactcggttg gatctcctga gcacagagca ataccccccct cacattcata tccgccacag  18540
aaaaaaagcg tcccagatac ccagcgggaa tatccaacga cagctgcaaa gacagcaaaa  18600
caatccctct gggagcaatc acaaaatcct ccggtgaaaa aagcacatac atattagaat  18660
aaccctgctg ctggggcaaa aaggcccgtc gtcccagcaa atgcacataa atatgttcat  18720
cagccattgc cccgtcttac cgcgtaaaca gccacgaaaa attcgagcta aaatccaccc  18780
```

```
aacagcctat agctatatat acactccgcc caatgacgct aataccgcac cacccaccgc  18840
caaagttcac ccacacccac gaaacccgcg aaaatccagc gccgtcagca cttccgcaat  18900
ttcagtctca caacgtcact tccgcgcgcc ttttcacatt cccacacccg cccacaaacc  18960
ccgcgtcacc gcccgtcacc ccggccccgc ctcgctcctc cccgctcatt atcatattgg  19020
cacgtttcca gaataaggta tattattgat gatgttaatt aattcgaacc cataataccc  19080
ataatagctg tttgccatcg accaattctc ccatattccc ggttgaattg tagtacatga  19140
gaccaataaa gttatttgaa gacgaaaggg cctcgtgata cgcctatttt tataggttaa  19200
tgtcatgata ataatggttt cttagacgtc aggtggcact tttcggggaa atgtgcgcgg  19260
aacccctatt tgtttatttt tctaaataca ttcaaatatg tatccgctca tgagacaata  19320
accctgataa atgcttcaat aatattgaaa aaggaagagt atgagtattc aacatttccg  19380
tgtcgccctt attccctttt ttgcggcatt ttgccttcct gtttttgctc acccagaaac  19440
gctggtgaaa gtaaaagatg ctgaagatca gttgggtgca cgagtgggtt acatcgaact  19500
ggatctcaac agcggtaaga tccttgagag ttttcgcccc gaagaacgtt ttccaatgat  19560
gagcactttt aaagttctgc tatgtggcgc ggtattatcc cgtgttgacg ccgggcaaga  19620
gcaactcggt cgccgcatac actattctca gaatgacttg gttgagtact caccagtcac  19680
agaaaagcat cttacggatg gcatgacagt aagagaatta tgcagtgctg ccataaccat  19740
gagtgataac actgcggcca acttacttct gacaacgatc ggaggaccga aggagctaac  19800
cgctttttg cacaacatgg gggatcatgt aactcgcctt gatcgttggg aaccggagct  19860
gaatgaagcc ataccaaacg acgagcgtga caccacgatg cctgcagcaa tggcaacaac  19920
gttgcgcaaa ctattaactg gcgaactact tactctagct tcccggcaac aattaataga  19980
ctggatggag gcggataaag ttgcaggacc acttctgcgc tcggcccttc cggctggctg  20040
gtttattgct gataaatctg gagccggtga gcgtgggtct cgcggtatca ttgcagcact  20100
ggggccagat ggtaagccct cccgtatcgt agttatctac acgacgggga gtcaggcaac  20160
tatggatgaa cgaaatagac agatcgctga gataggtgcc tcactgatta agcattggta  20220
actgtcagac caagtttact catatatact ttagattgat ttaaaacttc atttttaatt  20280
taaaaggatc taggtgaaga tccttttttga taatctcatg accaaaatcc cttaacgtga  20340
gttttcgttc cactgagcgt cagaccccgt agaaaagatc aaaggatctt cttgagatcc  20400
ttttttctg cgcgtaatct gctgcttgca aacaaaaaaa ccaccgctac cagcggtggt  20460
ttgtttgccg gatcaagagc taccaactct ttttccgaag gtaactggct tcagcagagc  20520
gcagatacca aatactgtcc ttctagtgta gccgtagtta ggccaccact tcaagaactc  20580
tgtagcaccg cctacatacc tcgctctgct aatcctgtta ccagtggctg ctgccagtgg  20640
cgataagtcg tgtcttaccg ggttggactc aagacgatag ttaccggata aggcgcagcg  20700
gtcgggctga acggggggtt cgtgcacaca gcccagcttg gagcgaacga cctacaccga  20760
actgagatac ctacagcgtg agctatgaga aagcgccacg cttcccgaag ggagaaaggc  20820
ggacaggtat ccggtaagcg gcagggtcgg aacaggagag cgcacgaggg agcttccagg  20880
gggaaacgcc tggtatcttt atagtcctgt cgggtttcgc cacctctgac ttgagcgtcg  20940
atttttgtga tgctcgtcag gggggcggag cctatggaaa aacgccagca acgcggcctt  21000
tttacggttc ctggcctttt gctggccttg aagctgtccc tgatggtcgt catctacctg  21060
cctggacagc atggcctgca acgcgggcat cccgatgccg ccggaagcga gaagaatcat  21120
aatggggaag gccatccagc ctcgcgtcga tggcaaacag ctattatggg tattatgggt  21180
tcgaattaat                                                         21190
```

```
SEQ ID NO: 38          moltype = DNA  length = 19781
FEATURE                Location/Qualifiers
source                 1..19781
                       mol_type = other DNA
                       note = Synthetic oligonucleotide
                        pBr/sAd4287.PsiI-rITR.dE3.dE4
                       organism = synthetic construct
SEQUENCE: 38
attaacccag gacctggaaa tagtgccttt aactaaagac agcaaagaca gaagctacaa  60
tattataaac aacacgacgg acaccctgta tcggagctgg tttctggctt acaactacgg  120
agaccccgag aaaggagtga gatcatggac catactcacc accacggacg tgacctgtgg  180
ctcgcagcaa gtgtactggt ccctgccgga tatgatgcaa gacccggtca ccttccgccc  240
ctccacccaa gtcagcaact tcccggtggt gggcaccgag ctgctgcccg tccatgccaa  300
gagcttctac aacgagcagg ccgtctactc gcaacttatt cgccagtcca ccgcgcttac  360
ccacgtgttc aatcgctttc ccgagaacca gattctggtg cgccctcccg ctcctaccat  420
taccaccgtc agtgaaaacg ttcccgccct cacagatcac ggaaccctgc cgctgcgcag  480
cagtatcagt ggagttcagc gcgtgaccat caccgacgcc agacgtcgaa cctgccccta  540
cgtttacaaa gcgcttggcg tggtggctcc taaagttctt tctagtcgca ccttctaaaa  600
acatgtccat cctcatctct cccgataaca acaccggctg gggactgggc tccggcaaga  660
tgtacggcgg agccaaaagg cgctccagtc agcacccagt tcgagttcgg ggccacttcc  720
gcgctccttg gggagcttac aagcgaggac tctcgggtcg aacggctgta gacgatacca  780
tagatgccgt gattgccgac gcccgccggt acaaccccgg accggtcgct agcgccgcct  840
ccaccgtgga ttccgtgatc gacagcgtgg tagccggcgc tcgggcctat gctcgccgca  900
agaggcggct gcatcggaga cgtcgcccca ccgccgccat gctggcagcc agagccgtgc  960
tgagacgggc ccggagggta ggcaggaggg ctatgcgccg cgctgccgcc aacgccgccg  1020
ccgggagggc ccgccgacag gctgcccgcc aggctgctgc cgccatcgct agcatggcca  1080
gacccaggag agggaacgtg tactgggtgc gcgattctgt gacgggagtc cgagtgccgg  1140
tgcgcagccg acctccccga agttagaaga tccaagctgc gaagacggcg gtactgagtc  1200
tccctgttgt tatcagccca acatgagcaa gcgcaagttt aaagaagaac tgctgcagac  1260
gctggtgcct gagatctatg gccctccgga cgtgaagcct gacattaagc cccgcgatat  1320
caagcgtgtt aaaaagcggg aaaagaaaga ggaactcgcg gtggtagacg atggcggagt  1380
ggaatttatt aggagtttcg ccccgcggcg cagggttcaa tggaaagggc gacgggtaca  1440
acgcgttttg aggccgggca ccgcggtagt ttttaccccg ggagagcggt cggccgttag  1500
gggttttaaa aggcagtacg acgaggtgta cggcgacgag gacatattgg aacaggcggc  1560
tcaacagatc ggagaatttg cctatggaaa gcgctcgcgt cgcgaagacc tggccatcgc  1620
cttagacagc ggcaacccca cgcccagcct caaacccgtg acgctgcagc aggtgcttcc  1680
cgtgagcgcc agcacggaca gcaagagggg aataaaaaga gaaatggaag atctgcagcc  1740
```

```
taccatccag ctcatggttc ctaaacggca gaggctggaa gaggtcctgg agaagatgaa  1800
agtggacccc agcatagagc cggacgttaa agtcaggccg atcaaagaag tggcccctgg  1860
actcggggtg cagacggtgg atatccagat ccccgtcacg tcagcttcga ccgccgtgga  1920
agccatggaa acgcaaaccg aaacccccgc cgtggttggt accaaagaag tggcgttgca  1980
aaccgacccc tggtacgaat ttgccgcccc ccggcgtcag aggcgacccg ctcgttacgg  2040
ccccgccaac gccatcatgc cagaatatgc gctgcatccg tctatcctgc ccacccccgg  2100
ctaccgggga gtgacgtatc gcccgtcagg aacccgccgc cgaacccgtc gccgccgccg  2160
ctcccgtcgc gctctggccc ccgtgtcggt gcgccgcgta acacgccggg gaaagacagt  2220
caccattccc aacccgcgct accaccctag catcctttaa tgactctgcc gttttgcaga  2280
tggctctgac ttgccgcgtg cgccttcccg ttccgcacta tcgaggaaga tctcgtcgta  2340
ggagaggcat ggcgggcagt ggtcgccggc gggctttgcg caggcgcatg aaaggcggaa  2400
ttttacccgc tttgataccc ataatcgccg ccgccatcgg tgccataccc ggcgtcgctt  2460
cagtggcctt gcaagcagct cgtaataaat aaacgaaggc ttttgcactt atgtcctggt  2520
cctgactatt ttatgcagaa agagcatgga agacatcaat tttacgtcgc tggctccgcg  2580
gcacggctcg cggccgctca tgggcacctg gaacgacatc ggcaccagtc agctcaacgg  2640
gggcgctttc aattgggggga gcctttggag cggcattaaa aactttggct ccacgattaa  2700
atcctacggc agcaaagcct ggaacagtag tgctggtcag atgctccgag ataaactgaa  2760
ggacaccaac ttccaagaaa aagtggtcaa tggggtggtg accggcatcc acggtgcggt  2820
agatctcgcc aaccaagcgg tgcagaaaga gattgacagg cgtttggaaa actcgcgggt  2880
gccgccgcag agggggggatg aggtggaggt cgaggaagta gaagtagagg aaaagctgcc  2940
cccgctggag aaagttcccg gtgcacctcc gaggccgcag aagcggccca ggccagaact  3000
agaagaaact ctggtgacgg agagcaagga gcctccctcg tacgagcaag ccttgaaaga  3060
gggcgcctct ccaccctcct acccgatgac taagccgatc gcacccatgg ctcgaccggt  3120
gtacggcaag gattacaagc ccgtcacgct agagctgccc ccaccgcccc cttcgcgtcc  3180
gacggtgcct ccgctgcctg ccccgtcggc gggtcccgag tctgcaccat ccgctgtgcc  3240
tctgccagcc gcccgtcccg tggccgtggc cactgccagg aaccccagag gccagagagg  3300
agccaactgg caaagcacgc tgaacagcat cgtgggcctg ggggtgaaaa gcctgaaacg  3360
ccgccgttgc tattattaaa aagtgtagct aaaaaatttc ccgttgtata cgcctcctat  3420
gttaccgcca gagacgcgtg actgtcgccg cgagcgccgc ttccaagatg gccaccccat  3480
cgatgatgcc gcagtggtct tacatgcaca tcgccggcca ggacgcctcg gagtacctga  3540
gtcccggcct cgtgcagttt gcccgcgcca ccgacaccta cttcagcttg ggaaacaagt  3600
ttagaaaccc caccgtggcc cccacccacg atgtgaccac ggaccgctcg cagaggctga  3660
ccctgcgctt tgtgcccgta gaccgggagg acaccgcgta ctcttacaaa gtgcgctaca  3720
cgctggccgt aggggacaac cgagtgctgg acatggccag cacctacttt gacatccggg  3780
gggtgctgga tcggggtccc agcttcaagc cctactccgg caccgcttac aactccctgg  3840
ctcccaaggg cgcccccaat cctgcagaat gggccgatac caacgacagc aacaaactga  3900
aagtgagggg tcaggcgcct tttgtcagta cttacggttc tgctacggcg cttacaaaag  3960
atgggataca ggtgggagtg gatacttccg aagcatctca ggctgtttat gccgacagaa  4020
gttaccagcc agaaccccaa attggagaga cagagtggaa cagcgaagtg ggtaatgacg  4080
acagagtggc gggaagggtg ctaaagaaaa caactcccat gttcccttgt tacggttcat  4140
atgccaagcc caccaacgaa aaaggcggac aagcaataca gcccaccgcc ggcaacggcg  4200
ataatcaggc tgtagagtta caattctttg ccactactag cactcccact gcgccaaagg  4260
cagtattgta cgcggaggac gtggccattg aagctccaga tactcactta gtgtttaagc  4320
caacagtagt cgcgggaact acaagttcgg aagctctgct aacccaacaa gccgcaccta  4380
accgcccaaa ctacattgcc tttagagata actttattgg tctcatgtac tacaattcaa  4440
ccgggaatat gggagtactg gccggacaag catctcagct caatgcagtg gttgatcttc  4500
aggacagaaa caccgaactg tcatatcagc taatgctgga tgctctggga gatcgcagtc  4560
ggtacttttc tatgtggaat caagctgtag atagctatga tccagatgta agaattgtag  4620
aaaaccacgg tgtggaagac gaactgccta attattgctt cccactaggc gggatggtag  4680
taacggacac ttacaaagcc ataaaggtaa atggaagcgg atggacggct aatactgacg  4740
ttttcagcga gagagtagaa ataggctcag gtaacctgtt tgccatggaa attaacttgc  4800
aagctaatct gtggcgcagt ttcttgtatt ccaacatagg actgtacctc ccggactctt  4860
taaaattaac ccctgacaac atcacgctcc ctgagaacaa aaatacctac cagtatatga  4920
acggtcgcgt aacaccaccc gggctcgtgg acacctacgt taacgtgggt gcgcgctggt  4980
cccccgatgt tatggacagc attaaccctt ttaaccacca ccgcaacgcc gggctccgct  5040
accgttccat gctcctggga aacggacgct acgtaccctt ccacattcag gtgccccaga  5100
aattctttgc aattaaaaac ctgctgctgc tccccggttc ctatacctac gagtggaatt  5160
tccgcaagga cgtgaacatg attttgcaaa gctcgctggg taacgacctg cgagttgacg  5220
gggccagcat acgcttcgac agcatcaacc tgtatgctaa ctttttcccc atggcccaca  5280
acacggcctc caccctggaa gccatgctgc gcaacgacac caatgaccag tccttcaacg  5340
actacctgtg cgcggccaac atgctgtatc ccatccccgc caacgccacc agcgtgccca  5400
tctccatccc gtctcgcaac tgggccgcct ttaggggttg gagtttcacc cgcctcaaaa  5460
ccaaggaaac cccctcgctg ggctctggct tcgacccccta cttcgtctac tcaggctcca  5520
ttccctacct ggacggcact ttctatctta accacacttt caaaaaggtg tctatcatgt  5580
tcgattcctc ggtcagctgg cccggcaacg accgcctgct gacgcccaac gagttcgaaa  5640
tcaagcgttc ggtggacggt gaagggtaca acgtggccca gagcaacatg accaaggact  5700
ggttcctggt tcaaatgctc agccattaca acatcggtta ccagggcttc tatgtgcccg  5760
agaactacaa ggaccgcatg tactccttct ttaggaactt ccaacccatg agtcgccaag  5820
tcgtggactc agtggcttac agggactact accaggacgt taagctcccc taccagcaca  5880
acaactcagg gttcgtgggc tacatgggtc ccaccatgcg agaggggcag gcctacccgg  5940
ccaactatcc ttatccccta atcggagaga ctgctgtacc cagcctgacg cagaaaaagt  6000
tcctctgcga ccgggtgatg tggaggatac ccttctctag caacttcatg tctatgggct  6060
ccctcaccga cctggggcag aacatgctgt acgccaactc cgctcacgcc ttggacatga  6120
cctttgaggt ggatcccatg gatgagccca cgcttctcta tgttctgttt gaagtcttcg  6180
acgtggtgcg catccaccag ccgcaccgcg gcgtcatcga ggccgtctac ctgcgcacac  6240
ctttctctgc cggtaacgcc accacctaaa gaagccgatg ggctccagcg aacaggagct  6300
gcaggccatt gttcgcgacc tgggctgcgg gccctacttt ttgggcacct tcgacaagcg  6360
gttccccggc ttcatgtccc ctcacaagcc ggcctgtgcc atcgttaaca cggccggacg  6420
ggaaaccggg ggggtccact ggctcgcctt cgcctggaac ccgcgtaacc gcacctgcta  6480
```

-continued

```
cctgttcgac ccttttggtt tctccgacga aaggctgaag cagatctacc agttcgagta  6540
cgaggggctc ctccagcgca gcgctctggc ctccacgccc gaccactgcg tcaccctgga  6600
aaagtccacc cagacggtcc aggggcccct ctcggccgcc tgcgggctct tctgttgcat  6660
gtttttgcac gccttcgtgc actggcctca cacccccatg gatcacaacc ccaccatgga  6720
tctgctcacc ggagtgccca acagcatgct tcacagcccc caggtcgccc ccaccctgcg  6780
ccgtaaccag gaacacctgt atcgctttct ggggaaacac tctgcctatt tccgccgcca  6840
tcggcagcgc atcgaacagg ccacggcctt cgaaagcatg agccaaagag tgtaatcaat  6900
aaaaaccatt tttatttgac atgatacgcg cttctggcgt ttttattaaa aatcgaaggg  6960
ttcgagggag gggtcctcgt gcccgctggg gagggacacg ttgcgatact ggaatcgggc  7020
gctccaacga aactcgggga tcaccagtcg cggcaggggc acgtcttcca ggttctgctt  7080
ccaaaactgt cgcaccagct gcagggctcc catcacgtcg ggcgccgata tcttgaagtc  7140
gcagttaggg ccggagctcc cgcggctgtt ccggaacacg gggttggcac actggaacac  7200
catcacgctg gggttgtgaa tactagccag ggccgtcgga tcggtcacct ccgacgcatc  7260
cagatcctcg gcgttgctca gggcgaacgg ggtcagcttg cacatctgcc gcccgatctg  7320
gggcaccagg tcgggtttgt tgaggcaatc gcagcgcaga gggatcagga tgcgtcgctg  7380
cccgcgttgc atgatagggt aactcgccgc caggaactcc tccatctgac ggaaggccat  7440
ctgggcctta acgccctcgg tgaaaaacag cccacaggac ttgctagaaa atacgttatt  7500
gccgcagtta atgtcttccg cgcagcagcg tgcatcttcg ttcttcagct gaaccacgtt  7560
acgcccccag cggttctgga ccaccttggc tttcgtagga tgctccttca gcgcccgctg  7620
cccgttctcg ctggtcacat ccatttccac cacgtgctcc ttgcagacca tctccactcc  7680
gtggaagcaa aacaggacgc cctcctgccg ggtattgcga tgctcccaaa cggcacaccc  7740
ggtgggctcc cagctcttgt gttttacccc cgcgtaggct tccatgtaag ccatgaggaa  7800
tctgcccatc agctcggtga aggtcttctg attggtgaag gttagcggca ggccgcggtg  7860
ctcctcgttc aaccaagttt gacagatctt gcggtacacc gttccctggt cggggcagaaa  7920
cttaaaagcc gctctgctgt cgttgtccac gtggaacttc tccattaaca tcatcatggt  7980
ttccataccc ttctcccacg ctgacaccag cggtttgctg tcggggttct tcaccaacac  8040
ggcggtagag gggccctcgc cggccccgac gtccttcatg gtcattcttt gaaactccac  8100
ggagccgtcc gcgcgacgta ctctgcgcac cggagggtag ctgaagccca cctccaccac  8160
ggtgccttcg ccctcgctgt cggaaacgat ctccggggat ggcggcggtg cgggtgtcgc  8220
cttgcgagcc ttcttcttgg gagggagctg aggcgcctcc tgctcgcgct cggggctcat  8280
ctcccgcaag taggggggtta tggagctgcc tgcttggttc tgacggttgg ccattgtatc  8340
ctaggcagaa agacatggag cttatgcgcg aggaaacttt aaccgccccg tcccccgtca  8400
gcgacgaaga tgtcatcgtc gaacaggacc cgggctacgt tacgccgccc gaggatctgg  8460
aggggcctga ccggcgcgac gctagtgagc ggcaggaaaa tgagaaagag gaggcctgct  8520
acctcctgga aggcgacgtt ttgctaaagc atttcgccag gcagagcacc atagttaagg  8580
aggccttgca agaccgctcc gaggtgccct tggacgtcgc cgcgctctcc caggcctacg  8640
aggcgaacct tttctcgcct cgagtgcctc cgaagagaca gcccaacggc acctgcgagc  8700
ccaacccgcg actcaacttc taccccgtgt tcgccgtacc agaggcgctg gccacctatc  8760
acattttttt caaaaaccaa cgcatccccc tatcgtgccg ggccaaccgc accgcggccg  8820
ataggaatct caggcttaaa aacggagcca acatacctga tatcacgtcg ctggaggaag  8880
tgcccaagat tttcgagggt ctgggtcgag atgagaagcg ggcggcgaac gctctgcaga  8940
aagaacagaa agagagtcag aacgtgctgg tggagctgga gggggacaac gcgcgtctgg  9000
ccgtcctcaa acgctgcata gaagtctccc acttcgccta ccccgccctc aacttgccac  9060
ccaaagttat gaaatcggtc atggatcagc tgctcatcaa gagagctgag cccctggatc  9120
ccgaccaccc cgaggcggaa aactcagagg acggaaagcc cgtcgtcagc gacgaggagc  9180
tcgagcggtg gctggaaacc agggaccccc aacagttgca agagaggcgc aagatgatga  9240
tggcggccgt gctggtcacc gtggagctgg aatgcctgca acggtttttc agcgacgtgg  9300
agacgctacg caaaatcggg gaatccctgc actacacctt ccgccagggc tacgtccgcc  9360
aggcctgcaa gatctccaac gtggagctca gcaacctggt ctcctacatg ggcatcctcc  9420
acgagaaccg gctggggcag agcgtgctgc actgcacctt gcaaggcgag gcgcggcggg  9480
actacgtgcg agactgcatc tacctcttcc tcaccctcac ctggcagacc gccatgggcg  9540
tctggcagca gtgcttggaa gagagaaacc tcaaagagct agacaaactc ctctgccgcc  9600
agcggcgcgc cctgtggtcc ggtttcagcg agcgcacggt cgccagcgct ctggcggaca  9660
tcatcttccc ggagcgcctg atgaaaacct tgcaaaacgg cctgccggat ttcatcagtc  9720
aaagcatttt gcaaaacttc cgctcttttg tcctggaacg ctccgggatc ttgcccgcca  9780
tgagctgcgc gctaccttct gactttgtcc ccctctccta ccgcgagtgc cctcccccac  9840
tgtggagcca ctgctacctc ttccaactgg ccaactttct ggcctaccac tccgacctca  9900
tggaagacgt aagcggagag ggtttactgg agtgccactg ccgctgcaac ctgtgcaccc  9960
cccacagatc gctggcctgc aacaccgagc tactcagcga aacccaggtc ataggtacct  10020
tcgagatcca ggggccccag cagcaagagg gtgcttccgg cttgaagctc actccggcgc  10080
tgtggacctc ggcttactta cgcaaatttg tagccgagga ctaccacgcc cacaaaattc  10140
agttttacga agaccaatct caaccaccga aagcccccct cacggcctgc gtcatcaccc  10200
agagcaagat cctggcccaa ttgcaatcca tcaaccaagc gcgccgcgat ttccttttga  10260
aaaagggtcg gggggtgtat ctggaccccc agaccggcga ggaactcaac ccgtccacac  10320
tctccgtcga agcagccccc ccgagacatg ccgcccaagg gaaccgccaa gcagctgatc  10380
gctcggcaga gagcgaagaa gcaagagctg ctccagcagc aggtggagga cgaggaagag  10440
atgtgggaca gccaggcaga ggaggtgtca gaggacgagg aggagatgga aagctgggac  10500
agcctagacg aggaggagga cgagctttca gaggaagagg cgaccgaaga aaaaccacct  10560
gcatccagcg cgccttctct gagccgacag ccgaagcccc ggcccccgac gcccccggcc  10620
ggctcactca aagccagccg taggtgggac gccaccgaat ctccagcggc agcggcaacg  10680
gcagcgggta aggccaaacg cgagcggcgg gggtattgct cctggcgggc ccacaaaagc  10740
agtattgtga actgcttgca acactgcggg ggaaacatct cctttgcccg acgctacctc  10800
ctcttccatc acggtgtggc cttccctcgc aacgttctct attattaccg tcatctctac  10860
agcccctacg aaacgctcgg agaaaaaagc taaggcctcc tccgccgcga ggaaaaactc  10920
cgccgccgct gccgccgcca aggatccacc ggccaccgag gagctgagaa agcgcatctt  10980
tcccactctg tatgctatct ttcagcaaag ccgcgggcag caccctcagc gcgaactgaa  11040
aataaaaaac cgctccttcc gctcgctcac ccgcagctgt ctgtaccaca agagagaaga  11100
ccagctgcag cgcaccctgg acgacgccga agcactgttc agcaaatact gctcagcgtc  11160
tcttaaagac taaaagaccc gcgctttttc cccctcggcc gccaaaaccc acgtcatcgc  11220
```

```
cagcatgagc aaggagattc ccacccccta catgtggagc tatcagcccc agatgggcct  11280
ggccgcgggg gccgcccagg actactccag caagatgaac tggctcagcg ccggccccca  11340
catgatctca cgagttaacg gcatccgagc ccaccgaaac cagattctct tagaacaggc  11400
ggcaatcacc gccacacccc ggcgccaact caacccgcct agttggcccg ccgcccaggt  11460
gtatcaggaa aatccccgcc cgaccacagt cctcctgcca cgcgacgcgg aggccgaagt  11520
cctcatgact aactctgggg tacaattagc gggcgggtcc aggtacgcca ggtacagagg  11580
tcgggccgct ccttactctc ccgggagtat aaagagggtg atcattcgag gccgaggtat  11640
ccagctcaac gacgagacgg tgagctcctc aaccggtctc agacctgacg gagtcttcca  11700
gctcggagga gcgggccgct cttccttcac cactcgccag gcctacctga ccctgcagag  11760
ctcttcctcg cagccgcgct ccgggggaat cggcactctc cagttcgtgg aagagttcgt  11820
tccctccgtc tacttcaacc ccttctccgg ctcgcctgga cgctacccgg acgccttcat  11880
tcccaacttt gacgcagtga gtgaatccgt ggacggctac gactgatgac agatggtgcg  11940
gccgtgagag ctcggctgcg acatctgcat cactgccgtc agcctcgctg ctacgctcgg  12000
gaggcgatcg tcttcagcta ctttgagctg ccggacgagc accctcaggg tccggctcac  12060
gggttgaaac tcgagatcga gaacgcgctc gagtctcgcc tcatcgacac cttcaccgcc  12120
cgacctctcc tggtagaaat cgaacgcggg atcactacca tcaccctgtt ctgcatctgc  12180
cccacgcccg gattacatga agatctgtgc tgtcatcttt gcgctcagtt taataaaaac  12240
tgaacttttt gccgcacctt caacgccacg cgtcgtttct ccaaaagttg tcgacagctc  12300
ttcagtcaga ggtatacgag aaactgttta tttttacaac tctactactt ttctcaccct  12360
taactgctcc tgcactaacg aactaattca gtggttcgcg aacggctcac tctgccaagt  12420
ctttttaat tctgctgttc ttcctgagtt tggctccttt gcgtgtggaa attctacact  12480
agtgggagct atcctgtgtc actgtcacgc gcctgattgt atgcccaaac taattagaac  12540
tctctgtgcc ttaggtgata tatttaaaat gtaagtcagt atcaataaac ttaccttaaa  12600
tttgacagca gtttttggt aacatcattc agcagcacca ctttaccctc ttcccaactc  12660
tcgtatggga cgtgatggtg ggcggcaaac ttcctccaaa ccctaaaaca aatattaata  12720
tccacttcct tgtccttacc cacaattttc atcttttcat agatgaaaag aaccagagtt  12780
gatgaagact tcaaccccgt ctacccttat gactccacat ccactcctgc ggtccccttt  12840
atatcccccc cgtttgtaaa cagcgatggt cttcaggaaa accctcctgg agtcttaagt  12900
ttacgaatag ctaaaccctt gtattttgac atggaaagga aactagcgct ttcacttgga  12960
agaggattgg caattacctc caccggacag ctagaaagca cacagagcgt gcaaaccacc  13020
cctccattag ttgtcaacaa cagcaacacg cttgtcctgc gttattcctc cccgttaggc  13080
ttatcgggtg acaatttaat actaaattgc tccgatcctc tccgcgtagt aaacaacagc  13140
ctgacattca gctacctatc tccacttcgt tttgaaggtg gcagtcttac attcaattac  13200
acatctcccc ttaaactgtt gaacagcagc cttgcgatcg gaataaattc caacaaaggt  13260
ctcggcaatg acagcgatga actttctgtc aaactaacat cagatctaaa gtttaacaac  13320
gatggaaaaa tagcttttgg tatacaaagc ctgtgtacca cccccacagc cgcctctaac  13380
tgtaccgttt ttaccaacgg tgattcttta ctctgtttat gtttaaccaa atgtggagct  13440
cacgtgttag gaagtgtgag tttaaccgga atgcaaggaa ccataacagc catgacacag  13500
aactacatta gtattcaatt tctatttgac aacaatggtg cgttgacttc atcaccgctc  13560
ctcaacaaca acacttgggg tatacggcaa aacgacactt cgtccgctaa ccccgcctac  13620
aatgctcttg catttatgcc taacagcact gtatatgtaa gaggtcaaag tggtgagccc  13680
agaaataact attacaccca aacatacctt aggggaaacg ttaaaaagcc aattatcctt  13740
accgttacct acaactcggc tgcttcaggt tattcactaa cttttaaatg ggatgctgta  13800
gtaacagaaa aatttgccac tccaacatct tctttttgct atattacaga acaataaatt  13860
cctattaccc caccaattcg tttttttcag atgaaacggg ccagagttga tgaagacttc  13920
aacccagtgt acccttatga ccccccatac gctcccgtta tgcccttcat tactccacct  13980
tttacctcct cggatgggtt gcaggaaaaa ccacttggag tgttaagttt aaactacaag  14040
gatcccatta ctacacaaaa tggatctctc acgttgaaaa taggaaacgg cctcactcta  14100
gacaaccagg gacaattaac atcaactgct ggggaagtag agcctccgct cactaatgct  14160
aacaacaaac ttgcactagc ctatagcgaa ccattagcag taaaaagcaa ccgcttaact  14220
ttatcacaca ccgcccccct tgtcgttgct aataattctt tagcgttgca agtttcagaa  14280
cctattttta taaatgacga tgacaagcta gccctgcaga cagccgcccc ccttgtaact  14340
aacgctggca cccttcgctt acagagcgcc gcccctttag gattggttga aaatactctt  14400
agactgctgt tttctaaacc cttgtatttg caaaatgatt ttcttgcatt aggcattgaa  14460
cgcccccctgg ctatagcagc cgcaggtact ctagcactac aactcactcc tccattaaag  14520
actaacgatg acgggctgac actatccaca gtcgagccat taactgtaaa aaacggaaac  14580
ttaggcttgc aaatatctcg ccctttggtt gttcaaaaca gcagcctttc gcttgctatt  14640
acccccccgc tgcgtctatt taacagcgac cccgttcttg gtttgggctt tacttttccc  14700
ctagccgtga cagacaacct actctcctta aacatgggag acggtgttaa actaacctat  14760
aataaactaa cagccaattt gggtagggat ttacaatttg aaaacggtgc cattgccgta  14820
acgcttactg ccgaatcacc tttgcaatac actaacaaac ttcaactgaa tattggagct  14880
ggccttcgtt acaatggagc cagcagaaaa ctagatgtaa acattaacca aaataagggc  14940
ttaacttggg acaacgatgc agttattccc aaattaggat caggtttaca attcgaccct  15000
aatggtaaca tcgctgttat ccctgaaacc gtaaagccgc aaacgttatg gacaactgca  15060
gatccatcgc ctaactgctc agtgtaccag gacttggacg ccaggctgtg gctcgctctt  15120
gttaaaagtg gtgacatggt tcatggaagc attgctctaa aagccctaaa aggaacgttg  15180
ctaaatccta cagcaagcta catctccatt gtgatatatt tttacagcaa cggagtcagg  15240
cgtaccaact atcccacgtt tgacaacgaa ggcaccttag ctaacagcgc tacctgggga  15300
taccgagagg ggcaatctgc taacactaat gtaaccaatg ccactgaatt tatgcccagc  15360
tcaaccaggt accccgtgaa taaaggagac aatattcaga atcaatcttt ttcatacacc  15420
tgtatcaaag gagatttcgc tatgcctgtc ccgttccgtg taacatataa tcatgccctg  15480
gaaggatact cccttaagtt cacctggcgc gttgtagcca accaagcttt tgatattcct  15540
tgctgttcct tttcatacat cacagaataa accacttttt aaaatttttc tttttatttt  15600
acacgcacag taaggcttcc tccccccttc catttgacag catacaccag cctctccccc  15660
ttcatggcag taaactgctg cgagccagtc cggtatttgg gagttaaaat ccaaacagtc  15720
tctttggtga tgaaacgtcg atccgtgatg gacacaaatc cctggggcag gttttccagc  15780
gtttcggtaa aaaactgcac accgccctac aaaacaaaca ggttcaggct ctccatgggt  15840
tatctccccg atcaaactca gacagggtaa aggtgcggtg atgttccact aaaccacgca  15900
ggtggcgctg tctgaacctc tcggtgcgac tcctgtgagg ctggtaagaa gttagattgt  15960
```

```
ccagtagcct cacagcatgg atgatcagtt tacgtgtacg tctggcgcaa cagcgcatct  16020
gaatctcact gagattccgg caagaatcgc acaccatcac aatcaggttg ttcatgatcc  16080
catagctgaa cacgctccag ccaaagctca ttcgctccaa cagcgccacc gcgtgtccgt  16140
ccaaccttac tttaacataa atcaggtgtc tgccgcgtac aaacatacta cccgcataca  16200
gaacttcccg gggcaaaccc ctgttcacca cctgcctgta ccagggaaac ctcacattta  16260
tcagggagcc atagatagcc attttaaacc aattagctaa caccgcccca ccagctctac  16320
actgaagaga accgggagag ttacaatgac agtgaataat ccatctctca taacccctga  16380
tggtctgatg gaaatccagc acaccgccct acaaaacaaa caggttcagg ctctccatgg  16440
gttatctccc cgatcaaact cagacagggt aaaggtgcgg tgatgttcca ctaaaccacg  16500
caggtggcgc tgtctgaacc tctcggtgcg actcctgtga ggctggtaag aagttagatt  16560
gtccagtagc ctcacagcat ggatgatcag tttacgtgta cgtctggcgc aacagcgcat  16620
ctgaatctca ctgagattcc ggcaagaatc gcacaccatc acaatcaggt tgttcatgat  16680
cccatagctg aacacgctcc agccaaagct cattcgctcc aacagcgcca ccgcgtgtcc  16740
gtccaacctt actttaacat aaatcaggtg tctgccgcgt acaaacatac tacccgcata  16800
cagaacttcc cggggcaaac ccctgttcac cacctgcctg taccagggaa acctcacatt  16860
tatcagggag ccatagatag ccattttaaa ccaattagct aacaccgccc caccagctct  16920
acactgaaga gaaccgggag agttacaatg acagtgaata atccatctct cataacccct  16980
gatggtctga tggaaatcca gatctaacgt ggcacagcag atacacactc tcatatacat  17040
tttcatcaca tggttttccc aggccgttaa aatacaatcc caatacacgg gccactcctg  17100
cagtacaata aagctaatac aagatggtat actcctcacc tcactaacat tgtgcatgtt  17160
catattttca cattctaagt accgagagtt ctcctctaca acagcactgc tgcggtcctc  17220
acaaggtggt agctggtgac gatcgtaagg agccagtctg caacgatacc gtctgtcgcg  17280
ctgcatcgta gaccagagac cgacgcacct cctggtactg ccccgtctta ccgcgtaaac  17340
agccacgaaa aattcgagct aaaatccacc caacagccta tagctatata tacactccgc  17400
ccaatgacgc taataccgca ccacccaccg ccaaagttca cccacaccca cgaaacccgc  17460
gaaaatccag cgccgtcagc acttccgcaa tttcagtctc acaacgtcac ttccgcgcgc  17520
cttttcacat tcccacaccc gcccacaaac cccgcgtcac cgcccgtcac cccggccccg  17580
cctcgctcct ccccgctcat tatcatattg gcacgtttcc agaataaggt atattattga  17640
tgatgttaat taattcgaac ccataatacc cataatagct gtttgccatc gaccaattct  17700
cccatattcc cggttgaatt gtagtacatg agaccaataa agttatttga agacgaaagg  17760
gcctcgtgat acgcctattt ttataggtta atgtcatgat aataatggtt tcttagacgt  17820
caggtggcac ttttcgggga aatgtgcgcg gaacccctat ttgtttattt ttctaaatac  17880
attcaaatat gtatccgctc atgagacaat aaccctgata aatgcttcaa taatattgaa  17940
aaaggaagag tatgagtatt caacatttcc gtgtcgccct tattcccttt tttgcggcat  18000
tttgccttcc tgtttttgct cacccagaaa cgctggtgaa agtaaaagat gctgaagatc  18060
agttgggtgc acgagtgggt tacatcgaac tggatctcaa cagcggtaag atccttgaga  18120
gttttcgccc cgaagaacgt tttccaatga tgagcacttt taaagttctg ctatgtggcg  18180
cggtattatc ccgtgttgac gccgggcaag agcaactcgg tcgccgcata cactattctc  18240
agaatgactt ggttgagtac tcaccagtca cagaaaagca tcttacggat ggcatgacag  18300
taagagaatt atgcagtgct gccataacca tgagtgataa cactgcggcc aacttacttc  18360
tgacaacgat cggaggaccg aaggagctaa ccgctttttt gcacaacatg ggggatcatg  18420
taactcgcct tgatcgttgg gaaccggagc tgaatgaagc cataccaaac gacgagcgtg  18480
acaccacgat gcctgcagca atggcaacaa cgttgcgcaa actattaact ggcgaactac  18540
ttactctagc ttcccggcaa caattaatag actggatgga ggcggataaa gttgcaggac  18600
cacttctgcg ctcggccctt ccggctggct ggtttattgc tgataaatct ggagccggtg  18660
agcgtgggtc tcgcggtatc attgcagcac tggggccaga tggtaagccc tcccgtatcg  18720
tagttatcta cacgacgggg agtcaggcaa ctatggatga acgaaataga cagatcgctg  18780
agataggtgc ctcactgatt aagcattggt aactgtcaga ccaagtttac tcatatatac  18840
tttagattga tttaaaactt catttttaat ttaaaaggat ctaggtgaag atccttttttg  18900
ataatctcat gaccaaaatc ccttaacgtg agttttcgtt ccactgagcg tcagaccccg  18960
tagaaaagat caaaggatct tcttgagatc ctttttttct gcgcgtaatc tgctgcttgc  19020
aaacaaaaaa accaccgcta ccagcggtgg tttgtttgcc ggatcaagag ctaccaactc  19080
tttttccgaa ggtaactggc ttcagcagag cgcagatacc aaatactgtc cttctagtgt  19140
agccgtagtt aggccaccac ttcaagaact ctgtagcacc gcctacatac ctcgctctgc  19200
taatcctgtt accagtggct gctgccagtg gcgataagtc gtgtcttacc gggttggact  19260
caagacgata gttaccggat aaggcgcagc ggtcgggctg aacgggggggt tcgtgcacac  19320
agcccagctt ggagcgaacg acctacaccg aactgagata cctacagcgt gagctatgag  19380
aaagcgccac gcttcccgaa gggagaaagg cggacaggta tccggtaagc ggcagggtcg  19440
gaacaggaga gcgcacgagg gagcttccag ggggaaacgc ctggtatctt tatagtcctg  19500
tcgggtttcg ccacctctga cttgagcgtc gatttttgtg atgctcgtca ggggggcgga  19560
gcctatggaa aaacgccagc aacgcggcct ttttacggtt cctggccttt tgctggcctt  19620
gaagctgtcc ctgatggtcg tcatctacct gcctggacag catggcctgc aacgcgggca  19680
tcccgatgcc gccggaagcg agaagaatca taatggggaa ggccatccag cctcgcgtcg  19740
atggcaaaca gctattatgg gtattatggg ttcgaattaa t                      19781
```

```
SEQ ID NO: 39          moltype = DNA  length = 8764
FEATURE                Location/Qualifiers
source                 1..8764
                       mol_type = other DNA
                       note = Synthetic oligonucleotide sAdApt4287.E1btg.Empty
                       organism = synthetic construct
SEQUENCE: 39
attaattcga acccataata cccataatag ctgtttgcca tcgacgcgag gctggatggc  60
cttccccatt atgattcttc tcgcttccgg cggcatcggg atgcccgcgt tgcaggccat  120
gctgtccagg caggtagatg acgaccatca gggacagctt caaggccagc aaaaggccag  180
gaaccgtaaa aaggccgcgt tgctggcgtt tttccatagg ctccgccccc ctgacgagca  240
tcacaaaaat cgacgctcaa gtcagaggtg gcgaaacccg acaggactat aaagatacca  300
ggcgtttccc cctggaagct ccctcgtgcg ctctcctgtt ccgaccctgc cgcttaccgg  360
atacctgtcc gcctttctcc cttcgggaag cgtggcgctt tctcatagct cacgctgtag  420
```

```
gtatctcagt tcggtgtagg tcgttcgctc caagctgggc tgtgtgcacg aaccccccgt  480
tcagcccgac cgctgcgcct tatccggtaa ctatcgtctt gagtccaacc cggtaagaca  540
cgacttatcg ccactggcag cagccactgg taacaggatt agcagagcga ggtatgtagg  600
cggtgctaca gagttcttga agtggtggcc taactacggc tacactagaa ggacagtatt  660
tggtatctgc gctctgctga agccagttac cttcggaaaa agagttggta gctcttgatc  720
cggcaaacaa accaccgctg gtagcggtgg tttttttgtt tgcaagcagc agattacgcg  780
cagaaaaaaa ggatctcaag aagatccttt gatcttttct acggggtctg acgctcagtg  840
gaacgaaaac tcacgttaag ggattttggt catgagatta tcaaaaagga tcttcaccta  900
gatcctttta aattaaaaat gaagttttaa atcaatctaa agtatatatg agtaaacttg  960
gtctgacagt taccaatgct taatcagtga ggcacctatc tcagcgatct gtctatttcg 1020
ttcatccata gttgcctgac tccccgtcgt gtagataact acgatacggg agggcttacc 1080
atctggcccc agtgctgcaa tgataccgcg agacccacgc tcaccggctc cagatttatc 1140
agcaataaac cagccagccg gaagggccga gcgcagaagt ggtcctgcaa ctttatccgc 1200
ctccatccag tctattaatt gttgccggga agctagagta agtagttcgc cagttaatag 1260
tttgcgcaac gttgttgcca ttgctgcagg catcgtggtg tcacgctcgt cgtttggtat 1320
ggcttcattc agctccggtt cccaacgatc aaggcgagtt acatgatccc ccatgttgtg 1380
caaaaaagcg gttagctcct tcggtcctcc gatcgttgtc agaagtaagt tggccgcagt 1440
gttatcactc atggttatgg cagcactgca taattctctt actgtcatgc catccgtaag 1500
atgcttttct gtgactggtg agtactcaac caagtcattc tgagaatagt gtatgcggcg 1560
accgagttgc tcttgcccgg cgtcaacacg ggataatacc gcgccacata gcagaacttt 1620
aaaagtgctc atcattggaa aacgttcttc ggggcgaaaa ctctcaagga tcttaccgct 1680
gttgagatcc agttcgatgt aacccactcg tgcacccaac tgatcttcag catcttttac 1740
tttcaccagc gtttctgggt gagcaaaaac aggaaggcaa aatgccgcaa aaaagggaat 1800
aagggcgaca cggaaatgtt gaatactcat actcttcctt tttcaatatt attgaagcat 1860
ttatcagggt tattgtctca tgagcggata catatttgaa tgtatttaga aaaataaaca 1920
aataggggtt ccgcgcacat ttccccgaaa agtgccacct gacgtctaag aaaccattat 1980
tatcatgaca ttaacctata aaaataggcg tatcacgagg ccctttcgtc ttcaagaatt 2040
ggtcgatggc aaacagctat tatgggtatt atgggttcga attaattaac atcatcaata 2100
atatacctta ttctggaaac gtgccaatat gataatgagc ggggaggagc gaggcggggc 2160
cggggtgacg tgcggtgacg cggggtgacg cggggtggcg cgagggcggg gcgggagtgg 2220
ggaggcgctt agtttttacg tatgcggaag gaggttttat accggaagtt gggtaatttg 2280
ggcgtatatt tgtaagtttt gtgtaatttg gcgcgaaaac cgggtaatga ggaagttgag 2340
gttaatatgt actttttatg actgggcgga atttctgctg atcagcagtg aactttgggc 2400
gctgacgggg aggtttcgct acgtggcagt accacgagaa ggctcaaagg tcccatttat 2460
tgtactcctc agcgttttcg ctgggtattt aaacgctgtc agatcatcaa gaggccactc 2520
ttgagtgccg gcgagtagag ttttctcctc cgcgctgccg cgatgaggct ggttcccgag 2580
atgtacggtg ttttctgcag cgagacggcc cggaactcag atgagctgct taatacagat 2640
ctgctggatg ttcccaactc gcctgtggct tcgcctccgt cgcttcatga tcttttcgat 2700
gtggaagtgg atccaccgca agatcccaac gaggacgcgg taaacagtat gttccctgaa 2760
tgtctgtttg aggcggctga ggagggttct cacagcagtg aagagagcag acggggagag 2820
gaactggact tgaaatgcta cgaggaatgt ctgccttcta gcgattctga aacggaacag 2880
acagggggag acggctgtga gtcggcaatg aaaaatgaac ttgtattaga ctgtccagaa 2940
catcctggtc atggctgccg tgcctgtgct tttcatagaa atgccagcgg aaatcctgag 3000
actctatgtg ctctgtgtta tctgcgcctt accagcgatt ttgtatacag taagtaaagt 3060
gttttcattg gcgtacggta ggggattcgt tgaagtgctt tgtgacttat tatgtgtcat 3120
tatttctagg tgacgtgtcc gacgtggaag gggaaggaga tagatcaggg gctgctaatt 3180
ctccttgcac tttgggggct gtggttccag ctggcattat taaacccgtg gcggtcagag 3240
tctcaggcag acggtgcgca gttgaaaaaa ttgaagactt gctgcaggaa gaacagacgc 3300
aacctttgga cctgtccatg aaacgcccta agctgactta agtgtgttta ttgtatgcaa 3360
taaaagtgtt gatctttgaa ctgtgtttat gtgttgggtg tgtctgtggg tatataagca 3420
ggtggatggg aagtgagagc acagctgctt cagatggatc tgctaggaga cctaagagaa 3480
tttggcgtgg ttcggcgctt gttggagttg gcctctgaca gaacttccaa gttttggagg 3540
ttttgttttg gctcaacgct tagcaacgtg ctatataggg tcaagaagga gcaggagacg 3600
cagtttgcta ggctgttggc cgatactcct ggagtttttg tggctctgga tctaggccat 3660
cactctcttt tccaagagaa aattatcaaa aacctaactt ttacgtctcc tggccgcacg 3720
gttgcttccg ctgcctttat tacctatatt ttggatcaat ggagcaacag cggcagccac 3780
ctgtcgtggg agtacatgct ggattacatg tcgatggcgc tgtggagggc catgctgcgg 3840
aggagggttt gcatttactt gcgggcgcag cctccgcggc tgggccgagt ggaggaggag 3900
gacgagccgg gagagatgga gaacctgagg gccgggctgg accctccaac ggaggactag 3960
gtgctgagga tgatcctgaa gaggggacta gtgggggagc taggaaaaag caaaaaactg 4020
agcctgaacc tagaaacttt ttgaatgagt tgactgtaag cctgatgaat cggcagcgtc 4080
ctgagacggt gttttgggct gagttggagg atgagttcaa gaagggggaa ttgaacctct 4140
tgtacaagta tgggtttgag cagttgaaaa ctcactggtt ggagccgtgg gaggacatgg 4200
aaatggctct agacaccttt gctaaagtgg ctctgcggcc ggataaagtt tacactattc 4260
gccgcactgt taatataaaa aagagtgttt atgttatcgg tcatggagct ctggtgcagg 4320
tgcagacccc agaccgggtg gctttcaatt gcggcatgca gagtttgggc cccggggtga 4380
taggtttgaa tggagttaca tttcaaaatg tcaggtttac tggtgatgat tttaatggct 4440
ctgtgtttgt gactagcacc cagctaaccc tccacggtgt ttactttttt aactttaaca 4500
atacatgtgt ggagtcatgg ggtagggtgt ctctgagggg ctgcagtttt catggttgct 4560
ggaaggcggt ggtgggaaga attaaaagtg tcatgtctgt gaagaaatgc atatttgaac 4620
gctgtgtgat agctctagca gtagaggggt acggacggat caggaataac gccgcatctg 4680
agaatggatg ttttcttttg ctgaaaggta cggccagcgt taagcataat atgatttgcg 4740
gcagcggcct gtgcccctcg cagctcttaa cttgcgcaga tggaaactgt cacaccttgc 4800
gcaccgtgca catagtgtcc cactcgcgcc gcacctggcc aacatttgag cacaatatgc 4860
tcatgcgttg cgccgttcac ctaggtgcta gacgcggcgt gtttatgcct tatcaatgta 4920
actttagtca tactaagatt ttgctggaaa ctgattcctt ccctcgagta tgtttcaatg 4980
gggtgtttga catgtcaatg gaacttttta aagtgataag atatgatgaa accaagtctc 5040
gttgtcgctc atgtgaatgc ggagctaatc atttgaggtt gtatcctgta accctgaacg 5100
tcaccgagga gctgaggacg gaccaccaca tgctgtcttg cctgcgtacc gactatgaat 5160
```

```
ccagtgatga ggagtgaggt gaggggcgga gccacaaagg gtataaaggg gcatgaaggg  5220
tggacggtcg actggtcaat attggccatt agccatatta ttcattggtt atatagcata  5280
aatcaatatt ggctattggc cattgcatac gttgtatcca tatcataata tgtacattta  5340
tattggctca tgtccaacat taccgccatg ttgacattga ttattgacta gttattaata  5400
gtaatcaatt acggggtcat tagttcatag cccatatatg gagttccgcg ttacataact  5460
tacggtaaat ggcccgcctg gctgaccgcc caacgacccc cgcccattga cgtcaataat  5520
gacgtatgtt cccatagtaa cgccaatagg gactttccat tgacgtcaat gggtggagta  5580
tttacggtaa actgcccact tggcagtaca tcaagtgtat catatgccaa gtacgccccc  5640
tattgacgtc aatgacggta aatggcccgc ctggcattat gcccagtaca tgaccttatg  5700
ggactttcct acttggcagt acatctacgt attagtcatc gctattacca tggtgatgcg  5760
gttttggcag tacatcaatg ggcgtggata gcggtttgac tcacggggat ttccaagtct  5820
ccaccccatt gacgtcaatg ggagtttgtt ttggcaccaa aatcaacggg actttccaaa  5880
atgtcgtaac aactccgccc cattgacgca aatgggcggt aggcgtgtac ggtgggaggt  5940
ctatataagc agagctcgtt tagtgaaccg tcagatcgcc tggagacgcc atccacgctg  6000
ttttgacctc catagaagac accgggaccg atccagcctc cgcggccggg aacggtgcat  6060
tggaagcttg gtaccggtga attcgctagc gttaacggat cctctagacg agatccgaac  6120
ttgtttattg cagcttataa tggttacaaa taaagcaata gcatcacaaa tttcacaaat  6180
aaagcatttt tttcactgca ttctagttgt ggtttgtcca aactcatcaa tgtatcttat  6240
catgtctaga tccttaagga atgcggagct aatcatttga ggttgtatcc tgtaaccctg  6300
aacgtcaccg aggagctgag gacggaccac cacatgctgt cttgcctgcg taccgactat  6360
gaatccagtg atgaggagtg aggtgagggg cggagccaca aagggtataa aggggcatga  6420
agggtggacg cggtgtttca aaatgagcgg gacgacggac ggcaatgcgt ttgagggggg  6480
agtgttcagc ccatatctga catctcgtct tccttcctgg gcaggagtgc gtcagaatgt  6540
agtgggctcc accgtggacg gacggccggt cgcccctgca aattccgcca ccctcaccta  6600
tgccaccgtg ggatcatcgt tggacactgc cgcggcagct gccgcttctg ctgccgcttc  6660
tactgctcgc ggcatggcgg ctgattttgg actatataac caactggcca ctgcagctgt  6720
ggcgtctcgg tctctggttc aagaagatgc cctgaatgtg atcttgactc gcctggagat  6780
catgtcacgt cgcctggacg aactggctgc gcagatatcc caagctaacc ccgataccgc  6840
ttcagaatct taaataaaga caaacaaatt tgttgaaaag taaaatggct ttatttgttt  6900
tttttggctc ggtaggctcg ggtccacctg tctcggtcgt taaggacttt gtgtatgttt  6960
tccaaaacac ggtacagatg ggcttggatg ttcaagtaca tgggcatgag gccatctttg  7020
gggtggagat aggaccactg aagagcgtca tgttccgggg tggtattgta aatcacccag  7080
tcgtagcagg gtttttgagc gtggaactgg aatatgtcct tcaggagcag gctaatggcc  7140
aagggcagcc ccttagtgta ggtgtttaca aagcggttga gctgggaggg atgcatgcgg  7200
ggggagatga tatgcatctt ggcttggatt ttgaggttag ctatgttacc acccaggtct  7260
ctgcgggggt tcatgttatg aaggaccacc agcacggtgt agccggtgca cttggggaac  7320
ttgtcatgca gtttggaggg gaaggcgtgg aagaatttag ataccccctt gtgcccccct  7380
aggttttcca tgcactcatc cataataatg gcaatgggac ccctggcggc cgctttagca  7440
aacacgtttt gggggttgga aacatcatag ttttgctcta gagtgagctc atcataggcc  7500
atctttacaa agcggggtag gagggtgccc gactggggga tgatagttcc atctgggcct  7560
ggagcgtagt tgccctcaca gatctgcatc tcccaggcct taatttccga gggggggatc  7620
atgtccacct gggggggcgat aaagaacacg gtttctggcg ggggattgat gagctgggtg  7680
gaaagcaagt tacgcaatag ctgggatttg ccgcaaccgg tggggccgta gatgaccccg  7740
atgacgggtt gcagctggta gttcagagag gaacagctgc cgtcggggcg caggaggggg  7800
gccacatcgt tcatcatgct tctgacatgt ttattttcac tcactaagtt ttgcaagagc  7860
ctctccccac ccagggataa gagttcttcc aggctgttga agtgtttcag cggtttcagg  7920
ccgtcggcca tgggcatctt ttcaagcgac tgacgaagca agtacagtcg gtcccagagc  7980
tcggtgacgt gctctatgga atctcgatcc agcagacttc ttggttgcgg gggttgggcc  8040
gactttcgct gtagggcacc agccggtggg cgtccagggc cgcgagggtt ctgtccttcc  8100
agggtctcag cgttcgggtg agggtggtct cggtgacggt gaagggatga gccccgggct  8160
gggcgcttgc gagggtgcgc ttcaggctca tcctgctggt gctgaagcgg gcgtcgtctc  8220
cctgtgagtc ggccagatag caacgaagca tgaggtcgta gctgagggac tcggccgcgt  8280
gtcccttggc gcgcagcttt cccttggaaa cgtgctgaca tttggtgcag tgcagacact  8340
tgagggcgta gagttttggg gccaggaaga ccgactcggg cgagtaggcg tcggctccgc  8400
actgagcgca gacggtctcg cactccacca gccacgtgag ctcgggttta gcgggatcaa  8460
aaaccaagtt gcctccattt tttttgatgc gtttcttacc ttgcgtctcc atgagtctgt  8520
gtcccgcttc cgtgacaaaa aggctgtcgg tgtccccgta gaccgacttg agggggcgat  8580
cttccaaagg tgttccgagg tcttccgcgt acaggaactg ggaccactcc gagacaaagg  8640
ctcgggtcca ggctaacacg aaggaggcga tctgcgaggg gtatctgtcg ttttcaatga  8700
gggggtccac cttttccagg gtgtgcagac acaggtcgtc ctcctccgcg tccacgaagt  8760
taat                                                               8764
```

SEQ ID NO: 40 moltype = DNA length = 6091
FEATURE Location/Qualifiers
source 1..6091
mol_type = other DNA
note = Synthetic oligonucleotide sAdApt4310A.Empty
organism = synthetic construct
SEQUENCE: 40

```
catcatcaat aatatacctt attctggaaa cgtgccaata tgataatgag cggggaggag  60
cgaggcgggg ccggggtgac gtgcggtgac gcggggtgac gcggggtggc gcgagggcgg  120
ggcgggtgtg cggaggcgct tagtttttac gtatgcggaa ggaggtttta taccggaagt  180
tgggtaattt gggcgtatac ttgtaagttt tgtgtagttt ggcgcgaaaa ccgggtaatg  240
aggaagttga ggttaatatg tactttttat gactgggcgg aatttctgct gatcagcagt  300
gaactttggg cgctgacggg gaggtttcgc tacgtggcag taccacgaga aggctcaaag  360
gtcccattta ttgtactcct cagcgttttc gctgggtatt taaacgctgt cagatcatca  420
agaggccact cttgagtgcc ggcgagtaga gttttctcct cgtcgactgg tcaatattgg  480
ccattagcca tattattcat tggttatata gcataaatca atattggcta ttggccattg  540
catacgttgt atccatatca taatatgtac atttatattg gctcatgtcc aacattaccg  600
```

-continued

```
ccatgttgac attgattatt gactagttat taatagtaat caattacggg gtcattagtt  660
catagcccat atatggagtt ccgcgttaca taacttacgg taaatggccc gcctggctga  720
ccgcccaacg acccccgccc attgacgtca ataatgacgt atgttcccat agtaacgcca  780
atagggactt tccattgacg tcaatgggtg gagtatttac ggtaaactgc ccacttggca  840
gtacatcaag tgtatcatat gccaagtacg ccccctattg acgtcaatga cggtaaatgg  900
cccgcctggc attatgccca gtacatgacc ttatgggact ttcctacttg gcagtacatc  960
tacgtattag tcatcgctat taccatggtg atgcggtttt ggcagtacat caatgggcgt 1020
ggatagcggt ttgactcacg gggatttcca agtctccacc ccattgacgt caatgggagt 1080
ttgttttggc accaaaatca acgggacttt ccaaaatgtc gtaacaactc cgccccattg 1140
acgcaaatgg gcggtaggcg tgtacggtgg gaggtctata taagcagagc tcgtttagtg 1200
aaccgtcaga tcgcctggag acgccatcca cgctgttttg acctccatag aagacaccgg 1260
gaccgatcca gcctccgcgg ccgggaacgg tgcattggaa gcttggtacc ggtgaattcg 1320
ctagcgttaa cggatcctct agacgagatc cgaacttgtt tattgcagct tataatggtt 1380
acaaataaag caatagcatc acaaatttca caaataaagc attttttca ctgcattcta 1440
gttgtggttt gtccaaactc atcaatgtat cttatcatgt ctagatcctt aaggacatgt 1500
caatggaact gtttaaagtg ataagatatg atgaatccaa gtctcgttgt cgcccatgtg 1560
aatgcggagc taatcatttg aggttgtatc ctgtaactct gaacgtcacc gaggagctga 1620
gaacggacca ccacatgctg tcttgcctgc gcactgacta tgaatccagc gacgaggagt 1680
gaggtgaggg gcggagccaa acgggtataa aggggcgtga ggggtcggtg cggtgtttca 1740
aaatgagcgg gacgacggac ggcaatgcgt ttgagggggg agtgttcagc ccatatctga 1800
catctcgtct tccttcctgg gcaggagtgc gtcagaatgt agtgggatcc accgtggacg 1860
gacgaccggt ggctcctgca aattccgcca ccctcaccta tgccaccgtg ggatcatcgt 1920
tggacactgc cgcggcagct gccgcttctg ctgccgcttc tactgctcgc ggcatggcgg 1980
ctgattttgg actgtataac caactggcca ctgcagctgt ggcgtctcgg tccctggttc 2040
aagaagatgc cctgaatgtg attctgactc gcctggagat catgtcacgc cgcctggacg 2100
aactggctgc gcagatatcc tcaactaacc ccgataccac ttcagaacct taaataaaga 2160
caaacaaatt tgttgaaaag taaaatggct ttatttgttt tttttggctc ggtaggctcg 2220
ggtccacctg tcccggtcgt taaggacctt gtgtatgttt tccaagaccc ggtacagatg 2280
ggcttggatg ttcaagtaca tgggcatgag gccatctcgg gggtggagat aggaccattg 2340
cagagcgtca tgctccgggg tggtgttgta aataacccag tcgtagcagg gtttctgagc 2400
gtggaactgg aagatgtcct ttaggagcag gctgatggcc aagggcagcc ccttagtgta 2460
ggtgttaaca aagcggttaa gctgggaggg atgcatgcgg ggggagatga tatgcatctt 2520
ggcttgaatt ttgaggttag ctatgttacc acctaggtcc ctgcgggggt tcatgttatg 2580
aaggaccacc agcacggtgt agccggtgca cttggggaac ttgtcatgca gtttggaggg 2640
gaaggcgtgg aagaatttag agaccccctt gtggcctcct aggttttcca tgcactcatc 2700
cataatgatg gcaatgggac ccctggcggc cgctttggca aacacgtttt gggggttgga 2760
aacatcatag ttttgctcta gagtgagctc atcataggcc atcttaacaa agcggggtag 2820
gagggtgccc gactgggggga tgatagttcc atctgggcct ggggcgtagt tgccctcaca 2880
aatctgcatt tcccaggcct taatttccga gggggggtatc atgtccacct gggggggcgat 2940
aaagaacacg gtttctggcg ggggattgat gagctgggtg gaaagcaagt tacgcaacag 3000
ttgggatttg ccgcaaccgg tgggaccgta gatgaccccg atgacgggtt gcagctggta 3060
gttgagagag gaacagctgc cgtcggggcg caggaggggg gctacatcgt tcatcatgct 3120
tctgacatgt ttattttcac tcactaagtt ttgcaagagc ctctccccac ccagggataa 3180
gagttcttcc aggctgttga agtgtttcag cggtttcagg ccgtctgcca tgggcatctt 3240
ttcaagcgac tgacgaagca agtacagtcg gtcccagagc tcggtgacgt gctctatgga 3300
atctcgatcc agcagacttc ttggttgcgg gggttgggcc gactttcgct gtagggcacc 3360
agccggtggg cgtccagggc cgcgagggtt ctgtccttcc agggtctcag cgttcgggtg 3420
agggtggtct cggtgacggt gaagggatga gccccgggct gggcgcttgc gagggtgcgc 3480
ttcaggctca tcctgctggt gctgaagcgg gcgtcgtctc cctgtgagtc ggccagatag 3540
caacgaagca tgaggtcgta gctgagggac tcggccgcgt gtcccttggc gcgcagcttt 3600
cccttggaaa cgtgctgaca tttggtgcag tgcagacact tgagggcgta gagtttgggg 3660
gccaggaaga ccgactcgga cgagtaggcg tcggctccgc actgagcgca gacggtctcg 3720
cactccacca gccacgtgag ctcgggttta gcgggatcaa aaaccaagtt gcctccattt 3780
tttttgatgc gtttcttacc ttgcgtctcc atgagtctgt gtcccgcttc cgtgacaaaa 3840
aggctgtcgg tgtccccgta gaccgacttg agggggcgat cttccaaagg tgttccgaga 3900
tcttccgcgt acaggaactg ggaccactcc gagacaaagg ctcgggtcca ggctaacacg 3960
aaggaggcga tctgcgaggg gtatctgtcg ttttcaatga ggttaattaa ttcgaaccca 4020
taatacccat aatagctgtt tgccatcgac gcgaggctgg atggccttcc ccattatgat 4080
tcttctcgct tccggcggca tcgggatgcc cgcgttgcag gccatgctgt ccaggcaggt 4140
agatgacgac catcagggac agcttcaagg ccagcaaaag gccaggaacc gtaaaaaggc 4200
cgcgttgctg gcgtttttcc ataggctccg cccccctgac gagcatcaca aaaatcgacg 4260
ctcaagtcag aggtggcgaa acccgacagg actataaaga taccaggcgt ttccccctgg 4320
aagctccctc gtgcgctctc ctgttccgac cctgccgctt accggatacc tgtccgcctt 4380
tctcccttcg ggaagcgtgg cgctttctca tagctcacgc tgtaggtatc tcagttcggt 4440
gtaggtcgtt cgctccaagc tgggctgtgt gcacgaaccc cccgttcagc ccgaccgctg 4500
cgccttatcc ggtaactatc gtcttgagtc caacccggta agacacgact tatcgccact 4560
ggcagcagcc actggtaaca ggattagcag agcgaggtat gtaggcggtg ctacagagtt 4620
cttgaagtgg tggcctaact acggctacac tagaaggaca gtatttggta tctgcgctct 4680
gctgaagcca gttaccttcg gaaaaagagt tggtagctct tgatccggca aacaaaccac 4740
cgctggtagc ggtggttttt ttgtttgcaa gcagcagatt acgcgcagaa aaaaaggatc 4800
tcaagaagat cctttgatct tttctacggg gtctgacgct cagtggaacg aaaactcacg 4860
ttaagggatt ttggtcatga gattatcaaa aaggatcttc acctagatcc ttttaaatta 4920
aaaatgaagt tttaaatcaa tctaaagtat atatgagtaa acttggtctg acagttacca 4980
atgcttaatc agtgaggcac ctatctcagc gatctgtcta tttcgttcat ccatagttgc 5040
ctgactcccc gtcgtgtaga taactacgat acgggagggc ttaccatctg gccccagtgc 5100
tgcaatgata ccgcgagacc cacgctcacc ggctccagat ttatcagcaa taaaccagcc 5160
agccggaagg gccgagcgca gaagtggtcc tgcaacttta tccgcctcca tccagtctat 5220
taattgttgc cgggaagcta gagtaagtag ttcgccagtt aatagtttgc gcaacgttgt 5280
tgccattgct gcaggcatcg tggtgtcacg ctcgtcgttt ggtatggctt cattcagctc 5340
```

```
cggttcccaa cgatcaaggc gagttacatg atcccccatg ttgtgcaaaa aagcggttag  5400
ctccttcggt cctccgatcg ttgtcagaag taagttggcc gcagtgttat cactcatggt  5460
tatggcagca ctgcataatt ctcttactgt catgccatcc gtaagatgct tttctgtgac  5520
tggtgagtac tcaaccaagt cattctgaga atagtgtatg cggcgaccga gttgctcttg  5580
cccggcgtca acacgggata ataccgcgcc acatagcaga actttaaaag tgctcatcat  5640
tggaaaacgt tcttcggggc gaaaactctc aaggatctta ccgctgttga gatccagttc  5700
gatgtaaccc actcgtgcac ccaactgatc ttcagcatct tttactttca ccagcgtttc  5760
tgggtgagca aaaacaggaa ggcaaaatgc cgcaaaaaag ggaataaggg cgacacggaa  5820
atgttgaata ctcatactct tcctttttca atattattga agcatttatc agggttattg  5880
tctcatgagc ggatacatat ttgaatgtat ttagaaaaat aaacaaatag gggttccgcg  5940
cacatttccc cgaaaagtgc cacctgacgt ctaagaaacc attattatca tgacattaac  6000
ctataaaaat aggcgtatca cgaggccctt tcgtcttcaa gaattggtcg atggcaaaca  6060
gctattatgg gtattatggg ttcgaattaa t                                 6091

SEQ ID NO: 41          moltype = DNA  length = 16580
FEATURE                Location/Qualifiers
source                 1..16580
                       mol_type = other DNA
                       note = Synthetic oligonucleotide pBr/sAd4310A.pIX-pV
                       organism = synthetic construct
SEQUENCE: 41
attaagacat gtcaatggaa ctgtttaaag tgataagata tgatgaatcc aagtctcgtt  60
gtcgcccatg tgaatgcgga gctaatcatt tgaggttgta tcctgtaact ctgaacgtca  120
ccgaggagct gagaacggac caccacatgc tgtcttgcct gcgcactgac tatgaatcca  180
gcgacgagga gtgaggtgag gggcggagcc aaacgggtat aaaggggcgt gaggggtcgg  240
tgcggtgttt caaaatgagc gggacgacgg acggcaatgc gtttgagggg ggagtgttca  300
gcccatatct gacatctcgt cttccttcct gggcaggagt gcgtcagaat gtagtgggat  360
ccaccgtgga cggacgaccg gtggctcctg caaattccgc caccctcacc tatgccaccg  420
tgggatcatc gttggacact gccgcggcag ctgccgcttc tgctgccgct tctactgctc  480
gcggcatggc ggctgatttt ggactgtata accaactggc cactgcagct gtggcgtctc  540
ggtccctggt tcaagaagat gccctgaatg tgattctgac tcgcctggag atcatgtcac  600
gccgcctgga cgaactggct gcgcagatat cctcaactaa ccccgatacc acttcagaac  660
cttaaataaa gacaaacaaa tttgttgaaa agtaaaatgg ctttatttgt tttttttggc  720
tcggtaggct cgggtccacc tgtcccggtc gttaaggacc ttgtgtatgt tttccaagac  780
ccggtacaga tgggcttgga tgttcaagta catgggcatg aggccatctc gggggtggag  840
ataggaccat tgcagagcgt catgctccgg ggtggtgttg taaataaccc agtcgtagca  900
gggtttctga gcgtggaact ggaagatgtc ctttaggagc aggctgatgg ccaagggcag  960
ccccttagtg taggtgttaa caaagcggtt aagctgggag ggatgcatgc ggggggagat  1020
gatatgcatc ttggcttgaa ttttgaggtt agctatgtta ccacctaggt ccctgcgggg  1080
gttcatgtta tgaaggacca ccagcacggt gtagccggtg cacttgggga acttgtcatg  1140
cagtttggag gggaaggcgt ggaagaattt agagaccccc ttgtggcctc ctaggttttc  1200
catgcactca tccataatga tggcaatggg acccctggcg gccgctttgg caaacacgtt  1260
ttgggggttg gaaacatcat agttttgctc tagagtgagc tcatcatagg ccatcttaac  1320
aaagcggggt aggagggtgc ccgactgggg gatgatagtt ccatctgggc ctggggcgta  1380
gttgccctca caaatctgca tttcccaggc cttaatttcc gagggggggta tcatgtccac  1440
ctgggggcg ataaagaaca cggtttctgg cgggggattg atgagctggg tggaaagcaa  1500
gttacgcaac agttgggatt tgccgcaacc ggtgggaccg tagatgaccc cgatgacggg  1560
ttgcagctgg tagttgagag aggaacagct gccgtcgggg cgcaggaggg gggctacatc  1620
gttcatcatg cttctgacat gtttattttc actcactaag ttttgcaaga gcctctcccc  1680
acccagggat aagagttctt ccaggctgtt gaagtgtttc agcggtttca ggccgtctgc  1740
catgggcatc ttttcaagcg actgacgaag caagtacagt cggtcccaga gctcggtgac  1800
gtgctctatg gaatctcgat ccagcagact tcttggttgc gggggttggg ccgactttcg  1860
ctgtagggca ccagccggtg ggcgtccagg gccgcgaggg ttctgtcctt ccagggtctc  1920
agcgttcggg tgagggtggt ctcggtgacg gtgaagggat gagccccggg ctgggcgctt  1980
gcgagggtgc gcttcaggct catcctgctg gtgctgaagc gggcgtcgtc tccctgtgag  2040
tcggccagat agcaacgaag catgaggtcg tagctgaggg actcggccgc gtgtcccttg  2100
gcgcgcagct ttcccttgga aacgtgctga catttggtgc agtgcagaca cttgagggcg  2160
tagagtttgg gggccaggaa gaccgactcg gacgagtagg cgtcggctcc gcactgagcg  2220
cagacggtct cgcactccac cagccacgtg agctcgggtt tagcgggatc aaaaaccaag  2280
ttgcctccat tttttttgat gcgtttctta ccttgcgtct ccatgagtct gtgtcccgct  2340
tccgtgacaa aaaggctgtc ggtgtccccg tagaccgact tgagggggcg atcttccaaa  2400
ggtgttccga gatcttccgc gtacaggaac tgggaccact ccgagacaaa ggctcgggtc  2460
caggctaaca cgaaggaggc gatctgcgag gggtatctgt cgttttcaat gagggggtcc  2520
acctttttcca gggtgtgcag acacaggtcg tcctcctccg cgtccacgaa ggtgattggc  2580
ttgtaagtgt aggtcacgtg acccgcaccc ccccaagggg tataaaaggg ggcgtgccca  2640
ctctccccgt cactttcttc cgcatcgctg tggaccagag ccagctgttc gggtgagtag  2700
gccctctcaa aagccggcat gatttcggcg ctcaagttgt cagtttctac aaacgaggag  2760
gatttgatat tcacgtgccc cgcggcgatg cttttgatgg tggaggggtc catctgatca  2820
gaaaacacga tctttttatt gtcaagtttg gtggcgaaag acccgtagag ggcgttggaa  2880
agcaacttgg cgatggagcg cagggtctga tttttctccc gatcggccct ctccttggcg  2940
gcgatgttga gttgcacgta ctcgcgagcc acgcaccgcc actcggggaa cacggcggtg  3000
cgctcgtcgg gcaggatgcg cacgtgccag ccgcggttgt gcagggtgat gaggtccacg  3060
ctggtggcca cctccccgcg gaggggctcg ttggtccaac acaatcgccc ccctttttctg  3120
gagcagaacg gaggcagggg atctagcaag ttggcgggcg gggggtcggc gtcgatggta  3180
aatatgccgg gtagcagaat tttattaaaa taatcgattt cggtgtccgt gtcttgcaac  3240
gcgtcttccc acttcttcac cgccagggcc ctttcgtagg gatttagggg cggtccccag  3300
ggcatggggt gggtcagggc cgaggcgtac atgccgcaga tgtcgtacac gtacaggggc  3360
tccctcaaca ccccgatgta agtggggtaa cagcgccccc cgcggatgct ggctcgcacg  3420
tagtcgtaca tctcgtgaga gggagccatg agcccgtctc ccaagtgggt cttgtggggt  3480
```

-continued

```
ttctcggccc ggtagaggat ctgcctgaag atggcgtggg agttggaaga gatggtgggg  3540
cgttggaaga cgttaaagtt ggctccgggc agtcccacgg agtcttggat gaattgggcg  3600
taggattccc ggagcttgtc caccagggct gcggttacca gcacgtcgag agcgcagtag  3660
tccaacgtct cgcggaccag gttgtaggcc gtctcttgtt ttttctccca cagttcgcgg  3720
ttgaggaggt attcctcgcg gtctttccag tactcttcgg cgggaaatcc tttttcgtcc  3780
gctcggtaag aacctaacat gtaaaattcg ttcacggctt tgtatggaca acagcctttt  3840
tctaccggca gggcgtacgc ttgagcggcc tttctgagag aggtgtgggt gagggcgaag  3900
gtgtcccgca ccatcacttt caggtactga tgtttgaagt ccgtgtcgtc gcaggcaccc  3960
tgttcccaca gcgtgaagtc ggtgcgcttt ttctgcctgg gattggggag ggcgaaggtg  4020
acgtcgttaa agaggatttt cccggcgcgg ggcatgaagt tgcgagagat cctgaagggt  4080
ccgggcacgt ccgagcggtt gttgatgact tgcgccgcca ggacgatctc atcgaagccg  4140
ttgatgttgt ggcccacgat gtaaagttcg ataaagcgcg gctgtccctt gagggccggc  4200
gctttttca actcctcgta ggtgagacag tccggcgagg acagacccag ctcagcccgg  4260
gcccagtcgg agagttgagg attagccgcg aggaaggaac tccatagatc caaggccagg  4320
agagtttgca agcggtcgcg gaactcgcgg aactttttgc ccacggccat tttctccggc  4380
gttaccacgt aaaaggtgtc ggggcggttg ttccagacgt cccatcggag ctctagggcc  4440
agctcgcagg cttggcgaac gagggtctcc tcgcccgaga cgtgcatgac cagcatgaag  4500
ggtaccaact gtttcccgaa cgagcccatc catgtgtagg tttctacgtc gtaggtgaca  4560
aagagccgct gggtgcgcgc gtgggagccg atcgggaaga agctgatctc ctgccaccag  4620
ctggaggaat gggtgttgat gtggtgaaag tagaagtccc gccggcgcac agagcattcg  4680
tgctgatgtt tgtaaaagcg accgcagtag tcgcagcgtt gcacgctctg tatctcctga  4740
atgagatgcg cttttcgccc gcgcaccaga aaccggaggg ggaagttgag actggggctt  4800
ggtggggcgg catccccttc gccttggcgg tgggagtctg cgtctgcgcc cttcttctct  4860
gggtggacga cggtggggac gacgacgccc cgggtgccgc aagtccagat ctccgccacg  4920
gaggggcgca ggcgctgcag gagggggcgc agctgcccgc tgtccaggga gtcgagggcg  4980
gccgcgctga ggtcgacggg aagcgtttgc aagttcactt tcagaagacc ggtaagagcg  5040
tgagccaggt gcagatggta cttgatttcc agggggggtgt tggaagaggc gtccacggcg  5100
tagaggaggc cgtgtccgcg cggggtcacc accgtgcccc gaggaggttt tatctcactc  5160
gtcgagggcg agcgccgggt ggtagaggcg gctctgcgcc ggggggcagc ggaggcagag  5220
gcacgttttc gtgaggattc ggcagcggtt gatgacgagc ccggagactg ctggcgtggg  5280
cgacgacgcg gcggttgagg tcctggatgt gctgtctctg cgtgaagacc accggtcccc  5340
gggtcctgaa cctgaaagag agttccacag aatcaatgtc tgcatcgtta acggcggcct  5400
gcctgaggat ctcctgtacg tcgcccgagt tgtcttgata ggcgatctcg gccatgaact  5460
gctccacttc ttcctcgcgg aggtcgccgt ggcccgctcg ctccacggtg gcggccaggt  5520
cgttggagat gcgacgcatg agttgagaga aggcgttgag gccgttctcg ttccacacgc  5580
ggctgtacac cacgtttccg aaggagtcgc gcgctcgcat gaccacctgg gccacgttga  5640
gttccacgtg gcgggcgaag acggcgtagt ttctgaggcg ctggaagagg tagttgagcg  5700
tggtggcgat gtgctcgcag acgaagaagt acatgatcca gcgccgcagg gtcatctcgt  5760
tgatgtctcc gatggcttcg agacgctcca tggcctcgta gaagtcgacg gcgaagttga  5820
aaaattggga gttgcgggcg gccaccgtga gttcttcttg caggaggcgg atgagatcgg  5880
cgaccgtgtc gcgcacctcc tgctcgaaag cgccccgagg cgcctctgct tcttcctccg  5940
gctcctcctc ttccaggggc acgggttcct ccggcagctc tgcgacgggg acggggcggc  6000
gacgtcgtcg tctgaccggc aggcggtcca cgaagcgctc gatcatttcg ccgcgccggc  6060
gacgcatggt ctcggtgacg gcgcgtccgt tttcgcgagg tcgcagttcg aagacgccgc  6120
cgcgcagagc gcccccgtgc agggagggta agtggttagg gccgtcgggc agggacacgg  6180
cgctgacgat gcattttatc aattgctgcg taggcactcc gtgcagggat ctgagaacgt  6240
cgaggtcgac gggatccgag aacttctcta ggaaagcgtc tatccaatcg caatcgcaag  6300
gtaagctgag gacggtgggc cgctgggggg cgtccgcggg cagttgggag gtgatgctgc  6360
tgatgatgta attaaagtag gcggtcttca ggcggcggat ggtggcgagg aggaccacgt  6420
ctttgggccc ggcctgttga atgcgcaggc gctcggccat gccccaggcc tcgctctgac  6480
agcgacgcag gtctttgtag tagtcttgca tcagtctctc caccggaacc tctgcttctc  6540
ccctgtctgc catgcgagtc gagccgaagc cccgcagggg ctgcagcaac gctaggtcgg  6600
ccacgaccct ctcggccagc acggcctgtt gaatctgcgt gagggtggtc tggaagtcgt  6660
ccaggtccac gaagcggtga taggcccccg tgttgatggt gtaggtgcag ttggccataa  6720
cggaccagtt gacgacttgc atgccgggtt gggtgatctc cgtgtacttg aggcgcgagt  6780
aggcgcggga ctcgaacacg tagtcgttgc atgtgcgcac cagatactgg tagccgacca  6840
ggaagtgagg aggcggttct cggtacaggg gccagccgac ggtggcgggg gcgccggggg  6900
acaggtcgtc cagcatgagg cggtggtagt ggtagatgta gcgggagagc caggtgatgc  6960
cggccgaggt ggtcgcggcc ctggtgaatt cgcggacgcg gttccagatg ttgcgcaggg  7020
ggcgaaagcg ctccatggtg ggcacgctct gccccgtgag gcgggcgcaa tcttgtacgc  7080
tctagatgga aaaaagacag ggcggtcatc gactcccttc cgtagctcgg ggggtaaagt  7140
cgcaagggtg cggcggcggg gaaccccggt tcgagaccgg ccggatccgc cgctcccgat  7200
gcgcctggcc ccgcatccac gacgtccgcg ccgagaccca gccgcgacgc tccgccccaa  7260
tacggagggg agtcttttgg tgtttttcg tagatgcatc cggtgctgcg gcagatgcga  7320
cctcagacgc ccaccaccac cgccgcggcg gcagtaaacc tgagcggagg cggtgacagg  7380
gaggaggagg agctggcttt agacctggaa gagggagagg ggttggcccg gctgggagcg  7440
ccgtccccag agagacaccc tagggttcag ctcgtgaggg acgccaggca ggcttttgtg  7500
ccgaagcaga acctgtttag ggaccgcagc ggtcaggagg cggaggagat gcgcgattgc  7560
aggtttcgcg cgggcagaga gctgagggcg ggcttcgatc gcgagcggct cctgagggcg  7620
gaggatttcg agcccgacga gcgttctggg gtgagcccgg cccgcgctca cgtctcggcg  7680
gccaacctgg tgagcgcgta cgagcagacg gtgaacgagg agcgcaactt ccaaaagagc  7740
tttaacaatc acgtgaggac cctgatcgcg agggaggagg tgaccatcgg gctgatgcat  7800
ctgtgggact tcgtggaggc ctacgtgcag aacccggcca gcaaacctct gacggcccag  7860
ctgttcctga tcgtgcagca cagccgcgac aacgagacgt tccgcgacgc catgttgaac  7920
atcgcggagc ccgagggtcg ctggctcttg gatctgatta acatcctgca gagcatcgtg  7980
gtgcaggaga gggggctgag tttagcggac aaggtggcgg ccattaacta ttcgatgcag  8040
agcctgggga agttctacgc tcgcaagatc tacaagagcc cttacgtgcc catagacaag  8100
gaggtgaaga tagacagctt ttacatgcgc atggcgctga aggtgctgac gctgagcgac  8160
gatctcggcg tgtaccgtaa cgacaagatc cacaaggcgg tgagcgccag ccgccggcgg  8220
```

```
gagctgagcg acagggagct gatgcacagc ctgcagaggg cgctggcggg cgccggggac  8280
gaggagcgcg aggcttactt cgacatggga gccgatctgc agtggcgtcc cagcgcgcgc  8340
gccttggagg cggcgggcta ccccgacgag gaggaccggg atgatttgga ggaggcaggc  8400
gagtacgagg acgaagcctg accgggcagg tgttgtttta gatgcagcgg ccggcggacg  8460
gggccaccgc ggatcccgca cttttggcat ccatgcagag tcaaccttcg ggcgtgaccg  8520
cctccgatga ctgggcggcg gccatggacc gcatcatggc gctgaccacc cgcaaccccg  8580
aggcttttag gcagcaaccc caggccaacc gtttttcggc catattggaa gcggtggtac  8640
cgtcgcgcac caaccccaca cacgagaaag tcctgactat cgtgaacgcc ctggtagaca  8700
gcaaagctat ccgccgcgac gaggcggggc tgatctacaa cgctctgttg gaacgggtgg  8760
cgcgctacaa cagcactaac ttgcagacca atctggatcg cctcaccacg gacgtgaagg  8820
aggcgctggc tcagaaggag cggtttctga gggatagcaa tctgggttct ctggtggcac  8880
tgaacgcctt tctgagcacg cagccggcca acgtgccccg cgggcaggag gattacgtga  8940
gcttcatcag cgctctgaga ctgctggtgt ccgaggtgcc ccagagcgag gtgtaccagt  9000
ctgggccgga ttactttttt cagacgtccc gacagggctt gcaaacggtg aacctgactc  9060
aggcctttaa aaacttgcaa ggtatgtggg gcgtcaaggc cccggtgggc gatcgcgcca  9120
ctatctccag tctgctgacc cccaacactc gcctgctgct gctcttgatc gcaccgttca  9180
ccaacagtag cactatcagc cgtgactcgt acctgggtca tctcatcact ctgtaccgcg  9240
aggccatcgg ccaggctcag atcgacgagc atacgtatca ggagatcact aacgtgagcc  9300
gggccctggg tcaggaagat accggcagcc tggaagccac gttgaacttt ttgctaacca  9360
accggaggca aaaaataccc tcccagttca cgttaagcgc cgaggaggag aggattctgc  9420
gatacgtgca gcagtccgtg agcctgtact tgatgcgcga gggcgccacc gcttccacgg  9480
ctttagacat gacggctcgg aacatggaac cgtcctttta ctccgcccac cggccgttca  9540
ttaaccgtct gatggactac ttccatcgtg cggccgccat gaacggggag tacttcacca  9600
atgccatcct gaatccgcat tggatgcccc cgtccggctt ctacaccggg gagtttgacc  9660
tgcccgaagc cgacgacggc tttctgtggg acgacgtgtc cgatagcatt ttcacgccgg  9720
ggaatcgccg attccagaag aaggagggcg gagacgagct ccccctctcc agcgtggagg  9780
ctgcctctag gggagagagc ccctttccca gtctgtcttc cgccagtagc ggtcgggtaa  9840
cgcgcccgcg gttgccgggg gagagcgact acctgaacga ccccttgctg cgaccggcta  9900
gaaagaaaaa tttccccaac aacggggtgg aaagcttggt ggataaaatg aatcgttgga  9960
agacctacgc ccaggagcag cgggagtggg aggacagtca gccgcgaccg ctggttccgc  10020
cgcactggcg tcgccagaga gaagacccgg acgactccgc agacgatagt agcgtgttgg  10080
acctgggagg gagcggagcc aaccccttg ctcacttgca acccaagggg cgttcgagtc  10140
gcctctacta ataaaaaaga cgcggaaact taccagagcc atggccacag cgtgtgtcct  10200
ttcttcctct ctttcttcct cggcgcggca gaatgagaag agcggtgaga gtcacgccgg  10260
cggcgtatga gggtccgccc ccttcttacg aaagcgtgat gggatcagcg aacgtgccgg  10320
ccacgctgga ggcgccttac gttcctccca gatacctggg acctaccgag ggcagaaaca  10380
gcatccgtta ctccgagctg gcgcccctgt acgataccac caaggtgtac ctggtggaca  10440
acaagtcggc ggacatcgcc tccctgaatt accaaaacga ccacagcaac tttctgacca  10500
ccgtggtgca gaacaatgac ttcaccccga cggaggcggg cacgcagacc attaactttg  10560
acgagcgttc ccgctggggc ggtcagctga aaaccatcct gcacaccaac atgcccaaca  10620
tcaacgagtt catgtccacc aacaagttca gggccaggct gatggttaaa aaggtagaaa  10680
accagcctcc cgagtacgaa tggtttgagt tcaccatccc cgagggcaac tattccgaga  10740
ctatgactat cgatctgatg aacaatgcga tcgtggacaa ttacctgcaa gtggggaggc  10800
agaacggggt attggaaagc gatatcggtg tgaaatttga taccagaaac ttccgactgg  10860
ggtgggatcc cgtgaccaag ctggtaatgc caggcgtgta caccaacgag gcttttcacc  10920
ccgacatcgt gctgctgccg gggtgcggcg tggatttcac tcagagccgc ttgagtaacc  10980
tgttaggaat caggaagcgc cgtcccttcc aggagggctt tcagatcatg tatgaggacc  11040
tggagggagg taacattccc gctctactag atgtgacaaa gtacgaacaa agtgtacagc  11100
gagccaaggc ggaagggcga gagattcgcg gagacacttt tgccgtgtct ccccaggatt  11160
tggttataga gccgttagag catgacagca aaaatcgtag ttacaatctt ttgcccaaca  11220
aaaccgacac ggcctatcgc agctggtttt tggcttacaa ctacggagac cccgagaaag  11280
gagtgagatc atggaccata ctcaccacca cggacgtgac ctgcggctcg cagcaagtgt  11340
actggtccct gccggatatg atgcaagacc cggtcacctt ccgcccctcc acccaagtca  11400
gcaacttccc ggtggtgggc accgagctgc tgcccgtcca tgccaagagc ttctacaacg  11460
agcaggccgt ctactcgcaa ctcattcgcc agtccaccgc gcttacccac gtgttcaatc  11520
gttttcccga gaaccagatt ctggtgcgcc ctcccgctcc taccattacc accgtcagtg  11580
aaaacgttcc cgccctcaca gatcacggaa ccctaccgct gcgcagcagt atcagtggag  11640
ttcagcgcgt gaccatcacc gacgccagac gtcgaacctg cccctacgtt tacaaagcgc  11700
tcggcgtggt ggcccctaaa gttctctcta gtcgcacctt ttaaacatgt ccattctcat  11760
ctctcccgat aacaacaccg gctggggatt gggctccggc aagatgtacg gcggggctaa  11820
gcgacgctcc agtcagcatc ccgttcgcgt tcggggtcac ttccgcgctc cctggggagc  11880
ttacaagcga ggactctctg gccgaacggc tgtagacgat accatagatg ccgtgattgc  11940
cgacgcccgc cggtacaacc ccggaccggt cgctagcgcc gcctccaccg tggattccgt  12000
gatcgacagc gtggtggcca gcgccagggc ctatgctcgc cgcaagaggc ggctgcatcg  12060
gaaacgtcgc cccaccgccg ccatgctagc agccagggcc gtgctgaggc gggcccggag  12120
ggtaggcagg agggctatgc gccgcgctgc cgccaacgcc gccgggaggg cccgcagaca  12180
agccgcccgc caggccgccg ctgccatcgc tagcatggcc agacccagga gagggaacgt  12240
gtactgggtg cgcgattctg taacgggagt ccgagtgccg gtgcgcagcc gacctccccg  12300
aagttagaag atccaagctg cgaagacggc ggtactgagt ctccctgttg ttattagccc  12360
aacatgagca agcgcaagtt taaagaagaa ctgctgcaga cgctggtgcc tgagatctat  12420
ggccctccgg acgtgaagcc tgacattaag ccccgcgata tcaagcgtgt taaaaagcgg  12480
gaaaaaaaag aggaacttgc ggcggtagac gatggcggtg tagaatttat taggagtttc  12540
gccccacggc gcagggttca atggaaaggg cggcgtgtac aacgcgttct gaggccgggc  12600
accgcggtag tttttacccc gggagagcgg tcggccgtta ggggtttcaa gcggcagtac  12660
gatgaggtgt acggcgacga agacatactg gaacaggcgg ctcagcagat tggagaattc  12720
gcttatggca aacgttctcg gcgcgaagac ctggccatcg ccttggacag cggcaatccc  12780
acacccagcc tcaaacccgt gacgctgcaa caggtgcttc ccgtgagcgc cagtactgac  12840
agcaaaaggg ggattaaaag agagatggaa gagctgcaac ccaccatcca acttatggtc  12900
cctaaacgac agaggttgga agaggtcctg gagaagatga aagtggaccc cagcatagag  12960
```

```
ccggatgtga aagtgaggcc tattaaggaa gtggcccccg gtcttggggt gcaaacggtg  13020
gacattcaaa tccccgtcac gtccgcttca acagcggtgg aagccatgga aacgcaaacg  13080
gaagcccccg ccgtcacggt cggtaccagg gaagtggcgt tgcaaacgga accctggtac  13140
gaatacgcca cccctaggcg tcagaggcgg tccgcccgtt acggacccgt caacgccatc  13200
atgcccgagt acgcgctaca tccgtctatc cggcccactc ccggctaccg gggagtgacg  13260
tatcgcccgt caggaactcg ccgccgttac cgtcgccgcc gtcgctctcg ccgcgctctg  13320
gccccagtgt cggtgcggcg cgtgacccgc caggggaaaa cagtcaccat ccccaacccg  13380
cgctaccacc ctagcattct ttaatgactc tgccgttttg cagatggctc tgacttgccg  13440
cgtgcgcctt cccgttctgc actatcgagg aagatctcgt cgtaggagag gcatggcggg  13500
cagtggtcgc cggcgggctt tgcgcaggcg catgaaaggc ggaattttac ccgccctaat  13560
acctataatc gccgccgcca taggcgccat acccggcgtc gcttcagtgg ccttgcaagc  13620
agctcgtaat aaataaacga aggcttttgc acttatgtcc tggtcctgac tattttatgc  13680
agaaaaagca tggaagacat caattttacg tcgctggctc cgcggcaagg ctcgcggccg  13740
ctcatgggca cctggaacga catcggcacc agtcagctca acgggggcgc tttcaattgg  13800
gggagccttt ggagcggcat taaaaacttt ggctccacga ttaaatccta cggcagcaaa  13860
gcctggaaca gtagtgctgg tcaaatgctc cgagataaac tgaaggacac caacttccaa  13920
gagaaagtgg tcaacggggt ggtgaccggc atacacggcg cggtagatct tgccaaccaa  13980
gcggtgcaga aagagattga caggcgattg gaaaactcgc gggtgccgcc gcagagaggg  14040
gatgaggtgg aggtcgagga agtagaagta gaggaaaagc tgccccccttt ggagaaagtt  14100
cccggtgcga ttccaaggcc gcagaagcgg ccaaggccag aactagaaga aactctggtg  14160
acggagagca aggagcctcc ctcgtacgag caagccttaa aagagggcgc ttcaccctac  14220
ccgatgacca aaccgatcgc gcctatggct cggccggtgt acgggaagga ctacaaacct  14280
gtcacgctag aacttcctcc gccactccct tcgcgtccta cggtgcctcc catgccagcg  14340
ccgtcggccg gtcccgtgtc tgcaccttcc gcagcgcctc tgccagccgc ccgcccagtg  14400
gccgtggcca ctgccagaaa ccccagaggc cagagaggag ccaactggca aaacacgctg  14460
aacagcatct taattaattc gaacccataa tacccataat agctgtttgc catcgacgcg  14520
aggctggatg gccttcccca ttatgattct tctcgcttcc ggcggcatcg ggatgcccgc  14580
gttgcaggcc atgctgtcca ggcaggtaga tgacgaccat cagggacagc ttcaaggatc  14640
gctcgcggct cttaccagcc cagcaaaagg ccaggaaccg taaaaaggcc gcgttgctgg  14700
cgtttttcca taggctccgc ccccctgacg agcatcacaa aaatcgacgc tcaagtcaga  14760
ggtggcgaaa cccgacagga ctataaagat accaggcgtt tccccctgga agctccctcg  14820
tgcgctctcc tgttccgacc ctgccgctta ccggatacct gtccgccttt ctcccttcgg  14880
gaagcgtggc gctttctcat agctcacgct gtaggtatct cagttcggtg taggtcgttc  14940
gctccaagct gggctgtgtg cacgaacccc ccgttcagcc cgaccgctgc gccttatccg  15000
gtaactatcg tcttgagtcc aacccggtaa gacacgactt atcgccactg gcagcagcca  15060
ctggtaacag gattagcaga gcgaggtatg taggcggtgc tacagagttc ttgaagtggt  15120
ggcctaacta cggctacact agaaggacag tatttggtat ctgcgctctg ctgaagccag  15180
ttaccttcgg aaaaagagtt ggtagctctt gatccggcaa acaaaccacc gctggtagcg  15240
gtggtttttt tgtttgcaag cagcagatta cgcgcagaaa aaaaggatct caagaagatc  15300
ctttgatctt ttctacgggg tctgacgctc agtggaacga aaactcacgt taagggattt  15360
tggtcatgag attatcaaaa aggatcttca cctagatcct tttaaattaa aaatgaagtt  15420
ttaaatcaat ctaaagtata tatgagtaaa cttggtctga cagttaccaa tgcttaatca  15480
gtgaggcacc tatctcagcg atctgtctat ttcgttcatc catagttgcc tgactccccg  15540
tcgtgtagat aactacgata cgggagggct taccatctgg ccccagtgct gcaatgatac  15600
cgcgagaccc acgctcaccg gctccagatt tatcagcaat aaaccagcca gccggaaggg  15660
ccgagcgcag aagtggtcct gcaactttat ccgcctccat ccagtctatt aattgttgcc  15720
gggaagctag agtaagtagt tcgccagtta atagtttgcg caacgttgtt gccattgctg  15780
caggcatcgt ggtgtcacgc tcgtcgtttg gtatggcttc attcagctcc ggttcccaac  15840
gatcaaggcg agttacatga tcccccatgt tgtgcaaaaa agcggttagc tccttcggtc  15900
ctccgatcgt tgtcagaagt aagttggccg cagtgttatc actcatggtt atggcagcac  15960
tgcataattc tcttactgtc atgccatccg taagatgctt ttctgtgact ggtgagtact  16020
caaccaagtc attctgagaa tagtgtatgc ggcgaccgag ttgctcttgc ccggcgtcaa  16080
cacgggataa taccgcgcca catagcagaa ctttaaaagt gctcatcatt ggaaaacgtt  16140
cttcggggcg aaaactctca aggatcttac cgctgttgag atccagttcg atgtaaccca  16200
ctcgtgcacc caactgatct tcagcatctt ttactttcac cagcgtttct gggtgagcaa  16260
aaacaggaag gcaaaatgcc gcaaaaaagg gaataagggc gacacggaaa tgttgaatac  16320
tcatactctt cctttttcaa tattattgaa gcatttatca gggttattgt ctcatgagcg  16380
gatacatatt tgaatgtatt tagaaaaata aacaaatagg ggttccgcgc acatttcccc  16440
gaaaagtgcc acctgacgtc taagaaacca ttattatcat gacattaacc tataaaaata  16500
ggcgtatcac gaggcccttt cgtcttcaag aattggtcga tggcaaacag ctattatggg  16560
tattatgggt tcgaattaat                                              16580
```

```
SEQ ID NO: 42          moltype = DNA  length = 21626
FEATURE                Location/Qualifiers
source                 1..21626
                       mol_type = other DNA
                       note = Synthetic oligonucleotide pBr/sAd4310A.RsrII-rITR
                       organism = synthetic construct
SEQUENCE: 42
attaacaccg tggattccgt gatcgacagc gtggtggcca gcgccagggc ctatgctcgc  60
cgcaagaggc ggctgcatcg gaaacgtcgc cccaccgccg ccatgctagc agccagggcc  120
gtgctgaggc gggcccggag ggtaggcagg agggctatgc gccgcgctgc cgccaacgcc  180
gccgggaggg cccgcagaca agccgcccgc caggccgccg ctgccatcgc tagcatggcc  240
agacccagga gagggaacgt gtactgggtg cgcgattctg taacgggagt ccgagtgccg  300
gtgcgcagcc gacctccccg aagttagaag atccaagctg cgaagacggc ggtactgagt  360
ctccctgttg ttattagccc aacatgagca agcgcaagtt taaagaagaa ctgctgcaga  420
cgctggtgcc tgagatctat ggccctccgg acgtgaagcc tgacattaag ccccgcgata  480
tcaagcgtgt taaaaagcgg gaaaaaaaag aggaacttgc ggcggtagac gatggcggtg  540
tagaatttat taggagtttc gccccacggc gcagggttca atggaaaggg cggcgtgtac  600
```

```
aacgcgttct gaggccgggc accgcggtag tttttacccc gggagagcgg tcggccgtta  660
ggggtttcaa gcggcagtac gatgaggtgt acggcgacga agacatactg gaacaggcgg  720
ctcagcagat tggagaattc gcttatggca aacgttctcg gcgcgaagac ctggccatcg  780
ccttggacag cggcaatccc acacccagcc tcaaacccgt gacgctgcaa caggtgcttc  840
ccgtgagcgc cagtactgac agcaaaaggg ggattaaaag agagatggaa gagctgcaac  900
ccaccatcca acttatggtc cctaaacgac agaggttgga agaggtcctg gagaagatga  960
aagtggaccc cagcatagag ccggatgtga aagtgaggcc tattaaggaa gtggcccccg 1020
gtcttggggt gcaaacggtg gacattcaaa tccccgtcac gtccgcttca acagcggtgg 1080
aagccatgga aacgcaaacg gaagcccccg ccgtcacggt cggtaccagg gaagtggcgt 1140
tgcaaacgga accctggtac gaatacgcca cccctaggcg tcagaggcgg tccgcccgtt 1200
acggacccgt caacgccatc atgcccgagt acgcgctaca tccgtctatc cggcccactc 1260
ccggctaccg gggagtgacg tatcgcccgt caggaactcg ccgccgttac cgtcgccgcc 1320
gtcgctctcg ccgcgctctg gccccagtgt cggtgcggcg cgtgacccgc caggggaaaa 1380
cagtcaccat ccccaacccg cgctaccacc ctagcattct ttaatgactc tgccgttttg 1440
cagatggctc tgacttgccg cgtgcgcctt cccgttctgc actatcgagg aagatctcgt 1500
cgtaggagag gcatggcggg cagtggtcgc cggcgggctt tgcgcaggcg catgaaaggc 1560
ggaattttac ccgccctaat acctataatc gccgccgcca taggcgccat acccggcgtc 1620
gcttcagtgg ccttgcaagc agctcgtaat aaataaacga aggcttttgc acttatgtcc 1680
tggtcctgac tattttatgc agaaaaagca tggaagacat caattttacg tcgctggctc 1740
cgcggcaagg ctcgcggccg ctcatgggca cctggaacga catcggcacc agtcagctca 1800
acgggggcgc tttcaattgg gggagccttt ggagcggcat taaaaacttt ggctccacga 1860
ttaaatccta cggcagcaaa gcctggaaca gtagtgctgg tcaaatgctc cgagataaac 1920
tgaaggacac caacttccaa gagaaagtgg tcaacggggt ggtgaccggc atacacggcg 1980
cggtagatct tgccaaccaa gcggtgcaga aagagattga caggcgattg gaaaactcgc 2040
gggtgccgcc gcagagaggg gatgaggtgg aggtcgagga agtagaagta gaggaaaagc 2100
tgccccccttt ggagaaagtt cccggtgcga ttccaaggcc gcagaagcgg ccaaggccag 2160
aactagaaga aactctggtg acggagagca aggagcctcc ctcgtacgag caagccttaa 2220
aagagggcgc ttcaccctac ccgatgacca aaccgatcgc gcctatggct cggccggtgt 2280
acgggaagga ctacaaacct gtcacgctag aacttcctcc gccactccct tcgcgtccta 2340
cggtgcctcc catgccagcg ccgtcggccg gtcccgtgtc tgcaccttcc gcagcgcctc 2400
tgccagccgc ccgcccagtg gccgtggcca ctgccagaaa ccccagaggc cagagaggag 2460
ccaactggca aaacacgctg aacagcatcg tgggcctggg agttaaaagc ctgaaacgcc 2520
gccgttgcta ttattaaaaa agtgtagcta aaaaatctcc cgttgtatac gcctcctatg 2580
ttaccgccag agacgtgtga ctgtcgtcgc gagcagcgct ttcaagatgg ccaccccatc 2640
gatgatgccg cagtggtctt acatgcacat cgccgggcag gacgcctcgg agtatctgag 2700
ccccggtctt gtgcagtttg cccgcgccac cgacacctac ttcagcttgg gaaacaagtt 2760
tagaaatccc accgtggccc ccacgcacga tgtgaccacg gatcgttcgc agaggctgac 2820
tctgcgcttt gtaccggtag accgtgagga tactgcctat tcttacaaag ttcggtatac 2880
gttagccgta ggagacaaca gggtgctgga catggccagt acttactttg acatccgcgg 2940
tgttcttgac cgcggtccaa gctttaaacc gtataccgga acggcataca atgccttggc 3000
tccaaagggc gctccaaatg cttgccagtg gacaacgacc aacgggggca ataaaacgaa 3060
cacttttgcc caagcccctt taataggcac ggctattgac ggaaccaacg gactgcagat 3120
tgggcaagat aatggacaag ctgtttatgc tgacaaaacc tttcaacccg aaccacaagt 3180
gggagaatct cagtggaata ctaatccaac cacaaacgca gcaggacgcg tgttaaaaac 3240
aactactcgc atgctgcctt gctatggttc ttttgcaagg cccaccaatg agaaaggggg 3300
tcaagcttca ggagacgtta ccttccaatt tttcgacact gcctcggaca atggcaacaa 3360
ccctaaggtg gtgctatatg gagaagacgt caacattgaa tcgcctgaca cacacttaat 3420
ctacaaaccc accgctgaca acacaaactc tgaaaacctt ttgggtcaac aggccgctcc 3480
aaacagagcc aattacattg cctttcggga caacttcatt ggactaatgt actataattc 3540
aacaggaaac atgggagtgt tggcagggca ggcttcccaa ctaaatgctg tggtagactt 3600
gcaagacaga aacactgagc tttcctacca actcatgtta gatgcaatag gagaccggag 3660
tcgttacttt tcaatgtgga accaagcagt ggacagctat gatccagatg tgcgaattat 3720
tgaaaatcat ggcgttgagg acgaactgcc aaattactgc ttccctctta acgctcaagg 3780
aattgctaac acctataaag gcgttaagaa aaacaacggc aattgggcga aagacgacgc 3840
agtagtagaa actaacgaaa ttggcatagg aaatgttttt gccatggaga taaatttaac 3900
tgctaacttg tggcgaaact ttctgtattc caatattgct ttgtacctgc cagactccta 3960
caagtattca ccgggaaaca taaccttacc cgaaaacaaa aacagttaca attacattaa 4020
tggtcgagta acagctcctg gtctggtaga cacctttgta aacattggcg cgcgatggtc 4080
tcccgacccc atggacaacg tgaatccttt taatcaccat cgcaatgctg gtctgcgtta 4140
tcgctccatg cttctaggca acggccgcta cgtgcccttc cacattcagg tgcctcaaaa 4200
attctttgcc attaagaacc tgcttctgct gcctgggtcc tacacctacg agtggaactt 4260
cagaaaagat gtaaacatga tcttgcagag cacgctgggc aacgacctcc gtgtcgacgg 4320
ggccagcgtc agattcgaca gcattaacct ctacgctaat ttcttcccca tggcacataa 4380
caccgcttcc accctggagg ctatgttacg caacgacacc aacgaccagt cctttaatga 4440
ctacctctgc gcggccaaca tgctataccc cattcctgcc aatgccacca gtgtgcccat 4500
ctccatcccc tctcgcaact gggcagcttt cagagggtgg agtttcaccc gcctcaaaac 4560
aaaagaaacc ccctcgctgg gttccggatt tgatccatac tttgtttact caggctccat 4620
tccctacctg gatggtacct tctacctgaa ccacaccttc aaaaaggtgt ctattatgtt 4680
cgactcttct gtgagctggc ccggcaacga ccgcctgctg acccctaatg agtttgaaat 4740
taagcgctcg gtggacggag aaggatacaa tgtagcccag agcaacatga ccaaagactg 4800
gttcttaatt caaatgctca gccactacaa cattggttac caagggtttt acgtgcccga 4860
ggcttacaaa gacagaatgt actccttttt tagaaacttc caacctatga gtagacaggt 4920
agtggatgca gatcggtatg aacaatacaa aaaagtcacc gttgagtatc aacataataa 4980
ttctggtttt gtgggataca tgggacccac catgagggaa gggcaggctt atccagcgaa 5040
ttacccttat cctcttattg gagacaccgc cgtgcccagc ctgacccaga aaaagttcct 5100
ctgtgaccgc accatgtgga gaatcccctt ctctagcaac ttcatgtcta tgggggccct 5160
caccgacctg gggcagaaca tgctgtacgc caattccgct cacgccttgg atatgacctt 5220
tgaggtggac cccatggatg agcccacgct tctctatgtt ctgtttgaag tcttcgacgt 5280
ggtgcgcatc caccagccgc accgcggcgt catcgaggcc gtctacctgc gcacaccttt 5340
```

```
ctctgccggt aacgccacca cataagaagc aaatgggctc cagcgaacag gagctgcggg  5400
ccattattcg cgacctgggc tgcggaccct actttttggg caccttcgac aagcgtttcc  5460
ccggattcat gtccccccag aagccggcct gtgccatagt caacacggcc gggcgggaga  5520
ccgggggggt tcactggctc gccttcgcct ggaacccgcg caaccgcacc tgctacctgt  5580
tcgacccttt tggtttttcc gacgaaaggc tgaagcaaat ctaccagttc gaatacgaag  5640
gactcctcaa gcgcagcgct ctggcctcca cgcccgacca ctgcgtcacc ctggaaaaat  5700
ccacccaaac ggtgcagggg cccctctcgg ccgcctgcgg gcttttctgt tgcatgtttt  5760
tgcacgcctt cgtgcactgg cctcacaacc ccatggagcg caaccccacc atggatctgc  5820
tcaccggagt gcccaacagc atgcttcaca gcccccaggt cgcccccacc ctgcgccgta  5880
accaggaaca cctgtatcgc tttctgggga aacactctgc ctatttccgc cgccaccggc  5940
agcgcatcga gcaggccacg gcctttgaaa gcatgagcca aagagtgtaa tcaataaaaa  6000
ccatttttat ttaacatgat acgcgcttct ggcgttttta ttaaaaatcg aacggttcga  6060
gggaggggtc ctcgtgcccg ctgggaaggg acacgttgcg gtactggaaa cgggcgctcc  6120
aacgaaactc ggggatcacc agccgcggca ggggcacgtc ttctaggttc tgcttccaga  6180
actgccgcac cagctgcagg gctcccatga cgtcgggcgc cgagatcttg aagtcgcagt  6240
tagggccgga gcccccgcgg ctgttgcgga acacggggtt ggcacactgg aacaccagca  6300
cgctggggtt gtaaatactg gccagggccg ttgggtcggt cacctccgac gcatccagat  6360
cctcggcatt gctcagggcg aacggagtca gcttgcacat ctgccgtccg atctggggca  6420
ccaggtcggg tttgttgagg caatcgcagc gcagagggat taggatgcga cgctgcccgc  6480
gttgcatgat agggtaactc gccgccagga actcctccat ctgacggaag gccatctggg  6540
ccttggtacc ctcggtgaaa aatagcccac aggacttgct agaaaatacg ttattgccgc  6600
agttgatgtc ttccgcgcag cagcgtgcat cttcgttctt cagctgaacc acgttacgcc  6660
cccagcggtt ctggaccacc ttggctttcg taggatgctc cttcaacgcc cgctgaccgt  6720
tctcgctggt cacatccatt tccaccacgt gctccttgca gaccatctcc actccgtgga  6780
agcagaacag gacgccctcc tgctgggtat tgcgatgctc ccaaacggca catccggtgg  6840
gctcccagct cttgcgtttc acccccgcgt atgcttccat gtaagccatg aggaatctgc  6900
ccatcagctc ggtgaaggtc ttctggttgg tgaaggttag cggcaggccg cggtgctcct  6960
cgttcaacca agtttgacag attttgcggt acacggctcc ctggtcgggc agaaacttaa  7020
aagccgctct gctctcgttg tccacgtgga acttctccat caacatcgtc atgacttcca  7080
tgcccttctc ccacgccgtc accaacggtt cggtcccggg gttcttcacc aacacggcgg  7140
tggaggggcc ctcgccggcc ccgacgtcct tcatggtcat tctttggaac tccacggtgc  7200
cgtccgcgcg gcgtactctg cgcatcggag ggtagctgaa gcccacctcc accacggtgc  7260
cttcgccctc gctgtcggaa acgatctccg gggatggcgg cggcgcgggt gtcgccttgc  7320
gagccttctt cttgggaggg agcggaggca cctcctgctc gcgctcgggg ctcatctccc  7380
gcaagtaggg ggtaatggag cttccgggtt ggttctgacg gttggccatt gtatcctagg  7440
cagaaagaca tggatcttat gcgcgaggaa actttaaccg ccccgtcccc cgtcagcgac  7500
gaagaggtca tcgtcgaaca ggacccgggc tacgttacgc cgcccgagga tctggagtcc  7560
cccttagacg accgacgcga cgctagtgag cggcaggaaa atgagaaaga ggaggaggag  7620
ggctgctacc tcctggaagg cgacgtcttg ctaaagcatt tcgccaggca gagcaccata  7680
ctcaaggagg ccttgcaaga ccgctccgag gtgcccttgg acgtcgccgc gctctcccag  7740
gcctacgagg cgaacctttt ctcgccccga gtgcctccga agagacagcc caacggcacc  7800
tgcgagccca acccgcgact caacttctac cccgtgttcg ccgtgcccga ggcgctggcc  7860
acctaccaca tctttttcaa aaaccagcgc attccccttt cctgccgggc caaccgcacc  7920
gcagccgata ggaagctaac actcagaaac ggagccagca tacctgatat cacgtcactg  7980
gaggaagtgc ctaagatctt cgagggtctg ggtcgagatg agaagcgggc ggcgaacgct  8040
ctgcagaaag aacagaaaga gagtcagaac gtgctggtgg agctggaggg ggacaacgcg  8100
cgtctggccg tcctcaaacg ctgcatagaa gtctcccact tcgcctaccc cgccctcaac  8160
ttgccaccca aagttatgaa atcggtcatg gatcagctgc tcatcaagag agctgagccc  8220
ctggatcccg accaccccga ggcggaaaac tcagaggacg gaaagcccgt cgtcagcgac  8280
gaggagctcg agcggtggct ggaaaccggg gacccccaac agttgcaaga gaggcgcaag  8340
atgatgatgg cggccgtgct ggtcaccgtg gagctggaat gcctgcaacg gtttttcagc  8400
gacgtggaga cgctacgcaa aatcggggag tccctgcact acaccttccg ccagggctac  8460
gtccgccagg cctgcaagat ctccaacgtg gagctcagca acctggtctc ctacatgggc  8520
atcctccacg agaaccggct ggggcagagc gtgctgcact gcaccttgca aggcgaggcg  8580
cggcgggact acgtccgcga ctgcatctac ctcttcctca ccctcacctg gcagaccgcc  8640
atgggcgtct ggcagcagtg cttggaagag agaaacctca aagagctaga caaactcctc  8700
tgccgccagc ggcgggccct ctggaccggt ttcagcgagc gcacggtcgc ctgcgccctg  8760
gcagacatta tcttcccgga gcgcctgatg aaaaccttgc agaacggcct gccggatttt  8820
atcagtcaaa gtattttgca aaacttccgc tccttcgttc tggagcgctc cgggatcttg  8880
cccgccatga gctgcgcgct gccttctgac tttgtccccc tttcctaccg cgagtgtcct  8940
cccccccctgt ggagccactg ctacctcttc caactggcca actttctggc ctaccactcc  9000
gacctcatgg aagacgtgag cggagagggg ctgctcgagt gccactgccg ctgcaacctc  9060
tgcacccccc acagatcgct ggcctgcaac accgagctgc tcagcgaaac ccaggtcata  9120
ggtaccttcg agatccaggg gccccagcag caagagggtg cttccggctt gaagctcact  9180
ccggcgctgt ggacctcggc ttacttacgc aaatttgtag ccgaggacta ccacgcccac  9240
aaaattcagt tctatgaaga ccaatctcga ccacccaaag ccccccctcac ggcctgcgtc  9300
atcactcaga gcaaaatcct ggcccaattg caatccatca accaagcgcg ccgagatttc  9360
cttttgaaaa agggtcgggg ggtgtaccta gacccccaga ccggcgagga actcaacccg  9420
tccacactct ccgtcgaagc agcccccccg agacatgccg cccaagggaa ccgccaagca  9480
gctgatcgct cggcagagag cgaagaagca agagctgctc cagcagcagc agcaggtgga  9540
ggacgaggaa gagctgtggg acagccaggc agaggaggtg tcagaggacg aggaggagat  9600
ggaaagctgg gacagcctag acgaggagga ggacgagctt tcagaggaag aggcgaccga  9660
agaaaaacca cctgcatcca gcgcgccttc tctgagccga cagccgaagc cccggccccc  9720
gacgcccccg gccggctcac tcaaagccag ccgtaggtgg gacgccaccg gatctccagc  9780
ggcagcggca acggcagcgg gtaaggccaa acgcgagcgg cgggggtatt gctcctggcg  9840
ggcccacaaa agcagtatcg tgaactgctt gcaacactgc gggggaaaca tctcctttgc  9900
ccgacgctac ctcctcttcc atcacggtgt ggccttccct cgcaacgttc tctattatta  9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
```

```
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttccccctcg ggcgccaaaa  10320
cccacgtcat tgccagcatg agcaaggaga ttcccacccc ttacatgtgg agctatcagc  10380
cccagatggg cctggccgcg ggggccgccc aggactactc cagcaagatg aactggctca  10440
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
acggagtctt ccagctcgga ggagcgggcc gctcttcctt caccactcgc caggcctacc  10860
tgaccctgca gagctcttcc tcgcagccgc gctccggggg aatcggcact ctccagttcg  10920
tggaagagtt cgtcccctcc gtctacttca acccgttttc cggctcacct ggacgctacc  10980
cggacgcctt cattcccaac tttgacgcag tgagtgaatc cgtggacggc tacgactgat  11040
gacagatggt gcggccgtga gagctcggct gcgacatctg catcactgcc gccagcctcg  11100
ctgctacgct cgggaggcga tcgtgttcag ctactttgag ctgccggacg agcaccctca  11160
ggggccggct cacgggttga aactcgagat cgagaacgcg ctcgagtctc gcctcatcga  11220
cgccttcacc gcccggcctc tcctggtaga aaccgaacgc gggatcacta ccatcaccct  11280
gttctgcatc tgccccacgc ccggattaca tgaagatctg tgttgtcatc tttgcgctca  11340
gtttaataaa aactgaactg tttgccgcac cttcaacgcc atctgtgatt tctacaacaa  11400
aaagttcttc tggcaaaggt acacaaactg tattttattc taattctacc tcatctattg  11460
tgctgaactg cgcctgcact aacgaactta tccagtggat tgcaaacggt agtgtgtgca  11520
agtacttttg ggggaacgag atagttagta gaaataacag cctttgcaag cactgcaact  11580
cctccacact aatcctttat cccccatttg ttactggatg gtatatgtgc gttggctccg  11640
gtttaaatcc tagttgcttt cataagtggt ttctacaaaa agagaccctt cccaacaatt  11700
ctgtttcttt tttcaccctg tcctactgct gttctccctc tggttactct ttcaaacctc  11760
taattggtat tttagctttg atactgataa tctttattaa ctttataata attaacaact  11820
tacagtaaac atgcttgtta tcctcctgct cgccacattt ttcgctctct ctcacgccag  11880
aacaagtatt gttggcgcag gttacaatgc aactcttcaa tctgcttaca tgccagattc  11940
cgaccagata ccccatatta cgtggtactt acaaacctcc aaacctaatt cttcatttta  12000
tgaaggaaac aaactctgcg atgactccga caacaggacg cacacatttc cccacccttc  12060
actacaattc gaatgcgtaa acaaaagctt gaagctttac aacttaaagc cttcagattc  12120
tggcttgtat catgctgtag ttgaaaaaag taatttagaa gtccacagtg attacattga  12180
attgatggtt gtggacctgc cacctccaaa atgtgaggtt tcctcctctt accttgaagt  12240
tcaaggcgtg gatgcctact gcctcataca cattaactgc agcaactcta aatatccagc  12300
tagaatttac tataatggac aggaaagtaa tctttttat tatttaacaa caagcgctgg  12360
taacggtaaa cagttacctg attattttac tgctgttgtt gaattttcca cctacagaga  12420
aacgtatgcc aagcggcctt acaatttctc atacccgttt aacgaccttt gcaatgaaat  12480
acaagcgctc gaaactggaa ctgattttac tccaattttc attgctgcca ttgttgtgag  12540
cttaattacc attattgtca gcctagcatt ttactgcttt tgcaagccca aaaaacctaa  12600
gtttgaaaaa cttaaactaa aacctgtcat tcaacaagtg tgattttgtt ttccagcatg  12660
gtagctgcat ttctacttct cctctgtcta cccatcattt tcgtctcttc aactttcgcc  12720
gcagtttccc acctggaacc agagtgccta ccgccttttg acgtgtatct gattctcacc  12780
tttgtttgtt gtatatccat ttgcagtata gcctgctttt ttataacaat ctttcaagcc  12840
gccgactatc tttacgtgcg aattgcttac tttagacacc atcctgaata cagaaatcaa  12900
aacgttgcct ccttactttg tttggcatga ttaagctatt gctaatactt aattatttac  12960
ccctaatcaa ctgtaattgt ccattcacca aaccctggtc attctacacc tgttatgata  13020
aaatccccga cactcctgtt gcttggcttt acgcagccac cgccgctttg gtatttgtat  13080
ctacttgcct tggagtaaaa ttgtatttta ttctacacac tgggtggcta catcccagag  13140
aagatttacc tagacatcct cttgtaaacg cttttcaatt acagcctctg cctcctcctg  13200
atcttcttcc tcgagctccc tctattgtga gctactttca actcaccggt ggagatgact  13260
gactctcagg acattaatat tagtgtggaa agaatagctg ctcagcgtca gcgagaaacg  13320
cgagtgttgg aatacctgga actacaacag cttaaggagt cccactggtg tgagaaagga  13380
gtgctgtgtc atgttaagca ggcagccctt tcctacgatg tcagcgttca gggacatgaa  13440
ctgtcttaca ctttgccttt gcagaaacaa accttctgca ccatgatggg ctctacctcc  13500
atcacaatca cccaacaagc cgggcctgta gagggggcta tcctctgtca ctgtcacgca  13560
cctgattgca tgtccaaact aatcaaaact ctctgtgctt taggtgatat ttttaaaatg  13620
taaatcataa taaacttacc ttaaatttga caacaatttt ctggtgacat cattcagcag  13680
caccacttta ccctcttccc agctctcgta tgggatgcga tagtgggtgg caaacttcct  13740
ccaaacccta aaagaaatat tggtatccac ttccttgtcc tcacccacaa ttttcatctt  13800
ttcatagatg aaaagaacca gagttgatga agacttcaac cccgtctacc cctatgacac  13860
cacaaccact cctgcagttc cctttatatc acccccccttt gtaaacagcg atggtcttca  13920
ggaaaacccc ccaggtgttt taagtctgcg aatagctaaa cccctatatt tcgacatgga  13980
gagaaaacta gccctttcac ttggaagagg gttgacaatt accgccgccg gacaattaga  14040
aagtacgcag agcgtacaaa ccaacccacc gttgataatt accaacaaca acacactgac  14100
cctacgtcat tctcccccct taaacctaac tgacaatagc ttagtgctag gctactcgag  14160
tccgctccgc gtcacagaca acaaacttac atttaacttc acatcaccac tccgttatga  14220
aaatgaaaac cttactttta actatacaga gcctcttaaa cttataaata acagccttgc  14280
cattgacatc aattcctcaa aaggccttag tagcgtcgga ggctcactag ctgtaaacct  14340
gagttcagac ttaaagtttg acagcaacgg atccatagct tttggcatac aaaccctgtg  14400
gaccgctccg acctcgactg gcaactgcac cgtctacagc gagggcgatt ccctacttag  14460
tctctgttta accaaatgcg gagctcacgt cttaggaagt gtaagtttaa ccggtttaac  14520
aggaaccata acccaaatga ctgatatttc tgtcaccatt caatttacat ttgacaacaa  14580
tggtaagcta ctaagctctc cgcttataaa caacgccttt agtattcgac agaatgacag  14640
tacggcctca aaccctacct acaacgccct ggcgtttatg cctaacagta ccatatatgc  14700
aagaggggga ggtggtgaac cacgaaacaa ctactacgtc caaacgtatc ttaggggaaa  14760
tgttcaaaaa ccaatcattc ttactgtaac ctacaactca gccgccacag gatattcctt  14820
```

```
atcttttaag tggactgctc ttgcacgtga aaagtttgca accccaacaa cttcgttttg  14880
ctacattaca gaacaataaa accgtgtacc ccaccgtttc gtttttttca gatgaaacgg  14940
gcgagagttg atgaagactt caacccagtg tacccttatg acccccccaca tgctcccgtt  15000
atgcccttca ttactccacc ttttacctcc tcggatgggt tgcaggaaaa accacttgga  15060
gtgttaagtt taaactacag agatcccatt actacgcaaa atgggtctct tacagttaaa  15120
ctaggaaacg gcctcactct agacaaccag ggacaactaa catcaaccgc tggggaagta  15180
gaacctccac tcactaacgc taacaacaaa cttgcactgg tctatagcga tcctttagca  15240
gtaaagcgca acagcctaac cttatcgcac accgctcccc ttgttattgc tgataactct  15300
ttagcattgc aagtttcaga gcctattttt ataaatgaca aggacaaact agccctgcaa  15360
acagccgcgc cccttgtaac taacgctggc acccttcgct tacaaagcgc cgccccttta  15420
ggcattgcag accaaaccct aaaactcctg tttaccaacc ctttgtactt gcagaataac  15480
tttctcacgt tagccattga acgacccctt gccattacca atagtggaaa gctggctcta  15540
cagctctccc caccgctaca aacagcagac acaggcttga ctttgcaaac caacgtgcca  15600
ttaactgtaa gcaacgggac cctaggctta gccataaagc gcccacttat tgttcaggac  15660
aacaacttgt ttttggactt cagagctccc ctgcgtcttt tcaacagcga ccccgtacta  15720
gggcttaact tttacacccc tcttgcagtg cgcgatgagg cgctcactgt taacacaggc  15780
cgcggcctca cagtgagtta cgatggttta attttaaatc ttggtaagga tcttcgcttt  15840
gacaacaaca ccgtttctgt cgctcttagt gctgctttgc ctttacaata cactgatcag  15900
cttcgcctta acgtgggcgc tgggctgcgt tacaatccag tgagtaaaaa attggacgtg  15960
aaccccaatc aaaacaaggg tttaacctgg gaaaatgact acctcattgt aaagctagga  16020
aatggattag gttttgatgg caatggaaac atagctgttt ctcctcaagt tacatcgcct  16080
gacaccttat ggaccactgc cgatccatcc cccaattgtt ccatctacac tgatttagat  16140
gccaaaatgt ggctctcgtt ggtaaaacaa gggggtgtgg ttcacggttc tgttgcttta  16200
aaagcattga aaggaaccct attgagtcct acggaaagtg ccattgttat tatactacat  16260
tttgacaatt atggagtgcg aattctcaat tatcccactt tgggcactca aggcacgttg  16320
ggaaataatg caacttgggg ttataggcag ggagaatctg cagacactaa tgtactcaat  16380
gcactagcat ttatgcccag ttcaaaaagg tacccaagag ggcgtggaag cgaagttcag  16440
aatcaaactg tgggctacac ttgtatacag ggtgaccttt ctatgcccgt accgtaccaa  16500
atacagtaca actatggacc aactggctac tcctttaaat ttatttggag aactgtttca  16560
agacaaccat ttgacatccc atgctgtttt ttctcttaca ttacggaaga ataaaacaac  16620
ttttcctttt tattttcttt ttattttaca cgcacagtaa ggcttcctcc acccttccat  16680
ttgacagcat acaccagcct ctccccccttc atggcagtaa actgctgcga gccagtccgg  16740
tatttgggag ttaagatcca aacagtctct ttggtaatca gatgtcgatc cgtgatggac  16800
acaaatccct ggggcaggtt ctccaacgtt tcggtgaaaa actgcatgcc gccctacaaa  16860
acaaacaggt tcaggctctc cacgggttat ctccccgatc aaactcagac agggtaaagg  16920
tgcgatgatg ttccactaaa ccacgcaggt ggcgctgtct gaacctctcg gtgcgactcc  16980
tgtgaggctg gtaagaagtt agattgtcca gcagcctcac agcatggatc atcagtctac  17040
gagtgcgtct ggcgcagcag cgcatctgaa tctcactgag attccggcaa gaatcgcaca  17100
ccatcacaat caggttgttc atgatcccat agctgaacac gctccagcca aagctcattc  17160
gctccaacag cgccaccgcg tgtccgtcca accttacttt aacataaatc aggtgtctgc  17220
cgcgtacaaa catgctaccc gcatacagaa cctcccgggg cagtcccctg ttcaccacct  17280
gcctgtacca gggaaacctc acatttatca gggagccata gatagccatc ttaaaccaat  17340
tagctaacac cgccccacca gctctacact gaagagaacc gggagagtta caatgacagt  17400
gaataatcca tctctcataa cccctaatgg tctgatggaa atccagatct aacgtggcac  17460
agcagataca cactttcata tacattttca tcacatgttt ttcccaggcc gttaaaatac  17520
aatcccaata cacgggccac tcctgcagta caataaagct aatacaagat ggtatactcc  17580
tcacctcact aacattgtgc atgttcatat tttcacattc taagtaccga gagctctcct  17640
ctacaacagc actgccgcgg tcctcacaag gtggtagctg gtgacaattg tagggagcca  17700
gtctgcagcg ataccgtctg tcgcgttgca tcgtagacca gggaccgacg cacttcctcg  17760
tacttgtagt agcagaacca cgtccgctgc cagcacgtct ccaagtaacg ccggtccctg  17820
cgtcgctcac gctccctcct caacgcaaag tgcaaccact cttgtaatcc acacagatcc  17880
ctctcggcct ccggggcgat gcacacctca aacctacaga tgtctcggta cagttccaaa  17940
cacgtagtga gggcgagttc caaccaagac agacagcctg atctatcccg acacactgga  18000
ggtggaggaa gacacggaag aggcatgtta ttccaagcga ttcaccaacg ggtcgaaatg  18060
aagatcccga agatgacaac ggtcgcctcc ggagccctga tggaatttaa cagccagatc  18120
aaacattatg cgattttcca ggctatcaat cgcggcctcc aaaagagcct ggacccgcac  18180
ttccacaaac accagcaaag caaaagcgtt attatcaaac tcttcgatca tcaagctgca  18240
ggactgtaca atgcccaagt aattttcatt tctccactcg cgaatgatgt cgcggcaaat  18300
agtctgaagg ttcatgccgt gcatattaaa aagctccgaa agggcgccct ctatagccat  18360
gcgtagacac accatcatga ctgcaagata tcgggctcct gagacacctg cagcagattt  18420
aacagaccca ggtcaggttg ctctccgcga tcgcgaatct ccatccgcaa ggtcatttgc  18480
aaataattaa atagatctgc gccgactaaa tctgttaact ccgcgctagg aactaaatca  18540
ggtgtggcta tgcagcacaa aagttccagg gatggcgcca aactcactag aaccgctccc  18600
gagtagcaaa actgatgaat gggagtaaca cagtgtaaaa tgttcagcca aaaatcacta  18660
agctgctcct ttaaaaagtc cagtacttct atattcagtc cgtgcaagta ctgaagcaac  18720
tgtgcgggaa tatgcacagc aaaaaaaata gggcggctca gatacatgtt gacctaaaat  18780
aaaaataaac attaaactaa agaagcttgg cgaacggtgg gatatatgac acgctccagc  18840
agcaggcaag caaccggctg tccccgggaa ccgcggtaaa attcatccga atgattaaaa  18900
agaacaacag aaacttccca ccatgtactc ggttggatct cctgagcaca cagcaatacc  18960
cccctcacat tcatatccgc cacagaaaaa aaacgtccca gatacccagt gggaatatcc  19020
aacgacagct gcaaagacag caaaataatc cctctgggag caagcacaaa atcctccggt  19080
gaaaaaagaa catacatatt agaataaccc tgttgctggg gcaaaaaggc ccgacgtccc  19140
agcaaatgca catatatgtg ttgatcagcc attgccccgt cttaccgcgt ataaagccac  19200
gaaaaagtcg agctaaaatc cacccaacag cctatagcta tatatacact ccgcccaatg  19260
acgctaacac cgtaccaccc acgaccaaag ttcacccaca cccacaaaac ccgcgaaaat  19320
ccagcgccgt cagcacttcc gcaatttcag tctcacaacg tcacttccgc gcgccttttt  19380
tcactattcc cacacccgcc ctcgcgccac cccgcgtcac cccgcgtcac cgcacgtcac  19440
cccggccccg cctcgctcct ccccgctcat tatcatattg gcacgtttcc agaataaggt  19500
atattattga tgatgttaat taattcgaac ccataatacc cataatagct gtttgccatc  19560
```

```
gacgcgaggc tggatggcct tccccattat gattcttctc gcttccggcg gcatcgggat  19620
gcccgcgttg caggccatgc tgtccaggca ggtagatgac gaccatcagg gacagcttca  19680
aggatcgctc gcggctctta ccagcccagc aaaaggccag gaaccgtaaa aaggccgcgt  19740
tgctggcgtt tttccatagg ctccgccccc ctgacgagca tcacaaaaat cgacgctcaa  19800
gtcagaggtg gcgaaacccg acaggactat aaagatacca ggcgtttccc cctggaagct  19860
ccctcgtgcg ctctcctgtt ccgaccctgc cgcttaccgg atacctgtcc gcctttctcc  19920
cttcgggaag cgtggcgctt tctcatagct cacgctgtag gtatctcagt tcggtgtagg  19980
tcgttcgctc caagctgggc tgtgtgcacg aaccccccgt tcagcccgac cgctgcgcct  20040
tatccggtaa ctatcgtctt gagtccaacc cggtaagaca cgacttatcg ccactggcag  20100
cagccactgg taacaggatt agcagagcga ggtatgtagg cggtgctaca gagttcttga  20160
agtggtggcc taactacggc tacactagaa ggacagtatt tggtatctgc gctctgctga  20220
agccagttac cttcggaaaa agagttggta gctcttgatc cggcaaacaa accaccgctg  20280
gtagcggtgg tttttttgtt tgcaagcagc agattacgcg cagaaaaaaa ggatctcaag  20340
aagatccttt gatcttttct acggggtctg acgctcagtg gaacgaaaac tcacgttaag  20400
ggattttggt catgagatta tcaaaaagga tcttcaccta gatcctttta aattaaaaat  20460
gaagttttaa atcaatctaa agtatatatg agtaaacttg gtctgacagt taccaatgct  20520
taatcagtga ggcacctatc tcagcgatct gtctatttcg ttcatccata gttgcctgac  20580
tccccgtcgt gtagataact acgatacggg agggcttacc atctggcccc agtgctgcaa  20640
tgataccgcg agacccacgc tcaccggctc cagatttatc agcaataaac cagccagccg  20700
gaagggccga gcgcagaagt ggtcctgcaa ctttatccgc ctccatccag tctattaatt  20760
gttgccggga agctagagta agtagttcgc cagttaatag tttgcgcaac gttgttgcca  20820
ttgctgcagg catcgtggtg tcacgctcgt cgtttggtat ggcttcattc agctccggtt  20880
cccaacgatc aaggcgagtt acatgatccc ccatgttgtg caaaaaagcg gttagctcct  20940
tcggtcctcc gatcgttgtc agaagtaagt tggccgcagt gttatcactc atggttatgg  21000
cagcactgca taattctctt actgtcatgc catccgtaag atgcttttct gtgactggtg  21060
agtactcaac caagtcattc tgagaatagt gtatgcggcg accgagttgc tcttgcccgg  21120
cgtcaacacg ggataatacc gcgccacata gcagaacttt aaaagtgctc atcattggaa  21180
aacgttcttc ggggcgaaaa ctctcaagga tcttaccgct gttgagatcc agttcgatgt  21240
aacccactcg tgcacccaac tgatcttcag catcttttac tttcaccagc gtttctgggt  21300
gagcaaaaac aggaaggcaa aatgccgcaa aaaagggaat aagggcgaca cggaaatgtt  21360
gaatactcat actcttcctt tttcaatatt attgaagcat ttatcagggt tattgtctca  21420
tgagcggata catatttgaa tgtatttaga aaaataaaca aataggggtt ccgcgcacat  21480
ttccccgaaa agtgccacct gacgtctaag aaaccattat tatcatgaca ttaacctata  21540
aaaataggcg tatcacgagg ccctttcgtc ttcaagaatt ggtcgatggc aaacagctat  21600
tatgggtatt atgggttcga attaat                                       21626
```

```
SEQ ID NO: 43          moltype = DNA  length = 19593
FEATURE                Location/Qualifiers
source                 1..19593
                       mol_type = other DNA
                       note = Synthetic oligonucleotide pBr/sAd4310A.RsrII-rITR.dE3
                       organism = synthetic construct
SEQUENCE: 43
attaacaccg tggattccgt gatcgacagc gtggtggcca gcgccagggc ctatgctcgc  60
cgcaagaggc ggctgcatcg gaaacgtcgc cccaccgccg ccatgctagc agccagggcc  120
gtgctgaggc gggcccggag ggtaggcagg agggctatgc gccgcgctgc cgccaacgcc  180
gccgggaggg cccgcagaca agccgcccgc caggccgccg ctgccatcgc tagcatggcc  240
agacccagga gagggaacgt gtactgggtg cgcgattctg taacgggagt ccgagtgccg  300
gtgcgcagcc gacctccccg aagttagaag atccaagctg cgaagacggc ggtactgagt  360
ctccctgttg ttattagccc aacatgagca agcgcaagtt taaagaagaa ctgctgcaga  420
cgctggtgcc tgagatctat ggccctccgg acgtgaagcc tgacattaag ccccgcgata  480
tcaagcgtgt taaaaagcgg gaaaaaaaag aggaacttgc ggcggtagac gatggcggtg  540
tagaatttat taggagtttc gccccacggc gcagggttca atggaaaggg cggcgtgtac  600
aacgcgttct gaggccgggc accgcggtag tttttacccc gggagagcgg tcggccgtta  660
ggggtttcaa gcggcagtac gatgaggtgt acggcgacga agacatactg gaacaggcgg  720
ctcagcagat tggagaattc gcttatggca aacgttctcg gcgcgaagac ctggccatcg  780
ccttggacag cggcaatccc acacccagcc tcaaacccgt gacgctgcaa caggtgcttc  840
ccgtgagcgc cagtactgac agcaaaaggg ggattaaaag agagatggaa gagctgcaac  900
ccaccatcca acttatggtc cctaaacgac agaggttgga agaggtcctg gagaagatga  960
aagtggaccc cagcatagag ccggatgtga aagtgaggcc tattaaggaa gtggcccccg  1020
gtcttggggt gcaaacggtg gacattcaaa tccccgtcac gtccgcttca acagcggtgg  1080
aagccatgga aacgcaaacg gaagcccccg ccgtcacggt cggtaccagg gaagtggcgt  1140
tgcaaacgga accctggtac gaatacgcca cccctaggcg tcagaggcgg tccgcccgtt  1200
acggacccgt caacgccatc atgcccgagt acgcgctaca tccgtctatc cggcccactc  1260
ccggctaccg gggagtgacg tatcgcccgt caggaactcg ccgccgttac cgtcgccgcc  1320
gtcgctctcg ccgcgctctg gccccagtgt cggtgcggcg cgtgacccgc caggggaaaa  1380
cagtcaccat ccccaacccg cgctaccacc ctagcattct ttaatgactc tgccgttttg  1440
cagatggctc tgacttgccg cgtgcgcctt cccgttctgc actatcgagg aagatctcgt  1500
cgtaggagag gcatggcggg cagtggtcgc cggcgggctt tgcgcaggcg catgaaaggc  1560
ggaattttac ccgccctaat acctataatc gccgccgcca taggcgccat acccggcgtc  1620
gcttcagtgg ccttgcaagc agctcgtaat aaataaacga aggcttttgc acttatgtcc  1680
tggtcctgac tattttatgc agaaaaagca tggaagacat caattttacg tcgctggctc  1740
cgcggcaagg ctcgcggccg ctcatgggca cctggaacga catcggcacc agtcagctca  1800
acgggggcgc tttcaattgg gggagccttt ggagcggcat taaaaacttt ggctccacga  1860
ttaaatccta cggcagcaaa gcctggaaca gtagtgctgg tcaaatgctc cgagataaac  1920
tgaaggacac caacttccaa gagaaagtgg tcaacggggt ggtgaccggc atacacggcg  1980
cggtagatct tgccaaccaa gcggtgcaga aagagattga caggcgattg gaaaactcgc  2040
gggtgccgcc gcagagaggg gatgaggtgg aggtcgagga agtagaagta gaggaaaagc  2100
tgcccccctt ggagaaagtt cccggtgcga ttccaaggcc gcagaagcgg ccaaggccag  2160
```

-continued

```
aactagaaga aactctggtg acggagagca aggagcctcc ctcgtacgag caagccttaa  2220
aagagggcgc ttcaccctac ccgatgacca aaccgatcgc gcctatggct cggccggtgt  2280
acgggaagga ctacaaacct gtcacgctag aacttcctcc gccactccct tcgcgtccta  2340
cggtgcctcc catgccagcg ccgtcggccg gtcccgtgtc tgcaccttcc gcagcgcctc  2400
tgccagccgc ccgcccagtg gccgtggcca ctgccagaaa ccccagaggc cagagaggag  2460
ccaactggca aaacacgctg aacagcatcg tgggcctggg agttaaaagc ctgaaacgcc  2520
gccgttgcta ttattaaaaa agtgtagcta aaaaatctcc cgttgtatac gcctcctatg  2580
ttaccgccag agacgtgtga ctgtcgtcgc gagcagcgct ttcaagatgg ccaccccatc  2640
gatgatgccg cagtggtctt acatgcacat cgccgggcag gacgcctcgg agtatctgag  2700
ccccggtctt gtgcagtttg cccgcgccac cgacacctac ttcagcttgg gaaacaagtt  2760
tagaaatccc accgtggccc ccacgcacga tgtgaccacg gatcgttcgc agaggctgac  2820
tctgcgcttt gtaccggtag accgtgagga tactgcctat tcttacaaag ttcggtatac  2880
gttagccgta ggagacaaca gggtgctgga catggccagt acttactttg acatccgcgg  2940
tgttcttgac cgcggtccaa gctttaaacc gtataccgga acggcataca atgccttggc  3000
tccaaagggc gctccaaatg cttgccagtg gacaacgacc aacgggggca ataaaacgaa  3060
cacttttgcc caagcccctt taataggcac ggctattgac ggaaccaacg gactgcagat  3120
tgggcaagat aatggacaag ctgtttatgc tgacaaaacc tttcaacccg aaccacaagt  3180
gggagaatct cagtggaata ctaatccaac cacaaacgca gcaggacgcg tgttaaaaac  3240
aactactcgc atgctgcctt gctatggttc ttttgcaagg cccaccaatg agaaaggggg  3300
tcaagcttca ggagacgtta ccttccaatt tttcgacact gcctcggaca atggcaacaa  3360
ccctaaggtg gtgctatatg gagaagacgt caacattgaa tcgcctgaca cacacttaat  3420
ctacaaaccc accgctgaca acacaaactc tgaaaacctt ttgggtcaac aggccgctcc  3480
aaacagagcc aattacattg cctttcggga caacttcatt ggactaatgt actataattc  3540
aacaggaaac atgggagtgt tggcagggca ggcttcccaa ctaaatgctg tggtagactt  3600
gcaagacaga aacactgagc tttcctacca actcatgtta gatgcaatag gagaccggag  3660
tcgttacttt tcaatgtgga accaagcagt ggacagctat gatccagatg tgcgaattat  3720
tgaaaatcat ggcgttgagg acgaactgcc aaattactgc ttccctctta acgctcaagg  3780
aattgctaac acctataaag gcgttaagaa aaacaacggc aattgggcga aagacgacgc  3840
agtagtagaa actaacgaaa ttggcatagg aaatgttttt gccatggaga taaatttaac  3900
tgctaacttg tggcgaaact ttctgtattc caatattgct ttgtacctgc cagactccta  3960
caagtattca ccgggaaaca taaccttacc cgaaaacaaa aacagttaca attacattaa  4020
tggtcgagta acagctcctg gtctggtaga cacctttgta aacattggcg cgcgatggtc  4080
tcccgacccc atggacaacg tgaatccttt taatcaccat cgcaatgctg gtctgcgtta  4140
tcgctccatg cttctaggca acggccgcta cgtgcccttc cacattcagg tgcctcaaaa  4200
attctttgcc attaagaacc tgcttctgct gcctgggtcc tacacctacg agtggaactt  4260
cagaaaagat gtaaacatga tcttgcagag cacgctgggc aacgacctcc gtgtcgacgg  4320
ggccagcgtc agattcgaca gcattaacct ctacgctaat ttcttcccca tggcacataa  4380
caccgcttcc accctggagg ctatgttacg caacgacacc aacgaccagt cctttaatga  4440
ctacctctgc gcggccaaca tgctataccc cattcctgcc aatgccacca gtgtgcccat  4500
ctccatcccc tctcgcaact gggcagcttt cagagggtgg agtttcaccc gcctcaaaac  4560
aaaagaaacc ccctcgctgg gttccggatt tgatccatac tttgtttact caggctccat  4620
tccctacctg gatggtacct tctacctgaa ccacaccttc aaaaaggtgt ctattatgtt  4680
cgactcttct gtgagctggc ccggcaacga ccgcctgctg acccctaatg agtttgaaat  4740
taagcgctcg gtggacggag aaggatacaa tgtagcccag agcaacatga ccaaagactg  4800
gttcttaatt caaatgctca gccactacaa cattggttac caagggtttt acgtgcccga  4860
ggcttacaaa gacagaatgt actccttttt tagaaacttc caacctatga gtagacaggt  4920
agtggatgca gatcggtatg aacaatacaa aaaagtcacc gttgagtatc aacataataa  4980
ttctggtttt gtgggataca tgggacccac catgagggaa gggcaggctt atccagcgaa  5040
ttacccttat cctcttattg gagacaccgc cgtgcccagc ctgacccaga aaaagttcct  5100
ctgtgaccgc accatgtgga gaatcccctt ctctagcaac ttcatgtcta tgggggccct  5160
caccgacctg gggcagaaca tgctgtacgc caattccgct cacgccttgg atatgacctt  5220
tgaggtggac cccatggatg agcccacgct tctctatgtt ctgtttgaag tcttcgacgt  5280
ggtgcgcatc caccagccgc accgcggcgt catcgaggcc gtctacctgc gcacaccttt  5340
ctctgccggt aacgccacca cataagaagc aaatgggctc cagcgaacag gagctgcggg  5400
ccattattcg cgacctgggc tgcggaccct actttttggg caccttcgac aagcgtttcc  5460
ccggattcat gtccccccag aagccggcct gtgccatagt caacacggcc gggcgggaga  5520
ccgggggggt tcactggctc gccttcgcct ggaacccgcg caaccgcacc tgctacctgt  5580
tcgacccttt tggtttttcc gacgaaaggc tgaagcaaat ctaccagttc gaatacgaag  5640
gactcctcaa gcgcagcgct ctggcctcca cgcccgacca ctgcgtcacc ctggaaaaat  5700
ccacccaaac ggtgcagggg cccctctcgg ccgcctgcgg gcttttctgt tgcatgtttt  5760
tgcacgcctt cgtgcactgg cctcacaacc ccatggagcg caaccccacc atggatctgc  5820
tcaccggagt gcccaacagc atgcttcaca gcccccaggt cgcccccacc ctgcgccgta  5880
accaggaaca cctgtatcgc tttctgggga aacactctgc ctatttccgc cgccaccggc  5940
agcgcatcga gcaggccacg gcctttgaaa gcatgagcca aagagtgtaa tcaataaaaa  6000
ccatttttat ttaacatgat acgcgcttct ggcgttttta ttaaaaatcg aacggttcga  6060
gggaggggtc ctcgtgcccg ctgggaaggg acacgttgcg gtactggaaa cgggcgctcc  6120
aacgaaactc ggggatcacc agccgcggca ggggcacgtc ttctaggttc tgcttccaga  6180
actgccgcac cagctgcagg gctcccatga cgtcgggcgc cgagatcttg aagtcgcagt  6240
tagggccgga gcccccgcgg ctgttgcgga acacggggtt ggcacactgg aacaccagca  6300
cgctggggtt gtaaatactg gccagggccg ttgggtcggt cacctccgac gcatccagat  6360
cctcggcatt gctcagggcg aacggagtca gcttgcacat ctgccgtccg atctggggca  6420
ccaggtcggg tttgttgagg caatcgcagc gcagagggat taggatgcga cgctgcccgc  6480
gttgcatgat agggtaactc gccgccagga actcctccat ctgacggaag gccatctggg  6540
ccttggtacc ctcggtgaaa aatagcccac aggacttgct agaaaatacg ttattgccgc  6600
agttgatgtc ttccgcgcag cagcgtgcat cttcgttctt cagctgaacc acgttacgcc  6660
cccagcggtt ctggaccacc ttggctttcg taggatgctc cttcaacgcc cgctgaccgt  6720
tctcgctggt cacatccatt tccaccacgt gctccttgca gaccatctcc actccgtgga  6780
agcagaacag gacgccctcc tgctgggtat tgcgatgctc ccaaacggca catccggtgg  6840
gctcccagct cttgcgtttc acccccgcgt atgcttccat gtaagccatg aggaatctgc  6900
```

-continued

```
ccatcagctc ggtgaaggtc ttctggttgg tgaaggttag cggcaggccg cggtgctcct  6960
cgttcaacca agtttgacag attttgcggt acacggctcc ctggtcgggc agaaacttaa  7020
aagccgctct gctctcgttg tccacgtgga acttctccat caacatcgtc atgacttcca  7080
tgcccttctc ccacgccgtc accaacggtt cggtcccggg gttcttcacc aacacggcgg  7140
tggaggggcc ctcgccggcc ccgacgtcct tcatggtcat tctttggaac tccacggtgc  7200
cgtccgcgcg gcgtactctg cgcatcggag ggtagctgaa gcccacctcc accacggtgc  7260
cttcgccctc gctgtcggaa acgatctccg gggatggcgg cggcgcgggt gtcgccttgc  7320
gagccttctt cttgggaggg agcggaggca cctcctgctc gcgctcgggg ctcatctccc  7380
gcaagtaggg ggtaatggag cttccgggtt ggttctgacg gttggccatt gtatcctagg  7440
cagaaagaca tggatcttat gcgcgaggaa actttaaccg ccccgtcccc cgtcagcgac  7500
gaagaggtca tcgtcgaaca ggacccgggc tacgttacgc cgcccgagga tctggagtcc  7560
cccttagacg accgacgcga cgctagtgag cggcaggaaa atgagaaaga ggaggaggag  7620
ggctgctacc tcctggaagg cgacgtcttg ctaaagcatt tcgccaggca gagcaccata  7680
ctcaaggagg ccttgcaaga ccgctccgag gtgcccttgg acgtcgccgc gctctcccag  7740
gcctacgagg cgaacctttt ctcgccccga gtgcctccga agagacagcc caacggcacc  7800
tgcgagccca acccgcgact caacttctac cccgtgttcg ccgtgcccga ggcgctggcc  7860
acctaccaca tctttttcaa aaaccagcgc attccccttt cctgccgggc caaccgcacc  7920
gcagccgata ggaagctaac actcagaaac ggagccagca tacctgatat cacgtcactg  7980
gaggaagtgc ctaagatctt cgagggtctg ggtcgagatg agaagcgggc ggcgaacgct  8040
ctgcagaaag aacagaaaga gagtcagaac gtgctggtgg agctggaggg ggacaacgcg  8100
cgtctggccg tcctcaaacg ctgcatagaa gtctcccact tcgcctaccc cgccctcaac  8160
ttgccaccca aagttatgaa atcggtcatg gatcagctgc tcatcaagag agctgagccc  8220
ctggatcccg accaccccga ggcggaaaac tcagaggacg gaaagcccgt cgtcagcgac  8280
gaggagctcg agcggtggct ggaaaccggg gacccccaac agttgcaaga gaggcgcaag  8340
atgatgatgg cggccgtgct ggtcaccgtg gagctggaat gcctgcaacg gtttttcagc  8400
gacgtggaga cgctacgcaa aatcggggag tccctgcact acaccttccg ccagggctac  8460
gtccgccagg cctgcaagat ctccaacgtg gagctcagca acctggtctc ctacatgggc  8520
atcctccacg agaaccggct ggggcagagc gtgctgcact gcaccttgca aggcgaggcg  8580
cggcgggact acgtccgcga ctgcatctac ctcttcctca ccctcacctg gcagaccgcc  8640
atgggcgtct ggcagcagtg cttggaagag agaaacctca aagagctaga caaactcctc  8700
tgccgccagc ggcgggccct ctggaccggt ttcagcgagc gcacggtcgc ctgcgccctg  8760
gcagacatta tcttcccgga gcgcctgatg aaaaccttgc agaacggcct gccggatttt  8820
atcagtcaaa gtattttgca aaacttccgc tccttcgttc tggagcgctc cgggatcttg  8880
cccgccatga gctgcgcgct gccttctgac tttgtccccc tttcctaccg cgagtgtcct  8940
cccccccctgt ggagccactg ctacctcttc caactggcca actttctggc ctaccactcc  9000
gacctcatgg aagacgtgag cggagagggg ctgctcgagt gccactgccg ctgcaacctc  9060
tgcacccccc acagatcgct ggcctgcaac accgagctgc tcagcgaaac ccaggtcata  9120
ggtaccttcg agatccaggg gccccagcag caagagggtg cttccggctt gaagctcact  9180
ccggcgctgt ggacctcggc ttacttacgc aaatttgtag ccgaggacta ccacgcccac  9240
aaaattcagt tctatgaaga ccaatctcga ccacccaaag ccccccctcac ggcctgcgtc  9300
atcactcaga gcaaaatcct ggcccaattg caatccatca accaagcgcg ccgagatttc  9360
cttttgaaaa agggtcgggg ggtgtaccta gacccccaga ccggcgagga actcaacccg  9420
tccacactct ccgtcgaagc agcccccccg agacatgccg cccaagggaa ccgccaagca  9480
gctgatcgct cggcagagag cgaagaagca agagctgctc cagcagcagc agcaggtgga  9540
ggacgaggaa gagctgtggg acagccaggc agaggaggtg tcagaggacg aggaggagat  9600
ggaaagctgg gacagcctag acgaggagga ggacgagctt tcagaggaag aggcgaccga  9660
agaaaaacca cctgcatcca gcgcgccttc tctgagccga cagccgaagc cccggccccc  9720
gacgcccccg gccggctcac tcaaagccag ccgtaggtgg gacgccaccg gatctccagc  9780
ggcagcggca acggcagcgg gtaaggccaa acgcgagcgg cgggggtatt gctcctggcg  9840
ggcccacaaa agcagtatcg tgaactgctt gcaacactgc gggggaaaca tctcctttgc  9900
ccgacgctac ctcctcttcc atcacggtgt ggccttccct cgcaacgttc tctattatta  9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttccccctcg ggcgccaaaa  10320
cccacgtcat tgccagcatg agcaaggaga ttcccacccc ttacatgtgg agctatcagc  10380
cccagatggg cctggccgcg ggggccgccc aggactactc cagcaagatg aactggctca  10440
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
acggagtctt ccagctcgga ggagcgggcc gctcttcctt caccactcgc caggcctacc  10860
tgaccctgca gagctcttcc tcgcagccgc gctccggggg aatcggcact ctccagttcg  10920
tggaagagtt cgtcccctcc gtctacttca acccgttttc cggctcacct ggacgctacc  10980
cggacgcctt cattcccaac tttgacgcag tgagtgaatc cgtggacggc tacgactgat  11040
gacagatggt gcggccgtga gagctcggct gcgacatctg catcactgcc gccagcctcg  11100
ctgctacgct cgggaggcga tcgtgttcag ctactttgag ctgccggacg agcaccctca  11160
ggggccggct cacgggttga aactcgagat cgagaacgcg ctcgagtctc gcctcatcga  11220
cgccttcacc gcccggcctc tcctggtaga aaccgaacgc gggatcacta ccatcaccct  11280
gttctgcatc tgccccacgc ccggattaca tgaagatctg tgttgtcatc tttgcgctca  11340
gtttaataaa aactgaactg tttgccgcac cttcaacgcc atctgtgatt tctacaacaa  11400
aaagttcttc tggcaaaggt acacaaactg tattttattc taattctacc tcatctattg  11460
tgctgaactg cgcctgcact aacgaactta tcctgtagag ggggctatcc tctgtcactg  11520
tcacgcacct gattgcatgt ccaaactaat caaaactctc tgtgctttag gtgatatttt  11580
taaaatgtaa atcataataa acttacctta aatttgacaa caattttctg gtgacatcat  11640
```

-continued

```
tcagcagcac cactttaccc tcttcccagc tctcgtatgg gatgcgatag tgggtggcaa  11700
acttcctcca aaccctaaaa gaaatattgg tatccacttc cttgtcctca cccacaattt  11760
tcatcttttc atagatgaaa agaaccagag ttgatgaaga cttcaacccc gtctacccct  11820
atgacaccac aaccactcct gcagttccct ttatatcacc ccccttttgta aacagcgatg  11880
gtcttcagga aaacccccca ggtgttttaa gtctgcgaat agctaaaccc ctatatttcg  11940
acatggagag aaaactagcc ctttcacttg gaagagggtt gacaattacc gccgccggac  12000
aattagaaag tacgcagagc gtacaaacca acccaccgtt gataattacc aacaacaaca  12060
cactgaccct acgtcattct cccccttaa acctaactga caatagctta gtgctaggct  12120
actcgagtcc gctccgcgtc acagacaaca aacttacatt taacttcaca tcaccactcc  12180
gttatgaaaa tgaaaacctt acttttaact atacagagcc tcttaaactt ataaataaca  12240
gccttgccat tgacatcaat tcctcaaaag gccttagtag cgtcggaggc tcactagctg  12300
taaacctgag ttcagactta aagtttgaca gcaacggatc catagctttt ggcatacaaa  12360
ccctgtggac cgctccgacc tcgactggca actgcaccgt ctacagcgag ggcgattccc  12420
tacttagtct ctgtttaacc aaatgcggag ctcacgtctt aggaagtgta agtttaaccg  12480
gtttaacagg aaccataacc caaatgactg atatttctgt caccattcaa tttacatttg  12540
acaacaatgg taagctacta agctctccgc ttataaacaa cgcctttagt attcgacaga  12600
atgacagtac ggcctcaaac cctacctaca acgccctggc gtttatgcct aacagtacca  12660
tatatgcaag agggggaggt ggtgaaccac gaaacaacta ctacgtccaa acgtatctta  12720
ggggaaatgt tcaaaaacca atcattctta ctgtaaccta caactcagcc gccacaggat  12780
attccttatc ttttaagtgg actgctcttg cacgtgaaaa gtttgcaacc ccaacaactt  12840
cgttttgcta cattacagaa caataaaacc gtgtacccca ccgtttcgtt tttttcagat  12900
gaaacgggcg agagttgatg aagacttcaa cccagtgtac ccttatgacc ccccacatgc  12960
tcccgttatg cccttcatta ctccaccttt tacctcctcg gatgggttgc aggaaaaacc  13020
acttggagtg ttaagtttaa actacagaga tcccattact acgcaaaatg ggtctcttac  13080
agttaaacta ggaaacggcc tcactctaga caaccaggga caactaacat caaccgctgg  13140
ggaagtagaa cctccactca ctaacgctaa caacaaactt gcactggtct atagcgatcc  13200
tttagcagta aagcgcaaca gcctaacctt atcgcacacc gctccccttg ttattgctga  13260
taactcttta gcattgcaag tttcagagcc tatttttata aatgacaagg acaaactagc  13320
cctgcaaaca gccgcgcccc ttgtaactaa cgctggcacc cttcgcttac aaagcgccgc  13380
ccctttaggc attgcagacc aaaccctaaa actcctgttt accaaccctt tgtacttgca  13440
gaataacttt ctcacgttag ccattgaacg acccccttgcc attaccaata gtggaaagct  13500
ggctctacag ctctccccac cgctacaaac agcagacaca ggcttgactt tgcaaaccaa  13560
cgtgccatta actgtaagca acgggaccct aggcttagcc ataaagcgcc cacttattgt  13620
tcaggacaac aacttgtttt tggacttcag agctcccctg cgtcttttca acagcgaccc  13680
cgtactaggg cttaactttt acacccctct tgcagtgcgc gatgaggcgc tcactgttaa  13740
cacaggccgc ggcctcacag tgagttacga tggtttaatt ttaaatcttg gtaaggatct  13800
tcgctttgac aacaacaccg tttctgtcgc tcttagtgct gctttgcctt tacaatacac  13860
tgatcagctt cgccttaacg tgggcgctgg gctgcgttac aatccagtga gtaaaaaatt  13920
ggacgtgaac cccaatcaaa acaagggttt aacctgggaa aatgactacc tcattgtaaa  13980
gctaggaaat ggattaggtt ttgatggcaa tggaaacata gctgtttctc ctcaagttac  14040
atcgcctgac accttatgga ccactgccga tccatccccc aattgttcca tctacactga  14100
tttagatgcc aaaatgtggc tctcgttggt aaaacaaggg ggtgtggttc acggttctgt  14160
tgctttaaaa gcattgaaag gaaccctatt gagtcctacg gaaagtgcca ttgttattat  14220
actacatttt gacaattatg gagtgcgaat tctcaattat cccactttgg gcactcaagg  14280
cacgttggga aataatgcaa cttggggtta taggcaggga gaatctgcag acactaatgt  14340
actcaatgca ctagcattta tgcccagttc aaaaaggtac ccaagagggc gtggaagcga  14400
agttcagaat caaactgtgg gctacacttg tatacagggt gacctttcta tgcccgtacc  14460
gtaccaaata cagtacaact atggaccaac tggctactcc tttaaattta tttggagaac  14520
tgtttcaaga caaccatttg acatcccatg ctgtttttc tcttacatta cggaagaata  14580
aaacaacttt tccttttat tttcttttta ttttacacgc acagtaaggc ttcctccacc  14640
cttccatttg acagcataca ccagcctctc ccccttcatg gcagtaaact gctgcgagcc  14700
agtccggtat ttgggagtta agatccaaac agtctctttg gtaatcagat gtcgatccgt  14760
gatggacaca aatccctggg gcaggttctc caacgtttcg gtgaaaaact gcatgccgcc  14820
ctacaaaaca aacaggttca ggctctccac gggttatctc cccgatcaaa ctcagacagg  14880
gtaaaggtgc gatgatgttc cactaaacca cgcaggtggc gctgtctgaa cctctcggtg  14940
cgactcctgt gaggctggta agaagttaga ttgtccagca gcctcacagc atggatcatc  15000
agtctacgag tgcgtctggc gcagcagcgc atctgaatct cactgagatt ccggcaagaa  15060
tcgcacacca tcacaatcag gttgttcatg atcccatagc tgaacacgct ccagccaaag  15120
ctcattcgct ccaacagcgc caccgcgtgt ccgtccaacc ttactttaac ataaatcagg  15180
tgtctgccgc gtacaaacat gctacccgca tacagaacct cccggggcag tcccctgttc  15240
accacctgcc tgtaccaggg aaacctcaca tttatcaggg agccatagat agccatctta  15300
aaccaattag ctaacaccgc cccaccagct ctacactgaa gagaaccggg agagttacaa  15360
tgacagtgaa taatccatct ctcataaccc ctaatggtct gatggaaatc cagatctaac  15420
gtggcacagc agatacacac tttcatatac attttcatca catgtttttc ccaggccgtt  15480
aaaatacaat cccaatacac gggccactcc tgcagtacaa taaagctaat acaagatggt  15540
atactcctca cctcactaac attgtgcatg ttcatatttt cacattctaa gtaccgagag  15600
ctctcctcta caacagcact gccgcggtcc tcacaaggtg gtagctggtg acaattgtag  15660
ggagccagtc tgcagcgata ccgtctgtcg cgttgcatcg tagaccaggg accgacgcac  15720
ttcctcgtac ttgtagtagc agaaccacgt ccgctgccag cacgtctcca agtaacgccg  15780
gtccctgcgt cgctcacgct ccctcctcaa cgcaaagtgc aaccactctt gtaatccaca  15840
cagatccctc tcggcctccg gggcgatgca cacctcaaac ctacagatgt ctcggtacag  15900
ttccaaacac gtagtgaggg cgagttccaa ccaagacaga cagcctgatc tatcccgaca  15960
cactggaggt ggaggaagac acggaagagg catgttattc caagcgattc accaacgggt  16020
cgaaatgaag atcccgaaga tgacaacggt cgcctccgga gccctgatgg aatttaacag  16080
ccagatcaaa cattatgcga ttttccaggc tatcaatcgc ggcctccaaa agagcctgga  16140
cccgcacttc cacaaacacc agcaaagcaa aagcgttatt atcaaactct tcgatcatca  16200
agctgcagga ctgtacaatg cccaagtaat tttcatttct ccactcgcga atgatgtcgc  16260
ggcaaatagt ctgaaggttc atgccgtgca tattaaaaag ctccgaaagg gcgccctcta  16320
tagccatgcg tagacacacc atcatgactg caagatatcg ggctcctgag acacctgcag  16380
```

```
cagatttaac agacccaggt caggttgctc tccgcgatcg cgaatctcca tccgcaaggt  16440
catttgcaaa taattaaata gatctgcgcc gactaaatct gttaactccg cgctaggaac  16500
taaatcaggt gtggctatgc agcacaaaag ttccagggat ggcgccaaac tcactagaac  16560
cgctcccgag tagcaaaact gatgaatggg agtaacacag tgtaaaatgt tcagccaaaa  16620
atcactaagc tgctccttta aaaagtccag tacttctata ttcagtccgt gcaagtactg  16680
aagcaactgt gcgggaatat gcacagcaaa aaaaataggg cggctcagat acatgttgac  16740
ctaaaataaa aataaacatt aaactaaaga agcttggcga acggtgggat atatgacacg  16800
ctccagcagc aggcaagcaa ccggctgtcc ccgggaaccg cggtaaaatt catccgaatg  16860
attaaaaaga acaacagaaa cttcccacca tgtactcggt tggatctcct gagcacacag  16920
caataccccc ctcacattca tatccgccac agaaaaaaaa cgtcccagat acccagtggg  16980
aatatccaac gacagctgca aagacagcaa aataatccct ctgggagcaa gcacaaaatc  17040
ctccggtgaa aaaagaacat acatattaga ataaccctgt tgctggggca aaaaggcccg  17100
acgtcccagc aaatgcacat atatgtgttg atcagccatt gccccgtctt accgcgtata  17160
aagccacgaa aaagtcgagc taaaatccac ccaacagcct atagctatat atacactccg  17220
cccaatgacg ctaacaccgt accacccacg accaaagttc acccacaccc acaaaacccg  17280
cgaaaatcca gcgccgtcag cacttccgca atttcagtct cacaacgtca cttccgcgcg  17340
cctttttca ctattcccac acccgccctc gcgccacccc gcgtcacccc gcgtcaccgc  17400
acgtcacccc ggccccgcct cgctcctccc cgctcattat catattggca cgtttccaga  17460
ataaggtata ttattgatga tgttaattaa ttcgaaccca taatacccat aatagctgtt  17520
tgccatcgac gcgaggctgg atggccttcc ccattatgat tcttctcgct tccggcggca  17580
tcgggatgcc cgcgttgcag gccatgctgt ccaggcaggt agatgacgac catcagggac  17640
agcttcaagg atcgctcgcg gctcttacca gcccagcaaa aggccaggaa ccgtaaaaag  17700
gccgcgttgc tggcgttttt ccataggctc cgcccccctg acgagcatca caaaaatcga  17760
cgctcaagtc agaggtggcg aaacccgaca ggactataaa gataccaggc gtttccccct  17820
ggaagctccc tcgtgcgctc tcctgttccg accctgccgc ttaccggata cctgtccgcc  17880
tttctccctt cgggaagcgt ggcgctttct catagctcac gctgtaggta tctcagttcg  17940
gtgtaggtcg ttcgctccaa gctgggctgt gtgcacgaac cccccgttca gcccgaccgc  18000
tgcgccttat ccggtaacta tcgtcttgag tccaacccgg taagacacga cttatcgcca  18060
ctggcagcag ccactggtaa caggattagc agagcgaggt atgtaggcgg tgctacagag  18120
ttcttgaagt ggtggcctaa ctacggctac actagaagga cagtatttgg tatctgcgct  18180
ctgctgaagc cagttacctt cggaaaaaga gttggtagct cttgatccgg caaacaaacc  18240
accgctggta gcggtggttt ttttgtttgc aagcagcaga ttacgcgcag aaaaaaagga  18300
tctcaagaag atcctttgat cttttctacg gggtctgacg ctcagtggaa cgaaaactca  18360
cgttaaggga ttttggtcat gagattatca aaaaggatct tcacctagat ccttttaaat  18420
taaaaatgaa gttttaaatc aatctaaagt atatatgagt aaacttggtc tgacagttac  18480
caatgcttaa tcagtgaggc acctatctca gcgatctgtc tatttcgttc atccatagtt  18540
gcctgactcc ccgtcgtgta gataactacg atacgggagg gcttaccatc tggccccagt  18600
gctgcaatga taccgcgaga cccacgctca ccggctccag atttatcagc aataaaccag  18660
ccagccggaa gggccgagcg cagaagtggt cctgcaactt tatccgcctc catccagtct  18720
attaattgtt gccgggaagc tagagtaagt agttcgccag ttaatagttt gcgcaacgtt  18780
gttgccattg ctgcaggcat cgtggtgtca cgctcgtcgt ttggtatggc ttcattcagc  18840
tccggttccc aacgatcaag gcgagttaca tgatccccca tgttgtgcaa aaaagcggtt  18900
agctccttcg gtcctccgat cgttgtcaga agtaagttgg ccgcagtgtt atcactcatg  18960
gttatggcag cactgcataa ttctcttact gtcatgccat ccgtaagatg cttttctgtg  19020
actggtgagt actcaaccaa gtcattctga gaatagtgta tgcggcgacc gagttgctct  19080
tgcccggcgt caacacggga taataccgcg ccacatagca gaactttaaa agtgctcatc  19140
attggaaaac gttcttcggg gcgaaaactc tcaaggatct taccgctgtt gagatccagt  19200
tcgatgtaac ccactcgtgc acccaactga tcttcagcat cttttacttt caccagcgtt  19260
tctgggtgag caaaaacagg aaggcaaaat gccgcaaaaa agggaataag ggcgacacgg  19320
aaatgttgaa tactcatact cttcctttt caatattatt gaagcattta tcagggttat  19380
tgtctcatga gcggatacat atttgaatgt atttagaaaa ataaacaaat aggggttccg  19440
cgcacatttc cccgaaaagt gccacctgac gtctaagaaa ccattattat catgacatta  19500
acctataaaa ataggcgtat cacgaggccc tttcgtcttc aagaattggt cgatggcaaa  19560
cagctattat gggtattatg ggttcgaatt aat                               19593
```

```
SEQ ID NO: 44          moltype = DNA  length = 18199
FEATURE                Location/Qualifiers
source                 1..18199
                       mol_type = other DNA
                       note = Synthetic oligonucleotide
                        pBr/sAd4310A.RsrII-rITR.dE3.dE4
                       organism = synthetic construct
SEQUENCE: 44
attaacaccg tggattccgt gatcgacagc gtggtggcca gcgccagggc ctatgctcgc  60
cgcaagaggc ggctgcatcg gaaacgtcgc cccaccgccg ccatgctagc agccagggcc  120
gtgctgaggc gggcccggag ggtaggcagg agggctatgc gccgcgctgc cgccaacgcc  180
gccgggaggg cccgcagaca agccgcccgc caggccgccg ctgccatcgc tagcatggcc  240
agacccagga gagggaacgt gtactgggtg cgcgattctg taacgggagt ccgagtgccg  300
gtgcgcagcc gacctccccg aagttagaag atccaagctg cgaagacggc ggtactgagt  360
ctccctgttg ttattagccc aacatgagca agcgcaagtt taaagaagaa ctgctgcaga  420
cgctggtgcc tgagatctat ggccctccgg acgtgaagcc tgacattaag ccccgcgata  480
tcaagcgtgt taaaaagcgg gaaaaaaaag aggaacttgc ggcggtagac gatggcggtg  540
tagaatttat taggagtttc gccccacggc gcagggttca atggaaaggg cggcgtgtac  600
aacgcgttct gaggccgggc accgcggtag tttttacccc gggagagcgg tcggccgtta  660
ggggtttcaa gcggcagtac gatgaggtgt acggcgacga agacatactg gaacaggcgg  720
ctcagcagat tggagaattc gcttatggca aacgttctcg gcgcgaagac ctggccatcg  780
ccttggacag cggcaatccc acacccagcc tcaaacccgt gacgctgcaa caggtgcttc  840
ccgtgagcgc cagtactgac agcaaaaggg ggattaaaag agagatggaa gagctgcaac  900
ccaccatcca acttatggtc cctaaacgac agaggttgga agaggtcctg gagaagatga  960
```

-continued

```
aagtggaccc cagcatagag ccggatgtga aagtgaggcc tattaaggaa gtggcccccg  1020
gtcttggggt gcaaacggtg gacattcaaa tccccgtcac gtccgcttca acagcggtgg  1080
aagccatgga aacgcaaacg gaagcccccg ccgtcacggt cggtaccagg gaagtggcgt  1140
tgcaaacgga accctggtac gaatacgcca cccctaggcg tcagaggcgg tccgcccgtt  1200
acggacccgt caacgccatc atgcccgagt acgcgctaca tccgtctatc cggcccactc  1260
ccggctaccg gggagtgacg tatcgcccgt caggaactcg ccgccgttac cgtcgccgcc  1320
gtcgctctcg ccgcgctctg gccccagtgt cggtgcggcg cgtgacccgc caggggaaaa  1380
cagtcaccat ccccaacccg cgctaccacc ctagcattct ttaatgactc tgccgttttg  1440
cagatggctc tgacttgccg cgtgcgcctt cccgttctgc actatcgagg aagatctcgt  1500
cgtaggagag gcatggcggg cagtggtcgc cggcgggctt tgcgcaggcg catgaaaggc  1560
ggaattttac ccgccctaat acctataatc gccgccgcca taggcgccat acccggcgtc  1620
gcttcagtgg ccttgcaagc agctcgtaat aaataaacga aggcttttgc acttatgtcc  1680
tggtcctgac tattttatgc agaaaaagca tggaagacat caattttacg tcgctggctc  1740
cgcggcaagg ctcgcggccg ctcatgggca cctggaacga catcggcacc agtcagctca  1800
acgggggcgc tttcaattgg gggagccttt ggagcggcat taaaaacttt ggctccacga  1860
ttaaatccta cggcagcaaa gcctggaaca gtagtgctgg tcaaatgctc cgagataaac  1920
tgaaggacac caacttccaa gagaaagtgg tcaacggggt ggtgaccggc atacacggcg  1980
cggtagatct tgccaaccaa gcggtgcaga aagagattga caggcgattg gaaaactcgc  2040
gggtgccgcc gcagagaggg gatgaggtgg aggtcgagga agtagaagta gaggaaaagc  2100
tgcccccctt ggagaaagtt cccggtgcga ttccaaggcc gcagaagcgg ccaaggccag  2160
aactagaaga aactctggtg acggagagca aggagcctcc ctcgtacgag caagccttaa  2220
aagagggcgc ttcaccctac ccgatgacca aaccgatcgc gcctatggct cggccggtgt  2280
acgggaagga ctacaaacct gtcacgctag aacttcctcc gccactccct tcgcgtccta  2340
cggtgcctcc catgccagcg ccgtcggccg gtcccgtgtc tgcaccttcc gcagcgcctc  2400
tgccagccgc ccgcccagtg gccgtggcca ctgccagaaa ccccagaggc cagagaggag  2460
ccaactggca aaacacgctg aacagcatcg tgggcctggg agttaaaagc ctgaaacgcc  2520
gccgttgcta ttattaaaaa agtgtagcta aaaaatctcc cgttgtatac gcctcctatg  2580
ttaccgccag agacgtgtga ctgtcgtcgc gagcagcgct ttcaagatgg ccaccccatc  2640
gatgatgccg cagtggtctt acatgcacat cgccgggcag gacgcctcgg agtatctgag  2700
ccccggtctt gtgcagtttg cccgcgccac cgacacctac ttcagcttgg gaaacaagtt  2760
tagaaatccc accgtggccc ccacgcacga tgtgaccacg gatcgttcgc agaggctgac  2820
tctgcgcttt gtaccggtag accgtgagga tactgcctat tcttacaaag ttcggtatac  2880
gttagccgta ggagacaaca gggtgctgga catggccagt acttactttg acatccgcgg  2940
tgttcttgac cgcggtccaa gctttaaacc gtataccgga acggcataca atgccttggc  3000
tccaaagggc gctccaaatg cttgccagtg gacaacgacc aacgggggca ataaaacgaa  3060
cacttttgcc caagcccctt taataggcac ggctattgac ggaaccaacg gactgcagat  3120
tgggcaagat aatggacaag ctgtttatgc tgacaaaacc tttcaacccg aaccacaagt  3180
gggagaatct cagtggaata ctaatccaac cacaaacgca gcaggacgcg tgttaaaaac  3240
aactactcgc atgctgcctt gctatggttc ttttgcaagg cccaccaatg agaaaggggg  3300
tcaagcttca ggagacgtta ccttccaatt tttcgacact gcctcggaca atggcaacaa  3360
ccctaaggtg gtgctatatg gagaagacgt caacattgaa tcgcctgaca cacacttaat  3420
ctacaaaccc accgctgaca acacaaactc tgaaaacctt ttgggtcaac aggccgctcc  3480
aaacagagcc aattacattg cctttcggga caacttcatt ggactaatgt actataattc  3540
aacaggaaac atgggagtgt tggcagggca ggcttcccaa ctaaatgctg tggtagactt  3600
gcaagacaga aacactgagc tttcctacca actcatgtta gatgcaatag gagaccggag  3660
tcgttacttt tcaatgtgga accaagcagt ggacagctat gatccagatg tgcgaattat  3720
tgaaaatcat ggcgttgagg acgaactgcc aaattactgc ttccctctta acgctcaagg  3780
aattgctaac acctataaag gcgttaagaa aaacaacggc aattgggcga aagacgacgc  3840
agtagtagaa actaacgaaa ttggcatagg aaatgttttt gccatggaga taaatttaac  3900
tgctaacttg tggcgaaact ttctgtattc caatattgct ttgtacctgc cagactccta  3960
caagtattca ccgggaaaca taaccttacc cgaaaacaaa aacagttaca attacattaa  4020
tggtcgagta acagctcctg gtctggtaga cacctttgta aacattggcg cgcgatggtc  4080
tcccgacccc atggacaacg tgaatccttt taatcaccat cgcaatgctg gtctgcgtta  4140
tcgctccatg cttctaggca acggccgcta cgtgcccttc cacattcagg tgcctcaaaa  4200
attctttgcc attaagaacc tgcttctgct gcctgggtcc tacacctacg agtggaactt  4260
cagaaaagat gtaaacatga tcttgcagag cacgctgggc aacgacctcc gtgtcgacgg  4320
ggccagcgtc agattcgaca gcattaacct ctacgctaat ttcttcccca tggcacataa  4380
caccgcttcc accctggagg ctatgttacg caacgacacc aacgaccagt cctttaatga  4440
ctacctctgc gcggccaaca tgctataccc cattcctgcc aatgccacca gtgtgcccat  4500
ctccatcccc tctcgcaact gggcagcttt cagagggtgg agtttcaccc gcctcaaaac  4560
aaaagaaacc ccctcgctgg gttccggatt tgatccatac tttgtttact caggctccat  4620
tccctacctg gatggtacct tctacctgaa ccacaccttc aaaaaggtgt ctattatgtt  4680
cgactcttct gtgagctggc ccggcaacga ccgcctgctg acccctaatg agtttgaaat  4740
taagcgctcg gtggacggag aaggatacaa tgtagcccag agcaacatga ccaaagactg  4800
gttcttaatt caaatgctca gccactacaa cattggttac caagggtttt acgtgcccga  4860
ggcttacaaa gacagaatgt actccttttt tagaaacttc caacctatga gtagacaggt  4920
agtggatgca gatcggtatg aacaatacaa aaaagtcacc gttgagtatc aacataataa  4980
ttctggtttt gtgggataca tgggacccac catgagggaa gggcaggctt atccagcgaa  5040
ttacccttat cctcttattg gagacaccgc cgtgcccagc ctgacccaga aaaagttcct  5100
ctgtgaccgc accatgtgga gaatcccctt ctctagcaac ttcatgtcta tgggggccct  5160
caccgacctg gggcagaaca tgctgtacgc caattccgct cacgccttgg atatgacctt  5220
tgaggtggac cccatggatg agcccacgct tctctatgtt ctgtttgaag tcttcgacgt  5280
ggtgcgcatc caccagccgc accgcggcgt catcgaggcc gtctacctgc gcacaccttt  5340
ctctgccggt aacgccacca cataagaagc aaatgggctc cagcgaacag gagctgcggg  5400
ccattattcg cgacctgggc tgcggaccct actttttggg caccttcgac aagcgtttcc  5460
ccggattcat gtccccccag aagccggcct gtgccatagt caacacggcc gggcgggaga  5520
ccgggggggt tcactggctc gccttcgcct ggaacccgcg caaccgcacc tgctacctgt  5580
tcgacccttt tggtttttcc gacgaaaggc tgaagcaaat ctaccagttc gaatacgaag  5640
gactcctcaa gcgcagcgct ctggcctcca cgcccgacca ctgcgtcacc ctggaaaaat  5700
```

```
ccacccaaac ggtgcagggg cccctctcgg ccgcctgcgg gcttttctgt tgcatgtttt  5760
tgcacgcctt cgtgcactgg cctcacaacc ccatggagcg caaccccacc atggatctgc  5820
tcaccggagt gcccaacagc atgcttcaca gcccccaggt cgcccccacc ctgcgccgta  5880
accaggaaca cctgtatcgc tttctgggga aacactctgc ctatttccgc cgccaccggc  5940
agcgcatcga gcaggccacg gcctttgaaa gcatgagcca aagagtgtaa tcaataaaaa  6000
ccatttttat ttaacatgat acgcgcttct ggcgttttta ttaaaaatcg aacggttcga  6060
gggaggggtc ctcgtgcccg ctgggaaggg acacgttgcg gtactggaaa cgggcgctcc  6120
aacgaaactc ggggatcacc agccgcggca ggggcacgtc ttctaggttc tgcttccaga  6180
actgccgcac cagctgcagg gctcccatga cgtcgggcgc cgagatcttg aagtcgcagt  6240
tagggccgga gcccccgcgg ctgttgcgga acacggggtt ggcacactgg aacaccagca  6300
cgctggggtt gtaaatactg gccagggccg ttgggtcggt cacctccgac gcatccagat  6360
cctcggcatt gctcagggcg aacggagtca gcttgcacat ctgccgtccg atctggggca  6420
ccaggtcggg tttgttgagg caatcgcagc gcagagggat taggatgcga cgctgcccgc  6480
gttgcatgat agggtaactc gccgccagga actcctccat ctgacggaag gccatctggg  6540
ccttggtacc ctcggtgaaa aatagcccac aggacttgct agaaaatacg ttattgccgc  6600
agttgatgtc ttccgcgcag cagcgtgcat cttcgttctt cagctgaacc acgttacgcc  6660
cccagcggtt ctggaccacc ttggctttcg taggatgctc cttcaacgcc cgctgaccgt  6720
tctcgctggt cacatccatt tccaccacgt gctccttgca gaccatctcc actccgtgga  6780
agcagaacag gacgccctcc tgctgggtat tgcgatgctc ccaaacggca catccggtgg  6840
gctcccagct cttgcgtttc acccccgcgt atgcttccat gtaagccatg aggaatctgc  6900
ccatcagctc ggtgaaggtc ttctggttgg tgaaggttag cggcaggccg cggtgctcct  6960
cgttcaacca agtttgacag attttgcggt acacggctcc ctggtcgggc agaaacttaa  7020
aagccgctct gctctcgttg tccacgtgga acttctccat caacatcgtc atgacttcca  7080
tgcccttctc ccacgccgtc accaacggtt cggtcccggg gttcttcacc aacacggcgg  7140
tggaggggcc ctcgccggcc ccgacgtcct tcatggtcat tctttggaac tccacggtgc  7200
cgtccgcgcg gcgtactctg cgcatcggag ggtagctgaa gcccacctcc accacggtgc  7260
cttcgccctc gctgtcggaa acgatctccg gggatggcgg cggcgcgggt gtcgccttgc  7320
gagccttctt cttgggaggg agcggaggca cctcctgctc gcgctcgggg ctcatctccc  7380
gcaagtaggg ggtaatggag cttccgggtt ggttctgacg gttggccatt gtatcctagg  7440
cagaaagaca tggatcttat gcgcgaggaa actttaaccg ccccgtcccc cgtcagcgac  7500
gaagaggtca tcgtcgaaca ggacccgggc tacgttacgc cgcccgagga tctggagtcc  7560
cccttagacg accgacgcga cgctagtgag cggcaggaaa atgagaaaga ggaggaggag  7620
ggctgctacc tcctggaagg cgacgtcttg ctaaagcatt tcgccaggca gagcaccata  7680
ctcaaggagg ccttgcaaga ccgctccgag gtgcccttgg acgtcgccgc gctctcccag  7740
gcctacgagg cgaacctttt ctcgccccga gtgcctccga agagacagcc caacggcacc  7800
tgcgagccca acccgcgact caacttctac cccgtgttcg ccgtgcccga ggcgctggcc  7860
acctaccaca tctttttcaa aaaccagcgc attccccttt cctgccgggc caaccgcacc  7920
gcagccgata ggaagctaac actcagaaac ggagccagca tacctgatat cacgtcactg  7980
gaggaagtgc ctaagatctt cgagggtctg ggtcgagatg agaagcgggc ggcgaacgct  8040
ctgcagaaag aacagaaaga gagtcagaac gtgctggtgg agctggaggg ggacaacgcg  8100
cgtctggccg tcctcaaacg ctgcatagaa gtctcccact tcgcctaccc cgccctcaac  8160
ttgccaccca aagttatgaa atcggtcatg gatcagctgc tcatcaagag agctgagccc  8220
ctggatcccg accaccccga ggcggaaaac tcagaggacg gaaagcccgt cgtcagcgac  8280
gaggagctcg agcggtggct ggaaaccggg gacccccaac agttgcaaga gaggcgcaag  8340
atgatgatgg cggccgtgct ggtcaccgtg gagctggaat gcctgcaacg gtttttcagc  8400
gacgtggaga cgctacgcaa aatcggggag tccctgcact acaccttccg ccagggctac  8460
gtccgccagg cctgcaagat ctccaacgtg gagctcagca acctggtctc ctacatgggc  8520
atcctccacg agaaccggct ggggcagagc gtgctgcact gcaccttgca aggcgaggcg  8580
cggcgggact acgtccgcga ctgcatctac ctcttcctca ccctcacctg gcagaccgcc  8640
atgggcgtct ggcagcagtg cttggaagag agaaacctca aagagctaga caaactcctc  8700
tgccgccagc ggcgggccct ctggaccggt ttcagcgagc gcacggtcgc ctgcgccctg  8760
gcagacatta tcttcccgga gcgcctgatg aaaaccttgc agaacggcct gccggatttt  8820
atcagtcaaa gtattttgca aaacttccgc tccttcgttc tggagcgctc cgggatcttg  8880
cccgccatga gctgcgcgct gccttctgac tttgtccccc tttcctaccg cgagtgtcct  8940
cccccctgt ggagccactg ctacctcttc caactggcca actttctggc ctaccactcc  9000
gacctcatgg aagacgtgag cggagagggg ctgctcgagt gccactgccg ctgcaacctc  9060
tgcacccccc acagatcgct ggcctgcaac accgagctgc tcagcgaaac ccaggtcata  9120
ggtaccttcg agatccaggg gccccagcag caagagggtg cttccggctt gaagctcact  9180
ccggcgctgt ggacctcggc ttacttacgc aaatttgtag ccgaggacta ccacgcccac  9240
aaaattcagt tctatgaaga ccaatctcga ccacccaaag cccccctcac ggcctgcgtc  9300
atcactcaga gcaaaatcct ggcccaattg caatccatca accaagcgcg ccgagatttc  9360
cttttgaaaa agggtcgggg ggtgtaccta gacccccaga ccggcgagga actcaacccg  9420
tccacactct ccgtcgaagc agcccccccg agacatgccg cccaagggaa ccgccaagca  9480
gctgatcgct cggcagagag cgaagaagca agagctgctc cagcagcagc agcaggtgga  9540
ggacgaggaa gagctgtggg acagccaggc agaggaggtg tcagaggacg aggaggagat  9600
ggaaagctgg gacagcctag acgaggagga ggacgagctt tcagaggaag aggcgaccga  9660
agaaaaacca cctgcatcca gcgcgccttc tctgagccga cagccgaagc cccggccccc  9720
gacgcccccg gccggctcac tcaaagccag ccgtaggtgg gacgccaccg gatctccagc  9780
ggcagcggca acggcagcgg gtaaggccaa acgcgagcgg cgggggtatt gctcctggcg  9840
ggcccacaaa agcagtatcg tgaactgctt gcaacactgc gggggaaaca tctcctttgc  9900
ccgacgctac ctcctcttcc atcacggtgt ggccttccct cgcaacgttc tctattatta  9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttccccctcg ggcgccaaaa  10320
cccacgtcat tgccagcatg agcaaggaga ttcccacccc ttacatgtgg agctatcagc  10380
cccagatggg cctggccgcg ggggccgccc aggactactc cagcaagatg aactggctca  10440
```

```
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
acggagtctt ccagctcgga ggagcgggcc gctcttcctt caccactcgc caggcctacc  10860
tgaccctgca gagctcttcc tcgcagccgc gctccggggg aatcggcact ctccagttcg  10920
tggaagagtt cgtcccctcc gtctacttca acccgttttc cggctcacct ggacgctacc  10980
cggacgcctt cattcccaac tttgacgcag tgagtgaatc cgtggacggc tacgactgat  11040
gacagatggt gcggccgtga gagctcggct gcgacatctg catcactgcc gccagcctcg  11100
ctgctacgct cgggaggcga tcgtgttcag ctactttgag ctgccggacg agcaccctca  11160
ggggccggct cacgggttga aactcgagat cgagaacgcg ctcgagtctc gcctcatcga  11220
cgccttcacc gcccggcctc tcctggtaga aaccgaacgc gggatcacta ccatcaccct  11280
gttctgcatc tgccccacgc ccggattaca tgaagatctg tgttgtcatc tttgcgctca  11340
gtttaataaa aactgaactg tttgccgcac cttcaacgcc atctgtgatt tctacaacaa  11400
aaagttcttc tggcaaaggt acacaaactg tattttattc taattctacc tcatctattg  11460
tgctgaactg cgcctgcact aacgaactta tcctgtagag ggggctatcc tctgtcactg  11520
tcacgcacct gattgcatgt ccaaactaat caaaactctc tgtgctttag gtgatatttt  11580
taaaatgtaa atcataataa acttacctta aatttgacaa caattttctg gtgacatcat  11640
tcagcagcac cactttaccc tcttcccagc tctcgtatgg gatgcgatag tgggtggcaa  11700
acttcctcca aaccctaaaa gaaatattgg tatccacttc cttgtcctca cccacaattt  11760
tcatcttttc atagatgaaa agaaccagag ttgatgaaga cttcaacccc gtctacccct  11820
atgacaccac aaccactcct gcagttccct ttatatcacc ccccttttgta aacagcgatg  11880
gtcttcagga aaacccccca ggtgttttaa gtctgcgaat agctaaaccc ctatatttcg  11940
acatggagag aaaactagcc ctttcacttg gaagagggtt gacaattacc gccgccggac  12000
aattagaaag tacgcagagc gtacaaacca acccaccgtt gataattacc aacaacaaca  12060
cactgaccct acgtcattct cccccttaa acctaactga caatagctta gtgctaggct  12120
actcgagtcc gctccgcgtc acagacaaca aacttacatt taacttcaca tcaccactcc  12180
gttatgaaaa tgaaaacctt acttttaact atacagagcc tcttaaactt ataaataaca  12240
gccttgccat tgacatcaat tcctcaaaag gccttagtag cgtcggaggc tcactagctg  12300
taaacctgag ttcagactta aagtttgaca gcaacggatc catagctttt ggcatacaaa  12360
ccctgtggac cgctccgacc tcgactggca actgcaccgt ctacagcgag ggcgattccc  12420
tacttagtct ctgtttaacc aaatgcggag ctcacgtctt aggaagtgta agtttaaccg  12480
gtttaacagg aaccataacc caaatgactg atatttctgt caccattcaa tttacatttg  12540
acaacaatgg taagctacta agctctccgc ttataaacaa cgcctttagt attcgacaga  12600
atgacagtac ggcctcaaac cctacctaca acgccctggc gtttatgcct aacagtacca  12660
tatatgcaag agggggaggt ggtgaaccac gaaacaacta ctacgtccaa acgtatctta  12720
ggggaaatgt tcaaaaacca atcattctta ctgtaaccta caactcagcc gccacaggat  12780
attccttatc ttttaagtgg actgctcttg cacgtgaaaa gtttgcaacc ccaacaactt  12840
cgttttgcta cattacagaa caataaaacc gtgtacccca ccgtttcgtt tttttcagat  12900
gaaacgggcg agagttgatg aagacttcaa cccagtgtac ccttatgacc ccccacatgc  12960
tcccgttatg cccttcatta ctccaccttt tacctcctcg gatgggttgc aggaaaaacc  13020
acttggagtg ttaagtttaa actacagaga tcccattact acgcaaaatg ggtctcttac  13080
agttaaacta ggaaacggcc tcactctaga caaccaggga caactaacat caaccgctgg  13140
ggaagtagaa cctccactca ctaacgctaa caacaaactt gcactggtct atagcgatcc  13200
tttagcagta aagcgcaaca gcctaacctt atcgcacacc gctccccttg ttattgctga  13260
taactcttta gcattgcaag tttcagagcc tatttttata aatgacaagg acaaactagc  13320
cctgcaaaca gccgcgcccc ttgtaactaa cgctggcacc cttcgcttac aaagcgccgc  13380
ccctttaggc attgcagacc aaaccctaaa actcctgttt accaaccctt tgtacttgca  13440
gaataacttt ctcacgttag ccattgaacg acccctttgcc attaccaata gtggaaagct  13500
ggctctacag ctctccccac cgctacaaac agcagacaca ggcttgactt tgcaaaccaa  13560
cgtgccatta actgtaagca acgggaccct aggcttagcc ataaagcgcc cacttattgt  13620
tcaggacaac aacttgtttt tggacttcag agctcccctg cgtcttttca acagcgaccc  13680
cgtactaggg cttaactttt acacccctct tgcagtgcgc gatgaggcgc tcactgttaa  13740
cacaggccgc ggcctcacag tgagttacga tggtttaatt ttaaatcttg gtaaggatct  13800
tcgctttgac aacaacaccg tttctgtcgc tcttagtgct gctttgcctt tacaatacac  13860
tgatcagctt cgccttaacg tgggcgctgg gctgcgttac aatccagtga gtaaaaaatt  13920
ggacgtgaac cccaatcaaa acaagggttt aacctgggaa aatgactacc tcattgtaaa  13980
gctaggaaat ggattaggtt ttgatggcaa tggaaacata gctgtttctc ctcaagttac  14040
atcgcctgac accttatgga ccactgccga tccatccccc aattgttcca tctacactga  14100
tttagatgcc aaaatgtggc tctcgttggt aaaacaaggg ggtgtggttc acggttctgt  14160
tgctttaaaa gcattgaaag gaaccctatt gagtcctacg gaaagtgcca ttgttattat  14220
actacatttt gacaattatg gagtgcgaat tctcaattat cccactttgg gcactcaagg  14280
cacgttggga aataatgcaa cttggggtta taggcaggga gaatctgcag acactaatgt  14340
actcaatgca ctagcattta tgcccagttc aaaaaggtac ccaagagggc gtggaagcga  14400
agttcagaat caaactgtgg gctacacttg tatacagggt gacctttcta tgcccgtacc  14460
gtaccaaata cagtacaact atggaccaac tggctactcc tttaaattta tttggagaac  14520
tgtttcaaga caaccatttg acatcccatg ctgtttttc tcttacatta cggaagaata  14580
aaacaacttt tcctttttat tttcttttta ttttacacgc acagtaaggc ttcctccacc  14640
cttccatttg acagcataca ccagcctctc ccccttcatg gcagtaaact gctgcgagcc  14700
agtccggtat ttgggagtta agatccaaac agtctctttg gtaatcagat gtcgatccgt  14760
gatggacaca aatccctggg gcaggttctc caacgtttcg gtgaaaaact gcatgccgcc  14820
ctacaaaaca aacaggttca ggctctccac gggttatctc cccgatcaaa ctcagacagg  14880
gtaaaggtgc gatgatgttc cactaaacca cgcaggtggc gctgtctgaa cctctcggtg  14940
cgactcctgt gaggctggta agaagttaga ttgtccagca gcctcacagc atggatcatc  15000
agtctacgag tgcgtctggc gcagcagcgc atctgaatct cactgagatt ccggcaagaa  15060
tcgcacacca tcacaatcag gttgttcatg atcccatagc tgaacacgct ccagccaaag  15120
ctcattcgct ccaacagcgc caccgcgtgt ccgtccaacc ttactttaac ataaatcagg  15180
```

```
tgtctgccgc gtacaaacat gctacccgca tacagaacct cccggggcag tcccctgttc  15240
accacctgcc tgtaccaggg aaacctcaca tttatcaggg agccatagat agccatctta  15300
aaccaattag ctaacaccgc cccaccagct ctacactgaa gagaaccggg agagttacaa  15360
tgacagtgaa taatccatct ctcataaccc ctaatggtct gatggaaatc cagatctaac  15420
gtggcacagc agatacacac tttcatatac attttcatca catgtttttc ccaggccgtt  15480
aaaatacaat cccaatacac gggccactcc tgcagtacaa taaagctaat acaagatggt  15540
atactcctca cctcactaac attgtgcatg ttcatatttt cacattctaa gtaccgagag  15600
ctctcctcta caacagcact gccgcggtcc tcacaaggtg gtagctggtg acaattgtag  15660
ggagccagtc tgcagcgata ccgtctgtcg cgttgcatcg tagaccaggg accgacgcac  15720
ttcctcgtac ttgtagtagc agaactgccc cgtcttaccg cgtataaagc cacgaaaaag  15780
tcgagctaaa atccacccaa cagcctatag ctatatatac actccgccca atgacgctaa  15840
caccgtacca cccacgacca aagttcaccc acacccacaa aacccgcgaa aatccagcgc  15900
cgtcagcact tccgcaattt cagtctcaca acgtcacttc cgcgcgcctt ttttcactat  15960
tcccacaccc gccctcgcgc caccccgcgt caccccgcgt caccgcacgt cacccccggcc  16020
ccgcctcgct cctccccgct cattatcata ttggcacgtt tccagaataa ggtatattat  16080
tgatgatgtt aattaattcg aacccataat acccataata gctgtttgcc atcgacgcga  16140
ggctggatgg ccttccccat tatgattctt ctcgcttccg gcggcatcgg gatgcccgcg  16200
ttgcaggcca tgctgtccag gcaggtagat gacgaccatc agggacagct tcaaggatcg  16260
ctcgcggctc ttaccagccc agcaaaaggc caggaaccgt aaaaaggccg cgttgctggc  16320
gtttttccat aggctccgcc cccctgacga gcatcacaaa aatcgacgct caagtcagag  16380
gtggcgaaac ccgacaggac tataaagata ccaggcgttt ccccctggaa gctccctcgt  16440
gcgctctcct gttccgaccc tgccgcttac cggatacctg tccgcctttc tcccttcggg  16500
aagcgtggcg ctttctcata gctcacgctg taggtatctc agttcggtgt aggtcgttcg  16560
ctccaagctg ggctgtgtgc acgaaccccc cgttcagccc gaccgctgcg ccttatccgg  16620
taactatcgt cttgagtcca acccggtaag acacgactta tcgccactgg cagcagccac  16680
tggtaacagg attagcagag cgaggtatgt aggcggtgct acagagttct tgaagtggtg  16740
gcctaactac ggctacacta gaaggacagt atttggtatc tgcgctctgc tgaagccagt  16800
taccttcgga aaaagagttg gtagctcttg atccggcaaa caaaccaccg ctggtagcgg  16860
tggtttttt gtttgcaagc agcagattac gcgcagaaaa aaaggatctc aagaagatcc  16920
tttgatcttt tctacggggt ctgacgctca gtggaacgaa aactcacgtt aagggatttt  16980
ggtcatgaga ttatcaaaaa ggatcttcac ctagatcctt ttaaattaaa aatgaagttt  17040
taaatcaatc taaagtatat atgagtaaac ttggtctgac agttaccaat gcttaatcag  17100
tgaggcacct atctcagcga tctgtctatt tcgttcatcc atagttgcct gactccccgt  17160
cgtgtagata actacgatac gggagggctt accatctggc cccagtgctg caatgatacc  17220
gcgagaccca cgctcaccgg ctccagattt atcagcaata aaccagccag ccggaagggc  17280
cgagcgcaga agtggtcctg caactttatc cgcctccatc cagtctatta attgttgccg  17340
ggaagctaga gtaagtagtt cgccagttaa tagtttgcgc aacgttgttg ccattgctgc  17400
aggcatcgtg gtgtcacgct cgtcgtttgg tatggcttca ttcagctccg gttcccaacg  17460
atcaaggcga gttacatgat cccccatgtt gtgcaaaaaa gcggttagct ccttcggtcc  17520
tccgatcgtt gtcagaagta agttggccgc agtgttatca ctcatggtta tggcagcact  17580
gcataattct cttactgtca tgccatccgt aagatgcttt tctgtgactg gtgagtactc  17640
aaccaagtca ttctgagaat agtgtatgcg gcgaccgagt tgctcttgcc cggcgtcaac  17700
acgggataat accgcgccac atagcagaac tttaaaagtg ctcatcattg gaaaacgttc  17760
ttcggggcga aaactctcaa ggatcttacc gctgttgaga tccagttcga tgtaacccac  17820
tcgtgcaccc aactgatctt cagcatcttt tactttcacc agcgtttctg ggtgagcaaa  17880
aacaggaagg caaaatgccg caaaaaaggg aataagggcg acacggaaat gttgaatact  17940
catactcttc ctttttcaat attattgaag catttatcag ggttattgtc tcatgagcgg  18000
atacatattt gaatgtattt agaaaaataa acaaataggg gttccgcgca catttccccg  18060
aaaagtgcca cctgacgtct aagaaaccat tattatcatg acattaacct ataaaaatag  18120
gcgtatcacg aggccctttc gtcttcaaga attggtcgat ggcaaacagc tattatgggt  18180
attatgggtt cgaattaat                                               18199
```

```
SEQ ID NO: 45          moltype = DNA  length = 8765
FEATURE                Location/Qualifiers
source                 1..8765
                       mol_type = other DNA
                       note = Synthetic oligonucleotide sAdApt4310A.E1btg.Empty
                       organism = synthetic construct
SEQUENCE: 45
attaacatca tcaataatat accttattct ggaaacgtgc caatatgata atgagcgggg  60
aggagcgagg cggggccggg gtgacgtgcg gtgacgcggg gtgacgcggg gtggcgcgag  120
ggcggggcgg gtgtgcggag gcgcttagtt tttacgtatg cggaaggagg ttttataccg  180
gaagttgggt aatttgggcg tatacttgta agttttgtgt agtttggcgc gaaaaccggg  240
taatgaggaa gttgaggtta atatgtactt tttatgactg ggcggaattt ctgctgatca  300
gcagtgaact ttgggcgctg acggggaggt ttcgctacgt ggcagtacca cgagaaggct  360
caaaggtccc atttattgta ctcctcagcg ttttcgctgg gtatttaaac gctgtcagat  420
catcaagagg ccactcttga gtgccggcga gtagagtttt ctcctccgcg ctgccgcgat  480
gaggctggtt cccgagatgt acggtgtttt ctgcagcgag acggcccgga actcagatga  540
gctgctgaat tcagacctgc tggaaatttc gaattcgcct gtgcttttgc cgccgtcact  600
tcacgacctg tttgatgtgg aagtggaccc tccggaagat cccaacgagg acgcggtaaa  660
tactatgttt ccagaatgtc tgtttgaggc ggctgaggag ggttcttaca gcggtgaaga  720
cggcgggcag ggagaggaag tggacctgaa gtgctacgag gaatgtctac cttctagcga  780
ttctgaaacg gaacagacag ggggagatgg ctgtgctgaa cctgttgtga aaaatgaact  840
tgtattagac tgtcctgata atcctggtca cggttgccgc gcctgtgatt ttcatagaaa  900
tgccagtgga aatcctgaga ctctatgtgc tctgtgttac ctgcgcctta ccagccattg  960
tgtatacagt aagtagaaac tttttcgctt tgtgcatgct ggtgggattt ttaaagtgcg  1020
ttgggcttat tgttgcgtaa tgttttacag gcgacgtgtc tgacgcggaa ggggatggag  1080
atagatcagg ctctgctggt tctccttgca ctttgggggc tgtggttcca gatggcatta  1140
ttaaacccgt ggcggtaaga gtttcaggca gacggtgtgc ggtcgaaaaa attgaagact  1200
```

```
tgctgcagga ggaacagatg caacctttgg acctgtccct gaaacgccct aagctgacct  1260
aagagtgttt attgtatgca ataaaaagtg ttgatctttg aactgtgttt atgtgttggg  1320
tgtgtctgtg ggtatataag caggtggatg ggaagtgaga gcacagctgc ttcagatgga  1380
tctgctagga gacctgaggg aatttggcgt ggttcggcgc ttgctggagt tggcctctga  1440
cagaacttcc aagttttgga ggttttgttt tggctcaacg cttagcaacg tgctatatag  1500
ggtcaagaag gagcaggaga cgcagtttgc taggctgttg gccgatactc ctggagtttt  1560
tgtggctctg gatctaggcc atcactctct tttccaagag aaaattatca aaaacttaac  1620
ttttacgtct cctggtcgca cggttgcttc cgctgccttt attacctata ttttggatca  1680
atggagcaac agcggcagtc acctgtcgtg ggagtacatg ctggattaca tgtcgatggc  1740
gctgtggagg gccatgctgc ggaggagggt ttgcatttac ttgcgggcgc agcctccgcg  1800
gctggaccga gtggaggagg aggacgagcc gggggagacc gagaacctga gggccgggct  1860
ggaccctcca acggaggact aggtgctgag gatgatcccg aagaggggac tagtggggct  1920
aggaagaagc aaaagactga gtctgaacct cgaaactttt tgaatgagtt gactgtgagt  1980
ttgatgaatc gtcagcgtcc ggagacaatt ttctggtctg aattggagga ggaattcagg  2040
agggggggaac tgaacctgct atacaagtat gggtttgaac agttgaaaac tcactggttg  2100
gagccgtggg aggattttga aaccgccttg gacacttttg ctaaagtggc tctgcgaccg  2160
gataaggttt acactatccg ccgcactgtt aacataaaga agagtgttta tgttataggc  2220
catggagctc tggtgcaggt gcaaaccgcc gaccgggtgg cctttagttg cggcatgcaa  2280
aatctgggcc ccggggtgat aggcttaaat ggtgtaacat ttcacaatgt aaggtttact  2340
ggtgaaagtt ttaacggctc tgtgtttgca aataacacac agctgacgct ccacggcgtt  2400
tactttttta actttaataa cacatgtgtg gagtcgtggg gcagggtgtc tttgaggggc  2460
tgctgttttc acggctgctg gaaggcggtg gtgggaagac ttaaaagtgt aacatctgta  2520
aaaaaatgcg tgtttgagcg ctgtgtgttg gctttaaccg tggagggctg tggacgcatt  2580
aggaataatg cagcgtctga gaatggatgt ttccttttgc taaaaggcac ggctagcgtt  2640
aagcataaca tgatatgcgg cagcggtttg tacccttcgc agctgttaac ttgcgcggat  2700
ggaaactgtc agaccctgcg caccgtgcac atagcgtccc accagcgacg cgcctggcca  2760
acattcgagc acaatatgct tatgcgctgt gccgttcacc tgggccctag gcgaggcgtg  2820
tttgtgcctt accagtgtaa ctttagccat accaagtttt tactagaacc tgacaccttc  2880
tctcgagtgt gtttcaacgg ggtttttgac atgtcaatgg aactgtttaa agtgataaga  2940
tatgatgaat ccaagtctcg ttgtcgccca tgtgaatgcg gagctaatca tttgaggttg  3000
tatcctgtaa ctctgaacgt caccgaggag ctgagaacgg accaccacat gctgtcttgc  3060
ctgcgcactg actatgaatc cagcgacgag gagtgaggtg aggggcggag ccaaacgggt  3120
ataaaggggc gtgaggtcga ctggtcaata ttggccatta gccatattat tcattggtta  3180
tatagcataa atcaatattg gctattggcc attgcatacg ttgtatccat atcataatat  3240
gtacatttat attggctcat gtccaacatt accgccatgt tgacattgat tattgactag  3300
ttattaatag taatcaatta cggggtcatt agttcatagc ccatatatgg agttccgcgt  3360
tacataactt acggtaaatg gcccgcctgg ctgaccgccc aacgaccccc gcccattgac  3420
gtcaataatg acgtatgttc ccatagtaac gccaataggg actttccatt gacgtcaatg  3480
ggtggagtat ttacggtaaa ctgcccactt ggcagtacat caagtgtatc atatgccaag  3540
tacgcccccct attgacgtca atgacggtaa atggcccgcc tggcattatg cccagtacat  3600
gaccttatgg gactttccta cttggcagta catctacgta ttagtcatcg ctattaccat  3660
ggtgatgcgg ttttggcagt acatcaatgg gcgtggatag cggtttgact cacggggatt  3720
tccaagtctc caccccattg acgtcaatgg gagtttgttt tggcaccaaa atcaacggga  3780
ctttccaaaa tgtcgtaaca actccgcccc attgacgcaa atgggcggta ggcgtgtacg  3840
gtgggaggtc tatataagca gagctcgttt agtgaaccgt cagatcgcct ggagacgcca  3900
tccacgctgt tttgacctcc atagaagaca ccgggaccga tccagcctcc gcggccggga  3960
acggtgcatt ggaagcttgg taccggtgaa ttcgctagcg ttaacggatc ctctagacga  4020
gatccgaact tgtttattgc agcttataat ggttacaaat aaagcaatag catcacaaat  4080
ttcacaaata aagcattttt ttcactgcat tctagttgtg gtttgtccaa actcatcaat  4140
gtatcttatc atgtctagat ccttaaggac atgtcaatgg aactgtttaa agtgataaga  4200
tatgatgaat ccaagtctcg ttgtcgccca tgtgaatgcg gagctaatca tttgaggttg  4260
tatcctgtaa ctctgaacgt caccgaggag ctgagaacgg accaccacat gctgtcttgc  4320
ctgcgcactg actatgaatc cagcgacgag gagtgaggtg aggggcggag ccaaacgggt  4380
ataaaggggc gtgaggggtc ggtgcggtgt ttcaaaatga gcgggacgac ggacggcaat  4440
gcgtttgagg ggggagtgtt cagcccatat ctgacatctc gtcttccttc ctgggcagga  4500
gtgcgtcaga atgtagtggg atccaccgtg gacggacgac cggtggctcc tgcaaattcc  4560
gccaccctca cctatgccac cgtgggatca tcgttggaca ctgccgcggc agctgccgct  4620
tctgctgccg cttctactgc tcgcggcatg gcggctgatt ttggactgta taaccaactg  4680
gccactgcag ctgtggcgtc tcggtccctg gttcaagaag atgccctgaa tgtgattctg  4740
actcgcctgg agatcatgtc acgccgcctg gacgaactgg ctgcgcagat atcctcaact  4800
aaccccgata ccacttcaga accttaaata aagacaaaca aatttgttga aaagtaaaat  4860
ggctttattt gtttttttg gctcggtagg ctcgggtcca cctgtcccgg tcgttaagga  4920
ccttgtgtat gttttccaag acccggtaca gatgggcttg gatgttcaag tacatgggca  4980
tgaggccatc tcgggggtgg agataggacc attgcagagc gtcatgctcc ggggtggtgt  5040
tgtaaataac ccagtcgtag cagggtttct gagcgtggaa ctggaagatg tcctttagga  5100
gcaggctgat ggccaagggc agccccttag tgtaggtgtt aacaaagcgg ttaagctggg  5160
agggatgcat gcgggggggag atgatatgca tcttggcttg aattttgagg ttagctatgt  5220
taccacctag gtccctgcgg gggttcatgt tatgaaggac caccagcacg gtgtagccgg  5280
tgcacttggg gaacttgtca tgcagtttgg aggggaaggc gtggaagaat ttagagaccc  5340
ccttgtggcc tcctaggttt tccatgcact catccataat gatggcaatg ggacccctgg  5400
cggccgcttt ggcaaacacg ttttgggggt tggaaacatc atagttttgc tctagagtga  5460
gctcatcata ggccatctta acaaagcggg gtaggagggt gcccgactgg gggatgatag  5520
ttccatctgg gcctggggcg tagttgccct cacaaatctg catttcccag gccttaattt  5580
ccgagggggg tatcatgtcc acctgggggg cgataaagaa cacggtttct ggcgggggat  5640
tgatgagctg ggtggaaagc aagttacgca acagttggga tttgccgcaa ccggtgggac  5700
cgtagatgac cccgatgacg ggttgcagct ggtagttgag agaggaacag ctgccgtcgg  5760
ggcgcaggag gggggctaca tcgttcatca tgcttctgac atgtttattt tcactcacta  5820
agttttgcaa gagcctctcc ccacccaggg ataagagttc ttccaggctg ttgaagtgtt  5880
tcagcggttt caggccgtct gccatgggca tcttttcaag cgactgacga agcaagtaca  5940
```

```
gtcggtccca gagctcggtg acgtgctcta tggaatctcg atccagcaga cttcttggtt  6000
gcgggggttg ggccgacttt cgctgtaggg caccagccgg tgggcgtcca gggccgcgag  6060
ggttctgtcc ttccagggtc tcagcgttcg ggtgagggtg gtctcggtga cggtgaaggg  6120
atgagccccg ggctgggcgc ttgcgagggt gcgcttcagg ctcatcctgc tggtgctgaa  6180
gcgggcgtcg tctccctgtg agtcggccag atagcaacga agcatgaggt cgtagctgag  6240
ggactcggcc gcgtgtccct tggcgcgcag ctttcccttg gaaacgtgct gacatttggt  6300
gcagtgcaga cacttgaggg cgtagagttt gggggccagg aagaccgact cggacgagta  6360
ggcgtcggct ccgcactgag cgcagacggt ctcgcactcc accagccacg tgagctcggg  6420
tttagcggga tcaaaaacca agttgcctcc atttttttg atgcgtttct taccttgcgt  6480
ctccatgagt ctgtgtcccg cttccgtgac aaaaaggctg tcggtgtccc cgtagaccga  6540
cttgaggggg cgatcttcca aaggtgttcc gagatcttcc gcgtacagga actgggacca  6600
ctccgagaca aaggctcggg tccaggctaa cacgaaggag gcgatctgcg aggggtatct  6660
gtcgttttca atgaggttaa ttaattcgaa cccataatac ccataatagc tgtttgccat  6720
cgacgcgagg ctggatggcc ttccccatta tgattcttct cgcttccggc ggcatcggga  6780
tgcccgcgtt gcaggccatg ctgtccaggc aggtagatga cgaccatcag ggacagcttc  6840
aaggccagca aaaggccagg aaccgtaaaa aggccgcgtt gctggcgttt ttccataggc  6900
tccgcccccc tgacgagcat cacaaaaatc gacgctcaag tcagaggtgg cgaaacccga  6960
caggactata aagataccag gcgtttcccc ctggaagctc cctcgtgcgc tctcctgttc  7020
cgaccctgcc gcttaccgga tacctgtccg cctttctccc ttcgggaagc gtggcgcttt  7080
ctcatagctc acgctgtagg tatctcagtt cggtgtaggt cgttcgctcc aagctgggct  7140
gtgtgcacga accccccgtt cagcccgacc gctgcgcctt atccggtaac tatcgtcttg  7200
agtccaaccc ggtaagacac gacttatcgc cactggcagc agccactggt aacaggatta  7260
gcagagcgag gtatgtaggc ggtgctacag agttcttgaa gtggtggcct aactacggct  7320
acactagaag gacagtattt ggtatctgcg ctctgctgaa gccagttacc ttcggaaaaa  7380
gagttggtag ctcttgatcc ggcaaacaaa ccaccgctgg tagcggtggt ttttttgttt  7440
gcaagcagca gattacgcgc agaaaaaaag gatctcaaga agatcctttg atcttttcta  7500
cggggtctga cgctcagtgg aacgaaaact cacgttaagg gattttggtc atgagattat  7560
caaaaaggat cttcacctag atccttttaa attaaaaatg aagttttaaa tcaatctaaa  7620
gtatatatga gtaaacttgg tctgacagtt accaatgctt aatcagtgag gcacctatct  7680
cagcgatctg tctatttcgt tcatccatag ttgcctgact ccccgtcgtg tagataacta  7740
cgatacggga gggcttacca tctggcccca gtgctgcaat gataccgcga gacccacgct  7800
caccggctcc agatttatca gcaataaacc agccagccgg aagggccgag cgcagaagtg  7860
gtcctgcaac tttatccgcc tccatccagt ctattaattg ttgccgggaa gctagagtaa  7920
gtagttcgcc agttaatagt ttgcgcaacg ttgttgccat tgctgcaggc atcgtggtgt  7980
cacgctcgtc gtttggtatg gcttcattca gctccggttc ccaacgatca aggcgagtta  8040
catgatcccc catgttgtgc aaaaaagcgg ttagctcctt cggtcctccg atcgttgtca  8100
gaagtaagtt ggccgcagtg ttatcactca tggttatggc agcactgcat aattctctta  8160
ctgtcatgcc atccgtaaga tgcttttctg tgactggtga gtactcaacc aagtcattct  8220
gagaatagtg tatgcggcga ccgagttgct cttgcccggc gtcaacacgg gataataccg  8280
cgccacatag cagaacttta aaagtgctca tcattggaaa acgttcttcg gggcgaaaac  8340
tctcaaggat cttaccgctg ttgagatcca gttcgatgta acccactcgt gcacccaact  8400
gatcttcagc atcttttact ttcaccagcg tttctgggtg agcaaaaaca ggaaggcaaa  8460
atgccgcaaa aaagggaata agggcgacac ggaaatgttg aatactcata ctcttccttt  8520
ttcaatatta ttgaagcatt tatcagggtt attgtctcat gagcggatac atatttgaat  8580
gtatttagaa aaataaacaa ataggggttc cgcgcacatt tccccgaaaa gtgccacctg  8640
acgtctaaga aaccattatt atcatgacat taacctataa aaataggcgt atcacgaggc  8700
cctttcgtct tcaagaattg gtcgatggca aacagctatt atgggtatta tgggttcgaa  8760
ttaat                                                              8765
```

```
SEQ ID NO: 46          moltype = DNA  length = 6174
FEATURE                Location/Qualifiers
source                 1..6174
                       mol_type = other DNA
                       note = Synthetic oligonucleotide sAdApt4312.Empty
                       organism = synthetic construct
SEQUENCE: 46
attaacatca tcaataatat accttattct ggaaacgtgc caatatgata atgagtgggg  60
aggagcgagg cggggccggg gtggggtgag gcggggccgg ggtggggtga gggtgacgtc  120
ggggcgggcg gggcggccga cgtgtgtggg gaggcgcgta gtgtttacgt atgcggaagg  180
aggttttata ccggaagatg ggtaatttgg gcgtatactt gtaagttttg tgtaatttgg  240
cgcgaaaact gggtaatgag gaagttgagg ttaatatgta ctttttatga ctgggcggaa  300
tttctgctgt tcagcagtga actttgggcg ctgacgggga ggtttcgcta cgtggcagta  360
ccacgagaag gctcaaaggt cccatttatt gtactcctca gcgttttcgc cgggtattta  420
aacgctgtca gatcatcaag aggccactct tgagtgctgg cgagtagagt tttctcctcc  480
ggtcgactgg tcaatattgg ccattagcca tattattcat tggttatata gcataaatca  540
atattggcta ttggccattg catacgttgt atccatatca taatatgtac atttatattg  600
gctcatgtcc aacattaccg ccatgttgac attgattatt gactagttat taatagtaat  660
caattacggg gtcattagtt catagcccat atatggagtt ccgcgttaca taacttacgg  720
taaatggccc gcctggctga ccgcccaacg acccccgccc attgacgtca ataatgacgt  780
atgttcccat agtaacgcca atagggactt tccattgacg tcaatgggtg gagtatttac  840
ggtaaactgc ccacttggca gtacatcaag tgtatcatat gccaagtacg ccccctattg  900
acgtcaatga cggtaaatgg cccgcctggc attatgccca gtacatgacc ttatgggact  960
ttcctacttg gcagtacatc tacgtattag tcatcgctat taccatggtg atgcggtttt  1020
ggcagtacat caatgggcgt ggatagcggt ttgactcacg gggatttcca agtctccacc  1080
ccattgacgt caatgggagt ttgttttggc accaaaatca acgggacttt ccaaaatgtc  1140
gtaacaactc cgccccattg acgcaaatgg gcggtaggcg tgtacggtgg gaggtctata  1200
taagcagagc tcgtttagtg aaccgtcaga tcgcctggag acgccatcca cgctgttttg  1260
acctccatag aagacaccgg gaccgatcca gcctccgcgg ccgggaacgg tgcattggaa  1320
gcttggtacc ggtgaattcg ctagcgttaa cggatcctct agacgagatc cgaacttgtt  1380
```

```
tattgcagct tataatggtt acaaataaag caatagcatc acaaatttca caaataaagc  1440
atttttttca ctgcattcta gttgtggttt gtccaaactc atcaatgtat cttatcatgt  1500
ctagatcctt aaggtgataa gatatgatga atccaagtct cgttgtcgcc cctgtgaatg  1560
cggagctaat catttgaggt tgtatcccgc gaccctgaac gtaaccgagg agctgagggc  1620
cgaccaccac atgttgtcct gcttgcgcac cgactatgag tccagcgacg aagagtgagg  1680
tgaggggcgg agccacaaag ggtataaagg gtcaggatgg gtgggcacag gtattcaaaa  1740
tgagcgggac gacggacggc aacgcgtttg agggggggagt gttcagccca tatctgacat  1800
ctcgtcttcc ttcctgggca ggagtgcgtc agaatgtagt gggctccacc gtggacggac  1860
ggccggtcgc ccctgcgaat tccgccaccc ttacctatgc caccgtggga tcaccgttgg  1920
acactgccgc ggcagccgca gcttctgctg ccgcttctac tgctcgcggt atggcggctg  1980
actttggact ttataaccaa ctggctaccg cggctgtggc atctcgcact ctggttcaag  2040
aagatgccct gagcgtggtt ctgcttcgac tggaagatct gtctcgtcgc ttggatcagc  2100
tggctgcgca gatatcccca cctaaccccg atactactca agaatcttaa ataaagacaa  2160
acagatttgt tgaaaataaa tggctttatt tgtttttttt ggctcgatag gctcgggtcc  2220
acctgtcccg gtcgttaagg actttgtgta tgctttccaa gacccggtac agatgggctt  2280
ggatgtttag atacatgggc atgaggccat cccgggggtg gagataggac cattgcagag  2340
cgtcatgctc cggggtggtg ttgtagatga cccagtcgta gcagggtttt tgggcgtgga  2400
actgaaaaat gtccttgaga agcaggctga tggccagggg cagaccctta gtgtaggtgt  2460
tcacaaagcg gttgagctgg gagggatgca tgcggggaga gatgatatgc atcttagcct  2520
ggattttcag gttagctatg ttgcccccca ggtcccttcg agggttcata ttgtggagga  2580
ccaccagaac ggtgtagccg gtacacttgg gaaacttatc gtgcagtttg gaggggaagg  2640
cgtgaaagaa tttggaaacc cctttgtgac cacctaagtt ttccatgcac tcgtccatga  2700
taatggcgat gggccccttg gcggcagctt tagcgaacac gttgtggggg ttggaaacat  2760
catagttttg ctctagagtt agctcgtcat aggccatttt tacgaagcgg ggtaggaggg  2820
tgccagactg agggacgata gttccatctg gccccggtgc gtaattaccc tcgcagatct  2880
gcatctccca agctttaatt tccgagggag ggatcatgtc cacctggggg gcgataaaga  2940
acacggtttc tggcggggga ttaatgagct gggtggaaag caggttgcgc aagagctgag  3000
acttgccgca accggtggga ccgtagatga ccccgatgac gggctgcagc tggtagttga  3060
gagaggagca gctgccgtcg gggcgtagga ggggagccac ctcgttcatc atgcttctta  3120
catgtttatt ttcactgact aagctttgca agagcctctc cccacccagg gacaagagtt  3180
cttccaggct gttgaagtgt ttcagcggtt tcaggccgtc ggccatgggc atcttttcaa  3240
gcgactgacg aagcaagtac agccggtccc agagctcggt gacgtgctct atggaatctc  3300
gatccagcag acttcttggt tgcgggggtt gggccgactt tcgctgtagg gtacgagccg  3360
gtgggcgtcc agggccgcga gggttttgtc cttccagggt ctcagcgtcc gggtgagggt  3420
ggtctcggtg acggtgaacg gatgagcccc gggctgggcg cttgccaggg tgcgcttcag  3480
gctcatccgg ctggtgctga agcgggcgtc gtctccctgg gaatcggcca gatagcaacg  3540
gagcatgagg tcgtagctaa gggattcggc cgcgtgtccc ttggcgcgca gttttccctt  3600
ggaaacatgc tggcatctgg tgcagtgtaa acacttgagg gcgtacagct tgggggcgag  3660
gaagacggac tcgggcgagt aggcgtcggc cccgcactcg gcgcagacgg tttcacactc  3720
caccagccac gtgagctcgg gtttgtcggg gtcaaaaacc aggttgcctc catttttttt  3780
gatgcgtttc ttaccttgcg tctccatgag cctgtgaccc gcttcggtga caaaaaggct  3840
gtctgtgtct ccgtagaccg acttgagggg gcgttcttcc aagggcgtgc cgcggtcttc  3900
tgcgtacaaa aactgggacc actccgaaac gaaggccctg gtccacgcta acacgaagga  3960
tgcgatctgc gaggggtatc tgtcgttctc aatgagggga tccacctttt ccagggtatg  4020
cagacacagg tcgtcctcct ccgcgtccac aaaggtgatt ggcttgtaag tgtaggtcac  4080
gtgacttaat taattcgaac ccataatacc cataatagct gtttgccatc gacgcgaggc  4140
tggatggcct tccccattat gattcttctc gcttccggcg gcatcgggat gcccgcgttg  4200
caggccatgc tgtccaggca ggtagatgac gaccatcagg gacagcttca aggccagcaa  4260
aaggccagga accgtaaaaa ggccgcgttg ctggcgtttt tccataggct ccgcccccct  4320
gacgagcatc acaaaaatcg acgctcaagt cagaggtggc gaaacccgac aggactataa  4380
agataccagg cgtttccccc tggaagctcc ctcgtgcgct ctcctgttcc gaccctgccg  4440
cttaccggat acctgtccgc ctttctccct tcgggaagcg tggcgctttc tcatagctca  4500
cgctgtaggt atctcagttc ggtgtaggtc gttcgctcca agctgggctg tgtgcacgaa  4560
ccccccgttc agcccgaccg ctgcgcctta tccggtaact atcgtcttga gtccaacccg  4620
gtaagacacg acttatcgcc actggcagca gccactggta acaggattag cagagcgagg  4680
tatgtaggcg gtgctacaga gttcttgaag tggtggccta actacggcta cactagaagg  4740
acagtatttg gtatctgcgc tctgctgaag ccagttacct tcggaaaaag agttggtagc  4800
tcttgatccg gcaaacaaac caccgctggt agcggtggtt tttttgtttg caagcagcag  4860
attacgcgca gaaaaaaagg atctcaagaa gatcctttga tcttttctac ggggtctgac  4920
gctcagtgga acgaaaactc acgttaaggg attttggtca tgagattatc aaaaaggatc  4980
ttcacctaga tccttttaaa ttaaaaatga agttttaaat caatctaaag tatatatgag  5040
taaacttggt ctgacagtta ccaatgctta atcagtgagg cacctatctc agcgatctgt  5100
ctatttcgtt catccatagt tgcctgactc cccgtcgtgt agataactac gatacgggag  5160
ggcttaccat ctggccccag tgctgcaatg ataccgcgag acccacgctc accggctcca  5220
gatttatcag caataaacca gccagccgga agggccgagc gcagaagtgg tcctgcaact  5280
ttatccgcct ccatccagtc tattaattgt tgccgggaag ctagagtaag tagttcgcca  5340
gttaatagtt tgcgcaacgt tgttgccatt gctgcaggca tcgtggtgtc acgctcgtcg  5400
tttggtatgg cttcattcag ctccggttcc caacgatcaa ggcgagttac atgatccccc  5460
atgttgtgca aaaaagcggt tagctccttc ggtcctccga tcgttgtcag aagtaagttg  5520
gccgcagtgt tatcactcat ggttatggca gcactgcata attctcttac tgtcatgcca  5580
tccgtaagat gcttttctgt gactggtgag tactcaacca agtcattctg agaatagtgt  5640
atgcggcgac cgagttgctc ttgcccggcg tcaacacggg ataataccgc gccacatagc  5700
agaactttaa aagtgctcat cattggaaaa cgttcttcgg ggcgaaaact ctcaaggatc  5760
ttaccgctgt tgagatccag ttcgatgtaa cccactcgtg cacccaactg atcttcagca  5820
tcttttactt tcaccagcgt ttctgggtga gcaaaaacag gaaggcaaaa tgccgcaaaa  5880
aagggaataa gggcgacacg gaaatgttga atactcatac tcttcctttt tcaatattat  5940
tgaagcattt atcagggtta ttgtctcatg agcggataca tatttgaatg tatttagaaa  6000
aataaacaaa taggggttcc gcgcacattt ccccgaaaag tgccacctga cgtctaagaa  6060
accattatta tcatgacatt aacctataaa aataggcgta tcacgaggcc ctttcgtctt  6120
```

```
caagaattgg tcgatggcaa acagctatta tgggtattat gggttcgaat taat        6174

SEQ ID NO: 47          moltype = DNA  length = 16854
FEATURE                Location/Qualifiers
source                 1..16854
                       mol_type = other DNA
                       note = Synthetic oligonucleotide pBr/sAd4312.pIX-pV
                       organism = synthetic construct
SEQUENCE: 47
attaagtgat aagatatgat gaatccaagt ctcgttgtcg cccctgtgaa tgcggagcta  60
atcatttgag gttgtatccc gcgaccctga acgtaaccga ggagctgagg gccgaccacc  120
acatgttgtc ctgcttgcgc accgactatg agtccagcga cgaagagtga ggtgaggggc  180
ggagccacaa agggtataaa gggtcaggat gggtgggcac aggtattcaa aatgagcggg  240
acgacggacg gcaacgcgtt tgagggggga gtgttcagcc catatctgac atctcgtctt  300
ccttcctggg caggagtgcg tcagaatgta gtgggctcca ccgtggacgg acggccggtc  360
gcccctgcga attccgccac ccttacctat gccaccgtgg gatcaccgtt ggacactgcc  420
gcggcagccg cagcttctgc tgccgcttct actgctcgcg gtatggcggc tgactttgga  480
ctttataacc aactggctac cgcggctgtg gcatctcgca ctctggttca agaagatgcc  540
ctgagcgtgg ttctgcttcg actggaagat ctgtctcgtc gcttggatca gctggctgcg  600
cagatatccc cacctaaccc cgatactact caagaatctt aaataaagac aaacagattt  660
gttgaaaata aatggcttta tttgtttttt ttggctcgat aggctcgggt ccacctgtcc  720
cggtcgttaa ggactttgtg tatgctttcc aagacccggt acagatgggc ttggatgttt  780
agatacatgg gcatgaggcc atcccggggg tggagatagg accattgcag agcgtcatgc  840
tccggggtgg tgttgtagat gacccagtcg tagcagggtt tttgggcgtg gaactgaaaa  900
atgtccttga gaagcaggct gatggccagg ggcagaccct tagtgtaggt gttcacaaag  960
cggttgagct gggagggatg catgcgggga gagatgatat gcatcttagc ctggattttc  1020
aggttagcta tgttgccccc caggtccctt cgagggttca tattgtggag gaccaccaga  1080
acggtgtagc cggtacactt gggaaactta tcgtgcagtt tggaggggaa ggcgtgaaag  1140
aatttggaaa cccctttgtg accacctaag ttttccatgc actcgtccat gataatggcg  1200
atgggcccct tggcggcagc tttagcgaac acgttgtggg ggttggaaac atcatagttt  1260
tgctctagag ttagctcgtc ataggccatt tttacgaagc ggggtaggag ggtgccagac  1320
tgagggacga tagttccatc tggccccggt gcgtaattac cctcgcagat ctgcatctcc  1380
caagctttaa tttccgaggg agggatcatg tccacctggg gggcgataaa gaacacggtt  1440
tctggcgggg gattaatgag ctgggtggaa agcaggttgc gcaagagctg agacttgccg  1500
caaccggtgg gaccgtagat gaccccgatg acgggctgca gctggtagtt gagagaggag  1560
cagctgccgt cggggcgtag gaggggagcc acctcgttca tcatgcttct tacatgttta  1620
ttttcactga ctaagctttg caagagcctc tccccaccca gggacaagag ttcttccagg  1680
ctgttgaagt gtttcagcgg tttcaggccg tcggccatgg gcatcttttc aagcgactga  1740
cgaagcaagt acagccggtc ccagagctcg gtgacgtgct ctatggaatc tcgatccagc  1800
agacttcttg gttgcggggg ttgggccgac tttcgctgta gggtacgagc cggtgggcgt  1860
ccagggccgc gagggttttg tccttccagg gtctcagcgt ccgggtgagg gtggtctcgg  1920
tgacggtgaa cggatgagcc ccgggctggg cgcttgccag ggtgcgcttc aggctcatcc  1980
ggctggtgct gaagcgggcg tcgtctccct gggaatcggc cagatagcaa cggagcatga  2040
ggtcgtagct aagggattcg gccgcgtgtc ccttggcgcg cagttttccc ttggaaacat  2100
gctggcatct ggtgcagtgt aaacacttga gggcgtacag cttgggggcg aggaagacgg  2160
actcgggcga gtaggcgtcg gccccgcact cggcgcagac ggtttcacac tccaccagcc  2220
acgtgagctc gggtttgtcg gggtcaaaaa ccaggttgcc tccatttttt ttgatgcgtt  2280
tcttaccttg cgtctccatg agcctgtgac ccgcttcggt gacaaaaagg ctgtctgtgt  2340
ctccgtagac cgacttgagg gggcgttctt ccaagggcgt gccgcggtct tctgcgtaca  2400
aaaactggga ccactccgaa acgaaggccc tggtccacgc taacacgaag gatgcgatct  2460
gcgaggggta tctgtcgttc tcaatgaggg gatccacctt ttccagggta tgcagacaca  2520
ggtcgtcctc ctccgcgtcc acaaaggtga ttggcttgta agtgtaggtc acgtgaccgg  2580
cgcccccccgg aggggtataa aagggggcgt gcccaccctc cccgtcactt tcttccgcat  2640
cgctgtggac cagagccagc tgttcgggtg agtaggccct ctcaaaggcc ggcatgactt  2700
cggcactcaa gttgtcagtt tctacaaacg aggaggattt gatgttcacg tgccccgcgg  2760
cgatgctttt gatggtggag tggtccatct ggtcagaaaa cacgatcttt ttgttgtcaa  2820
gtttggtggc aaaagaccca tagagggcgt tggaaagcaa cttggcgatg gagcgcaggg  2880
tctgattttt ttcccgatcg gccctttcct tcgcggcgat gtttaattgc acgtactcgc  2940
gggccacgca tcgccattcc gggaacacgg cggtgcgctc gtcgggcagg atgcgcacgc  3000
gccagccgcg attgtgcagg gtgatcatgt ccacgctggt ggccacctcc ccccggaggg  3060
gctcgttggt ccaacacaat ctccctcctt ttctggagca gaacggaggg aggggatcta  3120
ggaggttggc gtgcgggggg tcggcgtcga tggtgaagat gccaggcagg agaactttat  3180
taaagtaatc gatctcggtt tccacgtctt gcaacgcctc ctcccatctc tttaccgcca  3240
gggccctctc gtaggggttc aggggcgccc cccagggcat ggggtgggtg agagccgagg  3300
cgtacatgcc acagatgtca tagacgtaga ggggctcccg taggaccccg atgtaagtgg  3360
gataacagcg ccccccgcgg atgctggccc gcacgtagtc gtacatctcg tgagatgggg  3420
ccaggagacc ctctcccaag tgggtcttgt ggggcttctc cgcccggtag aggatctgcc  3480
tgaagatggc gtgggagttg gaagagatgg tgggccgttg gaagacgtta aagttggccc  3540
gcggcagccc caccgagtct tcgatgaact gggcgtagga ttcctggagt ttgttcacga  3600
gggcggcggt gaccagcacg tccagggcgc agtaatccag ggtctcgcgg accaggttgt  3660
aggagctctc ttgtttttc tcccacagtt cgcggttgag gaggtattcc tcgcggtctt  3720
tccagtactc ttcggcggga aatccttttt cgtccgctcg gtaagaacct aacatgtaaa  3780
actcgttcac cgctttgtat ggacaacagc ctttctctac cggcagggcg tacgcctgag  3840
cggcctttct gagagaagtg tgggtgaggg cgaaggtgtc ccgcaccatg actttcaggt  3900
actgatgttt gaagtccgtg tcgtcgcagc ttccttgttc ccacaggctg aagtcggtgc  3960
gctttttctg cctcgggttg gggagggcga aagtgacatc gttaaacaag attttcccgg  4020
cgcggggcat aaagttgcga gagattctga agggccctgg cacgtccgag cggttgttga  4080
tgacctgcgc cgccaggacg atctcgtcga agccgttgat gttatgcccc acgatgtaca  4140
gttctatgaa gcgcggctgt cccttgaggg cgggcgcttt tttcagttcc tcgtaggtga  4200
```

-continued

```
gggactcggg agaggcgagc cccagctccg cgcgggccca gtcggccagt tgagggttag  4260
ccgcgaggaa ggaattccag agctccgagg ccagaagagt ttgcaagcga tcgcgaaact  4320
cgcggaactt tttccccacg gccatttttt ctggcgtgac cacgtagaaa gtggcggagc  4380
gatcgttcca gacgtcccac ttgagctccc gggccagctc gcaggcctga cgcacgagag  4440
tttcctcgcc cgagacgtgc atgaccaaca tgaaaggcac taactgtttt ccgaacgcgc  4500
ccatccacgt gtaggtctct acatcgtagg tgacaaagag ccgttgggtg cgtgcgtggg  4560
agccgatcgg aaagaagctg atctcctgcc accagctgga ggaatgggtg ttgatgtggt  4620
gaaagtagaa gtcccgccgg cgcacagagc attcgtgctg gtgtttgtaa aagcgaccgc  4680
agtagtcgca gcgctgcacg ctctgtattt cttgaatgag atgcactttt cgcccgcgaa  4740
ccagaaatcg gaggggaaag ttgagcccgg gggatggtgg agtcgcgtcc ccttcgcctt  4800
ggcggtgggc gtctgcgtct gcgtcctgtt tttctgggtg gacgacggtg gggacgacga  4860
cgccccgggt tccgcaagtc cagatttcag cgacggaggg gcgcagacgc agaaggaggg  4920
ggcgcagttg cccgctgtcc agagagtcga ggaaagcgac gctgaggtca gcggggagcg  4980
tttgcaaatt cactttcaag agaccggtaa gagcgtgagc caggtggaga tgatacttga  5040
tttccagggg ggtgttggaa gaggcgtcca cgccgtacaa gaggccgtgt ccgcgcggag  5100
ccaccacggt tccccgcgga ggttttatct cactcgccga gggcgagcgc cgggggggtag  5160
aggcggctct gcgccgggtg gtagcggagg cagaggcacg ttttcgtgag gattcggcag  5220
cggctgatga cgcgctcgga gactgctggc gtgggcgacg acgcggcggt tgaggtcctg  5280
gatgtgctgc ctctgcgtga agaccaccgg tcccctggtc ctgaacctga aagagagttc  5340
cacagagtca atgtctgcat cgttaacggc cgcctgcctg aggatctcct gcacgtcgcc  5400
cgagttgtct tggtaggcga tctcggccat gaactgttcg acttcttctt cgcggaggtc  5460
gccgtggccc gcgcgttcta cggtggcggc caggtcgtta gagatgcgac gcatgagctg  5520
ggagaaggcg ttgaggccgt tctcgttcca cacgcggctg tacaccacgt taccgaagga  5580
gtcgcgcgct cgcatgacca cctgcgccac gttgagttcc acgtggcggg cgaagacggc  5640
gtagtttctg aggcgctgga agaggtagtt gagcgtggtg gcgatgtgct cgcagacgaa  5700
gaagtacatg atccagcgcc tcagagtctg ctcgttgatg tctccgatgg cttcgaggcg  5760
ttccatggcc tcgtagaagt cgacggcgaa gttgaaaaat tgggagttgc gggcggccac  5820
cgtgagttct tcttgcagga ggcggatgag atcggcgacg gtgtcgcgca cctcctgttc  5880
gaaagcgccc cgaggcgcct ctgcttcttc ctccagctcc tcctcttcca ggggcacagg  5940
ttcctccggc acctctgcgg cggggacggg gcggcgacgt cgtcgtctga ccggcagtcg  6000
gtccacgaag cgttcgatca tttcaccgcg ccggcgacgc atggtctcgg tgacggcgcg  6060
tccgttttcg cggggacgca gttcgaagac gccgccgcgc agagcgcccc cgtgcaggga  6120
gggtaagtgg ttagggccgt cgggcagaga cacggcgctg acgatgcatt ttatcaattg  6180
ttgcgtaggc actccgtgca gggatctgag aacgtcgagg tcgacgggat ccgaaaactt  6240
ctctaggaaa gcgtctatcc aatcgcaatc gcaaggtaag ctgaggacgg tgggccgctg  6300
gggggcgtcc gcgggtagtt gggaggtgat gctgctgatg atgtaattaa agtaggcggt  6360
tttcaggcgg cggatggtgg cgaggaggac cacgtctttg ggcccggcct gttgaatgcg  6420
caggcgctcg gccatccccc aggcctcgct ctgacagcga cgcaggtctt tgtagtagtc  6480
ttgcatcagt ctctccaccg gaatctctgc ttctcccctg tctgccatgc gagtcgagcc  6540
gtacccccgc aagggctgca gcaacgctag gtctgccact actctttcgg ccagcacggc  6600
ctgttgaatc tgcgtgaggg tggcctggaa gtcgtccagg tccacgaagc ggtggtaggc  6660
tcccgtgttg atggtgtagg tgcagttggc catgacggac cagttgacga cttggatgcc  6720
gggttgggtg atctccgtgt acttgaggcg cgagtaggcc ctggactcga acacgtagtc  6780
gttgcatgcg cgcaccagat actggtagcc gacgagaaag tgcggaggcg gttcccgata  6840
caggggccag cccacggtgg cgggggctcc gggggccagg tcttccagca tgaggcggtg  6900
gtagtggtac acgtatcgag agagccaggt gatgccggct gaggtggtgg cggccctggt  6960
gaactcgcgg acgcggttcc agatgttgcg cagggggcgg aagcgttcca tggtgggcac  7020
gctctgtccc gtcaggcgcg cgcaatcctg tacgctctag atggagaaaa gacagggcgg  7080
tcatcgactc ccgtccgtag ctgggaggta aagtcgcaag ggtgcggcgg cggggaaccc  7140
cggttcgaga ccggctggat ccgccgttcc cgatgcgcct ggccccgcat ccacgacgtt  7200
cgcgccgaga cccagccgcg gcacaccgcc ccaatacgga ggggagtctt ttggtgtttt  7260
ttcatagatg catccggtgc tgcgacagat gcgaccccag acgcccactg ctactaccgc  7320
cgcggcggca gtaaacctga gcggaggcgg tgacagggag gacgaagagc tggctttaga  7380
cctggaagag ggagagggtc tggcgcgact gggcgccccc tcccccgaga gacaccccag  7440
ggtccagctc gtgagggatg cgagacaggc ttttgtaccg cggcagaacc tgtttaggga  7500
ccgcagcggc caggaggcgg aggagatgcg cgattgtcgg tttcgggcgg gcagagagct  7560
gagggcgggg ttcgaccggg agcggttgct gcgggcggag gatttcgaac ccgacgagcg  7620
gtcgggggtg agtccggccc gagcccacgt gtcggccgcc aacctggtga gtgcgtatga  7680
gcagacggtg aacgaggagc gtaactttca aaagagcttt aataatcacg ttcggaccct  7740
catcgcgagg gaggaggtgg ccatcgggct gatgcatctg tgggacttcg tggaggccta  7800
cgtgcagaac ccggcgagca agcccctgac ggctcagctg ttcctgatcg tgcagcacag  7860
ccgcgacaac gagacgtttc gcgacgccat gctcaacatc gccgagcccg agggccgctg  7920
gctcttggat cttatcaaca tcttgcagag catcgtggtt caggagaggg gtctcagctt  7980
agcggacaag gtggcggcca ttaactactc catgcagagt ctgggaaaat tctacgctcg  8040
caagatctac aagagcccct acgtgcccat agacaaggag gtgaagatag acagctttta  8100
catgcgcatg gcgctgaagg tgctgacgct gagcgacgat ctcggcgtgt accgtaacga  8160
caagatccac aaggcggtga gcgccagccg ccggcgggag ctgagcgata gggagctgat  8220
gcacagcctg cagagggcgc tggcgggtgc cggggacgag gagcgcgaga cttacttcga  8280
tatgggagcg gacttacagt ggaaacccag cgcccgagcg ttggaggcgg cgggctaccg  8340
tggcgacgag gatcgggatg actttgagga ggcaggcgag tacgaggacg aagcctgacc  8400
gggcaggtgt tgttttagat gcagcgtccg gcggacgggg ccaccgtgga tcccgcgctt  8460
ttggcatcca tgcagagtca acctacgggc gtgaccgcct ccgatgactg ggcggcggcc  8520
atggaccgca tcatggcact gaccacccgc aaccccgagg cttttaggca gcaaccccag  8580
gccaaccgtt tttcggccat cttggaagcg gtagtgccgt ctcgcactaa tccgacccac  8640
gaaaaggttt taactatcgt gaacgcgctg gtagacagca aggccatccg ccgcgacgag  8700
gcggggctga tttacaacgc tctgctggaa cgcgtggcgc gctacaacag cactaacgtg  8760
cagaccaatc tggaccgcct caccacggac gtgaaggaag cgttggctca gaaggagcgg  8820
ttcttaaggg acagcaatct gggttctctg gtggcgctga acgcttttct gagcacgcag  8880
ccggcgaacg taccccgcgg gcaggaggac tacgtgagct tcatcagcgc tctgagactg  8940
```

-continued

```
ctcgtttccg aggtgccgca gagcgaggtg taccagtcgg gacctgacta cttcttccag  9000
acgtcccgac agggcttgca aacggtgaac ctgactcagg cttttaaaaa cttgcaaggc  9060
atgtggggcg tgaaggcgcc ggttggcgat cgcgcgacca tttccagcct gctgaccccc  9120
aacacgagac tgctgttgct tttaatcgcc ccgttcacca acagcagcac catcagccgc  9180
gactcgtacc tgggccatct catcactctg taccgagagg ccataggtca ggctcagatt  9240
gacgagcata cgtatcaaga gatcaccaat gtgagccgag ccctgggtca ggaagacacc  9300
ggcagtttgg aagccacgct aaactttctg ctgaccaatc ggagacaaaa gattccctcg  9360
cagtacacgt taagcgccga ggaggagagg attctgcgct acgtgcagca gtccgtgagc  9420
ctgtacttga tgcgggaggg tgctaccgct tccacggcct tggacatgac ggctcgaaac  9480
atggaaccgt ctttttactc agcccaccgt ccgttcatca atcgcctgat ggactacttc  9540
catcgcgcgg ccgccatgaa cggggagtat ttcaccaatg ccatcttgaa tccgcattgg  9600
atgcctccgt ccggtttcta caccggggag ttcgacctgc ccgaggccga cgacggcttt  9660
ctgtgggacg atgtgtccga cagcattttt acgccaggta acagtcgttt ccataaaaag  9720
gaagggggag acgaacttcc cctttcgagt gtggaggcgg cctccagggg ggagagcccc  9780
ttttccagct tgtcttccgt gagtagcggt cgggtgacgc gcccacgctt gccgggggag  9840
agcgactacc taaacgaccc tttgctgcga ccggctaaaa agaaaaattt tcccaacaac  9900
ggggtggaaa gcttggtgga taaaatgaat cgttggaaga cctacgctca ggagcagcgg  9960
gagtgggagg acagtcagcc ccgaccgctg gtcccgccgc actggcgccg ccagagagaa  10020
gacccggacg actccgcaga cgatagtagc gtgttggact tgggagggag cggagccaac  10080
ccctttgctc acttgcaacc caaggggcgc ttgagtcgcc tgtactaata aaaagaaagc  10140
ggaaacgtac cagagccatg gccacagcgt gtgtcctttc ttcctctctt tcctcctcgg  10200
cgcggcagaa tgagaagagc ggtgagagtc acgccggcgg tgtatgccga gggtccgccc  10260
ccttcttacg aaagcgtgat gggatcagcg aacgtgccgg ccacgctgga ggcgccttac  10320
gttcctccca gatacctggg acctaccgag ggcagaaaca gcatccgtta ctccgagctg  10380
gcccccctgt acgataccac caaggtgtac ctggtggaca acaagtcggc ggacatcgcc  10440
tccctgaatt accaaaacga ccacagcaac ttcctgacca ccgtggtgca gaacaatgac  10500
ttcaccccga cggaggcggg cacgcaaacc attaactttg acgagcgttc ccgctggggc  10560
ggtcagctga aaaccatcct gcacaccaac atgcccaaca tcaacgagtt tatgtccacc  10620
aacaagttta gggccaggtt gatggtagag aagactagcg gccagccgcc caaatacgag  10680
tggttcgagt tcaccattcc cgagggtaac tactccgaga ccatgactat cgatctcatg  10740
aataacgcga tcgtggacaa ttacctgcaa gttggaaggc aaaacggggt attggagagc  10800
gacataggag taaaatttga taccaggaac ttccgactgg ggtgggatcc ggtgaccaag  10860
ctggtgatgc ctggcgtgta caccaacgag gcttttcacc ccgatatcgt gctgcttccg  10920
gggtgcggag tggactttac gcagagccgc ttgagtaacc tgttaggaat caggaagcgc  10980
cgtccctttc aggagggctt tcagattatg tatgaggact tggagggagg taatattcca  11040
ggcctgctag acgtgccggc ctatgaacaa agcttacaac aggcccaaga ggagggaaga  11100
gtcactcgcg gagacacctt tgccacggct cccaacgagg tagtgattaa gcccttattg  11160
aaagacagta aggatagaag ttataatatt ataaccgaca ccacggacac tttgtaccgg  11220
agttggtttc tggcttacaa ctacggggac cccgaaaacg gagtgagatc atggaccata  11280
ctcaccacca cggacgtgac ctgcggctcg cagcaagtgt actggtccct gccggatatg  11340
atgcaagacc cagtcacctt ccgcccctcc acccaagtca gcaactttcc ggtggtgggc  11400
actgagctgt tgcccgttca cgccaagagc ttctacaacg agcaggctgt ttattcgcaa  11460
ctcattcgcc agtctaccgc gcttacccac gtattcaacc gtttccccga gaaccagatt  11520
ctcgtgcgcc ctcccgctcc taccattacc accgtgagtg aaaacgttcc cgccctcaca  11580
gatcacggaa ccctgccgct gcgcagcagt atcagtggag ttcagcgcgt gaccatcacc  11640
gacgccagac gtcgaacctg cccttacgtt tacaaagcgc tcggcgtagt ggccccaaaa  11700
gtgctctcta gtcgcacctt ctaaaacatg tccattctca tctctcccga taacaacacc  11760
ggctggggac tgggctccgg caagatgtat ggcggggcga agcggcgctc cagtcagcac  11820
cctgttcgcg ttcggggtca tttccgcgct ccctggggag cttacaaacg aggactctcg  11880
ggccgaacgg cggtagacga caccattgac gccgtcattg ccgatgcccg ccggtataac  11940
cccggaacgg tcgctagcgc cgcctccacc gtggattccg tgatcgacag cgtggtggcc  12000
ggcgccaggg cctacgctcg ccgcaaaagg cggctgcacc gcaggcgtcg acccacggcc  12060
gccatgctgg ccgccagggc cgtgctgaga cgggcccgca gggtaggcag gagggccatg  12120
cgccgcgcgg ccgccaacgc tgccgccggg agggcccgca ggcaagccgc cagccgggcc  12180
gccgccgcca tcgctaacat ggccagaccc aggagaggga acgtttactg ggtgcgcgat  12240
tctgtgacgg gagtcagagt gccggtgcgc agccgacctc cccgaagtta gaagaccaaa  12300
ggtgcgaaga cggcgtactg agtctccctg ttgttatcag cccaacatga gcaagcgcaa  12360
gtttaaagaa gaactcctgc agaccctggc tcctgaaatc tatggccctc cggacgtgaa  12420
gcccgacatt aagccccgcg atatcaagcg tgttaaaaag cgggaaaaaa aagaggaact  12480
cgcggtggta gacgatggcg gggtagaatt tattagaagt ttcgccccgc gacgcagggt  12540
gcagtggaaa gggcggcgcg tgcaacgcgt tctcaggcca ggcaccgcgg tagtttttac  12600
tccgggagag cggtcggctg tcaggggttt caagcggcaa tatgacgagg tgtacggcga  12660
cgaagacatc ctggaacagg cggctcagca gattggagaa ttcgcctacg gaaagcggtc  12720
tcgccgcgaa gacctggcca ttgccttgga cagtggcaac cccacccccca gcctcaaacc  12780
cgtcacgctg cagcaggtgc tccccgtgag cgcgagcacg gagagcaaaa ggggaatcaa  12840
gagagagatg gaagatctga agcccaccat ccaacttatg gtccctaaac gacagaagct  12900
ggaggaggtt ctggaaaaca tgaaagtgga ccccagcata gagccggatg taaaagtgag  12960
gcctattaag gaagtggctc cgggtctcgg ggtgcaaacg gtggacattc agatcccagt  13020
cagatccgct tcgaccgccg tggaagccat ggaaacgcaa accgaaactc cggtcgcggc  13080
cggtaccaga gaagtggctt tgcaaacgga gccctggtac gaatacaccg ctcctcggcg  13140
ccagaggcgg cgttacggcc cggcaaatgc catcatgcca gagtatgcgc tgcacccgtc  13200
tatccgaccc acccccggct accgggggt aacgtatcgc ccgtcgccaa cccgacgccg  13260
ttatcgtcgc cgccgccgtt ctcgtcgcgc tctggcgccc gtgtccgtgc gacgcgtaac  13320
gcgccgggga agaacagtca ccatccctaa cccgcgctac caccctagca ttctttaatg  13380
actctgccgt tttgcagatg gctctgactt gccgcgtgcg ccttcccgtt ctgcactatc  13440
gaggaagatc tcgtcgtagg agaggcatgg cggggagcgg ccgccgtcgg gctttacgca  13500
ggcgcatgaa aggcggaatt ttgcccgcac tgattcccat aattgccgcc gccattgggg  13560
cgatacccgg cgttgcttca gtggccttgc aagcagctcg taataaataa acgaaggctt  13620
ttcaacttat gacctggtcc tgactatttt atgcagaaaa agcatggaag acatcaattt  13680
```

```
tacgtcgctg gctccgcggc aaggctcacg cccgctcatg ggcacctgga acgacatcgg  13740
cagcagccag ctcaacgggg gcgctttcaa ttgggggagc ctttggagcg gcattaaaaa  13800
ctttggctcc gcgattaaat cctacggcag caaagcctgg aacagtagta ctggtcagat  13860
gctccgggat aaactgaagg acacaaactt tcaagagaaa gtggtcaacg gggtggtgac  13920
cggcatccac ggcgcggtgg atctcgctaa tcaagcggtg caaaaagaga tagacagacg  13980
atgggaaaac tcgcgggtgc ctccgcagag aggggacgaa gtggaggtgg aggaagtaga  14040
agtcgaggag aaactgcccc cgctagagaa agttcccggg gcgccgccca ggccacagaa  14100
gcgtccccgg ccggatctgg aagaaacttt agtgacggaa accatcgaac ctccctcgta  14160
cgaacaagct ttaaaggagg gcgcctctcc ttaccccatg actaagccca tcgcgcccat  14220
ggcgcgtccg gtgtacggaa aagatcacaa gccagtaacg ttagagctac cccaccacc  14280
cccttcccgt cctacggtgc ctccgttacc cgccccgtcg gcaggtccca gctctgcacc  14340
atccgcagct cctgcaccaa ccgctcgccc ggtggccgtg gcaaccgcca gagcccccag  14400
aggatccaac tggcaaagca cgctgaacag catcgtgggc ttgggagtga aaaccctaaa  14460
acgccgccgc tgctattatt aaagagtgta gctaaaaatt tcccgttgta tacgcctcct  14520
atgttaccgc cagagacgcg tgactggtcg ccgctccgcc gctttcaaga tggccacccc  14580
atcgatgatg ccgcagtggt cttacatgca catcgccggc caggacgcct cggagtacct  14640
gagtcccggc ctggtgcagt ttgcccgcgc caccgaaagc tacttcagct tgggaaacaa  14700
gtttagaaac cccaccgtgg cccccacgca cgatgtaacc acggaccgct cgcagaggct  14760
gacacttaat taattcgaac ccataatacc cataatagct gtttgccatc gacgcgaggc  14820
tggatggcct tccccattat gattcttctc gcttccggcg gcatcgggat gcccgcgttg  14880
caggccatgc tgtccaggca ggtagatgac gaccatcagg gacagcttca aggccagcaa  14940
aaggccagga accgtaaaaa ggccgcgttg ctggcgtttt tccataggct ccgcccccct  15000
gacgagcatc acaaaaatcg acgctcaagt cagaggtggc gaaacccgac aggactataa  15060
agataccagg cgtttccccc tggaagctcc ctcgtgcgct ctcctgttcc gaccctgccg  15120
cttaccggat acctgtccgc ctttctccct tcgggaagcg tggcgctttc tcatagctca  15180
cgctgtaggt atctcagttc ggtgtaggtc gttcgctcca agctgggctg tgtgcacgaa  15240
ccccccgttc agcccgaccg ctgcgcctta tccggtaact atcgtcttga gtccaacccg  15300
gtaagacacg acttatcgcc actggcagca gccactggta acaggattag cagagcgagg  15360
tatgtaggcg gtgctacaga gttcttgaag tggtggccta actacggcta cactagaagg  15420
acagtatttg gtatctgcgc tctgctgaag ccagttacct tcggaaaaag agttggtagc  15480
tcttgatccg gcaaacaaac caccgctggt agcggtggtt tttttgtttg caagcagcag  15540
attacgcgca gaaaaaaagg atctcaagaa gatcctttga tcttttctac ggggtctgac  15600
gctcagtgga acgaaaactc acgttaaggg attttggtca tgagattatc aaaaaggatc  15660
ttcacctaga tccttttaaa ttaaaaatga agttttaaat caatctaaag tatatatgag  15720
taaacttggt ctgacagtta ccaatgctta atcagtgagg cacctatctc agcgatctgt  15780
ctatttcgtt catccatagt tgcctgactc cccgtcgtgt agataactac gatacgggag  15840
ggcttaccat ctggccccag tgctgcaatg ataccgcgag acccacgctc accggctcca  15900
gatttatcag caataaacca gccagccgga agggccgagc gcagaagtgg tcctgcaact  15960
ttatccgcct ccatccagtc tattaattgt tgccgggaag ctagagtaag tagttcgcca  16020
gttaatagtt tgcgcaacgt tgttgccatt gctgcaggca tcgtggtgtc acgctcgtcg  16080
tttggtatgg cttcattcag ctccggttcc caacgatcaa ggcgagttac atgatccccc  16140
atgttgtgca aaaaagcggt tagctccttc ggtcctccga tcgttgtcag aagtaagttg  16200
gccgcagtgt tatcactcat ggttatggca gcactgcata attctcttac tgtcatgcca  16260
tccgtaagat gcttttctgt gactggtgag tactcaacca agtcattctg agaatagtgt  16320
atgcggcgac cgagttgctc ttgcccggcg tcaacacggg ataataccgc gccacatagc  16380
agaactttaa aagtgctcat cattggaaaa cgttcttcgg ggcgaaaact ctcaaggatc  16440
ttaccgctgt tgagatccag ttcgatgtaa cccactcgtg cacccaactg atcttcagca  16500
tcttttactt tcaccagcgt ttctgggtga gcaaaaacag gaaggcaaaa tgccgcaaaa  16560
aagggaataa gggcgacacg gaaatgttga atactcatac tcttcctttt tcaatattat  16620
tgaagcattt atcagggtta ttgtctcatg agcggataca tatttgaatg tatttagaaa  16680
aataaacaaa taggggttcc gcgcacattt ccccgaaaag tgccacctga cgtctaagaa  16740
accattatta tcatgacatt aacctataaa aataggcgta tcacgaggcc ctttcgtctt  16800
caagaattgg tcgatggcaa acagctatta tgggtattat gggttcgaat taat        16854
```

```
SEQ ID NO: 48          moltype = DNA  length = 21377
FEATURE                Location/Qualifiers
source                 1..21377
                       mol_type = other DNA
                       note = Synthetic oligonucleotide pBr/sAd4312.pV-rITR
                       organism = synthetic construct
SEQUENCE: 48
attaaccgaa gttagaagac caaaggtgcg aagacggcgt actgagtctc cctgttgtta  60
tcagcccaac atgagcaagc gcaagtttaa agaagaactc ctgcagaccc tggctcctga  120
aatctatggc cctccggacg tgaagcccga cattaagccc cgcgatatca agcgtgttaa  180
aaagcgggaa aaaaaagagg aactcgcggt ggtagacgat ggcggggtag aatttattag  240
aagtttcgcc ccgcgacgca gggtgcagtg gaaagggcgg cgcgtgcaac gcgttctcag  300
gccaggcacc gcggtagttt ttactccggg agagcggtcg gctgtcaggg gtttcaagcg  360
gcaatatgac gaggtgtacg gcgacgaaga catcctggaa caggcggctc agcagattgg  420
agaattcgcc tacggaaagc ggtctcgccg cgaagacctg gccattgcct tggacagtgg  480
caaccccacc cccagcctca aacccgtcac gctgcagcag gtgctccccg tgagcgcgag  540
cacggagagc aaaaggggaa tcaagagaga gatggaagat ctgaagccca ccatccaact  600
tatggtccct aaacgacaga agctggagga ggttctggaa aacatgaaag tggaccccag  660
catagagccg gatgtaaaag tgaggcctat taaggaagtg gctccgggtc tcggggtgca  720
aacggtggac attcagatcc cagtcagatc cgcttcgacc gccgtggaag ccatggaaac  780
gcaaaccgaa actccggtcg cggccggtac cagagaagtg gctttgcaaa cggagccctg  840
gtacgaatac accgctcctc ggcgccagag gcggcgttac ggcccggcaa atgccatcat  900
gccagagtat gcgctgcacc cgtctatccg acccaccccc ggctaccggg gggtaacgta  960
tcgcccgtcg ccaacccgac gccgttatcg tcgccgccgc cgttctcgtc gcgctctggc  1020
gcccgtgtcc gtgcgacgcg taacgcgccg gggaagaaca gtcaccatcc ctaacccgcg  1080
```

-continued

```
ctaccaccct agcattcttt aatgactctg ccgttttgca gatggctctg acttgccgcg  1140
tgcgccttcc cgttctgcac tatcgaggaa gatctcgtcg taggagaggc atggcgggga  1200
gcggccgccg tcgggcttta cgcaggcgca tgaaaggcgg aattttgccc gcactgattc  1260
ccataattgc cgccgccatt ggggcgatac ccggcgttgc ttcagtggcc ttgcaagcag  1320
ctcgtaataa ataaacgaag gcttttcaac ttatgacctg gtcctgacta ttttatgcag  1380
aaaaagcatg gaagacatca attttacgtc gctggctccg cggcaaggct cacgcccgct  1440
catgggcacc tggaacgaca tcggcagcag ccagctcaac gggggcgctt tcaattgggg  1500
gagcctttgg agcggcatta aaaactttgg ctccgcgatt aaatcctacg gcagcaaagc  1560
ctggaacagt agtactggtc agatgctccg ggataaactg aaggacacaa actttcaaga  1620
gaaagtggtc aacggggtgg tgaccggcat ccacggcgcg gtggatctcg ctaatcaagc  1680
ggtgcaaaaa gagatagaca gacgatggga aaactcgcgg gtgcctccgc agagagggga  1740
cgaagtggag gtggaggaag tagaagtcga ggagaaactg cccccgctag agaaagttcc  1800
cggggcgccg cccaggccac agaagcgtcc ccggccggat ctggaagaaa ctttagtgac  1860
ggaaaccatc gaacctccct cgtacgaaca agctttaaag gagggcgcct ctccttaccc  1920
catgactaag cccatcgcgc ccatggcgcg tccggtgtac ggaaaagatc acaagccagt  1980
aacgttagag ctacccccac cacccccttc ccgtcctacg gtgcctccgt tacccgcccc  2040
gtcggcaggt cccagctctg caccatccgc agctcctgca ccaaccgctc gcccggtggc  2100
cgtggcaacc gccagagccc ccagaggatc caactggcaa agcacgctga acagcatcgt  2160
gggcttggga gtgaaaaccc taaaacgccg ccgctgctat tattaaagag tgtagctaaa  2220
aatttcccgt tgtatacgcc tcctatgtta ccgccagaga cgcgtgactg gtcgccgctc  2280
cgccgctttc aagatggcca ccccatcgat gatgccgcag tggtcttaca tgcacatcgc  2340
cggccaggac gcctcggagt acctgagtcc cggcctggtg cagtttgccc gcgccaccga  2400
aagctacttc agcttgggaa acaagtttag aaaccccacc gtggccccca cgcacgatgt  2460
aaccacggac cgctcgcaga ggctgacact gcgcttcgtg cccgtagacc gggaggacac  2520
cgcgtactcc tacaaagtgc gcttcaccct cgccgtaggg gacaacaggg tgctggacat  2580
ggccagcacg tactttgaca tccggggaat gctggaccga gggcccagct ttaaacccta  2640
ctcgggaact gcctacaatt cgctggcacc taagggcgct cccaacccta gtcaatggac  2700
tactaccaac ggagggaata aaacaaattc atttgcccaa gcatcctaca taggtcaaag  2760
cctgtcgaaa gacggggtgc aagtagcagt agatacagcc gctgggggg ctgcagtata  2820
tgctgacaaa acgtttcaac cagaacccca agtaggaata tcacaatgga atgaaaatcc  2880
tactacaaat gctgcaggaa gaattttaaa gcctactacc gcaatgcgtc catgctacgg  2940
ttcatacgct taccccacca acgaaaaagg tgggcaggta aaaatcactg accctaacaa  3000
tgacaaaacc ggcgctaata acgttagctt aaatttttc aacactgccg ctgacaatgg  3060
gaataacaat ccaaaagtag tactctacag cgaagatgta aatttagaag ggccagatac  3120
ccaccttgtt tttaagccag atgtaactgg cgacgcaacc agtgcagaaa ccctgttagg  3180
tcaacaagca gctcccaatc gtccaaacta cattgggttc agggacaact ttattggcct  3240
gatgtactac aattcaactg gaaacatggg agtgctagca ggtcaggctt ctcagctaaa  3300
cgccgtagtg gatcttcaag acagaaatac cgaattgtca tatcagctaa tgcttgacgc  3360
tttgggtgac agaagtcggt acttttctat gtggaatcaa gcagtggaca gctacgatcc  3420
tgacgttaga atcatagaaa atcatggagt agaagacgaa cttccaaatt attgttttcc  3480
gttaaatgga caggggattt cgaatacata caaaggtgtg aaatataaca caaacacttg  3540
gacgcaagac actgatgtag tcacaaccaa tgaaatttcc attggcaaca tttttgccat  3600
ggaaataaac ctggcggcta acttgtggcg cagctttctg tactccaatg tcgccctgta  3660
cttgccagat tcctacaaat acactcccga caatattgaa cttcctacaa acaagaacag  3720
ctacggctac attaacggaa gggtaaccgc ccccactgcc atcgacactt acgttaacat  3780
cggcgcccgg tggtctccgg accccatgga caacgttaac cctttcaacc accaccgcaa  3840
cgccggcttg cgataccgct ccatgctgct gggcaacggt cgctacgtac ccttccacat  3900
tcaggtgccc cagaaatttt ttgccattaa aaacctgctt ctgcttcccg ggtcctacac  3960
ctacgagtgg aacttcagga aagatgtaaa catgatcttg cagagcacct tgggcaacga  4020
cctccgcgtt gacggagcta gcgtgaggtt tgacagcatt aacctctacg ctaacttctt  4080
ccccatggcc cacaacacgg cctccacctt ggaagccatg ctgcgcaacg acaccaacga  4140
ccagtccttt aatgattacc tgtgcgcggc caacatgctg taccccatcc ccgccaatgc  4200
caccagcgtg ccgatctcca ttccctcacg caactgggcc gccttcagag gttggagttt  4260
cactcgcctg aaaaccaagg agacccccctc gctgggctcc ggtttcgacc catactttgt  4320
ttactccggg agcattccct acctggacgg aactttctac ctgaaccaca ccttcaaaaa  4380
ggtgtctatt atgtttgact cctccgtgag ctggcccggt aacgaccgct tgctaacccc  4440
caacgagttc gaaatcaaac gctcggtgga cggagagggt tacaatgtag cccagagcaa  4500
catgaccaaa gactggtttt taattcaaat gctaagccac tataacattg gctaccaagg  4560
attctacgtg cctgaagcct acaaggacag aatgtactcc ttctttagaa acttccaacc  4620
catgagccgc caggtagtag acacggtaaa ctatgctaac tacaaggaag taacaatgcc  4680
attccagcac aacaactcag gcttcgtggg gtacatggga cctaccatga gagaggggca  4740
ggcctacccg gctaattatc cctacccccct aatcggagcc actgccgtgc ccagcctgac  4800
acagaaaaag tttctctgcg atcgaacaat gtggaggatt cccttctcta gcaacttcat  4860
gtccatgggg gctctcaccg acctggggca gaacatgctg tacgctaact ccgctcacgc  4920
cttggacatg acctttgagg tggaccccat ggatgagccc acgcttctct atgttctgtt  4980
tgaagtcttc gacgtggtgc gcattcacca gccgcaccgc ggcgtcatcg aggccgtcta  5040
cctgcgcaca cctttctctg ccggtaacgc caccacctaa gaagctgatg ggctccagcg  5100
aacaggagct gcgggccatt gttcgcgacc tgggctgcgg gccctacttt ttgggcacct  5160
tcgacaagcg cttccccggc ttcatgtccc cccacaagcc ggcctgcgcc atcgtcaaca  5220
cggccggacg cgagaccggg ggggttcact ggctcgcctt tgcctggaac ccgcgtaacc  5280
acacctgcta cctgttcgac ccttttggtt tttctgacga aaggcttaaa cagatttacc  5340
agttcgagta cgaggggctc cttaaacgca gcgctctggc ctccacgccc gaccactgcg  5400
tcaccctgga gaagtccacc caaacggttc agggtcccct ctcggcggcc tgcggactct  5460
tttgttgcat gtttttgcat gctttcgtcc actggccgaa cacccccatg gaccgcaacc  5520
ccactatgga tctgctcacg ggagtgccta acagcatgct tcacagccct caggtcgcac  5580
ccaccctgcg tcgcaatcag gaacagctgt atgcttttct gggaaaacat tctgcctact  5640
ttcgccgcca ccggcagcgc atagaacagg ccacggcctt tgaaagcatg agtcaaagag  5700
tgtaatcaat aaaatcaact tttattttac atcacacgcg cttctggcgt tttcttaaaa  5760
atcaaagggt tcgggggagg ggtcgtcgtg cccgctgggc agggacacgt tgcgatactg  5820
```

-continued

```
gaagcggggg ctccagcgga actcggggat cgccagccgg ggcagaggca cttcttccag  5880
gttctgcttc caaaactgcc gcaccagctg gagggctccc attacgtcgg gcgccgagat  5940
cttgaagtcg cagttggggc ccgagcttcc gcggctgttg cgaaacacgg ggttggcaca  6000
ctggaacacc agcacgctcg ggtagttgat actggccagg gccgttgcgt cggtcaccgc  6060
cgttacatcc agatcctccg cgttggtcag ggcgaaggga gtcagcttgc acatctgccg  6120
cccgatgtgg ggcacgccgt catgcttgtt gaggcagtcg caacgcaggg gaatcagaat  6180
gcgatgctgg ccgcgttgca tctgagggta gttggcccgc aagaacgctt ccatctgacg  6240
gaaggccgtc tgggctttca ttccctcggt gtagaaaaga ccgcaggact tgctagaaaa  6300
tacattattg ccgcaggtga cgtcttccgc gcagcagcgg gcgtcttcgt tctttagctg  6360
caccacgttg cgaccccacc ggttctgtac caccttggcc ctcgtgggct gctccttcag  6420
cgcccgctgg ccgttttcgc tggtcacatc catttccaac acgtgctcct tacacaccat  6480
ttccactccg tggaagcaga acaggacgcc ctcctgctgg gtattgcgat gctcccacac  6540
ggcgcagcct gtggcctccc agctcttatg cttcaccccc gcgtagtttt ccatgtaagc  6600
catcaggaat ctgcccatca tctcggtaaa ggttttctga ctggtgaagg tcaaaggcaa  6660
gccgcggtgc tcttcgttca gccacgtttg acagatcttg cggtacgtgg cgccctgatc  6720
cggcagaaac ttaaacgccc ccttgctctc gttgtccacg tggaactttt ccatcagcat  6780
tagcataact tccataccct tctcccacgc cgtcaccagc ggtgtgctgt cggggttctt  6840
caccaacatg gtagaagggc cctcgccggc cctgaagtcg ctcatactca ttttttgaaa  6900
ctccacagtg ccgtccgcac gacggacccg gcgcatcgga gggtagctga agccaacctc  6960
caccagggtg ccttcgctct cgctgtcgga gacgatctcc ggggagggcg gcggcgcggg  7020
tgtcgacttg cgagccttct tcttgggagg aagcggtggc gcctcttggt cgcgctcggg  7080
actcatctcc ctcaagtagg gggtgatgga gcttcctgct tggttctgac ggttggccat  7140
tgtatcctag gcagaaacac atggagctta tgcgcgagga aactttaacc gccccgtccc  7200
ccgtcaacga cgaagaggtc atcatcgaac aggacccggg ctacgttact ccgcccgagg  7260
atctggaggg gcctttagac gaccggcgcg acgctagtga gcagcaggaa aatgagaaag  7320
aggaagcctg ctacctcctg gaaggcgacg tgttgctaaa acatttcgcc aggcagagca  7380
ccatagtgaa ggaggctttg caagaccgct cggaggtgcc cttggacgtc gccgcgctct  7440
cccaggccta cgaggcgaac ctcttctcgc cccgagtgcc tccgaagaga cagcccaacg  7500
gcacctgcga gcccaacccg cgccttaact tctaccccgt gttcgccgtg cccgaggcgc  7560
tggccaccta ccacattttt ttcaagaacc agcgcatccc gctctcgtgc cgggccaacc  7620
gcaccgcggc cgatagaaag ctgagactca aaaacggagc tagcatacct gatatcacgt  7680
ccctggagga agtgcctaag atcttcgaag gtctgggtcg agacgagaaa cgggcggcaa  7740
acgctctgca gaaagaacag aaggacagtc agaacgtgct ggtggaactg gagggggaca  7800
atgcgcgtct ggccgttctc aagcgctgca tagaagtttc ccacttcgcc taccctgccc  7860
tgaacctgcc gcccaaagtc atgcgctcgg tcatggacca gctgctcatc aagagagctg  7920
agcccctgaa ccccgagcac cccgaggcgg agaactcgga ggacggaaag cccgtcgtca  7980
gcgacgagga gctcgagcgg tggctggaca gcacggaccc cgagcagttg caagagcggc  8040
gcaaaatgat gatggcggcc gtcctggtca ccgttgagct ggagtgcctg cagcggtttt  8100
ttagcgacgt ggaaacgctg cgtaaaatcg gagagtccct gcactacacc ttccgccagg  8160
gctacgtccg ccaggcctgc aagatctcca acgtggagct cagcaacctg gtctcctaca  8220
tgggcatcct ccacgagaac cggctgggac agagcgtgct gcactgcacc ttgcaaggcg  8280
aggcgcggcg ggactacgtg cgagactgcg tctacctctt cctcactctc acctggcaga  8340
ccgccatggg agtgtggcag cagtgcttgg aagacagaaa cctcaaagag ctagacaaac  8400
tcctctgccg ccagcggcgc gccctgtggt ccggtttcag cgagcgcacg gtcgccagcg  8460
ctctggcgga catcatcttc ccggagcgcc tgatgaaaac cttgcaaaac ggcctgccgg  8520
atttcatcag tcaaagcatt ttgcaaaact tccgctcttt tgtcctggaa cgctccggga  8580
tattgcccgc catgagctgc gcgctacctt ctgactttgt ccccctctcc taccgcgagt  8640
gccctccccc actgtggagc cactgctacc tcttccaact ggccaacttt ctggcctacc  8700
actccgacct catggaagac gtaagcggag agggtttact ggagtgccac tgccgctgca  8760
acctgtgcac cccccacaga tcgctggcct gcaacaccga gctactcagc gaaacccagg  8820
tcataggtac cttcgagatc caggggcccc agcagcaaga gggtgcttcc ggcttgaagc  8880
tcactccggc gctgtggacc tcggcttact tacgcaaatt tgtagccgag gactaccacg  8940
cccacaaaat tcagttttac gaagaccaat ctcgaccacc gaaagccccc ctcacggcct  9000
gcgtcatcac ccagagcaag atcctggccc aattgcaatc catcaaccaa gcgcgccgcg  9060
atttcctttt gaaaaagggt cgggggggtgt acctggaccc ccagaccggc gaggaactca  9120
acccgtccac actctccgtc gaagcagccc ccccgagaca tgccgcccaa gggaaccgcc  9180
aagcagctga tcgctcggca gagagcgaag aagcaagagc tgctccagca gcaggtggag  9240
gacgaggaag agatgtggga cagccaggca gaggaggtgt cagaggacga ggaggagatg  9300
gaaagctggg acagcctaga cgaggaggag gacgagcttt cagaggaaga ggcgaccgaa  9360
gaaaaaccac ctgcatccag cgcgccttct ctgagccgac agccgaagcc ccggcccccg  9420
acgcccccgg ccggctcact caaagccagc cgtaggtggg acgccaccga atctccagcg  9480
gcagcggcaa cggcagcggg taaggccaaa cgcgagcggc gggggtattg ctcctggcgg  9540
gcccacaaaa gcagtattgt gaactgcttg caacactgcg ggggaaacat ctcctttgcc  9600
cgacgctacc tcctcttcca tcacggtgtg gccttccctc gcaacgttct ctattattac  9660
cgtcatctct acagccccta cgaaacgctc ggagaaaaaa gctaaggcct cctccgccgc  9720
gaggaaaaac tccgccgccg ctgccgccgc caaggatcca ccggccaccg aagagctgag  9780
aaagcgcatc tttcccactc tgtatgctat ctttcagcaa agccgcgggc agcaccctca  9840
gcgcgaactg aaaataaaaa accgctcctt ccgctcgctc acccgcagct gtctgtacca  9900
caagagagaa gaccagctgc agcgcaccct ggacgacgcc gaagcactgt tcagcaaata  9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
cttagaacag gcggcaatca ccgccacacc ccggcgccaa ctcaacccgc ctagttggcc  10260
cgccgcccag gtgtatcagg aaaatccccg cccgaccaca gtcctcctgc cacgcgacgc  10320
ggaggccgaa gtcctcatga ctaactctgg ggtacaatta gcgggcgggt ccaggtacgc  10380
caggtacaga ggtcgggccg ctccttactc tcccgggagt ataaagaggg tgatcattcg  10440
aggccgaggt atccagctca acgacgagac ggtgagctcc tcaaccggtc tcagacctga  10500
cggagtcttc cagctcggag gagcaggccg ctcttccttc accactcgcc aggcctacct  10560
```

```
gaccctgcag agctcttcct cgcagccgcg ctccggggga atcggcactc tccagttcgt  10620
ggaagagttc gttccctccg tctacttcaa ccccttctcc ggctcgcctg gacgctaccc  10680
ggacgccttc attcccaact ttgacgcagt gagtgaatcc gtggacggct acgactgatg  10740
acagatggtg cggccgtgag agctcggctg cgacatctgc atcactgccg tcagcctcgc  10800
tgctacgctc gggaggcgat cgtgttcagc tactttgagc tgccggacga gcaccctcag  10860
ggtccggctc acgggttgaa actcgagatc gagaacgcgc tcgagtctcg cctcatcgac  10920
accttcaccg cccgacctct cctggtagaa atccaacggg ggatcactac catcaccctg  10980
ttctgcatct gccccacgcc cggattacat gaagatctgt gttgtcatct ttgcgctcag  11040
tttaataaaa actgaacttt ttgccgcacc ttcaacgcca cgcgttgttt ctccaacagt  11100
cgacgatagc tcttcaatta aaggtacccg agaaactgtt tattttgaca attctactac  11160
ttctcttatc cttaactgtt cttgcactaa cgaactaatt cagtggttcg ccaacggttc  11220
actctgcaaa gttttccttg actctgcgat acttcccgga tttagcagct ctgcgtgtga  11280
taattctacc ccctccacct taaccatcac aaagccattt tcagaagtcc agtatttttg  11340
tattggagcg gggggtaaac cgggctgtat tcaccgcttc tttctggaga catttgttgc  11400
ttcgattccc attaacactt cactttcctc taatacatac ttaactacct tacattctac  11460
tcacccctcc tggaaacctc ttattggcct cacagctttt atttccgttg ttttactaaa  11520
ctttataatt cttaacaaac tttcttaaac atgcttgcca ttttgcttct gctcgttact  11580
ttaacctccg cagattacca caatgcaatt gtacgagaaa acagtttaca aaacccatca  11640
caggtatatg ttaaagcagg ttctaactta actctacaat ccttctattc gccttaccct  11700
gaggacatgc cacgtgtcac ctggtactta gaagtttttg attcgctatt tgaaagacat  11760
acaattcctc catttttac aggcgttata ctttgtgaca tttctggtga catacagcat  11820
gtgtggaacc attggccttt acaatttaat tgcataaata aaagcttaca tattatcaat  11880
ctcaaaccaa gtgatgaagg cctttacaat gtgaaggttt taaagggcag cattcagcat  11940
aatacatact ttcgtgtgca tgtagtaagt tttccaaaac ctgaatgtaa catcaccact  12000
acatatcttt cagatgacta ctgccttatt aacattgatt gctctcaatt accataccct  12060
gctaaggtct attataatgg caatgaaagt aagctgcatt actacttatc tgaacgcggt  12120
ggccaaccaa accttccaaa ttactttact gttgggtatc gatatagaga tctccgacag  12180
aattatacag ttgaatatcc atttaatgaa ctctgtacag atataattgc tcttgaaaca  12240
gggtctgatt ttacgccaat ttttatagtt accctagtgg tgagcattat agttattgtg  12300
atgggcatca catatcttat ttatcactgt aggactttaa aaaccaaaac caaaaccaag  12360
cctcctgaaa tccgtctgct ttaatttttt ccagaatggt agctgctttc ttcattctcc  12420
tctgtatacc aatcatctgc gcctccacaa cttttgccgc tgtttcccac ctggaaccag  12480
actgtctacc acctttgtt gtatacctaa tactgacttt tgtggtctgt acagccatta  12540
ccagtatagc ctgctttttt gtaacaattt tccaagccgc cgattacctc tacgtacggt  12600
ttgcttactt tagacatcac cccgagtatc ggaatcaaaa cgtagcctct ctgctttgtt  12660
tagcatgatt cgcattttta tactttgtaa gctctttacc accacaatat gtcaatgccc  12720
ttttaccaaa ccctggtcct tttacacttg ttataatgta ttacccgaaa cccccattgc  12780
ctggctttac gtagccacag cggctttagt ttttgtagca acctgcattg gcgttaaact  12840
gtacttttac ttaaaaattg gatggcttca tcccccagaa gatttacccc gatatcctct  12900
tgttaataac tttcaacagc ctctaccgcc tcctgatctt ccgcgagctc cctccgttgt  12960
tagctacttt caactcaccg gtggagatga ctgacactca ggacattaac attactgtgg  13020
aaagaatagc tgctcagcgt cagcgagaga cgcgggtgat ggagtacgtg gaactacagc  13080
agcttaaaga gtcccactgg tgtgaaaaag gagtgctttg ccatgttaag caagcagccc  13140
tttcttacga tgtcagcact cagggacatg aactgtccta cactttgcct ttacagaaac  13200
aaaccttctg caccatgatg ggctctacct ccattacaat cagccaacaa accggacctg  13260
tcgagggggc tatcctgtgt cactgtcacg cgcctgattg tatgcccaaa ctaatcagaa  13320
ctctttgtgc tttaggtgat atatttaaaa tatagatagt atcaataaac ttaccttaaa  13380
tttgacagca atttttggt atcatcattc agcagcacca ctttaccctc ttcccaactc  13440
tcatatggga tatgatggtg ggcggcaaac ttcctccaaa ccctgaaaga aatatcggta  13500
tccacttcct tgtcctcacc cacaattttc atcttttcat agatgaaaag aacccgagtt  13560
gatgaagact tcaaccccgt ctacccttat gacaccacaa ccactccagc cgttcctttc  13620
atatcacccc cgtttgtaaa cagtgacggt cttcaggaaa accccccggg agttttaagc  13680
ctgcgaatag ctaaacccct gtattttgac atggagagaa aactagccct ttcacttgga  13740
agagggttaa caattaccgc gaacggacaa ttagaaagca cccagagcgt gcagactaac  13800
ccgccgttaa ctgtcaccaa taacaacaca cttatcctac gccactcctc ccctttaatc  13860
ctaactgaca ataatttaac cgtaggcttc tcaagtcctc tccgtgttat agacaacaaa  13920
ctgacattca cttttacctc acctctccgt tatgaaaacg aaacccttac cttcaattac  13980
acagagcccc ttacacttat gaacagcaac cttgcgctta acgtaaactc ctctaaaggc  14040
cttagggttg acgggggctc actaggtaca aacttaagtc cggacttaag gtttaacagc  14100
agtggagcca tagcttttgg tatacaaacc ctatggacac ccccgacctc aaatcctaac  14160
tgcaccgttt acaccgaaag cgattcctta cttagtctct gcttaactaa atgcggagct  14220
cacgttttag gaagtgtaag cttaaccggg gtagcaggta ccatgataaa catggctgaa  14280
acttcgcttg ctattgaatt tacgtttgac gacactggaa aactacttca ctcaccactt  14340
gttaacacca cttttagcat tcgtcagggc gacagccccg cctcaaatcc tacctacaat  14400
gctctagcat ttatgccaaa cagtaccctc tacgctagag gaggaagtgg tgaaccccga  14460
aacaattact acgtccaaac atacctcagg ggaaatgttc agagaccgat taccctcact  14520
gttactttca actcagccgc cacgggatat tccttatctt ttaagtggac tgctgttgca  14580
cgtgaaaaat ttgcagctcc tgcaacttca ttttgctaca ttaccgaaca ataaaaccct  14640
gtgttcccac cgtttcgttt tttccagatg aaacgggcca gagttgatga agacttcaat  14700
cccgtgtacc cttacgatcc cccttacgcc cccattatgc cgtttattac cccgccgttt  14760
acatcttcag atgggttaca ggaaaaacca cttggtgttt taagtttaaa atacaaggat  14820
cctatcacta cacaaaatgg ttctctaacc cttaaattag gaaacgggct gaacattaac  14880
aaccagggcc aacttacatc atctgctggg gaagtcgagc ctcccctcac caatgctgac  14940
aacaagctgg ccttagccta cagcgaccct ctgacattaa aaaacagccg tctaacactg  15000
tctcacaatg ccccacttgc aattaacaat aattctctaa gtttggaagt atcagagcct  15060
atatttataa ataacgacaa caaactgtct ctgaaagctg acgcccccct gacaaccagc  15120
gctggaaccc tccgcctgca aagcgctgct ccattaggac ttgctgaaca gacactaaag  15180
ctgctgtttt ctaacccttt gtacttgcga ggtgacttcc ttacattagc cattgaacgc  15240
ccattggctg taacagcaga cgggctatta tcacttgccc tcaaccctcc gctcacaaca  15300
```

```
actaacacag gcttagctct ctctaccgcg gttccattaa ctgttaccaa cgggaacctt  15360
agcctaaacg taaaacggcc gtttattata caggacggca gcctttacat ggattttaga  15420
cccccactat atctgtttaa cagcgagcca caacttggtg ttaattttaa tgcccctcta  15480
actgttagag ataacggcct agctataaac accggagacg ggctaacagt aacgtataat  15540
aaactaacat taaacctcgg tagagacttg caatatgaaa atggagctgc agctgttaag  15600
ctaagtaccg cccctcctct acagtatact actcaactgc agctgaattt gggagcgggc  15660
ttacgtctag gtcctactag gaacttagac gtggccatta accacaataa agggttagcg  15720
tgggaaaaca atgaagtggt tactaaatta ggacaaggcc tttactttga ttcctccgga  15780
agcatagctt tatcgcctac aaaccccaga ccagatactt tatggaccac ggccgatcct  15840
tcgccaaact gcactgtata tgaatcactt gactctagac tgtggctagc gcttgttaaa  15900
tgtgggggaa tggtacacgg cagcatagcc ctacaagctg aaaaaggcca attgctgcgt  15960
cctactgcta gttttatctc catcgtaatt tacttctaca gtgatggggt ccgtcgcacc  16020
aactacccta caattggcaa tgatgagggt actctggcca acagcgctac ttggggctac  16080
agacaagggc aatctgcaga caccaacgtc accaatgctg ttgaattcat gcctagttta  16140
cacagatatc ctataaatca gggagacaat attaaaaacc aaatgataac ttacacttgc  16200
atacaaggca acgtgaacat gccagtaccc ttgaaaatca cgttcaatca tgctcttgaa  16260
ggctactcct taaagtttac atggcgtgtg gtggctaatg aaaagtttga tattccttgc  16320
tgttcgtttt cttacattac agaacaataa aacaactttt ttatttttca tttcttttat  16380
tttacacgca cagtaagact tcctcccccc ttccatttaa cagcgtacac cagcctttcc  16440
cccttcatgg cggtaaactt ctgtgagtta gtccggtatt tgggagttaa aatccaaaca  16500
ggctctttgg tgattaaacg ttgatccgtg atggacacaa atccctgaga caggtcctcc  16560
aacgttgcgg taaaaaactg aacgccgccc tacaaaacaa acagttcagg ctctccacgg  16620
gttatcaccc cgatcaaact cagacagagt aaaggtgcgg tgatgttcca caagaccgcg  16680
caagtggcgc tgtctaaagc tctcagtgcg acttctatgc ggctggtagg atgttacatt  16740
atccaacagc ctcacagcgc ggattattag tctacgagtg cgcctggcgc agcagcgcat  16800
ctgaatttca gtcaagtctt gacaagaagc gcataccata acaatcaggt tgttcatgat  16860
cccatagcta aacgcgctcc agccaaaact cattcgctcc aacagcacca ccgcgtgtcc  16920
gtcaagtctt acttttacat aaacaaggtg tctgccacgt acatacatgc tacccgcata  16980
caaaacttcc cggggcaaac ctctattcac cacctgtctg taccagggaa acctgatgtt  17040
tatcagggaa ccatagatgg ccattttaaa ccagttagcc agcaccaccc cgccagctct  17100
acactgaagg gaaccgggag agttacaatg acagtggatc atccacctct cgtaacccct  17160
aattacctga ttaaaatcca aatctaacgt ggcacaacag atacacactc tcataaacat  17220
tttcatgaca tgtttttccc aggatgttaa aatacaatcc caatacacgg gccactcctg  17280
taatacaata aagctaatgc atgatggaac gctcctcacc tcactaacat tgtgcatgtt  17340
tacattttca cactctaagt accgagtcct ctcctcaaca gccgcagtgt cgcgctcctc  17400
acacggtggt agctgatgac aattgtaagg ggccagtctg cagcgatatc gtctgtcgcg  17460
ctgcatcgta aaacagggac cgtctcactt cctcgtactt ccaatagcag aaccacgtcc  17520
gctgccagca ggtttccacg aaccgccgat cccttcgtcg ttcacgctcc ctcctcaacg  17580
caaaatgcag ccactcctgc aatccacaca aatccctctc ggcctccgga gtcatgcaca  17640
cctcatacct atatatgtct cggtacagtt ccaaacacga agtaagggcg agctccaacc  17700
aacacaaaca ggctgattta tcccgacaca ctggaggtgg aggaagacac ggaagaggca  17760
tgttattcca agcgatccgg caaaggatca aagtgcagat cccgaagatg gcaacgctcg  17820
cctccggagc cctggtgaaa tttaacggcc aaatcaaaca ttatgcggtt ttccaaacta  17880
tcaatcgccg cctccaaaag ggcctgaacc cgcacttcca caatcaccag caaagcaaaa  17940
gcgtgattat caaagtcttc aatcatcaga tggcatgact gtacaatgcc caaataattc  18000
tcatttctcc actcgcgaat agtgtcgcgg cagatcgtct gaaggtccat gccatgcatg  18060
ttaaaaagct cccagagggc gccctctacc gacatgcgta gacacaccat catgactgca  18120
aaatatcagg ctcctgagac acctgcagca gatttaacag atcaaagtca ggttgctgtc  18180
cgcggtcacg aatctccatg cgcaaagcca tttgcaaaaa attatatagg tctgtgccaa  18240
ctagctctgt taattccgcg ttaggaagca aatcaggtga ggctatgcag cacaaaagtt  18300
gcagggaagg cgccaaactc agtaaaaccg ctccagaata acaaaattga tgaagcggag  18360
tcacacagtg taaaatgtgc aaccaaaaat cattcagctg ctcttttaaa tagtccagta  18420
cttctatatt caatccgtgc aagtactgaa gcaactgcgc gggaacagtc acattaaaaa  18480
aaatggggcg gctcaaatac atgtcgacct aaaataaaaa taatcattaa accagagaag  18540
cttgacgaat ggaaggataa aatacacgct ccagcaaaag gcaggcaacc ggctgtcccc  18600
gagaaccgta aaaaaattca tccgaatgat taaaaagaac cacagaaatt tcccaccatg  18660
tactcggttg taactcctga gcacacagca acacccccct aacgttcatg tccgccactg  18720
aaaaaagacg tcccaaatac ccaggtggaa tgtcaagaga caactgcaga gacagcaaaa  18780
caacccctct gggagcgatc ataaactcct ccggtgagaa aagcgcatac aaattagaat  18840
aaccctgttg ctggggcaaa atagcccggc ggcccagcaa atggacataa atatgttcag  18900
cagccatcgc cccgtcttac cgcgtaaaaa gccagaaaaa tccagctaac tacactctac  18960
agcctattac tatatatact ctcctcccac tgacgctata ccaccccgcc cacgtccaaa  19020
gttcacccac gcccaaaaaa cccgcgaaaa tccagcgccg tcagcacttc cgcaattgta  19080
gtctctcaac gtcacttccg cgcgcctttt ccctattccc acacacgccc gcggacttcg  19140
ccccgcccgc cctcgcgcca ccccgcgtca ccccgcgtca ccgcacgtca ccccggcccc  19200
gcctcgctcc tccccactca ttatcatatt ggcacgtttc cagaataagg tatattattg  19260
atgatgttaa ttaattcgaa cccataatac ccataatagc tgtttgccat cgacgcgagg  19320
ctggatggcc ttccccatta tgattcttct cgcttccggc ggcatcggga tgcccgcgtt  19380
gcaggccatg ctgtccaggc aggtagatga cgaccatcag ggacagcttc aaggatcgct  19440
cgcggctctt accagcccag caaaaggcca ggaaccgtaa aaaggccgcg ttgctggcgt  19500
ttttccatag gctccgcccc cctgacgagc atcacaaaaa tcgacgctca agtcagaggt  19560
ggcgaaaccc gacaggacta taaagatacc aggcgtttcc ccctggaagc tccctcgtgc  19620
gctctcctgt tccgaccctg ccgcttaccg gatacctgtc cgcctttctc ccttcgggaa  19680
gcgtggcgct ttctcatagc tcacgctgta ggtatctcag ttcggtgtag gtcgttcgct  19740
ccaagctggg ctgtgtgcac gaaccccccg ttcagcccga ccgctgcgcc ttatccggta  19800
actatcgtct tgagtccaac ccggtaagac acgacttatc gccactggca gcagccactg  19860
gtaacaggat tagcagagcg aggtatgtag gcggtgctac agagttcttg aagtggtggc  19920
ctaactacgg ctacactaga aggacagtat ttggtatctg cgctctgctg aagccagtta  19980
ccttcggaaa aagagttggt agctcttgat ccggcaaaca aaccaccgct ggtagcggtg  20040
```

```
gtttttttgt ttgcaagcag cagattacgc gcagaaaaaa aggatctcaa gaagatcctt  20100
tgatcttttc tacggggtct gacgctcagt ggaacgaaaa ctcacgttaa gggattttgg  20160
tcatgagatt atcaaaaagg atcttcacct agatcctttt aaattaaaaa tgaagtttta  20220
aatcaatcta aagtatatat gagtaaactt ggtctgacag ttaccaatgc ttaatcagtg  20280
aggcacctat ctcagcgatc tgtctatttc gttcatccat agttgcctga ctccccgtcg  20340
tgtagataac tacgatacgg gagggcttac catctggccc cagtgctgca atgataccgc  20400
gagacccacg ctcaccggct ccagatttat cagcaataaa ccagccagcc ggaagggccg  20460
agcgcagaag tggtcctgca actttatccg cctccatcca gtctattaat tgttgccggg  20520
aagctagagt aagtagttcg ccagttaata gtttgcgcaa cgttgttgcc attgctgcag  20580
gcatcgtggt gtcacgctcg tcgtttggta tggcttcatt cagctccggt tcccaacgat  20640
caaggcgagt tacatgatcc cccatgttgt gcaaaaaagc ggttagctcc ttcggtcctc  20700
cgatcgttgt cagaagtaag ttggccgcag tgttatcact catggttatg gcagcactgc  20760
ataattctct tactgtcatg ccatccgtaa gatgcttttc tgtgactggt gagtactcaa  20820
ccaagtcatt ctgagaatag tgtatgcggc gaccgagttg ctcttgcccg gcgtcaacac  20880
gggataatac cgcgccacat agcagaactt taaaagtgct catcattgga aaacgttctt  20940
cggggcgaaa actctcaagg atcttaccgc tgttgagatc cagttcgatg taacccactc  21000
gtgcacccaa ctgatcttca gcatctttta ctttcaccag cgtttctggg tgagcaaaaa  21060
caggaaggca aaatgccgca aaaaagggaa taagggcgac acggaaatgt tgaatactca  21120
tactcttcct ttttcaatat tattgaagca tttatcaggg ttattgtctc atgagcggat  21180
acatatttga atgtatttag aaaaataaac aaataggggt tccgcgcaca tttccccgaa  21240
aagtgccacc tgacgtctaa gaaaccatta ttatcatgac attaacctat aaaaataggc  21300
gtatcacgag gccctttcgt cttcaagaat tggtcgatgg caaacagcta ttatgggtat  21360
tatgggttcg aattaat                                                 21377
```

```
SEQ ID NO: 49          moltype = DNA  length = 19308
FEATURE                Location/Qualifiers
source                 1..19308
                       mol_type = other DNA
                       note = Synthetic oligonucleotide pBr/sAd4312.pV-rITR.dE3
                       organism = synthetic construct
SEQUENCE: 49
attaaccgaa gttagaagac caaaggtgcg aagacggcgt actgagtctc cctgttgtta  60
tcagcccaac atgagcaagc gcaagtttaa agaagaactc ctgcagaccc tggctcctga  120
aatctatggc cctccggacg tgaagcccga cattaagccc cgcgatatca agcgtgttaa  180
aaagcgggaa aaaaaagagg aactcgcggt ggtagacgat ggcggggtag aatttattag  240
aagtttcgcc ccgcgacgca gggtgcagtg gaaagggcgg cgcgtgcaac gcgttctcag  300
gccaggcacc gcggtagttt ttactccggg agagcggtcg gctgtcaggg gtttcaagcg  360
gcaatatgac gaggtgtacg gcgacgaaga catcctggaa caggcggctc agcagattgg  420
agaattcgcc tacggaaagc ggtctcgccg cgaagacctg gccattgcct tggacagtgg  480
caaccccacc cccagcctca aacccgtcac gctgcagcag gtgctccccg tgagcgcgag  540
cacggagagc aaaaggggaa tcaagagaga gatggaagat ctgaagccca ccatccaact  600
tatggtccct aaacgacaga agctggagga ggttctggaa aacatgaaag tggaccccag  660
catagagccg gatgtaaaag tgaggcctat taaggaagtg gctccgggtc tcggggtgca  720
aacggtggac attcagatcc cagtcagatc cgcttcgacc gccgtggaag ccatggaaac  780
gcaaaccgaa actccggtcg cggccggtac cagagaagtg gctttgcaaa cggagccctg  840
gtacgaatac accgctcctc ggcgccagag gcggcgttac ggcccggcaa atgccatcat  900
gccagagtat gcgctgcacc cgtctatccg acccaccccc ggctaccggg gggtaacgta  960
tcgcccgtcg ccaacccgac gccgttatcg tcgccgccgc cgttctcgtc gcgctctggc  1020
gcccgtgtcc gtgcgacgcg taacgcgccg gggaagaaca gtcaccatcc ctaacccgcg  1080
ctaccaccct agcattcttt aatgactctg ccgttttgca gatggctctg acttgccgcg  1140
tgcgccttcc cgttctgcac tatcgaggaa gatctcgtcg taggagaggc atggcgggga  1200
gcggccgccg tcgggcttta cgcaggcgca tgaaaggcgg aattttgccc gcactgattc  1260
ccataattgc cgccgccatt ggggcgatac ccggcgttgc ttcagtggcc ttgcaagcag  1320
ctcgtaataa ataaacgaag gcttttcaac ttatgacctg gtcctgacta ttttatgcag  1380
aaaaagcatg gaagacatca attttacgtc gctggctccg cggcaaggct cacgcccgct  1440
catgggcacc tggaacgaca tcggcagcag ccagctcaac gggggcgctt tcaattgggg  1500
gagcctttgg agcggcatta aaaactttgg ctccgcgatt aaatcctacg gcagcaaagc  1560
ctggaacagt agtactggtc agatgctccg ggataaactg aaggacacaa actttcaaga  1620
gaaagtggtc aacggggtgg tgaccggcat ccacggcgcg gtggatctcg ctaatcaagc  1680
ggtgcaaaaa gagatagaca gacgatggga aaactcgcgg gtgcctccgc agagagggga  1740
cgaagtggag gtggaggaag tagaagtcga ggagaaactg cccccgctag agaaagttcc  1800
cggggcgccg cccaggccac agaagcgtcc ccggccggat ctggaagaaa ctttagtgac  1860
ggaaaccatc gaacctccct cgtacgaaca agctttaaag gagggcgcct ctccttaccc  1920
catgactaag cccatcgcgc ccatggcgcg tccggtgtac ggaaaagatc acaagccagt  1980
aacgttagag ctacccccac cacccccttc ccgtcctacg gtgcctccgt tacccgcccc  2040
gtcggcaggt cccagctctg caccatccgc agctcctgca ccaaccgctc gcccggtggc  2100
cgtggcaacc gccagagccc ccagaggatc caactggcaa agcacgctga acagcatcgt  2160
gggcttggga gtgaaaaccc taaaacgccg ccgctgctat tattaaagag tgtagctaaa  2220
aatttcccgt tgtatacgcc tcctatgtta ccgccagaga cgcgtgactg gtcgccgctc  2280
cgccgctttc aagatggcca ccccatcgat gatgccgcag tggtcttaca tgcacatcgc  2340
cggccaggac gcctcggagt acctgagtcc cggcctggtg cagtttgccc gcgccaccga  2400
aagctacttc agcttgggaa acaagtttag aaaccccacc gtggcccccca cgcacgatgt  2460
aaccacggac cgctcgcaga ggctgacact gcgcttcgtg cccgtagacc gggaggacac  2520
cgcgtactcc tacaaagtgc gcttcaccct cgccgtaggg gacaacaggg tgctggacat  2580
ggccagcacg tactttgaca tccggggaat gctggaccga gggcccagct ttaaacccta  2640
ctcgggaact gcctacaatt cgctggcacc taagggcgct cccaacccta gtcaatggac  2700
tactaccaac ggagggaata aaacaaattc atttgcccaa gcatcctaca taggtcaaag  2760
cctgtcgaaa gacggggtgc aagtagcagt agatacagcc gctgggggg ctgcagtata  2820
tgctgacaaa acgtttcaac cagaacccca agtaggaata tcacaatgga atgaaaatcc  2880
```

```
tactacaaat gctgcaggaa gaattttaaa gcctactacc gcaatgcgtc catgctacgg  2940
ttcatacgct taccccacca acgaaaaagg tgggcaggta aaaatcactg accctaacaa  3000
tgacaaaacc ggcgctaata acgttagctt aaatttttc aacactgccg ctgacaatgg  3060
gaataacaat ccaaaagtag tactctacag cgaagatgta aatttagaag ggccagatac  3120
ccaccttgtt tttaagccag atgtaactgg cgacgcaacc agtgcagaaa ccctgttagg  3180
tcaacaagca gctcccaatc gtccaaacta cattgggttc agggacaact ttattggcct  3240
gatgtactac aattcaactg gaaacatggg agtgctagca ggtcaggctt ctcagctaaa  3300
cgccgtagtg gatcttcaag acagaaatac cgaattgtca tatcagctaa tgcttgacgc  3360
tttgggtgac agaagtcggt acttttctat gtggaatcaa gcagtggaca gctacgatcc  3420
tgacgttaga atcatagaaa atcatggagt agaagacgaa cttccaaatt attgttttcc  3480
gttaaatgga caggggattt cgaatacata caaaggtgtg aaatataaca caaacacttg  3540
gacgcaagac actgatgtag tcacaaccaa tgaaatttcc attggcaaca tttttgccat  3600
ggaaataaac ctggcggcta acttgtggcg cagctttctg tactccaatg tcgccctgta  3660
cttgccagat tcctacaaat acactcccga caatattgaa cttcctacaa acaagaacag  3720
ctacggctac attaacggaa gggtaaccgc ccccactgcc atcgacactt acgttaacat  3780
cggcgcccgg tggtctccgg accccatgga caacgttaac cctttcaacc accaccgcaa  3840
cgccggcttg cgataccgct ccatgctgct gggcaacggt cgctacgtac ccttccacat  3900
tcaggtgccc cagaaatttt ttgccattaa aaacctgctt ctgcttcccg ggtcctacac  3960
ctacgagtgg aacttcagga aagatgtaaa catgatcttg cagagcacct tgggcaacga  4020
cctccgcgtt gacggagcta gcgtgaggtt tgacagcatt aacctctacg ctaacttctt  4080
ccccatggcc cacaacacgg cctccacctt ggaagccatg ctgcgcaacg acaccaacga  4140
ccagtccttt aatgattacc tgtgcgcggc caacatgctg taccccatcc ccgccaatgc  4200
caccagcgtg ccgatctcca ttccctcacg caactgggcc gccttcagag gttggagttt  4260
cactcgcctg aaaaccaagg agaccccctc gctgggctcc ggtttcgacc catactttgt  4320
ttactccggg agcattccct acctggacgg aactttctac ctgaaccaca ccttcaaaaa  4380
ggtgtctatt atgtttgact cctccgtgag ctggcccggt aacgaccgct tgctaacccc  4440
caacgagttc gaaatcaaac gctcggtgga cggagagggt tacaatgtag cccagagcaa  4500
catgaccaaa gactggtttt taattcaaat gctaagccac tataacattg gctaccaagg  4560
attctacgtg cctgaagcct acaaggacag aatgtactcc ttctttagaa acttccaacc  4620
catgagccgc caggtagtag acacggtaaa ctatgctaac tacaaggaag taacaatgcc  4680
attccagcac aacaactcag gcttcgtggg gtacatggga cctaccatga gagaggggca  4740
ggcctacccg gctaattatc cctacccccct aatcggagcc actgccgtgc ccagcctgac  4800
acagaaaaag tttctctgcg atcgaacaat gtggaggatt cccttctcta gcaacttcat  4860
gtccatgggg gctctcaccg acctggggca gaacatgctg tacgctaact ccgctcacgc  4920
cttggacatg acctttgagg tggaccccat ggatgagccc acgcttctct atgttctgtt  4980
tgaagtcttc gacgtggtgc gcattcacca gccgcaccgc ggcgtcatcg aggccgtcta  5040
cctgcgcaca cctttctctg ccggtaacgc caccacctaa gaagctgatg ggctccagcg  5100
aacaggagct gcgggccatt gttcgcgacc tgggctgcgg gccctacttt ttgggcacct  5160
tcgacaagcg cttccccggc ttcatgtccc cccacaagcc ggcctgcgcc atcgtcaaca  5220
cggccggacg cgagaccggg ggggttcact ggctcgcctt tgcctggaac ccgcgtaacc  5280
acacctgcta cctgttcgac ccttttggtt tttctgacga aaggcttaaa cagatttacc  5340
agttcgagta cgaggggctc cttaaacgca gcgctctggc ctccacgccc gaccactgcg  5400
tcaccctgga gaagtccacc caaacggttc agggtcccct ctcggcggcc tgcggactct  5460
tttgttgcat gtttttgcat gctttcgtcc actggccgaa cacccccatg gaccgcaacc  5520
ccactatgga tctgctcacg ggagtgccta acagcatgct tcacagccct caggtcgcac  5580
ccaccctgcg tcgcaatcag gaacagctgt atgcttttct gggaaaacat tctgcctact  5640
ttcgccgcca ccggcagcgc atagaacagg ccacggcctt tgaaagcatg agtcaaagag  5700
tgtaatcaat aaaatcaact tttattttac atcacacgcg cttctggcgt tttcttaaaa  5760
atcaaagggt tcgggggagg ggtcgtcgtg cccgctgggc agggacacgt tgcgatactg  5820
gaagcggggg ctccagcgga actcggggat cgccagccgg ggcagaggca cttcttccag  5880
gttctgcttc caaaactgcc gcaccagctg gagggctccc attacgtcgg gcgccgagat  5940
cttgaagtcg cagttggggc ccgagcttcc gcggctgttg cgaaacacgg ggttggcaca  6000
ctggaacacc agcacgctcg ggtagttgat actggccagg gccgttgcgt cggtcaccgc  6060
cgttacatcc agatcctccg cgttggtcag ggcgaaggga gtcagcttgc acatctgccg  6120
cccgatgtgg ggcacgccgt catgcttgtt gaggcagtcg caacgcaggg gaatcagaat  6180
gcgatgctgg ccgcgttgca tctgagggta gttggcccgc aagaacgctt ccatctgacg  6240
gaaggccgtc tgggctttca ttccctcggt gtagaaaaga ccgcaggact tgctagaaaa  6300
tacattattg ccgcaggtga cgtcttccgc gcagcagcgg gcgtcttcgt tctttagctg  6360
caccacgttg cgaccccacc ggttctgtac caccttggcc ctcgtgggct gctccttcag  6420
cgcccgctgg ccgttttcgc tggtcacatc catttccaac acgtgctcct tacacaccat  6480
ttccactccg tggaagcaga acaggacgcc ctcctgctgg gtattgcgat gctcccacac  6540
ggcgcagcct gtggcctccc agctcttatg cttcaccccc gcgtagtttt ccatgtaagc  6600
catcaggaat ctgcccatca tctcggtaaa ggttttctga ctggtgaagg tcaaaggcaa  6660
gccgcggtgc tcttcgttca gccacgtttg acagatcttg cggtacgtgg cgccctgatc  6720
cggcagaaac ttaaacgccc ccttgctctc gttgtccacg tggaactttt ccatcagcat  6780
tagcataact tccataccct tctcccacgc cgtcaccagc ggtgtgctgt cggggttctt  6840
caccaacatg gtagaagggc cctcgccggc cctgaagtcg ctcatactca ttttttgaaa  6900
ctccacagtg ccgtccgcac gacggacccg gcgcatcgga gggtagctga agccaacctc  6960
caccagggtg ccttcgctct cgctgtcgga gacgatctcc ggggagggcg gcggcgcggg  7020
tgtcgacttg cgagccttct tcttgggagg aagcggtggc gcctcttggt cgcgctcggg  7080
actcatctcc ctcaagtagg gggtgatgga gcttcctgct tggttctgac ggttggccat  7140
tgtatcctag gcagaaacac atggagctta tgcgcgagga aactttaacc gccccgtccc  7200
ccgtcaacga cgaagaggtc atcatcgaac aggacccggg ctacgttact ccgcccgagg  7260
atctggaggg gcctttagac gaccggcgcg acgctagtga gcagcaggaa aatgagaaag  7320
aggaagcctg ctacctcctg gaaggcgacg tgttgctaaa acatttcgcc aggcagagca  7380
ccatagtgaa ggaggctttg caagaccgct cggaggtgcc cttggacgtc gccgcgctct  7440
cccaggccta cgaggcgaac ctcttctcgc cccgagtgcc tccgaagaga cagcccaacg  7500
gcacctgcga gcccaacccg cgccttaact tctaccccgt gttcgccgtg cccgaggcgc  7560
tggccaccta ccacattttt ttcaagaacc agcgcatccc gctctcgtgc cgggccaacc  7620
```

```
gcaccgcggc cgatagaaag ctgagactca aaaacggagc tagcatacct gatatcacgt  7680
ccctggagga agtgcctaag atcttcgaag gtctgggtcg agacgagaaa cgggcggcaa  7740
acgctctgca gaaagaacag aaggacagtc agaacgtgct ggtggaactg gagggggaca  7800
atgcgcgtct ggccgttctc aagcgctgca tagaagtttc ccacttcgcc taccctgccc  7860
tgaacctgcc gcccaaagtc atgcgctcgg tcatggacca gctgctcatc aagagagctg  7920
agcccctgaa ccccgagcac cccgaggcgg agaactcgga ggacggaaag cccgtcgtca  7980
gcgacgagga gctcgagcgg tggctggaca gcacggaccc cgagcagttg caagagcggc  8040
gcaaaatgat gatggcggcc gtcctggtca ccgttgagct ggagtgcctg cagcggtttt  8100
ttagcgacgt ggaaacgctg cgtaaaatcg gagagtccct gcactacacc ttccgccagg  8160
gctacgtccg ccaggcctgc aagatctcca acgtggagct cagcaacctg gtctcctaca  8220
tgggcatcct ccacgagaac cggctgggac agagcgtgct gcactgcacc ttgcaaggcg  8280
aggcgcggcg ggactacgtg cgagactgcg tctacctctt cctcactctc acctggcaga  8340
ccgccatggg agtgtggcag cagtgcttgg aagacagaaa cctcaaagag ctagacaaac  8400
tcctctgccg ccagcggcgc gccctgtggt ccggtttcag cgagcgcacg gtcgccagcg  8460
ctctggcgga catcatcttc ccggagcgcc tgatgaaaac cttgcaaaac ggcctgccgg  8520
atttcatcag tcaaagcatt ttgcaaaact tccgctcttt tgtcctggaa cgctccggga  8580
tattgcccgc catgagctgc gcgctacctt ctgactttgt ccccctctcc taccgcgagt  8640
gccctccccc actgtggagc cactgctacc tcttccaact ggccaacttt ctggcctacc  8700
actccgacct catggaagac gtaagcggag agggtttact ggagtgccac tgccgctgca  8760
acctgtgcac cccccacaga tcgctggcct gcaacaccga gctactcagc gaaacccagg  8820
tcataggtac cttcgagatc caggggcccc agcagcaaga gggtgcttcc ggcttgaagc  8880
tcactccggc gctgtggacc tcggcttact tacgcaaatt tgtagccgag gactaccacg  8940
cccacaaaat tcagttttac gaagaccaat ctcgaccacc gaaagccccc ctcacggcct  9000
gcgtcatcac ccagagcaag atcctggccc aattgcaatc catcaaccaa gcgcgccgcg  9060
atttcctttt gaaaaagggt cgggggtgt acctggaccc ccagaccggc gaggaactca  9120
acccgtccac actctccgtc gaagcagccc ccccgagaca tgccgcccaa gggaaccgcc  9180
aagcagctga tcgctcggca gagagcgaag aagcaagagc tgctccagca gcaggtggag  9240
gacgaggaag agatgtggga cagccaggca gaggaggtgt cagaggacga ggaggagatg  9300
gaaagctggg acagcctaga cgaggaggag gacgagcttt cagaggaaga ggcgaccgaa  9360
gaaaaaccac ctgcatccag cgcgccttct ctgagccgac agccgaagcc ccggcccccg  9420
acgcccccgg ccggctcact caaagccagc cgtaggtggg acgccaccga atctccagcg  9480
gcagcggcaa cggcagcggg taaggccaaa cgcgagcggc gggggtattg ctcctggcgg  9540
gcccacaaaa gcagtattgt gaactgcttg caacactgcg ggggaaacat ctcctttgcc  9600
cgacgctacc tcctcttcca tcacggtgtg gccttccctc gcaacgttct ctattattac  9660
cgtcatctct acagccccta cgaaacgctc ggagaaaaaa gctaaggcct cctccgccgc  9720
gaggaaaaac tccgccgccg ctgccgccgc caaggatcca ccggccaccg aagagctgag  9780
aaagcgcatc tttcccactc tgtatgctat ctttcagcaa agccgcgggc agcaccctca  9840
gcgcgaactg aaaataaaaa accgctcctt ccgctcgctc acccgcagct gtctgtacca  9900
caagagagaa gaccagctgc agcgcaccct ggacgacgcc gaagcactgt tcagcaaata  9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
cttagaacag gcggcaatca ccgccacacc ccggcgccaa ctcaacccgc ctagttggcc  10260
cgccgcccag gtgtatcagg aaaatccccg cccgaccaca gtcctcctgc cacgcgacgc  10320
ggaggccgaa gtcctcatga ctaactctgg ggtacaatta gcgggcgggt ccaggtacgc  10380
caggtacaga ggtcgggccg ctccttactc tcccgggagt ataaagaggg tgatcattcg  10440
aggccgaggt atccagctca acgacgagac ggtgagctcc tcaaccggtc tcagacctga  10500
cggagtcttc cagctcggag gagcaggccg ctcttccttc accactcgcc aggcctacct  10560
gaccctgcag agctcttcct cgcagccgcg ctccggggga atcggcactc tccagttcgt  10620
ggaagagttc gttccctccg tctacttcaa ccccttctcc ggctcgcctg gacgctaccc  10680
ggacgccttc attcccaact ttgacgcagt gagtgaatcc gtggacggct acgactgatg  10740
acagatggtg cggccgtgag agctcggctg cgacatctgc atcactgccg tcagcctcgc  10800
tgctacgctc gggaggcgat cgtgttcagc tactttgagc tgccggacga gcaccctcag  10860
ggtccggctc acgggttgaa actcgagatc gagaacgcgc tcgagtctcg cctcatcgac  10920
accttcaccg cccgacctct cctggtagaa atccaacggg ggatcactac catcaccctg  10980
ttctgcatct gccccacgcc cggattacat gaagatctgt gttgtcatct ttgcgctcag  11040
tttaataaaa actgaacttt ttgccgcacc ttcaacgcca cgcgttgttt ctccaacagt  11100
cgacgatagc tcttcaatta aaggtacccg agaaactgtt tattttgaca attctactac  11160
ttctcttatc cttaactgtt cttgcacact agtgaggggg ctatcctgtg tcactgtcac  11220
gcgcctgatt gtatgcccaa actaatcaga actctttgtg ctttaggtga tatatttaaa  11280
atatagatag tatcaataaa cttaccttaa atttgacagc aatttttgg tatcatcatt  11340
cagcagcacc actttaccct cttcccaact ctcatatggg atatgatggt gggcggcaaa  11400
cttcctccaa accctgaaag aaatatcggt atccacttcc ttgtcctcac ccacaatttt  11460
catcttttca tagatgaaaa gaacccgagt tgatgaagac ttcaaccccg tctaccctta  11520
tgacaccaca accactccag ccgttccttt catatcaccc ccgtttgtaa acagtgacgg  11580
tcttcaggaa aaccccccg gagttttaag cctgcgaata gctaaacccc tgtattttga  11640
catggagaga aaactagccc tttcacttgg aagagggtta acaattaccg cgaacggaca  11700
attagaaagc acccagagcg tgcagactaa cccgccgtta actgtcacca ataacaacac  11760
acttatccta cgccactcct ccccttttaat cctaactgac aataatttaa ccgtaggctt  11820
ctcaagtcct ctccgtgtta tagacaacaa actgacattc acttttacct cacctctccg  11880
ttatgaaaac gaaaccctta ccttcaatta cacagagccc cttacactta tgaacagcaa  11940
ccttgcgctt aacgtaaact cctctaaagg ccttagggtt gacgggggct cactaggtac  12000
aaacttaagt ccggacttaa ggtttaacag cagtggagcc atagcttttg gtatacaaac  12060
cctatggaca cccccgacct caaatcctaa ctgcaccgtt tacaccgaaa gcgattcctt  12120
acttagtctc tgcttaacta aatgcggagc tcacgtttta ggaagtgtaa gcttaaccgg  12180
ggtagcaggt accatgataa acatggctga aacttcgctt gctattgaat ttacgtttga  12240
cgacactgga aaactacttc actcaccact tgttaacacc acttttagca ttcgtcaggg  12300
cgacagcccc gcctcaaatc ctacctacaa tgctctagca tttatgccaa acagtaccct  12360
```

```
ctacgctaga ggaggaagtg gtgaaccccg aaacaattac tacgtccaaa catacctcag  12420
gggaaatgtt cagagaccga ttaccctcac tgttactttc aactcagccg ccacgggata  12480
ttccttatct tttaagtgga ctgctgttgc acgtgaaaaa tttgcagctc ctgcaacttc  12540
attttgctac attaccgaac aataaaaccc tgtgttccca ccgtttcgtt ttttccagat  12600
gaaacgggcc agagttgatg aagacttcaa tcccgtgtac ccttacgatc ccccttacgc  12660
ccccattatg ccgtttatta ccccgccgtt tacatcttca gatgggttac aggaaaaacc  12720
acttggtgtt ttaagtttaa aatacaagga tcctatcact acacaaaatg gttctctaac  12780
ccttaaatta ggaaacgggc tgaacattaa caaccagggc caacttacat catctgctgg  12840
ggaagtcgag cctcccctca ccaatgctga caacaagctg gccttagcct acagcgaccc  12900
tctgacatta aaaaacagcc gtctaacact gtctcacaat gccccacttg caattaacaa  12960
taattctcta agtttggaag tatcagagcc tatatttata aataacgaca acaaactgtc  13020
tctgaaagct gacgcccccc tgacaaccag cgctggaacc ctccgcctgc aaagcgctgc  13080
tccattagga cttgctgaac agacactaaa gctgctgttt tctaaccctt tgtacttgcg  13140
aggtgacttc cttacattag ccattgaacg cccattggct gtaacagcag acgggctatt  13200
atcacttgcc ctcaaccctc cgctcacaac aactaacaca ggcttagctc tctctaccgc  13260
ggttccatta actgttacca acgggaacct tagcctaaac gtaaaacggc cgtttattat  13320
acaggacggc agcctttaca tggattttag acccccacta tatctgttta acagcgagcc  13380
acaacttggt gttaatttta atgcccctct aactgttaga gataacggcc tagctataaa  13440
caccggagac gggctaacag taacgtataa taaactaaca ttaaacctcg gtagagactt  13500
gcaatatgaa aatggagctg cagctgttaa gctaagtacc gcccctcctc tacagtatac  13560
tactcaactg cagctgaatt tgggagcggg cttacgtcta ggtcctacta ggaacttaga  13620
cgtggccatt aaccacaata aagggttagc gtgggaaaac aatgaagtgg ttactaaatt  13680
aggacaaggc ctttactttg attcctccgg aagcatagct ttatcgccta caaaccccag  13740
accagatact ttatggacca cggccgatcc ttcgccaaac tgcactgtat atgaatcact  13800
tgactctaga ctgtggctag cgcttgttaa atgtggggga atggtacacg gcagcatagc  13860
cctacaagct gaaaaaggcc aattgctgcg tcctactgct agttttatct ccatcgtaat  13920
ttacttctac agtgatgggg tccgtcgcac caactaccct acaattggca atgatgaggg  13980
tactctggcc aacagcgcta cttggggcta cagacaaggg caatctgcag acaccaacgt  14040
caccaatgct gttgaattca tgcctagttt acacagatat cctataaatc agggagacaa  14100
tattaaaaac caaatgataa cttacacttg catacaaggc aacgtgaaca tgccagtacc  14160
cttgaaaatc acgttcaatc atgctcttga aggctactcc ttaaagttta catggcgtgt  14220
ggtggctaat gaaaagtttg atattccttg ctgttcgttt tcttacatta cagaacaata  14280
aaacaacttt tttatttttc atttctttta ttttacacgc acagtaagac ttcctccccc  14340
cttccattta acagcgtaca ccagcctttc ccccttcatg gcggtaaact tctgtgagtt  14400
agtccggtat ttgggagtta aaatccaaac aggctctttg gtgattaaac gttgatccgt  14460
gatggacaca aatccctgag acaggtcctc caacgttgcg gtaaaaaact gaacgccgcc  14520
ctacaaaaca aacagttcag gctctccacg ggttatcacc ccgatcaaac tcagacagag  14580
taaaggtgcg gtgatgttcc acaagaccgc gcaagtggcg ctgtctaaag ctctcagtgc  14640
gacttctatg cggctggtag gatgttacat tatccaacag cctcacagcg cggattatta  14700
gtctacgagt gcgcctggcg cagcagcgca tctgaatttc agtcaagtct tgacaagaag  14760
cgcataccat aacaatcagg ttgttcatga tcccatagct aaacgcgctc cagccaaaac  14820
tcattcgctc caacagcacc accgcgtgtc cgtcaagtct tacttttaca taaacaaggt  14880
gtctgccacg tacatacatg ctacccgcat acaaaacttc ccggggcaaa cctctattca  14940
ccacctgtct gtaccaggga aacctgatgt ttatcaggga accatagatg gccattttaa  15000
accagttagc cagcaccacc ccgccagctc tacactgaag ggaaccggga gagttacaat  15060
gacagtggat catccacctc tcgtaacccc taattacctg attaaaatcc aaatctaacg  15120
tggcacaaca gatacacact ctcataaaca ttttcatgac atgtttttcc caggatgtta  15180
aaatacaatc ccaatacacg ggccactcct gtaatacaat aaagctaatg catgatggaa  15240
cgctcctcac ctcactaaca ttgtgcatgt ttacattttc acactctaag taccgagtcc  15300
tctcctcaac agccgcagtg tcgcgctcct cacacggtgg tagctgatga caattgtaag  15360
gggccagtct gcagcgatat cgtctgtcgc gctgcatcgt aaaacaggga ccgtctcact  15420
tcctcgtact tccaatagca gaaccacgtc cgctgccagc aggtttccac gaaccgccga  15480
tcccttcgtc gttcacgctc cctcctcaac gcaaaatgca gccactcctg caatccacac  15540
aaatccctct cggcctccgg agtcatgcac acctcatacc tatatatgtc tcggtacagt  15600
tccaaacacg aagtaagggc gagctccaac caacacaaac aggctgattt atcccgacac  15660
actggaggtg gaggaagaca cggaagaggc atgttattcc aagcgatccg gcaaaggatc  15720
aaagtgcaga tcccgaagat ggcaacgctc gcctccggag ccctggtgaa atttaacggc  15780
caaatcaaac attatgcggt tttccaaact atcaatcgcc gcctccaaaa gggcctgaac  15840
ccgcacttcc acaatcacca gcaaagcaaa agcgtgatta tcaaagtctt caatcatcag  15900
atggcatgac tgtacaatgc ccaaataatt ctcatttctc cactcgcgaa tagtgtcgcg  15960
gcagatcgtc tgaaggtcca tgccatgcat gttaaaaagc tcccagaggg cgccctctac  16020
cgacatgcgt agacacacca tcatgactgc aaaatatcag gctcctgaga cacctgcagc  16080
agatttaaca gatcaaagtc aggttgctgt ccgcggtcac gaatctccat gcgcaaagcc  16140
atttgcaaaa aattatatag gtctgtgcca actagctctg ttaattccgc gttaggaagc  16200
aaatcaggtg aggctatgca gcacaaaagt tgcagggaag gcgccaaact cagtaaaacc  16260
gctccagaat aacaaaattg atgaagcgga gtcacacagt gtaaaatgtg caaccaaaaa  16320
tcattcagct gctcttttaa atagtccagt acttctatat tcaatccgtg caagtactga  16380
agcaactgcg cgggaacagt cacattaaaa aaaatggggc ggctcaaata catgtcgacc  16440
taaaataaaa ataatcatta aaccagagaa gcttgacgaa tggaaggata aaatacacgc  16500
tccagcaaaa ggcaggcaac cggctgtccc cgagaaccgt aaaaaaattc atccgaatga  16560
ttaaaaagaa ccacagaaat ttcccaccat gtactcggtt gtaactcctg agcacacagc  16620
aacacccccc taacgttcat gtccgccact gaaaaaagac gtcccaaata cccaggtgga  16680
atgtcaagag acaactgcag agacagcaaa acaacccctc tgggagcgat cataaactcc  16740
tccggtgaga aaagcgcata caaattagaa taaccctgtt gctggggcaa aatagcccgg  16800
cggcccagca aatggacata aatatgttca gcagccatcg ccccgtctta ccgcgtaaaa  16860
agccagaaaa atccagctaa ctacactcta cagcctatta ctatatatac tctcctccca  16920
ctgacgctat accaccccgc ccacgtccaa agttcaccca cgcccaaaaa acccgcgaaa  16980
atccagcgcc gtcagcactt ccgcaattgt agtctctcaa cgtcacttcc gcgcgccttt  17040
tccctattcc cacacacgcc cgcggacttc gccccgcccg ccctcgcgcc accccgcgtc  17100
```

```
accccgcgtc accgcacgtc accccggccc cgcctcgctc ctccccactc attatcatat  17160
tggcacgttt ccagaataag gtatattatt gatgatgtta attaattcga acccataata  17220
cccataatag ctgtttgcca tcgacgcgag gctggatggc cttccccatt atgattcttc  17280
tcgcttccgg cggcatcggg atgcccgcgt tgcaggccat gctgtccagg caggtagatg  17340
acgaccatca gggacagctt caaggatcgc tcgcggctct taccagccca gcaaaaggcc  17400
aggaaccgta aaaaggccgc gttgctggcg tttttccata ggctccgccc ccctgacgag  17460
catcacaaaa atcgacgctc aagtcagagg tggcgaaacc cgacaggact ataaagatac  17520
caggcgtttc cccctggaag ctccctcgtg cgctctcctg ttccgaccct gccgcttacc  17580
ggatacctgt ccgcctttct cccttcggga agcgtggcgc tttctcatag ctcacgctgt  17640
aggtatctca gttcggtgta ggtcgttcgc tccaagctgg gctgtgtgca cgaacccccc  17700
gttcagcccg accgctgcgc cttatccggt aactatcgtc ttgagtccaa cccggtaaga  17760
cacgacttat cgccactggc agcagccact ggtaacagga ttagcagagc gaggtatgta  17820
ggcggtgcta cagagttctt gaagtggtgg cctaactacg gctacactag aaggacagta  17880
tttggtatct gcgctctgct gaagccagtt accttcggaa aaagagttgg tagctcttga  17940
tccggcaaac aaaccaccgc tggtagcggt ggtttttttg tttgcaagca gcagattacg  18000
cgcagaaaaa aaggatctca agaagatcct ttgatctttt ctacggggtc tgacgctcag  18060
tggaacgaaa actcacgtta agggattttg gtcatgagat tatcaaaaag gatcttcacc  18120
tagatccttt taaattaaaa atgaagtttt aaatcaatct aaagtatata tgagtaaact  18180
tggtctgaca gttaccaatg cttaatcagt gaggcaccta tctcagcgat ctgtctattt  18240
cgttcatcca tagttgcctg actccccgtc gtgtagataa ctacgatacg ggagggctta  18300
ccatctggcc ccagtgctgc aatgataccg cgagacccac gctcaccggc tccagattta  18360
tcagcaataa accagccagc cggaagggcc gagcgcagaa gtggtcctgc aactttatcc  18420
gcctccatcc agtctattaa ttgttgccgg gaagctagag taagtagttc gccagttaat  18480
agtttgcgca acgttgttgc cattgctgca ggcatcgtgg tgtcacgctc gtcgtttggt  18540
atggcttcat tcagctccgg ttcccaacga tcaaggcgag ttacatgatc ccccatgttg  18600
tgcaaaaaag cggttagctc cttcggtcct ccgatcgttg tcagaagtaa gttggccgca  18660
gtgttatcac tcatggttat ggcagcactg cataattctc ttactgtcat gccatccgta  18720
agatgctttt ctgtgactgg tgagtactca accaagtcat tctgagaata gtgtatgcgg  18780
cgaccgagtt gctcttgccc ggcgtcaaca cgggataata ccgcgccaca tagcagaact  18840
ttaaaagtgc tcatcattgg aaaacgttct tcggggcgaa aactctcaag gatcttaccg  18900
ctgttgagat ccagttcgat gtaacccact cgtgcaccca actgatcttc agcatctttt  18960
actttcacca gcgtttctgg gtgagcaaaa acaggaaggc aaaatgccgc aaaaaaggga  19020
ataagggcga cacggaaatg ttgaatactc atactcttcc tttttcaata ttattgaagc  19080
atttatcagg gttattgtct catgagcgga tacatatttg aatgtattta gaaaaataaa  19140
caaatagggg ttccgcgcac atttccccga aaagtgccac ctgacgtcta agaaaccatt  19200
attatcatga cattaaccta taaaaatagg cgtatcacga ggccctttcg tcttcaagaa  19260
ttggtcgatg gcaaacagct attatgggta ttatgggttc gaattaat               19308
```

SEQ ID NO: 50 moltype = DNA length = 17915
FEATURE Location/Qualifiers
source 1..17915
mol_type = other DNA
note = Synthetic oligonucleotide pBr/sAd4312.pV-rITR.dE3.dE4
organism = synthetic construct
SEQUENCE: 50

```
attaaccgaa gttagaagac caaaggtgcg aagacggcgt actgagtctc cctgttgtta  60
tcagcccaac atgagcaagc gcaagtttaa agaagaactc ctgcagaccc tggctcctga  120
aatctatggc cctccggacg tgaagcccga cattaagccc cgcgatatca agcgtgttaa  180
aaagcgggaa aaaaaagagg aactcgcggt ggtagacgat ggcggggtag aatttattag  240
aagtttcgcc ccgcgacgca gggtgcagtg gaaagggcgg cgcgtgcaac gcgttctcag  300
gccaggcacc gcggtagttt ttactccggg agagcggtcg gctgtcaggg gtttcaagcg  360
gcaatatgac gaggtgtacg gcgacgaaga catcctggaa caggcggctc agcagattgg  420
agaattcgcc tacggaaagc ggtctcgccg cgaagacctg gccattgcct tggacagtgg  480
caaccccacc cccagcctca aacccgtcac gctgcagcag gtgctccccg tgagcgcgag  540
cacggagagc aaaaggggaa tcaagagaga gatggaagat ctgaagccca ccatccaact  600
tatggtccct aaacgacaga agctggagga ggttctggaa aacatgaaag tggaccccag  660
catagagccg gatgtaaaag tgaggcctat taaggaagtg gctccgggtc tcggggtgca  720
aacggtggac attcagatcc cagtcagatc cgcttcgacc gccgtggaag ccatggaaac  780
gcaaaccgaa actccggtcg cggccggtac cagagaagtg gctttgcaaa cggagccctg  840
gtacgaatac accgctcctc ggcgccagag gcggcgttac ggcccggcaa atgccatcat  900
gccagagtat gcgctgcacc cgtctatccg acccaccccc ggctaccggg gggtaacgta  960
tcgcccgtcg ccaacccgac gccgttatcg tcgccgccgc cgttctcgtc gcgctctggc  1020
gcccgtgtcc gtgcgacgcg taacgcgccg gggaagaaca gtcaccatcc ctaacccgcg  1080
ctaccaccct agcattcttt aatgactctg ccgttttgca gatggctctg acttgccgcg  1140
tgcgccttcc cgttctgcac tatcgaggaa gatctcgtcg taggagaggc atggcgggga  1200
gcggccgccg tcgggcttta cgcaggcgca tgaaaggcgg aattttgccc gcactgattc  1260
ccataattgc cgccgccatt ggggcgatac ccggcgttgc ttcagtggcc ttgcaagcag  1320
ctcgtaataa ataaacgaag gcttttcaac ttatgacctg gtcctgacta ttttatgcag  1380
aaaaagcatg gaagacatca attttacgtc gctggctccg cggcaaggct cacgcccgct  1440
catgggcacc tggaacgaca tcggcagcag ccagctcaac gggggcgctt tcaattgggg  1500
gagcctttgg agcggcatta aaaactttgg ctccgcgatt aaatcctacg gcagcaaagc  1560
ctggaacagt agtactggtc agatgctccg ggataaactg aaggacacaa actttcaaga  1620
gaaagtggtc aacggggtgg tgaccggcat ccacggcgcg gtggatctcg ctaatcaagc  1680
ggtgcaaaaa gagatagaca gacgatggga aaactcgcgg gtgcctccgc agagagggga  1740
cgaagtggag gtggaggaag tagaagtcga ggagaaactg cccccgctag agaaagttcc  1800
cggggcgccg cccaggccac agaagcgtcc ccggccggat ctggaagaaa ctttagtgac  1860
ggaaaccatc gaacctccct cgtacgaaca agctttaaag gagggcgcct ctccttaccc  1920
catgactaag cccatcgcgc ccatggcgcg tccggtgtac ggaaaagatc acaagccagt  1980
aacgttagag ctacccccac cacccccttc ccgtcctacg gtgcctccgt tacccgcccc  2040
```

-continued

```
gtcggcaggt cccagctctg caccatccgc agctcctgca ccaaccgctc gcccggtggc  2100
cgtggcaacc gccagagccc ccagaggatc caactggcaa agcacgctga acagcatcgt  2160
gggcttggga gtgaaaaccc taaaacgccg ccgctgctat tattaaagag tgtagctaaa  2220
aatttcccgt tgtatacgcc tcctatgtta ccgccagaga cgcgtgactg gtcgccgctc  2280
cgccgctttc aagatggcca ccccatcgat gatgccgcag tggtcttaca tgcacatcgc  2340
cggccaggac gcctcggagt acctgagtcc cggcctggtg cagtttgccc gcgccaccga  2400
aagctacttc agcttgggaa acaagtttag aaaccccacc gtggcccccca cgcacgatgt  2460
aaccacggac cgctcgcaga ggctgacact gcgcttcgtg cccgtagacc gggaggacac  2520
cgcgtactcc tacaaagtgc gcttcaccct cgccgtaggg gacaacaggg tgctggacat  2580
ggccagcacg tactttgaca tccggggaat gctggaccga gggcccagct ttaaacccta  2640
ctcgggaact gcctacaatt cgctggcacc taagggcgct cccaacccta gtcaatggac  2700
tactaccaac ggagggaata aaacaaattc atttgcccaa gcatcctaca taggtcaaag  2760
cctgtcgaaa gacggggtgc aagtagcagt agatacagcc gctgggggg ctgcagtata  2820
tgctgacaaa acgtttcaac cagaacccca agtaggaata tcacaatgga atgaaaatcc  2880
tactacaaat gctgcaggaa gaattttaaa gcctactacc gcaatgcgtc catgctacgg  2940
ttcatacgct taccccacca acgaaaaagg tgggcaggta aaaatcactg accctaacaa  3000
tgacaaaacc ggcgctaata acgttagctt aaatttttc aacactgccg ctgacaatgg  3060
gaataacaat ccaaaagtag tactctacag cgaagatgta aatttagaag ggccagatac  3120
ccaccttgtt tttaagccag atgtaactgg cgacgcaacc agtgcagaaa ccctgttagg  3180
tcaacaagca gctcccaatc gtccaaacta cattgggttc agggacaact ttattggcct  3240
gatgtactac aattcaactg gaaacatggg agtgctagca ggtcaggctt ctcagctaaa  3300
cgccgtagtg gatcttcaag acagaaatac cgaattgtca tatcagctaa tgcttgacgc  3360
tttgggtgac agaagtcggt acttttctat gtggaatcaa gcagtggaca gctacgatcc  3420
tgacgttaga atcatagaaa atcatggagt agaagacgaa cttccaaatt attgttttcc  3480
gttaaatgga caggggattt cgaatacata caaaggtgtg aaatataaca caaacacttg  3540
gacgcaagac actgatgtag tcacaaccaa tgaaatttcc attggcaaca tttttgccat  3600
ggaaataaac ctggcggcta acttgtggcg cagctttctg tactccaatg tcgccctgta  3660
cttgccagat tcctacaaat acactcccga caatattgaa cttcctacaa acaagaacag  3720
ctacggctac attaacggaa gggtaaccgc ccccactgcc atcgacactt acgttaacat  3780
cggcgcccgg tggtctccgg accccatgga caacgttaac cctttcaacc accaccgcaa  3840
cgccggcttg cgataccgct ccatgctgct gggcaacggt cgctacgtac ccttccacat  3900
tcaggtgccc cagaaatttt ttgccattaa aaacctgctt ctgcttcccg ggtcctacac  3960
ctacgagtgg aacttcagga aagatgtaaa catgatcttg cagagcacct tgggcaacga  4020
cctccgcgtt gacggagcta gcgtgaggtt tgacagcatt aacctctacg ctaacttctt  4080
ccccatggcc cacaacacgg cctccacctt ggaagccatg ctgcgcaacg acaccaacga  4140
ccagtccttt aatgattacc tgtgcgcggc caacatgctg taccccatcc ccgccaatgc  4200
caccagcgtg ccgatctcca ttccctcacg caactgggcc gccttcagag gttggagttt  4260
cactcgcctg aaaaccaagg agaccccctc gctgggctcc ggtttcgacc catactttgt  4320
ttactccggg agcattccct acctggacgg aactttctac ctgaaccaca ccttcaaaaa  4380
ggtgtctatt atgtttgact cctccgtgag ctggcccggt aacgaccgct tgctaacccc  4440
caacgagttc gaaatcaaac gctcggtgga cggagagggt tacaatgtag cccagagcaa  4500
catgaccaaa gactggtttt taattcaaat gctaagccac tataacattg gctaccaagg  4560
attctacgtg cctgaagcct acaaggacag aatgtactcc ttctttagaa acttccaacc  4620
catgagccgc caggtagtag acacggtaaa ctatgctaac tacaaggaag taacaatgcc  4680
attccagcac aacaactcag gcttcgtggg gtacatggga cctaccatga gagaggggca  4740
ggcctacccg gctaattatc cctacccccct aatcggagcc actgccgtgc ccagcctgac  4800
acagaaaaag tttctctgcg atcgaacaat gtggaggatt cccttctcta gcaacttcat  4860
gtccatgggg gctctcaccg acctggggca gaacatgctg tacgctaact ccgctcacgc  4920
cttggacatg acctttgagg tggaccccat ggatgagccc acgcttctct atgttctgtt  4980
tgaagtcttc gacgtggtgc gcattcacca gccgcaccgc ggcgtcatcg aggccgtcta  5040
cctgcgcaca cctttctctg ccggtaacgc caccacctaa gaagctgatg ggctccagcg  5100
aacaggagct gcgggccatt gttcgcgacc tgggctgcgg gccctacttt ttgggcacct  5160
tcgacaagcg cttccccggc ttcatgtccc cccacaagcc ggcctgcgcc atcgtcaaca  5220
cggccggacg cgagaccggg ggggttcact ggctcgcctt tgcctggaac ccgcgtaacc  5280
acacctgcta cctgttcgac ccttttggtt tttctgacga aaggcttaaa cagatttacc  5340
agttcgagta cgaggggctc cttaaacgca gcgctctggc ctccacgccc gaccactgcg  5400
tcaccctgga gaagtccacc caaacggttc agggtcccct ctcggcggcc tgcggactct  5460
tttgttgcat gtttttgcat gctttcgtcc actggccgaa cacccccatg gaccgcaacc  5520
ccactatgga tctgctcacg ggagtgccta acagcatgct tcacagccct caggtcgcac  5580
ccaccctgcg tcgcaatcag gaacagctgt atgcttttct gggaaaacat tctgcctact  5640
ttcgccgcca ccggcagcgc atagaacagg ccacggcctt tgaaagcatg agtcaaagag  5700
tgtaatcaat aaaatcaact tttattttac atcacacgcg cttctggcgt tttcttaaaa  5760
atcaaagggt tcgggggagg ggtcgtcgtg cccgctgggc agggacacgt tgcgatactg  5820
gaagcggggg ctccagcgga actcggggat cgccagccgg ggcagaggca cttcttccag  5880
gttctgcttc caaaactgcc gcaccagctg gagggctccc attacgtcgg gcgccgagat  5940
cttgaagtcg cagttggggc ccgagcttcc gcggctgttg cgaaacacgg ggttggcaca  6000
ctggaacacc agcacgctcg ggtagttgat actggccagg gccgttgcgt cggtcaccgc  6060
cgttacatcc agatcctccg cgttggtcag ggcgaaggga gtcagcttgc acatctgccg  6120
cccgatgtgg ggcacgccgt catgcttgtt gaggcagtcg caacgcaggg gaatcagaat  6180
gcgatgctgg ccgcgttgca tctgagggta gttggcccgc aagaacgctt ccatctgacg  6240
gaaggccgtc tgggctttca ttccctcggt gtagaaaaga ccgcaggact tgctagaaaa  6300
tacattattg ccgcaggtga cgtcttccgc gcagcagcgg gcgtcttcgt tctttagctg  6360
caccacgttg cgaccccacc ggttctgtac caccttggcc ctcgtgggct gctccttcag  6420
cgcccgctgg ccgttttcgc tggtcacatc catttccaac acgtgctcct tacacaccat  6480
ttccactccg tggaagcaga acaggacgcc ctcctgctgg gtattgcgat gctcccacac  6540
ggcgcagcct gtggcctccc agctcttatg cttcaccccc gcgtagtttt ccatgtaagc  6600
catcaggaat ctgcccatca tctcggtaaa ggttttctga ctggtgaagg tcaaaggcaa  6660
gccgcggtgc tcttcgttca gccacgtttg acagatcttg cggtacgtgg cgccctgatc  6720
cggcagaaac ttaaacgccc ccttgctctc gttgtccacg tggaactttt ccatcagcat  6780
```

```
tagcataact tccataccct tctcccacgc cgtcaccagc ggtgtgctgt cggggttctt  6840
caccaacatg gtagaagggc cctcgccggc cctgaagtcg ctcatactca ttttttgaaa  6900
ctccacagtg ccgtccgcac gacggacccg gcgcatcgga gggtagctga agccaacctc  6960
caccagggtg ccttcgctct cgctgtcgga gacgatctcc ggggagggcg gcggcgcggg  7020
tgtcgacttg cgagccttct tcttgggagg aagcggtggc gcctcttggt cgcgctcggg  7080
actcatctcc ctcaagtagg gggtgatgga gcttcctgct tggttctgac ggttggccat  7140
tgtatcctag gcagaaacac atggagctta tgcgcgagga aactttaacc gccccgtccc  7200
ccgtcaacga cgaagaggtc atcatcgaac aggacccggg ctacgttact ccgcccgagg  7260
atctggaggg gcctttagac gaccggcgcg acgctagtga gcagcaggaa aatgagaaag  7320
aggaagcctg ctacctcctg gaaggcgacg tgttgctaaa acatttcgcc aggcagagca  7380
ccatagtgaa ggaggctttg caagaccgct cggaggtgcc cttggacgtc gccgcgctct  7440
cccaggccta cgaggcgaac ctcttctcgc cccgagtgcc tccgaagaga cagcccaacg  7500
gcacctgcga gcccaacccg cgccttaact tctaccccgt gttcgccgtg cccgaggcgc  7560
tggccaccta ccacattttt ttcaagaacc agcgcatccc gctctcgtgc cgggccaacc  7620
gcaccgcggc cgatagaaag ctgagactca aaaacggagc tagcatacct gatatcacgt  7680
ccctggagga agtgcctaag atcttcgaag gtctgggtcg agacgagaaa cgggcggcaa  7740
acgctctgca gaaagaacag aaggacagtc agaacgtgct ggtggaactg gagggggaca  7800
atgcgcgtct ggccgttctc aagcgctgca tagaagtttc ccacttcgcc taccctgccc  7860
tgaacctgcc gcccaaagtc atgcgctcgg tcatggacca gctgctcatc aagagagctg  7920
agcccctgaa ccccgagcac cccgaggcgg agaactcgga ggacggaaag cccgtcgtca  7980
gcgacgagga gctcgagcgg tggctggaca gcacggaccc cgagcagttg caagagcggc  8040
gcaaaatgat gatggcggcc gtcctggtca ccgttgagct ggagtgcctg cagcggtttt  8100
ttagcgacgt ggaaacgctg cgtaaaatcg gagagtccct gcactacacc ttccgccagg  8160
gctacgtccg ccaggcctgc aagatctcca acgtggagct cagcaacctg gtctcctaca  8220
tgggcatcct ccacgagaac cggctgggac agagcgtgct gcactgcacc ttgcaaggcg  8280
aggcgcggcg ggactacgtg cgagactgcg tctacctctt cctcactctc acctggcaga  8340
ccgccatggg agtgtggcag cagtgcttgg aagacagaaa cctcaaagag ctagacaaac  8400
tcctctgccg ccagcggcgc gccctgtggt ccggtttcag cgagcgcacg gtcgccagcg  8460
ctctggcgga catcatcttc ccggagcgcc tgatgaaaac cttgcaaaac ggcctgccgg  8520
atttcatcag tcaaagcatt ttgcaaaact tccgctcttt tgtcctggaa cgctccggga  8580
tattgcccgc catgagctgc gcgctacctt ctgactttgt ccccctctcc taccgcgagt  8640
gccctccccc actgtggagc cactgctacc tcttccaact ggccaacttt ctggcctacc  8700
actccgacct catggaagac gtaagcggag agggtttact ggagtgccac tgccgctgca  8760
acctgtgcac cccccacaga tcgctggcct gcaacaccga gctactcagc gaaacccagg  8820
tcataggtac cttcgagatc caggggcccc agcagcaaga gggtgcttcc ggcttgaagc  8880
tcactccggc gctgtggacc tcggcttact tacgcaaatt tgtagccgag gactaccacg  8940
cccacaaaat tcagttttac gaagaccaat ctcgaccacc gaaagccccc ctcacggcct  9000
gcgtcatcac ccagagcaag atcctggccc aattgcaatc catcaaccaa gcgcgccgcg  9060
atttcctttt gaaaaagggt cgggggtgt acctggaccc ccagaccggc gaggaactca  9120
acccgtccac actctccgtc gaagcagccc ccccgagaca tgccgcccaa gggaaccgcc  9180
aagcagctga tcgctcggca gagagcgaag aagcaagagc tgctccagca gcaggtggag  9240
gacgaggaag agatgtggga cagccaggca gaggaggtgt cagaggacga ggaggagatg  9300
gaaagctggg acagcctaga cgaggaggag gacgagcttt cagaggaaga ggcgaccgaa  9360
gaaaaaccac ctgcatccag cgcgccttct ctgagccgac agccgaagcc ccggcccccg  9420
acgcccccgg ccggctcact caaagccagc cgtaggtggg acgccaccga atctccagcg  9480
gcagcggcaa cggcagcggg taaggccaaa cgcgagcggc gggggtattg ctcctggcgg  9540
gcccacaaaa gcagtattgt gaactgcttg caacactgcg ggggaaacat ctcctttgcc  9600
cgacgctacc tcctcttcca tcacggtgtg gccttccctc gcaacgttct ctattattac  9660
cgtcatctct acagccccta cgaaacgctc ggagaaaaaa gctaaggcct cctccgccgc  9720
gaggaaaaac tccgccgccg ctgccgccgc caaggatcca ccggccaccg aagagctgag  9780
aaagcgcatc tttcccactc tgtatgctat ctttcagcaa agccgcgggc agcaccctca  9840
gcgcgaactg aaaataaaaa accgctcctt ccgctcgctc acccgcagct gtctgtacca  9900
caagagagaa gaccagctgc agcgcaccct ggacgacgcc gaagcactgt tcagcaaata  9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
cttagaacag gcggcaatca ccgccacacc ccggcgccaa ctcaacccgc ctagttggcc  10260
cgccgcccag gtgtatcagg aaaatccccg cccgaccaca gtcctcctgc cacgcgacgc  10320
ggaggccgaa gtcctcatga ctaactctgg ggtacaatta gcgggcgggt ccaggtacgc  10380
caggtacaga ggtcgggccg ctccttactc tcccgggagt ataaagaggg tgatcattcg  10440
aggccgaggt atccagctca acgacgagac ggtgagctcc tcaaccggtc tcagacctga  10500
cggagtcttc cagctcggag gagcaggccg ctcttccttc accactcgcc aggcctacct  10560
gaccctgcag agctcttcct cgcagccgcg ctccggggga atcggcactc tccagttcgt  10620
ggaagagttc gttccctccg tctacttcaa ccccttctcc ggctcgcctg gacgctaccc  10680
ggacgccttc attcccaact ttgacgcagt gagtgaatcc gtggacggct acgactgatg  10740
acagatggtg cggccgtgag agctcggctg cgacatctgc atcactgccg tcagcctcgc  10800
tgctacgctc gggaggcgat cgtgttcagc tactttgagc tgccggacga gcaccctcag  10860
ggtccggctc acgggttgaa actcgagatc gagaacgcgc tcgagtctcg cctcatcgac  10920
accttcaccg cccgacctct cctggtagaa atccaacggg ggatcactac catcaccctg  10980
ttctgcatct gccccacgcc cggattacat gaagatctgt gttgtcatct ttgcgctcag  11040
tttaataaaa actgaacttt ttgccgcacc ttcaacgcca cgcgttgttt ctccaacagt  11100
cgacgatagc tcttcaatta aaggtacccg agaaactgtt tattttgaca attctactac  11160
ttctcttatc cttaactgtt cttgcacact agtgaggggg ctatcctgtg tcactgtcac  11220
gcgcctgatt gtatgcccaa actaatcaga actctttgtg ctttaggtga tatatttaaa  11280
atatagatag tatcaataaa cttaccttaa atttgacagc aatttttgg tatcatcatt  11340
cagcagcacc actttaccct cttcccaact ctcatatggg atatgatggt gggcggcaaa  11400
cttcctccaa accctgaaag aaatatcggt atccacttcc ttgtcctcac ccacaatttt  11460
catcttttca tagatgaaaa gaacccgagt tgatgaagac ttcaaccccg tctacccttta  11520
```

```
tgacaccaca accactccag ccgttccttt catatcaccc ccgtttgtaa acagtgacgg  11580
tcttcaggaa aaccccccg gagttttaag cctgcgaata gctaaacccc tgtattttga  11640
catggagaga aaactagccc tttcacttgg aagagggtta acaattaccg cgaacggaca  11700
attagaaagc acccagagcg tgcagactaa cccgccgtta actgtcacca ataacaacac  11760
acttatccta cgccactcct ccccttaat cctaactgac aataatttaa ccgtaggctt  11820
ctcaagtcct ctccgtgtta tagacaacaa actgacattc acttttacct cacctctccg  11880
ttatgaaaac gaaaccctta ccttcaatta cacagagccc cttacactta tgaacagcaa  11940
ccttgcgctt aacgtaaact cctctaaagg ccttagggtt gacgggggct cactaggtac  12000
aaacttaagt ccggacttaa ggtttaacag cagtggagcc atagcttttg gtatacaaac  12060
cctatggaca cccccgacct caaatcctaa ctgcaccgtt tacaccgaaa gcgattcctt  12120
acttagtctc tgcttaacta aatgcggagc tcacgtttta ggaagtgtaa gcttaaccgg  12180
ggtagcaggt accatgataa acatggctga aacttcgctt gctattgaat ttacgtttga  12240
cgacactgga aaactacttc actcaccact tgttaacacc acttttagca ttcgtcaggg  12300
cgacagcccc gcctcaaatc ctacctacaa tgctctagca tttatgccaa acagtaccct  12360
ctacgctaga ggaggaagtg gtgaaccccg aaacaattac tacgtccaaa catacctcag  12420
gggaaatgtt cagagaccga ttaccctcac tgttactttc aactcagccg ccacgggata  12480
ttccttatct tttaagtgga ctgctgttgc acgtgaaaaa tttgcagctc ctgcaacttc  12540
attttgctac attaccgaac aataaaaccc tgtgttccca ccgtttcgtt ttttccagat  12600
gaaacgggcc agagttgatg aagacttcaa tcccgtgtac ccttacgatc ccccttacgc  12660
ccccattatg ccgtttatta ccccgccgtt tacatcttca gatgggttac aggaaaaacc  12720
acttggtgtt ttaagtttaa aatacaagga tcctatcact acacaaaatg gttctctaac  12780
ccttaaatta ggaaacgggc tgaacattaa caaccagggc caacttacat catctgctgg  12840
ggaagtcgag cctcccctca ccaatgctga caacaagctg gccttagcct acagcgaccc  12900
tctgacatta aaaaacagcc gtctaacact gtctcacaat gccccacttg caattaacaa  12960
taattctcta agtttggaag tatcagagcc tatatttata aataacgaca acaaactgtc  13020
tctgaaagct gacgccccccc tgacaaccag cgctggaacc ctccgcctgc aaagcgctgc  13080
tccattagga cttgctgaac agacactaaa gctgctgttt tctaaccctt tgtacttgcg  13140
aggtgacttc cttacattag ccattgaacg cccattggct gtaacagcag acgggctatt  13200
atcacttgcc ctcaaccctc cgctcacaac aactaacaca ggcttagctc tctctaccgc  13260
ggttccatta actgttacca acgggaacct tagcctaaac gtaaaacggc cgtttattat  13320
acaggacggc agcctttaca tggattttag acccccacta tatctgttta acagcgagcc  13380
acaacttggt gttaatttta atgcccctct aactgttaga gataacggcc tagctataaa  13440
caccggagac gggctaacag taacgtataa taaactaaca ttaaacctcg gtagagactt  13500
gcaatatgaa aatggagctg cagctgttaa gctaagtacc gcccctcctc tacagtatac  13560
tactcaactg cagctgaatt tgggagcggg cttacgtcta ggtcctacta ggaacttaga  13620
cgtggccatt aaccacaata aagggttagc gtgggaaaac aatgaagtgg ttactaaatt  13680
aggacaaggc ctttactttg attcctccgg aagcatagct ttatcgccta caaaccccag  13740
accagatact ttatggacca cggccgatcc ttcgccaaac tgcactgtat atgaatcact  13800
tgactctaga ctgtggctag cgcttgttaa atgtggggga atggtacacg gcagcatagc  13860
cctacaagct gaaaaaggcc aattgctgcg tcctactgct agttttatct ccatcgtaat  13920
ttacttctac agtgatgggg tccgtcgcac caactaccct acaattggca atgatgaggg  13980
tactctggcc aacagcgcta cttggggcta cagacaaggg caatctgcag acaccaacgt  14040
caccaatgct gttgaattca tgcctagttt acacagatat cctataaatc agggagacaa  14100
tattaaaaac caaatgataa cttacacttg catacaaggc aacgtgaaca tgccagtacc  14160
cttgaaaatc acgttcaatc atgctcttga aggctactcc ttaaagttta catggcgtgt  14220
ggtggctaat gaaaagtttg atattccttg ctgttcgttt tcttacatta cagaacaata  14280
aaacaacttt tttatttttc atttctttta ttttacacgc acagtaagac ttcctccccc  14340
cttccattta acagcgtaca ccagcctttc ccccttcatg gcggtaaact tctgtgagtt  14400
agtccggtat ttgggagtta aaatccaaac aggctctttg gtgattaaac gttgatccgt  14460
gatggacaca aatccctgag acaggtcctc caacgttgcg gtaaaaaact gaacgccgcc  14520
ctacaaaaca aacagttcag gctctccacg ggttatcacc ccgatcaaac tcagacagag  14580
taaaggtgcg gtgatgttcc acaagaccgc gcaagtggcg ctgtctaaag ctctcagtgc  14640
gacttctatg cggctggtag gatgttacat tatccaacag cctcacagcg cggattatta  14700
gtctacgagt gcgcctggcg cagcagcgca tctgaatttc agtcaagtct tgacaagaag  14760
cgcataccat aacaatcagg ttgttcatga tcccatagct aaacgcgctc cagccaaaac  14820
tcattcgctc caacagcacc accgcgtgtc cgtcaagtct tacttttaca taaacaaggt  14880
gtctgccacg tacatacatg ctacccgcat acaaaacttc ccggggcaaa cctctattca  14940
ccacctgtct gtaccaggga aacctgatgt ttatcaggga accatagatg gccattttaa  15000
accagttagc cagcaccacc ccgccagctc tacactgaag ggaaccggga gagttacaat  15060
gacagtggat catccacctc tcgtaacccc taattacctg attaaaatcc aaatctaacg  15120
tggcacaaca gatacacact ctcataaaca ttttcatgac atgtttttcc caggatgtta  15180
aaatacaatc ccaatacacg ggccactcct gtaatacaat aaagctaatg catgatggaa  15240
cgctcctcac ctcactaaca ttgtgcatgt ttacattttc acactctaag taccgagtcc  15300
tctcctcaac agccgcagtg tcgcgctcct cacacggtgg tagctgatga caattgtaag  15360
gggccagtct gcagcgatat cgtctgtcgc gctgcatcgt aaaacaggga ccgtctcact  15420
tcctcgtact tccaatagca gaacccgccc cgtcttaccg cgtaaaaagc cagaaaaatc  15480
cagctaacta cactctacag cctattacta tatatactct cctcccactg acgctatacc  15540
accccgccca cgtccaaagt tcacccacgc ccaaaaaacc cgcgaaaatc cagcgccgtc  15600
agcacttccg caattgtagt ctctcaacgt cacttccgcg cgccttttcc ctattcccac  15660
acacgcccgc ggacttcgcc ccgcccgccc tcgcgccacc ccgcgtcacc ccgcgtcacc  15720
gcacgtcacc ccggccccgc ctcgctcctc cccactcatt atcatattgg cacgtttcca  15780
gaataaggta tattattgat gatgttaatt aattcgaacc cataataccc ataatagctg  15840
tttgccatcg acgcgaggct ggatggcctt ccccattatg attcttctcg cttccggcgg  15900
catcgggatg cccgcgttgc aggccatgct gtccaggcag gtagatgacg accatcaggg  15960
acagcttcaa ggatcgctcg cggctcttac cagcccagca aaaggccagg aaccgtaaaa  16020
aggccgcgtt gctggcgttt ttccataggc tccgcccccc tgacgagcat cacaaaaatc  16080
gacgctcaag tcagaggtgg cgaaacccga caggactata aagataccag gcgtttcccc  16140
ctggaagctc cctcgtgcgc tctcctgttc cgaccctgcc gcttaccgga tacctgtccg  16200
cctttctccc ttcgggaagc gtggcgcttt ctcatagctc acgctgtagg tatctcagtt  16260
```

```
cggtgtaggt cgttcgctcc aagctgggct gtgtgcacga accccccgtt cagcccgacc  16320
gctgcgcctt atccggtaac tatcgtcttg agtccaaccc ggtaagacac gacttatcgc  16380
cactggcagc agccactggt aacaggatta gcagagcgag gtatgtaggc ggtgctacag  16440
agttcttgaa gtggtggcct aactacggct acactagaag gacagtattt ggtatctgcg  16500
ctctgctgaa gccagttacc ttcggaaaaa gagttggtag ctcttgatcc ggcaaacaaa  16560
ccaccgctgg tagcggtggt ttttttgttt gcaagcagca gattacgcgc agaaaaaaag  16620
gatctcaaga agatcctttg atcttttcta cggggtctga cgctcagtgg aacgaaaact  16680
cacgttaagg gattttggtc atgagattat caaaaaggat cttcacctag atccttttaa  16740
attaaaaatg aagttttaaa tcaatctaaa gtatatatga gtaaacttgg tctgacagtt  16800
accaatgctt aatcagtgag gcacctatct cagcgatctg tctatttcgt tcatccatag  16860
ttgcctgact ccccgtcgtg tagataacta cgatacggga gggcttacca tctggcccca  16920
gtgctgcaat gataccgcga gacccacgct caccggctcc agatttatca gcaataaacc  16980
agccagccgg aagggccgag cgcagaagtg gtcctgcaac tttatccgcc tccatccagt  17040
ctattaattg ttgccgggaa gctagagtaa gtagttcgcc agttaatagt ttgcgcaacg  17100
ttgttgccat tgctgcaggc atcgtggtgt cacgctcgtc gtttggtatg gcttcattca  17160
gctccggttc ccaacgatca aggcgagtta catgatcccc catgttgtgc aaaaaagcgg  17220
ttagctcctt cggtcctccg atcgttgtca gaagtaagtt ggccgcagtg ttatcactca  17280
tggttatggc agcactgcat aattctctta ctgtcatgcc atccgtaaga tgcttttctg  17340
tgactggtga gtactcaacc aagtcattct gagaatagtg tatgcggcga ccgagttgct  17400
cttgcccggc gtcaacacgg gataataccg cgccacatag cagaacttta aaagtgctca  17460
tcattggaaa acgttcttcg gggcgaaaac tctcaaggat cttaccgctg ttgagatcca  17520
gttcgatgta acccactcgt gcacccaact gatcttcagc atcttttact ttcaccagcg  17580
tttctgggtg agcaaaaaca ggaaggcaaa atgccgcaaa aaagggaata agggcgacac  17640
ggaaatgttg aatactcata ctcttccttt ttcaatatta ttgaagcatt tatcagggtt  17700
attgtctcat gagcggatac atatttgaat gtatttagaa aaataaacaa ataggggttc  17760
cgcgcacatt tccccgaaaa gtgccacctg acgtctaaga aaccattatt atcatgacat  17820
taacctataa aaataggcgt atcacgaggc cctttcgtct tcaagaattg gtcgatggca  17880
aacagctatt atgggtatta tgggttcgaa ttaat                             17915
```

```
SEQ ID NO: 51          moltype = DNA  length = 8865
FEATURE                Location/Qualifiers
source                 1..8865
                       mol_type = other DNA
                       note = Synthetic oligonucleotide sAdApt4312.E1btg.Empty
                       organism = synthetic construct
SEQUENCE: 51
attaacatca tcaataaagg gtcaggatgg gtgggcacag gtattgtcga ctggtcaata  60
ttggccattg agcgaggcgg ggccggggtg gggtgaggcg gggccggggt ggggtgaggg  120
tgacgtcggg gcgggcgggg cggccgacgt gtgtggggag gcgcgtagtg tttacgtatg  180
cggaaggagg ttttataccg gaagatgggt aatttgggcg tatacttgta agttttgtgt  240
aatttggcgc gaaaactggg taatgaggaa gttgaggtta atatgtactt tttatgactg  300
ggcggaattt ctgctgttca gcagtgaact ttgggcgctg acggggaggt ttcgctacgt  360
ggcagtacca cgagaaggct caaaggtccc atttattgta ctcctcagcg ttttcgccgg  420
gtatttaaac gctgtcagat catcaagagg ccactcttga gtgctggcga gtagagtttt  480
ctcctccgcg ctgccacaat gaggctggtc cccgagatgt ttggtgtttt ttgcgacgag  540
gcggcgcgga actcagatga cctgctgaat tcagatttgc tggaaattcc caattcgcct  600
gtggcttcgc ctccgtcact tcacgacctt ttcgatgtgg aagtggatcc tccggcagat  660
cccaacgagg acgcggtaaa tagtatgttt cccgaatgtc tgttcgaggc ggctgacgag  720
ggtagcgaca gcggtggaga gagtggacag ggtgaggaac tggacttaaa atgctacgag  780
gaatgcatac cgtctagcga ttctgaaacg gaacaaacag ggggagatgg ctgcgctgag  840
ccaactgaga aaaatgaact tatattagac tgtcctgaac atcctggtca tggctgccgt  900
gcctgtgctt ttcatagaga tgccagtgga aatcctgaaa ctctatgtgc tctgtgttac  960
ctgcgtctta ccggcaattt tgtatacagt aagtaggttt tttactttgt gtacggtagg  1020
gaagtttttg taaagtgtgt tatgacttat tgcttgtgta atgttttaca ggtgacgtgt  1080
ctgatgtgga ggagggagat aagtcagtcc atactagttc tccttgcact ttgggggctg  1140
tggttccaga taatgttatt aaacccgtgg cggtcagagt atcaggcagg cggtgtgcag  1200
tcgaaaaaat tgaagacttg ctgcaggaag agcagatgca acctttggac ctgtccctca  1260
aacgccctaa gatgacctaa gcctgtttat tgagtgcaat aaaactgttg atctttgaac  1320
tgtgtttatg tgttgggtgt gtctgtggat atataagcag gtggatggga agtgagagca  1380
catctgcctt gatggatctg ttggggaact tgcgggaatt tgacgtggtt cgtcgcttgc  1440
tggagttggc ctccgacaaa acttccaggc tttggaggtt ttggtttggc tcaacgctta  1500
gcagcgtagt gtacagggtc aagaaggagc aggaggggca attttctagg ctgttggctg  1560
atattcctgg agtttttgtg gctctggatt taggccatca cagtcttttt caagagaaaa  1620
ttgtcaaaag cttaactttc tcgtctcctg gccgcacggt tgtttcagca gcctttatta  1680
cctatatttt ggatcaatgg agcagcagcg gcagccacct gtcgtgggat tacatgctgg  1740
attacctggc aatggccctg tggagggcca tgctgcggag gagggtttgc atttactcgc  1800
gggcgcagcc tccgcggctg gatcgagtgg tggaggagga cgagccggac gagaccgaga  1860
acctgagagc cggcctggac cctccaatgg aagactaggt gcagaggata atcctgaaga  1920
gggaactagt gggggtgcta gaaaaaagca aaaaaccgag actgagccta gaaacttttt  1980
gaatgagctg actgtgagtt tgatgaatcg ccatcgtccc gagacaattt tctggtctga  2040
gttggaggaa gagtttagga agggggattt gaacctgctg tacaagtatg ggttcgaaca  2100
gttgaagact cactggttgg agccgtggga ggattttgaa accgctctgg acacttttgc  2160
taaagtggct ttgcggccgg ataaagttta tactatccgc tgcactgtta atataaggaa  2220
aagtgtttat gttataggcc atggagcact ggtgcaggtg gagaccgccg atcgggtggc  2280
tttcaactgc ggcatgcaga atctgggccc tggggtgata ggtgttaatg gtgtcacgtt  2340
tcagaacgtg aggttcgcgg gtgaaagctt tagcggctcc gtgtttgcaa ataacacaca  2400
gctcactctc cacggcgttt actttttaa ctttaacaat acatgtgtgg agtcgtgggg  2460
cagggcgtcc ttgaggggct gcacttttca cggttgctgg aaggcggtgg tgggaagact  2520
gaaaagtgta acgtctgtga aaaaatgcat attcgagcgg tgtgtgctag ctgtaaccgt  2580
```

```
ggaagggcat ggacgcatta gaaacaacgc agcgtctgag aatgggtgtt ttcttttact  2640
gaaaggcacg gccagcgtta agcataacat gatctgtggc agtgggctgt acccgtcgca  2700
gttgttaacc tgcgcggatg gaaactgcca gacattgcgc accgtgcaca tagtgtctca  2760
cccgcgtcgc cactggccaa cgtttgagca caacttgctt atgcgttgta cggtccatct  2820
ggggcctaga cggggcatgt ttgtgccttt tcagtgtaac tttagccaca ctaagatctt  2880
actagaagca gatgccttca ctcgagtgtg tttcaatggg gtgtttgaca tgtcggtgga  2940
aatttttaaa gtgataagat atgatgaatc caagtctcgt tgtcgcccct gtgaatgcgg  3000
agctaatcat ttgaggttgt atcccgcgac cctgaacgta accgaggagc tgagggccga  3060
ccaccacatg ttgtcctgct tgcgcaccga ctatgagtcc agcgacgaag agtgaggtga  3120
ggggcggagc cacaaagggt ataaagggtc aggatgggtg ggcacaggta ttgtcgactg  3180
gtcaatattg gccattagcc atattattca ttggttatat agcataaatc aatattggct  3240
attggccatt gcatacgttg tatccatatc ataatatgta catttatatt ggctcatgtc  3300
caacattacc gccatgttga cattgattat tgactagtta ttaatagtaa tcaattacgg  3360
ggtcattagt tcatagccca tatatggagt tccgcgttac ataacttacg gtaaatggcc  3420
cgcctggctg accgcccaac gacccccgcc cattgacgtc aataatgacg tatgttccca  3480
tagtaacgcc aatagggact ttccattgac gtcaatgggt ggagtattta cggtaaactg  3540
cccacttggc agtacatcaa gtgtatcata tgccaagtac gccccctatt gacgtcaatg  3600
acggtaaatg gcccgcctgg cattatgccc agtacatgac cttatgggac tttcctactt  3660
ggcagtacat ctacgtatta gtcatcgcta ttaccatggt gatgcggttt tggcagtaca  3720
tcaatgggcg tggatagcgg tttgactcac ggggatttcc aagtctccac cccattgacg  3780
tcaatgggag tttgttttgg caccaaaatc aacgggactt tccaaaatgt cgtaacaact  3840
ccgccccatt gacgcaaatg ggcggtaggc gtgtacggtg ggaggtctat ataagcagag  3900
ctcgtttagt gaaccgtcag atcgcctgga gacgccatcc acgctgtttt gacctccata  3960
gaagacaccg ggaccgatcc agcctccgcg gccgggaacg gtgcattgga agcttggtac  4020
cggtgaattc gctagcgtta acggatcctc tagacgagat ccgaacttgt ttattgcagc  4080
ttataatggt tacaaataaa gcaatagcat cacaaatttc acaaataaag catttttttc  4140
actgcattct agttgtggtt tgtccaaact catcaatgta tcttatcatg tctagatcct  4200
taaggtgata agatatgatg aatccaagtc tcgttgtcgc ccctgtgaat gcggagctaa  4260
tcatttgagg ttgtatcccg cgaccctgaa cgtaaccgag gagctgaggg ccgaccacca  4320
catgttgtcc tgcttgcgca ccgactatga gtccagcgac gaagagtgag gtgaggggcg  4380
gagccacaaa gggtataaag ggtcaggatg ggtgggcaca ggtattcaaa atgagcggga  4440
cgacggacgg caacgcgttt gagggggggag tgttcagccc atatctgaca tctcgtcttc  4500
cttcctgggc aggagtgcgt cagaatgtag tgggctccac cgtggacgga cggccggtcg  4560
cccctgcgaa ttccgccacc cttacctatg ccaccgtggg atcaccgttg gacactgccg  4620
cggcagccgc agcttctgct gccgcttcta ctgctcgcgg tatggcggct gactttggac  4680
tttataacca actggctacc gcggctgtgg catctcgcac tctggttcaa gaagatgccc  4740
tgagcgtggt tctgcttcga ctggaagatc tgtctcgtcg cttggatcag ctggctgcgc  4800
agatatcccc acctaacccc gatactactc aagaatctta aataaagaca aacagatttg  4860
ttgaaaataa atggctttat ttgttttttt tggctcgata ggctcgggtc cacctgtccc  4920
ggtcgttaag gactttgtgt atgctttcca agacccggta cagatgggct tggatgttta  4980
gatacatggg catgaggcca tcccgggggt ggagatagga ccattgcaga gcgtcatgct  5040
ccggggtggt gttgtagatg acccagtcgt agcagggttt ttgggcgtgg aactgaaaaa  5100
tgtccttgag aagcaggctg atggccaggg gcagaccctt agtgtaggtg ttcacaaagc  5160
ggttgagctg ggagggatgc atgcggggag agatgatatg catcttagcc tggattttca  5220
ggttagctat gttgcccccc aggtcccttc gagggttcat attgtggagg accaccagaa  5280
cggtgtagcc ggtacacttg ggaaacttat cgtgcagttt ggaggggaag gcgtgaaaga  5340
atttggaaac ccctttgtga ccacctaagt tttccatgca ctcgtccatg ataatggcga  5400
tgggcccctt ggcggcagct ttagcgaaca cgttgtgggg gttggaaaca tcatagtttt  5460
gctctagagt tagctcgtca taggccattt ttacgaagcg gggtaggagg gtgccagact  5520
gagggacgat agttccatct ggccccggtg cgtaattacc ctcgcagatc tgcatctccc  5580
aagctttaat ttccgaggga gggatcatgt ccacctgggg ggcgataaag aacacggttt  5640
ctggcggggg attaatgagc tgggtggaaa gcaggttgcg caagagctga gacttgccgc  5700
aaccggtggg accgtagatg accccgatga cgggctgcag ctggtagttg agagaggagc  5760
agctgccgtc ggggcgtagg aggggagcca cctcgttcat catgcttctt acatgtttat  5820
tttcactgac taagctttgc aagagcctct ccccacccag ggacaagagt tcttccaggc  5880
tgttgaagtg tttcagcggt ttcaggccgt cggccatggg catcttttca agcgactgac  5940
gaagcaagta cagccggtcc cagagctcgg tgacgtgctc tatggaatct cgatccagca  6000
gacttcttgg ttgcgggggt tgggccgact ttcgctgtag ggtacgagcc ggtgggcgtc  6060
cagggccgcg agggttttgt ccttccaggg tctcagcgtc cgggtgaggg tggtctcggt  6120
gacggtgaac ggatgagccc cgggctgggc gcttgccagg gtgcgcttca ggctcatccg  6180
gctggtgctg aagcgggcgt cgtctccctg ggaatcggcc agatagcaac ggagcatgag  6240
gtcgtagcta agggattcgg ccgcgtgtcc cttggcgcgc agttttccct tggaaacatg  6300
ctggcatctg gtgcagtgta aacacttgag ggcgtacagc ttgggggcga ggaagacgga  6360
ctcgggcgag taggcgtcgg ccccgcactc ggcgcagacg gtttcacact ccaccagcca  6420
cgtgagctcg ggtttgtcgg ggtcaaaaac caggttgcct ccattttttt tgatgcgttt  6480
cttaccttgc gtctccatga gcctgtgacc cgcttcggtg acaaaaaggc tgtctgtgtc  6540
tccgtagacc gacttgaggg ggcgttcttc caagggcgtg ccgcggtctt ctgcgtacaa  6600
aaactgggac cactccgaaa cgaaggccct ggtccacgct aacacgaagg atgcgatctg  6660
cgaggggtat ctgtcgttct caatgagggg atccaccttt tccagggtat gcagacacag  6720
gtcgtcctcc tccgcgtcca caaaggtgat tggcttgtaa gtgtaggtca cgtgacttaa  6780
ttaattcgaa cccataatac ccataatagc tgtttgccat cgacgcgagg ctggatggcc  6840
ttccccatta tgattcttct cgcttccggc ggcatcggga tgcccgcgtt gcaggccatg  6900
ctgtccaggc aggtagatga cgaccatcag ggacagcttc aaggccagca aaaggccagg  6960
aaccgtaaaa aggccgcgtt gctggcgttt ttccataggc tccgcccccc tgacgagcat  7020
cacaaaaatc gacgctcaag tcagaggtgg cgaaacccga caggactata aagataccag  7080
gcgtttcccc ctggaagctc cctcgtgcgc tctcctgttc cgaccctgcc gcttaccgga  7140
tacctgtccg cctttctccc ttcgggaagc gtggcgcttt ctcatagctc acgctgtagg  7200
tatctcagtt cggtgtaggt cgttcgctcc aagctgggct gtgtgcacga accccccgtt  7260
cagcccgacc gctgcgcctt atccggtaac tatcgtcttg agtccaaccc ggtaagacac  7320
```

```
gacttatcgc cactggcagc agccactggt aacaggatta gcagagcgag gtatgtaggc  7380
ggtgctacag agttcttgaa gtggtggcct aactacggct acactagaag gacagtattt  7440
ggtatctgcg ctctgctgaa gccagttacc ttcggaaaaa gagttggtag ctcttgatcc  7500
ggcaaacaaa ccaccgctgg tagcggtggt ttttttgttt gcaagcagca gattacgcgc  7560
agaaaaaaag gatctcaaga agatcctttg atcttttcta cggggtctga cgctcagtgg  7620
aacgaaaact cacgttaagg gattttggtc atgagattat caaaaaggat cttcacctag  7680
atccttttaa attaaaaatg aagttttaaa tcaatctaaa gtatatatga gtaaacttgg  7740
tctgacagtt accaatgctt aatcagtgag gcacctatct cagcgatctg tctatttcgt  7800
tcatccatag ttgcctgact ccccgtcgtg tagataacta cgatacggga gggcttacca  7860
tctggcccca gtgctgcaat gataccgcga gacccacgct caccggctcc agatttatca  7920
gcaataaacc agccagccgg aagggccgag cgcagaagtg gtcctgcaac tttatccgcc  7980
tccatccagt ctattaattg ttgccgggaa gctagagtaa gtagttcgcc agttaatagt  8040
ttgcgcaacg ttgttgccat tgctgcaggc atcgtggtgt cacgctcgtc gtttggtatg  8100
gcttcattca gctccggttc ccaacgatca aggcgagtta catgatcccc catgttgtgc  8160
aaaaaagcgg ttagctcctt cggtcctccg atcgttgtca gaagtaagtt ggccgcagtg  8220
ttatcactca tggttatggc agcactgcat aattctctta ctgtcatgcc atccgtaaga  8280
tgcttttctg tgactggtga gtactcaacc aagtcattct gagaatagtg tatgcggcga  8340
ccgagttgct cttgcccggc gtcaacacgg gataataccg cgccacatag cagaacttta  8400
aaagtgctca tcattggaaa acgttcttcg gggcgaaaac tctcaaggat cttaccgctg  8460
ttgagatcca gttcgatgta acccactcgt gcacccaact gatcttcagc atcttttact  8520
ttcaccagcg tttctgggtg agcaaaaaca ggaaggcaaa atgccgcaaa aaagggaata  8580
agggcgacac ggaaatgttg aatactcata ctcttccttt ttcaatatta ttgaagcatt  8640
tatcagggtt attgtctcat gagcggatac atatttgaat gtatttagaa aaataaacaa  8700
ataggggttc cgcgcacatt tccccgaaaa gtgccacctg acgtctaaga aaccattatt  8760
atcatgacat taacctataa aaataggcgt atcacgaggc cctttcgtct tcaagaattg  8820
gtcgatggca aacagctatt atgggtatta tgggttcgaa ttaat                  8865
```

SEQ ID NO: 52 moltype = DNA length = 40
FEATURE Location/Qualifiers
source 1..40
mol_type = other DNA
note = Synthetic oligonucleotide sAd4287.1A.fwd
organism = synthetic construct
SEQUENCE: 52

```
tctcacttaa ttaacatcat caataatata ccttattctg                        40
```

SEQ ID NO: 53 moltype = DNA length = 35
FEATURE Location/Qualifiers
source 1..35
mol_type = other DNA
note = Synthetic oligonucleotide sAd4287.1A.rev
organism = synthetic construct
SEQUENCE: 53

```
ttatgagtcg acaggagaaa actctactcg ccggc                             35
```

SEQ ID NO: 54 moltype = DNA length = 36
FEATURE Location/Qualifiers
source 1..36
mol_type = other DNA
note = Synthetic oligonucleotide sAd4287.1B.fwd
organism = synthetic construct
SEQUENCE: 54

```
tatactctta aggaatgcgg agctaatcat ttgagg                            36
```

SEQ ID NO: 55 moltype = DNA length = 36
FEATURE Location/Qualifiers
source 1..36
mol_type = other DNA
note = Synthetic oligonucleotide sAd4287.1B.rev
organism = synthetic construct
SEQUENCE: 55

```
tctcacttaa ttaacttcgt ggacgcggag gaggac                            36
```

SEQ ID NO: 56 moltype = DNA length = 36
FEATURE Location/Qualifiers
source 1..36
mol_type = other DNA
note = Synthetic oligonucleotide sAd4287.TGC.fwd
organism = synthetic construct
SEQUENCE: 56

```
ttatgagtcg actggtcaat attggccatt agccat                            36
```

SEQ ID NO: 57 moltype = DNA length = 37
FEATURE Location/Qualifiers
source 1..37
mol_type = other DNA
note = Synthetic oligonucleotide sAd4287.TGC.rev
organism = synthetic construct
SEQUENCE: 57

```
tatactctta aggatctaga catgataaga tacattg                          37

SEQ ID NO: 58          moltype = DNA  length = 36
FEATURE                Location/Qualifiers
source                 1..36
                       mol_type = other DNA
                       note = Synthetic oligonucleotide sAd4287.2A.rev
                       organism = synthetic construct
SEQUENCE: 58
tctcaccctg caggcaggag atcctcaggc aggccg                           36

SEQ ID NO: 59          moltype = DNA  length = 37
FEATURE                Location/Qualifiers
source                 1..37
                       mol_type = other DNA
                       note = Synthetic oligonucleotide sAd4287.2A.fwd
                       organism = synthetic construct
SEQUENCE: 59
tctcaccctg caggcgacta cctgaacgac cccttgc                          37

SEQ ID NO: 60          moltype = DNA  length = 35
FEATURE                Location/Qualifiers
source                 1..35
                       mol_type = other DNA
                       note = Synthetic oligonucleotide sAd4287.2B.fwd
                       organism = synthetic construct
SEQUENCE: 60
tctcacatta atcgactacc tgaacgaccc cttgc                            35

SEQ ID NO: 61          moltype = DNA  length = 37
FEATURE                Location/Qualifiers
source                 1..37
                       mol_type = other DNA
                       note = Synthetic oligonucleotide sAd4287.2B.rev
                       organism = synthetic construct
SEQUENCE: 61
tctcacttaa ttaactgact ggtgccgatg tcgttcc                          37

SEQ ID NO: 62          moltype = DNA  length = 37
FEATURE                Location/Qualifiers
source                 1..37
                       mol_type = other DNA
                       note = Synthetic oligonucleotide sAd4287.3A.fwd
                       organism = synthetic construct
SEQUENCE: 62
tctcacttaa ttaacccagg acctggaaat agtgcct                          37

SEQ ID NO: 63          moltype = DNA  length = 37
FEATURE                Location/Qualifiers
source                 1..37
                       mol_type = other DNA
                       note = Synthetic oligonucleotide sAd4287.3A.rev
                       organism = synthetic construct
SEQUENCE: 63
tctcaccctg caggggtggg ctgtattgct tgtccgc                          37

SEQ ID NO: 64          moltype = DNA  length = 38
FEATURE                Location/Qualifiers
source                 1..38
                       mol_type = other DNA
                       note = Synthetic oligonucleotide sAd4287.3B.fwd
                       organism = synthetic construct
SEQUENCE: 64
tctcaccctg caggggttgc aggaaaaacc acttggag                         38

SEQ ID NO: 65          moltype = DNA  length = 40
FEATURE                Location/Qualifiers
source                 1..40
                       mol_type = other DNA
                       note = Synthetic oligonucleotide sAd4287.3B.rev
                       organism = synthetic construct
SEQUENCE: 65
tctcacttaa ttaacatcat caataatata ccttattctg                       40

SEQ ID NO: 66          moltype = DNA  length = 23
FEATURE                Location/Qualifiers
source                 1..23
                       mol_type = other DNA
                       note = Synthetic oligonucleotide sAd4287.dE3A.fwd
```

```
                        organism = synthetic construct
SEQUENCE: 66
gagctagaca aactcctctg ccg                                          23

SEQ ID NO: 67           moltype = DNA  length = 36
FEATURE                 Location/Qualifiers
source                  1..36
                        mol_type = other DNA
                        note = Synthetic oligonucleotide sAd4287.dE3A.rev
                        organism = synthetic construct
SEQUENCE: 67
ttcctaacta gtgtagaatt tccacacgca aaggag                            36

SEQ ID NO: 68           moltype = DNA  length = 35
FEATURE                 Location/Qualifiers
source                  1..35
                        mol_type = other DNA
                        note = Synthetic oligonucleotide sAd4287.dE3B.fwd
                        organism = synthetic construct
SEQUENCE: 68
ttcctaacta gtgggagcta tcctgtgtca ctgtc                             35

SEQ ID NO: 69           moltype = DNA  length = 24
FEATURE                 Location/Qualifiers
source                  1..24
                        mol_type = other DNA
                        note = Synthetic oligonucleotide sAd4287.dE3B.rev
                        organism = synthetic construct
SEQUENCE: 69
cagcagttga tgttaattgt ccct                                         24

SEQ ID NO: 70           moltype = DNA  length = 24
FEATURE                 Location/Qualifiers
source                  1..24
                        mol_type = other DNA
                        note = Synthetic oligonucleotide sAd4287.E1.fwd
                        organism = synthetic construct
SEQUENCE: 70
cgctgtcaga tcatcaagag gcca                                         24

SEQ ID NO: 71           moltype = DNA  length = 54
FEATURE                 Location/Qualifiers
source                  1..54
                        mol_type = other DNA
                        note = Synthetic oligonucleotide sAd4287.E1.rev
                        organism = synthetic construct
SEQUENCE: 71
atggctaatg gccaatattg accagtcgac cgtccaccct tcatgcccct ttat        54

SEQ ID NO: 72           moltype = DNA  length = 55
FEATURE                 Location/Qualifiers
source                  1..55
                        mol_type = other DNA
                        note = Synthetic oligonucleotide sAd4287.dE4A.fwd
                        organism = synthetic construct
SEQUENCE: 72
ctcacgttga aaataggaaa cggcctcact ctagacaacc agggacaatt aacat       55

SEQ ID NO: 73           moltype = DNA  length = 38
FEATURE                 Location/Qualifiers
source                  1..38
                        mol_type = other DNA
                        note = Synthetic oligonucleotide sAd4287.dE4A.rev
                        organism = synthetic construct
SEQUENCE: 73
cggtaagacg gggcagtacc aggaggtgcg tcggtctc                          38

SEQ ID NO: 74           moltype = DNA  length = 38
FEATURE                 Location/Qualifiers
source                  1..38
                        mol_type = other DNA
                        note = Synthetic oligonucleotide sAd4287.dE4B.fwd
                        organism = synthetic construct
SEQUENCE: 74
cgcacctcct ggtactgccc cgtcttaccg cgtaaaca                          38

SEQ ID NO: 75           moltype = DNA  length = 53
FEATURE                 Location/Qualifiers
source                  1..53
```

```
                        mol_type = other DNA
                        note = Synthetic oligonucleotide sAd4287.dE4B.rev
                        organism = synthetic construct
SEQUENCE: 75
tgccgatgtc gttccaggtg cccatgagcg gccgcgagcc gtgccgcgga gcc         53

SEQ ID NO: 76           moltype = DNA  length = 40
FEATURE                 Location/Qualifiers
source                  1..40
                        mol_type = other DNA
                        note = Synthetic oligonucleotide sAd4310A.1A.fwd
                        organism = synthetic construct
SEQUENCE: 76
tctcacttaa ttaacatcat caataatata ccttattctg                        40

SEQ ID NO: 77           moltype = DNA  length = 35
FEATURE                 Location/Qualifiers
source                  1..35
                        mol_type = other DNA
                        note = Synthetic oligonucleotide sAd4310A.1A.rev
                        organism = synthetic construct
SEQUENCE: 77
ttatgagtcg acgaggagaa aactctactc gccgg                             35

SEQ ID NO: 78           moltype = DNA  length = 37
FEATURE                 Location/Qualifiers
source                  1..37
                        mol_type = other DNA
                        note = Synthetic oligonucleotide sAd4310A.1B.fwd
                        organism = synthetic construct
SEQUENCE: 78
tatactctta aggacatgtc aatggaactg tttaaag                           37

SEQ ID NO: 79           moltype = DNA  length = 38
FEATURE                 Location/Qualifiers
source                  1..38
                        mol_type = other DNA
                        note = Synthetic oligonucleotide sAd4310A.1B.rev
                        organism = synthetic construct
SEQUENCE: 79
tctcacttaa ttaacctcat tgaaaacgac agataccc                          38

SEQ ID NO: 80           moltype = DNA  length = 36
FEATURE                 Location/Qualifiers
source                  1..36
                        mol_type = other DNA
                        note = Synthetic oligonucleotide sAd4310A.TGC.fwd
                        organism = synthetic construct
SEQUENCE: 80
ttatgagtcg actggtcaat attggccatt agccat                            36

SEQ ID NO: 81           moltype = DNA  length = 37
FEATURE                 Location/Qualifiers
source                  1..37
                        mol_type = other DNA
                        note = Synthetic oligonucleotide sAd4310A.TGC.rev
                        organism = synthetic construct
SEQUENCE: 81
tatactctta aggatctaga catgataaga tacattg                           37

SEQ ID NO: 82           moltype = DNA  length = 39
FEATURE                 Location/Qualifiers
source                  1..39
                        mol_type = other DNA
                        note = Synthetic oligonucleotide sAd4310A.2A.fwd
                        organism = synthetic construct
SEQUENCE: 82
tctcacttaa ttaagacatg tcaatggaac tgtttaaag                         39

SEQ ID NO: 83           moltype = DNA  length = 38
FEATURE                 Location/Qualifiers
source                  1..38
                        mol_type = other DNA
                        note = Synthetic oligonucleotide sAd4310A.2A.rev
                        organism = synthetic construct
SEQUENCE: 83
tctcaccctg caggcaaact ctcctggcct tggatcta                          38

SEQ ID NO: 84           moltype = DNA  length = 37
```

```
FEATURE                 Location/Qualifiers
source                  1..37
                        mol_type = other DNA
                        note = Synthetic oligonucleotide sAd4310A.2B.fwd
                        organism = synthetic construct
SEQUENCE: 84
tctcaccctg cagggtgact cgtacctggg tcatctc                          37

SEQ ID NO: 85           moltype = DNA  length = 38
FEATURE                 Location/Qualifiers
source                  1..38
                        mol_type = other DNA
                        note = Synthetic oligonucleotide sAd4310A.2B.rev
                        organism = synthetic construct
SEQUENCE: 85
tctcacttaa ttaagatgct gttcagcgtg ttttgcca                         38

SEQ ID NO: 86           moltype = DNA  length = 37
FEATURE                 Location/Qualifiers
source                  1..37
                        mol_type = other DNA
                        note = Synthetic oligonucleotide sAd4310A.3A.fwd
                        organism = synthetic construct
SEQUENCE: 86
tctcacttaa ttaacaccgt ggattccgtg atcgaca                          37

SEQ ID NO: 87           moltype = DNA  length = 38
FEATURE                 Location/Qualifiers
source                  1..38
                        mol_type = other DNA
                        note = Synthetic oligonucleotide sAd4310A.3A.rev
                        organism = synthetic construct
SEQUENCE: 87
tctcaccctg cagggttaat gctgtcgaat ctgacgct                         38

SEQ ID NO: 88           moltype = DNA  length = 38
FEATURE                 Location/Qualifiers
source                  1..38
                        mol_type = other DNA
                        note = Synthetic oligonucleotide sAd4310A.3B.fwd
                        organism = synthetic construct
SEQUENCE: 88
tctcaccctg cagggaagac ttcaacccag tgtaccct                         38

SEQ ID NO: 89           moltype = DNA  length = 40
FEATURE                 Location/Qualifiers
source                  1..40
                        mol_type = other DNA
                        note = Synthetic oligonucleotide sAd4310A.3B.rev
                        organism = synthetic construct
SEQUENCE: 89
tctcacttaa ttaacatcat caataatata ccttattctg                       40

SEQ ID NO: 90           moltype = DNA  length = 23
FEATURE                 Location/Qualifiers
source                  1..23
                        mol_type = other DNA
                        note = Synthetic oligonucleotide sAd4310A.dE3A.fwd.G
                        organism = synthetic construct
SEQUENCE: 90
gttgcatgat agggtaactc gcc                                         23

SEQ ID NO: 91           moltype = DNA  length = 47
FEATURE                 Location/Qualifiers
source                  1..47
                        mol_type = other DNA
                        note = Synthetic oligonucleotide sAd4310A.dE3A.rev.G
                        organism = synthetic construct
SEQUENCE: 91
agagaggata gccccctcta caggataagt tcgttagtgc aggcgca               47

SEQ ID NO: 92           moltype = DNA  length = 47
FEATURE                 Location/Qualifiers
source                  1..47
                        mol_type = other DNA
                        note = Synthetic oligonucleotide sAd4310A.dE3B.fwd.G
                        organism = synthetic construct
SEQUENCE: 92
tgcgcctgca ctaacgaact tatcctgtag agggggctat cctctgt               47
```

```
SEQ ID NO: 93          moltype = DNA  length = 23
FEATURE                Location/Qualifiers
source                 1..23
                       mol_type = other DNA
                       note = Synthetic oligonucleotide sAd4310A.dE3B.rev.G
                       organism = synthetic construct
SEQUENCE: 93
gttctacttc cccagcggtt gat                                          23

SEQ ID NO: 94          moltype = DNA  length = 24
FEATURE                Location/Qualifiers
source                 1..24
                       mol_type = other DNA
                       note = Synthetic oligonucleotide sAd4310A.E1.fwd
                       organism = synthetic construct
SEQUENCE: 94
cgtatgcgga aggaggtttt atac                                         24

SEQ ID NO: 95          moltype = DNA  length = 54
FEATURE                Location/Qualifiers
source                 1..54
                       mol_type = other DNA
                       note = Synthetic oligonucleotide sAd4310A.E1.rev
                       organism = synthetic construct
SEQUENCE: 95
atggctaatg gccaatattg accagtcgac ctcacgcccc tttatacccg tttg        54

SEQ ID NO: 96          moltype = DNA  length = 53
FEATURE                Location/Qualifiers
source                 1..53
                       mol_type = other DNA
                       note = Synthetic oligonucleotide sAd4310A.dE4A.fwd
                       organism = synthetic construct
SEQUENCE: 96
ttacagttaa actaggaaac ggcctcactc tagacaacca gggacaacta aca         53

SEQ ID NO: 97          moltype = DNA  length = 43
FEATURE                Location/Qualifiers
source                 1..43
                       mol_type = other DNA
                       note = Synthetic oligonucleotide sAd4310A.dE4A.rev
                       organism = synthetic construct
SEQUENCE: 97
gcggtaagac ggggcagttc tgctactaca agtacgagga agt                    43

SEQ ID NO: 98          moltype = DNA  length = 39
FEATURE                Location/Qualifiers
source                 1..39
                       mol_type = other DNA
                       note = Synthetic oligonucleotide sAd4310A.dE4B.fwd
                       organism = synthetic construct
SEQUENCE: 98
ttgtagtagc agaactgccc cgtcttaccg cgtataaag                         39

SEQ ID NO: 99          moltype = DNA  length = 51
FEATURE                Location/Qualifiers
source                 1..51
                       mol_type = other DNA
                       note = Synthetic oligonucleotide sAd4310A.dE4B.rev
                       organism = synthetic construct
SEQUENCE: 99
gtgccgatgt cgttccaggt gcccatgagc ggccgcgagc cttgccgcgg a           51

SEQ ID NO: 100         moltype = DNA  length = 40
FEATURE                Location/Qualifiers
source                 1..40
                       mol_type = other DNA
                       note = Synthetic oligonucleotide sAd4312.1A.fwd
                       organism = synthetic construct
SEQUENCE: 100
tctcacttaa ttaacatcat caataatata ccttattctg                        40

SEQ ID NO: 101         moltype = DNA  length = 35
FEATURE                Location/Qualifiers
source                 1..35
                       mol_type = other DNA
                       note = Synthetic oligonucleotide sAd4312.1A.rev
                       organism = synthetic construct
```

```
SEQUENCE: 101
ttatgagtcg accggaggag aaaactctac tcgcc                              35

SEQ ID NO: 102          moltype = DNA  length = 38
FEATURE                 Location/Qualifiers
source                  1..38
                        mol_type = other DNA
                        note = Synthetic oligonucleotide sAd4312.1B.fwd
                        organism = synthetic construct
SEQUENCE: 102
tatactctta aggtgataag atatgatgaa tccaagtc                           38

SEQ ID NO: 103          moltype = DNA  length = 38
FEATURE                 Location/Qualifiers
source                  1..38
                        mol_type = other DNA
                        note = Synthetic oligonucleotide sAd4312.1B.rev
                        organism = synthetic construct
SEQUENCE: 103
tctcacttaa ttaagtcacg tgacctacac ttacaagc                           38

SEQ ID NO: 104          moltype = DNA  length = 36
FEATURE                 Location/Qualifiers
source                  1..36
                        mol_type = other DNA
                        note = Synthetic oligonucleotide sAd4312.TGC.fwd
                        organism = synthetic construct
SEQUENCE: 104
ttatgagtcg actggtcaat attggccatt agccat                             36

SEQ ID NO: 105          moltype = DNA  length = 37
FEATURE                 Location/Qualifiers
source                  1..37
                        mol_type = other DNA
                        note = Synthetic oligonucleotide sAd4312.TGC.rev
                        organism = synthetic construct
SEQUENCE: 105
tatactctta aggatctaga catgataaga tacattg                            37

SEQ ID NO: 106          moltype = DNA  length = 40
FEATURE                 Location/Qualifiers
source                  1..40
                        mol_type = other DNA
                        note = Synthetic oligonucleotide sAd4312.2A.fwd
                        organism = synthetic construct
SEQUENCE: 106
tctcacttaa ttaagtgata agatatgatg aatccaagtc                         40

SEQ ID NO: 107          moltype = DNA  length = 35
FEATURE                 Location/Qualifiers
source                  1..35
                        mol_type = other DNA
                        note = Synthetic oligonucleotide sAd4312.2A.rev
                        organism = synthetic construct
SEQUENCE: 107
tctcaccata tgcttctctc agaaaggccg ctcag                              35

SEQ ID NO: 108          moltype = DNA  length = 36
FEATURE                 Location/Qualifiers
source                  1..36
                        mol_type = other DNA
                        note = Synthetic oligonucleotide sAd4312.2B.fwd
                        organism = synthetic construct
SEQUENCE: 108
tctcaccata tgcaagcggc aatatgacga ggtgta                             36

SEQ ID NO: 109          moltype = DNA  length = 36
FEATURE                 Location/Qualifiers
source                  1..36
                        mol_type = other DNA
                        note = Synthetic oligonucleotide sAd4312.2B.rev
                        organism = synthetic construct
SEQUENCE: 109
tctcacttaa ttaagtgtca gcctctgcga gcggtc                             36

SEQ ID NO: 110          moltype = DNA  length = 38
FEATURE                 Location/Qualifiers
source                  1..38
                        mol_type = other DNA
```

```
                        note = Synthetic oligonucleotide sAd4312.3A.fwd
                        organism = synthetic construct
SEQUENCE: 110
tctcacttaa ttaaccgaag ttagaagacc aaaggtgc                          38

SEQ ID NO: 111          moltype = DNA  length = 36
FEATURE                 Location/Qualifiers
source                  1..36
                        mol_type = other DNA
                        note = Synthetic oligonucleotide sAd4312.3A.rev
                        organism = synthetic construct
SEQUENCE: 111
tctcaccctg cagggtgtca gcctctgcga gcggtc                            36

SEQ ID NO: 112          moltype = DNA  length = 38
FEATURE                 Location/Qualifiers
source                  1..38
                        mol_type = other DNA
                        note = Synthetic oligonucleotide sAd4312.3B.fwd
                        organism = synthetic construct
SEQUENCE: 112
tctcaccctg caggccagac cagatacttt atggacca                          38

SEQ ID NO: 113          moltype = DNA  length = 40
FEATURE                 Location/Qualifiers
source                  1..40
                        mol_type = other DNA
                        note = Synthetic oligonucleotide sAd4312.3B.rev
                        organism = synthetic construct
SEQUENCE: 113
tctcacttaa ttaacatcat caataatata ccttattctg                        40

SEQ ID NO: 114          moltype = DNA  length = 24
FEATURE                 Location/Qualifiers
source                  1..24
                        mol_type = other DNA
                        note = Synthetic oligonucleotide sAd4312.dE3A.fwd
                        organism = synthetic construct
SEQUENCE: 114
ggaagacaga aacctcaaag agct                                         24

SEQ ID NO: 115          moltype = DNA  length = 37
FEATURE                 Location/Qualifiers
source                  1..37
                        mol_type = other DNA
                        note = Synthetic oligonucleotide sAd4312.dE3A.rev
                        organism = synthetic construct
SEQUENCE: 115
ttcctaacta gtgtgcaaga acagttaagg ataagag                           37

SEQ ID NO: 116          moltype = DNA  length = 35
FEATURE                 Location/Qualifiers
source                  1..35
                        mol_type = other DNA
                        note = Synthetic oligonucleotide sAd4312.dE3B.fwd
                        organism = synthetic construct
SEQUENCE: 116
ttcctaacta gtgagggggc tatcctgtgt cactg                             35

SEQ ID NO: 117          moltype = DNA  length = 24
FEATURE                 Location/Qualifiers
source                  1..24
                        mol_type = other DNA
                        note = Synthetic oligonucleotide sAd4312.dE3B.rev
                        organism = synthetic construct
SEQUENCE: 117
ccacatttaa caagcgctag ccac                                         24

SEQ ID NO: 118          moltype = DNA  length = 24
FEATURE                 Location/Qualifiers
source                  1..24
                        mol_type = other DNA
                        note = Synthetic oligonucleotide sAd4312.E1.fwd
                        organism = synthetic construct
SEQUENCE: 118
gaaggaggtt ttataccgga agat                                         24

SEQ ID NO: 119          moltype = DNA  length = 53
FEATURE                 Location/Qualifiers
```

-continued

```
source                  1..53
                        mol_type = other DNA
                        note = Synthetic oligonucleotide sAd4312.E1.rev
                        organism = synthetic construct
SEQUENCE: 119
atggctaatg gccaatattg accagtcgac aatacctgtg cccacccatc ctg         53

SEQ ID NO: 120          moltype = DNA  length = 53
FEATURE                 Location/Qualifiers
source                  1..53
                        mol_type = other DNA
                        note = Synthetic oligonucleotide sAd4312.dE4A.fwd
                        organism = synthetic construct
SEQUENCE: 120
agcaccactt taccctcttc ccaactctca tatgggatat gatggtgggc ggc         53

SEQ ID NO: 121          moltype = DNA  length = 40
FEATURE                 Location/Qualifiers
source                  1..40
                        mol_type = other DNA
                        note = Synthetic oligonucleotide sAd4312.dE4A.rev
                        organism = synthetic construct
SEQUENCE: 121
gcggtaagac ggggcgggtt ctgctattgg aagtacgagg                        40

SEQ ID NO: 122          moltype = DNA  length = 38
FEATURE                 Location/Qualifiers
source                  1..38
                        mol_type = other DNA
                        note = Synthetic oligonucleotide sAd4312.dE4B.fwd
                        organism = synthetic construct
SEQUENCE: 122
tccaatagca gaacccgccc cgtcttaccg cgtaaaaa                          38

SEQ ID NO: 123          moltype = DNA  length = 50
FEATURE                 Location/Qualifiers
source                  1..50
                        mol_type = other DNA
                        note = Synthetic oligonucleotide sAd4312.dE4B.rev
                        organism = synthetic construct
SEQUENCE: 123
ctttcatgcg cctgcgtaaa gcccgacggc ggccgctccc cgccatgcct             50

SEQ ID NO: 124          moltype = AA  length = 11
FEATURE                 Location/Qualifiers
source                  1..11
                        mol_type = protein
                        organism = SIVmac239
SEQUENCE: 124
AAVKNWMTQT L                                                       11

SEQ ID NO: 125          moltype = AA  length = 9
FEATURE                 Location/Qualifiers
source                  1..9
                        mol_type = protein
                        organism = SIVmac239
SEQUENCE: 125
KSLYNTVCV                                                          9

SEQ ID NO: 126          moltype = AA  length = 13
FEATURE                 Location/Qualifiers
source                  1..13
                        mol_type = protein
                        organism = SIVmac239
SEQUENCE: 126
DRFYKSLRAE QTD                                                     13
```

What is claimed is:

1. A recombinant adenovirus comprising a nucleotide sequence having at least 90% sequence identity over the entire sequence of any one of SEQ ID NOs: 10 and 12, or a complementary sequence to a nucleotide sequence having at least 90% sequence identity over the entire sequence of any one of SEQ ID NOs: 10 and 12;

wherein said recombinant adenovirus comprises a deletion in or of an E1 region, an E3 region, and/or an E4 region, said deletion rendering said recombinant adenovirus a replication-defective virus.

2. The recombinant adenovirus of claim 1, wherein said nucleotide sequence further comprises all or a portion of any one of SEQ ID NOs: 4, 6, 7, 9, 13, 15, 16, and 18, or a complementary sequence to all or a portion of any one of SEQ ID NOs: 4, 6, 7, 9, 13, 15, 16, and 18.

3. The recombinant adenovirus of claim 1, further comprising a nucleotide sequence having at least 90% sequence identity to the sequence of any one of SEQ ID NOs: 1 and 3 or a complementary sequence to a nucleotide sequence having at least 90% sequence identity over the entire sequence of any one of SEQ ID NOs: 1 and 3.

4. The recombinant adenovirus of claim 2, wherein said nucleotide sequence comprises the nucleotide sequence of any one of SEQ ID NOs: 34-39 and 46-51.

5. The recombinant adenovirus of claim 1, further comprising a heterologous nucleotide sequence encoding an antigenic or therapeutic gene product of interest, or fragment thereof, wherein said antigenic gene product, or fragment thereof, comprises a bacterial, viral, parasitic, or fungal protein, or fragment thereof.

6. The recombinant adenovirus of claim 5, wherein:

(i) said bacterial protein, or fragment thereof, is from Mycobacterium tuberculosis, Mycobacterium bovis, Mycobacterium africanum, Mycobacterium microti, Mycobacterium leprae, Pseudomonas aeruginosa, Salmonella typhimurium, Escherichia coli, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani, or Bacillus anthracis;

(ii) said parasitic protein, or fragment thereof, is from Toxoplasma gondii, Plasmodium falciparum, Plasmodium vivax, Plasmodium ovale, Plasmodium malariae, Trypanosoma spp., or Legionella spp; or (iii) said fungal protein, or fragment thereof, is from Aspergillus, Blastomyces dermatitidis, Candida, Coccidioides immitis, Cryptococcus neoformans, Histoplasma capsulatum var. capsulatum, Paracoccidioides brasiliensis, Sporothrix schenckii, Zygomycetes spp., Absidia corymbifera, Rhizomucor pusillus, or Rhizopus arrhizus.

7. The recombinant adenovirus of claim 5, wherein said viral protein, or fragment thereof, is from a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae, and Reoviridae, or said viral protein, or fragment thereof, is from human immunodeficiency virus (HIV), human papillomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, Zika virus, or Marburg virus.

8. The recombinant adenovirus of claim 7, wherein said viral protein, or fragment thereof, from HIV is Gag, Pol, Env, Nef, Tat, Rev, Vif, Vpr, or Vpu.

9. A method of treating a subject having a disease, said method comprising administering the recombinant adenovirus of claim 5 to said subject.

10. The method of claim 9, wherein said recombinant adenovirus comprises an antigenic gene product, or fragment thereof, that promotes an immune response in said subject against an infective agent, wherein said infective agent is a bacterium, a virus, a parasite, or a fungus.

11. The method of claim 9, wherein:

(a) said subject is human;

(b) said adenovirus is administered intramuscularly; and/or (c) said adenovirus is administered as a pharmaceutical composition comprising a pharmaceutically acceptable carrier.

12. The method of claim 11, wherein:

(i) said subject is administered at least one dose of said pharmaceutical composition;

(ii) said subject is administered at least two doses of said pharmaceutical composition; *or*

(iii) said pharmaceutical composition is administered to said subject as a prime boost.

13. A method of producing a recombinant adenovirus comprising transfecting a cell with: (a) an isolated polynucleotide comprising a nucleotide sequence having at least 90% sequence identity over the entire sequence of any one of SEQ ID NOs: 10 and 12, or a complementary sequence to a nucleotide sequence having at least 90% sequence identity over the entire sequence of any one of SEQ ID NOs: 10 and 12 or (b) a recombinant vector comprising said polynucleotide; culturing said cell in a suitable medium to allow replication of said polynucleotide or vector in said cell; and harvesting produced recombinant adenovirus from said medium and/or said cell.

14. The method of claim 13, wherein said cell is a bacterial, plant, or mammalian cell[, wherein optionally said mammalian cell is a PER.55K cell or a Chinese hamster ovary (CHO) cell].

15. The recombinant adenovirus of claim 5, wherein the viral gene product is an envelope glycoprotein or fragment thereof.

16. A method of inducing an immune response against a flavivirus in a subject comprising administering the recombinant adenovirus of claim 5 to said subject, wherein the antigenic gene product, or fragment thereof, is a viral gene product from the flavivirus.

17. The method of claim 16, wherein the viral gene product is an envelope glycoprotein or fragment thereof.

18. The method of claim 16, wherein the subject is a human.

19. The method of claim 16, wherein the adenovirus is administered intramuscularly.

20. The method of claim 16, wherein the adenovirus is administered as a pharmaceutical composition comprising a pharmaceutically acceptable carrier.

21. The method of claim 20, wherein the subject is administered at least one or two doses of the pharmaceutical composition[, optionally wherein the pharmaceutical composition is administered to the subject as a prime boost].

22. A method of inducing an immune response against a retrovirus in a subject comprising administering the recombinant adenovirus of claim 5 to the subject, wherein the antigenic gene product, or fragment thereof, is a viral gene product from the retrovirus.

23. The method of claim 22, wherein the retrovirus is human immunodeficiency virus (HIV).

24. The method of claim 22, wherein the subject is a human.

25. The method of claim 22, wherein the viral gene product is an envelope glycoprotein or fragment thereof.

26. The method of claim 25, wherein the viral gene product is a protein or fragment thereof from HIV.

27. The method of claim 22, wherein the recombinant adenovirus is administered intramuscularly.

28. The method of claim 22, wherein the recombinant adenovirus is administered as a pharmaceutical composition comprising a pharmaceutically acceptable carrier.

29. The method of claim 28, wherein the subject is administered at least one or two doses of the pharmaceutical composition[, optionally wherein the pharmaceutical composition is administered to the subject as a prime boost].

*30. A vector comprising an E1 region of sAd4287, sAd4310A or sAd4312.*

*31. The vector of claim 30, wherein the E1 region is the E1 region of sAd4287.*

*32. The vector of claim 31, wherein the E1 region comprises nucleotides 474 to 3085 of SEQ ID NO: 1.*

*33. The vector of claim 30, wherein the E1 region is the E1 region of sAd4310A.*

*34. The vector of claim 33, wherein the E1 region comprises nucleotides 474 to 3088 of SEQ ID NO: 2.*

*35. The vector of claim 30, wherein the E1 region is the E1 region of sAd4312.*

*36. The vector of claim 35, wherein the E1 reoion comprises nucleotides 487 to 3100 of SEQ ID NO: 3.*

*37. A cell comprising a vector which comprises an E1 region of sAd4287, sAd4310A or sAd43120.*

*38. The cell of claim 37, wherein the E1 region is the E1 region of sAd4287.*

*39. The cell of claim 38, wherein the E1 region comprises nucleotides 474 to 3085 of SEQ ID NO: 1.*

*40. The cell of claim 37, wherein the E1 region is the E1 region of sAd4310A.*

*41. The cell of claim 40, wherein the E1 region comprises nucleotides 474 to 3088 of SEQ ID NO: 2.*

*42. The cell of claim 37, wherein the E1 region is the E1 region of sAd4312.*

*43. The cell of claim 42, wherein the E1 region comprises nucleotides 487 to 3100 of SEQ ID NO: 3.*

*44. A cell line comprising a portion of sAd4287, sAd4310A or sAd4312 that complements an E1-deficient sAd4287, sAd4310A or sAd4312, respectively.*

*45. The cell line of claim 44, which is a PER.55K cell line.*

*46. The cell line of claim 44, which is a 293 cell line.*

*47. The cell line of claim 44, which complements an E1-deficient sAd4287.*

*48. The cell line of claim 47, which comprises an sAd4287 E1 region.*

*49. The cell line of claim 44, which complements an E1-deficient sAd4310A.*

*50. The cell line of claim 49, which comprises an sAd4310A E1 reqion.*

*51. The cell line of claim 44, which complements an E1-deficient sAd4312.*

*52. The cell line of claim 51, which comprises an sAd4312 E1 region.*

*53. The method of claim 13, wherein the isolated polynucleotide comprises a deletion in or of an E1 region as compared to sAd4287 or sAd4312, and wherein the cell comprises a rescue vector comprising an E1 region of sAd4287 or sAd4312.*

*54. The method of claim 53, wherein the rescue vector comprises an E1 region of sAd4287.*

*55. The method of claim 54, wherein the rescue vector comprises nucleotides 474 to 3085 of SEQ ID NO:1.*

*56. The method of claim 53, wherein the rescue vector comprises an E1 region of sAd4312.*

*57. The method of claim 56, wherein the rescue vector comprises nucleotides 487 to 3100 of SEQ ID NO:3.*

*58. A method of producinq a recombinant adenovirus comprisinq:*

*(a) transfecting a cell with an isolated polynucleotide having a deletion in or of an E1 region as compared to sAd4310 and comprising a nucleotide sequence havinq at least 90% sequence identity over the entire sequence of SEQ ID NO:11, or a complementary sequence to a nucleotide sequence havinq at least 90% sequence identity over the entire sequence of SEQ ID NO:11, wherein the cell comprises a rescue vector comprising an E1 region of sAd4310;*

*(b) culturing said cell in a suitable medium to allow replication of said polynucleotide in said cell; and*

*(c) harvesting produced recombinant adenovirus from said medium and/or said cell.*

*59. The method of claim 58, wherein the vector comprises nucleotides 474 to 3088 of SEQ ID NO:2.*

*60. A replication-defective recombinant adenovirus whose genome comprises:*

*(a) a nucleotide sequence encoding a hexon protein comprising the amino acid sequence of any one of SEQ ID NQs: 25, 26 and 27;*

*(b) a deletion in or of an E1 region; and*

*(c) an expression cassette for a transgene in the deleted E1 region.*

*61. The replication-defective recombinant adenovirus of claim 60, wherein the nucleotide sequence encodes a hexon protein comprising the amino acid sequence of SEQ ID NO:25.*

*62. The replication-defective recombinant adenovirus of claim 60, wherein the nucleotide sequence encodes a hexon protein comprising the amino acid sequence of SEQ ID NO:26.*

*63. The replication-defective recombinant adenovirus of claim 60, wherein the nucleotide sequence encodes a hexon protein comprising the amino acid sequence of SEQ ID NO:27.*

*64. A method of producing the replication-defective recombinant adenovirus of claim 60, comprising:*

*(a) transfecting a cell that is enqineered to rescue the E1 deletion with a polynucleotide comprising the nucleotide sequence of the adenovirus genome;*

*(b) culturing said cell in a suitable medium to allow replication of said polynucleotide in said cell; and*

*(c) harvesting produced recombinant adenovirus from said medium and/or said cell.*

*65. The method of claim 64, wherein the cell is a PER.55K cell.*

*66. The method of claim 64, wherein the cell is a 293 cell.*

*67. The method of claim 14, wherein said mammalian cell is a PER.55K cell or a Chinese hamster ovary (CHO) cell.*

*68. The method of claim 21, wherein the pharmaceutical composition is administered to the subject as a prime boost.*

*69. The method of claim 29, wherein the pharmaceutical composition is administered to the subject as a prime boost.*

* * * * *